US012760312B2

(12) United States Patent
Flasinski

(10) Patent No.: US 12,760,312 B2
(45) Date of Patent: Oct. 13, 2026

(54) PLANT REGULATORY ELEMENTS AND USES THEREOF

(71) Applicant: Monsanto Technology LLC, St. Louis, MO (US)

(72) Inventor: Stanislaw Flasinski, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 94 days.

(21) Appl. No.: 18/773,700

(22) Filed: Jul. 16, 2024

(65) Prior Publication Data

US 2024/0425870 A1 Dec. 26, 2024

Related U.S. Application Data

(62) Division of application No. 17/821,123, filed on Aug. 19, 2022, now Pat. No. 12,071,628, which is a division of application No. 16/900,717, filed on Jun. 12, 2020, now Pat. No. 11,466,282, which is a division of application No. 15/798,319, filed on Oct. 30, 2017, now Pat. No. 10,752,910, which is a division of application No. 14/686,602, filed on Apr. 14, 2015, now Pat. No. 9,834,777, which is a division of application No. 13/428,994, filed on Mar. 23, 2012, now Pat. No. 9,062,316.

(60) Provisional application No. 61/467,875, filed on Mar. 25, 2011.

(51) Int. Cl.
*C12N 15/82* (2006.01)
*C12N 15/113* (2010.01)

(52) U.S. Cl.
CPC ........ *C12N 15/8216* (2013.01); *C12N 15/113* (2013.01); *C12N 15/8222* (2013.01)

(58) Field of Classification Search
None
See application file for complete search history.

(56) References Cited

U.S. PATENT DOCUMENTS

| | | | | |
|---|---|---|---|---|
| 5,633,441 | A | 5/1997 | De Greef et al. | |
| 6,054,574 | A | 4/2000 | Quail et al. | |
| 6,596,925 | B1 | 7/2003 | Perera et al. | |
| 6,878,818 | B1 | 4/2005 | Goldsbrough et al. | |
| 7,211,711 | B2 | 5/2007 | Perera et al. | |
| 7,518,034 | B2 | 4/2009 | Perera et al. | |
| 7,622,641 | B2 | 11/2009 | McCutchen et al. | |
| 7,750,207 | B2 * | 7/2010 | Wu .......................... | C12Q 1/68 435/468 |
| 7,816,581 | B2 | 10/2010 | Gilbertson et al. | |
| 7,932,374 | B2 | 4/2011 | Perera et al. | |
| 9,062,316 | B2 | 6/2015 | Flasinski | |
| 10,752,910 | B2 | 8/2020 | Flasinski | |
| 11,466,282 | B2 | 10/2022 | Flasinski | |
| 12,071,628 | B2 | 8/2024 | Flasinski | |
| 2002/0042932 | A1 | 4/2002 | Back et al. | |
| 2002/0046415 | A1 | 4/2002 | Albert et al. | |
| 2002/0192813 | A1 | 12/2002 | Conner et al. | |
| 2003/0154509 | A1 | 8/2003 | Pascal et al. | |
| 2005/0198712 | A1 | 9/2005 | Betts et al. | |
| 2008/0263721 | A9 | 10/2008 | Boukharov et al. | |
| 2010/0058495 | A1 | 3/2010 | Abbitt | |
| 2010/0199371 | A1 | 8/2010 | Castle et al. | |
| 2011/0023183 | A1 | 1/2011 | Neal et al. | |
| 2011/0177228 | A1 | 7/2011 | Alexandrov et al. | |
| 2015/0167012 | A1 | 6/2015 | Flasinski | |
| 2016/0289693 | A1 | 10/2016 | Flasinski | |
| 2018/0057833 | A1 | 3/2018 | Flasinski | |
| 2018/0105823 | A1 | 4/2018 | Flasinski | |
| 2020/0032289 | A1 | 1/2020 | Anderson et al. | |
| 2020/0080096 | A1 | 3/2020 | Flasinski et al. | |

FOREIGN PATENT DOCUMENTS

| | | | |
|---|---|---|---|
| CA | 2822289 | | 6/2012 |
| CL | 1646-04 | | 6/2004 |
| EP | 1953232 | | 8/2008 |
| RU | 2181380 | | 4/2002 |
| RU | 2326167 | | 6/2008 |
| WO | WO 99/46976 | | 9/1999 |
| WO | WO 99/58659 | A2 | 11/1999 |
| WO | WO 01/94394 | A2 | 12/2001 |
| WO | WO 2006/101938 | | 9/2006 |
| WO | WO 2006/101938 | A1 | 9/2006 |
| WO | WO 2007/112326 | | 10/2007 |
| WO | WO 2008/064289 | A2 | 5/2008 |
| WO | WO 2009/126470 | | 10/2009 |
| WO | WO 2009/149304 | A2 | 12/2009 |
| WO | WO 2010/144385 | A1 | 12/2010 |

OTHER PUBLICATIONS

U.S. Appl. No. 15/668,668, filed Aug. 3, 2017, Flasinski.

Christensen et al., "Maize polyubiquitin genes: structure, thermal perturbation of expression and transcript splicing, and promoter activity following transfer to protoplasts by electroporation," *Plant Molec Biol*, 18(4):675-689. 1992.

EMBL Accession No. CW082733, dated May 19, 2010.

EMBL Accession No. CW0938, XP002685119, dated May 19, 2010.

Frank et al., "Drought and rust effects on gene expression in the dominant plant species of tallgrass prairie, Andropogon gerardii," abstract 16, <http://www.k-state.edu/ecogen/PosterAbstracts-2006.pdf>, 2006.

Frank, "Rust and drought effects on the gene expression and phytohormone concentration in Big Bluestem," thesis, Kansas State University, p. 24, <http://hdl.handle.net/2097/393>, 2007.

(Continued)

*Primary Examiner* — Medina A Ibrahim

(74) *Attorney, Agent, or Firm* — Dentons US LLP; Judith Koehler

(57) ABSTRACT

The present invention provides novel DNA molecules and constructs, including their nucleotide sequences, useful for modulating gene expression in plants and plant cells. The invention also provides transgenic plants, plant cells, plant parts, seeds, and commodity products comprising the DNA molecules operably linked to heterologous transcribable polynucleotides, along with methods of their use.

22 Claims, 31 Drawing Sheets

Specification includes a Sequence Listing.

(56) References Cited

OTHER PUBLICATIONS

GenBank Accession No. X04753, "Potato light-inducible tissue-specific ST-LS1 gene," <http://www.ncbi.nlm.nih.gov/nuccore/X04753>, accessed on Nov. 1, 2012.
International Search Report and Written Opinion issued in PCT/US2012/029990 dated Oct. 29, 2012.
Kim et al., "A 20 nucleotide upstream element is essential for the nopaline synthase (nos) promoter activity," *Plant Molecular Biology* 24:105-117, 1994.
Vettore et al., "The molecular and functional characterization of an Opaque2 homologue gene from Coix and a new classification of plant bZIP proteins," *Plant Molecular Biology* 36(2):249-263, 1998.
Wang et al., "Rice ubiquitin promoters: deletion analysis and potential usefulness in plant transformation systems," *Plant Cell Reproduction* 22:129-134, 2003.
Chilean Office Action regarding Jul. 27, 2013, dated Feb. 16, 2015.
Kosugi et al., "Two of three promoter elements identified in a rice gene for proliferating cell nuclear antigen are essential for meristematic tissue-specific expression," The Plant Journal 7(6):877-886, 1995.
Dolferus et al., "Differential interactions of promoter elements in stress response of the *Arabidopsis* Adh gene", *Plant Physiol.*, 105:1075-1087, 1994.
Donald et al., "Mutation of either G box or I box sequences profoundly affects expression from the *Arabidopsis* rbcS-1A promoter", *The EMBO Journal*, 9(6):1717-1726, 1990.
USPTO: Non-final Office Action regarding U.S. Appl. No. 14/625,566 dated Jan. 20, 2017.
Christensen, et al., "Maize polyubiquitin genes: structure, thermal perturbation of expression and transcript splicing, and promoter activity following transfer to protoplasts by electroporation", *Plant Molecular Biology* 18: 675-689, 1992.
GenBank Accession No. EU161568, dated Dec. 7, 2007.
GenBank Accession No. EU161573, dated Dec. 7, 2007.
Himmelbach et al., "A Set of Modular Binary Vecgtors for Transformation of Cereals," *Plant Physiology* 145:1192-1200, 2007.
Response to Non-Final Office Action regarding U.S. Appl. No. 14/625,566, dated Apr. 19, 2017.
USPTO: Notice of Allowance and Fee(s) Due regarding U.S. Appl. No. 14/625,566, dated May 26, 2017.
USPTO: Notice of Allowability regarding U.S. Appl. No. 14/686,602, dated Oct. 12, 2017.
Decision on Grant of Patent for Invention regarding Russian Application No. 2013147604, dated Nov. 14, 2017.
USPTO: Non-Final Office Action regarding U.S. Appl. No. 15/179,635, dated Nov. 22, 2017.
GenBank Accession No. AY37338, dated Nov. 25, 2003.
GenBank Accession No. DQ141598, dated Sep. 6, 2005.
Lee et al., "Enhanced octopamine synthesis through the ectopic expression of tyrosine decarboxylase in rice plants," *Plant Science* 176:46-50, 2009.
USPTO: Final Office Action regarding U.S. Appl. No. 15/179,635, dated Apr. 6, 2018.
Doebley, "Molecular Evidence for Gene Flow among *Zea* Species," *BioScience* 40(6):443-448, 1990.
Streatfield et al., "Analysis of the maize polyubiquitin-1 promoter heat shock elements and generation of promoter variants with modified expression characteristics," *Transgenic Research* 13:299-312, 2004.
Response to Final Office Action regarding U.S. Appl. No. 15/179,635, dated Jul. 6, 2018.
USPTO: Advisory Action regarding U.S. Appl. No. 15/179,635, dated Jul. 23, 2018.
USPTO: Non-Final Office Action regarding U.S. Appl. No. 15/179,635, dated Sep. 11, 2018.
USPTO: Notice of Allowance and Fee(s) Due regarding U.S. Appl. No. 15/668,668, dated Oct. 1, 2018.
Christensen et al., "Ubiquitin promoter-based vectors for high-level expression of selectable and/or screenable marker genes in monocotyledonous plants," *Transgenic Research* 5:213-218, 1996.
USPTO: Non-Final Office Action regarding U.S. Appl. No. 15/798,326, dated Nov. 28, 2018.
Response to Non-Final Office Action regarding U.S. Appl. No. 15/179,635, dated Dec. 11, 2018.
Response to Non-Final Office Action regarding U.S. Appl. No. 15/798,326, dated Feb. 25, 2019.
USPTO: Final Office Action regarding U.S. Appl. No. 15/179,635, dated Jan. 23, 2019.
Response to Final Office Action regarding U.S. Appl. No. 15/179,635, dated Jul. 1, 2019.
USPTO: Final Office Action regarding U.S. Appl. No. 15/798,326, dated May 24, 2019.
Response to Final Office Action regarding U.S. Appl. No. 15/798,326, dated Aug. 22, 2019.
Notice of Allowance regarding U.S. Appl. No. 15/798,326, dated Sep. 6, 2019.
USPTO: Non-Final Office Action regarding U.S. Appl. No. 15/179,635, dated Nov. 4, 2019.
Response to Non-Final Office Action regarding U.S. Appl. No. 15/179,635, dated Mar. 2, 2020.
USPTO: Notice of Allowance regarding U.S. Appl. No. 15/179,635, dated Mar. 27, 2020.
GenBank Accession No. AY342393. Zea diploperennis polyubiquitin-1 (Ubi-1) gene, promoter region and 5' UTR. Published Aug. 1, 2004. pp. 1-2.
Response to Non-Final Office Action regarding U.S. Appl. No. 15/179,635, dated Feb. 2, 2018.
USPTO: Corrected Notice of Allowability regarding U.S. Appl. No. 15/798,319, dated Jul. 2, 2020.
GenBank Accession No. NC_012879.1, dated Nov. 16, 2009.
Office Action regarding Ukraine App. No. a201803687, mailed Feb. 8, 2024.

* cited by examiner

```
P-ANDge.Ubq1-1:1:9     ------------------------------------------------------------
P-ANDge.Ubq1-1:1:8     ------------------------------------------------------------
P-ANDge.Ubq1-1:1:11    AGCAGACTCGCATTATCGATGGAGGGGTGGGTTTAGAACCCTGAAAACTGGTACTGTTTC
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    ------------------------------------------------------------

P-ANDge.Ubq1-1:1:9     ------------------------------------------------------------
P-ANDge.Ubq1-1:1:8     ------------------------------------------------------------
P-ANDge.Ubq1-1:1:11    GAACTGAAAAACACTGTAGCACTTTTCGTTTGTTTGTGGTAAATATTATCTTACTATGGT
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    ------------------------------------------------------------

P-ANDge.Ubq1-1:1:9     ------------------------------------------------------------
P-ANDge.Ubq1-1:1:8     ------------------------------------------------------------
P-ANDge.Ubq1-1:1:11    CTAACTAGGCTCAAAAGAATCGTCTCGCAATGTACATCTAAATTATGCAATTAGTTATTT
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    ------------------------------------------------------------

P-ANDge.Ubq1-1:1:9     ------------------------------------------------------------
P-ANDge.Ubq1-1:1:8     ------------------------------------------------------------
P-ANDge.Ubq1-1:1:11    TGTTTACCTGCATTTCATACTCCGAGCATGCGTCTTTTGGTACATTTAATGCTTCGATGT
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    ------------------------------------------------------------

P-ANDge.Ubq1-1:1:9     ------------------------------------------------------------
P-ANDge.Ubq1-1:1:8     ------------------------------------------------------------
P-ANDge.Ubq1-1:1:11    GATGGGAATTTTAAAAATTTTGGAGAAAAGTTGGTTTCTAAACACCCCCGAGGACGAAAT
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    ------------------------------------------------------------

P-ANDge.Ubq1-1:1:9     ------------------------------------------------------------
P-ANDge.Ubq1-1:1:8     ------------------------------------------------------------
P-ANDge.Ubq1-1:1:11    TGGATTCGGTCTTTGACGCGGATGCAGCAACTGCAGTGCGCAGGATACCATCTTAGCCGT
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    ------------------------------------------------------------
```

FIG. 1a

```
P-ANDge.Ubq1-1:1:9     ------------------------------------------------------------
P-ANDge.Ubq1-1:1:8     ------------------------------------------------------------
P-ANDge.Ubq1-1:1:11    TGCGTCGAAGTTCGCTTTGCTAACGTTTTGAGAAAATTAAACCAGCTTTGACCAACGTGA
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    ------------------------------------------------------------

P-ANDge.Ubq1-1:1:9     ------------------------------------------------------------
P-ANDge.Ubq1-1:1:8     ------------------------------------------------------------
P-ANDge.Ubq1-1:1:11    GACGAGCGCCTTACGTGGCAGTGTAATGGAACCGGGCACGGCAAGTTTGACGCTGTAGTG
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    ------------------------------------------------------------

P-ANDge.Ubq1-1:1:9     ---------CTCGTTACGTTTGGCACAACTTAGTTGAATCCGGCTTCCGGCAAACTATAT
P-ANDge.Ubq1-1:1:8     ------------------------------------------------------------
P-ANDge.Ubq1-1:1:11    TTAGCCGGTCTCGTTACGTTTGGCACAACTTAGTTGAATCCGGCTTCCGGCAAACTATAT
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    ------------------------------------------------------------

P-ANDge.Ubq1-1:1:9     GGCAAGTTAGACCCAAGTGTGAGCCGGCCACCGCAAGTTATTGGGACATTATACGTAGGA
P-ANDge.Ubq1-1:1:8     ------------------------------------------------------------
P-ANDge.Ubq1-1:1:11    GGCAAGTTAGACCCAAGTGTGAGCCGGCCACCGCAAGTTATTGGGACATTATACGTAGGA
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    ------------------------------------------------------------

P-ANDge.Ubq1-1:1:9     AGCAAGTGTATAATAAGAATATGAGATAATGTAAGCAGCTATATGAATCATCACGTCATA
P-ANDge.Ubq1-1:1:8     ------------------------------------------------------------
P-ANDge.Ubq1-1:1:11    AGCAAGTGTATAATAAGAATATGAGATAATGTAAGCAGCTATATGAATCATCACGTCATA
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    ------------------------------------------------------------

P-ANDge.Ubq1-1:1:9     TTTATGTTAAGATGAAGAGGATAGAATAAACGGTATGTAAATTTATAGCGAGTGATAGAC
P-ANDge.Ubq1-1:1:8     ------------------------------------------------------------
P-ANDge.Ubq1-1:1:11    TTTATGTTAAGATGAAGAGGATAGAATAAACGGTATGTAAATTTATAGCGAGTGATAGAC
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    ------------------------------------------------------------
```

FIG. 1b

```
P-ANDge.Ubq1-1:1:9     GGGCACAAGGCCTCCTAGCTATTTCCATAAATCGGATTTTGTAAGAACAAAAAAGAGGAC
P-ANDge.Ubq1-1:1:8     ------------------------------------------------------------
P-ANDge.Ubq1-1:1:11    GGGCACAAGGCCTCCTAGCTATTTCCATAAATCGGATTTTGTAAGAACAAAAAAGAGGAC
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    ------------------------------------------------------------

P-ANDge.Ubq1-1:1:9     TTATTATAAGAGAATGTGGTAAGTAAGTATACTCTCTCCGTTTCAAATTATAAGTTGTTT
P-ANDge.Ubq1-1:1:8     ------------------------------------------------------------
P-ANDge.Ubq1-1:1:11    TTATTATAAGAGAATGTGGTAAGTAAGTATACTCTCTCCGTTTCAAATTATAAGTTGTTT
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    ------------------------------------------------------------

P-ANDge.Ubq1-1:1:9     TGATTTTTTTGGTACATCTATTTTACTATGCATTAGATATAATAATGTGTCTAGATACAT
P-ANDge.Ubq1-1:1:8     ------------------------------------------------------------
P-ANDge.Ubq1-1:1:11    TGATTTTTTTGGTACATCTATTTTACTATGCATTAGATATAATAATGTGTCTAGATACAT
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    ------------------------------------------------------------

P-ANDge.Ubq1-1:1:9     AACAAAATGGATGAATCAAAAAAGTCAAAGTGATTTACAATTTGGAACGGAGAGAGTAAG
P-ANDge.Ubq1-1:1:8     ------------------------------------------------------------
P-ANDge.Ubq1-1:1:11    AACAAAATGGATGAATCAAAAAAGTCAAAGTGATTTACAATTTGGAACGGAGAGAGTAAG
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    -----------------------------------------------------------G

P-ANDge.Ubq1-1:1:9     TTCAAGCCGTCAAGGCACTTCTATGCAACCACAGTCAACTTGAATGCCGCTTGAGTGCCT
P-ANDge.Ubq1-1:1:8     ------------------------------------------------------------
P-ANDge.Ubq1-1:1:11    TTCAAGCCGTCAAGGCACTTCTATGCAACCACAGTCAACTTGAATGCCGCTTGAGTGCCT
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    TTCAAGCCGTCAAGGCACTTCTATGCAACCACAGTCAACTTGAATGCCGCTTGAGTGCCT

P-ANDge.Ubq1-1:1:9     TCTCAAGTTTTTTTTTCTTGCAAAAATCATTTCTTTTTTTTAAAAAAAGTATAATTTGGA
P-ANDge.Ubq1-1:1:8     ------------------------------------------------------------
P-ANDge.Ubq1-1:1:11    TCTCAAGTTTTTTTTTCTTGCAAAAATCATTTCTTTTTTTTAAAAAAAGTATAATTTGGA
P-ANDge.Ubq1-1:1:12    ------------------------------------------------------------
P-ANDge.Ubq1-1:1:13    ------------------------------------------------------------
P-ANDge.Ubq1-1:1:14    ------------------------------------------------------------
P-ANDge.Ubq1-1:1:10    TCTCAAGTTTTTTTTTCTTGCAAAAATCATTTCTTTTTTTTAAAAAAAGTATAATTTGGA
```

FIG. 1c

```
P-ANDge.Ubq1-1:1:9     TCGTGCAAATTTCTCTCTAGGTGTGTGTGTGACTGTGTGAGTAACAATTTCTCTAGTTGT
P-ANDge.Ubq1-1:1:8     ------------------------------------------------------------
P-ANDge.Ubq1-1:1:11    TCGTGCAAATTTCTCTCTAGGTGTGTGTGTGACTGTGTGAGTAACAATTTCTCTAGTTGT
P-ANDge.Ubq1-1:1:12    ---------------------------------------------------TCTAGTTGT
P-ANDge.Ubq1-1:1:13    ------------------------------------------------------------
P-ANDge.Ubq1-1:1:14    ------------------------------------------------------------
P-ANDge.Ubq1-1:1:10    TCGTGCAAATTTCTCTCTAGGTGTGTGTGTGACTGTGTGAGTAACAATTTCTCTAGTTGT

P-ANDge.Ubq1-1:1:9     GCGCGACTGCTGCTTACTTTGGAGATTACAATATCTTTCTAAAATGCTTCGATTACTTAT
P-ANDge.Ubq1-1:1:8     ------------------------------------------------------------
P-ANDge.Ubq1-1:1:11    GCGCGACTGCTGCTTACTTTGGAGATTACAATATCTTTCTAAAATGCTTCGATTACTTAT
P-ANDge.Ubq1-1:1:12    GCGCGACTGCTGCTTACTTTGGAGATTACAATATCTTTCTAAAATGCTTCGATTACTTAT
P-ANDge.Ubq1-1:1:13    ------------------------------------------------------------
P-ANDge.Ubq1-1:1:14    ------------------------------------------------------------
P-ANDge.Ubq1-1:1:10    GCGCGACTGCTGCTTACTTTGGAGATTACAATATCTTTCTAAAATGCTTCGATTACTTAT

P-ANDge.Ubq1-1:1:9     TTATAAACCGTCTCTAAGGCCAATTGCTCAAGATTCATTCAACAATTGAAACGTCTCACA
P-ANDge.Ubq1-1:1:8     ------------------------------------------------------------
P-ANDge.Ubq1-1:1:11    TTATAAACCGTCTCTAAGGCCAATTGCTCAAGATTCATTCAACAATTGAAACGTCTCACA
P-ANDge.Ubq1-1:1:12    TTATAAACCGTCTCTAAGGCCAATTGCTCAAGATTCATTCAACAATTGAAACGTCTCACA
P-ANDge.Ubq1-1:1:13    ------------------------------------------------------------
P-ANDge.Ubq1-1:1:14    ------------------------------------------------------------
P-ANDge.Ubq1-1:1:10    TTATAAACCGTCTCTAAGGCCAATTGCTCAAGATTCATTCAACAATTGAAACGTCTCACA

P-ANDge.Ubq1-1:1:9     TGATTAAATCATATAAAGTTTCTAAGTCTTGTTTGACAAGATTTTTTTAGATTTTCATCT
P-ANDge.Ubq1-1:1:8     ------------------------------------------------------------
P-ANDge.Ubq1-1:1:11    TGATTAAATCATATAAAGTTTCTAAGTCTTGTTTGACAAGATTTTTTTAGATTTTCATCT
P-ANDge.Ubq1-1:1:12    TGATTAAATCATATAAAGTTTCTAAGTCTTGTTTGACAAGATTTTTTTAGATTTTCATCT
P-ANDge.Ubq1-1:1:13    ------------------------------------------------------------
P-ANDge.Ubq1-1:1:14    ------------------------------------------------------------
P-ANDge.Ubq1-1:1:10    TGATTAAATCATATAAAGTTTCTAAGTCTTGTTTGACAAGATTTTTTTAGATTTTCATCT

P-ANDge.Ubq1-1:1:9     AAATTGGATGAAACTATCAAACACTAATTTTAAAAAATATAAGAGAAGCTCCGGAGATAA
P-ANDge.Ubq1-1:1:8     ------------------------------------------------------------
P-ANDge.Ubq1-1:1:11    AAATTGGATGAAACTATCAAACACTAATTTTAAAAAATATAAGAGAAGCTCCGGAGATAA
P-ANDge.Ubq1-1:1:12    AAATTGGATGAAACTATCAAACACTAATTTTAAAAAATATAAGAGAAGCTCCGGAGATAA
P-ANDge.Ubq1-1:1:13    ------------------------------------------------------------
P-ANDge.Ubq1-1:1:14    ------------------------------------------------------------
P-ANDge.Ubq1-1:1:10    AAATTGGATGAAACTATCAAACACTAATTTTAAAAAATATAAGAGAAGCTCCGGAGATAA

P-ANDge.Ubq1-1:1:9     AAGGTCGTCTATGTTATTATAAGAGTAAAGTCGTCTATTCTCTTCGTCCCAACATATATA
P-ANDge.Ubq1-1:1:8     ------------------------------------------------------------
P-ANDge.Ubq1-1:1:11    AAGGTCGTCTATGTTATTATAAGAGTAAAGTCGTCTATTCTCTTCGTCCCAACATATATA
P-ANDge.Ubq1-1:1:12    AAGGTCGTCTATGTTATTATAAGAGTAAAGTCGTCTATTCTCTTCGTCCCAACATATATA
P-ANDge.Ubq1-1:1:13    ------------------------------------------------------------
P-ANDge.Ubq1-1:1:14    ------------------------------------------------------------
P-ANDge.Ubq1-1:1:10    AAGGTCGTCTATGTTATTATAAGAGTAAAGTCGTCTATTCTCTTCGTCCCAACATATATA
```

FIG. 1d

```
P-ANDge.Ubq1-1:1:9     ATTCTAAGCATGAATTGCTTTCTTTTTGGACAAAAGGAGCATGCCACAACACAAGAATGA
P-ANDge.Ubq1-1:1:8     --------------------------------------------------CACAAGAATGA
P-ANDge.Ubq1-1:1:11    ATTCTAAGCATGAATTGCTTTCTTTTTGGACAAAAGGAGCATGCCACAACACAAGAATGA
P-ANDge.Ubq1-1:1:12    ATTCTAAGCATGAATTGCTTTCTTTTTGGACAAAAGGAGCATGCCACAACACAAGAATGA
P-ANDge.Ubq1-1:1:13    ------------------------------------------------------------
P-ANDge.Ubq1-1:1:14    ------------------------------------------------------------
P-ANDge.Ubq1-1:1:10    ATTCTAAGCATGAATTGCTTTCTTTTTGGACAAAAGGAGCATGCCACAACACAAGAATGA

P-ANDge.Ubq1-1:1:9     TGTCACCGTCATGCTTGGATCCTTTTATGGTAAAGCTTCACCTTCTATAATCTAACAATA
P-ANDge.Ubq1-1:1:8     TGTCACCGTCATGCTTGGATCCTTTTATGGTAAAGCTTCACCTTCTATAATCTAACAATA
P-ANDge.Ubq1-1:1:11    TGTCACCGTCATGCTTGGATCCTTTTATGGTAAAGCTTCACCTTCTATAATCTAACAATA
P-ANDge.Ubq1-1:1:12    TGTCACCGTCATGCTTGGATCCTTTTATGGTAAAGCTTCACCTTCTATAATCTAACAATA
P-ANDge.Ubq1-1:1:13    ------------------------------------------------------------
P-ANDge.Ubq1-1:1:14    ------------------------------------------------------------
P-ANDge.Ubq1-1:1:10    TGTCACCGTCATGCTTGGATCCTTTTATGGTAAAGCTTCACCTTCTATAATCTAACAATA

P-ANDge.Ubq1-1:1:9     GAGAAATCAGGGAAAAATCATGTTTTGGTTGTTTTTATTTCTAACCTCCACAATAACTTT
P-ANDge.Ubq1-1:1:8     GAGAAATCAGGGAAAAATCATGTTTTGGTTGTTTTTATTTCTAACCTCCACAATAACTTT
P-ANDge.Ubq1-1:1:11    GAGAAATCAGGGAAAAATCATGTTTTGGTTGTTTTTATTTCTAACCTCCACAATAACTTT
P-ANDge.Ubq1-1:1:12    GAGAAATCAGGGAAAAATCATGTTTTGGTTGTTTTTATTTCTAACCTCCACAATAACTTT
P-ANDge.Ubq1-1:1:13    ------------------------------------------------------------
P-ANDge.Ubq1-1:1:14    ------------------------------------------------------------
P-ANDge.Ubq1-1:1:10    GAGAAATCAGGGAAAAATCATGTTTTGGTTGTTTTTATTTCTAACCTCCACAATAACTTT

P-ANDge.Ubq1-1:1:9     GGTTTACCATTTTTTTGTTTGATTTTAGTTTTAGAGAAGCGTTTATAACAGGACCTAAAAT
P-ANDge.Ubq1-1:1:8     GGTTTACCATTTTTTTGTTTGATTTTAGTTTTAGAGAAGCGTTTATAACAGGACCTAAAAT
P-ANDge.Ubq1-1:1:11    GGTTTACCATTTTTTTGTTTGATTTTAGTTTTAGAGAAGCGTTTATAACAGGACCTAAAAT
P-ANDge.Ubq1-1:1:12    GGTTTACCATTTTTTTGTTTGATTTTAGTTTTAGAGAAGCGTTTATAACAGGACCTAAAAT
P-ANDge.Ubq1-1:1:13    ------------------------------------------------------------
P-ANDge.Ubq1-1:1:14    ------------------------------------------------------------
P-ANDge.Ubq1-1:1:10    GGTTTACCATTTTTTTGTTTGATTTTAGTTTTAGAGAAGCGTTTATAACAGGACCTAAAAT

P-ANDge.Ubq1-1:1:9     CTTTTTTCAGTACACAGTACAACGCAGACGCTCATACACGCACGCACACTCACCTCTATG
P-ANDge.Ubq1-1:1:8     CTTTTTTCAGTACACAGTACAACGCAGACGCTCATACACGCACGCACACTCACCTCTATG
P-ANDge.Ubq1-1:1:11    CTTTTTTCAGTACACAGTACAACGCAGACGCTCATACACGCACGCACACTCACCTCTATG
P-ANDge.Ubq1-1:1:12    CTTTTTTCAGTACACAGTACAACGCAGACGCTCATACACGCACGCACACTCACCTCTATG
P-ANDge.Ubq1-1:1:13    ------------------------------------------------------------
P-ANDge.Ubq1-1:1:14    ------------------------------------------------------------
P-ANDge.Ubq1-1:1:10    CTTTTTTCAGTACACAGTACAACGCAGACGCTCATACACGCACGCACACTCACCTCTATG

P-ANDge.Ubq1-1:1:9     AACACACGTAAGAAAACCCTACACCTTGAGCACCTTCGAAGGACTGAGCCGGTAAATATA
P-ANDge.Ubq1-1:1:8     AACACACGTAAGAAAACCCTACACCTTGAGCACCTTCGAAGGACTGAGCCGGTAAATATA
P-ANDge.Ubq1-1:1:11    AACACACGTAAGAAAACCCTACACCTTGAGCACCTTCGAAGGACTGAGCCGGTAAATATA
P-ANDge.Ubq1-1:1:12    AACACACGTAAGAAAACCCTACACCTTGAGCACCTTCGAAGGACTGAGCCGGTAAATATA
P-ANDge.Ubq1-1:1:13    ------------------------------------------------------------
P-ANDge.Ubq1-1:1:14    ------------------------------------------------------------
P-ANDge.Ubq1-1:1:10    AACACACGTAAGAAAACCCTACACCTTGAGCACCTTCGAAGGACTGAGCCGGTAAATATA
```

FIG. 1e

```
P-ANDge.Ubq1-1:1:9     GAGATTCTCGAAGTCACTATTAGCGCCTCGTTGTCAACGGGAATGTCGCTTACCACTTAA
P-ANDge.Ubq1-1:1:8     GAGATTCTCGAAGTCACTATTAGCGCCTCGTTGTCAACGGGAATGTCGCTTACCACTTAA
P-ANDge.Ubq1-1:1:11    GAGATTCTCGAAGTCACTATTAGCGCCTCGTTGTCAACGGGAATGTCGCTTACCACTTAA
P-ANDge.Ubq1-1:1:12    GAGATTCTCGAAGTCACTATTAGCGCCTCGTTGTCAACGGGAATGTCGCTTACCACTTAA
P-ANDge.Ubq1-1:1:13    --------------------------------GTCAACGGGAATGTCGCTTACCACTTAA
P-ANDge.Ubq1-1:1:14    ------------------------------------------------------------
P-ANDge.Ubq1-1:1:10    GAGATTCTCGAAGTCACTATTAGCGCCTCGTTGTCAACGGGAATGTCGCTTACCACTTAA

P-ANDge.Ubq1-1:1:9     AGCATAACGCCGAGAAATCCCGTAATAAATCCAGTAAAATACGAGCACCCGTGCCAAGTT
P-ANDge.Ubq1-1:1:8     AGCATAACGCCGAGAAATCCCGTAATAAATCCAGTAAAATACGAGCACCCGTGCCAAGTT
P-ANDge.Ubq1-1:1:11    AGCATAACGCCGAGAAATCCCGTAATAAATCCAGTAAAATACGAGCACCCGTGCCAAGTT
P-ANDge.Ubq1-1:1:12    AGCATAACGCCGAGAAATCCCGTAATAAATCCAGTAAAATACGAGCACCCGTGCCAAGTT
P-ANDge.Ubq1-1:1:13    AGCATAACGCCGAGAAATCCCGTAATAAATCCAGTAAAATACGAGCACCCGTGCCAAGTT
P-ANDge.Ubq1-1:1:14    ------------------------------------------------------------
P-ANDge.Ubq1-1:1:10    AGCATAACGCCGAGAAATCCCGTAATAAATCCAGTAAAATACGAGCACCCGTGCCAAGTT

P-ANDge.Ubq1-1:1:9     GAATATTTGAACCCGAGTGGGTAGATTCCACCGCAAAGGACCTAACCAGATCATTTCGCA
P-ANDge.Ubq1-1:1:8     GAATATTTGAACCCGAGTGGGTAGATTCCACCGCAAAGGACCTAACCAGATCATTTCGCA
P-ANDge.Ubq1-1:1:11    GAATATTTGAACCCGAGTGGGTAGATTCCACCGCAAAGGACCTAACCAGATCATTTCGCA
P-ANDge.Ubq1-1:1:12    GAATATTTGAACCCGAGTGGGTAGATTCCACCGCAAAGGACCTAACCAGATCATTTCGCA
P-ANDge.Ubq1-1:1:13    GAATATTTGAACCCGAGTGGGTAGATTCCACCGCAAAGGACCTAACCAGATCATTTCGCA
P-ANDge.Ubq1-1:1:14    ------------------------------------------------------------
P-ANDge.Ubq1-1:1:10    GAATATTTGAACCCGAGTGGGTAGATTCCACCGCAAAGGACCTAACCAGATCATTTCGCA

P-ANDge.Ubq1-1:1:9     AACAGGAACTAAAATCGGTAGAGAGCCCAGACAAAAGCCTTTCCTAAGAGCCACTCCAGT
P-ANDge.Ubq1-1:1:8     AACAGGAACTAAAATCGGTAGAGAGCCCAGACAAAAGCCTTTCCTAAGAGCCACTCCAGT
P-ANDge.Ubq1-1:1:11    AACAGGAACTAAAATCGGTAGAGAGCCCAGACAAAAGCCTTTCCTAAGAGCCACTCCAGT
P-ANDge.Ubq1-1:1:12    AACAGGAACTAAAATCGGTAGAGAGCCCAGACAAAAGCCTTTCCTAAGAGCCACTCCAGT
P-ANDge.Ubq1-1:1:13    AACAGGAACTAAAATCGGTAGAGAGCCCAGACAAAAGCCTTTCCTAAGAGCCACTCCAGT
P-ANDge.Ubq1-1:1:14    ------------------------------------------------------------
P-ANDge.Ubq1-1:1:10    AACAGGAACTAAAATCGGTAGAGAGCCCAGACAAAAGCCTTTCCTAAGAGCCACTCCAGT

P-ANDge.Ubq1-1:1:9     GGAAGCCCCTACTTTAGGTATAAAATGCAATACTAGTGGGGCTCCTAAATAAACTTCTAT
P-ANDge.Ubq1-1:1:8     GGAAGCCCCTACTTTAGGTATAAAATGCAATACTAGTGGGGCTCCTAAATAAACTTCTAT
P-ANDge.Ubq1-1:1:11    GGAAGCCCCTACTTTAGGTATAAAATGCAATACTAGTGGGGCTCCTAAATAAACTTCTAT
P-ANDge.Ubq1-1:1:12    GGAAGCCCCTACTTTAGGTATAAAATGCAATACTAGTGGGGCTCCTAAATAAACTTCTAT
P-ANDge.Ubq1-1:1:13    GGAAGCCCCTACTTTAGGTATAAAATGCAATACTAGTGGGGCTCCTAAATAAACTTCTAT
P-ANDge.Ubq1-1:1:14    ------------------------------------------------------------
P-ANDge.Ubq1-1:1:10    GGAAGCCCCTACTTTAGGTATAAAATGCAATACTAGTGGGGCTCCTAAATAAACTTCTAT

P-ANDge.Ubq1-1:1:9     TTTTCATGGCCTTCTAAAATTCACTCCCAAACCCCTAGCTATAGAAGTCTCTTATCCATC
P-ANDge.Ubq1-1:1:8     TTTTCATGGCCTTCTAAAATTCACTCCCAAACCCCTAGCTATAGAAGTCTCTTATCCATC
P-ANDge.Ubq1-1:1:11    TTTTCATGGCCTTCTAAAATTCACTCCCAAACCCCTAGCTATAGAAGTCTCTTATCCATC
P-ANDge.Ubq1-1:1:12    TTTTCATGGCCTTCTAAAATTCACTCCCAAACCCCTAGCTATAGAAGTCTCTTATCCATC
P-ANDge.Ubq1-1:1:13    TTTTCATGGCCTTCTAAAATTCACTCCCAAACCCCTAGCTATAGAAGTCTCTTATCCATC
P-ANDge.Ubq1-1:1:14    ---------------------CACTCCCAAACCCCTAGCTATAGAAGTCTCTTATCCATC
P-ANDge.Ubq1-1:1:10    TTTTCATGGCCTTCTAAAATTCACTCCCAAACCCCTAGCTATAGAAGTCTCTTATCCATC
                                            ***************************************
```

FIG. 1f

```
P-ANDge.Ubq1-1:1:9       CTCTAAATAAAAATGGGAGTCTATTTTATTTCACCAGAGTTGATCGTAAATTTAGTCTCT
P-ANDge.Ubq1-1:1:8       CTCTAAATAAAAATGGGAGTCTATTTTATTTCACCAGAGTTGATCGTAAATTTAGTCTCT
P-ANDge.Ubq1-1:1:11      CTCTAAATAAAAATGGGAGTCTATTTTATTTCACCAGAGTTGATCGTAAATTTAGTCTCT
P-ANDge.Ubq1-1:1:12      CTCTAAATAAAAATGGGAGTCTATTTTATTTCACCAGAGTTGATCGTAAATTTAGTCTCT
P-ANDge.Ubq1-1:1:13      CTCTAAATAAAAATGGGAGTCTATTTTATTTCACCAGAGTTGATCGTAAATTTAGTCTCT
P-ANDge.Ubq1-1:1:14      CTCTAAATAAAAATGGGAGTCTATTTTATTTCACCAGAGTTGATCGTAAATTTAGTCTCT
P-ANDge.Ubq1-1:1:10      CTCTAAATAAAAATGGGAGTCTATTTTATTTCACCAGAGTTGATCGTAAATTTAGTCTCT
                         ************************************************************

P-ANDge.Ubq1-1:1:9       CAAATTTTATAAGTTGAGGGTAGAGGATGACTGGAGTTGCTCTAAACGGACCTATCTTCA
P-ANDge.Ubq1-1:1:8       CAAATTTTATAAGTTGAGGGTAGAGGATGACTGGAGTTGCTCTAAACGGACCTATCTTCA
P-ANDge.Ubq1-1:1:11      CAAATTTTATAAGTTGAGGGTAGAGGATGACTGGAGTTGCTCTAAACGGACCTATCTTCA
P-ANDge.Ubq1-1:1:12      CAAATTTTATAAGTTGAGGGTAGAGGATGACTGGAGTTGCTCTAAACGGACCTATCTTCA
P-ANDge.Ubq1-1:1:13      CAAATTTTATAAGTTGAGGGTAGAGGATGACTGGAGTTGCTCTAAACGGACCTATCTTCA
P-ANDge.Ubq1-1:1:14      CAAATTTTATAAGTTGAGGGTAGAGGATGACTGGAGTTGCTCTAAACGGACCTATCTTCA
P-ANDge.Ubq1-1:1:10      CAAATTTTATAAGTTGAGGGTAGAGGATGACTGGAGTTGCTCTAAACGGACCTATCTTCA
                         ************************************************************

P-ANDge.Ubq1-1:1:9       AGTGACCTCAGTGAGCCCGTTTAACGGCGTCGACAAGTTTAATCTAACGGACACCAACCA
P-ANDge.Ubq1-1:1:8       AGTGACCTCAGTGAGCCCGTTTAACGGCGTCGACAAGTTTAATCTAACGGACACCAACCA
P-ANDge.Ubq1-1:1:11      AGTGACCTCAGTGAGCCCGTTTAACGGCGTCGACAAGTTTAATCTAACGGACACCAACCA
P-ANDge.Ubq1-1:1:12      AGTGACCTCAGTGAGCCCGTTTAACGGCGTCGACAAGTTTAATCTAACGGACACCAACCA
P-ANDge.Ubq1-1:1:13      AGTGACCTCAGTGAGCCCGTTTAACGGCGTCGACAAGTTTAATCTAACGGACACCAACCA
P-ANDge.Ubq1-1:1:14      AGTGACCTCAGTGAGCCCGTTTAACGGCGTCGACAAGTTTAATCTAACGGACACCAACCA
P-ANDge.Ubq1-1:1:10      AGTGACCTCAGTGAGCCCGTTTAACGGCGTCGACAAGTTTAATCTAACGGACACCAACCA
                         ************************************************************

P-ANDge.Ubq1-1:1:9       GAGAAGAGAACCACCGCCAGCGCCGAGCCAAGCGACGTTGACATCTTGGCGCGGCACGGC
P-ANDge.Ubq1-1:1:8       GAGAAGAGAACCACCGCCAGCGCCGAGCCAAGCGACGTTGACATCTTGGCGCGGCACGGC
P-ANDge.Ubq1-1:1:11      GAGAAGAGAACCACCGCCAGCGCCGAGCCAAGCGACGTTGACATCTTGGCGCGGCACGGC
P-ANDge.Ubq1-1:1:12      GAGAAGAGAACCACCGCCAGCGCCGAGCCAAGCGACGTTGACATCTTGGCGCGGCACGGC
P-ANDge.Ubq1-1:1:13      GAGAAGAGAACCACCGCCAGCGCCGAGCCAAGCGACGTTGACATCTTGGCGCGGCACGGC
P-ANDge.Ubq1-1:1:14      GAGAAGAGAACCACCGCCAGCGCCGAGCCAAGCGACGTTGACATCTTGGCGCGGCACGGC
P-ANDge.Ubq1-1:1:10      GAGAAGAGAACCACCGCCAGCGCCGAGCCAAGCGACGTTGACATCTTGGCGCGGCACGGC
                         ************************************************************

P-ANDge.Ubq1-1:1:9       ATCTCCCTGGCGTCTGGCCCCCTCTCGAGACTTCCGCTCCACCTCCCACCGGTGGCGGTT
P-ANDge.Ubq1-1:1:8       ATCTCCCTGGCGTCTGGCCCCCTCTCGAGACTTCCGCTCCACCTCCCACCGGTGGCGGTT
P-ANDge.Ubq1-1:1:11      ATCTCCCTGGCGTCTGGCCCCCTCTCGAGACTTCCGCTCCACCTCCCACCGGTGGCGGTT
P-ANDge.Ubq1-1:1:12      ATCTCCCTGGCGTCTGGCCCCCTCTCGAGACTTCCGCTCCACCTCCCACCGGTGGCGGTT
P-ANDge.Ubq1-1:1:13      ATCTCCCTGGCGTCTGGCCCCCTCTCGAGACTTCCGCTCCACCTCCCACCGGTGGCGGTT
P-ANDge.Ubq1-1:1:14      ATCTCCCTGGCGTCTGGCCCCCTCTCGAGACTTCCGCTCCACCTCCCACCGGTGGCGGTT
P-ANDge.Ubq1-1:1:10      ATCTCCCTGGCGTCTGGCCCCCTCTCGAGACTTCCGCTCCACCTCCCACCGGTGGCGGTT
                         ************************************************************
```

FIG. 1g

```
P-ANDge.Ubq1-1:1:9      TCCAAGTCCGTTCCGCCTCCTCTCACACGGCACGAAACCGTGACGGGCACCGGCAGCACG
P-ANDge.Ubq1-1:1:8      TCCAAGTCCGTTCCGCCTCCTCTCACACGGCACGAAACCGTGACGGGCACCGGCAGCACG
P-ANDge.Ubq1-1:1:11     TCCAAGTCCGTTCCGCCTCCTCTCACACGGCACGAAACCGTGACGGGCACCGGCAGCACG
P-ANDge.Ubq1-1:1:12     TCCAAGTCCGTTCCGCCTCCTCTCACACGGCACGAAACCGTGACGGGCACCGGCAGCACG
P-ANDge.Ubq1-1:1:13     TCCAAGTCCGTTCCGCCTCCTCTCACACGGCACGAAACCGTGACGGGCACCGGCAGCACG
P-ANDge.Ubq1-1:1:14     TCCAAGTCCGTTCCGCCTCCTCTCACACGGCACGAAACCGTGACGGGCACCGGCAGCACG
P-ANDge.Ubq1-1:1:10     TCCAAGTCCGTTCCGCCTCCTCTCACACGGCACGAAACCGTGACGGGCACCGGCAGCACG
                        ************************************************************

P-ANDge.Ubq1-1:1:9      GGGGGATTCCTTTCCCACCGCTCCTTCCCTTTCCCTTCCTCTCCCGCCGCTATAAATAGC
P-ANDge.Ubq1-1:1:8      GGGGGATTCCTTTCCCACCGCTCCTTCCCTTTCCCTTCCTCTCCCGCCGCTATAAATAGC
P-ANDge.Ubq1-1:1:11     GGGGGATTCCTTTCCCACCGCTCCTTCCCTTTCCCTTCCTCTCCCGCCGCTATAAATAGC
P-ANDge.Ubq1-1:1:12     GGGGGATTCCTTTCCCACCGCTCCTTCCCTTTCCCTTCCTCTCCCGCCGCTATAAATAGC
P-ANDge.Ubq1-1:1:13     GGGGGATTCCTTTCCCACCGCTCCTTCCCTTTCCCTTCCTCTCCCGCCGCTATAAATAGC
P-ANDge.Ubq1-1:1:14     GGGGGATTCCTTTCCCACCGCTCCTTCCCTTTCCCTTCCTCTCCCGCCGCTATAAATAGC
P-ANDge.Ubq1-1:1:10     GGGGGATTCCTTTCCCACCGCTCCTTCCCTTTCCCTTCCTCTCCCGCCGCTATAAATAGC
                        ************************************************************

P-ANDge.Ubq1-1:1:9      CAGCCCCATCCCCAGCTTCTTTC
P-ANDge.Ubq1-1:1:8      CAGCCCCATCCCCAGCTTCTTTC
P-ANDge.Ubq1-1:1:11     CAGCCCCATCCCCAGCTTCTTTC
P-ANDge.Ubq1-1:1:12     CAGCCCCATCCCCAGCTTCTTTC
P-ANDge.Ubq1-1:1:13     CAGCCCCATCCCCAGCTTCTTTC
P-ANDge.Ubq1-1:1:14     CAGCCCCATCCCCAGCTTCTTTC
P-ANDge.Ubq1-1:1:10     CAGCCCCATCCCCAGCTTCTTTC
                        ***********************
```

FIG. 1h

```
P-ERIra.Ubq1-1:1:9      ------------------------------------------------------------
P-ERIra.Ubq1-1:1:10     GTGGCCAGCTTTTGTTCTAGTTCAACGGCCCCGGCCTTCCGGGCACCTAATACCCTAATT
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------

P-ERIra.Ubq1-1:1:9      ------------------------------------------------------------
P-ERIra.Ubq1-1:1:10     AATCTATTGCAGCTAACCTCAAAAGAAATGCATTTGCAGTTGTCTGTCCCAATCAATCTA
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------

P-ERIra.Ubq1-1:1:9      ------------------------------------------------------------
P-ERIra.Ubq1-1:1:10     CTAGCAGACTTACATTATAGATGGAGGAAATTAAATTCAGCCTTTGACGTGGATGCAACA
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------

P-ERIra.Ubq1-1:1:9      ------------------------------------------------------------
P-ERIra.Ubq1-1:1:10     ACTGCACTGCACAGGATACCATCTTAGCCGTTGTGTCAAAGTTTGCTTTGCTAAACGTTT
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------

P-ERIra.Ubq1-1:1:9      ------------------------------------------------------------
P-ERIra.Ubq1-1:1:10     TGAGAAAACCAGCTTTGACCAACGCGAGATGAGCGCCTTACGTTTGGCACAATGTAATGT
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------

P-ERIra.Ubq1-1:1:9      ------------------------------------------------------------
P-ERIra.Ubq1-1:1:10     AATCCGGCACGGCAAGTTAGACTCTGTAGTGTTAGCCGGCCTCTTTACGTTTGGCATAGT
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------
```

FIG. 2a

```
P-ERIra.Ubq1-1:1:9      ------------------------------------------------------------
P-ERIra.Ubq1-1:1:10     TTAATTGAATCCGGCATGGCAAGTTAGACCGTAGTGTGAGCCGGCCAACGCAAGTTATTA
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------

P-ERIra.Ubq1-1:1:9      --------GTATAAGAGCAAGTGTATTGTCACGTGATATTTATGTTGAGATGAAGAAGAG
P-ERIra.Ubq1-1:1:10     TGACATATGTATAAGAGCAAGTGTATTGTCACGTGATATTTATGTTGAGATGAAGAAGAG
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------

P-ERIra.Ubq1-1:1:9      AAAATAAACAGCCTGCAAATTTATAGCGAGTGATAGATGGGCACAAGGCTTCCTATTTCT
P-ERIra.Ubq1-1:1:10     AAAATAAACAGCCTGCAAATTTATAGCGAGTGATAGATGGGCACAAGGCTTCCTATTTCT
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------

P-ERIra.Ubq1-1:1:9      TAAATCAGACTTTGTAAGAACAAAAAAAGGACTTATAAGAGAATGGGATAAACCATATAT
P-ERIra.Ubq1-1:1:10     TAAATCAGACTTTGTAAGAACAAAAAAAGGACTTATAAGAGAATGGGATAAACCATATAT
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------

P-ERIra.Ubq1-1:1:9      CAATGGTGTAGTATGTTAGTATGCATTAAGATCTGACTATTATATGAGTGAGTTGTTAAA
P-ERIra.Ubq1-1:1:10     CAATGGTGTAGTATGTTAGTATGCATTAAGATCTGACTATTATATGAGTGAGTTGTTAAA
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------

P-ERIra.Ubq1-1:1:9      TTCATTTTAGGTGACATGGCCCGGTTAAATTATTAGCCATACCCTAACAGCTCTAAAAAA
P-ERIra.Ubq1-1:1:10     TTCATTTTAGGTGACATGGCCCGGTTAAATTATTAGCCATACCCTAACAGCTCTAAAAAA
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------
```

FIG. 2b

```
P-ERIra.Ubq1-1:1:9     GATATATTCGTTGAGGCACTTTTATGCAACCACATAGTCAACTTGAATGCCGCTTGAGTG
P-ERIra.Ubq1-1:1:10    GATATATTCGTTGAGGCACTTTTATGCAACCACATAGTCAACTTGAATGCCGCTTGAGTG
P-ERIra.Ubq1-1:1:8     ------------------------------------------------------------
P-ERIra.Ubq1-1:1:11    ------------------------------------------------------------
P-ERIra.Ubq1-1:1:12    ------------------------------------------------------------
P-ERIra.Ubq1-1:1:13    ------------------------------------------------------------

P-ERIra.Ubq1-1:1:9     CGTTCTCAAGTTTTTTTTCTTGCAAATTACGCTTTTTTAAGAAAGTATAATTTGGATCGT
P-ERIra.Ubq1-1:1:10    CGTTCTCAAGTTTTTTTTCTTGCAAATTACGCTTTTTTAAGAAAGTATAATTTGGATCGT
P-ERIra.Ubq1-1:1:8     ------------------------------------------------------------
P-ERIra.Ubq1-1:1:11    ------------------------------------------------------------
P-ERIra.Ubq1-1:1:12    ------------------------------------------------------------
P-ERIra.Ubq1-1:1:13    ------------------------------------------------------------

P-ERIra.Ubq1-1:1:9     GCGATTTTTTTTCTCTAGGTGTGCGTGACTGTGTGAGTAACAATTTTGGATCTCAGAAAG
P-ERIra.Ubq1-1:1:10    GCGATTTTTTTTCTCTAGGTGTGCGTGACTGTGTGAGTAACAATTTTGGATCTCAGAAAG
P-ERIra.Ubq1-1:1:8     ------------------------------------------------------------
P-ERIra.Ubq1-1:1:11    ------------------------------------------------------------
P-ERIra.Ubq1-1:1:12    ------------------------------------------------------------
P-ERIra.Ubq1-1:1:13    ------------------------------------------------------------

P-ERIra.Ubq1-1:1:9     GTAATAAAAGAATAATACTGCTGCCTACTTTGAGGATTACAATATCTTTCTCTAAAATGT
P-ERIra.Ubq1-1:1:10    GTAATAAAAGAATAATACTGCTGCCTACTTTGAGGATTACAATATCTTTCTCTAAAATGT
P-ERIra.Ubq1-1:1:8     ------------------------------------------------------------
P-ERIra.Ubq1-1:1:11    -----------------CTGCTGCCTACTTTGAGGATTACAATATCTTTCTCTAAAATGT
P-ERIra.Ubq1-1:1:12    ------------------------------------------------------------
P-ERIra.Ubq1-1:1:13    ------------------------------------------------------------

P-ERIra.Ubq1-1:1:9     TTTGGTTTGTTATTTAAACCGTCTTTAAGGCCAATTGCTCAAGATTCATTCAACAATTGA
P-ERIra.Ubq1-1:1:10    TTTGGTTTGTTATTTAAACCGTCTTTAAGGCCAATTGCTCAAGATTCATTCAACAATTGA
P-ERIra.Ubq1-1:1:8     ------------------------------------------------------------
P-ERIra.Ubq1-1:1:11    TTTGGTTTGTTATTTAAACCGTCTTTAAGGCCAATTGCTCAAGATTCATTCAACAATTGA
P-ERIra.Ubq1-1:1:12    ------------------------------------------------------------
P-ERIra.Ubq1-1:1:13    ------------------------------------------------------------

P-ERIra.Ubq1-1:1:9     AACGTCTCACATGATTAAATCATATAAGGTTGCTAAGGTCTTGTTTGACAAGGTTTTTTT
P-ERIra.Ubq1-1:1:10    AACGTCTCACATGATTAAATCATATAAGGTTGCTAAGGTCTTGTTTGACAAGGTTTTTTT
P-ERIra.Ubq1-1:1:8     ------------------------------------------------------------
P-ERIra.Ubq1-1:1:11    AACGTCTCACATGATTAAATCATATAAGGTTGCTAAGGTCTTGTTTGACAAGGTTTTTTT
P-ERIra.Ubq1-1:1:12    ------------------------------------------------------------
P-ERIra.Ubq1-1:1:13    ------------------------------------------------------------
```

FIG. 2c

```
P-ERIra.Ubq1-1:1:9     TGTGGAAATTTCATCTAAATTTTTGAGTGAAACTATCAAATACTAATTTAAAAAAGGCAA
P-ERIra.Ubq1-1:1:10    TGTGGAAATTTCATCTAAATTTTTGAGTGAAACTATCAAATACTAATTTAAAAAAGGCAA
P-ERIra.Ubq1-1:1:8     ------------------------------------------------------------
P-ERIra.Ubq1-1:1:11    TGTGGAAATTTCATCTAAATTTTTGAGTGAAACTATCAAATACTAATTTAAAAAAGGCAA
P-ERIra.Ubq1-1:1:12    ------------------------------------------------------------
P-ERIra.Ubq1-1:1:13    ------------------------------------------------------------

P-ERIra.Ubq1-1:1:9     ATTTTGCTGGAGGACACTGCAGAAACGTGTAATTGGCCGGCACAAACCGCCAAACGGAGA
P-ERIra.Ubq1-1:1:10    ATTTTGCTGGAGGACACTGCAGAAACGTGTAATTGGCCGGCACAAACCGCCAAACGGAGA
P-ERIra.Ubq1-1:1:8     ------------------------------------------------------------
P-ERIra.Ubq1-1:1:11    ATTTTGCTGGAGGACACTGCAGAAACGTGTAATTGGCCGGCACAAACCGCCAAACGGAGA
P-ERIra.Ubq1-1:1:12    ------------------------------------------------------------
P-ERIra.Ubq1-1:1:13    ------------------------------------------------------------

P-ERIra.Ubq1-1:1:9     ATTTGCCCAGTACCATTATAAATTCATGATAAATTCATGGTTGTTTGCCAGTGGGGCTAG
P-ERIra.Ubq1-1:1:10    ATTTGCCCAGTACCATTATAAATTCATGATAAATTCATGGTTGTTTGCCAGTGGGGCTAG
P-ERIra.Ubq1-1:1:8     ------------------------------------------------------------
P-ERIra.Ubq1-1:1:11    ATTTGCCCAGTACCATTATAAATTCATGATAAATTCATGGTTGTTTGCCAGTGGGGCTAG
P-ERIra.Ubq1-1:1:12    ------------------------------------------------------------
P-ERIra.Ubq1-1:1:13    ------------------------------------------------------------

P-ERIra.Ubq1-1:1:9     GGTTCCTCGCGTATGGTGCGGAATGTGGTTTGGTTCGACCAACTCGAACTCAATCCGATC
P-ERIra.Ubq1-1:1:10    GGTTCCTCGCGTATGGTGCGGAATGTGGTTTGGTTCGACCAACTCGAACTCAATCCGATC
P-ERIra.Ubq1-1:1:8     ------------------------------------------------------------
P-ERIra.Ubq1-1:1:11    GGTTCCTCGCGTATGGTGCGGAATGTGGTTTGGTTCGACCAACTCGAACTCAATCCGATC
P-ERIra.Ubq1-1:1:12    ------------------------------------------------------------
P-ERIra.Ubq1-1:1:13    ------------------------------------------------------------

P-ERIra.Ubq1-1:1:9     CAAAGGGGCATCAATAGTCATTTTAGAAAGTTTCTCTCTCCCGAGCAGTGGAAATGATTA
P-ERIra.Ubq1-1:1:10    CAAAGGGGCATCAATAGTCATTTTAGAAAGTTTCTCTCTCCCGAGCAGTGGAAATGATTA
P-ERIra.Ubq1-1:1:8     ------------------------------------------------------------
P-ERIra.Ubq1-1:1:11    CAAAGGGGCATCAATAGTCATTTTAGAAAGTTTCTCTCTCCCGAGCAGTGGAAATGATTA
P-ERIra.Ubq1-1:1:12    ------------------------------------------------------------
P-ERIra.Ubq1-1:1:13    ------------------------------------------------------------

P-ERIra.Ubq1-1:1:9     TTCTATTTGGCGCGATGTCCACCGGCAAACAACCACGAATTTGTAATGGTACTAGGCAAA
P-ERIra.Ubq1-1:1:10    TTCTATTTGGCGCGATGTCCACCGGCAAACAACCACGAATTTGTAATGGTACTAGGCAAA
P-ERIra.Ubq1-1:1:8     ------------------CCACCGGCAAACAACCACGAATTTGTAATGGTACTAGGCAAA
P-ERIra.Ubq1-1:1:11    TTCTATTTGGCGCGATGTCCACCGGCAAACAACCACGAATTTGTAATGGTACTAGGCAAA
P-ERIra.Ubq1-1:1:12    ------------------------------------------------------------
P-ERIra.Ubq1-1:1:13    ------------------------------------------------------------
```

FIG. 2d

```
P-ERIra.Ubq1-1:1:9      TTCTCCGTTTGGCGGTGTGTGCCGGCCAATTACACGTTTTTGCGGTGTCCTCCGACAAAA
P-ERIra.Ubq1-1:1:10     TTCTCCGTTTGGCGGTGTGTGCCGGCCAATTACACGTTTTTGCGGTGTCCTCCGACAAAA
P-ERIra.Ubq1-1:1:8      TTCTCCGTTTGGCGGTGTGTGCCGGCCAATTACACGTTTTTGCGGTGTCCTCCGACAAAA
P-ERIra.Ubq1-1:1:11     TTCTCCGTTTGGCGGTGTGTGCCGGCCAATTACACGTTTTTGCGGTGTCCTCCGACAAAA
P-ERIra.Ubq1-1:1:12     ------------------------------------------------------------
P-ERIra.Ubq1-1:1:13     ------------------------------------------------------------

P-ERIra.Ubq1-1:1:9      TTTGCCTTTTAAAAACAATTTTATAAGAGAAGCTCCGGAGATAAAAGGCCGTCAATGTTA
P-ERIra.Ubq1-1:1:10     TTTGCCTTTTAAAAACAATTTTATAAGAGAAGCTCCGGAGATAAAAGGCCGTCAATGTTA
P-ERIra.Ubq1-1:1:8      TTTGCCTTTTAAAAACAATTTTATAAGAGAAGCTCCGGAGATAAAAGGCCGTCAATGTTA
P-ERIra.Ubq1-1:1:11     TTTGCCTTTTAAAAACAATTTTATAAGAGAAGCTCCGGAGATAAAAGGCCGTCAATGTTA
P-ERIra.Ubq1-1:1:12     ------------------------------------------------------------
P-ERIra.Ubq1-1:1:13     ------------------------------------------------------------

P-ERIra.Ubq1-1:1:9      CAAGAGTGAAGTCGTCTACTCCCTCCATCCCAAAAAATGTAATTCTAAGTATGAGTTGTA
P-ERIra.Ubq1-1:1:10     CAAGAGTGAAGTCGTCTACTCCCTCCATCCCAAAAAATGTAATTCTAAGTATGAGTTGTA
P-ERIra.Ubq1-1:1:8      CAAGAGTGAAGTCGTCTACTCCCTCCATCCCAAAAAATGTAATTCTAAGTATGAGTTGTA
P-ERIra.Ubq1-1:1:11     CAAGAGTGAAGTCGTCTACTCCCTCCATCCCAAAAAATGTAATTCTAAGTATGAGTTGTA
P-ERIra.Ubq1-1:1:12     ------------------------------------------------------------
P-ERIra.Ubq1-1:1:13     ------------------------------------------------------------

P-ERIra.Ubq1-1:1:9      TTATTATTTTTGGACAAAAGGAGTATACCACAAGAATGATATCATCGTCATGCTTAGATC
P-ERIra.Ubq1-1:1:10     TTATTATTTTTGGACAAAAGGAGTATACCACAAGAATGATATCATCGTCATGCTTAGATC
P-ERIra.Ubq1-1:1:8      TTATTATTTTTGGACAAAAGGAGTATACCACAAGAATGATATCATCGTCATGCTTAGATC
P-ERIra.Ubq1-1:1:11     TTATTATTTTTGGACAAAAGGAGTATACCACAAGAATGATATCATCGTCATGCTTAGATC
P-ERIra.Ubq1-1:1:12     --------------------------ACCACAAGAATGATATCATCGTCATGCTTAGATC
P-ERIra.Ubq1-1:1:13     ------------------------------------------------------------

P-ERIra.Ubq1-1:1:9      CTTTTTAGTAAAGCTTGAGCTTCTCTAAAAGTAGAGAAATTAGAAAAAAAATCACGTTTTT
P-ERIra.Ubq1-1:1:10     CTTTTTAGTAAAGCTTGAGCTTCTCTAAAAGTAGAGAAATTAGAAAAAAAATCACGTTTTT
P-ERIra.Ubq1-1:1:8      CTTTTTAGTAAAGCTTGAGCTTCTCTAAAAGTAGAGAAATTAGAAAAAAAATCACGTTTTT
P-ERIra.Ubq1-1:1:11     CTTTTTAGTAAAGCTTGAGCTTCTCTAAAAGTAGAGAAATTAGAAAAAAAATCACGTTTTT
P-ERIra.Ubq1-1:1:12     CTTTTTAGTAAAGCTTGAGCTTCTCTAAAAGTAGAGAAATTAGAAAAAAAATCACGTTTTT
P-ERIra.Ubq1-1:1:13     ------------------------------------------------------------

P-ERIra.Ubq1-1:1:9      GTGGTCTTGATTTCTAGCCTCCACAAAATCTTTGGTTTTACATTTTTTGTTTGATTTTGG
P-ERIra.Ubq1-1:1:10     GTGGTCTTGATTTCTAGCCTCCACAAAATCTTTGGTTTTACATTTTTTGTTTGATTTTGG
P-ERIra.Ubq1-1:1:8      GTGGTCTTGATTTCTAGCCTCCACAAAATCTTTGGTTTTACATTTTTTGTTTGATTTTGG
P-ERIra.Ubq1-1:1:11     GTGGTCTTGATTTCTAGCCTCCACAAAATCTTTGGTTTTACATTTTTTGTTTGATTTTGG
P-ERIra.Ubq1-1:1:12     GTGGTCTTGATTTCTAGCCTCCACAAAATCTTTGGTTTTACATTTTTTGTTTGATTTTGG
P-ERIra.Ubq1-1:1:13     ------------------------------------------------------------
```

FIG. 2e

```
P-ERIra.Ubq1-1:1:9      TTTCAGAAGTCCTTATTTATATGTGCTAGTTTGGCAGCACTTAAAATCGTTAGAGAGAGC
P-ERIra.Ubq1-1:1:10     TTTCAGAAGTCCTTATTTATATGTGCTAGTTTGGCAGCACTTAAAATCGTTAGAGAGAGC
P-ERIra.Ubq1-1:1:8      TTTCAGAAGTCCTTATTTATATGTGCTAGTTTGGCAGCACTTAAAATCGTTAGAGAGAGC
P-ERIra.Ubq1-1:1:11     TTTCAGAAGTCCTTATTTATATGTGCTAGTTTGGCAGCACTTAAAATCGTTAGAGAGAGC
P-ERIra.Ubq1-1:1:12     TTTCAGAAGTCCTTATTTATATGTGCTAGTTTGGCAGCACTTAAAATCGTTAGAGAGAGC
P-ERIra.Ubq1-1:1:13     ------------------------------------------------------------

P-ERIra.Ubq1-1:1:9      CTAAACAAAAGCCTTTTCAAAACGACCTTGAGCCAGATTGGTTGATGGCCAAAATTTGAT
P-ERIra.Ubq1-1:1:10     CTAAACAAAAGCCTTTTCAAAACGACCTTGAGCCAGATTGGTTGATGGCCAAAATTTGAT
P-ERIra.Ubq1-1:1:8      CTAAACAAAAGCCTTTTCAAAACGACCTTGAGCCAGATTGGTTGATGGCCAAAATTTGAT
P-ERIra.Ubq1-1:1:11     CTAAACAAAAGCCTTTTCAAAACGACCTTGAGCCAGATTGGTTGATGGCCAAAATTTGAT
P-ERIra.Ubq1-1:1:12     CTAAACAAAAGCCTTTTCAAAACGACCTTGAGCCAGATTGGTTGATGGCCAAAATTTGAT
P-ERIra.Ubq1-1:1:13     ------------------------------------------------------------

P-ERIra.Ubq1-1:1:9      TGTCAAAACTTAGGCAAGCCAAGATTTTAGCAGCTATTTGGTTTGGTACCAAAATTTGCC
P-ERIra.Ubq1-1:1:10     TGTCAAAACTTAGGCAAGCCAAGATTTTAGCAGCTATTTGGTTTGGTACCAAAATTTGCC
P-ERIra.Ubq1-1:1:8      TGTCAAAACTTAGGCAAGCCAAGATTTTAGCAGCTATTTGGTTTGGTACCAAAATTTGCC
P-ERIra.Ubq1-1:1:11     TGTCAAAACTTAGGCAAGCCAAGATTTTAGCAGCTATTTGGTTTGGTACCAAAATTTGCC
P-ERIra.Ubq1-1:1:12     TGTCAAAACTTAGGCAAGCCAAGATTTTAGCAGCTATTTGGTTTGGTACCAAAATTTGCC
P-ERIra.Ubq1-1:1:13     ------------AGGCAAGCCAAGATTTTAGCAGCTATTTGGTTTGGTACCAAAATTTGCC
                                    ************************************************

P-ERIra.Ubq1-1:1:9      AATGATCTGTTCTTTTGCCTTTTCAACCGGTTTATCAGCCGTACTTCAGCTTATTCTCTC
P-ERIra.Ubq1-1:1:10     AATGATCTGTTCTTTTGCCTTTTCAACCGGTTTATCAGCCGTACTTCAGCTTATTCTCTC
P-ERIra.Ubq1-1:1:8      AATGATCTGTTCTTTTGCCTTTTCAACCGGTTTATCAGCCGTACTTCAGCTTATTCTCTC
P-ERIra.Ubq1-1:1:11     AATGATCTGTTCTTTTGCCTTTTCAACCGGTTTATCAGCCGTACTTCAGCTTATTCTCTC
P-ERIra.Ubq1-1:1:12     AATGATCTGTTCTTTTGCCTTTTCAACCGGTTTATCAGCCGTACTTCAGCTTATTCTCTC
P-ERIra.Ubq1-1:1:13     AATGATCTGTTCTTTTGCCTTTTCAACCGGTTTATCAGCCGTACTTCAGCTTATTCTCTC
                        ************************************************************

P-ERIra.Ubq1-1:1:9      TCACAGAACACTATTGAATCAGCCGAAAAGCCACCGCAGAACAGGACCAGTATCTCACAA
P-ERIra.Ubq1-1:1:10     TCACAGAACACTATTGAATCAGCCGAAAAGCCACCGCAGAACAGGACCAGTATCTCACAA
P-ERIra.Ubq1-1:1:8      TCACAGAACACTATTGAATCAGCCGAAAAGCCACCGCAGAACAGGACCAGTATCTCACAA
P-ERIra.Ubq1-1:1:11     TCACAGAACACTATTGAATCAGCCGAAAAGCCACCGCAGAACAGGACCAGTATCTCACAA
P-ERIra.Ubq1-1:1:12     TCACAGAACACTATTGAATCAGCCGAAAAGCCACCGCAGAACAGGACCAGTATCTCACAA
P-ERIra.Ubq1-1:1:13     TCACAGAACACTATTGAATCAGCCGAAAAGCCACCGCAGAACAGGACCAGTATCTCACAA
                        ************************************************************

P-ERIra.Ubq1-1:1:9      ATGGCATGCCAAATATACTCACCGTCAGTGAGCCCGTTTAACGGCGTCGACAAGTCTAAC
P-ERIra.Ubq1-1:1:10     ATGGCATGCCAAATATACTCACCGTCAGTGAGCCCGTTTAACGGCGTCGACAAGTCTAAC
P-ERIra.Ubq1-1:1:8      ATGGCATGCCAAATATACTCACCGTCAGTGAGCCCGTTTAACGGCGTCGACAAGTCTAAC
P-ERIra.Ubq1-1:1:11     ATGGCATGCCAAATATACTCACCGTCAGTGAGCCCGTTTAACGGCGTCGACAAGTCTAAC
P-ERIra.Ubq1-1:1:12     ATGGCATGCCAAATATACTCACCGTCAGTGAGCCCGTTTAACGGCGTCGACAAGTCTAAC
P-ERIra.Ubq1-1:1:13     ATGGCATGCCAAATATACTCACCGTCAGTGAGCCCGTTTAACGGCGTCGACAAGTCTAAC
                        ************************************************************
```

FIG. 2f

```
P-ERIra.Ubq1-1:1:9     GGCCACCAACCAGCGAACCACCAGCGTCAAGCTAGCCAAGCGAAGCAGACGGCCGAGACG
P-ERIra.Ubq1-1:1:10    GGCCACCAACCAGCGAACCACCAGCGTCAAGCTAGCCAAGCGAAGCAGACGGCCGAGACG
P-ERIra.Ubq1-1:1:8     GGCCACCAACCAGCGAACCACCAGCGTCAAGCTAGCCAAGCGAAGCAGACGGCCGAGACG
P-ERIra.Ubq1-1:1:11    GGCCACCAACCAGCGAACCACCAGCGTCAAGCTAGCCAAGCGAAGCAGACGGCCGAGACG
P-ERIra.Ubq1-1:1:12    GGCCACCAACCAGCGAACCACCAGCGTCAAGCTAGCCAAGCGAAGCAGACGGCCGAGACG
P-ERIra.Ubq1-1:1:13    GGCCACCAACCAGCGAACCACCAGCGTCAAGCTAGCCAAGCGAAGCAGACGGCCGAGACG
                       ************************************************************

P-ERIra.Ubq1-1:1:9     TTGACACCTTGGCGCGGGCATCTCTCTGGCCCCCTCTCGAGAGTTCCGCTCCACCTCCAC
P-ERIra.Ubq1-1:1:10    TTGACACCTTGGCGCGGGCATCTCTCTGGCCCCCTCTCGAGAGTTCCGCTCCACCTCCAC
P-ERIra.Ubq1-1:1:8     TTGACACCTTGGCGCGGGCATCTCTCTGGCCCCCTCTCGAGAGTTCCGCTCCACCTCCAC
P-ERIra.Ubq1-1:1:11    TTGACACCTTGGCGCGGGCATCTCTCTGGCCCCCTCTCGAGAGTTCCGCTCCACCTCCAC
P-ERIra.Ubq1-1:1:12    TTGACACCTTGGCGCGGGCATCTCTCTGGCCCCCTCTCGAGAGTTCCGCTCCACCTCCAC
P-ERIra.Ubq1-1:1:13    TTGACACCTTGGCGCGGGCATCTCTCTGGCCCCCTCTCGAGAGTTCCGCTCCACCTCCAC
                       ************************************************************

P-ERIra.Ubq1-1:1:9     TGGTGGCGGTTTCCAAGTCCGTTCCGCCTCCTGCTCCTCCTCACACGGCACGAAACCGTC
P-ERIra.Ubq1-1:1:10    TGGTGGCGGTTTCCAAGTCCGTTCCGCCTCCTGCTCCTCCTCACACGGCACGAAACCGTC
P-ERIra.Ubq1-1:1:8     TGGTGGCGGTTTCCAAGTCCGTTCCGCCTCCTGCTCCTCCTCACACGGCACGAAACCGTC
P-ERIra.Ubq1-1:1:11    TGGTGGCGGTTTCCAAGTCCGTTCCGCCTCCTGCTCCTCCTCACACGGCACGAAACCGTC
P-ERIra.Ubq1-1:1:12    TGGTGGCGGTTTCCAAGTCCGTTCCGCCTCCTGCTCCTCCTCACACGGCACGAAACCGTC
P-ERIra.Ubq1-1:1:13    TGGTGGCGGTTTCCAAGTCCGTTCCGCCTCCTGCTCCTCCTCACACGGCACGAAACCGTC
                       ************************************************************

P-ERIra.Ubq1-1:1:9     ACGGCACCGGCAGCACGGGGGATTCCTTTCCCACCGCTCCTTCCCTTTCCCTTCCTCGCC
P-ERIra.Ubq1-1:1:10    ACGGCACCGGCAGCACGGGGGATTCCTTTCCCACCGCTCCTTCCCTTTCCCTTCCTCGCC
P-ERIra.Ubq1-1:1:8     ACGGCACCGGCAGCACGGGGGATTCCTTTCCCACCGCTCCTTCCCTTTCCCTTCCTCGCC
P-ERIra.Ubq1-1:1:11    ACGGCACCGGCAGCACGGGGGATTCCTTTCCCACCGCTCCTTCCCTTTCCCTTCCTCGCC
P-ERIra.Ubq1-1:1:12    ACGGCACCGGCAGCACGGGGGATTCCTTTCCCACCGCTCCTTCCCTTTCCCTTCCTCGCC
P-ERIra.Ubq1-1:1:13    ACGGCACCGGCAGCACGGGGGATTCCTTTCCCACCGCTCCTTCCCTTTCCCTTCCTCGCC
                       ************************************************************

P-ERIra.Ubq1-1:1:9     CGCCGTTTTAAATAGCCAGCCCCATCCCCAGCTTCTCTCCCC
P-ERIra.Ubq1-1:1:10    CGCCGTTTTAAATAGCCAGCCCCATCCCCAGCTTCTCTCCCC
P-ERIra.Ubq1-1:1:8     CGCCGTTTTAAATAGCCAGCCCCATCCCCAGCTTCTCTCCCC
P-ERIra.Ubq1-1:1:11    CGCCGTTTTAAATAGCCAGCCCCATCCCCAGCTTCTCTCCCC
P-ERIra.Ubq1-1:1:12    CGCCGTTTTAAATAGCCAGCCCCATCCCCAGCTTCTCTCCCC
P-ERIra.Ubq1-1:1:13    CGCCGTTTTAAATAGCCAGCCCCATCCCCAGCTTCTCTCCCC
                       ******************************************
```

FIG. 2g

```
P-Sv.Ubq1-1:1:2    ------------------------------------------------------------
P-Sv.Ubq1-1:1:1    ACTGCCGCGACACGCCTCACTGGCGGGAGGGCTCCGAGCGCTCTCTCCCCGGCGGCCGGC
P-Sv.Ubq1-1:1:3    ------------------------------------------------------------

P-Sv.Ubq1-1:1:2    ------------------------------------------------------------
P-Sv.Ubq1-1:1:1    GGAGCAGCGATCTGGATTGGAGAGAATAGAGGAAAGAGAGGGAAAAGGAGAGAGATAGCG
P-Sv.Ubq1-1:1:3    ------------------------------------------------------------

P-Sv.Ubq1-1:1:2    ------------------------------------------------------------
P-Sv.Ubq1-1:1:1    CAAAGAGCTGAAAAGATAAGGTTGTGCGGGCTGTGGTGATTAGAGGACCACTAATCCCTC
P-Sv.Ubq1-1:1:3    ------------------------------------------------------------

P-Sv.Ubq1-1:1:2    ------------------------------------------------------------
P-Sv.Ubq1-1:1:1    CATCTCCTAATGACGCGGTGCCCAAGACCAGTGCCGCGGCACACCAGCGTCTAAGTGAAC
P-Sv.Ubq1-1:1:3    ------------------------------------------------------------

P-Sv.Ubq1-1:1:2    ------------------------------------------------------------
P-Sv.Ubq1-1:1:1    TTCCGCTAACCTTCCGGTCATTGCGCCTGAAAGATGTCATGTGGCGAGGCCCCCCTCTCA
P-Sv.Ubq1-1:1:3    ------------------------------------------------------------

P-Sv.Ubq1-1:1:2    ------------------------------------------------------------
P-Sv.Ubq1-1:1:1    GTAGATTGCCAACTGCCTACCGTGCCACTCTTCCATGCATGATTGCTCCCGTCTATCCCG
P-Sv.Ubq1-1:1:3    ------------------------------------------------------------

P-Sv.Ubq1-1:1:2    ------------------------------------------------------------
P-Sv.Ubq1-1:1:1    TTTCTCACAACAGATAGACAACAGTAAGCATCACTAAAGCAAGCATGTGTAGAACCTTAA
P-Sv.Ubq1-1:1:3    ------------------------------------------------------------

P-Sv.Ubq1-1:1:2    --------------------------------------GCCGTTTTTGAAGTATCCAGGA
P-Sv.Ubq1-1:1:1    AAAAAGGCTTATACTACCAGTATACTATCAACCAGCATGCCGTTTTTGAAGTATCCAGGA
P-Sv.Ubq1-1:1:3    ------------------------------------------------------------

P-Sv.Ubq1-1:1:2    TTAGAAGCTTCTACTGCGCTTTTATATTATAGCTGTGGACCTGTGGTAACCTTTCTCTTT
P-Sv.Ubq1-1:1:1    TTAGAAGCTTCTACTGCGCTTTTATATTATAGCTGTGGACCTGTGGTAACCTTTCTCTTT
P-Sv.Ubq1-1:1:3    ------------------------------------------------------------

P-Sv.Ubq1-1:1:2    TGGCGCTTGCTTAATCTCGGCCGTGCTGGTCCATGCTTAGGCACTAGGCAGAGATAGAGC
P-Sv.Ubq1-1:1:1    TGGCGCTTGCTTAATCTCGGCCGTGCTGGTCCATGCTTAGGCACTAGGCAGAGATAGAGC
P-Sv.Ubq1-1:1:3    ------------------------------------------------------------

P-Sv.Ubq1-1:1:2    CGGGGGTGAATGGGGCTAAAGCTCAGCTGCTCGAGGGGCCGTGGGCTGGTTTCCACTAGC
P-Sv.Ubq1-1:1:1    CGGGGGTGAATGGGGCTAAAGCTCAGCTGCTCGAGGGGCCGTGGGCTGGTTTCCACTAGC
P-Sv.Ubq1-1:1:3    ------------------------------------------------------------

P-Sv.Ubq1-1:1:2    CTACAGCTGTGCCACGTGCGGCCGCGCAAGCCGAAGCAAGCACGCTGAGCCGTTGGACAG
P-Sv.Ubq1-1:1:1    CTACAGCTGTGCCACGTGCGGCCGCGCAAGCCGAAGCAAGCACGCTGAGCCGTTGGACAG
P-Sv.Ubq1-1:1:3    ------------------------------------------------------------
```

FIG. 3a

```
P-Sv.Ubq1-1:1:2     CTTGTCATAATGCCATTACGTGGATTACAGGTAACTGGCCCTGTAACTACTCGTTCGGCC
P-Sv.Ubq1-1:1:1     CTTGTCATAATGCCATTACGTGGATTACAGGTAACTGGCCCTGTAACTACTCGTTCGGCC
P-Sv.Ubq1-1:1:3     ------------------------------------------------------------

P-Sv.Ubq1-1:1:2     ATCATCAAACGACGACGTCCGCTAGGCGACGACACGGGTAATGCACGCAGCCACCCAGGC
P-Sv.Ubq1-1:1:1     ATCATCAAACGACGACGTCCGCTAGGCGACGACACGGGTAATGCACGCAGCCACCCAGGC
P-Sv.Ubq1-1:1:3     --------------------------------CACGGGTAATGCACGCAGCCACCCAGGC
                                                    ****************************

P-Sv.Ubq1-1:1:2     GCGCGCGCTAGCGGAGCACGGTCAGGTGACACGGGCGTCGTGACGCTTCCGAGTTGAAGG
P-Sv.Ubq1-1:1:1     GCGCGCGCTAGCGGAGCACGGTCAGGTGACACGGGCGTCGTGACGCTTCCGAGTTGAAGG
P-Sv.Ubq1-1:1:3     GCGCGCGCTAGCGGAGCACGGTCAGGTGACACGGGCGTCGTGACGCTTCCGAGTTGAAGG
                    ************************************************************

P-Sv.Ubq1-1:1:2     GGTTAACGCCAGAAACAGTGTTTGGCCAGGGTATGAACATAACAAAAAATATTCACACGA
P-Sv.Ubq1-1:1:1     GGTTAACGCCAGAAACAGTGTTTGGCCAGGGTATGAACATAACAAAAAATATTCACACGA
P-Sv.Ubq1-1:1:3     GGTTAACGCCAGAAACAGTGTTTGGCCAGGGTATGAACATAACAAAAAATATTCACACGA
                    ************************************************************

P-Sv.Ubq1-1:1:2     AAGAATGGAAGTATGGAGCTGCTACTGTGTAAATGCCAAGCAGGAAACTCACGCCCGCTA
P-Sv.Ubq1-1:1:1     AAGAATGGAAGTATGGAGCTGCTACTGTGTAAATGCCAAGCAGGAAACTCACGCCCGCTA
P-Sv.Ubq1-1:1:3     AAGAATGGAAGTATGGAGCTGCTACTGTGTAAATGCCAAGCAGGAAACTCACGCCCGCTA
                    ************************************************************

P-Sv.Ubq1-1:1:2     ACATCCAACGGCCAACAGCTCGACGTGCCGGTCAGCAGAGACATCGGAACACTGGTGATT
P-Sv.Ubq1-1:1:1     ACATCCAACGGCCAACAGCTCGACGTGCCGGTCAGCAGAGACATCGGAACACTGGTGATT
P-Sv.Ubq1-1:1:3     ACATCCAACGGCCAACAGCTCGACGTGCCGGTCAGCAGAGACATCGGAACACTGGTGATT
                    ************************************************************

P-Sv.Ubq1-1:1:2     GGTGGAGCCGGCAGTATGCGCCCCAGCACGGCCGAGGTGGTGGTGGCCCGTGGCCCTGCT
P-Sv.Ubq1-1:1:1     GGTGGAGCCGGCAGTATGCGCCCCAGCACGGCCGAGGTGGTGGTGGCCCGTGGCCCTGCT
P-Sv.Ubq1-1:1:3     GGTGGAGCCGGCAGTATGCGCCCCAGCACGGCCGAGGTGGTGGTGGCCCGTGGCCCTGCT
                    ************************************************************

P-Sv.Ubq1-1:1:2     GTCTGCGCGGCTCGGGACAACTTGAAACTGGGCCACCGCCTCGTCGCAACTCGCAACCCG
P-Sv.Ubq1-1:1:1     GTCTGCGCGGCTCGGGACAACTTGAAACTGGGCCACCGCCTCGTCGCAACTCGCAACCCG
P-Sv.Ubq1-1:1:3     GTCTGCGCGGCTCGGGACAACTTGAAACTGGGCCACCGCCTCGTCGCAACTCGCAACCCG
                    ************************************************************

P-Sv.Ubq1-1:1:2     TTGGCGGAAGAAAGGAATGGCTCGTAGGGGGCCCGGGTAGAATCCAAGAATGTTGCGCTGG
P-Sv.Ubq1-1:1:1     TTGGCGGAAGAAAGGAATGGCTCGTAGGGGGCCCGGGTAGAATCCAAGAATGTTGCGCTGG
P-Sv.Ubq1-1:1:3     TTGGCGGAAGAAAGGAATGGCTCGTAGGGGGCCCGGGTAGAATCCAAGAATGTTGCGCTGG
                    ************************************************************

P-Sv.Ubq1-1:1:2     GCTTCGATTCACATAACATGGGCCTGAAGCTCTAAAACGACGGCCCGGTCACCGGGCGAT
P-Sv.Ubq1-1:1:1     GCTTCGATTCACATAACATGGGCCTGAAGCTCTAAAACGACGGCCCGGTCACCGGGCGAT
P-Sv.Ubq1-1:1:3     GCTTCGATTCACATAACATGGGCCTGAAGCTCTAAAACGACGGCCCGGTCACCGGGCGAT
                    ************************************************************
```

FIG. 3b

```
P-Sv.Ubq1-1:1:2        GGAAAGAGACCGGATCCTCCTCGTGAATTCTGGAAGGCCACACGAGAGCGACCCACCACC
P-Sv.Ubq1-1:1:1        GGAAAGAGACCGGATCCTCCTCGTGAATTCTGGAAGGCCACACGAGAGCGACCCACCACC
P-Sv.Ubq1-1:1:3        GGAAAGAGACCGGATCCTCCTTGTGAATTCTGGAAGGCCACACGAGAGCGACCCACCACC
                       ********************* **************************************

P-Sv.Ubq1-1:1:2        GACGCGGAGGAGTCGTGCGTGGTCCAACACGGCCGGCGGGCTGGGCTGCGACCTTAACCA
P-Sv.Ubq1-1:1:1        GACGCGGAGGAGTCGTGCGTGGTCCAACACGGCCGGCGGGCTGGGCTGCGACCTTAACCA
P-Sv.Ubq1-1:1:3        GACGCGGAGGAGTCGTGCGTGGTCCAACACGGCCGGCGGGCTGGGCTGCGACCTTAACCA
                       ************************************************************

P-Sv.Ubq1-1:1:2        GCAAGGCACGCCACGACCCGCCTCGCCCTCGAGGCATAAATACCCTCCCATCC
P-Sv.Ubq1-1:1:1        GCAAGGCACGCCACGACCCGCCTCGCCCTCGAGGCATAAATACCCTCCCATCC
P-Sv.Ubq1-1:1:3        GCAAGGCACGCCACGACCCGCCTCGCCCTCGAGGCATAAATACCCTCCCATCC
                       *****************************************************
```

FIG. 3c

```
EXP-Zm.UbqM1:1:2    GTCGTGCCCCTCTCTAGAGATAAAGAGCATTGCATGTCTAAAGTATAAAAAATTACCACA
EXP-Zm.UbqM1:1:5    GTCGTGCCCCTCTCTAGAGATAAAGAGCATTGCATGTCTAAAGTATAAAAAATTACCACA
EXP-Zm.UbqM1:1:1    GTCGTGCCCCTCTCTAGAGATAATGAGCATTGCATGTCTAAGTTATAAAAAATTACCACA
EXP-Zm.UbqM1:1:4    GTCGTGCCCCTCTCTAGAGATAAAGAGCATTGCATGTCTAAGTTATAAAAAATTACCACA
                    *********************** *****************  *****************

EXP-Zm.UbqM1:1:2    TA--TTTTTTTGTCACACT--TATTTGAAGTGTAGTTTATCTATCTCTATACATATATTT
EXP-Zm.UbqM1:1:5    TA--TTTTTTTGTCACACT--TATTTGAAGTGTAGTTTATCTATCTCTATACATATATTT
EXP-Zm.UbqM1:1:1    TATTTTTTTTTGTCACACTTGTGTTTGAAGTGCAGTTTATCTATCTCTATACATATATTT
EXP-Zm.UbqM1:1:4    TA-TTTTTTTTGTCACACT--TGTTTGAAGTGCAGTTTATCTATCTTTATACATATATTT
                    **  ***************  * ********* ************* *************

EXP-Zm.UbqM1:1:2    AAACTTCACTCTACAAATAATATAGTCTATAATACTAAAATAATATTAGTGTTTTAGAGG
EXP-Zm.UbqM1:1:5    AAACTTCACTCTACAAATAATATAGTCTATAATACTAAAATAATATTAGTGTTTTAGAGG
EXP-Zm.UbqM1:1:1    AAACTTCACTATATGAATAATATAGTCTATAGTATTAAAATAATATCAATGTTTTAGATG
EXP-Zm.UbqM1:1:4    AAACTTTACTCTACGAATAATATAATCTATAGTACTACAATAATATCAGTGTTTTAGAGA
                    ****** *** **  ********* ****** ** ** ******** * *********

EXP-Zm.UbqM1:1:2    ATCATATAAATAAACTGCTAGACATGGTCTAAAGGATAATTGAATATTTTGACAA-----
EXP-Zm.UbqM1:1:5    ATCATATAAATAAACTGCTAGACATGGTCTAAAGGATAATTGAATATTTTGACAA-----
EXP-Zm.UbqM1:1:1    ATTATATAACTGAACTGCTAGACATGGTCTAAAGGACAACCGAGTATTTTGACAACATGA
EXP-Zm.UbqM1:1:4    ATCATATAAATGAACAGTTAGACATGGTCTAAAGGACAATTGAGTATTTTGACAACAGGA
                    ** ****** * *** * ****************** **  ** ***********

EXP-Zm.UbqM1:1:2    -TCTACAGTTTTATCTTTTTAGTGTGCATGTGATCTCTCTGTTTTTTTTGCAAATAGCTT
EXP-Zm.UbqM1:1:5    -TCTACAGTTTTATCTTTTTAGTGTGCATGTGATCTCTCTGTTTTTTTTGCAAATAGCTT
EXP-Zm.UbqM1:1:1    CTCTACAGTTTTATCTTTTTAGTGTGCATGTGTTCTTT----TTACTTTGCAAATAGCTT
EXP-Zm.UbqM1:1:4    CTCTACAGTTTTATCTTTTTAGTGTGCATGTGTTCTCCTT-TTTTTTTTGCAAATAGCTT
                     ******************************* ***      **  **************

EXP-Zm.UbqM1:1:2    GACCTATATAATACTTCATCCATTTTATTAGTACATCCATTTAGGATTTAGGGTTGATGG
EXP-Zm.UbqM1:1:5    GACCTATATAATACTTCATCCATTTTATTAGTACATCCATTTAGGATTTAGGGTTGATGG
EXP-Zm.UbqM1:1:1    CACCTATATAATACTTCATCCATTTTATTAGTACATCCATTT------------------
EXP-Zm.UbqM1:1:4    CACCTATATAATACTTCATCCATTTTATTAGTACATCCATTTAGGGTTTAGGGTTAATGG
                     *****************************************

EXP-Zm.UbqM1:1:2    TTTCTATAGACTAA--TTTTTAGTACATCCATTTTATTCT-TTTTAGTCTCTAAATTTTT
EXP-Zm.UbqM1:1:5    TTTCTATAGACTAA--TTTTTAGTACATCCATTTTATTCT-TTTTAGTCTCTAAATTTTT
EXP-Zm.UbqM1:1:1    ---------ACTAAA-TTTTTAGTACATCTATTTTATTCTATTTTAGCCTCTAAA-TTAA
EXP-Zm.UbqM1:1:4    TTTTTATAGACTAATTTTTTTAGTACATCTATTTTATTCTATTTTAGCCTCTAAA-TTAA
                             *****  ************* ********** ****** ******* **

EXP-Zm.UbqM1:1:2    TAAAACTAAAACTCTATTTTAG-TTTTTTATTTAATAATTTAGATATAAAATGAAATAAA
EXP-Zm.UbqM1:1:5    TAAAACTAAAACTCTATTTTAG-TTTTTTATTTAATAATTTAGATATAAAATGAAATAAA
EXP-Zm.UbqM1:1:1    GAAAACTTAAACTCTATTTTAG-TTTTTTATTTAATAATTTAGATATAAAATAGAATAAA
EXP-Zm.UbqM1:1:4    GAAAACTAAAACTCTATTTTAGTTTTTTTATTTAATAATTTAGATATAAAATAGAATAAA
                     ****** ************** *****************************  ******
```

FIG. 4a

```
EXP-Zm.UbqM1:1:2    ATAAATTGACTACAAATAAAACAAATACCCTTTAAGAAA-TAAAAAAACTAAGCAAACAT
EXP-Zm.UbqM1:1:5    ATAAATTGACTACAAATAAAACAAATACCCTTTAAGAAA-TAAAAAAACTAAGCAAACAT
EXP-Zm.UbqM1:1:1    ATAAAGTGACTAAAAAATAACTAAATACCTTTTAAGAAA-TAAAAAAACTAAGGAACCAT
EXP-Zm.UbqM1:1:4    ATAAAGTGACTAAAAATTAAACAAATACCCTTTAAGAAATTAAAAAAACTAAGGAAACAT
                    ***** ****** ***  **  ******* ********* ************* ** ***

EXP-Zm.UbqM1:1:2    TTTTCTTGTTTCGAGTAGATAATGACAGGCTGTTCAACGCCGTCGACGAGTCTAACGGAC
EXP-Zm.UbqM1:1:5    TTTTCTTGTTTCGAGTAGATAATGACAGGCTGTTCAACGCCGTCGACGAGTCTAACGGAC
EXP-Zm.UbqM1:1:1    TTTTCTTGTTCCGAGTAGATAATGACAGCCTGTTCAACGCCGTCGACGAGTCTAACGGAC
EXP-Zm.UbqM1:1:4    TTTTCTTGTTTCGAGTAGATAATGCCAGCCTGTTAAACGCCGTCGACGAGTCTAACGGAC
                    ********** ************* *** ***** *************************

EXP-Zm.UbqM1:1:2    ACCAACCAGCGAACCAGCAGCGTCGCGTCGGGCCAAGCGAAGCAGACGGCACGGCATCTC
EXP-Zm.UbqM1:1:5    ACCAACCAGCGAACCAGCAGCGTCGCGTCGGGCCAAGCGAAGCAGACGGCACGGCATCTC
EXP-Zm.UbqM1:1:1    ACCAACCAGCGAACCAGCAGCGTCGCGTCGGGCCAAGCGAAGCAGACGGCACGGCATCTC
EXP-Zm.UbqM1:1:4    ACCAACCAGCGAACCAGCAGCGTCGCGTCGGGCCAAGCGAAGCAGACGGCACGGCATCTC
                    ************************************************************

EXP-Zm.UbqM1:1:2    TGTAGCTGCCTCTGGACCCCTCTCGAGAGTTCCGCTCCACCGTTGGACTTGCTCCGCTGT
EXP-Zm.UbqM1:1:5    TGTAGCTGCCTCTGGACCCCTCTCGAGAGTTCCGCTCCACCGTTGGACTTGCTCCGCTGT
EXP-Zm.UbqM1:1:1    TGTAGCTGCCTCTGGACCCCTCTCGAGAGTTCCGCTCCACCGTTGGACTTGCTCCGCTGT
EXP-Zm.UbqM1:1:4    TGTCGCTGCCTCTGGACCCCTCTCGAGAGTTCCGCTCCACCGTTGGACTTGCTCCGCTGT
                    *** ********************************************************

EXP-Zm.UbqM1:1:2    CGGCATCCAGAAATTGCGTGGCGGAGCGGCAGACGTGAGGCGGCACGGCAGGCGGCCTCT
EXP-Zm.UbqM1:1:5    CGGCATCCAGAAATTGCGTGGCGGAGCGGCAGACGTGAGGCGGCACGGCAGGCGGCCTCT
EXP-Zm.UbqM1:1:1    CGGCATCCAGAAATTGCGTGGCGGAGCGGCAGACGTGAGCCGGCACGGCAGGCGG-----
EXP-Zm.UbqM1:1:4    CGGCATCCAGAAATTGCGTGGCGGAGCGGCAGACGTGAGCCGGCACGGCAGGCGGCCTCC
                    *************************************** ***************

EXP-Zm.UbqM1:1:2    TCCTCCTCTCACGGCACCGGCAGCTACGGGGGATTCCTTTCCCACCGCTCCTTCGCTTTC
EXP-Zm.UbqM1:1:5    TCCTCCTCTCACGGCACCGGCAGCTACGGGGGATTCCTTTCCCACCGCTCCTTCGCTTTC
EXP-Zm.UbqM1:1:1    -CCTCCTCTCACGGCACCGGCAGCTACGGGGGATTCCTTTCCCACCGCTCCTTCGCTTTC
EXP-Zm.UbqM1:1:4    TCCTCCTCTCACGGCACCGGCAGCTACGGGGGATTCCTTTCCCACCGCTCCTTCGCTTTC
                     ***********************************************************
EXP-Zm.UbqM1:1:2    CCTTCCTCGCCCGCCGTAATAAATAGACACCCCCTCCACACCCTCTTTCCCCAACCTCGT
EXP-Zm.UbqM1:1:5    CCTTCCTCGCCCGCCGTAATAAATAGACACCCCCTCCACACCCTCTTTCCCCAACCTCGT
EXP-Zm.UbqM1:1:1    CCTTCCTCGCCCGCCGTAATAAATAG--ACCCCCTCCACACCCTCTTTCCCCAACCTCGT
EXP-Zm.UbqM1:1:4    CCTTCCTCGCCCGCCGTAATAAATAGACACCCCCTCCACACCTTCTTTCCCCAACCTCGT
                    **************************  ************** *****************

EXP-Zm.UbqM1:1:2    GTTCGTTCGGAGCGCACACACACGCAACCAGATCTCCCCCAAATCCAGCCGTCGGCACCT
EXP-Zm.UbqM1:1:5    GTTCGTTCGGAGCGCACACACACGCAACCAGATCTCCCCCAAATCCAGCCGTCGGCACCT
EXP-Zm.UbqM1:1:1    GTTCGTTCGGAGCGCGCACACACACAACCAGATCTCCCCCAAATCCACCCGTCGGCACCT
EXP-Zm.UbqM1:1:4    GTT-GTTCGGAGCGCACACACACACAACCAGATCTCCCCCAAATCCACCCGTCGGCACCT
                    *** *********** ******* *********************** ************
```

FIG. 4b

```
EXP-Zm.UbqM1:1:2      CCGCTTCAAGGTACGCCGCTCATCCTCCCCCCCCCCCTCTCTCTACCTTCTCTAGATCGG
EXP-Zm.UbqM1:1:5      CCGCTTCAAGGTACGCCGCTCATCCTCCCCCCCCCCCTCTCTCTACCTTCTCTAGATCGG
EXP-Zm.UbqM1:1:1      CCGCTTCAAGGTACGCCGCTCATCCTCCTCCCCCCCCTCTCTCTACCTTCTCTAGATCGG
EXP-Zm.UbqM1:1:4      CCGCTTCAAGGTACGCCGCTCATCCTCCCCCCCCC---CTCTCTACCTTCTCTAGATCGG
                      **************************** ******   **********************

EXP-Zm.UbqM1:1:2      CGATCCGGTCCATGGTTAGGGCCCGGTAGTTCTACTTCTGTTCATGTTTGTGTTAGAGCA
EXP-Zm.UbqM1:1:5      CGATCCGGTCCATGGTTAGGGCCCGGTAGTTCTACTTCTGTTCATGTTTGTGTTAGAGCA
EXP-Zm.UbqM1:1:1      CGTTTCGGTCCATGGTTAGGGCCCGGTAGTTCTACTTCTGTTCATGTTTGTGTTAGATC-
EXP-Zm.UbqM1:1:4      CGTTCCGGTCCATGGTTAGGGCCCGGTAGTTCTACTTCTGTTCATGTTTGTGTTAGATC-
                      ** * **************************************************** * 

EXP-Zm.UbqM1:1:2      AACATGTTCATGTT------------------------CATGTTTGTGAT----------
EXP-Zm.UbqM1:1:5      AACATGTTCATGTT------------------------CATGTTTGTGAT----------
EXP-Zm.UbqM1:1:1      --CGTGTTTGTGTTAGATCCGTGCTGCTAGATTTCGTACACGGATGCGACCTGTACATCA
EXP-Zm.UbqM1:1:4      --CGTGTTTGTGTTAGATCCGTGCTGCTAGCGTTCGTACACGGATGCGACCTGTACGTCA
                        * ****  ****                        ** *  ** **

EXP-Zm.UbqM1:1:2      GATGTGGTCTGGTTG-------GGCGGTCGTTCTAGATCGGAG----TAGGATACTGTTT
EXP-Zm.UbqM1:1:5      GATGTGGTCTGGTTG-------GGCGGTCGTTCTAGATCGGAG----TAGGATACTGTTT
EXP-Zm.UbqM1:1:1      GACATGTTCTGATTGCTAACTTGCCAGTGTTTCTCTTTGGGGAATCCTGGGA---TGGCT
EXP-Zm.UbqM1:1:4      GACACGTTCTGATTGCTAACTTGCCAGTGTTTCTCTTTGGGGAATCCTGGGA---TGGCT
                      **   * **** ***       * * **  ****   * **      * ***   **  *

EXP-Zm.UbqM1:1:2      CAAGCT---------ACCTGGTGGATTT-----ATTAATTTTGTATCTGTATGT------
EXP-Zm.UbqM1:1:5      CAAGCT---------ACCTGGTGGATTT-----ATTAATTTTGTATCTGTATGT------
EXP-Zm.UbqM1:1:1      CTAGCCGTTCCGCAGACGGGATCGATTTCATGAATTTTTTTTGTTTCGTTGCATAGGGTT
EXP-Zm.UbqM1:1:4      CTAGCCGTTCCGCAGACGGGATCGATTTCATG-ATTTTTTTTGTTTCGTTGCATAGGGTT
                      * ***          **  * * *****     ***  ****** **  *   *

EXP-Zm.UbqM1:1:2      --GTGTGCCATACATCTTCATAGTTACGAGTTTAAGATGATGGATGGAAATATCGATCTA
EXP-Zm.UbqM1:1:5      --GTGTGCCATACATCTTCATAGTTACGAGTTTAAGATGATGGATGGAAATATCGATCTA
EXP-Zm.UbqM1:1:1      TGGTTTGCCCTTTTCCTTTAT---------TTCAATAT-----------ATGCC------
EXP-Zm.UbqM1:1:4      TGGTTTGCCCTTTTCCTTTAT---------TTCAATAT-----------ATGCC------
                        ** **** *    *** **         ** ** **           **  *

EXP-Zm.UbqM1:1:2      GGATAGGTATACATGTTGATGCGGGT--TTTACTGATGCATATACAGAGATGCTTTTTTT
EXP-Zm.UbqM1:1:5      GGATAGGTATACATGTTGATGCGGGT--TTTACTGATGCATATACAGAGATGCTTTTTTT
EXP-Zm.UbqM1:1:1      ------GTGCACTTGTTTGT-CGGGTCATCTTTTCATG----------------TTTTTT
EXP-Zm.UbqM1:1:4      ------GTGCACTTGTTTGT-CGGGTCATCTTTTCATGC---------------TTTTTT
                            **  ** ****  * *****  * *  * ***                ******

EXP-Zm.UbqM1:1:2      CTCGCTTGGTTGTGATGATATGGTCTGGTTGGGCGGTCGTTCTAGATCGGAGTAGAATAC
EXP-Zm.UbqM1:1:5      CTCGCTTGGTTGTGATGATATGGTCTGGTTGGGCGGTCGTTCTAGATCGGAGTAGAATAC
EXP-Zm.UbqM1:1:1      TTGGCTTGGTTGTGATGATGTGGTCTGGTTGGGCGGTCGTTCTAGATCGGAGTAGAATAC
EXP-Zm.UbqM1:1:4      TTGTCTTGGTTGTGATGATGTGGTCTGGTTGGGCGGTCGTTCTAGATCGGAGAAGAATTC
                       *  *************** ******************************** ***** *
```

FIG. 4c

```
EXP-Zm.UbqM1:1:2        TGTTTCAAACTACCTGGTGGATTTATTAAAGGATAAAGGGTCGTTCTAGATCGGAGTAGA
EXP-Zm.UbqM1:1:5        TGTTTCAAACTACCTGGTGGATTTATTAAAGGATAAAGGGTCGTTCTAGATCGGAGTAGA
EXP-Zm.UbqM1:1:1        TGTTTCAAACTACCTGGTGGATTTATTAA-------------------------------
EXP-Zm.UbqM1:1:4        TGTTTCAAACTACCTGGTGGATTTATTAA-------------------------------
                        *****************************

EXP-Zm.UbqM1:1:2        ATACTGTTTCAAACTACCTGGTGGATTTATTAAAGGATCTGTATGTATGTGCC-TACATC
EXP-Zm.UbqM1:1:5        ATACTGTTTCAAACTACCTGGTGGATTTATTAAAGGATCTGTATGTATGTGCC-TACATC
EXP-Zm.UbqM1:1:1        ---------------------------------AGGATCTGTATGTATGTGCCATACATC
EXP-Zm.UbqM1:1:4        ------------------------------TTTTGGATCTGTATGTGTGTGCCATACATA
                                                          ************ ****** *****

EXP-Zm.UbqM1:1:2        TTCATAGTTACGAGTTTAAGATGATGGATGGAAATATCGATCTAGGATAGGTATACATGT
EXP-Zm.UbqM1:1:5        TTCATAGTTACGAGTTTAAGATGATGGATGGAAATATCGATCTAGGATAGGTATACATGT
EXP-Zm.UbqM1:1:1        TTCATAGTTACGAGTTTAAGATGATGGATGGAAATATCGATCTAGGATAGGTATACATGT
EXP-Zm.UbqM1:1:4        TTCATAGTTACGAATTGAAGATGATGGATGGAAATATCGATCTAGGATAGGTATACATGT
                        ************* ** *******************************************

EXP-Zm.UbqM1:1:2        TGATGCGGGTTTTACTGATGCATATACAGAGATGCTTTTT-TTCGCTTGGTTGTGATGAT
EXP-Zm.UbqM1:1:5        TGATGCGGGTTTTACTGATGCATATACAGAGATGCTTTTT-TTCGCTTGGTTGTGATGAT
EXP-Zm.UbqM1:1:1        TGATGCGGGTTTTACTGATGCATATACAGAGATGCTTTTTTTTCGCTTGGTTGTGATGAT
EXP-Zm.UbqM1:1:4        TGATGCGGGTTTTACTGATGCATATACAGAGATGCTTTTTGTTCGCTTGGTTGTGATGAT
                        **************************************** *******************

EXP-Zm.UbqM1:1:2        GTGGTCTGGTTGGGCGG--------TCGTTCTAGATCGGAGTAGAATACTGTTTCAAACT
EXP-Zm.UbqM1:1:5        GTGGTCTGGTTGGGCGG--------TCGTTCTAGATCGGAGTAGAATACTGTTTCAAACT
EXP-Zm.UbqM1:1:1        GTGGTCTGGTCGGGCGG--------TCGTTCTAGATCGGAGTAGAATACTGTTTCAAACT
EXP-Zm.UbqM1:1:4        GTGGTCTGGTTGGGCGGTCGTTCATTCGTTCTAGATCGGAGTAGAATACTGTTTCAAACT
                        ********** ******        ***********************************

EXP-Zm.UbqM1:1:2        ACCTGGTGGATTTATTAATTTTGTATCTTTATGTGTGTGCCATACATCTTCATAGTTACG
EXP-Zm.UbqM1:1:5        ACCTGGTGGATTTATTAATTTTGTATCTTTATGTGTGTGCCATACATCTTCATAGTTACG
EXP-Zm.UbqM1:1:1        ACCTGGTGGATTTATTAATTTTGGATCTGTATGTGTGT--CATACATCTTCATAGTTACG
EXP-Zm.UbqM1:1:4        ACCTGGTGTATTTATTAATTTTGGAACTGTATGTGTGTGTCATACATCTTCATAGTTACG
                        ******** ************** * ** *********  ********************

EXP-Zm.UbqM1:1:2        AGTTTAAGATGATGGATGGAAATATTGATCTAGGATAGGTATACATGTTGATGTGGGTTT
EXP-Zm.UbqM1:1:5        AGTTTAAGATGATGGATGGAAATATTGATCTAGGATAGGTATACATGTTGATGTGGGTTT
EXP-Zm.UbqM1:1:1        AGTTTAA---GATCGATGGAAATATCGATCTAGGATAGGTATACATGTTGATGTGGGTTT
EXP-Zm.UbqM1:1:4        AGTTTAA---GATGGATGGAAATATCGATCTAGGATAGGTATACATGTTGATGTGGGTTT
                        *******   *** *********** **********************************

EXP-Zm.UbqM1:1:2        TACTGATGCATATACATGATGGCATATGCGGCATCTATTCATATGCTCTAACCTTGAGTA
EXP-Zm.UbqM1:1:5        TACTGATGCATATACATGATGGCATATGCGGCATCTATTCATATGCTCTAACCTTGAGTA
EXP-Zm.UbqM1:1:1        TACTGATGCATATAC---ATGGCATATGCAGCATCTATTCATATGCTCTAACCTTGAGTA
EXP-Zm.UbqM1:1:4        TACTGATGCATATACATGATGGCATATGCAGCATCTATTCATATGCTCTAACCTTGAGTA
                        ***************   *********** ******************************
```

FIG. 4d

```
EXP-Zm.UbqM1:1:2        CCTATCTATTATAATAAACAAGTATGTTTTATAATTATTTTGATCTTGATATACTTGGAT
EXP-Zm.UbqM1:1:5        CCTATCTATTATAATAAACAAGTATGTTTTATAATTATTTTGATCTTGATATACTTGGAT
EXP-Zm.UbqM1:1:1        CCTATCTATTATAATAAACAAGTATGTTTTATAATTATTTTGATCTTGATATACTTGGAT
EXP-Zm.UbqM1:1:4        CCTATCTATTATAATAAACAAGTATGTTTTATAATTATTTTGATCTTGATATACTTGGAT
                        ************************************************************

EXP-Zm.UbqM1:1:2        GATGGCATATGCAGCAGCTATATGTGGA-TTTTTTAGCCCTGCCTTCATACGCTATTTAT
EXP-Zm.UbqM1:1:5        GATGGCATATGCAGCAGCTATATGTGGA-TTTTTTAGCCCTGCCTTCATACGCTATTTAT
EXP-Zm.UbqM1:1:1        GATGGCATATGCAGCAGCTATATGTGGATTTTTTTAGCCCTGCCTTCATACGCTATTTAT
EXP-Zm.UbqM1:1:4        GATGGCATATGCAGCAGCTATATGTGGATTTTTTTAGCCCTGCCTTCATACGCTATTTAT
                        **************************** *******************************

EXP-Zm.UbqM1:1:2        TTGCTTGGTACTGTTTCTTTTGTCCGATGCTCACCCTGTTGTTGGGTGATACTTCTGCAG
EXP-Zm.UbqM1:1:5        TTGCTTGGTACTGTTTCTTTTGTCCGATGCTCACCCTGTTGTTTGGTGATACTTCTGCAG
EXP-Zm.UbqM1:1:1        TTGCTTGGTACTGTTTCTTTTGT-CGATGCTCACCCTGTTGTTTGGTGATACTTCTGCAG
EXP-Zm.UbqM1:1:4        TTGCTTGGTACTGTTTCTTTTGT-CGATGCTCACCCTGTTGTTTGGTGATACTTCTGCAG
                        *********************** ******************* ****************
```

FIG. 4e

```
P-Sb.Ubq6-1:1:2          ------------------------------------------------------------
P-Sb.Ubq6-1:1:1          CATTAAAAGTCATTATGTGCATGCGTCGTAACTAACATGGATATGTTGCTGCACTATCTC

P-Sb.Ubq6-1:1:2          -----CACTAGCTGCGCATGATAAAGCCACAAGCCAAAATTAATTATTATGGGTGAGAATA
P-Sb.Ubq6-1:1:1          CTCGCACTAGCTGCGCATGATAAAGCCACAAGCCAAAATTAATTATTATGGGTGAGAATA
                              *******************************************************

P-Sb.Ubq6-1:1:2          AATACGTACCAGCACCGGCCATAGAAAAAGTACATTATTAAAGGTCTAATTTGGAAACAG
P-Sb.Ubq6-1:1:1          AATACGTACCAGCACCGGCCATAGAAAAAGTACATTATTAAAGGTCTAATTTGGAAACAG
                         ************************************************************

P-Sb.Ubq6-1:1:2          TCTGAAAACGACGTGCGCTGCAGAGGTAAATGTAATTTTCGGCACTAAAACCATTATCAA
P-Sb.Ubq6-1:1:1          TCTGAAAACGACGTGCGCTGCAGAGGTAAATGTAATTTTCGGCACTAAAACCATTATCAA
                         ************************************************************

P-Sb.Ubq6-1:1:2          CTAATTCATTCAATAACAGTTATTTAGAAAATGTATAGCTCGCTCTAAAAAAACAGTTTA
P-Sb.Ubq6-1:1:1          CTAATTCATTCAATAACAGTTATTTAGAAAATGTATAGCTCGCTCTAAAAAAACAGTTTA
                         ************************************************************

P-Sb.Ubq6-1:1:2          GAAAAACAGTCAAAATAATTCGACCAACAAACAGTTAATAAGGTTCATTAAATATATAAT
P-Sb.Ubq6-1:1:1          GAAAAACAGTCAAAATAATTCGACCAACAAACAGTTAATAAGGTTCATTAAATATATAAT
                         ************************************************************

P-Sb.Ubq6-1:1:2          GCACGGTGCTATTTGATCTTTTAAAGGAAAAAGAGGAATAGTCGTGGGCGCCAGGCGGGA
P-Sb.Ubq6-1:1:1          GCACGGTGCTATTTGATCTTTTAAAGGAAAAAGAGGAATAGTCGTGGGCGCCAGGCGGGA
                         ************************************************************

P-Sb.Ubq6-1:1:2          ATTGGGGCGCGGGAGTCTGCCGGACGACGCGTTCCGTCCGAACGGCCGGACCCGACGAGG
P-Sb.Ubq6-1:1:1          ATTGGGGCGCGGGAGTCTGCCGGACGACGCGTTCCGTCCGAACGGCCGGACCCGACGAGG
                         ************************************************************

P-Sb.Ubq6-1:1:2          CCCCCCCGCCGCCCCACGTCGCAGAACCGTCCGTGGGTGGTAATCTGGCCGGGTACACCA
P-Sb.Ubq6-1:1:1          CCCCCCCGCCGCCCCACGTCGCAGAACCGTCCGTGGGTGGTAATCTGGCCGGGTACACCA
                         ************************************************************

P-Sb.Ubq6-1:1:2          GCCGTCCCCTTGGGCGGCCTCACAGCACTGGGCTCACACGTGAGTTTTGTTCTGGGCTTC
P-Sb.Ubq6-1:1:1          GCCGTCCCCTTGGGCGGCCTCACAGCACTGGGCTCACACGTGAGTTTTGTTCTGGGCTTC
                         ************************************************************

P-Sb.Ubq6-1:1:2          GGATCGCACCATATGGGCCTCGGCATCAGAAAGACGGGGCCCGTCTGGGATAGAAGAGAC
P-Sb.Ubq6-1:1:1          GGATCGCACCATATGGGCCTCGGCATCAGAAAGACGGGGCCCGTCTGGGATAGAAGAGAC
                         ************************************************************
```

FIG. 5a

```
P-Sb.Ubq6-1:1:2      AGGAACCTCCTCGTGGATTCCAGAAGCCAGCCACGAGCGACCACCGACGCGGAGGATACT
P-Sb.Ubq6-1:1:1      AGGAACCTCCTCGTGGATTCCAGAAGCCAGCCACGAGCGACCACCGACGCGGAGGATACT
                     ************************************************************

P-Sb.Ubq6-1:1:2      CGTCGTCCAAGTCCAACACGGCGGGCGGGCGGGCGGACGCGTGGGCTGGGCTAACTGCCT
P-Sb.Ubq6-1:1:1      CGTCGTCCAAGTCCAACACGGCGGGCGGGCGGGCGGACGCGTGGGCTGGGCTAACTGCCT
                     ************************************************************

P-Sb.Ubq6-1:1:2      AACCTTAACCTCCAAGGCACGCCAAGGCCCGCTTCTCCCACCCGACATAAATATCCCCCC
P-Sb.Ubq6-1:1:1      AACCTTAACCTCCAAGGCACGCCAAGGCCCGCTTCTCCCACCCGACATAAATATCCCCCC
                     ************************************************************

P-Sb.Ubq6-1:1:2      ATCCAGGCAAGGCGC
P-Sb.Ubq6-1:1:1      ATCCAGGCAAGGCGC
                     ***************
```

FIG. 5b

```
P-SETit.Ubq1-1:1:4     ACTGCCGCGACACGCCTCACTGGCGGGAGGGCTCCGAGCGCTCTCTCCCCGGCGGCCGGC
P-SETit.Ubq1-1:1:3     ------------------------------------------------------------
P-SETit.Ubq1-1:1:1     ACTGCCGCGACACGCCTCACTGGCGGGAGGGCTCCGAGCGCTCTCTCCCCGGCGGCCGGC
P-SETit.Ubq1-1:1:2     ------------------------------------------------------------

P-SETit.Ubq1-1:1:4     GGAGCAGCGATCTGGATTGGAGAGAATAGAGGAAAGAGAGGGAAAAGGAGAGAGATAGCG
P-SETit.Ubq1-1:1:3     ------------------------------------------------------------
P-SETit.Ubq1-1:1:1     GGAGCAGCGATCTGGATTGGAGAGAATAGAGGAAAGAGAGGGAAAAGGAGAGAGATAGCG
P-SETit.Ubq1-1:1:2     ------------------------------------------------------------

P-SETit.Ubq1-1:1:4     CAAAGAGCTGAAAAGATAAGGTTGTGCGGGCTGTGGTGATTAGAGGACCACTAATCCCTC
P-SETit.Ubq1-1:1:3     ------------------------------------------------------------
P-SETit.Ubq1-1:1:1     CAAAGAGCTGAAAAGATAAGGTTGTGCGGGCTGTGGTGATTAGAGGACCACTAATCCCTC
P-SETit.Ubq1-1:1:2     ------------------------------------------------------------

P-SETit.Ubq1-1:1:4     CATCTCCTAATGACGCGGTGCCCAAGACCAGTGCCGCGGCACACCAGCGTCTAAGTGAAC
P-SETit.Ubq1-1:1:3     ------------------------------------------------------------
P-SETit.Ubq1-1:1:1     CATCTCCTAATGACGCGGTGCCCAAGACCAGTGCCGCGGCACACCAGCGTCTAAGTGAAC
P-SETit.Ubq1-1:1:2     ------------------------------------------------------------

P-SETit.Ubq1-1:1:4     TTCCGCTAACCTTCCGGTCATTGCGCCTGAAAGATGTCATGTGGCGAGGCCCCCCTCTCA
P-SETit.Ubq1-1:1:3     ------------------------------------------------------------
P-SETit.Ubq1-1:1:1     TTCCGCTAACCTTCCGGTCATTGCGCCTGAAAGATGTCATGTGGCGAGGCCCCCCTCTCA
P-SETit.Ubq1-1:1:2     ------------------------------------------------------------

P-SETit.Ubq1-1:1:4     GTAGATTGCCAACTGCCTACCGTGCCACTCTTCCATGCATGATTGCTCCCGTCTATCCCG
P-SETit.Ubq1-1:1:3     ------------------------------------------------------------
P-SETit.Ubq1-1:1:1     GTAGATTGCCAACTGCCTACCGTGCCACTCTTCCATGCATGATTGCTCCCGTCTATCCCG
P-SETit.Ubq1-1:1:2     ------------------------------------------------------------

P-SETit.Ubq1-1:1:4     TTTCTCACAACAGATAGACAACAGTAAGCATCACTAAAGCAAGCATGTGTAGAACCTTAA
P-SETit.Ubq1-1:1:3     ------------------------------------------------------------
P-SETit.Ubq1-1:1:1     TTTCTCACAACAGATAGACAACAGTAAGCATCACTAAAGCAAGCATGTGTAGAACCTTAA
P-SETit.Ubq1-1:1:2     ------------------------------------------------------------

P-SETit.Ubq1-1:1:4     AAAAAGGCTTATACTACCAGTATACTATCAACCAGCATGCCGTTTTTGAAGTATCCAGGA
P-SETit.Ubq1-1:1:3     ------------------------------------------------------------
P-SETit.Ubq1-1:1:1     AAAAAGGCTTATACTACCAGTATACTATCAACCAGCATGCCGTTTTTGAAGTATCCAGGA
P-SETit.Ubq1-1:1:2     --------------------------------------GCCGTTTTTGAAGTATCCAGGA

P-SETit.Ubq1-1:1:4     TTAGAAGCTTCTACTGCGCTTTTATATTATAGCTGTGGACCCGTGGTAACCTTTCTCTTT
P-SETit.Ubq1-1:1:3     ------------------------------------------------------------
P-SETit.Ubq1-1:1:1     TTAGAAGCTTCTACTGCGCTTTTATATTATAGCTGTGGACCTGTGGTAACCTTTCTCTTT
P-SETit.Ubq1-1:1:2     TTAGAAGCTTCTACTGCGCTTTTATATTATAGCTGTGGACCTGTGGTAACCTTTCTCTTT

P-SETit.Ubq1-1:1:4     TGGCGCTTGCTTAATCTCGGCCGTGCTGGTCCATGCTTAGGCACTAGGCAGAGATAGAGC
P-SETit.Ubq1-1:1:3     ------------------------------------------------------------
P-SETit.Ubq1-1:1:1     TGGCGCTTGCTTAATCTCGGCCGTGCTGGTCCATGCTTAGGCACTAGGCAGAGATAGAGC
P-SETit.Ubq1-1:1:2     TGGCGCTTGCTTAATCTCGGCCGTGCTGGTCCATGCTTAGGCACTAGGCAGAGATAGAGC
```

FIG. 6a

```
P-SETit.Ubq1-1:1:4     CGGGGGTGAATGGGGCTAAAGCTCAGCTGCTCGAGGGGCCGTGGGCTGGTTTCCACTAGC
P-SETit.Ubq1-1:1:3     ------------------------------------------------------------
P-SETit.Ubq1-1:1:1     CGGGGGTGAATGGGGCTAAAGCTCAGCTGCTCGAGGGGCCGTGGGCTGGTTTCCACTAGC
P-SETit.Ubq1-1:1:2     CGGGGGTGAATGGGGCTAAAGCTCAGCTGCTCGAGGGGCCGTGGGCTGGTTTCCACTAGC

P-SETit.Ubq1-1:1:4     CTACAGCTGTGCCACGTGCGGCCGCGCAAGCCGAAGCAAGCACGCTGAGCCGTTGGACAG
P-SETit.Ubq1-1:1:3     ------------------------------------------------------------
P-SETit.Ubq1-1:1:1     CTACAGCTGTGCCACGTGCGGCCGCGCAAGCCGAAGCAAGCACGCTGAGCCGTTGGACAG
P-SETit.Ubq1-1:1:2     CTACAGCTGTGCCACGTGCGGCCGCGCAAGCCGAAGCAAGCACGCTGAGCCGTTGGACAG

P-SETit.Ubq1-1:1:4     CTTGTCATAATGCCATTACGTGGATTACACGTAACTGGCCCTGTAACTACTCGTTCGGCC
P-SETit.Ubq1-1:1:3     ------------------------------------------------------------
P-SETit.Ubq1-1:1:1     CTTGTCATAATGCCATTACGTGGATTACACGTAACTGGCCCTGTAACTACTCGTTCGGCC
P-SETit.Ubq1-1:1:2     CTTGTCATAATGCCATTACGTGGATTACACGTAACTGGCCCTGTAACTACTCGTTCGGCC

P-SETit.Ubq1-1:1:4     ATCATCAAACGACGACGTCCGCTAGGCGACGACACGGGTAATGCACGCAGCCACCCAGGC
P-SETit.Ubq1-1:1:3     --------------------------------CACGGGTAATGCACGCAGCCACCCAGGC
P-SETit.Ubq1-1:1:1     ATCATCAAACGACGACGTCCGCTAGGCGACGACACGGGTAATGCACGCAGCCACCCAGGC
P-SETit.Ubq1-1:1:2     ATCATCAAACGACGACGTCCGCTAGGCGACGACACGGGTAATGCACGCAGCCACCCAGGC
                                                       ****************************

P-SETit.Ubq1-1:1:4     GCGCGCGCTAGCGGAGCACGGTCAGGTGACACGGGCGTCGTGACGCTTCCGAGTTGAAGG
P-SETit.Ubq1-1:1:3     GCGCGCGCTAGCGGAGCACGGTCAGGTGACACGGGCGTCGTGACGCTTCCGAGTTGAAGG
P-SETit.Ubq1-1:1:1     GCGCGCGCTAGCGGAGCACGGTCAGGTGACACGGGCGTCGTGACGCTTCCGAGTTGAAGG
P-SETit.Ubq1-1:1:2     GCGCGCGCTAGCGGAGCACGGTCAGGTGACACGGGCGTCGTGACGCTTCCGAGTTGAAGG
                       ************************************************************

P-SETit.Ubq1-1:1:4     GGTTAACGCCAGAAACAGTGTTTGGCCAGGGTATGAACATAACAAAAAATATTCACACGA
P-SETit.Ubq1-1:1:3     GGTTAACGCCAGAAACAGTGTTTGGCCAGGGTATGAACATAACAAAAAATATTCACACGA
P-SETit.Ubq1-1:1:1     GGTTAACGCCAGAAACAGTGTTTGGCCAGGGTATGAACATAACAAAAAATATTCACACGA
P-SETit.Ubq1-1:1:2     GGTTAACGCCAGAAACAGTGTTTGGCCAGGGTATGAACATAACAAAAAATATTCACACGA
                       ************************************************************

P-SETit.Ubq1-1:1:4     AAGAATGGAAGTATGGAGCTGCTACTGTGTAAATGCCAAGCAGGAAACTCACGCCCGCTA
P-SETit.Ubq1-1:1:3     AAGAATGGAAGTATGGAGCTGCTACTGTGTAAATGCCAAGCAGGAAACTCACGCCCGCTA
P-SETit.Ubq1-1:1:1     AAGAATGGAAGTATGGAGCTGCTACTGTGTAAATGCCAAGCAGGAAACTCACGCCCGCTA
P-SETit.Ubq1-1:1:2     AAGAATGGAAGTATGGAGCTGCTACTGTGTAAATGCCAAGCAGGAAACTCACGCCCGCTA
                       ************************************************************

P-SETit.Ubq1-1:1:4     ACATCCAACGGCCAACAGCTCGACGTGCCGGTCAGCAGAGCATCGGAACACTGGTGATTG
P-SETit.Ubq1-1:1:3     ACATCCAACGGCCAACAGCTCGACGTGCCGGTCAGCAGAGCATCGGAACACTGGTGATTG
P-SETit.Ubq1-1:1:1     ACATCCAACGGCCAACAGCTCGACGTGCCGGTCAGCAGAGCATCGGAACACTGGTGATTG
P-SETit.Ubq1-1:1:2     ACATCCAACGGCCAACAGCTCGACGTGCCGGTCAGCAGAGCATCGGAACACTGGTGATTG
                       ************************************************************

P-SETit.Ubq1-1:1:4     GTGGAGCCGGCAGTATGCGCCCCAGCACGGCCGAGGTGGTGGTGGCCCGTGGCCCTGCTG
P-SETit.Ubq1-1:1:3     GTGGAGCCGGCAGTATGCGCCCCAGCACGGCCGAGGTGGTGGTGGCCCGTGGCCCTGCTG
P-SETit.Ubq1-1:1:1     GTGGAGCCGGCAGTATGCGCCCCAGCACGGCCGAGGTGGTGGTGGCCCGTGGCCCTGCTG
P-SETit.Ubq1-1:1:2     GTGGAGCCGGCAGTATGCGCCCCAGCACGGCCGAGGTGGTGGTGGCCCGTGGCCCTGCTG
                       ************************************************************
```

FIG. 6b

```
P-SETit.Ubq1-1:1:4      TCTGCGCGGCTCGGGACAACTTGAAACTGGGCCACCGCCTCGTCGCAACTCGCAACCCGT
P-SETit.Ubq1-1:1:3      TCTGCGCGGCTCGGGACAACTTGAAACTGGGCCACCGCCTCGTCGCAACTCGCAACCCGT
P-SETit.Ubq1-1:1:1      TCTGCGCGGCTCGGGACAACTTGAAACTGGGCCACCGCCTCGTCGCAACTCGCAACCCGT
P-SETit.Ubq1-1:1:2      TCTGCGCGGCTCGGGACAACTTGAAACTGGGCCACCGCCTCGTCGCAACTCGCAACCCGT
                        ************************************************************

P-SETit.Ubq1-1:1:4      TGGCGGAAGAAAGGAATGGCTCGTAGGGGCCCGGGTAGAATCGAAGAATGTTGCGCTGGG
P-SETit.Ubq1-1:1:3      TGGCGGAAGAAAGGAATGGCTCGTAGGGGCCCGGGTAGAATCGAAGAATGTTGCGCTGGG
P-SETit.Ubq1-1:1:1      TGGCGGAAGAAAGGAATGGCTCGTAGGGGCCCGGGTAGAATCGAAGAATGTTGCGCTGGG
P-SETit.Ubq1-1:1:2      TGGCGGAAGAAAGGAATGGCTCGTAGGGGCCCGGGTAGAATCGAAGAATGTTGCGCTGGG
                        ************************************************************

P-SETit.Ubq1-1:1:4      CTTCGATTCACATAACATGGGCCTGAAGCTCTAAAACGACGGCCCGGTCGCCGCGCGATG
P-SETit.Ubq1-1:1:3      CTTCGATTCACATAACATGGGCCTGAAGCTCTAAAACGACGGCCCGGTCGCCGCGCGATG
P-SETit.Ubq1-1:1:1      CTTCGATTCACATAACATGGGCCTGAAGCTCTAAAACGACGGCCCGGTCGCCGCGCGATG
P-SETit.Ubq1-1:1:2      CTTCGATTCACATAACATGGGCCTGAAGCTCTAAAACGACGGCCCGGTCGCCGCGCGATG
                        ************************************************************

P-SETit.Ubq1-1:1:4      GAAAGAGACCGGATCCTCCTCGTGAATTCTGGAAGGCCACACGAGAGCGACCCACCACCG
P-SETit.Ubq1-1:1:3      GAAAGAGACCGGATCCTCCTCGTGAATTCTGGAAGGCCACACGAGAGCGACCCACCACCG
P-SETit.Ubq1-1:1:1      GAAAGAGACCGGATCCTCCTCGTGAATTCTGGAAGGCCACACGAGAGCGACCCACCACCG
P-SETit.Ubq1-1:1:2      GAAAGAGACCGGATCCTCCTCGTGAATTCTGGAAGGCCACACGAGAGCGACCCACCACCG
                        ************************************************************

P-SETit.Ubq1-1:1:4      ACGCGGAGGAGTCGTGCGTGGTCCAACACGGCCGGCGGGCTGGGCTGCGACCTTAACCAG
P-SETit.Ubq1-1:1:3      ACGCGGAGGAGTCGTGCGTGGTCCAACACGGCCGGCGGGCTGGGCTGCGACCTTAACCAG
P-SETit.Ubq1-1:1:1      ACGCGGAGGAGTCGTGCGTGGTCCAACACGGCCGGCGGGCTGGGCTGCGACCTTAACCAG
P-SETit.Ubq1-1:1:2      ACGCGGAGGAGTCGTGCGTGGTCCAACACGGCCGGCGGGCTGGGCTGCGACCTTAACCAG
                        ************************************************************

P-SETit.Ubq1-1:1:4      CAAGGCACGCCACGACCCGCCCCGCCCTCGAGGCATAAATACCCTCCCATCC
P-SETit.Ubq1-1:1:3      CAAGGCACGCCACGACCCGCCCCGCCCTCGAGGCATAAATACCCTCCCATCC
P-SETit.Ubq1-1:1:1      CAAGGCACGCCACGACCCGCCCCGCCCTCGAGGCATAAATACCCTCCCATCC
P-SETit.Ubq1-1:1:2      CAAGGCACGCCACGACCCGCCCCGCCCTCGAGGCATAAATACCCTCCCATCC
                        ****************************************************
```

FIG. 6c

```
E-Cl.Ubq1-1:1:1        AGCAGACTCGCATTATCGATGGAGCTCTACCAAACTGGCCCTAGGCATTAACCTACCATG
P-Cl.Ubq1-1:1:1        AGCAGACTCGCATTATCGATGGAGCTCTACCAAACTGGCCCTAGGCATTAACCTACCATG
P-Cl.Ubq1-1:1:3        ------------------------------------------------------------
P-Cl.Ubq1-1:1:4        ------------------------------------------------------------
P-Cl.Ubq1-1:1:5        ------------------------------------------------------------

E-Cl.Ubq1-1:1:1        GATCACATCGTAAAAAAAAAACCCTACCATGGATCCTATCTGTTTTCTTTTTGCCCTGAA
P-Cl.Ubq1-1:1:1        GATCACATCGTAAAAAAAAAACCCTACCATGGATCCTATCTGTTTTCTTTTTGCCCTGAA
P-Cl.Ubq1-1:1:3        ------------------------------------------------------------
P-Cl.Ubq1-1:1:4        -----------------------------------CTATCTGTTTTCTTTTTGCCCTGAA
P-Cl.Ubq1-1:1:5        ------------------------------------------------------------

E-Cl.Ubq1-1:1:1        AGAGTGAAGTCATCATCATATTTACCATGGCGCGCGTAGGAGCGCTTCGTCGAAGACCCA
P-Cl.Ubq1-1:1:1        AGAGTGAAGTCATCATCATATTTACCATGGCGCGCGTAGGAGCGCTTCGTCGAAGACCCA
P-Cl.Ubq1-1:1:3        ------------------------------------------------------------
P-Cl.Ubq1-1:1:4        AGAGTGAAGTCATCATCATATTTACCATGGCGCGCGTAGGAGCGCTTCGTCGAAGACCCA
P-Cl.Ubq1-1:1:5        ------------------------------------------------------------

E-Cl.Ubq1-1:1:1        TAGGGGGGCGGTACTCGCACCGTGGTTGTTTCCTGTTATGTAATATCGGATGGGGGAGCA
P-Cl.Ubq1-1:1:1        TAGGGGGGCGGTACTCGCACCGTGGTTGTTTCCTGTTATGTAATATCGGATGGGGGAGCA
P-Cl.Ubq1-1:1:3        ------------------------------------------------------------
P-Cl.Ubq1-1:1:4        TAGGGGGGCGGTACTCGCACCGTGGTTGTTTCCTGTTATGTAATATCGGATGGGGGAGCA
P-Cl.Ubq1-1:1:5        ------------------------------------------------------------

E-Cl.Ubq1-1:1:1        GTCGGCTAGGTTGGTCCCATCGGTACTGGTCGTCCCCTAGTGCGCTAGATGCGCGATGTT
P-Cl.Ubq1-1:1:1        GTCGGCTAGGTTGGTCCCATCGGTACTGGTCGTCCCCTAGTGCGCTAGATGCGCGATGTT
P-Cl.Ubq1-1:1:3        ------------------------------------------------------------
P-Cl.Ubq1-1:1:4        GTCGGCTAGGTTGGTCCCATCGGTACTGGTCGTCCCCTAGTGCGCTAGATGCGCGATGTT
P-Cl.Ubq1-1:1:5        ------------------------------------------------------------

E-Cl.Ubq1-1:1:1        TGTCCTCAAAAACTCTTTTCTTCTTAATAACAATCATACGCAAATTTTTTGCGTATTCGA
P-Cl.Ubq1-1:1:1        TGTCCTCAAAAACTCTTTTCTTCTTAATAACAATCATACGCAAATTTTTTGCGTATTCGA
P-Cl.Ubq1-1:1:3        ------------------------------------------------------------
P-Cl.Ubq1-1:1:4        TGTCCTCAAAAACTCTTTTCTTCTTAATAACAATCATACGCAAATTTTTTGCGTATTCGA
P-Cl.Ubq1-1:1:5        ------------------------------------------------------------

E-Cl.Ubq1-1:1:1        GAAAAAAAGAAGATTCTATCTGTTTTTTTTTTGAAATGGCTCCAATTTATAGGAGGAGCC
P-Cl.Ubq1-1:1:1        GAAAAAAAGAAGATTCTATCTGTTTTTTTTTTGAAATGGCTCCAATTTATAGGAGGAGCC
P-Cl.Ubq1-1:1:3        ------------------------------------------------------------
P-Cl.Ubq1-1:1:4        GAAAAAAAGAAGATTCTATCTGTTTTTTTTTTGAAATGGCTCCAATTTATAGGAGGAGCC
P-Cl.Ubq1-1:1:5        ------------------------------------------------------------

E-Cl.Ubq1-1:1:1        CGTTTAACGGCGTCGACAAATCTAACGGACACCAACCAGCGAATGAGCGAACCCACCAGC
P-Cl.Ubq1-1:1:1        CGTTTAACGGCGTCGACAAATCTAACGGACACCAACCAGCGAATGAGCGAACCCACCAGC
P-Cl.Ubq1-1:1:3        ----------------CAAATCTAACGGACACCAACCAGCGAATGAGCGAACCCACCAGC
P-Cl.Ubq1-1:1:4        CGTTTAACGGCGTCGACAAATCTAACGGACACCAACCAGCGAATGAGCGAACCCACCAGC
P-Cl.Ubq1-1:1:5        ------------------------------------------------------------
```

FIG. 7a

```
E-Cl.Ubq1-1:1:1      GCCAAGCTAGCCAAGCGAAGCAGACGGCCGAGACGCTGACACCCTTGCCTTGGCGCGGCA
P-Cl.Ubq1-1:1:1      GCCAAGCTAGCCAAGCGAAGCAGACGGCCGAGACGCTGACACCCTTGCCTTGGCGCGGCA
P-Cl.Ubq1-1:1:3      GCCAAGCTAGCCAAGCGAAGCAGACGGCCGAGACGCTGACACCCTTGCCTTGGCGCGGCA
P-Cl.Ubq1-1:1:4      GCCAAGCTAGCCAAGCGAAGCAGACGGCCGAGACGCTGACACCCTTGCCTTGGCGCGGCA
P-Cl.Ubq1-1:1:5      ------------------------------------------------------------

E-Cl.Ubq1-1:1:1      TCTCCGTCGCTGGCTCGCTGGCTCTGGCCCCTTCGCGAGAGTTCCGGTCCACCTCCACCT
P-Cl.Ubq1-1:1:1      TCTCCGTCGCTGGCTCGCTGGCTCTGGCCCCTTCGCGAGAGTTCCGGTCCACCTCCACCT
P-Cl.Ubq1-1:1:3      TCTCCGTCGCTGGCTCGCTGGCTCTGGCCCCTTCGCGAGAGTTCCGGTCCACCTCCACCT
P-Cl.Ubq1-1:1:4      TCTCCGTCGCTGGCTCGCTGGCTCTGGCCCCTTCGCGAGAGTTCCGGTCCACCTCCACCT
P-Cl.Ubq1-1:1:5      ------------------------------------------------------------

E-Cl.Ubq1-1:1:1      GTGTCGGTTTCCAACTCCGTTCCGCCTTCGCGTGGGACTTGTTCCGTTCATCCGTTGGCG
P-Cl.Ubq1-1:1:1      GTGTCGGTTTCCAACTCCGTTCCGCCTTCGCGTGGGACTTGTTCCGTTCATCCGTTGGCG
P-Cl.Ubq1-1:1:3      GTGTCGGTTTCCAACTCCGTTCCGCCTTCGCGTGGGACTTGTTCCGTTCATCCGTTGGCG
P-Cl.Ubq1-1:1:4      GTGTCGGTTTCCAACTCCGTTCCGCCTTCGCGTGGGACTTGTTCCGTTCATCCGTTGGCG
P-Cl.Ubq1-1:1:5      ------------------------------------------------------------

E-Cl.Ubq1-1:1:1      GCATCCGGAAATTGCGTGGCGTAGAGCACGGGGCCCTCCTCTCACACGGCACGGAACCGT
P-Cl.Ubq1-1:1:1      GCATCCGGAAATTGCGTGGCGTAGAGCACGGGGCCCTCCTCTCACACGGCACGGAACCGT
P-Cl.Ubq1-1:1:3      GCATCCGGAAATTGCGTGGCGTAGAGCACGGGGCCCTCCTCTCACACGGCACGGAACCGT
P-Cl.Ubq1-1:1:4      GCATCCGGAAATTGCGTGGCGTAGAGCACGGGGCCCTCCTCTCACACGGCACGGAACCGT
P-Cl.Ubq1-1:1:5      ------------------------------------------------------------

E-Cl.Ubq1-1:1:1      CACGAGCTCACGGCACCGGCAGCACGGCGGGGATTCCTTCCCCACCACCGCTCCTTCCCT
P-Cl.Ubq1-1:1:1      CACGAGCTCACGGCACCGGCAGCACGGCGGGGATTCCTTCCCCACCACCGCTCCTTCCCT
P-Cl.Ubq1-1:1:3      CACGAGCTCACGGCACCGGCAGCACGGCGGGGATTCCTTCCCCACCACCGCTCCTTCCCT
P-Cl.Ubq1-1:1:4      CACGAGCTCACGGCACCGGCAGCACGGCGGGGATTCCTTCCCCACCACCGCTCCTTCCCT
P-Cl.Ubq1-1:1:5      ------------------------------------------------------------

E-Cl.Ubq1-1:1:1      TTCCCTTCCTCGCCCGCC---------------------------------------
P-Cl.Ubq1-1:1:1      TTCCCTTCCTCGCCCGCCATCATAAATAGCCACCCCTCCCAGCTTCCTTCGCCACAT
P-Cl.Ubq1-1:1:3      TTCCCTTCCTCGCCCGCCATCATAAATAGCCACCCCTCCCAGCTTCCTTCGCCACAT
P-Cl.Ubq1-1:1:4      TTCCCTTCCTCGCCCGCCATCATAAATAGCCACCCCTCCCAGCTTCCTTCGCCACAT
P-Cl.Ubq1-1:1:5      ---CCTTCCTCGCCCGCCATCATAAATAGCCACCCCTCCCAGCTTCCTTCGCCACAT
                        ***************
```

FIG. 7b

PLANT REGULATORY ELEMENTS AND USES THEREOF

CROSS-REFERENCE TO RELATED APPLICATIONS

This application is a divisional of U.S. patent application Ser. No. 17/821,123, filed Aug. 19, 2022, which is a divisional of U.S. patent application Ser. No. 16/900,717, filed Jun. 12, 2020, now U.S. Pat. No. 11,466,282, which is a divisional of U.S. patent application Ser. No. 15/798,319, filed Oct. 30, 2017, now U.S. Pat. No. 10,752,910, which is a divisional of U.S. patent application Ser. No. 14/686,602, filed Apr. 14, 2015, now U.S. Pat. No. 9,834,777, which is a divisional of U.S. patent application Ser. No. 13/428,994, filed Mar. 23, 2012, now U.S. Pat. No. 9,062,316, which claims the benefit of U.S. Provisional Application No. 61/467,875, filed Mar. 25, 2011, each of which is herein incorporated by reference in its entirety.

INCORPORATION OF SEQUENCE LISTING

The sequence listing that is contained in the file named "MONS282USD8_ST26.xml", which is 421 KB (as measured in Microsoft Windows®) and was created on Jul. 12, 2024, is filed herewith by electronic submission and is incorporated by reference herein.

FIELD OF THE INVENTION

The invention relates to the field of plant molecular biology and plant genetic engineering, and DNA molecules useful for modulating gene expression in plants.

BACKGROUND

Regulatory elements are genetic elements that regulate gene activity by modulating the transcription of an operably linked transcribable polynucleotide molecule. Such elements include promoters, leaders, introns, and 3' untranslated regions and are useful in the field of plant molecular biology and plant genetic engineering.

SUMMARY OF THE INVENTION

The present invention provides novel gene regulatory elements for use in plants. The present invention also provides DNA constructs comprising the regulatory elements. The present invention also provides transgenic plant cells, plants, and seeds comprising the regulatory elements. The sequences may be provided operably linked to a transcribable polynucleotide molecule. In one embodiment, the transcribable polynucleotide molecule may be heterologous with respect to a regulatory sequence provided herein. A regulatory element sequence provided by the invention thus may, in particular embodiments, be defined as operably linked to a heterologous transcribable polynucleotide molecule. The present invention also provides methods of making and using the regulatory elements, the DNA constructs comprising the regulatory elements, and the transgenic plant cells, plants, and seeds comprising the regulatory elements operably linked to a transcribable polynucleotide molecule.

Thus, in one aspect, the present invention provides a DNA molecule comprising a DNA sequence selected from the group consisting of: a) a sequence with at least about 85 percent sequence identity to any of SEQ ID NOs: 1-158 and 180-183; b) a sequence comprising any of SEQ ID NOs: 1-158 and 180-183; and c) a fragment of any of SEQ ID NOs: 1-158 and 180-183, wherein the fragment has gene-regulatory activity; wherein the sequence is operably linked to a heterologous transcribable polynucleotide molecule. In specific embodiments, the DNA molecule comprises at least about 90 percent, at least about 95 percent, at least about 98 percent, or at least about 99 percent sequence identity to the DNA sequence of any of SEQ ID NOs: 1-158 and 180-183. In certain embodiments of the DNA molecule, the DNA sequence comprises a regulatory element. In some embodiments the regulatory element comprises a promoter. In particular embodiments, the heterologous transcribable polynucleotide molecule comprises a gene of agronomic interest, such as a gene capable of providing herbicide resistance in plants, or a gene capable of providing plant pest resistance in plants.

The invention also provides a transgenic plant cell comprising a heterologous DNA construct provided by the invention, including a sequence of any of SEQ ID NOs: 1-158 and 180-183, or a fragment or variant thereof, wherein said sequence is operably linked to a heterologous transcribable polynucleotide molecule. In certain embodiments, the transgenic plant cell is a monocotyledonous plant cell. In other embodiments, the transgenic plant cell is a dicotyledonous plant cell.

Further provided by the invention is a transgenic plant, or part thereof, comprising a DNA molecule as provided herein, including a DNA sequence selected from the group consisting of: a) a sequence with at least 85 percent sequence identity to any of SEQ ID NOs: 1-158 and 180-183; b) a sequence comprising any of SEQ ID NOs: 1-158 and 180-183; and c) a fragment of any of SEQ ID NOs: 1-158 and 180-183, wherein the fragment has gene-regulatory activity; wherein the sequence is operably linked to a heterologous transcribable polynucleotide molecule. In specific embodiments, the transgenic plant may be a progeny plant of any generation that comprises the DNA molecule, relative to a starting transgenic plant comprising the DNA molecule. Still further provided is a transgenic seed comprising a DNA molecule according to the invention.

In yet another aspect, the invention provides a method of producing a commodity product comprising obtaining a transgenic plant or part thereof according to the invention and producing the commodity product therefrom. In one embodiment, a commodity product of the invention is protein concentrate, protein isolate, grain, starch, seeds, meal, flour, biomass, or seed oil. In another aspect, the invention provides a commodity produced using the above method. For instance, in one embodiment the invention provides a commodity product comprising a DNA molecule as provided herein, including a DNA sequence selected from the group consisting of: a) a sequence with at least 85 percent sequence identity to any of SEQ ID NOs: 1-158 and 180-183; b) a sequence comprising any of SEQ ID NOs: 1-158 and 180-183; and c) a fragment of any of SEQ ID NOs: 1-158 and 180-183, wherein the fragment has gene-regulatory activity; wherein the sequence is operably linked to a heterologous transcribable polynucleotide molecule.

In still yet another aspect, the invention provides a method of expressing a transcribable polynucleotide molecule that comprises obtaining a transgenic plant according to the invention, such as a plant comprising a DNA molecule as described herein, and cultivating plant, wherein a transcribable polynucleotide in the DNA molecule is expressed.

Throughout this specification and the claims, unless the context requires otherwise, the word "comprise" and its variations, such as "comprises" and "comprising," will be understood to imply the inclusion of a stated composition, step, and/or value, or group thereof, but not the exclusion of any other composition, step, and/or value, or group thereof.

BRIEF DESCRIPTION OF THE FIGURES

FIGS. 1*a*-1*h* depict alignment of promoter size variants corresponding to promoter elements isolated from the grass species *Andropogon gerardii*. In particular, FIGS. 1*a*-1*h* show alignment of the 2603 bp promoter sequence P-ANDge.Ubq1-1:1:11 (SEQ ID NO: 2), found in the transcriptional regulatory expression element group EXP-ANDge.Ubq1:1:9 (SEQ ID NO: 1), with promoter sequences derived via deletion analysis of P-ANDge.Ubq1-1:1:11. Deletion, for instance of the 5' end of P-ANDge.Ubq1-1:1:11, produced the promoter P-ANDge.Ubq1-1:1:9 (SEQ ID NO: 6), a 2114 bp sequence which is found within EXP-ANDge.Ubq1:1:7 (SEQ ID NO: 5). Other promoter sequences in FIG. 1 include P-ANDge.Ubq1-1:1:10 (SEQ ID NO: 9), a 1644 bp sequence comprised within EXP-ANDge.Ubq1:1:8 (SEQ ID NO: 8); P-ANDge.Ubq1-1:1:12 (SEQ ID NO: 11), a 1472 bp sequence comprised within EXP-ANDge.Ubq1:1:10 (SEQ ID NO: 10); P-ANDge.Ubq1-1:1:8 (SEQ ID NO: 13), a 1114 bp sequence comprised within EXP-ANDge.Ubq1:1:6 (SEQ ID NO: 12); P-ANDge.Ubq1-1:1:13 (SEQ ID NO: 15), a 771 bp sequence comprised within EXP-ANDge.Ubq1:1:11 (SEQ ID NO: 14); and P-ANDge.Ubq1-1:1:14 (SEQ ID NO: 17), a 482 bp sequence comprised within EXP-ANDge.Ubq1:1:12 (SEQ ID NO: 16). Asterisks indicate bases which are identical between the aligned sequences.

FIGS. 2*a*-2*g* depict alignment of promoter variants isolated from the grass *Saccharum ravennae* (*Erianthus ravennae*). In particular, FIGS. 2*a*-2*g* show an alignment of the 2536 bp promoter sequence P-ERIra.Ubq1-1:1:10 (SEQ ID NO: 19) (found, for instance, within the transcriptional regulatory expression element group EXP-ERIra.Ubq1 (SEQ ID NO: 18)) with promoter sequences derived from deletion analysis of P-ERIra.Ubq1-1:1:10: a 2014 bp promoter sequence P-ERIra.Ubq1-1:1:9 (SEQ ID NO: 23); a 1525 bp promoter sequence P-ERIra.Ubq1-1:1:11 (SEQ ID NO: 26); a 1044 bp promoter sequence P-ERIra.Ubq1-1:1:8 (SEQ ID NO: 28); a 796 bp sequence P-ERIra.Ubq1-1:1:12 (SEQ ID NO: 30); and a 511 bp sequence P-ERIra.Ubq1-1:1:13 (SEQ ID NO: 32). Asterisks indicate bases which are identical between the aligned sequences.

FIGS. 3*a*-3*c* depict alignment of promoter size variants corresponding to promoter elements isolated from the grass species *Setaria viridis*. In particular, FIGS. 3*a*-3*c* show an alignment of a 1493 bp promoter sequence, P-Sv.Ubq1-1:1:1 (SEQ ID NO: 34) with promoters derived from deletion analysis of the 5' end of P-Sv.Ubq1-1:1:1: a 1035 bp sized promoter P-Sv.Ubq1-1:1:2 (SEQ ID NO: 38); and a 681 bp promoter sequence P-Sv.Ubq1-1:1:3 (SEQ ID NO: 40). Asterisks indicate bases which are identical between the aligned sequences.

FIGS. 4*a*-4*e* depict alignment of transcriptional regulatory expression element group variants derived from the grass *Zea mays* subsp. *mexicana*. In particular, FIGS. 4*a*-4*e* compare a 2005 bp transcriptional regulatory expression element group termed EXP-Zm.UbgM1:1:2 (SEQ ID NO: 49) with allelic variant EXP-Zm.UbgM1:1:5 (SEQ ID NO: 53), as well as with size variants EXP-Zm.UbgM1:1:1 (SEQ ID NO: 41), which is 1922 bps in length, and EXP-Zm.UbgM1:1:4 (SEQ ID NO: 45), which is 1971 bps in length. Asterisks indicate bases which are identical between the aligned sequences.

FIGS. 5*a*-5*b* depict alignment of promoter size variants isolated from the grass *Sorghum bicolor*. In particular, FIGS. 5*a*-5*b* shows alignment of the 791 bp sized promoter element, P-Sb.Ubg6-1:1:2 (SEQ ID NO: 60) comprised within the transcriptional regulatory expression element group EXP-Sb.Ubg6 (SEQ ID NO: 59), with 855 bp promoter element P-Sb.Ubg6-1:1:1 (SEQ ID NO: 64) comprised within EXP-Sb.Ubg6:1:1 (SEQ ID NO: 63). Asterisks indicate bases which are identical between the aligned sequences.

FIGS. 6*a*-6*c* depict alignment of promoter size variants corresponding to promoter elements isolated from the grass *Setaria italica*. In particular, FIGS. 6*a*-6*c* show an alignment of the 1492 bp promoter variant P-SETit.Ubq1-1:1:1 (SEQ ID NO: 70) with 1492 bp promoter variant P-SETit.Ubq1-1:1:4 (SEQ ID NO: 74), 1034 bp promoter element P-SETit.Ubq1-1:1:2 (SEQ ID NO: 76), and 680 bp promoter element P-SETit.Ubq1-1:1:3 (SEQ ID NO: 78). Asterisks indicate bases which are identical between the aligned sequences.

FIGS. 7*a*-7*b* depict alignment of promoter size variants and an enhancer element corresponding to promoter elements isolated from the grass species *Coix lachryma-jobi*. In particular, FIGS. 7*a* and 7*b* show an alignment of the 837 bp promoter variant, P-Cl.Ubq1-1:1:1 (SEQ ID NO: 80) found within transcriptional regulatory expression element group EXP-Cl.Ubq1:1:1 (SEQ ID NO: 79), with an enhancer fragment derived from P-Cl.Ubq1-1:1:1, termed E-Cl.Ubq1:1:1 (SEQ ID NO: 89) that is 798 bp in length, as well as with three 5' end deletion variants of P-Cl.Ubq1-1:1:1: a 742 bp element P-Cl.Ubq1-1:1:4 (SEQ ID NO: 84); a 401 bp element P-Cl.Ubq1-1:1:3 (SEQ ID NO: 86); and a 54 bp minimal promoter element P-Cl.Ubq1-1:1:5 (SEQ ID NO: 88). Asterisks indicate bases which are identical between the aligned sequences.

BRIEF DESCRIPTION OF THE SEQUENCES

Figure 8:
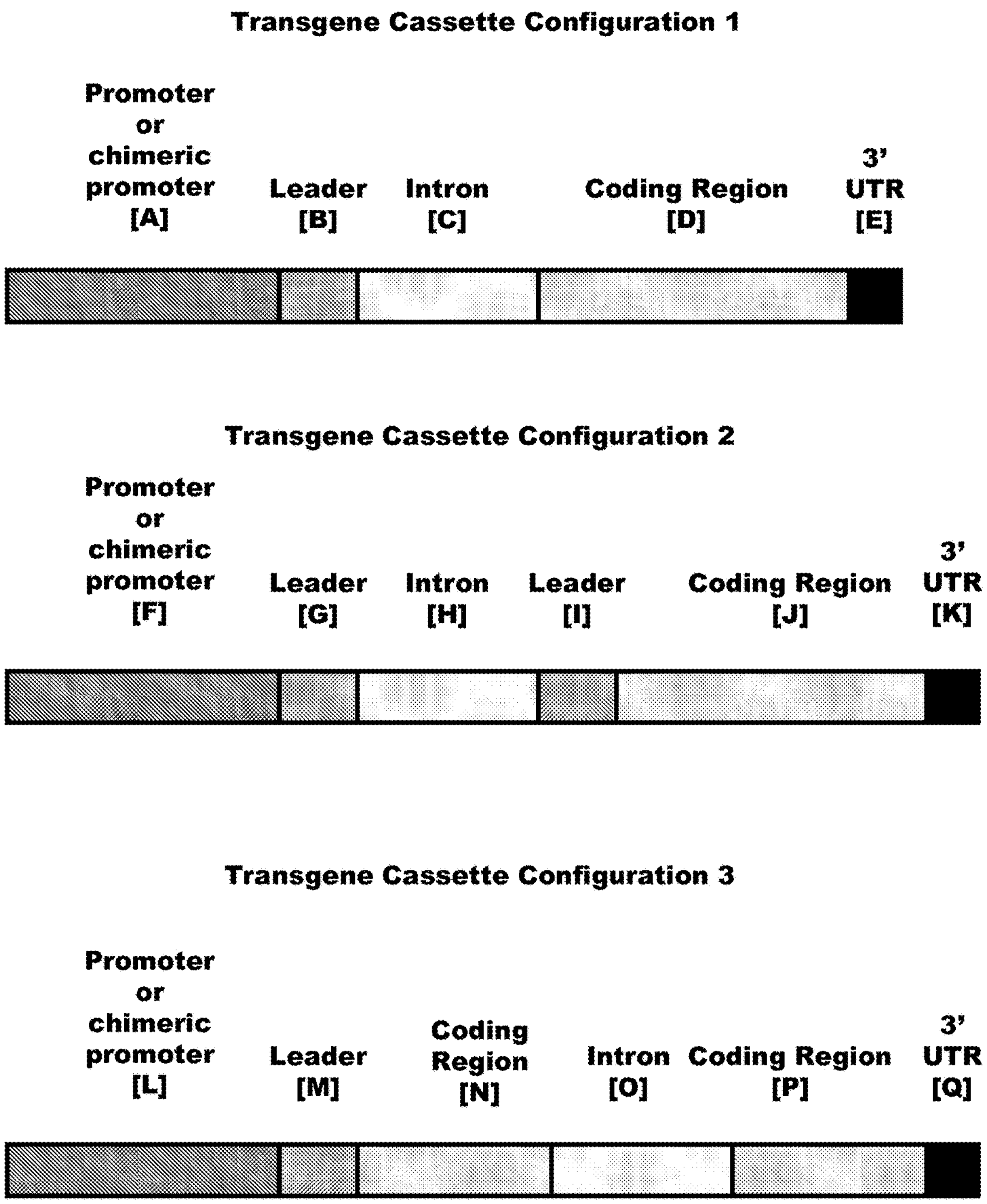
FIG. 8 depicts transgene cassette configurations of the present invention.

SEQ ID NOS: 1, 5, 8, 10, 12, 14, 16, 18, 22, 25, 27, 29, 31, 33, 37, 39, 41, 45, 49, 53, 55, 59, 63, 65, 69, 73, 75, 77, 79, 83, 85, 87, 90, 93, 95, 97, 98, 99, 100, 102, 104, 106, 108, 110, 112, 114, 115, 116, 117, 119, 121, 123, 124, 125, 126, 128, 130, 132, 133, 134, 136, 137, 139, 141, 143, 145, 147, 149, 151, 153, 155, 157, 180, 181 and 183 are sequences of transcriptional regulatory expression element groups or EXP sequences comprising a promoter sequence operably linked 5' to a leader sequence which is operably linked 5' to an intron sequence.

SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135 are promoter sequences.

SEQ ID NOS: 3, 20, 35, 43, 47, 51, 57, 61, 67, 71 and 81 are leader sequences.

SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182 are intron sequences.

SEQ ID NO: 89 is the sequence of an enhancer.

DETAILED DESCRIPTION OF THE INVENTION

The invention disclosed herein provides polynucleotide molecules having beneficial gene regulatory activity from plant species. The design, construction, and use of these polynucleotide molecules are provided by the invention. The nucleotide sequences of these polynucleotide molecules are provided among SEQ ID NOs: 1-158 and 180-183. These polynucleotide molecules are, for instance, capable of affecting the expression of an operably linked transcribable polynucleotide molecule in plant tissues, and therefore selectively regulating gene expression, or activity of an encoded gene product, in transgenic plants. The present invention also provides methods of modifying, producing, and using the same. The invention also provides compositions, transformed host cells, transgenic plants, and seeds containing the promoters and/or other disclosed nucleotide sequences, and methods for preparing and using the same.

The following definitions and methods are provided to better define the present invention and to guide those of ordinary skill in the art in the practice of the present invention. Unless otherwise noted, terms are to be understood according to conventional usage by those of ordinary skill in the relevant art.

DNA Molecules

As used herein, the term "DNA" or "DNA molecule" refers to a double-stranded DNA molecule of genomic or synthetic origin, i.e. a polymer of deoxyribonucleotide bases or a polynucleotide molecule, read from the 5' (upstream) end to the 3' (downstream) end. As used herein, the term "DNA sequence" refers to the nucleotide sequence of a DNA molecule. The nomenclature used herein corresponds to that of by Title 37 of the United States Code of Federal Regulations § 1.822, and set forth in the tables in WIPO Standard ST.25 (1998), Appendix 2, Tables 1 and 3.

As used herein, the term "isolated DNA molecule" refers to a DNA molecule at least partially separated from other molecules normally associated with it in its native or natural state. In one embodiment, the term "isolated" refers to a DNA molecule that is at least partially separated from some of the nucleic acids which normally flank the DNA molecule in its native or natural state. Thus, DNA molecules fused to regulatory or coding sequences with which they are not normally associated, for example as the result of recombinant techniques, are considered isolated herein. Such molecules are considered isolated when integrated into the chromosome of a host cell or present in a nucleic acid solution with other DNA molecules, in that they are not in their native state.

Any number of methods well known to those skilled in the art can be used to isolate and manipulate a DNA molecule, or fragment thereof, disclosed in the present invention. For example, PCR (polymerase chain reaction) technology can be used to amplify a particular starting DNA molecule and/or to produce variants of the original molecule. DNA molecules, or fragment thereof, can also be obtained by other techniques such as by directly synthesizing the fragment by chemical means, as is commonly practiced by using an automated oligonucleotide synthesizer.

As used herein, the term "sequence identity" refers to the extent to which two optimally aligned polynucleotide sequences or two optimally aligned polypeptide sequences are identical. An optimal sequence alignment is created by manually aligning two sequences, e.g. a reference sequence and another sequence, to maximize the number of nucleotide matches in the sequence alignment with appropriate internal nucleotide insertions, deletions, or gaps. As used herein, the term "reference sequence" refers to a sequence provided as the polynucleotide sequences of SEQ ID NOs: 1-158 and 180-183.

As used herein, the term "percent sequence identity" or "percent identity" or "% identity" is the identity fraction times 100. The "identity fraction" for a sequence optimally aligned with a reference sequence is the number of nucleotide matches in the optimal alignment, divided by the total number of nucleotides in the reference sequence, e.g. the total number of nucleotides in the full length of the entire reference sequence. Thus, one embodiment of the invention is a DNA molecule comprising a sequence that when optimally aligned to a reference sequence, provided herein as SEQ ID NOs: 1-158 and 180-183, has at least about 85 percent identity, at least about 90 percent identity, at least about 95 percent identity, at least about 96 percent identity, at least about 97 percent identity, at least about 98 percent identity, or at least about 99 percent identity to the reference sequence. In particular embodiments such sequences may be defined as having gene-regulatory activity.

Regulatory Elements

A regulatory element is a DNA molecule having gene regulatory activity, i.e. one that has the ability to affect the transcription and/or translation of an operably linked transcribable polynucleotide molecule. The term "gene regulatory activity" thus refers to the ability to affect the expression pattern of an operably linked transcribable polynucleotide molecule by affecting the transcription and/or translation of that operably linked transcribable polynucleotide molecule. As used herein, a transcriptional regulatory expression element group or "EXP" sequence may be comprised of expression elements, such as enhancers, promoters, leaders and introns, operably linked. Thus a transcriptional regulatory expression element group may be comprised, for instance, of a promoter operably linked 5' to a leader sequence, which is in turn operably linked 5' to an intron sequence. The intron sequence may be comprised of a sequence beginning at the point of the first intron/exon splice junction of the native sequence and further may be comprised of a small leader fragment comprising the second intron/exon splice junction so as to provide for proper intron/exon processing to facilitate transcription and proper processing of the resulting transcript. Leaders and introns may positively affect transcription of an operably linked transcribable polynucleotide molecule as well as translation of the resulting transcribed RNA. The pre-processed RNA molecule comprises leaders and introns, which may affect the post-transcriptional processing of the transcribed RNA and/or the export of the transcribed RNA molecule from the cell nucleus into the cytoplasm. Following post-transcriptional processing of the transcribed RNA molecule, the leader sequence may be retained as part of the final messenger RNA and may positively affect the translation of the messenger RNA molecule.

Regulatory elements such as promoters, leaders, introns, and transcription termination regions (or 3' UTRs) are DNA molecules that have gene regulatory activity and play an integral part in the overall expression of genes in living cells. The term "regulatory element" refers to a DNA molecule having gene regulatory activity, i.e. one that has the ability to affect the transcription and/or translation of an operably linked transcribable polynucleotide molecule. Isolated regulatory elements, such as promoters and leaders that function in plants are therefore useful for modifying plant phenotypes through the methods of genetic engineering.

Regulatory elements may be characterized by their expression pattern effects (qualitatively and/or quantitatively), e.g. positive or negative effects and/or constitutive or other effects such as by their temporal, spatial, developmental, tissue, environmental, physiological, pathological, cell cycle, and/or chemically responsive expression pattern, and any combination thereof, as well as by quantitative or qualitative indications. A promoter is useful as a regulatory element for modulating the expression of an operably linked transcribable polynucleotide molecule.

As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a dsRNA, a tRNA, an rRNA, a miRNA, and the like.

As used herein, the term "protein expression" is any pattern of translation of a transcribed RNA molecule into a protein molecule. Protein expression may be characterized by its temporal, spatial, developmental, or morphological qualities as well as by quantitative or qualitative indications.

As used herein, the term "promoter" refers generally to a DNA molecule that is involved in recognition and binding of RNA polymerase II and other proteins (trans-acting transcription factors) to initiate transcription. A promoter may be initially isolated from the 5' untranslated region (5' UTR) of a genomic copy of a gene. Alternately, promoters may be synthetically produced or manipulated DNA molecules. Promoters may also be chimeric, that is a promoter produced through the fusion of two or more heterologous DNA molecules. Promoters useful in practicing the present invention include SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135, or fragments or variants thereof. In specific embodiments of the invention, such molecules and any variants or derivatives thereof as described herein, are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" which provides a basal level of transcription and is comprised of a TATA box or equivalent sequence for recognition and binding of the RNA polymerase II complex for initiation of transcription.

In one embodiment, fragments are provided of a promoter sequence disclosed herein. Promoter fragments may comprise promoter activity, as described above, and may be useful alone or in combination with other promoters and promoter fragments, such as in constructing chimeric promoters. In specific embodiments, fragments of a promoter are provided comprising at least about 50, 95, 150, 250, 500, 750, or at least about 1000 contiguous nucleotides, or longer, of a polynucleotide molecule having promoter activity disclosed herein.

Compositions derived from any of the promoters presented as SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135, such as internal or 5' deletions, for example, can be produced using methods known in the art to improve or alter expression, including by removing elements that have either positive or negative effects on expression; duplicating elements that have positive or negative effects on expression; and/or duplicating or removing elements that have tissue or cell specific effects on expression. Compositions derived from any of the promoters presented as SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135 comprised of 3' deletions in which the TATA box element or equivalent sequence thereof and downstream sequence is removed can be used, for example, to make enhancer elements. Further deletions can be made to remove any elements that have positive or negative; tissue specific; cell specific; or timing specific (such as, but not limited to, circadian rhythms) effects on expression. Any of the promoters presented as SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135 and fragments or enhancers derived there from can be used to make chimeric transcriptional regulatory element compositions comprised of any of the promoters presented as SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135 and the fragments or enhancers derived therefrom operably linked to other enhancers and promoters. The efficacy of the modifications, duplications or deletions described herein on the desired expression aspects of a particular transgene may be tested empirically in stable and transient plant assays, such as those described in the working examples herein, so as to validate the results, which may vary depending upon the changes made and the goal of the change in the starting molecule.

As used herein, the term "leader" refers to a DNA molecule isolated from the untranslated 5' region (5' UTR) of a genomic copy of a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable polynucleotide molecule. Leader molecules may be used with a heterologous promoter or with their native promoter. Promoter molecules of the present invention may thus be operably linked to their native leader or may be operably linked to a heterologous leader. Leaders useful in practicing the present invention include SEQ ID NOS: 3, 20, 35, 43, 47, 51, 57, 61, 67, 71 and 81 or fragments or variants thereof. In specific embodiments, such sequences may be provided defined as being capable of acting as a leader in a host cell, including, for example, a transgenic plant cell. In one embodiment such sequences are decoded as comprising leader activity.

The leader sequences (5' UTR) presented as SEQ ID NOS: 3, 20, 35, 43, 47, 51, 57, 61, 67, 71 and 81 may be comprised of regulatory elements or may adopt secondary structures that can have an effect on transcription or translation of a transgene. The leader sequences presented as SEQ ID NOS: 3, 20, 35, 43, 47, 51, 57, 61, 67, 71 and 81 can be used in accordance with the invention to make chimeric regulatory elements that affect transcription or translation of a transgene. In addition, the leader sequences presented as SEQ ID NOS: 3, 20, 35, 43, 47, 51, 57, 61, 67, 71 and 81 can be used to make chimeric leader sequences that affect transcription or translation of a transgene.

The introduction of a foreign gene into a new plant host does not always result in a high expression of the incoming gene. Furthermore, if dealing with complex traits, it is sometimes necessary to modulate several genes with spatially or temporarily different expression pattern. Introns can principally provide such modulation. However multiple use of the same intron in one plant has shown to exhibit disadvantages. In those cases it is necessary to have a collection of basic control elements for the construction of appropriate recombinant DNA elements. As the available collection of introns known in the art with expression enhancing properties is limited, alternatives are needed.

Compositions derived from any of the introns presented as SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182 can be comprised of internal deletions or duplications of cis regulatory elements; and/or alterations of the 5' and 3' sequences comprising the intron/exon splice junctions can be used to improve expression or specificity of expression when operably linked to a promoter+leader or chimeric promoter+leader and coding sequence. Alterations of the 5' and 3' regions comprising the intron/exon splice junction can also be made to reduce the potential for introduction of false start and stop codons being produced in the resulting transcript after processing and splicing of the messenger RNA. The introns can be tested empirically as described in the working examples to determine the intron's effect on expression of a transgene.

In accordance with the invention a promoter or promoter fragment may be analyzed for the presence of known promoter elements, i.e. DNA sequence characteristics, such as a TATA-box and other known transcription factor binding site motifs. Identification of such known promoter elements may be used by one of skill in the art to design variants of the promoter having a similar expression pattern to the original promoter.

As used herein, the term "enhancer" or "enhancer element" refers to a cis-acting transcriptional regulatory element, a.k.a. cis-element, which confers an aspect of the overall expression pattern, but is usually insufficient alone to drive transcription, of an operably linked polynucleotide sequence. Unlike promoters, enhancer elements do not usually include a transcription start site (TSS) or TATA box or equivalent sequence. A promoter may naturally comprise one or more enhancer elements that affect the transcription of an operably linked polynucleotide sequence. An isolated enhancer element may also be fused to a promoter to produce a chimeric promoter cis-element, which confers an aspect of the overall modulation of gene expression. A promoter or promoter fragment may comprise one or more enhancer elements that effect the transcription of operably linked genes. Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e. deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis using known cis-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable polynucleotide molecules are encompassed by the present invention.

In plants, the inclusion of some introns in gene constructs leads to increased mRNA and protein accumulation relative to constructs lacking the intron.

This effect has been termed "intron mediated enhancement" (IME) of gene expression (Mascarenhas et al., (1990) *Plant Mol. Biol.* 15:913-920). Introns known to stimulate expression in plants have been identified in maize genes (e.g. tubA1, Adh1, Sh1, Ubi1 (Jeon et al. (2000) *Plant Physiol.* 123:1005-1014; Callis et al. (1987) *Genes Dev.* 1:1183-1200; Vasil et al. (1989) *Plant Physiol.* 91:1575-1579; Christiansen et al. (1992) *Plant Mol. Biol.* 18:675-689) and in rice genes (e.g. salt, tpi: McElroy et al., *Plant Cell* 2:163-171 (1990); Xu et al., *Plant Physiol.* 106:459-467 (1994)). Similarly, introns from dicotyledonous plant genes like those from *petunia* (e.g. rbcS), potato (e.g. st-ls1) and from *Arabidopsis thaliana* (e.g. ubq3 and pat1) have been found to elevate gene expression rates (Dean et al. (1989) *Plant Cell* 1:201-208; Leon et al. (1991) *Plant Physiol.* 95:968-972; Norris et al. (1993) *Plant Mol Biol* 21:895-906; Rose and Last (1997) *Plant J.* 11:455-464). It has been shown that deletions or mutations within the splice sites of an intron reduce gene expression, indicating that splicing might be needed for IME (Mascarenhas et al. (1990) *Plant Mol Biol.* 15:913-920; Clancy and Hannah (2002) *Plant Physiol.* 130:918-929). However, that splicing per se is not required for a certain IME in dicotyledonous plants has been shown by point mutations within the splice sites of the pat1 gene from *A. thaliana* (Rose and Beliakoff (2000) *Plant Physiol.* 122:535-542).

Enhancement of gene expression by introns is not a general phenomenon because some intron insertions into recombinant expression cassettes fail to enhance expression (e.g. introns from dicot genes (rbcS gene from pea, phaseolin gene from bean and the stls-1 gene from *Solanum tuberosum*) and introns from maize genes (adh1 gene the ninth intron, hsp81 gene the first intron)) (Chee et al. (1986) *Gene* 41:47-57; Kuhlemeier et al. (1988) *Mol Gen Genet* 212:405-411; Mascarenhas et al. (1990) *Plant Mol. Biol.* 15:913-920; Sinibaldi and Mettler (1992) In WE Cohn, K Moldave, eds, *Progress in Nucleic Acid Research and Molecular Biology*, Vol 42. Academic Press, New York, pp 229-257; Vancanneyt et al. 1990 *Mol. Gen. Genet.* 220:245-250). Therefore, not each intron can be employed in order to manipulate the gene expression level of non-endogenous genes or endogenous genes in transgenic plants. What characteristics or specific sequence features must be present in an intron sequence in order to enhance the expression rate of a given gene is not known in the prior art and therefore from the prior art it is not possible to predict whether a given plant intron, when used heterologously, will cause enhancement of expression at the DNA level or at the transcript level (IME).

As used herein, the term "chimeric" refers to a single DNA molecule produced by fusing a first DNA molecule to a second DNA molecule, where neither first nor second DNA molecule would normally be found in that configuration, i.e. fused to the other. The chimeric DNA molecule is thus a new DNA molecule not otherwise normally found in nature. As used herein, the term "chimeric promoter" refers to a promoter produced through such manipulation of DNA molecules. A chimeric promoter may combine two or more DNA fragments; an example would be the fusion of a promoter to an enhancer element. Thus, the design, construction, and use of chimeric promoters according to the methods disclosed herein for modulating the expression of operably linked transcribable polynucleotide molecules are encompassed by the present invention.

As used herein, the term "variant" refers to a second DNA molecule that is in composition similar, but not identical to, a first DNA molecule and yet the second DNA molecule still maintains the general functionality, i.e. same or similar expression pattern, of the first DNA molecule. A variant may be a shorter or truncated version of the first DNA molecule and/or an altered version of the sequence of the first DNA molecule, such as one with different restriction enzyme sites and/or internal deletions, substitutions, and/or insertions. A "variant" can also encompass a regulatory element having a nucleotide sequence comprising a substitution, deletion and/or insertion of one or more nucleotides of a reference sequence, wherein the derivative regulatory element has more or less or equivalent transcriptional or translational activity than the corresponding parent regulatory molecule. The regulatory element "variants" will also encompass variants arising from mutations that naturally occur in bacterial and plant cell transformation. In the present invention, a polynucleotide sequence provided as SEQ ID NOs: 1-158 and 180-183 may be used to create variants that are in composition similar, but not identical to, the polynucleotide sequence of the original regulatory element, while still maintaining the general functionality, i.e. same or similar expression pattern, of the original regulatory element. Production of such variants of the present invention is well within the ordinary skill of the art in light of the disclosure and is encompassed within the scope of the present invention. Chimeric regulatory element "variants" comprise the same constituent elements as a reference sequence but the constituent elements comprising the chimeric regulatory element may be operatively linked by various methods known in the art such as, restriction enzyme digestion and ligation, ligation independent cloning, modular assembly of PCR products during amplification, or direct chemical synthesis of the regulatory element as well as other methods known in the art. The resulting chimeric regulatory element "variant" can be comprised of the same, or variants of the same, constituent elements of the reference sequence but differ in the sequence or sequences that comprise the linking sequence or sequences which allow the constituent parts to be operatively linked. In the present invention, a polynucleotide sequence provided as SEQ ID NOs: 1-158 and 180-183 provide a reference sequence wherein the constituent elements that comprise the reference sequence may be joined by methods known in the art and may comprise substitutions, deletions and/or insertions of one or more nucleotides or mutations that naturally occur in bacterial and plant cell transformation.

Constructs

As used herein, the term "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. As used herein, the term "vector" means any recombinant polynucleotide construct that may be used for the purpose of transformation, i.e. the introduction of heterologous DNA into a host cell. The term includes an expression cassette isolated from any of the aforementioned molecules.

As used herein, the term "operably linked" refers to a first molecule joined to a second molecule, wherein the molecules are so arranged that the first molecule affects the function of the second molecule. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell. A leader, for example, is operably linked to coding sequence when it is capable of serving as a leader for the polypeptide encoded by the coding sequence.

The constructs of the present invention may be provided, in one embodiment, as double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *A. tumefaciens* cells, permit the integration of the T-DNA into the genome of a plant cell (see, for example, U.S. Pat. No. 6,603,061). The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *A. tumefaciens* ABI, C58, or LBA4404; however, other strains known to those skilled in the art of plant transformation can function in the present invention.

Methods are known in the art for assembling and introducing constructs into a cell in such a manner that the transcribable polynucleotide molecule is transcribed into a functional mRNA molecule that is translated and expressed as a protein product. For the practice of the present invention, conventional compositions and methods for preparing and using constructs and host cells are well known to one skilled in the art, see, for example, *Molecular Cloning: A Laboratory Manual, 3rd edition Volumes* 1, 2, *and* 3 (2000) J. Sambrook, D. W. Russell, and N. Irwin, Cold Spring Harbor Laboratory Press. Methods for making recombinant vectors particularly suited to plant transformation include, without limitation, those described in U.S. Pat. Nos. 4,971,908; 4,940,835; 4,769,061; and 4,757,011 in their entirety. These types of vectors have also been reviewed in the scientific literature (see, for example, Rodriguez, et al., *Vectors: A Survey of Molecular Cloning Vectors and Their Uses*, Butterworths, Boston, (1988) and Glick, et al., *Methods in Plant Molecular Biology and Biotechnology*, CRC Press, Boca Raton, FL. (1993)). Typical vectors useful for expression of nucleic acids in higher plants are well known in the art and include vectors derived from the tumor-inducing (Ti) plasmid of *Agrobacterium tumefaciens* (Rogers, et al., *Methods in Enzymology* 153: 253-277 (1987)). Other recombinant vectors useful for plant transformation, including the pCaMVCN transfer control vector, have also been described in the scientific literature (see, for example, Fromm, et al., *Proc. Natl. Acad. Sci. USA* 82: 5824-5828 (1985)).

Various regulatory elements may be included in a construct including any of those provided herein. Any such regulatory elements may be provided in combination with other regulatory elements. Such combinations can be designed or modified to produce desirable regulatory features. In one embodiment, constructs of the present invention comprise at least one regulatory element operably linked to a transcribable polynucleotide molecule operably linked to a 3'UTR.

Constructs of the present invention may include any promoter or leader provided herein or known in the art. For example, a promoter of the present invention may be operably linked to a heterologous non-translated 5' leader such as one derived from a heat shock protein gene (see, for example, U.S. Pat. Nos. 5,659,122 and 5,362,865). Alternatively, a leader of the present invention may be operably linked to a heterologous promoter such as the Cauliflower Mosaic Virus 35S transcript promoter (see, U.S. Pat. No. 5,352,605).

As used herein, the term "intron" refers to a DNA molecule that may be isolated or identified from the genomic copy of a gene and may be defined generally as a region spliced out during mRNA processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable polynucleotide molecule. A DNA construct may comprise an intron, and the intron may or may not be heterologous with respect to the transcribable polynucleotide molecule sequence. Examples of introns in the art include the rice actin intron (U.S. Pat. No. 5,641,876) and the corn HSP70 intron (U.S. Pat. No. 5,859,347). Introns useful in practicing the present invention include SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182. Further, when modifying intron/exon boundary sequences, it may be preferable to avoid using the nucleotide sequence AT or the nucleotide A just prior to the 5' end of the splice site (GT) and the nucleotide G or the nucleotide sequence TG, respectively just after 3' end of the splice site (AG) to eliminate the potential of unwanted start codons from being formed during processing of the messenger RNA into the final transcript. The sequence around the 5' or 3' end splice junction sites of the intron can thus be modified in this manner.

As used herein, the term "3' transcription termination molecule" or "3' UTR" refers to a DNA molecule that is used during transcription to produce the 3' untranslated region (3' UTR) of an mRNA molecule. The 3' untranslated region of an mRNA molecule may be generated by specific cleavage and 3' polyadenylation, a.k.a. polyA tail. A 3' UTR may be operably linked to and located downstream of a transcribable polynucleotide molecule and may include polynucleotides that provide a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region (see, Fraley, et al., *Proc. Natl. Acad. Sci. USA,* 80: 4803-4807 (1983)); wheat hsp17 3' region; pea rubisco small subunit 3' region; cotton E6 3' region (U.S. Pat. No. 6,096,950); 3' regions disclosed in WO0011200A2; and the coixin 3' UTR (U.S. Pat. No. 6,635,806).

3' UTRs typically find beneficial use for the recombinant expression of specific genes. In animal systems, a machinery of 3' UTRs has been well defined (e.g. Zhao et al., *Microbiol Mol Biol Rev* 63:405-445 (1999); Proudfoot, *Nature* 322: 562-565 (1986); Kim et al., *Biotechnology Progress* 19:1620-1622 (2003); Yonaha and Proudfoot, *EMBO J.* 19:3770-3777 (2000); Cramer et al., *FEBS Letters* 498:179-182 (2001); Kuerstem and Goodwin, *Nature Reviews Genetics* 4:626-637 (2003)). Effective termination of RNA transcription is required to prevent unwanted transcription of trait-unrelated (downstream) sequences, which may interfere with trait performance. Arrangement of multiple gene expression cassettes in local proximity to one another (e.g. within one T-DNA) may cause suppression of gene expression of one or more genes in said construct in comparison to independent insertions (Padidam and Cao, BioTechniques 31:328-334 (2001). This may interfere with achieving adequate levels of expression, for instance in cases were strong gene expression from all cassettes is desired.

In plants, clearly defined polyadenylation signal sequences are not known. Hasegawa et al., *Plant J.* 33:1063-1072, (2003)) were not able to identify conserved polyadenylation signal sequences in both in vitro and in vivo systems in *Nicotiana sylvestris* and to determine the actual length of the primary (non-polyadenylated) transcript. A weak 3' UTR has the potential to generate read-through, which may affect the expression of the genes located in the neighboring expression cassettes (Padidam and Cao, *BioTechniques* 31:328-334 (2001)). Appropriate control of transcription termination can prevent read-through into sequences (e.g. other expression cassettes) localized downstream and can further allow efficient recycling of RNA polymerase, to improve gene expression. Efficient termination of transcription (release of RNA Polymerase II from the DNA) is pre-requisite for re-initiation of transcription and thereby directly affects the overall transcript level. Subsequent to transcription termination, the mature mRNA is released from the site of synthesis and template to the cytoplasm. Eukaryotic mRNAs are accumulated as poly(A) forms in vivo, so that it is difficult to detect transcriptional termination sites by conventional methods. However, prediction of functional and efficient 3' UTRs by bioinformatics methods is difficult in that there are no conserved sequences which would allow easy prediction of an effective 3' UTR.

From a practical standpoint, it is typically beneficial that a 3' UTR used in a transgene cassette possesses the following characteristics. The 3' UTR should be able to efficiently and effectively terminate transcription of the transgene and prevent read-through of the transcript into any neighboring DNA sequence which can be comprised of another transgene cassette as in the case of multiple cassettes residing in one T-DNA, or the neighboring chromosomal DNA into which the T-DNA has inserted. The 3' UTR should not cause a reduction in the transcriptional activity imparted by the promoter, leader and introns that are used to drive expression of the transgene. In plant biotechnology, the 3' UTR is often used for priming of amplification reactions of reverse transcribed RNA extracted from the transformed plant and used to (1) assess the transcriptional activity or expression of the transgene cassette once integrated into the plant chromosome; (2) assess the copy number of insertions within the plant DNA; and (3) assess zygosity of the resulting seed after breeding. The 3' UTR is also used in amplification reactions of DNA extracted from the transformed plant to characterize the intactness of the inserted cassette.

3' UTRs useful in providing expression of a transgene in plants may be identified based upon the expression of expressed sequence tags (ESTs) in cDNA libraries made from messenger RNA isolated from seed, flower and other tissues derived from Big bluestem (*Andropogon gerardii*), Plume grass (*Saccharum ravennae* (*Erianthus ravennae*)), Green bristlegrass (*Setaria viridis*), Teosinte (*Zea mays* subsp. *mexicana*), Foxtail millet (*Setaria italica*), or *Coix* (*Coix lacryma-jobi*). Libraries of cDNA are made from tissues isolated from selected plant species using methods known to those skilled in the art from flower tissue, seed, leaf and root. The resulting cDNAs are sequenced using various sequencing methods known in the art. The resulting ESTs are assembled into clusters using bioinformatics software such as clc_ref_assemble_complete version 2.01.37139 (CLC bio USA, Cambridge, Massachusetts 02142). Transcript abundance of each cluster is determined by counting the number of cDNA reads for each cluster. The identified 3' UTRs may be comprised of sequence derived from cDNA sequence as well as sequence derived from genomic DNA. The cDNA sequence is used to design primers, which are then used with GenomeWalker™ (Clontech Laboratories, Inc, Mountain View, CA) libraries constructed following the manufacturer's protocol to clone the 3' region of the corresponding genomic DNA sequence to provide a longer termination sequence. Analysis of relative transcript abundance either by direct counts or normalized counts of observed sequence reads for each tissue library can be used to infer properties about patters of expression. For example, some 3' UTRs may be found in transcripts seen in higher abundance in root tissue as opposed to leaf. This is suggestive that the transcript is highly expressed in root and that the properties of root expression may be attributable to the transcriptional regulation of the promoter, the lead, the introns or the 3' UTR. Empirical testing of 3' UTRs identified by the properties of expression within specific organs, tissues or cell types can result in the identification of 3' UTRs that enhance expression in those specific organs, tissues or cell types.

Constructs and vectors may also include a transit peptide coding sequence that expresses a linked peptide that is useful for targeting of a protein product, particularly to a chloroplast, leucoplast, or other plastid organelle; mitochondria; peroxisome; vacuole; or an extracellular location. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (See, Klee et al., *Mol. Gen. Genet.* 210:437-442 (1987)) or the *Petunia hybrida* EPSPS CTP (CTP4) (See, della-Cioppa et al., *Proc. Natl. Acad. Sci. USA* 83:6873-6877 (1986)) has been show to target heterologous EPSPS protein sequences to chloroplasts in transgenic plants (See, U.S. Pat. Nos. 5,627,061; 5,633,435; and 5,312,910 and EP 0218571; EP 189707; EP 508909; and EP 924299).

Transcribable Polynucleotide Molecules

As used herein, the term "transcribable polynucleotide molecule" refers to any DNA molecule capable of being transcribed into a RNA molecule, including, but not limited to, those having protein coding sequences and those producing RNA molecules having sequences useful for gene suppression. A "transgene" refers to a transcribable polynucleotide molecule heterologous to a host cell at least with respect to its location in the genome and/or a transcribable polynucleotide molecule artificially incorporated into a host cell's genome in the current or any prior generation of the cell.

A promoter of the present invention may be operably linked to a transcribable polynucleotide molecule that is heterologous with respect to the promoter molecule. As used herein, the term "heterologous" refers to the combination of two or more polynucleotide molecules when such a combination is not normally found in nature. For example, the two molecules may be derived from different species and/or the two molecules may be derived from different genes, e.g. different genes from the same species or the same genes from different species. A promoter is thus heterologous with respect to an operably linked transcribable polynucleotide molecule if such a combination is not normally found in nature, i.e. that transcribable polynucleotide molecule is not naturally occurring operably linked in combination with that promoter molecule.

The transcribable polynucleotide molecule may generally be any DNA molecule for which expression of a RNA transcript is desired. Such expression of an RNA transcript may result in translation of the resulting mRNA molecule and thus protein expression. Alternatively, for example, a transcribable polynucleotide molecule may be designed to ultimately cause decreased expression of a specific gene or protein. In one embodiment, this may be accomplished by using a transcribable polynucleotide molecule that is oriented in the antisense direction. One of ordinary skill in the art is familiar with using such antisense technology. Briefly, as the antisense transcribable polynucleotide molecule is transcribed, the RNA product hybridizes to and sequesters a complimentary RNA molecule inside the cell. This duplex RNA molecule cannot be translated into a protein by the cell's translational machinery and is degraded in the cell. Any gene may be negatively regulated in this manner.

Thus, one embodiment of the invention is a regulatory element of the present invention, such as those provided as SEQ ID NOs: 1-158 and 180-183, operably linked to a transcribable polynucleotide molecule so as to modulate transcription of the transcribable polynucleotide molecule at a desired level or in a desired pattern when the construct is integrated in the genome of a plant cell. In one embodiment, the transcribable polynucleotide molecule comprises a protein-coding region of a gene, and the promoter affects the transcription of an RNA molecule that is translated and expressed as a protein product. In another embodiment, the transcribable polynucleotide molecule comprises an antisense region of a gene, and the promoter affects the transcription of an antisense RNA molecule, double stranded RNA or other similar inhibitory RNA molecule in order to inhibit expression of a specific RNA molecule of interest in a target host cell.

Genes of Agronomic Interest

Transcribable polynucleotide molecules may be genes of agronomic interest. As used herein, the term "gene of agronomic interest" refers to a transcribable polynucleotide molecule that when expressed in a particular plant tissue, cell, or cell type confers a desirable characteristic, such as associated with plant morphology, physiology, growth, development, yield, product, nutritional profile, disease or pest resistance, and/or environmental or chemical tolerance. Genes of agronomic interest include, but are not limited to, those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, a pesticidal protein, or any other agent such as an antisense or RNAi molecule targeting a particular gene for suppression. The product of a gene of agronomic interest may act within the plant in order to cause an effect upon the plant physiology or metabolism or may be act as a pesticidal agent in the diet of a pest that feeds on the plant.

In one embodiment of the invention, a promoter of the present invention is incorporated into a construct such that the promoter is operably linked to a transcribable polynucleotide molecule that is a gene of agronomic interest. The expression of the gene of agronomic interest is desirable in order to confer an agronomically beneficial trait. A beneficial agronomic trait may be, for example, but is not limited to, herbicide tolerance, insect control, modified yield, fungal disease resistance, virus resistance, nematode resistance, bacterial disease resistance, plant growth and development, starch production, modified oils production, high oil production, modified fatty acid content, high protein production, fruit ripening, enhanced animal and human nutrition, biopolymers, environmental stress resistance, pharmaceutical peptides and secretable peptides, improved processing traits, improved digestibility, enzyme production, flavor, nitrogen fixation, hybrid seed production, fiber production, and biofuel production. Examples of genes of agronomic interest known in the art include those for herbicide resistance (U.S. Pat. Nos. 6,803,501; 6,448,476; 6,248,876; 6,225,114; 6,107,549; 5,866,775; 5,804,425; 5,633,435; and 5,463,175), increased yield (U.S. Pat. Nos. RE38,446; 6,716,474; 6,663,906; 6,476,295; 6,441,277; 6,423,828; 6,399,330; 6,372,211; 6,235,971; 6,222,098; and 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; and 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; and 6,506,962), virus resistance (U.S. Pat. Nos. 6,617,496; 6,608,241; 6,015,940; 6,013,864; 5,850,023; and 5,304,730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; 6,476,295), modified oils production (U.S. Pat. Nos. 6,444,876; 6,426,447; and 6,380,462), high oil production (U.S. Pat. Nos. 6,495,739; 5,608,149; 6,483,008; and 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; and 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; and 6,171,640), biopolymers (U.S. Pat. Nos. RE37,543; 6,228,623; and U.S. Pat. Nos. 5,958,745, and 6,946,588), environmental stress resistance (U.S. Pat. No. 6,072,103), pharmaceutical peptides and secretable peptides (U.S. Pat. Nos. 6,812,379; 6,774,283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998,700).

Alternatively, a gene of agronomic interest can affect the above mentioned plant characteristic or phenotype by encoding a RNA molecule that causes the targeted modulation of gene expression of an endogenous gene, for example via antisense (see e.g. U.S. Pat. No. 5,107,065); inhibitory RNA ("RNAi", including modulation of gene expression via miRNA-, siRNA-, trans-acting siRNA-, and phased sRNA-mediated mechanisms, e.g. as described in published applications US 2006/0200878 and US 2008/0066206, and in U.S. patent application Ser. No. 11/974,469); or cosuppression-mediated mechanisms. The RNA could also be a catalytic RNA molecule (e.g. a ribozyme or a riboswitch; see e.g. US 2006/0200878) engineered to cleave a desired endogenous mRNA product. Thus, any transcribable polynucleotide molecule that encodes a transcribed RNA molecule that affects an agronomically important phenotype or morphology change of interest may be useful for the practice of the present invention. Methods are known in the art for constructing and introducing constructs into a cell in such a manner that the transcribable polynucleotide molecule is transcribed into a molecule that is capable of causing gene suppression. For example, posttranscriptional gene suppression using a construct with an anti-sense oriented transcribable polynucleotide molecule to regulate gene expression in plant cells is disclosed in U.S. Pat. Nos. 5,107,065 and 5,759,829, and posttranscriptional gene suppression using a construct with a sense-oriented transcribable polynucleotide molecule to regulate gene expression in plants is disclosed in U.S. Pat. Nos. 5,283,184 and 5,231,020. Expression of a transcribable polynucleotide in a plant cell can also be used to suppress plant pests feeding on the plant cell, for example, compositions isolated from coleopteran pests (U.S. Patent Publication No. US20070124836) and compositions isolated from nematode pests (U.S. Patent Publication No. US20070250947). Plant pests include, but are not limited to arthropod pests, nematode pests, and fungal or microbial pests. Exemplary transcribable polynucleotide molecules for incorporation into constructs of the present invention include, for example, DNA molecules or genes from a species other than the target species or genes that originate with or are present in the same species, but are incorporated into recipient cells by genetic engineering methods rather than classical reproduction or breeding techniques. The type of polynucleotide molecule can include, but is not limited to, a polynucleotide molecule that is already present in the plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

Selectable Markers

As used herein the term "marker" refers to any transcribable polynucleotide molecule whose expression, or lack thereof, can be screened for or scored in some way. Marker genes for use in the practice of the present invention include, but are not limited to transcribable polynucleotide molecules encoding β-glucuronidase (GUS described in U.S. Pat. No. 5,599,670), green fluorescent protein and variants thereof (GFP described in U.S. Pat. Nos. 5,491,084 and 6,146,826), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep) and gentamycin (aac3 and aacC4) are known in the art. Herbicides for which transgenic plant tolerance has been demonstrated and the method of the present invention can be applied, include, but are not limited to: amino-methyl-phosphonic acid, glyphosate, glufosinate, sulfonylureas, imidazolinones, bromoxynil, dalapon, dicamba, cyclohexanedione, protoporphyrinogen oxidase inhibitors, and isoxasflutole herbicides. Transcribable polynucleotide molecules encoding proteins involved in herbicide tolerance are known in the art, and include, but are not limited to, a transcribable polynucleotide molecule encoding 5-enolpyruvylshikimate-3-phosphate synthase (EPSPS for glyphosate tolerance described in U.S. Pat. Nos. 5,627,061; 5,633,435; 6,040,497; and 5,094,945); a transcribable polynucleotide molecule encoding a glyphosate oxidoreductase and a glyphosate-N-acetyl transferase (GOX described in U.S. Pat. No. 5,463,175; GAT described in U.S. Patent publication No. 20030083480, and dicamba monooxygenase U.S. Patent publication No. 20030135879); a transcribable polynucleotide molecule encoding bromoxynil nitrilase (Bxn for Bromoxynil tolerance described in U.S. Pat. No. 4,810,648); a transcribable polynucleotide molecule encoding phytoene desaturase (crtl) described in Misawa, et al., *Plant Journal* 4:833-840 (1993) and Misawa, et al., *Plant Journal* 6:481-489 (1994) for norflurazon tolerance; a transcribable polynucleotide molecule encoding acetohydroxyacid synthase (AHAS, aka ALS) described in Sathasiivan, et al., *Nucl. Acids Res.* 18:2188-2193 (1990) for tolerance to sulfonylurea herbicides; and the bar gene described in DeBlock, et al., *EMBO Journal* 6:2513-2519 (1987) for glufosinate and bialaphos tolerance. The promoter molecules of the present invention can express linked transcribable polynucleotide molecules that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, aryloxyalkanoate dioxygenases, acetyl CoA carboxylase, glyphosate oxidoreductase, and glyphosate-N-acetyl transferase.

Included within the term "selectable markers" are also genes which encode a secretable marker whose secretion can be detected as a means of identifying or selecting for transformed cells. Examples include markers that encode a secretable antigen that can be identified by antibody interaction, or even secretable enzymes which can be detected catalytically. Selectable secreted marker proteins fall into a number of classes, including small, diffusible proteins which are detectable, (e.g. by ELISA), small active enzymes which are detectable in extracellular solution (e.g, alpha-amylase, beta-lactamase, phosphinothricin transferase), or proteins which are inserted or trapped in the cell wall (such as proteins which include a leader sequence such as that found in the expression unit of extension or tobacco pathogenesis related proteins also known as tobacco PR-S). Other possible selectable marker genes will be apparent to those of skill in the art and are encompassed by the present invention.

Cell Transformation

The invention is also directed to a method of producing transformed cells and plants which comprise a promoter operably linked to a transcribable polynucleotide molecule.

The term "transformation" refers to the introduction of nucleic acid into a recipient host. As used herein, the term "host" refers to bacteria, fungi, or plant, including any cells, tissue, organs, or progeny of the bacteria, fungi, or plant. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign polynucleotide molecule, such as a construct, has been introduced. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic organism as a parent in a cross and exhibiting an altered phenotype resulting from the presence of a foreign polynucleotide molecule. The term "transgenic" refers to a bacteria, fungi, or plant containing one or more heterologous polynucleic acid molecules.

There are many methods for introducing polynucleic acid molecules into plant cells. The method generally comprises the steps of selecting a suitable host cell, transforming the host cell with a recombinant vector, and obtaining the transformed host cell. Suitable methods include bacterial infection (e.g. *Agrobacterium*), binary bacterial artificial chromosome vectors, direct delivery of DNA (e.g. via PEG-mediated transformation, desiccation/inhibition-mediated DNA uptake, electroporation, agitation with silicon carbide fibers, and acceleration of DNA coated particles, etc. (reviewed in Potrykus, et al., *Ann. Rev. Plant Physiol. Plant Mol. Biol.* 42: 205 (1991)).

Technology for introduction of a DNA molecule into cells is well known to those of skill in the art. Methods and materials for transforming plant cells by introducing a plant DNA construct into a plant genome in the practice of this invention can include any of the well-known and demonstrated methods. Any transformation methods may be utilized to transform a host cell with one or more promoters and/or constructs of the present. Host cells may be any cell or organism such as a plant cell, algae cell, algae, fungal cell, fungi, bacterial cell, or insect cell. Preferred hosts and transformed cells include cells from: plants, *Aspergillus*, yeasts, insects, bacteria and algae.

Regenerated transgenic plants can be self-pollinated to provide homozygous transgenic plants. Alternatively, pollen obtained from the regenerated transgenic plants may be crossed with non-transgenic plants, preferably inbred lines of agronomically important species. Descriptions of breeding methods that are commonly used for different traits and crops can be found in one of several reference books, see, for example, Allard, *Principles of Plant Breeding*, John Wiley & Sons, NY, U. of CA, Davis, CA, 50-98 (1960); Simmonds, *Principles of crop improvement*, Longman, Inc., NY, 369-399 (1979); Sneep and Hendriksen, Plant breeding perspectives, Wageningen (ed), Center for Agricultural Publishing and Documentation (1979); Fehr, *Soybeans: Improvement, Production and Uses,* 2nd Edition, Monograph, 16:249 (1987); Fehr, *Principles of variety development, Theory and Technique*, (Vol. 1) and *Crop Species Soybean* (Vol 2), Iowa State Univ., Macmillan Pub. Co., NY, 360-376 (1987). Conversely, pollen from non-transgenic plants may be used to pollinate the regenerated transgenic plants.

The transformed plants may be analyzed for the presence of the genes of interest and the expression level and/or profile conferred by the regulatory elements of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays. The expression of a transcribable polynucleotide molecule can be measured using TaqMan® (Applied Biosystems, Foster City, CA) reagents and methods as described by the manufacturer and PCR cycle times determined using the TaqMan® Testing Matrix. Alternatively, the Invader® (Third Wave Technologies, Madison, WI) reagents and methods as described by the manufacturer can be used transgene expression.

The seeds of the plants of this invention can be harvested from fertile transgenic plants and be used to grow progeny generations of transformed plants of this invention including hybrid plant lines comprising the construct of this invention and expressing a gene of agronomic interest.

The present invention also provides for parts of the plants of the present invention. Plant parts, without limitation, include leaves, stems, roots, tubers, seeds, endosperm, ovule, and pollen. The invention also includes and provides transformed plant cells which comprise a nucleic acid molecule of the present invention.

The transgenic plant may pass along the transgenic polynucleotide molecule to its progeny. Progeny includes any regenerable plant part or seed comprising the transgene derived from an ancestor plant. The transgenic plant is preferably homozygous for the transformed polynucleotide molecule and transmits that sequence to all offspring as a result of sexual reproduction. Progeny may be grown from seeds produced by the transgenic plant. These additional plants may then be self-pollinated to generate a true breeding line of plants. The progeny from these plants are evaluated, among other things, for gene expression. The gene expression may be detected by several common methods such as western blotting, northern blotting, immunoprecipitation, and ELISA.

Commodity Products

The present invention provides a commodity product comprising DNA molecules according to the invention. As used herein, a "commodity product" refers to any composition or product which is comprised of material derived from a plant, seed, plant cell or plant part comprising a DNA molecule of the invention. Commodity products may be sold to consumers and may be viable or nonviable. Nonviable commodity products include but are not limited to nonviable seeds and grains; processed seeds, seed parts, and plant parts; dehydrated plant tissue, frozen plant tissue, and processed plant tissue; seeds and plant parts processed for animal feed for terrestrial and/or aquatic animals consumption, oil, meal, flour, flakes, bran, fiber, milk, cheese, paper, cream, wine, and any other food for human consumption; and biomasses and fuel products. Viable commodity products include but are not limited to seeds and plant cells. Plants comprising a DNA molecule according to the invention can thus be used to manufacture any commodity product typically acquired from plants or parts thereof.

Having now generally described the invention, the same will be more readily understood through reference to the following examples which are provided by way of illustration, and are not intended to be limiting of the present invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1: Identification and Cloning of Regulatory Elements

Novel ubiquitin transcriptional regulatory elements, or transcriptional regulatory expression element group (EXP) sequences were identified and isolated from genomic DNA of the monocot species Big bluestem (*Andropogon gerardii*), Plume Grass (*Saccharum ravennae* (*Erianthus ravennae*)), Green bristlegrass (*Setaria viridis*), Teosinte (*Zea mays* subsp. *mexicana*), Foxtail millet (*Setaria italica*), and *Coix* (*Coix lacryma-jobi*).

Ubiquitin 1 transcript sequences were identified from each of the above species. The 5' untranslated region (5' UTR) of each of the Ubiquitin 1 transcripts was used to design primers to amplify the corresponding transcriptional regulatory elements for the identified Ubiquitin gene, which comprises a promoter, leader (5' UTR) and first intron operably linked. The primers were used with GenomeWalker™ (Clontech Laboratories, Inc, Mountain View, CA) libraries constructed following the manufacturer's protocol to clone the 5' region of the corresponding genomic DNA sequence. Ubiquitin transcriptional regulatory elements were also isolated from the monocot *Sorghum bicolor* using public sequences that are homologs to the Ubiquitin 4, 6 and 7 genes of *Zea mays*.

Using the identified sequences, a bioinformatic analysis was conducted to identify regulatory elements within the amplified DNA. Using the results of this analysis, regulatory elements were defined within the DNA sequences and primers designed to amplify the regulatory elements. The corresponding DNA molecule for each regulatory element was amplified using standard polymerase chain reaction conditions with primers containing unique restriction enzyme sites and genomic DNA isolated from *A. gerardii, S. ravennae, S. viridis, Z. mays* subsp. *mexicana, S. italica, C. lacryma-jobi*, and *S. bicolor*. The resulting DNA fragments were ligated into base plant expression vectors and sequenced. An analysis of the regulatory element TSS and intron/exon splice junctions was then done using transformed plant protoplasts. Briefly, the protoplasts were transformed with the plant expression vectors comprising the cloned DNA fragments operably linked to a heterologous transcribable polynucleotide molecule and the 5' RACE System for Rapid Amplification of cDNA Ends, Version 2.0 (Invitrogen, Carlsbad, California 92008) was used to confirm the regulatory element TSS and intron/exon splice junctions by analyzing the sequence of the mRNA transcripts produced thereby.

Sequences of the identified transcriptional regulatory expression element groups ("EXP's") are provided herein as SEQ ID NOS: 1, 5, 8, 10, 12, 14, 16, 18, 22, 25, 27, 29, 31, 33, 37, 39, 41, 45, 49, 53, 55, 59, 63, 65, 69, 73, 75, 77, 79, 83, 85, 87, 90, 93, 95, 97, 98, 99, 100, 102, 104, 106, 108, 110, 112, 114, 115, 116, 117, 119, 121, 123, 124, 125, 126, 128, 130, 132, 133, 134, 136, 137, 139, 141, 143, 145, 147, 149, 151, 153, 155, 157, 180, 181 and 183, as listed in Table 1 below. Promoter sequences are provided herein as SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135. Leader sequences are provided herein as SEQ ID NOS: 3, 20, 35, 43, 47, 51, 57, 61, 67,71 and 81. Intron sequences are provided herein as SEQ ID NOS: 4,7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182. An enhancer sequence is provided as SEQ ID NO: 89.

TABLE 1

Transcriptional regulatory expression element groups ("EXP's"), promoters, enhancers, leaders and introns isolated from various grass species.

| Annotation | SEQ ID NO: | Size (bp) | Source Genus/species | Description and/or regulatory elements of EXP linked in 5' → 3' direction (SEQ ID NOs): | Plasmid Construct(s) and Amplicons comprising EXP |
|---|---|---|---|---|---|
| EXP-ANDge.Ubq1:1:9 | 1 | 3741 | *A. gerardii* | EXP: P-ANDge.Ubq1-1:1:11 (SEQ ID NO: 2); L-ANDge.Ubq1-1:1:2 (SEQ ID NO: 3); I-ANDge.Ubq1-1:1:3 (SEQ ID NO: 4). | |
| P-ANDge.Ubq1-1:1:11 | 2 | 2603 | *A. gerardii* | promoter | |
| L-ANDge.Ubq1-1:1:2 | 3 | 99 | *A. gerardii* | leader | |
| I-ANDge.Ubq1-1:1:3 | 4 | 1039 | *A. gerardii* | intron | |
| EXP-ANDge.Ubq1:1:7 | 5 | 3255 | *A. gerardii* | EXP: P-ANDge.Ubq1-1:1:9 (SEQ ID NO: 6); L-ANDge.Ubq1-1:1:2 (SEQ ID NO: 3); I-ANDge.Ubq1-1:1:4 (SEQ ID NO: 7). | pMON136264, PCR0145892, pMON140896, PCR41 |
| P-ANDge.Ubq1-1:1:9 | 6 | 2114 | *A. gerardii* | promoter | |
| I-ANDge.Ubq1-1:1:4 | 7 | 1042 | *A. gerardii* | intron | |
| EXP-ANDge.Ubq1:1:8 | 8 | 2785 | *A. gerardii* | EXP: P-ANDge.Ubq1-1:1:10 (SEQ ID NO: 9); L-ANDge.Ubq1-1:1:2 (SEQ ID NO: 3); I-ANDge.Ubq1-1:1:4 (SEQ ID NO: 7). | pMON140917, PCR42 |
| P-ANDge.Ubq1-1:1:10 | 9 | 1644 | *A. gerardii* | promoter | |
| EXP-ANDge.Ubq1:1:10 | 10 | 2613 | *A. gerardii* | EXP: P-ANDge.Ubq1-1:1:12 (SEQ ID NO: 11); L-ANDge.Ubq1-1:1:2 (SEQ ID NO: 3); I-ANDge.Ubq1-1:1:4 (SEQ ID NO: 7). | PCR0145815, PCR43 |
| P-ANDge.Ubq1-1:1:12 | 11 | 1472 | *A. gerardii* | promoter | |
| EXP-ANDge.Ubq1:1:6 | 12 | 2255 | *A. gerardii* | EXP: P-ANDge.Ubq1-1:1:8 (SEQ ID NO: 13); L-ANDge.Ubq1-1:1:2 (SEQ ID NO: 3); I-ANDge.Ubq1-1:1:4 (SEQ ID NO: 7). | pMON136259, PCR0145893, pMON140898, PCR44 |
| P-ANDge.Ubq1-1:1:8 | 13 | 1114 | *A. gerardii* | promoter | |
| EXP-ANDge.Ubq1:1:11 | 14 | 1912 | *A. gerardii* | EXP: P-ANDge.Ubq1-1:1:13 (SEQ ID NO: 15); L-ANDge.Ubq1-1:1:2 (SEQ ID NO: 3); I-ANDge.Ubq1-1:1:4 (SEQ ID NO: 7). | PCR0145817, pMON140899, PCR45 |
| P-ANDge.Ubq1-1:1:13 | 15 | 771 | *A. gerardii* | promoter | |
| EXP-ANDge.Ubq1:1:12 | 16 | 1623 | *A. gerardii* | EXP: P-ANDge.Ubq1-1:1:14 (SEQ ID NO: 17); L-ANDge.Ubq1-1:1:2 (SEQ ID NO: 3); I-ANDge.Ubq1-1:1:4 (SEQ ID NO: 7). | PCR0145819, pMON140900, PCR46 |
| P-ANDge.Ubq1-1:1:14 | 17 | 482 | *A. gerardii* | promoter | |
| EXP-ERIra.Ubq1 | 18 | 3483 | *E. ravennae* | EXP: P-ERIra.Ubq1-1:1:10 (SEQ ID NO: 19); L-ERIra.Ubq1-1:1:2 (SEQ ID NO: 20); I-ERIra.Ubq1-1:1:1 (SEQ ID NO: 21). | |
| P-ERIra.Ubq1-1:1:10 | 19 | 2536 | *E. ravennae* | promoter | |
| L-ERIra.Ubq1-1:1:2 | 20 | 94 | *E. ravennae* | leader | |
| I-ERIra.Ubq1-1:1:1 | 21 | 1041 | *E. ravennae* | intron | |
| EXP-ERIra.Ubq1:1:9 | 22 | 3152 | *E. ravennae* | EXP: P-ERIra.Ubq1-1:1:9 (SEQ ID NO: 23); L-ERIra.Ubq1-1:1:2 (SEQ ID NO: 20); I-ERIra.Ubq1-1:1:2 (SEQ ID NO: 24). | pMON136263, PCR0145896, pMON140904, PCR50 |
| P-ERIra.Ubq1-1:1:9 | 23 | 2014 | *E. ravennae* | promoter | |
| I-ERIra.Ubq1-1:1:2 | 24 | 1044 | *E. ravennae* | intron | |
| EXP-ERIra.Ubq1:1:10 | 25 | 2663 | *E. ravennae* | EXP: P-ERIra.Ubq1-1:1:11 (SEQ ID NO: 26); L-ERIra.Ubq1-1:1:2 (SEQ ID NO: 20); I-ERIra.Ubq1-1:1:2 (SEQ ID NO: 24). | PCR0145820, pMON140905, PCR51 |
| P-ERIra.Ubq1-1:1:11 | 26 | 1525 | *E. ravennae* | promoter | |
| EXP-ERIra.Ubq1:1:8 | 27 | 2182 | *E. ravennae* | EXP: P-ERIra.Ubq1-1:1:8 (SEQ ID NO: 28); L-ERIra.Ubq1-1:1:2 (SEQ ID NO: 20); I-ERIra.Ubq1-1:1:2 (SEQ ID NO: 24). | pMON136258, PCR0145897, pMON140906, PCR52, pMON142864, pMON142862 |
| P-ERIra.Ubq1-1:1:8 | 28 | 1044 | *E. ravennae* | promoter | |
| EXP-ERIra.Ubq1:1:11 | 29 | 1934 | *E. ravennae* | EXP: P-ERIra.Ubq1-1:1:12 (SEQ ID NO: 30); L-ERIra.Ubq1-1:1:2 (SEQ ID NO: 20); I-ERIra.Ubq1-1:1:2 (SEQ ID NO: 24). | PCR0145821, pMON140907, PCR53 |
| P-ERIra.Ubq1-1:1:12 | 30 | 796 | *E. ravennae* | promoter | |
| EXP-ERIra.Ubq1:1:12 | 31 | 1649 | *E. ravennae* | EXP: P-ERIra.Ubq1-1:1:13 (SEQ ID NO: 32); L-ERIra.Ubq1-1:1:2 (SEQ ID NO: 20); I-ERIra.Ubq1-1:1:2 (SEQ ID NO: 24). | PCR0145822, pMON140908, PCR54 |

TABLE 1-continued

Transcriptional regulatory expression element groups ("EXP's"), promoters, enhancers, leaders and introns isolated from various grass species.

| Annotation | SEQ ID NO: | Size (bp) | Source Genus/species | Description and/or regulatory elements of EXP linked in 5' → 3' direction (SEQ ID NOs): | Plasmid Construct(s) and Amplicons comprising EXP |
|---|---|---|---|---|---|
| P-ERIra.Ubq1-1:1:13 | 32 | 511 | *E. ravennae* | promoter | |
| EXP-Sv.Ubq1:1:2 | 33 | 2631 | *S. viridis* | EXP: P-Sv.Ubq1-1:1:1 (SEQ ID NO: 34); L-Sv.Ubq1-1:1:2 (SEQ ID NO: 35); I-Sv.Ubq1-1:1:1 (SEQ ID NO: 36). | pMON140878, PCR0145909, pMON129203, pMON131958 |
| P-Sv.Ubq1-1:1:1 | 34 | 1493 | *S. viridis* | promoter | |
| L-Sv.Ubq1-1:1:2 | 35 | 127 | *S. viridis* | leader | |
| I-Sv.Ubq1-1:1:1 | 36 | 1011 | *S. viridis* | intron | |
| EXP-Sv.Ubq1:1:3 | 37 | 2173 | *S. viridis* | EXP: P-Sv.Ubq1-1:1:2 (SQ ID NO: 38); L-Sv.Ubq1-1:1:2 (SEQ ID NO: 35); I-Sv.Ubq1-1:1:1 (SEQ ID NO: 36). | PCR0145929, pMON129204 |
| P-Sv.Ubq1-1:1:2 | 38 | 1035 | *S. viridis* | promoter | |
| EXP-Sv.Ubq1:1:5 | 39 | 1819 | *S. viridis* | EXP: P-Sv.Ubq1-1:1:3 (SEQ ID NO: 40); L-Sv.Ubq1-1:1:2 (SEQ ID NO: 35); I-Sv.Ubq1-1:1:1 (SEQ ID NO: 36). | pMON129205, pMON131959 |
| P-Sv.Ubq1-1:1:3 | 40 | 681 | *S. viridis* | promoter | |
| EXP-Zm.UbqM1:1:1 (Allele-1) | 41 | 1922 | *Z. mays* subsp. *mexicana* | EXP: P-Zm.UbqM1-1:1:1 (SEQ ID NO: 42); L-Zm.UbqM1-1:1:1 (SEQ ID NO: 43); I-Zm.UbqM1-1:1:5 (SEQ ID NO: 44). | pMON140881, PCR0145914, pMON129210, pMON131961 |
| P-Zm.UbqM1-1:1:1 (Allele-1) | 42 | 850 | *Z. mays* subsp. *mexicana* | promoter | |
| L-Zm.UbqM1-1:1:1 (Allele-1) | 43 | 78 | *Z. mays* subsp. *mexicana* | leader | |
| I-Zm.UbqM1-1:1:5 (Allele-1) | 44 | 994 | *Z. mays* subsp. *mexicana* | intron | |
| EXP-Zm.UbqM1:1:4 (Allele-2) | 45 | 1971 | *Z. mays* subsp. *mexicana* | EXP: P-Zm.UbqM1-1:1:4 (SEQ ID NO: 46); L-Zm.UbqM1-1:1:5 (SEQ ID NO: 47); I-Zm.UbqM1-1:1:4 (SEQ ID NO: 48). | pMON140882, PCR0145915, pMON129212, pMON131963 |
| P-Zm.UbqM1-1:1:4 (Allele-2) | 46 | 887 | *Z. mays* subsp. *mexicana* | promoter | |
| L-Zm.UbqM1-1:1:5 (Allele-2) | 47 | 77 | *Z. mays* subsp. *mexicana* | leader | |
| I-Zm.UbqM1-1:1:4 (Allele-2) | 48 | 1007 | *Z. mays* subsp. *mexicana* | intron | |
| EXP-Zm.UbqM1:1:2 (Allele-3) | 49 | 2005 | *Z. mays* subsp. *mexicana* | EXP: P-Zm.UbqM1-1:1:5 (SEQ ID NO: 50); L-Zm.UbqM1-1:1:4 (SEQ ID NO: 51); I-Zm.UbqM1-1:1:11 (SEQ ID NO: 52). | PCR0145916, pMON129211, pMON131962, pMON132047 |
| P-Zm.UbqM1-1:1:5 (Allele-3) | 50 | 877 | *Z. mays* subsp. *mexicana* | promoter | |
| L-Zm.UbqM1-1:1:4 (Allele-3) | 51 | 78 | *Z. mays* subsp. *mexicana* | leader | |
| I-Zm.UbqM1-1:1:11 (Allele-3) | 52 | 1050 | *Z. mays* subsp. *mexicana* | intron | |
| EXP-Zm.UbqM1:1:5 (Allele-3) | 53 | 2005 | *Z. mays* subsp. *mexicana* | EXP: P-Zm.UbqM1-1:1:5 (SEQ ID NO: 50); L-Zm.UbqM1-1:1:4 (SEQ ID NO: 51); I-Zm.UbqM1-1:1:12 (SEQ ID NO: 54). | |
| I-Zm.UbqM1-1:1:12 (Allele-3) | 54 | 1050 | *Z. mays* subsp. *mexicana* | intron | |
| EXP-Sb.Ubq4:1:1 | 55 | 1632 | *S. bicolor* | EXP: P-Sb.Ubq4-1:1:1 (SEQ ID NO: 56); L-Sb.Ubq4-1:1:1 (SEQ ID NO: 57); I-Sb.Ubq4-1:1:1 (SEQ ID NO: 58). | pMON140886, PCR0145921, pMON129219, pMON132932 |
| P-Sb.Ubq4-1:1:1 | 56 | 401 | *S. bicolor* | promoter | |
| L-Sb.Ubq4-1:1:1 | 57 | 154 | *S. bicolor* | leader | |
| I-Sb.Ubq4-1:1:1 | 58 | 1077 | *S. bicolor* | intron | |
| EXP-Sb.Ubq6 | 59 | 2000 | *S. bicolor* | EXP: P-Sb.Ubq6-1:1:2 (SEQ ID NO: 60); L-Sb.Ubq6-1:1:1 (SEQ ID NO: 61); I-Sb.Ubq6-1:1:1 (SEQ ID NO: 62). | |
| P-Sb.Ubq6-1:1:2 | 60 | 791 | *S. bicolor* | promoter | |
| L-Sb.Ubq6-1:1:1 | 61 | 136 | *S. bicolor* | leader | |
| I-Sb.Ubq6-1:1:1 | 62 | 1073 | *S. bicolor* | intron | |
| EXP-Sb.Ubq6:1:1 | 63 | 2064 | *S. bicolor* | EXP: P-Sb.Ubq6-1:1:1 (SEQ ID NO: 64); L-Sb.Ubq6-1:1:1 (SEQ ID NO: 61); I-Sb.Ubq6-1:1:1 (SEQ ID NO: 62). | pMON140887, PCR0145920, pMON129218 |
| P-Sb.Ubq6-1:1:1 | 64 | 855 | *S. bicolor* | promoter | |
| EXP-Sb.Ubq7:1:1 | 65 | 2000 | *S. bicolor* | EXP: P-Sb.Ubq7-1:1:1 (SEQ ID NO: 66); L-Sb.Ubq7-1:1:1 (SEQ ID NO: 67); I-Sb.Ubq7-1:1:1 (SEQ ID NO: 68). | pMON132974 |
| P-Sb.Ubq7-1:1:1 | 66 | 565 | *S. bicolor* | promoter | |
| L-Sb.Ubq7-1:1:1 | 67 | 77 | *S. bicolor* | leader | |

TABLE 1-continued

Transcriptional regulatory expression element groups ("EXP's"), promoters, enhancers, leaders and introns isolated from various grass species.

| Annotation | SEQ ID NO: | Size (bp) | Source Genus/species | Description and/or regulatory elements of EXP linked in 5' → 3' direction (SEQ ID NOs): | Plasmid Construct(s) and Amplicons comprising EXP |
|---|---|---|---|---|---|
| I-Sb.Ubq7-1:1:1 | 68 | 1358 | *S. bicolor* | intron | |
| EXP-SETit.Ubq1:1:1 | 69 | 2622 | *S. italica* | EXP: P-SETit.Ubq1-1:1:1 (SEQ ID NO: 70); L-SETit.Ubq1-1:1:1 (SEQ ID NO: 71); I-SETit.Ubq1-1:1:1 (SEQ ID NO: 72). | pMON140877, PCR0145900, pMON129200 |
| P-SETit.Ubq1-1:1:1 | 70 | 1492 | *S. italica* | promoter | |
| L-SETit.Ubq1-1:1:1 | 71 | 127 | *S. italica* | leader | |
| I-SETit.Ubq1-1:1:1 | 72 | 1003 | *S. italica* | intron | |
| EXP-SETit.Ubq1:1:4 | 73 | 2622 | *S. italica* | EXP: P-SETit.Ubq1-1:1:4 (SEQ ID NO: 74); L-SETit.Ubq1-1:1:1 (SEQ ID NO: 71); I-SETit.Ubq1-1:1:1 (SEQ ID NO: 72). | pMON132037 |
| P-SETit.Ubq1-1:1:4 | 74 | 1492 | *S. italica* | promoter | |
| EXP-SETit.Ubq1:1:2 | 75 | 2164 | *S. italica* | EXP: P-SETit.Ubq1-1:1:2 (SEQ ID NO: 76); L-SETit.Ubq1-1:1:1 (SEQ ID NO: 71); I-SETit.Ubq1-1:1:1 (SEQ ID NO: 72). | |
| P-SETit.Ubq1-1:1:2 | 76 | 1034 | *S. italica* | promoter | |
| EXP-SETit.Ubq1:1:3 | 77 | 1810 | *S. italica* | EXP: P-SETit.Ubq1-1:1:3 (SEQ ID NO: 78); L-SETit.Ubq1-1:1:1 (SEQ ID NO: 71); I-SETit.Ubq1-1:1:1 (SEQ ID NO: 72). | PCR0145905, pMON129202, pMON131957 |
| P-SETit.Ubq1-1:1:3 | 78 | 680 | *S. italica* | promoter | |
| EXP-Cl.Ubq1:1:1 | 79 | 1940 | *C. lacryma-jobi* | EXP: P-Cl.Ubq1-1:1:1 (SEQ ID NO: 80); L-Cl.Ubq1-1:1:1 (SEQ ID NO: 81); I-Cl.Ubq1-1:1:1 (SEQ ID NO: 82). | pMON140889, PCR0145922, pMON140913, PCR19, pMON129221, pMON146795, pMON146796, pMON146797, pMON146798, pMON146799, pMON132047, pMON146800, pMON146801, pMON146802 |
| P-Cl.Ubq1-1:1:1 | 80 | 837 | *C. lacryma-jobi* | promoter | |
| L-Cl.Ubq1-1:1:1 | 81 | 86 | *C. lacryma-jobi* | leader | |
| I-Cl.Ubq1-1:1:1 | 82 | 1017 | *C. lacryma-jobi* | intron | |
| EXP-Cl.Ubq1:1:3 | 83 | 1845 | *C. lacryma-jobi* | EXP: P-Cl.Ubq1-1:1:4 (SEQ ID NO: 84); L-Cl.Ubq1-1:1:1 (SEQ ID NO: 81); I-Cl.Ubq1-1:1:1 (SEQ ID NO: 82). | PCR0145945, pMON140914, PCR20 |
| P-Cl.Ubq1-1:1:4 | 84 | 742 | *C. lacryma-jobi* | promoter | |
| EXP-Cl.Ubq1:1:4 | 85 | 1504 | *C. lacryma-jobi* | EXP: P-Cl.Ubq1-1:1:3 (SEQ ID NO: 86); L-Cl.Ubq1-1:1:1 (SEQ ID NO: 81); I-Cl.Ubq1-1:1:1 (SEQ ID NO: 82). | PCR0145946, pMON140915, PCR21 |
| P-Cl.Ubq1-1:1:3 | 86 | 401 | *C. lacryma-jobi* | promoter | |
| EXP-Cl.Ubq1:1:5 | 87 | 1157 | *C. lacryma-jobi* | EXP: P-Cl.Ubq1-1:1:5 (SEQ ID NO: 88); L-Cl.Ubq1-1:1:1 (SEQ ID NO: 81); I-Cl.Ubq1-1:1:1 (SEQ ID NO: 82). | PCR0145947, pMON140916, PCR22 |
| P-Cl.Ubq1-1:1:5 | 88 | 54 | *C. lacryma-jobi* | promoter | |
| E-Cl.Ubq1-1:1:1 | 89 | 798 | *C. lacryma-jobi* | enhancer | |
| EXP-Cl.Ubq1:1:12 | 90 | 3393 | *C. lacryma-jobi* | EXP: P-Cl.Ubq1-1:1:9 (SEQ ID NO: 91); L-Cl.Ubq1-1:1:1 (SEQ ID NO: 81); I-Cl.Ubq1-1:1:7 (SEQ ID NO: 92) | pMON142729 |
| P-Cl.Ubq1-1:1:9 | 91 | 2287 | *C. lacryma-jobi* | Promoter | |
| I-Cl.Ubq1-1:1:7 | 92 | 1020 | *C. lacryma-jobi* | Intron | |
| EXP-Cl.Ubq1:1:16 | 93 | 3393 | *C. lacryma-jobi* | EXP: P-Cl.Ubq1-1:1:9 (SEQ ID NO: 91); L-Cl.Ubq1-1:1:1 (SEQ ID NO: 81); I-Cl.Ubq1-1:1:6 (SEQ ID NO: 94) | pMON146750, pMON142748 |
| I-Cl.Ubq1-1:1:6 | 94 | 1020 | *C. lacryma-jobi* | Intron | |
| EXP-Cl.Ubq1:1:11 | 95 | 2166 | *C. lacryma-jobi* | EXP: P-Cl.Ubq1-1:1:10 (SEQ ID NO: 96); L-Cl.Ubq1-1:1:1 (SEQ ID NO: 81); I-Cl.Ubq1-1:1:7 (SEQ ID NO: 92) | pMON142730 |
| P-Cl.Ubq1-1:1:10 | 96 | 1060 | *C. lacryma-jobi* | Promoter | |
| EXP-Cl.Ubq1:1:17 | 97 | 2166 | *C. lacryma-jobi* | EXP: P-Cl.Ubq1-1:1:10 (SEQ ID NO: 96); L-Cl.Ubq1-1:1:1 (SEQ ID NO: 81); I-Cl.Ubq1-1:1:6 (SEQ ID NO: 94) | pMON146751, pMON142749 |
| EXP-Cl.Ubq1:1:10 | 98 | 1943 | *C. lacryma-jobi* | EXP: P-Cl.Ubq1-1:1:1 (SEQ ID NO: 80); L-Cl.Ubq1-1:1:1 (SEQ ID NO: 81); I-Cl.Ubq1-1:1:6 (SEQ ID NO: 94) | pMON140889, PCR0145922, pMON140913, PCR19, pMON129221 |
| EXP-Cl.Ubq1:1:18 | 99 | 1943 | *C. lacryma-jobi* | EXP: P-Cl.Ubq1-1:1:1 (SEQ ID NO: 80); L-Cl.Ubq1-1:1:1 (SEQ ID NO: 81); I-Cl.Ubq1-1:1:7 (SEQ ID NO: 92) | pMON146795 |

TABLE 1-continued

Transcriptional regulatory expression element groups ("EXP's"), promoters, enhancers, leaders and introns isolated from various grass species.

| Annotation | SEQ ID NO: | Size (bp) | Source Genus/species | Description and/or regulatory elements of EXP linked in 5' → 3' direction (SEQ ID NOs): | Plasmid Construct(s) and Amplicons comprising EXP |
|---|---|---|---|---|---|
| EXP-Cl.Ubq1:1:19 | 100 | 1943 | *C. lacryma-jobi* | EXP: P-Cl.Ubq1-1:1:1 (SEQ ID NO: 80); L-Cl.Ubq1-1:1:1 (SEQ ID NO: 81); I-Cl.Ubq1-1:1:8 (SEQ ID NO: 101) | pMON146796 |
| I-Cl.Ubq1-1:1:8 | 101 | 1020 | *C. lacryma-jobi* | Intron | |
| EXP-Cl.Ubq1:1:20 | 102 | 1943 | *C. lacryma-jobi* | EXP: P-Cl.Ubq1-1:1:1 (SEQ ID NO: 80); L-Cl.Ubq1-1:1:1 (SEQ ID NO: 81); I-Cl.Ubq1-1:1:9 (SEQ ID NO: 103) | pMON146797 |
| I-Cl.Ubq1-1:1:9 | 103 | 1020 | *C. lacryma-jobi* | Intron | |
| EXP-Cl.Ubq1:1:21 | 104 | 1943 | *C. lacryma-jobi* | EXP: P-Cl.Ubq1-1:1:1 (SEQ ID NO: 80); L-Cl.Ubq1-1:1:1 (SEQ ID NO: 81); I-Cl.Ubq1-1:1:10 (SEQ ID NO: 105) | pMON146798 |
| I-Cl.Ubq1-1:1:10 | 105 | 1020 | *C. lacryma-jobi* | Intron | |
| EXP-Cl.Ubq1:1:22 | 106 | 1943 | *C. lacryma-jobi* | EXP: P-Cl.Ubq1-1:1:1 (SEQ ID NO: 80); L-Cl.Ubq1-1:1:1 (SEQ ID NO: 81); I-Cl.Ubq1-1:1:11 (SEQ ID NO: 107) | pMON146799 |
| I-Cl.Ubq1-1:1:11 | 107 | 1020 | *C. lacryma-jobi* | Intron | |
| EXP-Cl.Ubq1:1:23 | 108 | 1943 | *C. lacryma-jobi* | EXP: P-Cl.Ubq1-1:1:1 (SEQ ID NO: 80); L-Cl.Ubq1-1:1:1 (SEQ ID NO: 81); I-Cl.Ubq1-1:1:12 (SEQ ID NO: 109) | pMON132047, pMON146800 |
| I-Cl.Ubq1-1:1:12 | 109 | 1020 | *C. lacryma-jobi* | Intron | |
| EXP-Cl.Ubq1:1:24 | 110 | 1943 | *C. lacryma-jobi* | EXP: P-Cl.Ubq1-1:1:1 (SEQ ID NO: 80); L-Cl.Ubq1-1:1:1 (SEQ ID NO: 81); I-Cl.Ubq1-1:1:13 (SEQ ID NO: 111) | pMON146801 |
| I-Cl.Ubq1-1:1:13 | 111 | 1020 | *C. lacryma-jobi* | Intron | |
| EXP-Cl.Ubq1:1:25 | 112 | 1943 | *C. lacryma-jobi* | EXP: P-Cl.Ubq1-1:1:1 (SEQ ID NO: 80); L-Cl.Ubq1-1:1:1 (SEQ ID NO: 81); I-Cl.Ubq1-1:1:14 (SEQ ID NO: 113) | pMON146802 |
| I-Cl.Ubq1-1:1:14 | 113 | 1020 | *C. lacryma-jobi* | Intron | |
| EXP-Cl.Ubq1:1:13 | 114 | 1848 | *C. lacryma-jobi* | EXP: P-Cl.Ubq1-1:1:4 (SEQ ID NO: 84); L-Cl.Ubq1-1:1:1 (SEQ ID NO: 81); I-Cl.Ubq1-1:1:6 (SEQ ID NO: 94) | PCR0145945, pMON140914, PCR20 |
| EXP-Cl.Ubq1:1:14 | 115 | 1507 | *C. lacryma-jobi* | EXP: P-Cl.Ubq1-1:1:3 (SEQ ID NO: 86); L-C1.Ubq1-1:1:1 (SEQ ID NO: 81); I-Cl.Ubq1-1:1:6 (SEQ ID NO: 94) | PCR0145946, pMON140915, PCR21 |
| EXP-Cl.Ubq1:1:15 | 116 | 1160 | *C. lacryma-jobi* | EXP: P-Cl.Ubq1-1:1:5 (SEQ ID NO: 88); L-Cl.Ubq1-1:1:1 (SEQ ID NO: 81); I-Cl.Ubq1-1:1:6 (SEQ ID NO: 94) | PCR0145947, pMON140916, PCR22 |
| EXP-SETit.Ubq1:1:5 | 117 | 2625 | *S. italica* | EXP: P-SETit.Ubq1-1:1:1 (SEQ ID NO: 70); L-SETit.Ubq1-1:1:1 (SEQ ID NO: 71); I-SETit.Ubq1-1:1:2 (SEQ ID NO: 118) | pMON140877, PCR0145900, pMON129200 |
| I-SETit.Ubq1-1:1:2 | 118 | 1006 | *S. italica* | Intron | |
| EXP-SETit.Ubq1:1:10 | 119 | 2625 | *S. italica* | EXP: P-SETit.Ubq1-1:1:4 (SEQ ID NO: 64); L-SETit.Ubq1-1:1:1 (SEQ ID NO: 71); I-SETit.Ubq1-1:1:3 (SEQ ID NO: 120) | pMON132037 |
| I-SETit.Ubq1-1:1:3 | 120 | 1006 | *S. italica* | Intron | |
| EXP-SETit.Ubq1:1:12 | 121 | 2625 | *S. italica* | EXP: P-SETit.Ubq1-1:1:4 (SEQ ID NO: 64); L-SETit.Ubq1-1:1:1 (SEQ ID NO: 71); I-SETit.Ubq1-1:1:4 (SEQ ID NO: 122) | |
| I-SETit.Ubq1-1:1:4 | 122 | 1006 | *S. italica* | Intron | |
| EXP-SETit.Ubq1:1:7 | 123 | 2167 | *S. italica* | EXP: P-SETit.Ubq1-1:1:2 (SEQ ID NO: 71); L-SETit.Ubq1-1:1:1 (SEQ ID NO: 71); I-SETit.Ubq1-1:1:2 (SEQ ID NO: 118) | PCR0145928, pMON129201 |
| EXP-SETit.Ubq1:1:6 | 124 | 1813 | *S. italica* | EXP: P-SETit.Ubq1-1:1:3 (SEQ ID NO: 73); L-SETit.Ubq1-1:1:1 (SEQ ID NO: 71); I-SETit.Ubq1-1:1:2 (SEQ ID NO: 118) | PCR0145905, pMON129202 |
| EXP-SETit.Ubq1:1:11 | 125 | 1813 | *S. italica* | EXP: P-SETit.Ubq1-1:1:3 (SEQ ID NO: 73); L-SETit.Ubq1-1:1:1 (SEQ ID NO: 71); I-SETit.Ubq1-1:1:3 (SEQ ID NO: 120) | pMON131957 |
| EXP-SETit.Ubq1:1:13 | 126 | 1813 | *S. italica* | EXP: P-SETit.Ubq1-1:1:3 (SEQ ID NO: 73); L-SETit.Ubq1-1:1:1 (SEQ ID NO: 71); I-SETit.Ubq1-1:1:5 (SEQ ID NO: 127) | |
| I-SETit.Ubq1-1:1:5 | 127 | 1006 | *S. italica* | Intron | |
| EXP-Sv.Ubq1:1:7 | 128 | 2634 | *S. viridis* | EXP: P-Sv.Ubq1-1:1:1 (SEQ ID NO: 34); L-Sv.Ubq1-1:1:2 (SEQ ID NO: 35); I-Sv.Ubq1-1:1:2 (SEQ ID NO: 129) | pMON140878, PCR0145909, pMON129203 |
| I-Sv.Ubq1-1:1:2 | 129 | 1014 | *S. viridis* | Intron | |
| EXP-Sv.Ubq1:1:11 | 130 | 2634 | *S. viridis* | EXP: P-Sv.Ubq1-1:1:1 (SEQ ID NO: 34); L-Sv.Ubq1-1:1:2 (SEQ ID NO: 35); I-Sv.Ubq1-1:1:3 (SEQ ID NO: 131) | pMON131958 |
| I-Sv.Ubq1-1:1:3 | 131 | 1014 | *S. viridis* | Intron | |
| EXP-Sv.Ubq1:1:8 | 132 | 2176 | *S. viridis* | EXP: P-Sv.Ubq1-1:1:2 (SEQ ID NO: 38); L-Sv.Ubq1-1:1:2 (SEQ ID NO: 35); I-Sv.Ubq1-1:1:2 (SEQ ID NO: 129) | PCR0145929, pMON129204 |

TABLE 1-continued

Transcriptional regulatory expression element groups ("EXP's"), promoters, enhancers, leaders and introns isolated from various grass species.

| Annotation | SEQ ID NO: | Size (bp) | Source Genus/species | Description and/or regulatory elements of EXP linked in 5' → 3' direction (SEQ ID NOs): | Plasmid Construct(s) and Amplicons comprising EXP |
|---|---|---|---|---|---|
| EXP-Sv.Ubq1:1:9 | 133 | 1822 | *S. viridis* | EXP: P-Sv.Ubq1-1:1:3 (SEQ ID NO: 40); L-Sv.Ubq1-1:1:2 (SEQ ID NO: 35); I-Sv.Ubq1-1:1:2 (SEQ ID NO: 129) | pMON129205 |
| EXP-Sv.Ubq1:1:10 | 134 | 1822 | *S. viridis* | EXP: P-Sv.Ubq1-1:1:4 (SEQ ID NO: 135); L-Sv.Ubq1-1:1:2 (SEQ ID NO: 35); I-Sv.Ubq1-1:1:2 (SEQ ID NO: 129) | PCR0145911 |
| P-Sv.Ubq1-1:1:4 | 135 | 681 | *S. viridis* | Promoter | |
| EXP-Sv.Ubq1:1:12 | 136 | 1822 | *S. viridis* | EXP: P-Sv.Ubq1-1:1:3 (SEQ ID NO: 40); L-Sv.Ubq1-1:1:2 (SEQ ID NO: 35); I-Sv.Ubq1-1:1:3 (SEQ ID NO: 131) | pMON131959 |
| EXP-Zm.UbqM1:1:6 (Allele-1) | 137 | 1925 | *Z. mays* subsp. *Mexicana* | EXP: P-Zm.UbqM1-1:1:1 (SEQ ID NO: 42); L-Zm.UbqM1-1:1:1 (SEQ ID NO: 43); I-Zm.UbqM1-1:1:13 (SEQ ID NO: 138) | pMON140881, PCR0145914, pMON129210 |
| I-Zm.UbqM1-1:1:13 (Allele-1) | 138 | 997 | *Z. mays* subsp. *Mexicana* | Intron | |
| EXP-Zm.UbqM1:1:10 (Allele-1) | 139 | 1925 | *Z. mays* subsp. *Mexicana* | EXP: P-Zm.UbqM1-1:1:1 (SEQ ID NO: 42); L-Zm.UbqM1-1:1:1 (SEQ ID NO: 43); I-Zm.UbqM1-1:1:17 (SEQ ID NO: 140) | pMON131961 |
| I-Zm.UbqM1-1:1:17 (Allele-1) | 140 | 997 | *Z. mays* subsp. *Mexicana* | Intron | |
| EXP-Zm.UbqM1:1:7 (Allele-2) | 141 | 1974 | *Z. mays* subsp. *Mexicana* | EXP: P-Zm.UbqM1-1:1:4 (SEQ ID NO: 46); L-Zm.UbqM1-1:1:5 (SEQ ID NO: 47); I-Zm.UbqM1-1:1:14 (SEQ ID NO: 142) | pMON140882, PCR0145915, pMON129212 |
| I-Zm.UbqM1-1:1:14 (Allele-2) | 142 | 1010 | *Z. mays* subsp. *Mexicana* | Intron | |
| EXP-Zm.UbqM1:1:12 (Allele-2) | 143 | 1974 | *Z. mays* subsp. *Mexicana* | EXP: P-Zm.UbqM1-1:1:4 (SEQ ID NO: 46); L-Zm.UbqM1-1:1:5 (SEQ ID NO: 47); I-Zm.UbqM1-1:1:19 (SEQ ID NO: 144) | pMON131963 |
| I-Zm.UbqM1-1:1:19 (Allele-2) | 144 | 1010 | *Z. mays* subsp. *Mexicana* | Intron | |
| EXP-Zm.UbqM1:1:8 (Allele-3) | 145 | 2008 | *Z. mays* subsp. *Mexicana* | EXP: P-Zm.UbqM1-1:1:5 (SEQ ID NO: 50); L-Zm.UbqM1-1:1:4 (SEQ ID NO: 51); I-Zm.UbqM1-1:1:15 (SEQ ID NO: 146) | PCR0145916, pMON129211 |
| I-Zm.UbqM1-1:1:15 (Allele-3) | 146 | 1053 | *Z. mays* subsp. *Mexicana* | Intron | |
| EXP-Zm.UbqM1:1:9 (Allele-3) | 147 | 2008 | *Z. mays* subsp. *Mexicana* | EXP: P-Zm.UbqM1-1:1:5 (SEQ ID NO: 50); L-Zm.UbqM1-1:1:4 (SEQ ID NO: 51); I-Zm.UbqM1-1:1:16 (SEQ ID NO: 148) | |
| I-Zm.UbqM1-1:1:16 (Allele-3) | 148 | 1053 | *Z. mays* subsp. *Mexicana* | Intron | |
| EXP-Zm.UbqM1:1:11 (Allele-3) | 149 | 2008 | *Z. mays* subsp. *Mexicana* | EXP: P-Zm.UbqM1-1:1:5 (SEQ ID NO: 50); L-Zm.UbqM1-1:1:4 (SEQ ID NO: 51); I-Zm.UbqM1-1:1:18 (SEQ ID NO: 150) | pMON131962, pMON132047 |
| I-Zm.UbqM1-1:1:18 (Allele-3) | 150 | 1053 | *Z. mays* subsp. *Mexicana* | Intron | |
| EXP-Sb.Ubq4:1:2 | 151 | 1635 | *S. bicolor* | EXP: P-Sb.Ubq4-1:1:1 (SEQ ID NO: 56); L-Sb.Ubq4-1:1:1 (SEQ ID NO: 57); I-Sb.Ubq4-1:1:2 (SEQ ID NO: 152) | pMON140886, PCR0145921, pMON129219, pMON132932 |
| I-Sb.Ubq4-1:1:2 | 152 | 1080 | *S. bicolor* | Intron | |
| EXP-Sb.Ubq6:1:2 | 153 | 2067 | *S. bicolor* | EXP: P-Sb.Ubq6-1:1:1 (SEQ ID NO: 64); L-Sb.Ubq6-1:1:1 (SEQ ID NO: 57); I-Sb.Ubq6-1:1:2 (SEQ ID NO: 154) | pMON140887, PCR0145920, pMON129218, pMON132931 |
| I-Sb.Ubq6-1:1:2 | 154 | 1076 | *S. bicolor* | Intron | |
| EXP-Sb.Ubq6:1:3 | 155 | 2067 | *S. bicolor* | EXP: P-Sb.Ubq6-1:1:1 (SEQ ID NO: 64); L-Sb.Ubq6-1:1:1 (SEQ ID NO: 57); I-Sb.Ubq6-1:1:3 (SEQ ID NO: 1569) | pMON132931 |
| I-Sb.Ubq6-1:1:3 | 156 | 1076 | *S. bicolor* | Intron | |
| EXP-Sb.Ubq7:1:2 | 157 | 2003 | *S. bicolor* | EXP: P-Sb.Ubq7-1:1:1 (SEQ ID NO: 66); L-Sb.Ubq7-1:1:1 (SEQ ID NO: 67); I-Sb.Ubq7-1:1:A (SEQ ID NO: 158) | pMON132974 |
| I-Sb.Ubq7-1:1:2 | 158 | 1361 | *S. bicolor* | Intron | |
| EXP-SETit.Ubq1:1:E | 180 | 2625 | *S. italica* | EXP: P-SETit.Ubq1-1:1:4 (SEQ ID NO: 64); L-SETit.Ubq1-1:1:1 (SEQ ID NO: 71); I-SETit.Ubq1-1:1:5 (SEQ ID NO: 127) | |
| EXP-Zm.UbqM1:1:13 (Allele-3) | 181 | 2008 | *Z. mays* subsp. *Mexicana* | EXP: P-Zm.UbqM1-1:1:5 (SEQ ID NO: 50); L-Zm.UbqM1-1:1:4 (SEQ ID NO: 51); I-Zm.UbqM1-1:1:20 (SEQ ID NO: 182) | |

TABLE 1-continued

| Transcriptional regulatory expression element groups ("EXP's"), promoters, enhancers, leaders and introns isolated from various grass species. | | | | | |
|---|---|---|---|---|---|
| Annotation | SEQ ID NO: | Size (bp) | Source Genus/species | Description and/or regulatory elements of EXP linked in 5' → 3' direction (SEQ ID NOs): | Plasmid Construct(s) and Amplicons comprising EXP |
| I-Zm.UbqM1-1:1:20 (Allele-3) | 182 | 1053 | *Z. mays* subsp. *Mexicana* | Intron | |
| EXP-SETit.Ubq1:1:9 | 183 | 2625 | *S. italica* | EXP: P-SETit.Ubq1-1:1:4 (SEQ ID NO: 64); L-SETit.Ubq1-1:1:1 (SEQ ID NO: 71); I-SETit.Ubq1-1:1:2 (SEQ ID NO: 118) | |

As shown in Table 1, for example, the transcriptional regulatory EXP sequence designated EXP-ANDge.Ubq1:1:9 (SEQ ID NO: 1), with components isolated from *A. gerardii*, comprises a promoter element, P-ANDge.Ubq1-1:1:11 (SEQ ID NO: 2), operably linked 5' to a leader element, L-ANDge.Ubq1-1:1:2 (SEQ ID NO: 3), operably linked 5' to an intron element, I-ANDge.Ubq1-1:1:3 (SEQ ID NO: 4). Other EXP's are linked similarly, as outlined in Table 1.

As shown in Table 1, the sequence listing and FIGS. 1-7, variants of promoter sequences from the species *A. gerardii, E. ravennae, Z. mays* subsp. *mexicana, S. bicolor, C. lacryma-jobi, S. italica*, and *S. viridis* were engineered which comprise shorter promoter fragments of, for instance, P-ANDge.Ubq1-1:1:11 (SEQ ID NO:2), P-ERIra.Ubq1-1:1:10 (SEQ ID NO:19) or other respective promoters from other species, and for instance resulting in P-ANDge.Ubq1-1:1:9 (SEQ ID NO: 6), P-ERIra.Ubq1-1:1:9 (SEQ ID NO: 23), P-Cl.Ubq1-1:1:10 (SEQ ID NO: 96), P-SETit.Ubq1-1:1:2 (SEQ ID NO: 76) and P-Sv.Ubq1-1:1:2 (SEQ ID NO: 38), as well as other promoter fragments. P-SETit.Ubq1-1:1:4 (SEQ ID NO: 74) comprises a single nucleotide change relative to P-SETit.Ubq1-1:1:1 (SEQ ID NO: 70). Likewise, P-Sv.Ubq1-1:1:3 (SEQ ID NO: 40) comprises a single nucleotide change relative to P-Sv.Ubq1-1:1:4 (SEQ ID NO: 135).

In some instances, variants of specific introns were created by altering the last 3' nucleotides of each respective intron following the sequence 5'-AG-3' of the 3' intron splice junction. These intron variants are shown in Table 2 below.

TABLE 2

| 3' end sequence of intron variants. | | |
|---|---|---|
| Annotation | SEQ ID NO: | Intron 3' end nucleotides immediately following 3' splice site AG |
| I-Cl.Ubq1-1:1:7 | 92 | GTG |
| I-Cl.Ubq1-1:1:6 | 94 | GTC |
| I-Cl.Ubq1-1:1:8 | 101 | GCG |
| I-Cl.Ubq1-1:1:9 | 103 | GAC |
| I-Cl.Ubq1-1:1:10 | 105 | ACC |
| I-Cl.Ubq1-1:1:11 | 107 | GGG |
| I-Cl.Ubq1-1:1:12 | 109 | GGT |
| I-Cl.Ubq1-1:1:13 | 111 | CGT |

TABLE 2-continued

| 3' end sequence of intron variants. | | |
|---|---|---|
| Annotation | SEQ ID NO: | Intron 3' end nucleotides immediately following 3' splice site AG |
| I-Cl.Ubq1-1:1:14 | 113 | TGT |
| I-SETit.Ubq1-1:1:2 | 118 | GTG |
| I-SETit.Ubq1-1:1:3 | 120 | GGT |
| I-SETit.Ubq1-1:1:4 | 122 | ACC |
| I-SETit.Ubq1-1:1:5 | 127 | GGC |
| I-Sv.Ubq1-1:1:2 | 129 | GTG |
| I-Sv.Ubq1-1:1:3 | 131 | GGT |
| I-Zm.UbqM1-1:1:13 (Allele-1) | 138 | GTC |
| I-Zm.UbqM1-1:1:17 (Allele-1) | 140 | GGT |
| I-Zm.UbqM1-1:1:14 (Allele-2) | 142 | GTC |
| I-Zm.UbqM1-1:1:19 (Allele-2) | 144 | GGT |
| I-Zm.UbqM1-1:1:15 (Allele-3) | 146 | GTC |
| I-Zm.UbqM1-1:1:18 (Allele-3) | 148 | GGT |
| I-Sb.Ubq6-1:1:2 | 154 | GTG |
| I-Sb.Ubq6-1:1:3 | 156 | GGT |
| I-Zm.UbqM1-1:1:20 (Allele-3) | 182 | CGG |

Also listed in Table 1 are three allelic variants isolated using the same primer sets designed for amplification of genomic DNA from *Z. mays* subsp. *mexicana*. Allelic variants of the EXP sequences are comprised of sequence that shares some identity within various regions of other sequences, but insertions, deletions and nucleotide mismatches may also be apparent within each promoter, leader and/or intron of each of the EXP sequences. The EXP sequence designated EXP-Zm.UbgM1:1:1 (SEQ ID NO: 41) represents a first allele (Allele-1) of the *Z. mays* subsp. *mexicana* Ubq1 gene transcriptional regulatory expression element group. The EXP sequences designated EXP-Zm.UbgM1:1:6 (SEQ ID NO: 137) and EXP-Zm.UbgM1:1:10 (SEQ ID NO: 139) represent a first allele (Allele-1), with the only difference between the two EXPs occurring in the last 3' nucleotides of each respective intron following the sequence 5'-AG-3' of the 3' intron splice junction. The EXP sequence designated EXP-Zm.UbgM1:1:4 (SEQ ID NO: 45) represents a second allele (Allele-2) of the *Z. mays* subsp. *mexicana* Ubq1 gene transcriptional regulatory expression element group. The EXP sequences designated EXP-Zm.UbgM1:1:7 (SEQ ID NO: 141) and EXP-Zm.UbgM1:1:12 (SEQ ID NO: 143) represent a second allele (Allele-2), with the only difference between the two EXPs occurring in the last 3' nucleotides of each respective intron following the sequence 5'-AG-3' of the 3' intron splice junction. The EXP sequences EXP-Zm.UbgM1:1:2 (SEQ ID NO: 49) and EXP-Zm.UbgM1:1:5 (SEQ ID NO: 53) represents a third allel (Allele-3) of the *Z. mays* subsp. *mexicana* Ubq1 gene transcriptional regulatory expression element group and comprise a single nucleotide difference at position 1034 within their respective introns (G for I-Zm.UbgM1-1:1:11, SEQ ID NO: 52 and T for I-Zm.UbgM1-1:1:12, SEQ ID NO: 54). The EXP sequences designated EXP-Zm.UbgM1:1:8 (SEQ ID NO: 145), EXP-Zm.UbgM1:1:9 (SEQ ID NO: 147), EXP-Zm.UbgM1:1:11 (SEQ ID NO: 149) and EXP-Zm.UbgM1:1:13 (SEQ ID NO: 181) also represent a third allele (Allele-3). The intron of EXP-Zm.UbgM1:1:9, I-Zm.UbgM1-1:1:16 (SEQ ID NO: 148) comprises a thymine residue at position 1034, while the introns of EXP-Zm.UbgM1:1:8, EXP-Zm.UbgM1:1:11 and EXP-Zm.UbgM1:1:13 (I-Zm.UbgM1-1:1:15, SEQ ID NO: 146; I-Zm.UbgM1-1:1:18, SEQ ID NO: 11 and; I-Zm.UbgM1-1:1:20, SEQ ID NO: 182) each comprise a guanine residue at position 1034. In addition, the last 3, 3' end nucleotides of EXP-Zm.UbgM1:1:8 (SEQ ID NO: 145) and EXP-Zm.UbgM1:1:9 (SEQ ID NO: 147) differ from those of EXP-Zm.UbgM1:1:11 (SEQ ID NO: 149) and EXP-Zm.UbgM1:1:13 (SEQ ID NO: 181).

Example 2: Analysis of Regulatory Elements Driving GUS in Corn Protoplasts

Corn leaf protoplasts were transformed with plant expression vectors containing an EXP sequence driving expression of the β-glucuronidase (GUS) transgene and compared to GUS expression in leaf protoplasts in which expression of GUS is driven by known constitutive promoters.

Expression of a transgene driven by EXP-ANDge.Ubq1:1:7 (SEQ ID NO: 5), EXP-ANDge.Ubq1:1:6 (SEQ ID NO: 12), EXP-ERIra.Ubq1:1:9 (SEQ ID NO: 22) or EXP-ERIra.Ubq1:1:8 (SEQ ID NO: 27) was compared with expression from known constitutive promoters. The foregoing EXP sequences were cloned into plant expression vectors as shown in Table 3 below to yield vectors in which an EXP sequence is operably linked 5' to a β-glucuronidase (GUS) reporter that contained a processable intron (referred to as GUS-2, SEQ ID NO: 160) derived from the potato light-inducible tissue-specific ST-LS1 gene (GenBank Accession: X04753) or a contiguous GUS coding sequence (GUS-1, SEQ ID NOS: 159), which was operably linked 5' to a 3' UTR derived from the *A. tumefaciens* Nopaline synthase gene (T-AGRtu.nos-1:1:13, SEQ ID NO: 161) or the wheat Hsp17 gene (T-Ta.Hsp17-1:1:1, SEQ ID NO: 162).

TABLE 3

GUS plant expression plasmid construct and corresponding EXP sequence, GUS coding sequence and 3' UTR used for transformation of corn leaf protoplasts. "SEQ ID NO:" refers to given EXP sequence.

| Plasmid | EXP sequence | SEQ ID NO: | GUS | 3' UTR |
|---|---|---|---|---|
| pMON19469 | EXP-CaMV.35S-enh + Zm.DnaK:1:1 | 170 | GUS-1 | T-AGRtu.nos-1:1:13 |
| pMON65328 | EXP-CaMV.35S-enh + Ta.Lhcb1 + Os.Act1:1:1 | 163 | GUS-2 | T-Ta.Hsp17-1:1:1 |
| pMON25455 | EXP-Os.Act1:1:9 | 179 | GUS-1 | T-AGRtu.nos-1:1:13 |
| pMON122605 | EXP-Os.TubA-3:1:1 | 165 | GUS-1 | T-AGRtu.nos-1:1:13 |
| pMON136264 | EXP-ANDge.Ubq1:1:7 | 5 | GUS-1 | T-AGRtu.nos-1:1:13 |
| pMON136259 | EXP-ANDge.Ubq1:1:6 | 12 | GUS-1 | T-AGRtu.nos-1:1:13 |
| pMON136263 | EXP-ERIra.Ubq1:1:9 | 22 | GUS-1 | T-AGRtu.nos-1:1:13 |
| pMON136258 | EXP-ERIra.Ubq1:1:8 | 27 | GUS-1 | T-AGRtu.nos-1:1:13 |

Control plasmids (pMON19469, pMON65328, pMON25455 and pMON122605) used for comparison were constructed as described above and contain a known EXP sequence: EXP-CaMV.35S-enh+Zm.DnaK:1:1 (SEQ ID NO: 170), EXP-CaMV.35S-enh+Ta.Lhcb1+Os.Act1:1:1 (SEQ ID NO: 163), EXP-Os.Act1:1:9 (SEQ ID NO: 179), or EXP-Os.TubA-3:1:1 (SEQ ID NO: 165), respectively, operably linked 5' to a GUS coding sequence and 3' UTR. Three additional controls were provided to assess background GUS and luciferase expression: a no DNA control, an empty vector which is not designed for transgene expression, and an expression vector used to express green fluorescent protein (GFP).

Two plasmids, for use in co-transformation and normalization of data, were also constructed using methods known in the art. Each plasmid contained a specific luciferase coding sequence that was driven by a constitutive EXP sequence. The plant vector pMON19437 comprises a transgene cassette with a constitutive promoter operably linked 5' to an intron, (EXP-CaMV.35S-enh+Zm.DnaK:1:1, SEQ ID NO: 170), operably linked 5' to a firefly (Photinus pyralis) luciferase coding sequence (LUCIFERASE:1:3, SEQ ID NO: 166), operably linked 5' to a 3' UTR from the *Agrobacterium tumefaciens* nopaline synthase gene (T-AGRtu.nos-1:1:13, SEQ ID NO: 161). The plant vector pMON63934 comprises a transgene cassette with a constitutive EXP sequence (EXP-CaMV.35S-enh-Lhcb1, SEQ ID NO: 168), operably linked 5' to a sea pansy (*Renilla reniformis*) luciferase coding sequence (CR-Ren.hRenilla Lucife-0:0:1, SEQ ID NO: 167), operably linked 5' to a 3' UTR from the *Agrobacterium tumefaciens* nopaline synthase gene (T-AGRtu.nos-1:1:13, SEQ ID NO: 161).

Corn leaf protoplasts were transformed using a PEG-based transformation method, as is well known in the art. Protoplast cells were transformed with pMON19437 plasmid DNA, pMON63934 plasmid DNA, and an equimolar quantity of one of the plasmids presented in Table 3 and incubated overnight in total darkness. Measurements of both GUS and luciferase were conducted by placing aliquots of a lysed preparation of cells transformed as above into two different small-well trays. One tray was used for GUS measurements, and a second tray was used to perform a dual luciferase assay using the dual luciferase reporter assay system (Promega Corp., Madison, WI; see for example, *Promega Notes* Magazine, No: 57, 1996, p. 02). One or two transformations for each EXP sequence were performed and the mean expression values for each EXP sequence determined from several samples from each transformation experiment. Sample measurements were made using four replicates of each EXP sequence construct transformation, or alternatively, three replicates of each EXP sequence construct per one of two transformation experiments. The mean GUS and luciferase expression levels are provided in Table 4. In this table, the firefly luciferase values (e.g. from expression of pMON19437) are provided in the column labeled "FLuc" and the *Renilla* luciferase values are provided as in the column labeled "RLuc."

TABLE 4

Mean GUS and Luciferase activity in transformed corn leaf protoplast cells.

| Plasmid | EXP sequence | SEQ ID NO: | Gus | RLuc | FLuc |
|---|---|---|---|---|---|
| pMON19469 | EXP-CaMV.35S-enh + Zm.DnaK:1:1 | 170 | 789147 | 298899 | 36568 |
| pMON65328 | EXP-CaMV.35S-enh + Ta.Lhcb1 + Os.Act1:1:1 | 163 | 508327 | 158227 | 17193 |
| pMON25455 | EXP-Os.Act1:1:9 | 179 | 460579 | 183955 | 53813 |
| pMON122605 | EXP-Os.TubA-3:1:1 | 165 | 25082 | 25821 | 21004 |
| pMON136264 | EXP-ANDge.Ubq1:1:7 | 5 | 926083 | 101213 | 23704 |
| pMON136259 | EXP-ANDge.Ubq1:1:6 | 12 | 845274 | 193153 | 51479 |
| pMON136263 | EXP-ERIra.Ubq1:1:9 | 22 | 901985 | 132765 | 41313 |
| pMON136258 | EXP-ERIra.Ubq1:1:8 | 27 | 1011447 | 210635 | 66803 |

To compare the relative activity of each EXP sequence, GUS values were expressed as a ratio of GUS to luciferase activity and normalized with respect to the expression levels observed for the EXP sequence EXP-Os.TubA-3:1:1 (SEQ ID NO: 165). Table 5 below shows the GUS/RLuc ratios of expression normalized with respect to EXP-Os.TubA-3:1:1 expression in corn protoplasts.

As can be seen in Table 5, GUS expression, driven by EXP-ANDge.Ubq1:1:7 (SEQ ID NO: 5), EXP-ANDge.Ubq1:1:6 (SEQ ID NO: 12), EXP-ERIra.Ubq1:1:9 (SEQ ID NO: 22) or EXP-ERIra.Ubq1:1:8 (SEQ ID NO: 27) was 4.51 to 9.42 fold higher than GUS expression driven by EXP-Os.TubA-3:1:1 (SEQ ID NO: 165). GUS expression driven by EXP-ANDge.Ubq1:1:7 (SEQ ID NO: 5), EXP-ANDge.Ubq1:1:6 (SEQ ID NO: 12), EXP-ERIra.Ubq1:1:9 (SEQ ID NO: 22) or EXP-ERIra.Ubq1:1:8 (SEQ ID NO: 27) was also higher than that of EXP-CaMV.35S-enh+Zm.DnaK:1:1 (SEQ ID NO: 170), EXP-CaMV.35S-enh+Ta.Lhcb1+Os.Act1:1:1 (SEQ ID NO: 163), or EXP-Os.Act1:1:9 (SEQ ID NO: 179).

TABLE 5

GUS/RLuc fold expression as relative to EXP-Os.TubA-3:1:1 expression in corn leaf protoplast cells.

| Plasmid | EXP sequence | SEQ ID NO: | Gus/RLuc | Gus/RLuc Normalized with respect to EXP-Os.TubA-3:1:1 |
|---|---|---|---|---|
| pMON19469 | EXP-CaMV.35S-enh + Zm.DnaK:1:1 | 170 | 2.640000 | 2.72 |
| pMON65328 | EXP-CaMV.35S-enh + Ta.Lhcb1 + Os.Act1:1:1 | 163 | 3.210000 | 3.31 |
| pMON25455 | EXP-Os.Act1:1:9 | 179 | 2.500000 | 2.57 |
| pMON122605 | EXP-Os.TubA-3:1:1 | 165 | 0.971000 | 1.00 |
| pMON136264 | EXP-ANDge.Ubq1:1:7 | 5 | 9.150000 | 9.42 |
| pMON136259 | EXP-ANDge.Ubq1:1:6 | 12 | 4.380000 | 4.51 |
| pMON136263 | EXP-ERIra.Ubq1:1:9 | 22 | 6.790000 | 6.99 |
| pMON136258 | EXP-ERIra.Ubq1:1:8 | 27 | 4.800000 | 4.94 |

Table 6 below show GUS/FLuc ratios of expression normalized with respect to EXP-Os.TubA-3:1:1 expression in corn protoplasts.

TABLE 6

GUS/FLuc fold expression as relative to EXP-Os.TubA-3:1:1 expression in corn leaf protoplast cells.

| Plasmid | EXP sequence | SEQ ID NO: | Gus/FLuc | Normalized with respect to EXP-Os.TubA-3:1:1 |
|---|---|---|---|---|
| pMON19469 | EXP-CaMV.35S-enh + Zm.DnaK:1:1 | 170 | 21.600000 | 18.15 |
| pMON65328 | EXP-CaMV.35S-enh + Ta.Lhcb1 + Os.Act1:1:1 | 163 | 29.600000 | 24.87 |
| pMON25455 | EXP-Os.Act1:1:9 | 179 | 8.560000 | 7.19 |
| pMON122605 | EXP-Os.TubA-3:1:1 | 165 | 1.190000 | 1.00 |
| pMON136264 | EXP-ANDge.Ubq1:1:7 | 5 | 39.100000 | 32.86 |
| pMON136259 | EXP-ANDge.Ubq1:1:6 | 12 | 16.400000 | 13.78 |
| pMON136263 | EXP-ERIra.Ubq1:1:9 | 22 | 21.800000 | 18.32 |
| pMON136258 | EXP-ERIra.Ubq1:1:8 | 27 | 15.100000 | 12.69 |

As can be seen in Table 6, GUS expression, driven by EXP-ANDge.Ubq1:1:7 (SEQ ID NO: 5), EXP-ANDge.Ubq1:1:6 (SEQ ID NO: 12), EXP-ERIra.Ubq1:1:9 (SEQ ID NO: 22) or EXP-ERIra.Ubq1:1:8 (SEQ ID NO: 27) demonstrated the same general trend when expressed as ratio of GUS/FLuc values and is normalized with respect to EXP-Os.TubA-3:1:1 (SEQ ID NO: 165). Expression was 12.69 to 32.86 fold higher than GUS expression driven by EXP-Os.TubA-3:1:1 (SEQ ID NO: 165). GUS expression driven by EXP-ANDge.Ubq1:1:7 (SEQ ID NO: 5), EXP-ANDge.Ubq1:1:6 (SEQ ID NO: 12), EXP-ERIra.Ubq1:1:9 (SEQ ID NO: 22) or EXP-ERIra.Ubq1:1:8 (SEQ ID NO: 27) was also higher in certain comparisons than that of EXP-CaMV.35S-enh+Zm.DnaK:1:1 (SEQ ID NO: 170), EXP-CaMV.35S-enh+Ta.Lhcb1+Os.Act1:1:1 (SEQ ID NO: 163), or EXP-Os.Act1:1:9 (SEQ ID NO: 179).

Example 3: Analysis of Regulatory Elements Driving GUS in Corn Protoplasts Using GUS Transgene Cassette Amplicons Corn leaf protoplasts were transformed with DNA amplicons derived from plant expression vectors containing an EXP sequence, driving expression of the β-glucuronidase (GUS) transgene, and compared to leaf protoplast in which expression of GUS is driven by known constitutive promoters in a series of experiments presented below.

In a first set of experiments, corn protoplast cells, derived from leaf tissue were transformed as above with amplicons produced from amplification of GUS transgene cassettes comprising plant expression vectors to compare expression of a transgene (GUS) driven by one of EXP-ANDge.Ubq1:1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sv.Ubq1:1:7 (SEQ ID NO: 128), EXP-Sv.Ubq1:1:8 (SEQ ID NO: 132), EXP-Sv.Ubq1:1:10 (SEQ ID NO: 134), EXP-Zm.UbgM1:1:6 (SEQ ID NO: 137), EXP-Zm.UbgM1:1:7 (SEQ ID NO: 141), EXP-Sb.Ubg4:1:2 (SEQ ID NO: 151), EXP-Sb.Ubg6:1:2 (SEQ ID NO: 153) and EXP-Cl.Ubq1:1:10 (SEQ ID NO: 98) with that of known constitutive promoters. Each EXP sequence comprising the amplification template from which the transgene cassette amplicon is produced was cloned using methods known in the art into a plant expression vector shown in Table 7 below under the heading of "Amplicon Template." The resulting plant expression vectors comprise a transgene cassette comprised of a EXP sequence, operably linked 5' to a coding sequence for β-glucuronidase (GUS) that either contains a processable intron ("GUS-2" as discussed in Example 2 above), or a contiguous GUS coding sequence ("GUS-1", as discussed above), operably linked 5' to a 3' UTR T-AGRtu.nos-1:1:13 or T-Ta.Hsp17-1:1:1, as also noted above. Amplicons were produced using methods known to those skilled in the art using the plasmid construct templates presented in Table 7 below. Briefly, a 5' oligonucleotide primer was designed to anneal to the promoter sequence and a 3' oligonucleotide primer, which anneals at the 3' end of the 3' UTR was used for amplification of each transgene cassette. Successive 5' deletions were introduced into the promoter sequences comprising the transgene cassettes, giving rise to different EXP sequences, by the use of different oligonucleotide primers which were designed to anneal at different positions within the promoter sequence comprising each amplicon template.

TABLE 7

GUS plant expression amplicons and corresponding plasmid construct amplicon templates, EXP sequence, GUS coding sequence and 3' UTR used for transformation of corn leaf protoplasts.

| Amplicon ID | Amplicon Template | EXP sequence | SEQ ID NO: | GUS Coding Sequence | 3' UTR |
|---|---|---|---|---|---|
| PCR0145942 | pMON25455 | EXP-Os.Act1:1:9 | 179 | GUS-1 | T-AGRtu.nos-1:1:13 |
| PCR0145941 | pMON33449 | P-CAMV.35S-ENH-1:1:102/L-CAMV.35S-1:1:2 | 169 | GUS-1 | T-AGRtu.nos-1:1:13 |
| PCR0145943 | pMON65328 | EXP-CaMV.35S-enh + Ta.Lhcb1 + Os.Act1:1:1 | 163 | GUS-2 | T-Ta.Hsp17-1:1:1 |
| PCR0145944 | pMON81552 | EXP-CaMV.35S-enh + Zm.DnaK:1:1 | 170 | GUS-1 | T-AGRtu.nos-1:1:13 |
| PCR0145892 | pMON136264 | EXP-ANDge.Ubq1:1:7 | 5 | GUS-1 | T-AGRtu.nos-1:1:13 |
| PCR0145815 | pMON136264 | EXP-ANDge.Ubq1:1:10 | 10 | GUS-1 | T-AGRtu.nos-1:1:13 |
| PCR0145893 | pMON136259 | EXP-ANDge.Ubq1:1:6 | 12 | GUS-1 | T-AGRtu.nos-1:1:13 |
| PCR0145817 | pMON136264 | EXP-ANDge.Ubq1:1:11 | 14 | GUS-1 | T-AGRtu.nos-1:1:13 |
| PCR0145819 | pMON136264 | EXP-ANDge.Ubq1:1:12 | 16 | GUS-1 | T-AGRtu.nos-1:1:13 |
| PCR0145896 | pMON136263 | EXP-ERIra.Ubq1:1:9 | 22 | GUS-1 | T-AGRtu.nos-1:1:13 |
| PCR0145820 | pMON136263 | EXP-ERIra.Ubq1:1:10 | 25 | GUS-1 | T-AGRtu.nos-1:1:13 |
| PCR0145897 | pMON136258 | EXP-ERIra.Ubq1:1:8 | 27 | GUS-1 | T-AGRtu.nos-1:1:13 |
| PCR0145821 | pMON136263 | EXP-ERIra.Ubq1:1:11 | 29 | GUS-1 | T-AGRtu.nos-1:1:13 |
| PCR0145822 | pMON136263 | EXP-ERIra.Ubq1:1:12 | 31 | GUS-1 | T-AGRtu.nos-1:1:13 |
| PCR0145900 | pMON140877 | EXP-SETit.Ubq1:1:5 | 117 | GUS-1 | T-AGRtu.nos-1:1:13 |
| PCR0145928 | pMON140877 | EXP-SETit.Ubq1:1:7 | 123 | GUS-1 | T-AGRtu.nos-1:1:13 |
| PCR0145905 | pMON140877 | EXP-SETit.Ubq1:1:6 | 124 | GUS-1 | T-AGRtu.nos-1:1:13 |
| PCR0145909 | pMON140878 | EXP-Sv.Ubq1:1:7 | 128 | GUS-1 | T-AGRtu.nos-1:1:13 |
| PCR0145929 | pMON140878 | EXP-Sv.Ubq1:1:8 | 132 | GUS-1 | T-AGRtu.nos-1:1:13 |

TABLE 7-continued

GUS plant expression amplicons and corresponding plasmid construct amplicon templates, EXP sequence, GUS coding sequence and 3' UTR used for transformation of corn leaf protoplasts.

| Amplicon ID | Amplicon Template | EXP sequence | SEQ ID NO: | GUS Coding Sequence | 3' UTR |
|---|---|---|---|---|---|
| PCR0145911 | pMON140878 | EXP-Sv.Ubq1:1:10 | 134 | GUS-1 | T-AGRtu.nos-1:1:13 |
| PCR0145914 | pMON140881 | EXP-Zm.UbqM1:1:6 | 137 | GUS-1 | T-AGRtu.nos-1:1:13 |
| PCR0145915 | pMON140882 | EXP-Zm.UbqM1:1:7 | 141 | GUS-1 | T-AGRtu.nos-1:1:13 |
| PCR0145921 | pMON140886 | EXP-Sb.Ubq4:1:2 | 151 | GUS-1 | T-AGRtu.nos-1:1:13 |
| PCR0145920 | pMON140887 | EXP-Sb.Ubq6:1:2 | 153 | GUS-1 | T-AGRtu.nos-1:1:13 |
| PCR0145922 | pMON140889 | EXP-Cl.Ubq1:1:10 | 98 | GUS-1 | T-AGRtu.nos-1:1:13 |

Plasmid constructs listed as amplicon templates in Table 7 served as templates for amplification of transgene expression cassettes comprising the listed EXP sequences of Table 7. Control plasmids used to generate GUS transgene amplicons for comparison were constructed as previously described with known constitutive EXP sequences described in Example 2. Negative controls for determination of GUS and luciferase background, a no DNA control, and a control sample in which the two luciferase plasmids are used in transformation along with a plasmid DNA that does not express a coding sequence were also used. Plasmids pMON19437 and pMON63934, as discussed in Example 2, were also employed for co-transformation and normalization of data.

Corn leaf protoplasts were transformed using a PEG-based transformation method as described in Example 2, above. Table 8 below shows the average GUS and luciferase expression values determined for each transgene cassette.

TABLE 8

Mean GUS and Luciferase activity in transformed corn leaf protoplast cells.

| EXP sequence | SEQ ID NO: | GUS | RLuc | FLuc |
|---|---|---|---|---|
| EXP-Os.Act1:1:9 | 179 | 1540.3 | 105416.8 | 2671.8 |
| P-CAMV.35S-ENH-1:1:102/L-CAMV.35S-1:1:2 | 169 | 10426.3 | 344088.6 | 8604.1 |
| EXP-CaMV.35S-enh + Ta.Lhcb1 + Os.Act1:1:1 | 163 | 12530.8 | 137722.6 | 3067.1 |
| EXP-CaMV.35S-enh + Zm.DnaK:1:1 | 170 | 61036.1 | 208125.3 | 5787.6 |
| EXP-ANDge.Ubq1:1:7 | 5 | 59447.4 | 84667.6 | 2578.4 |
| EXP-ANDge.Ubq1:1:10 | 10 | 40123.3 | 76753.8 | 2419.8 |
| EXP-ANDge.Ubq1:1:6 | 12 | 42621.0 | 121751.3 | 3974.8 |
| EXP-ANDge.Ubq1:1:11 | 14 | 44358.5 | 87105.8 | 2687.1 |
| EXP-ANDge.Ubq1:1:12 | 16 | 48219.0 | 107762.1 | 3279.6 |
| EXP-ERIra.Ubq1:1:9 | 22 | 31253.0 | 171684.1 | 6476.1 |
| EXP-ERIra.Ubq1:1:10 | 25 | 7905.8 | 21235.6 | 462.4 |
| EXP-ERIra.Ubq1:1:8 | 27 | 39935.8 | 173766.6 | 5320.3 |
| EXP-ERIra.Ubq1:1:11 | 29 | 34141.3 | 111626.8 | 3377.6 |
| EXP-ERIra.Ubq1:1:12 | 31 | 11540.3 | 42362.1 | 1045.3 |
| EXP-SETit.Ubq1:1:5 | 117 | 20496.5 | 88695.8 | 2358.8 |
| EXP-SETit.Ubq1:1:7 | 123 | 75728.5 | 185223.8 | 4723.1 |

TABLE 8-continued

Mean GUS and Luciferase activity in transformed corn leaf protoplast cells.

| EXP sequence | SEQ ID NO: | GUS | RLuc | FLuc |
|---|---|---|---|---|
| EXP-SETit.Ubq1:1:6 | 124 | 44148.3 | 161216.3 | 4962.1 |
| EXP-Sv.Ubq1:1:7 | 128 | 15043.8 | 74670.6 | 1888.3 |
| EXP-Sv.Ubq1:1:8 | 132 | 31997.8 | 113787.1 | 3219.8 |
| EXP-Sv.Ubq1:1:10 | 134 | 38952.8 | 220208.6 | 7011.3 |
| EXP-Zm.UbqM1:1:6 | 137 | 30528.3 | 90113.1 | 2453.6 |
| EXP-Zm.UbqM1:1:7 | 141 | 34986.3 | 105724.7 | 2553.8 |
| EXP-Sb.Ubq4:1:2 | 151 | 9982.3 | 72593.8 | 2171.6 |
| EXP-Sb.Ubq6:1:2 | 153 | 33689.0 | 114709.6 | 3879.6 |
| EXP-Cl.Ubq1:1:10 | 98 | 50622.3 | 107084.3 | 2621.3 |

To compare the relative activity of each EXP sequence GUS values were expressed as a ratio of GUS to luciferase activity and normalized with respect to the expression levels observed for EXP-Os.Act1:1:1 and EXP-CaMV.35S-enh+Ta.Lhcb1+Os.Act1:1:1. Table 9 below shows the GUS/RLuc ratios of expression normalized with respect to EXP-Os.Act1:1:1 and EXP-CaMV.35S-enh+Ta.Lhcb1+Os.Act1:1:1 driven expression in corn protoplasts. Table 10 below shows the GUS/FLuc ratios of expression normalized with respect to EXP-Os.Act1:1:1 and EXP-CaMV.35S-enh+Ta.Lhcb1+Os.Act1:1:1 driven expression in corn protoplasts.

TABLE 9

GUS/RLuc and GUS/FLuc ratios of expression normalized with respect to EXP-CaMV.35S-enh + Ta.Lhcb1 + Os.Act1:1:1 (SEQ ID NO: 163) in corn protoplasts.

| EXP sequence | SEQ ID NO: | GUS/RLuc Relative to EXP-CaMV.35S-enh + Ta.Lhcb1 + Os.Act1:1:1 | GUS/FLuc Relative to EXP-CaMV.35S-enh + Ta.Lhcb1 + Os.Act1:1:1 |
|---|---|---|---|
| EXP-Os.Act1:1:9 | 179 | 0.16 | 0.14 |
| P-CAMV.35S-ENH-1:1:102/L-CAMV.35S-1:1:2 | 169 | 0.33 | 0.30 |

TABLE 9-continued

GUS/RLuc and GUS/FLuc ratios of expression normalized with respect to EXP-CaMV.35S-enh + Ta.Lhcb1 + Os.Act1:1:1 (SEQ ID NO: 163) in corn protoplasts.

| EXP sequence | SEQ ID NO: | GUS/RLuc Relative to EXP-CaMV.35S-enh + Ta.Lhcb1 + Os.Act1:1:1 | GUS/FLuc Relative to EXP-CaMV.35S-enh + Ta.Lhcb1 + Os.Act1:1:1 |
|---|---|---|---|
| EXP-CaMV.35S-enh + Ta.Lhcb1 + Os.Act1:1:1 | 163 | 1.00 | 1.00 |
| EXP-CaMV.35S-enh + Zm.DnaK:1:1 | 170 | 3.22 | 2.58 |
| EXP-ANDge.Ubq1:1:7 | 5 | 7.72 | 5.64 |
| EXP-ANDge.Ubq1:1:10 | 10 | 5.75 | 4.06 |
| EXP-ANDge.Ubq1:1:6 | 12 | 3.85 | 2.62 |
| EXP-ANDge.Ubq1:1:11 | 14 | 5.60 | 4.04 |
| EXP-ANDge.Ubq1:1:12 | 16 | 4.92 | 3.60 |
| EXP-ERIra.Ubq1:1:9 | 22 | 2.00 | 1.18 |
| EXP-ERIra.Ubq1:1:10 | 25 | 4.09 | 4.18 |
| EXP-ERIra.Ubq1:1:8 | 27 | 2.53 | 1.84 |
| EXP-ERIra.Ubq1:1:11 | 29 | 3.36 | 2.47 |
| EXP-ERIra.Ubq1:1:12 | 31 | 2.99 | 2.70 |
| EXP-SETit.Ubq1:1:5 | 117 | 2.54 | 2.13 |
| EXP-SETit.Ubq1:1:7 | 123 | 4.49 | 3.92 |
| EXP-SETit.Ubq1:1:6 | 124 | 3.01 | 2.18 |
| EXP-Sv.Ubq1:1:7 | 128 | 2.21 | 1.95 |
| EXP-Sv.Ubq1:1:8 | 132 | 3.09 | 2.43 |
| EXP-Sv.Ubq1:1:10 | 134 | 1.94 | 1.36 |
| EXP-Zm.UbqM1:1:6 | 137 | 3.72 | 3.05 |
| EXP-Zm.UbqM1:1:7 | 141 | 3.64 | 3.35 |
| EXP-Sb.Ubq4:1:2 | 151 | 1.51 | 1.13 |
| EXP-Sb.Ubq6:1:2 | 153 | 3.23 | 2.13 |
| EXP-Cl.Ubq1:1:10 | 98 | 5.20 | 4.73 |

TABLE 10

GUS/RLuc and GUS/FLuc ratios of expression normalized with respect to EXP-Os.Act1:1:9 (SEQ ID NO: 179) in corn leaf protoplasts.

| EXP sequence | SEQ ID NO: | GUS/RLuc Relative to EXP-Os.Act1:1:9 | GUS/FLuc Relative to EXP-Os.Act1:1:9 |
|---|---|---|---|
| EXP-Os.Act1:1:9 | 179 | 1.00 | 1.00 |
| P-CAMV.35S-ENH-1:1:102/L-CAMV.35S-1:1:2 | 169 | 2.07 | 2.10 |
| EXP-CaMV.35S-enh + Ta.Lhcb1 + Os.Act1:1:1 | 163 | 6.23 | 7.09 |
| EXP-CaMV.35S-enh + Zm.DnaK:1:1 | 170 | 20.07 | 18.29 |
| EXP-ANDge.Ubq1:1:7 | 5 | 48.05 | 39.99 |
| EXP-ANDge.Ubq1:1:10 | 10 | 35.78 | 28.76 |
| EXP-ANDge.Ubq1:1:6 | 12 | 23.96 | 18.60 |
| EXP-ANDge.Ubq1:1:11 | 14 | 34.85 | 28.64 |
| EXP-ANDge.Ubq1:1:12 | 16 | 30.62 | 25.50 |
| EXP-ERIra.Ubq1:1:9 | 22 | 12.46 | 8.37 |
| EXP-ERIra.Ubq1:1:10 | 25 | 25.48 | 29.66 |
| EXP-ERIra.Ubq1:1:8 | 27 | 15.73 | 13.02 |
| EXP-ERIra.Ubq1:1:11 | 29 | 20.93 | 17.53 |
| EXP-ERIra.Ubq1:1:12 | 31 | 18.64 | 19.15 |
| EXP-SETit.Ubq1:1:5 | 117 | 15.82 | 15.07 |
| EXP-SETit.Ubq1:1:7 | 123 | 27.98 | 27.81 |
| EXP-SETit.Ubq1:1:6 | 124 | 18.74 | 15.43 |

TABLE 10-continued

GUS/RLuc and GUS/FLuc ratios of expression normalized with respect to EXP-Os.Act1:1:9 (SEQ ID NO: 179) in corn leaf protoplasts.

| EXP sequence | SEQ ID NO: | GUS/RLuc Relative to EXP-Os.Act1:1:9 | GUS/FLuc Relative to EXP-Os.Act1:1:9 |
|---|---|---|---|
| EXP-Sv.Ubq1:1:7 | 128 | 13.79 | 13.82 |
| EXP-Sv.Ubq1:1:8 | 132 | 19.25 | 17.24 |
| EXP-Sv.Ubq1:1:10 | 134 | 12.11 | 9.64 |
| EXP-Zm.UbqM1:1:6 | 137 | 23.19 | 21.58 |
| EXP-Zm.UbqM1:1:7 | 141 | 22.65 | 23.76 |
| EXP-Sb.Ubq4:1:2 | 151 | 9.41 | 7.97 |
| EXP-Sb.Ubq6:1:2 | 153 | 20.10 | 15.06 |
| EXP-Cl.Ubq1:1:10 | 98 | 32.35 | 33.50 |

As can be seen in Tables 9 and 10, nearly all of the EXP sequences were capable of driving GUS transgene expression in corn cells. Average GUS expression was higher for EXP-ANDge.Ubq1:1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sv.Ubq1:1:7 (SEQ ID NO: 128), EXP-Sv.Ubq1:1:8 (SEQ ID NO: 132), EXP-Sv.Ubq1:1:10 (SEQ ID NO: 134), EXP-Zm.UbgM1:1:6 (SEQ ID NO: 137), EXP-Zm.UbgM1:1:7 (SEQ ID NO: 141), EXP-Sb.Ubg4:1:2 (SEQ ID NO: 151), EXP-Sb.Ubg6:1:2 (SEQ ID NO: 153) and EXP-Cl.Ubq1:1:10 (SEQ ID NO: 98) when compared to GUS expression driven by EXP-Os.Act1:1:1 or EXP-CaMV.35S-enh+Ta.Lhcb1+Os.Act1:1:1.

In a second set of experiments, a GUS cassette amplicon comprising the EXP sequence EXP-Zm.UbgM1:1:8 (SEQ ID NO: 145) was compared to the control amplicons, PCR0145942 (EXP-Os.Act1:1:9, SEQ ID NO: 179) and PCR0145944 (EXP-CaMV.35S-enh+Zm.DnaK:1:1, SEQ ID NO: 170) with respect to GUS expression. GUS expression driven by the EXP sequence EXP-Zm.UbgM1:1:8 was higher than that of the two controls. Table 11 below shows the mean GUS and luciferase values determined for each amplicon. Table 12 below shows the GUS/RLuc and GUS/FLuc ratios of expression normalized with respect to EXP-Os.Act1:1:9 and EXP-CaMV.35S-enh+Zm.DnaK:1:1 driven expression in corn protoplasts.

TABLE 11

Mean GUS and Luciferase activity in transformed corn leaf protoplast cells.

| Amplicon | EXP sequence | SEQ ID NO: | GUS | RLuc | FLuc |
|---|---|---|---|---|---|
| PCR0145942 | EXP-Os.Act1:1:9 | 179 | 1512.25 | 190461 | 11333.8 |
| PCR0145944 | EXP-CaMV.35S-enh + Zm.DnaK:1:1 | 170 | 41176.5 | 330837 | 13885.8 |
| PCR0145916 | EXP-Zm.UbqM1:1:8 | 145 | 79581.5 | 330756 | 15262.5 |

TABLE 12

GUS/RLuc and GUS/FLuc ratios of expression normalized with respect to EXP-Os.Act1:1:9 (SEQ ID NO: 179) and EXP-CaMV.35S-enh + Zm.DnaK:1:1 (SEQ ID NO: 170) in corn leaf protoplasts.

| EXP sequence | SEQ ID NO: | GUS/RLuc relative to EXP-Os.Act1:1:9 | GUS/FLuc relative to EXP-Os.Act1:1:9 | GUS/RLuc relative to EXP-CaMV.35S-enh + Zm.DnaK:1:1 | GUS/FLuc relative to EXP-CaMV.35S-enh + Zm.DnaK:1:1 |
|---|---|---|---|---|---|
| EXP-Os.Act1:1:9 | 179 | 1.00 | 1.00 | 0.06 | 0.04 |
| EXP-CaMV.35S-enh + Zm.DnaK:1:1 | 170 | 15.68 | 22.22 | 1.00 | 1.00 |
| EXP-Zm.UbqM1:1:8 | 145 | 30.30 | 39.08 | 1.93 | 1.76 |

In a third set of experiments, amplicon GUS transgene cassettes were made as described above and assayed for expression driven by the EXP sequences, EXP-ANDge.Ubq1:1:8 (SEQ ID NO: 8), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116). The amplicons were comprised of an EXP sequence operably linked to the GUS-1 coding sequence which was operably linked to the T-AGRtu.nos-1:1:13 3' UTR. Expression was compared to the controls EXP-Os.Act1:1:9 (SEQ ID NO: 179) and EXP-CaMV.35S-enh+Zm.DnaK:1:1 (SEQ ID NO: 170). Table 13 below shows the mean GUS and luciferase values determined for each amplicon. Table 14 below shows the GUS/RLuc ratios of expression normalized with respect to EXP-Os.Act1:1:9 and EXP-CaMV.35S-enh+Zm.DnaK:1:1 driven expression in corn protoplasts.

TABLE 13

Mean GUS and Luciferase activity in transformed corn leaf protoplast cells.

| Amplicon ID | EXP sequence | SEQ ID NO: | GUS | RLuc |
|---|---|---|---|---|
| PCR0145942 | EXP-Os.Act1:1:9 | 179 | 9445.25 | 929755 |
| PCR0145944 | EXP-CaMV.35S-enh+ Zm.DnaK:1:1 | 170 | 78591.25 | 445127 |
| PCR0146628 | EXP-ANDge.Ubq1:1:8 | 8 | 192056.75 | 972642 |
| PCR0145922 | EXP-Cl.Ubq1:1:10 | 98 | 175295.25 | 395563 |
| PCR0145945 | EXP-Cl.Ubq1:1:13 | 114 | 173674.5 | 402966 |
| PCR0145946 | EXP-Cl.Ubq1:1:14 | 115 | 185987.5 | 390052 |
| PCR0145947 | EXP-Cl.Ubq1:1:15 | 116 | 9435 | 320749 |

TABLE 14

GUS/RLuc and GUS/FLuc ratios of expression normalized with respect to EXP-Os.Act1:1:9 (SEQ ID NO: 179) and EXP-CaMV.35S-enh+Zm.DnaK:1:1 (SEQ ID NO: 170) in corn leaf protoplasts.

| EXP sequence | SEQ ID NO: | GUS/RLuc relative to EXP-Os.Act1:1:9 | GUS/RLuc relative to EXP-CaMV.35S-enh + Zm.DnaK:1:1 |
|---|---|---|---|
| EXP-Os.Act1:1:9 | 179 | 1.00 | 0.06 |
| EXP-CaMV.35S-enh+Zm.DnaK:1:1 | 170 | 17.38 | 1.00 |
| EXP-ANDge.Ubq1:1:8 | 8 | 19.44 | 1.12 |
| EXP-Cl.Ubq1:1:10 | 98 | 43.62 | 2.51 |

TABLE 14-continued

GUS/RLuc and GUS/FLuc ratios of expression normalized with respect to EXP-Os.Act1:1:9 (SEQ ID NO: 179) and EXP-CaMV.35S-enh+Zm.DnaK:1:1 (SEQ ID NO: 170) in corn leaf protoplasts.

| EXP sequence | SEQ ID NO: | GUS/RLuc relative to EXP-Os.Act1:1:9 | GUS/RLuc relative to EXP-CaMV.35S-enh + Zm.DnaK:1:1 |
|---|---|---|---|
| EXP-Cl.Ubq1:1:13 | 114 | 42.43 | 2.44 |
| EXP-Cl.Ubq1:1:14 | 115 | 46.94 | 2.70 |
| EXP-Cl.Ubq1:1:15 | 116 | 2.90 | 0.17 |

As can be seen in Table 14 above, the EXP sequences EXP-ANDge.Ubq1:1:8 (SEQ ID NO: 8), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) are capable of driving transgene expression. Expression driven by EXP-ANDge.Ubq1:1:8 (SEQ ID NO: 8), EXP-Cl.Ubq1:1:10 (SEQ ID NO: 98), EXP-Cl.Ubq1:1:13 (SEQ ID NO: 114) and EXP-Cl.Ubq1:1:14 (SEQ ID NO: 115) was higher than that of both controls. Expression driven by EXP-Cl.Ubq1:1:15 (SEQ ID NO: 116) was lower than EXP-CaMV.35S-enh+Zm.DnaK:1:1 (SEQ ID NO: 170) but higher than the control, EXP-Os.Act1:1:9 (SEQ ID NO: 179).

In a fourth set of experiments, amplicon GUS transgene cassettes were made as described above and assayed for expression driven by the EXP sequences, EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97). Expression was compared to the controls EXP-Os.Act1:1:9 (SEQ ID NO: 179) and EXP-CaMV.35S-enh+Zm.DnaK:1:1 (SEQ ID NO: 170). Table 15 below shows the mean GUS and luciferase values determined for each amplicon. Table 16 below shows the GUS/RLuc and GUS/FLuc ratios of expression normalized with respect to EXP-Os.Act1:1:9 and EXP-CaMV.35S-enh+Zm.DnaK:1:1 driven expression in corn protoplasts.

TABLE 15

Mean GUS and Luciferase activity in transformed corn leaf protoplast cells.

| Amplicon ID | EXP sequence | SEQ ID NO: | GUS | RLuc | FLuc |
|---|---|---|---|---|---|
| PCR0145942 | EXP-Os.Act1:1:9 | 179 | 5333.5 | 171941.75 | 77817.88 |
| PCR0145944 | EXP-CaMV.35S-enh+Zm.DnaK:1:1 | 170 | 88517 | 177260.25 | 54207.38 |
| PCR0145922 | EXP-Cl.Ubq1:1:10 | 98 | 130125.75 | 194216 | 32055 |
| pMON146750 | EXP-Cl.Ubq1:1:16 | 93 | 134101.75 | 182317.5 | 32434.5 |
| pMON146751 | EXP-Cl.Ubq1:1:17 | 97 | 107122.5 | 151783.25 | 51354.38 |

TABLE 16

GUS/RLuc and GUS/FLuc ratios of expression normalized with respect to EXP-Os.Act1:1:9 (SEQ ID NO: 179) and EXP-CaMV.35S-enh+Zm.DnaK:1:1 (SEQ ID NO: 170) in corn leaf protoplasts.

| Amplicon ID | EXP sequence | SEQ ID NO: | GUS/RLuc relative to EXP-Os.Act1:1:9 | GUS/FLuc relative to EXP-Os.Act1:1:9 | GUS/RLuc relative to EXP-CaMV.35S-enh+Zm.DnaK:1:1 | GUS/FLuc relative to EXP-CaMV.35S-enh+Zm.DnaK:1:1 |
|---|---|---|---|---|---|---|
| PCR0145942 | EXP-Os.Act1:1:9 | 179 | 1.00 | 1.00 | 0.06 | 0.04 |
| PCR0145944 | EXP-CaMV.35S-enh+Zm.DnaK:1:1 | 170 | 16.10 | 23.83 | 1.00 | 1.00 |
| PCR0145922 | EXP-Cl.Ubq1:1:10 | 98 | 21.60 | 59.23 | 1.34 | 2.49 |
| pMON146750 | EXP-Cl.Ubq1:1:16 | 93 | 23.71 | 60.32 | 1.47 | 2.53 |
| PMON146751 | EXP-Cl.Ubq1:1:17 | 97 | 22.75 | 30.43 | 1.41 | 1.28 |

As can be seen in Table 16, the EXP sequences EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97) were able to drive transgene expression. Expression driven by each of the EXP sequences was higher than that of both controls.

In a fifth set of experiments, amplicon GUS transgene cassettes were made as described above assay expression driven by the EXP sequences, EXP-Zm.UbqM1:1:11 (SEQ ID NO: 149) and EXP-Cl.Ubq1:1:23 (SEQ ID NO: 108). Expression was compared to the controls EXP-Os.Act1:1:9 (SEQ ID NO: 179) and EXP-CaMV.35S-enh+Ta.Lhcb1+Os.Act1:1:1 (SEQ ID NO: 163). Table 17 below shows the mean GUS and luciferase values determined for each amplicon. Table 18 below shows the GUS/RLuc ratios of expression normalized with respect to EXP-Os.Act1:1:9 and EXP-CaMV.35S-enh+Ta.Lhcb1+Os.Act1:1:1 driven expression in corn protoplasts.

TABLE 17

Mean GUS and Luciferase activity in transformed corn leaf protoplast cells.

| Template | Amplicon | EXP sequence | SEQ ID NO: | GUS | RLuc |
|---|---|---|---|---|---|
| PMON65328 | PCR0145943 | EXP-CaMV.35S-enh+Ta.Lhcb1+Os.Act1:1:1 | 163 | 70352.00 | 79028.75 |
| pMON25455 | PCR0145942 | EXP-Os.Act1:1:9 | 179 | 33155.25 | 92337.00 |
| pMON131962 | pMON131962 | EXP-Zm.UbqM1:1:11 | 149 | 18814.75 | 33663.00 |
| pMON132047 | pMON132047 | EXP-Cl.Ubq1:1:23 | 108 | 15387.50 | 40995.50 |

TABLE 18

GUS/RLuc ratios of expression normalized with respect to EXP-Os.Act1:1:9 (SEQ ID NO: 179) and EXP-CaMV.35S-enh+Ta.Lhcb1+Os.Act1:1:1 (SEQ ID NO: 163) in corn leaf protoplasts.

| Amplicon | EXP sequence | SEQ ID NO: | GUS/RLuc relative to EXP-Os.Act1:1:9 | GUS/RLuc relative to EXP-CaMV.35S-enh+Ta.Lhcb1+Os.Act1:1:1 |
|---|---|---|---|---|
| PCR0145943 | EXP-CaMV.35S-enh+Ta.Lhcb1+Os.Act1:1:1 | 163 | 2.48 | 1.00 |

TABLE 18-continued

GUS/RLuc ratios of expression normalized with respect to EXP-Os.Act1:1:9 (SEQ ID NO: 179) and EXP-CaMV.35S-enh+Ta.Lhcb1+Os.Act1:1:1 (SEQ ID NO: 163) in corn leaf protoplasts.

| Amplicon | EXP sequence | SEQ ID NO: | GUS/RLuc relative to EXP-Os.Act1:1:9 | GUS/RLuc relative to EXP-CaMV.35S-enh+Ta.Lhcb1+Os.Act1:1:1 |
|---|---|---|---|---|
| PCR0145942 | EXP-Os.Act1:1:9 | 179 | 1.00 | 0.40 |
| pMON131962 | EXP-Zm.UbqM1:1:11 | 149 | 1.56 | 0.63 |
| pMON132047 | EXP-Cl.Ubq1:1:23 | 108 | 1.05 | 0.42 |

As can be seen in Table 18 above, the EXP sequences, EXP-Zm.UbqM1:1:11 (SEQ ID NO: 149) and EXP-Cl.Ubq1:1:23 (SEQ ID NO: 108) were able to drive GUS expression in corn leaf protoplasts. Expression was similar to that of the control, EXP-Os.Act1:1:9 (SEQ ID NO: 179) and lower than that of EXP-CaMV.35S-enh+Ta.Lhcb1+Os.Act1:1:1 (SEQ ID NO: 163).

The efficacy of regulatory elements driving GUS expression from amplicons can be similarly studied in sugarcane leaf protoplasts. For instance, sugarcane protoplasts may be transformed with DNA amplicons derived from plant expression vectors containing an EXP sequence, driving expression of the β-glucuronidase (GUS) transgene, and compared to leaf protoplast in which expression of GUS is driven by known constitutive promoters. Likewise, regulatory elements driving CP4 expression from amplicons in corn or wheat protoplasts may be similarly studied.

Example 4: Analysis of Regulatory Elements Driving GUS in Wheat Protoplasts Using GUS Transgene Cassette Amplicons Wheat leaf protoplasts were transformed with DNA amplicons derived from plant expression vectors containing an EXP sequence, driving expression of the β-glucuronidase (GUS) transgene, and compared to leaf protoplast in which expression of GUS was driven by known constitutive promoters.

Wheat protoplast cells derived from leaf tissue were transformed using methods known in the art with amplicons produced from amplification of GUS transgene cassettes comprising plant expression vectors to compare expression of a transgene (GUS) driven by the EXP sequences listed in Tables 10-11 with that of known constitutive promoters with methodology as described in a previous example (Example 3), using the same GUS cassette amplicons as that used for assay in Corn in Example 3 above. Control GUS cassette amplicons and Luciferase plasmids used for wheat protoplast transformation were also the same as those presented in the previous example and provided in Table 7 above in Example 3. Likewise, negative controls were used for the determination of GUS and luciferase background, as described above. Wheat leaf protoplasts were transformed using a PEG-based transformation method, as described in Example 3 above. Table 19 lists mean GUS and LUC activity seen in transformed wheat leaf protoplast cells, and Table 20 shows normalized GUS/RLuc ratios of expression in wheat protoplasts.

TABLE 19

Mean GUS and Luciferase activity in transformed wheat leaf protoplast cells

| EXP sequence | SEQ ID NO: | GUS | RLuc | GUS/RLuc |
|---|---|---|---|---|
| EXP-Os.Act1:1:9 | 179 | 2976.33 | 53334.8 | 0.0558047 |
| P-CaMV.35S-ENH-1:1:102/L-CaMV.35S-1:1:2 | 169 | 1431.33 | 55996.1 | 0.0255612 |
| EXP-CaMV.35S-enh+Ta.Lhcb1+Os.Act1:1:1 | 163 | 29299.3 | 50717.4 | 0.5776973 |
| EXP-CaMV.35S-enh+Zm.DnaK:1:1 | 170 | 34294.3 | 63307.9 | 0.5417066 |
| EXP-ANDge.Ubq1:1:7 | 5 | 68444.3 | 60329.1 | 1.1345158 |
| EXP-ANDge.Ubq1:1:10 | 10 | 60606.3 | 60659.4 | 0.9991245 |
| EXP-ANDge.Ubq1:1:6 | 12 | 33386.3 | 56712.1 | 0.5886984 |
| EXP-ANDge.Ubq1:1:11 | 14 | 43237.3 | 48263.4 | 0.8958609 |
| EXP-ANDge.Ubq1:1:12 | 16 | 51712.7 | 64702.8 | 0.7992341 |
| EXP-ERIra.Ubq1:1:9 | 22 | 20998.3 | 60273.4 | 0.3483845 |
| EXP-ERIra.Ubq1:1:10 | 25 | 17268.3 | 25465.4 | 0.6781084 |
| EXP-ERIra.Ubq1:1:8 | 27 | 34635.7 | 59467.1 | 0.5824341 |
| EXP-ERIra.Ubq1:1:11 | 29 | 28979 | 56153.8 | 0.516065 |
| EXP-ERIra.Ubq1:1:12 | 31 | 41409.7 | 55152.4 | 0.7508221 |
| EXP-SETit.Ubq1:1:5 | 117 | 39427.7 | 57463.1 | 0.6861388 |
| EXP-SETit.Ubq1:1:7 | 123 | 108091 | 49330.4 | 2.191169 |
| EXP-SETit.Ubq1:1:6 | 124 | 58703 | 46110.1 | 1.2731047 |
| EXP-Sv.Ubq1:1:7 | 128 | 29330 | 43367.1 | 0.676319 |
| EXP-Sv.Ubq1:1:8 | 132 | 53359 | 40076.4 | 1.3314306 |
| EXP-Sv.Ubq1:1:10 | 134 | 49122.7 | 53180.8 | 0.9236922 |
| EXP-Zm.UbqM1:1:6 | 137 | 37268 | 54088.1 | 0.6890239 |
| EXP-Zm.UbqM1:1:7 | 141 | 51408 | 47297.4 | 1.0869087 |
| EXP-Sb.Ubq4:1:2 | 151 | 35660.3 | 62591.1 | 0.5697347 |
| EXP-Sb.Ubq6:1:2 | 153 | 27543 | 57826.4 | 0.4763046 |
| EXP-Cl.Ubq1:1:10 | 98 | 54493.3 | 41964.1 | 1.2985699 |

TABLE 20

GUS/RLuc ratios of expression normalized with respect to EXP-Os.Act1:1:9 (SEQ ID NO: 179) and EXP-CaMV.35S-enh+Ta.Lhcb1+Os.Act1:1:1 (SEQ ID NO: 163) in wheat leaf protoplasts.

| EXP sequence | SEQ ID NO: | GUS/RLuc Relative to EXP-Os.Act1:1:9 | GUS/RLuc Relative to EXP-CaMV.35S-enh+Ta.Lhcb1+Os.Act1:1:1 |
|---|---|---|---|
| EXP-Os.Act1:1:9 | 179 | 1.00 | 0.10 |
| P-CaMV.35S-ENH-1:1:102/L-CaMV.35S-1:1:2 | 169 | 0.46 | 0.04 |

TABLE 20-continued

GUS/RLuc ratios of expression normalized with respect to EXP-Os.Act1:1:9 (SEQ ID NO: 179) and EXP-CaMV.35S-enh+Ta.Lhcb1+Os.Act1:1:1 (SEQ ID NO: 163) in wheat leaf protoplasts.

| EXP sequence | SEQ ID NO: | GUS/RLuc Relative to EXP-Os.Act1:1:9 | GUS/RLuc Relative to EXP-CaMV.35S-enh+Ta.Lhcb1+Os.Act1:1:1 |
|---|---|---|---|
| EXP-CaMV.35S-enh+Ta.Lhcb1+Os.Act1:1:1 | 163 | 10.35 | 1.00 |
| EXP-CaMV.35S-enh+Zm.DnaK:1:1 | 170 | 9.71 | 0.94 |
| EXP-ANDge.Ubq1:1:7 | 5 | 20.33 | 1.96 |
| EXP-ANDge.Ubq1:1:10 | 10 | 17.90 | 1.73 |
| EXP-ANDge.Ubq1:1:6 | 12 | 10.55 | 1.02 |
| EXP-ANDge.Ubq1:1:11 | 14 | 16.05 | 1.55 |
| EXP-ANDge.Ubq1:1:12 | 16 | 14.32 | 1.38 |
| EXP-ERIra.Ubq1:1:9 | 22 | 6.24 | 0.60 |
| EXP-ERIra.Ubq1:1:10 | 25 | 12.15 | 1.17 |
| EXP-ERIra.Ubq1:1:8 | 27 | 10.44 | 1.01 |
| EXP-ERIra.Ubq1:1:11 | 29 | 9.25 | 0.89 |
| EXP-ERIra.Ubq1:1:12 | 31 | 13.45 | 1.30 |
| EXP-SETit.Ubq1:1:5 | 117 | 12.30 | 1.19 |
| EXP-SETit.Ubq1:1:7 | 123 | 39.26 | 3.79 |
| EXP-SETit.Ubq1:1:6 | 124 | 22.81 | 2.20 |
| EXP-Sv.Ubq1:1:7 | 128 | 12.12 | 1.17 |
| EXP-Sv.Ubq1:1:8 | 132 | 23.86 | 2.30 |
| EXP-Sv.Ubq1:1:10 | 134 | 16.55 | 1.60 |
| EXP-Zm.UbqM1:1:6 | 137 | 12.35 | 1.19 |
| EXP-Zm.UbqM1:1:7 | 141 | 19.48 | 1.88 |
| EXP-Sb.Ubq4:1:2 | 151 | 10.21 | 0.99 |
| EXP-Sb.Ubq6:1:2 | 153 | 8.54 | 0.82 |
| EXP-Cl.Ubq1:1:10 | 98 | 23.27 | 2.25 |

As can be seen in Table 20 above, nearly all of the EXP sequences were capable of driving GUS transgene expression in wheat cells. GUS transgene expression driven by EXP-ANDge.Ubq1:1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sv.Ubq1:1:7 (SEQ ID NO: 128), EXP-Sv.Ubq1:1:8 (SEQ ID NO: 132), EXP-Sv.Ubq1:1:10 (SEQ ID NO: 134), EXP-Zm.UbgM1:1:6 (SEQ ID NO: 137), EXP-Zm.UbgM1:1:7 (SEQ ID NO: 141), EXP-Sb.Ubg4:1:2 (SEQ ID NO: 151), EXP-Sb.Ubg6:1:2 (SEQ ID NO: 153) and EXP-Cl.Ubq1:1:10 (SEQ ID NO: 98) was much higher than GUS expression driven by EXP-Os.Act1:1:9. GUS expression of the amplicons in wheat leaf protoplast cells relative to EXP-CaMV.35S-enh+Ta.Lhcb1+Os-.Act1:1:1 was slightly different from the expression observed in corn protoplast cells. Each of EXP-ANDge.Ubq1:1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:10 (SEQ ID NO: 25), EXP-ERIra.Ubq1:1:8 (SEQ ID NO: 27), EXP-ERIra.Ubq1:1:12 (SEQ ID NO: 31), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sv.Ubq1:1:7 (SEQ ID NO: 128), EXP-Sv.Ubq1:1:8 (SEQ ID NO: 132), EXP-Sv.Ubq1:1:10 (SEQ ID NO: 134), EXP-Zm.UbgM1:1:6 (SEQ ID NO: 137), EXP-Zm.UbgM1:1:7 (SEQ ID NO: 141) and EXP-Cl.Ubq1:1:10 (SEQ ID NO: 98) demonstrated higher levels of GUS expression relative to EXP-CaMV.35S-enh+Ta.Lhcb1+Os.Act1:1:1. The EXP sequences EXP-ERIra.Ubq1:1:9 (SEQ ID NO: 22), EXP-ERIra.Ubq1:1:11 (SEQ ID NO: 29), EXP-Sb.Ubg4:1:2 (SEQ ID NO: 151) and EXP-Sb.Ubg6:1:2 (SEQ ID NO: 153) demonstrated lower levels of GUS expression relative to EXP-CaMV.35S-enh+Ta.Lhcb1+Os.Act1:1:1.

In a second set of experiments, amplicon GUS transgene cassettes were made as described above and assayed for expression driven by the EXP sequences, EXP-ANDge.Ubq1:1:8 (SEQ ID NO: 8), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116). The amplicons were comprised of an EXP sequence operably linked to the GUS-1 coding sequence which was operably linked to the T-AGRtu.nos-1:1:13 3' UTR. Expression was compared to the controls EXP-Os.Act1:1:9 (SEQ ID NO: 179) and EXP-CaMV.35S-enh+Zm.DnaK:1:1 (SEQ ID NO: 170). Table 21 below shows the mean GUS and luciferase values determined for each amplicon. Table 22 below shows the GUS/RLuc ratios of expression normalized with respect to EXP-Os.Act1:1:9 and EXP-CaMV.35S-enh+Zm.DnaK:1:1 driven expression in corn protoplasts.

TABLE 21

Mean GUS and Luciferase activity in transformed wheat leaf protoplast cells.

| Amplicon ID | EXP sequence | SEQ ID NO: | GUS | RLuc |
|---|---|---|---|---|
| PCR0145942 | EXP-Os.Act1:1:9 | 179 | 1234 | 176970.5 |
| PCR0145944 | EXP-CaMV.35S-enh + Zm.DnaK:1:1 | 170 | 12883.5 | 119439 |

TABLE 21-continued

| Mean GUS and Luciferase activity in transformed wheat leaf protoplast cells. | | | | |
|---|---|---|---|---|
| Amplicon ID | EXP sequence | SEQ ID NO: | GUS | RLuc |
| PCR0146628 | EXP-ANDge.Ubq1:1:8 | 8 | 38353.3 | 171535.3 |
| PCR0145922 | EXP-Cl.Ubq1:1:10 | 98 | 34938 | 154245.8 |
| PCR0145945 | EXP-Cl.Ubq1:1:13 | 114 | 32121 | 122220.8 |
| PCR0145946 | EXP-Cl.Ubq1:1:14 | 115 | 56814 | 143318.3 |
| PCR0145947 | EXP-Cl.Ubq1:1:15 | 116 | 1890.5 | 167178.5 |

TABLE 22

GUS/RLuc and GUS/FLuc ratios of expression normalized with respect to EXP-Os.Act1:1:9 (SEQ ID NO: 179) and EXP-CaMV.35S-enh+Zm.DnaK:1:1 (SEQ ID NO: 170) in wheat leaf protoplasts.

| EXP sequence | SEQ ID NO: | GUS/RLuc relative to EXP-Os.Act1:1:9 | GUS/RLuc relative to EXP-CaMV.35S-enh+Zm.DnaK:1:1 |
|---|---|---|---|
| EXP-Os.Act1:1:9 | 179 | 1.00 | 0.06 |
| EXP-CaMV.35S-enh+Zm.DnaK:1:1 | 170 | 15.47 | 1.00 |
| EXP-ANDge.Ubq1:1:8 | 8 | 32.07 | 2.07 |
| EXP-Cl.Ubq1:1:10 | 98 | 32.48 | 2.10 |
| EXP-Cl.Ubq1:1:13 | 114 | 37.69 | 2.44 |
| EXP-Cl.Ubq1:1:14 | 115 | 56.85 | 3.68 |
| EXP-Cl.Ubq1:1:15 | 116 | 1.62 | 0.10 |

As can be seen in Table 22 above, the EXP sequences EXP-ANDge.Ubq1:1:8 (SEQ ID NO: 8), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) are capable of driving transgene expression. Expression driven by EXP-ANDge.Ubq1:1:8 (SEQ ID NO: 8), EXP-Cl.Ubq1:1:10 (SEQ ID NO: 98), EXP-Cl.Ubq1:1:13 (SEQ ID NO: 114) and EXP-Cl.Ubq1:1:14 (SEQ ID NO: 115) was higher than that of both controls. Expression driven by EXP-Cl.Ubq1:1:15 (SEQ ID NO: 116) was lower than EXP-CaMV.35S-enh+Zm.DnaK:1:1 (SEQ ID NO: 170) but higher than the control, EXP-Os.Act1:1:9 (SEQ ID NO: 179).

In a third set of experiments, amplicon GUS transgene cassettes were made as described above to assay expression driven by the EXP sequences, EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97). Expression was compared to the controls EXP-Os.Act1:1:9 (SEQ ID NO: 179) and EXP-CaMV.35S-enh+Zm.DnaK:1:1 (SEQ ID NO: 170). Table 23 below shows the mean GUS and luciferase values determined for each amplicon. Table 24 below shows the GUS/RLuc and GUS/FLuc ratios of expression normalized with respect to EXP-Os.Act1:1:9 and EXP-CaMV.35S-enh+Zm.DnaK:1:1 driven expression in corn protoplasts.

TABLE 23

| Mean GUS and Luciferase activity in transformed wheat leaf protoplast cells. | | | | | |
|---|---|---|---|---|---|
| Amplicon ID | EXP sequence | SEQ ID NO: | GUS | RLuc | FLuc |
| PCR0145942 | EXP-Os.Act1:1:9 | 179 | 478 | 46584.5 | 2709.75 |
| PCR0145944 | EXP-CaMV.35S-enh+Zm.DnaK:1:1 | 170 | 8178.5 | 43490.8 | 2927.25 |
| PCR0145922 | EXP-Cl.Ubq1:1:10 | 98 | 22068.3 | 47662.3 | 1289 |
| pMON146750 | EXP-Cl.Ubq1:1:16 | 93 | 34205 | 45064.5 | 1379.63 |
| pMON146751 | EXP-Cl.Ubq1:1:17 | 97 | 31758 | 45739.3 | 2820.75 |

TABLE 24

GUS/RLuc and GUS/FLuc ratios of expression normalized with respect to EXP-Os.Act1:1:9 (SEQ ID NO: 179) and EXP-CaMV.35S-enh+Zm.DnaK:1:1 (SEQ ID NO: 170) in wheat leaf protoplasts.

| Amplicon ID | EXP sequence | SEQ ID NO: | GUS/RLuc relative to EXP-Os.Act1:1:9 | GUS/FLuc relative to EXP-Os.Act1:1:9 | GUS/RLuc relative to EXP-CaMV.35S-enh+Zm.DnaK:1:1 | GUS/FLuc relative to EXP-CaMV.35S-enh+Zm.DnaK:1:1 |
|---|---|---|---|---|---|---|
| PCR0145942 | EXP-Os.Act1:1:9 | 179 | 1.00 | 1.00 | 0.05 | 0.06 |
| PCR0145944 | EXP-CaMV.35S-enh+Zm.DnaK:1:1 | 170 | 18.33 | 15.84 | 1.00 | 1.00 |
| PCR0145922 | EXP-Cl.Ubq1:1:10 | 98 | 45.12 | 97.05 | 2.46 | 6.13 |
| pMON146750 | EXP-Cl.Ubq1:1:16 | 93 | 73.97 | 140.55 | 4.04 | 8.87 |
| pMON146751 | EXP-Cl.Ubq1:1:17 | 97 | 67.67 | 63.82 | 3.69 | 4.03 |

As can be seen in Table 24 above, the EXP sequences EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97) were able to drive transgene expression. Expression driven by each of the EXP sequences was higher than that of both controls.

In a fourth set of experiments, amplicon GUS transgene cassettes were made as described above to assay expression driven by the EXP sequences, EXP-Zm.UbqM1:1:11 (SEQ ID NO: 149) and EXP-Cl.Ubq1:1:23 (SEQ ID NO: 108). Expression was compared to the controls EXP-Os.Act1:1:9 (SEQ ID NO: 179) and EXP-CaMV.35S-enh+Ta.Lhcb1+Os.Act1:1:1 (SEQ ID NO: 163). Table 25 below shows the mean GUS and luciferase values determined for each amplicon. Table 26 below shows the GUS/RLuc ratios of expression normalized with respect to EXP-Os.Act1:1:9 and EXP-CaMV.35S-enh+Ta.Lhcb1+Os.Act1:1:1 driven expression in corn protoplasts.

TABLE 25

Mean GUS and Luciferase activity in transformed wheat leaf protoplast cells.

| Template | Amplicon ID | EXP sequence | SEQ ID NO: | GUS | RLuc |
|---|---|---|---|---|---|
| pMON65328 | PCR0145943 | EXP-CaMV.35S-enh+Ta.Lhcb1+Os.Act1:1:1 | 163 | 67459.13 | 11682.00 |
| PMON25455 | PCR0145942 | EXP-Os.Act1:1:9 | 179 | 56618.33 | 16654.83 |
| pMON131962 | pMON131962 | EXP-Zm.UbqM1:1:11 | 149 | 53862.13 | 10313.75 |
| pMON132047 | pMON132047 | EXP-Cl.Ubq1:1:23 | 108 | 38869.38 | 12279.00 |

TABLE 26

GUS/RLuc ratios of expression normalized with respect to EXP-Os.Act1:1:9 (SEQ ID NO: 179) and EXP-CaMV.35S-enh+Ta.Lhcb1+Os.Act1:1:1 (SEQ ID NO: 163) in wheat leaf protoplasts.

| Amplicon ID | EXP sequence | SEQ ID NO: | GUS/RLuc relative to EXP-Os.Act1:1:9 | GUS/RLuc relative to EXP-CaMV.35S-enh+Ta.Lhcb1+Os.Act1:1:1 |
|---|---|---|---|---|
| PCR0145943 | EXP-CaMV.35S-enh+Ta.Lhcb1+Os.Act1:1:1 | 163 | 1.70 | 1.00 |
| PCR0145942 | EXP-Os.Act1:1:9 | 179 | 1.00 | 0.59 |
| PMON131962 | EXP-Zm.UbqM1:1:11 | 149 | 1.54 | 0.90 |
| pMON132047 | EXP-Cl.Ubq1:1:23 | 108 | 0.93 | 0.55 |

As can be seen in Table 26 above, the EXP sequences, EXP-Zm.UbqM1:1:11 (SEQ ID NO: 149) and EXP-Cl.Ubq1:1:23 (SEQ ID NO: 108) were able to drive GUS expression in wheat leaf protoplasts. Expression was similar to that of the control, EXP-Os.Act1:1:9 (SEQ ID NO: 179) and lower than that of EXP-CaMV.35S-enh+Ta.Lhcb1+Os.Act1:1:1 (SEQ ID NO: 163).

Example 5: Analysis of Regulatory Elements Driving GUS in Sugarcane Protoplasts Using GUS Transgene Cassette Amplicons Sugarcane leaf protoplasts were transformed with DNA amplicons derived from plant expression vectors containing an EXP sequence, driving expression of the β-glucuronidase (GUS) transgene, and compared to leaf protoplast in which expression of GUS was driven by known constitutive promoters.

Sugarcane protoplast cells derived from leaf tissue were transformed using a PEG-based transformation method, as described in Example 3 above with amplicons produced from amplification of GUS transgene cassettes comprising plant expression vectors to compare expression of a transgene (GUS) driven by one of EXP-ANDge.Ubq1:1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) and presented in Table 27 below, with that of known constitutive promoters.

TABLE 27

GUS plant expression amplicons and corresponding plasmid construct amplicon template and EXP sequence.

| Amplicon ID | Amplicon Template | EXP sequence | SEQ ID NO: |
|---|---|---|---|
| PCR0145942 | pMON25455 | EXP-Os.Act1:1:9 | 179 |
| PCR0145944 | pMON81552 | EXP-CaMV.35S-enh+Zm.DnaK:1:1 | 170 |
| PCR0145892 | pMON136264 | EXP-ANDge.Ubq1:1:7 | 5 |
| PCR0145815 | pMON136264 | EXP-ANDge.Ubq1:1:10 | 10 |
| PCR0145893 | pMON136259 | EXP-ANDge.Ubq1:1:6 | 12 |
| PCR0145817 | pMON136264 | EXP-ANDge.Ubq1:1:11 | 14 |

TABLE 27-continued

GUS plant expression amplicons and corresponding plasmid construct amplicon template and EXP sequence.

| Amplicon ID | Amplicon Template | EXP sequence | SEQ ID NO: |
|---|---|---|---|
| PCR0145819 | pMON136264 | EXP-ANDge.Ubq1:1:12 | 16 |
| PCR0145896 | pMON136263 | EXP-ERIra.Ubq1:1:9 | 22 |
| PCR0145820 | pMON136263 | EXP-ERIra.Ubq1:1:10 | 25 |
| PCR0145897 | pMON136258 | EXP-ERIra.Ubq1:1:8 | 27 |
| PCR0145821 | pMON136263 | EXP-ERIra.Ubq1:1:11 | 29 |
| PCR0145822 | pMON136263 | EXP-ERIra.Ubq1:1:12 | 31 |
| PCR0145922 | pMON140889 | EXP-Cl.Ubq1:1:10 | 98 |
| PCR0145945 | pMON140889 | EXP-Cl.Ubq1:1:13 | 114 |
| PCR0145946 | pMON140889 | EXP-Cl.Ubq1:1:14 | 115 |
| PCR0145947 | pMON140889 | EXP-Cl.Ubq1:1:15 | 116 |

Control GUS cassette amplicons and Luciferase plasmids used for sugarcane protoplast transformation were also the same as those presented in Examples 2 through 4 and provided in Table 7 above in Example 3. Likewise, negative controls were used for the determination of GUS and luciferase background, as described above. Table 28 lists mean GUS and Luc activity seen in transformed sugarcane leaf protoplast cells, and Table 29 shows normalized GUS/RLuc ratios of expression in sugarcane leaf protoplasts.

TABLE 28

Mean GUS and Luciferase activity in transformed wheat leaf protoplast cells.

| EXP sequence | SEQ ID NO: | GUS | RLuc | FLuc |
|---|---|---|---|---|
| EXP-Os.Act1:1:9 | 179 | 6667.5 | 3024.5 | 1129.25 |
| EXP-CaMV.35S-enh+Zm.DnaK:1:1 | 170 | 14872.8 | 5171 | 2019.5 |
| EXP-ANDge.Ubq1:1:7 | 5 | 15225 | 4618.25 | 1775.75 |
| EXP-ANDge.Ubq1:1:10 | 10 | 17275.3 | 4333 | 1678 |
| EXP-ANDge.Ubq1:1:6 | 12 | 17236 | 5633.25 | 2240 |
| EXP-ANDge.Ubq1:1:11 | 14 | 22487.8 | 6898.25 | 2878 |
| EXP-ANDge.Ubq1:1:12 | 16 | 22145.3 | 6240.25 | 2676.5 |
| EXP-ERIra.Ubq1:1:9 | 22 | 16796.5 | 7759.75 | 3179 |
| EXP-ERIra.Ubq1:1:10 | 25 | 16267.5 | 5632.75 | 2436.75 |
| EXP-ERIra.Ubq1:1:8 | 27 | 25351 | 9019.5 | 4313.5 |
| EXP-ERIra.Ubq1:1:11 | 29 | 16652.3 | 3672.25 | 1534 |
| EXP-ERIra.Ubq1:1:12 | 31 | 12654.5 | 3256.75 | 1261.5 |
| EXP-Cl.Ubq1:1:10 | 98 | 22383.8 | 7097.5 | 3109.25 |
| EXP-Cl.Ubq1:1:13 | 114 | 14532.3 | 2786.5 | 1198.25 |
| EXP-Cl.Ubq1:1:14 | 115 | 19244.5 | 3455.25 | 1475 |
| EXP-Cl.Ubq1:1:15 | 116 | 6676.5 | 3870.25 | 1497.75 |

TABLE 29

GUS/RLuc and GUS/FLuc ratios of expression normalized with respect to EXP-Os.Act1:1:9 (SEQ ID NO: 179) and EXP-CaMV.35S-enh+Zm.DnaK:1:1 (SEQ ID NO: 170) in sugarcane leaf protoplasts.

| EXP sequence | SEQ ID NO: | GUS/RLuc relative to EXP-Os.Act1:1:9 | GUS/FLuc relative to EXP-Os.Act1:1:9 | GUS/RLuc relative to EXP-CaMV.35S-enh+Zm.DnaK:1:1 | GUS/FLuc relative to EXP-CaMV.35S-enh+Zm.DnaK:1:1 |
|---|---|---|---|---|---|
| EXP-Os.Act1:1:9 | 179 | 1.00 | 1.00 | 0.77 | 0.80 |
| EXP-CaMV.35S-enh+Zm.DnaK:1:1 | 170 | 1.30 | 1.25 | 1.00 | 1.00 |
| EXP-ANDge.Ubq1:1:7 | 5 | 1.50 | 1.45 | 1.15 | 1.16 |
| EXP-ANDge.Ubq1:1:10 | 10 | 1.81 | 1.74 | 1.39 | 1.40 |
| EXP-ANDge.Ubq1:1:6 | 12 | 1.39 | 1.30 | 1.06 | 1.04 |
| EXP-ANDge.Ubq1:1:11 | 14 | 1.48 | 1.32 | 1.13 | 1.06 |

TABLE 29-continued

GUS/RLuc and GUS/FLuc ratios of expression normalized with respect to EXP-Os.Act1:1:9 (SEQ ID NO: 179) and EXP-CaMV.35S-enh+Zm.DnaK:1:1 (SEQ ID NO: 170) in sugarcane leaf protoplasts.

| EXP sequence | SEQ ID NO: | GUS/RLuc relative to EXP-Os.Act1:1:9 | GUS/FLuc relative to EXP-Os.Act1:1:9 | GUS/RLuc relative to EXP-CaMV.35S-enh+Zm.DnaK:1:1 | GUS/FLuc relative to EXP-CaMV.35S-enh+Zm.DnaK:1:1 |
|---|---|---|---|---|---|
| EXP-ANDge.Ubq1:1:12 | 16 | 1.61 | 1.40 | 1.23 | 1.12 |
| EXP-ERIra.Ubq1:1:9 | 22 | 0.98 | 0.89 | 0.75 | 0.72 |
| EXP-ERIra.Ubq1:1:10 | 25 | 1.31 | 1.13 | 1.00 | 0.91 |
| EXP-ERIra.Ubq1:1:8 | 27 | 1.27 | 1.00 | 0.98 | 0.80 |
| EXP-ERIra.Ubq1:1:11 | 29 | 2.06 | 1.84 | 1.58 | 1.47 |
| EXP-ERIra.Ubq1:1:12 | 31 | 1.76 | 1.70 | 1.35 | 1.36 |
| EXP-Cl.Ubq1:1:10 | 98 | 1.43 | 1.22 | 1.10 | 0.98 |
| EXP-Cl.Ubq1:1:13 | 114 | 2.37 | 2.05 | 1.81 | 1.65 |
| EXP-Cl.Ubq1:1:14 | 115 | 2.53 | 2.21 | 1.94 | 1.77 |
| EXP-Cl.Ubq1:1:15 | 116 | 0.78 | 0.75 | 0.60 | 0.61 |

As can be seen in Table 29 above, the EXP sequences EXP-ANDge.Ubq1:1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) were all capable of driving transgene expression in sugarcane protoplasts. The EXP sequences, EXP-ANDge.Ubq1:1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:10 (SEQ ID NO: 25), EXP-ERIra.Ubq1:1:8 (SEQ ID NO: 27), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114) and EXP-Cl.Ubq1:1:14 (SEQ ID NO: 115) expressed GUS higher than EXP-CaMV.35S-enh+Zm.DnaK:1:1 (SEQ ID NO: 170) in this experiment.

Example 6: Analysis of Regulatory Elements Driving CP4 in Corn Protoplasts

This example illustrates the ability of EXP-Sv.Ubq1:1:7 (SEQ ID NO: 128), EXP-Sv.Ubq1:1:8 (SEQ ID NO: 132), EXP-Sv.Ubq1:1:9 (SEQ ID NO: 133), EXP-Zm.UbgM1:1:6 (SEQ ID NO: 137), EXP-Zm.UbgM1:1:8 (SEQ ID NO: 145), EXP-Zm.UbgM1:1:7 (SEQ ID NO: 141), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sb.Ubg4:1:2 (SEQ ID NO: 151) and EXP-Sb.Ubg6:1:2 (SEQ ID NO: 153) in driving expression of glyphosate tolerance gene CP4 in corn protoplasts. These EXP sequences were cloned into plant binary transformation plasmid constructs using methods known in the art. The resulting plant expression vectors contained a right border region from *A. tumefaciens*, an ubiquitin EXP sequence operably linked 5' to a plastid targeted glyphosate tolerant EPSPS coding sequence (CP4, U.S. RE39247), operably linked 5' to the T-AGRtu.nos-1:1:13 3' UTR and a left border region from *A. tumefaciens* (B-AGRtu.left border). The resulting plasmid constructs were used to transform corn leaf protoplasts cells using methods known in the art.

Plasmid constructs listed in Table 30, with EXP sequences as defined in Table 1, were utilized. Three control plasmids (pMON30098, pMON42410, and pMON30167), with known constitutive regulatory elements driving either CP4 or GFP, were constructed and used to compare the relative CP4 expression levels driven by these EXP sequences with CP4 expression driven by known constitutive expression elements. Two other plasmids (pMON19437 and pMON63934) were also used as described above to evaluate transformation efficiency and viability. Each plasmid contains a specific luciferase coding sequence driven by a constitutive EXP sequence.

Corn leaf protoplasts were transformed using a PEG-based transformation method, as described in Example 2 above. Measurements of both CP4 and luciferase were conducted similarly to Example 2 above. The average levels of CP4 protein expression expressed as part per million (ppm) is shown in Table 30 below.

TABLE 30

Average CP4 protein expression in corn leaf protoplasts.

| Plasmid | EXP sequence | SEQ ID NO: | CP4 Average ppm | CP4 STDEV ppm |
|---|---|---|---|---|
| No DNA | No DNA | | 0 | 0 |
| pMON30098 | GFP | | 0 | 0 |
| pMON42410 | EXP-CaMV.35S-enh + Ta.Lhcb1 + Os.Act1:1:1 | 163 | 34.1 | 15.6 |
| pMON30167 | EXP-Os.Act1:1:1 | 164 | 40.4 | 11.6 |
| pMON129203 | EXP-Sv.Ubq1:1:7 | 128 | 45.2 | 6.2 |
| pMON129204 | EXP-Sv.Ubq1:1:8 | 132 | 101.9 | 13.8 |
| pMON129205 | EXP-Sv.Ubq1:1:9 | 133 | 71.1 | 8.7 |
| pMON129210 | EXP-Zm.UbqM1:1:6 | 137 | 137.1 | 14.8 |
| pMON129211 | EXP-Zm.UbqM1:1:8 | 145 | 136.5 | 12.3 |
| pMON129212 | EXP-Zm.UbqM1:1:7 | 141 | 170.2 | 18.1 |
| pMON129200 | EXP-SETit.Ubq1:1:5 | 117 | 44.3 | 9.5 |
| pMON129201 | EXP-SETit.Ubq1:1:7 | 123 | 105.1 | 8.4 |
| pMON129202 | EXP-SETit.Ubq1:1:6 | 124 | 124.9 | 33.7 |
| pMON129219 | EXP-Sb.Ubq4:1:2 | 151 | 14.3 | 1 |
| pMON129218 | EXP-Sb.Ubq6:1:2 | 153 | 75.7 | 8.9 |

As can be seen in Table 30, EXP-Sv.Ubq1:1:7 (SEQ ID NO: 128), EXP-Sv.Ubq1:1:8 (SEQ ID NO: 132), EXP-Sv.Ubq1:1:9 (SEQ ID NO: 133), EXP-Zm.UbgM1:1:6 (SEQ ID NO: 137), EXP-Zm.UbgM1:1:8 (SEQ ID NO:

145), EXP-Zm.UbgM1:1:7 (SEQ ID NO: 141), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124) and EXP-Sb.Ubg6:1:2 (SEQ ID NO: 153) drove expression of the CP4 transgene at levels close to or higher than CP4 expression levels driven by EXP-CaMV.35S-enh+Ta.Lhcb1+Os.Act1:1:1 and EXP-Os.Act1:1:1. The EXP sequence, EXP-Sb.Ubg4:1:2 (SEQ ID NO: 151) demonstrated the ability to drive expression of CP4, but the level of expression was lower than that of the constitutive controls.

Similar data to that above may also be obtained from plants stably transformed with plasmid constructs described above, for instance, plants of progeny generation(s) $R_0$, $R_1$ or $F_1$ or later. Likewise, expression from other plasmid constructs may be studied. For instance, pMON141619, comprises the EXP sequence EXP-ANDge.Ubq1:1:8, while pMON142862 is comprised of the EXP sequence EXP-ERIra.Ubq1:1:8. These and other constructs may be analyzed in this manner.

Example 7: Analysis of Regulatory Elements Driving CP4 in Corn Protoplasts Using CP4 Transgene Cassette Amplicons This example illustrates the ability of EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115), EXP-Cl.Ubq1:1:15 (SEQ ID NO: 116), EXP-Cl.Ubq1:1:16 (SEQ ID NO: 93) and EXP-Cl.Ubq1:1:17 (SEQ ID NO: 97) in driving expression of glyphosate tolerance gene CP4 in corn protoplasts. These EXP sequences were cloned into plant binary transformation plasmid constructs. The resulting plant expression vectors were used as amplification templates to produce a transgene cassette amplicon comprised of an ubiquitin EXP sequence operably linked 5' to a plastid targeted glyphosate tolerant EPSPS coding sequence (CP4, U.S. RE39247), operably linked 5' to the T-AGRtu.nos-1:1:13 3' UTR and a left border region from *A. tumefaciens*. The resulting amplicons were used to transform corn leaf protoplasts cells.

Corn leaf protoplasts were transformed using a PEG-based transformation method, as described in Example 2 above. Measurements of both CP4 were conducted using an ELISA-based assay. The average levels of CP4 protein expression expressed as part per million (ppm) is shown in Tables 31 and 32 below.

In a first series of experiments, expression of CP4 driven by amplicons comprised of the EXP sequences EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) were assayed in transformed corn leaf protoplasts and compared to CP4 expression levels driven by the constitutive controls, EXP-CaMV.35S-enh+Zm.DnaK:1:1 (SEQ ID NO: 170) and EXP-Os.Act1:1:1 (SEQ ID NO: 164). The average levels of CP4 protein expression expressed as part per million (ppm) is shown in Tables 31 below.

TABLE 31

Average CP4 protein expression in corn leaf protoplasts.

| Amplicon Template | Amplicon ID | EXP sequence | SEQ ID NO: | CP4 ng/mg total protein Average | CP4 ng/mg total protein STDEV |
|---|---|---|---|---|---|
| | | no DNA | | 0.0 | 0.0 |
| pMON30098 | | GFP (negative control) | | 0.0 | 0.0 |
| pMON19469 | PCR24 | EXP-CaMV.35S-enh + Zm.DnaK:1:1 | 170 | 605.5 | 27.6 |
| pMON30167 | PCR25 | EXP-Os.Act1:1:1 | 164 | 50.6 | 14.2 |
| pMON140896 | PCR41 | EXP-ANDge.Ubq1:1:7 | 5 | 459.0 | 60.9 |
| pMON140917 | PCR42 | EXP-ANDge.Ubq1:1:8 | 8 | 258.2 | 38.4 |
| pMON140897 | PCR43 | EXP-ANDge.Ubq1:1:10 | 10 | 324.8 | 21.6 |
| pMON140898 | PCR44 | EXP-ANDge.Ubq1:1:6 | 12 | 394.9 | 66.4 |
| pMON140899 | PCR45 | EXP-ANDge.Ubq1:1:11 | 14 | 508.7 | 89.6 |
| pMON140900 | PCR46 | EXP-ANDge.Ubq1:1:12 | 16 | 329.3 | 14.5 |
| pMON140904 | PCR50 | EXP-ERIra.Ubq1:1:9 | 22 | 148.6 | 24.4 |
| pMON140905 | PCR51 | EXP-ERIra.Ubq1:1:10 | 25 | 215.8 | 22.6 |
| pMON140906 | PCR52 | EXP-ERIra.Ubq1:1:8 | 27 | 376.6 | 44.1 |
| pMON140907 | PCR53 | EXP-ERIra.Ubq1:1:11 | 29 | 459.9 | 104.7 |
| pMON140908 | PCR54 | EXP-ERIra.Ubq1:1:12 | 31 | 221.6 | 15.9 |
| pMON140913 | PCR19 | EXP-Cl.Ubq1:1:10 | 98 | 287.8 | 50.9 |
| pMON140914 | PCR20 | EXP-Cl.Ubq1:1:13 | 114 | 585.8 | 47.9 |
| pMON140915 | PCR21 | EXP-Cl.Ubq1:1:14 | 115 | 557.5 | 76.6 |
| pMON140916 | PCR22 | EXP-Cl.Ubq1:1:15 | 116 | 33.2 | 9.5 |

As can be seen in Table 31 above, the EXP sequences EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) were able to drive CP4 expression. All of the EXP sequences with the exception of one EXP-Cl.Ubq1:1:15 (SEQ ID NO: 116) drove CP4 expression levels at a much higher level than the constitutive control, EXP-Os.Act1:1:1 (SEQ ID NO: 164). Expression levels were lower than that of EXP-CaMV.35S-enh+Zm.DnaK:1:1 (SEQ ID NO: 170).

In a second series of experiments, expression of CP4 driven by amplicons comprised of the EXP sequences EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97) were assayed in transformed corn leaf protoplasts and compared to CP4 expression levels driven by the constitutive control, EXP-Os.Act1:1:1 (SEQ ID NO: 164). The average levels of CP4 protein expression expressed as part per million (ppm) is shown in Tables 32 below.

TABLE 32

Average CP4 protein expression in corn leaf protoplasts.

| Amplicon Template | Amplicon ID | EXP sequence | SEQ ID NO: | Maize Leaf CP4 mg/total protein Avg | Maize Leaf CP4 mg/total protein StdDev |
|---|---|---|---|---|---|
| pMON30167 | PCR25 | EXP-Os.Act1:1:1 | 164 | 12.2 | 1.69 |
| pMON140913 | PCR19 | EXP-Cl.Ubq1:1:10 | 98 | 307.5 | 24.21 |
| pMON142748 | pMON142748 | EXP-Cl.Ubq1:1:16 | 93 | 245.95 | 30.14 |
| pMON142749 | pMON142749 | EXP-Cl.Ubq1:1:17 | 97 | 302.85 | 25.32 |

As can be seen in Table 32 above, the EXP sequences EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97) were able to drive CP4 expression. Expression levels driven by all three EXP sequences were higher than that of the constitutive control, EXP-Os.Act1:1:1 (SEQ ID NO: 164).

Example 8: Analysis of Regulatory Elements Driving CP4 in Wheat Protoplasts

This example illustrates the ability of EXP-Sv.Ubq1:1:7 (SEQ ID NO: 128), EXP-Sv.Ubq1:1:8 (SEQ ID NO: 132), EXP-Sv.Ubq1:1:9 (SEQ ID NO: 133), EXP-Zm.UbgM1:1:6 (SEQ ID NO: 137), EXP-Zm.UbgM1:1:8 (SEQ ID NO: 145), EXP-Zm.UbgM1:1:7 (SEQ ID NO: 141), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sb.Ubq4:1:2 (SEQ ID NO: 151) and EXP-Sb.Ubq6:1:2 (SEQ ID NO: 153) to drive CP4 expression in wheat leaf protoplasts. These EXP sequences were cloned into plant binary transformation plasmid constructs using methods known in the art, and as described in Examples 2 and 5 above.

Three control plasmids (pMON30098, pMON4241, as previously described, and pMON43647 comprising a right border region from *Agrobacterium tumefaciens* with EXP-Os.Act1+CaMV.35S.2xA1-B3+Cs.Act1:5:1 (SEQ ID NO: 138) operably linked 5' to a plastid targeted glyphosate tolerance coding sequence (CP4, U.S. RE39247), operably linked 5' to T-AGRtu.nos-1:1:13, and a left border region (B-AGRtu.left border) with known constitutive regulatory elements driving either CP4 or GFP were constructed as outlined in Example 5.

Wheat leaf protoplasts were transformed using a PEG-based transformation method as described in the previous examples with the exception that $1.5 \times 10^5$ protoplast cells per assay were used. Assays of luciferase and CP4 transgene expression were performed as described in Example 6 above. The mean CP4 expression levels determined by CP4 ELISA are presented in Table 34 below.

TABLE 34

Mean CP4 Protein Expression in Wheat Leaf Protoplast Cells.

| Plasmid | EXP sequence | SEQ ID NO: | CP4 Average ppm | CP4 STDEV ppm |
|---|---|---|---|---|
| No DNA | No DNA | | 0 | 0 |
| pMON30098 | GFP | | 0 | 0 |
| pMON43647 | EXP-Os.Act1 + CaMV.35S.2xA1-B3 + Os.Act1:1:1 | 172 | 656.2 | 124.5 |
| pMON42410 | EXP-CaMV.35S-enh + Ta.Lhcb1 + Os.Act1:1:1 | 163 | 438.3 | 78.9 |
| pMON30167 | EXP-Os.Act1:1:1 | 164 | 583 | 107.4 |
| pMON129203 | EXP-Sv.Ubq1:1:7 | 128 | 156.9 | 25.1 |
| pMON129204 | EXP-Sv.Ubq1:1:8 | 132 | 39.5 | 7 |
| pMON129205 | EXP-Sv.Ubq1:1:9 | 133 | 154.5 | 56.5 |
| pMON129210 | EXP-Zm.UbqM1:1:6 | 137 | 1500 | 0 |
| pMON129211 | EXP-Zm.UbqM1:1:8 | 145 | 199.7 | 64.9 |
| pMON129212 | EXP-Zm.UbqM1:1:7 | 141 | 234.6 | 66.9 |
| pMON129200 | EXP-SETit.Ubq1:1:5 | 117 | 725.7 | 149.7 |
| pMON129201 | EXP-SETit.Ubq1:1:7 | 123 | 64.9 | 14.5 |
| pMON129202 | EXP-SETit.Ubq1:1:6 | 124 | 122.9 | 48.7 |
| pMON129219 | EXP-Sb.Ubq4:1:2 | 151 | 113.1 | 32.8 |

The total amount of CP4 expression in wheat protoplasts driven by the EXP sequences and the known constitutive EXP sequence EXP-CaMV.35S-enh+Ta.Lhcb1+Os.Act1:1:1 demonstrated different levels of CP4 expression in wheat protoplasts when compared to corn protoplasts.

Several EXP sequences drove CP4 expression at lower levels in wheat protoplasts than the known constitutive EXP sequences EXP-Os.Act1+CaMV.35S.2xA1-B3+Os.Act1:1:1 and EXP-CaMV.35S-enh+Ta.Lhcb1+Os.Act1:1:1. Two EXP sequences, EXP-Zm.UbgM1:1:6 (SEQ ID NO: 137), and EXP-SETit.Ubq1:1:5 (SEQ ID NO: 117), provide higher levels of CP4 expression in wheat protoplasts than the known constitutive, EXP sequences in this assay. EXP-Zm.UbgM1:1:2 drove expression of CP4 at the highest level, with expression levels being 2.2 to 3.4 fold higher than EXP-Os.Act1+CaMV.35S.2xA1-B3+Os.Act1:1:1 and EXP-CaMV.35S-enh+Ta.Lhcb1+Os.Act1:1:1, respectively. All EXP sequences assayed demonstrated the capacity to drive expression of CP4 in wheat cells.

Example 9: Analysis of Regulatory Elements Driving CP4 in Wheat Protoplasts Using CP4 Transgene Cassette Amplicons This example illustrates the ability of EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115), EXP-Cl.Ubq1:1:15 (SEQ ID NO: 116), EXP-Cl.Ubq1:1:16 (SEQ ID NO: 93) and EXP-Cl.Ubq1:1:17 (SEQ ID NO: 97) in driving expression of glyphosate tolerance gene CP4 in wheat protoplasts. These EXP sequences were cloned into plant binary transformation plasmid constructs. The resulting plant expression vectors were used as amplification templates to produce a transgene cassette amplicon comprised of an ubiquitin EXP sequence operably linked 5' to a plastid targeted glyphosate tolerant EPSPS coding sequence (CP4, U.S. RE39247), operably linked 5' to the T-AGRtu.nos-1:1:13 3' UTR and a left border region from *A. tumefaciens*. The resulting amplicons were used to transform corn leaf protoplasts cells.

Wheat leaf protoplasts were transformed using a PEG-based transformation method, as described in Example 2 above. Measurements of both CP4 were conducted using an ELISA-based assay. The average levels of CP4 protein expression expressed as part per million (ppm) is shown in Tables 35 and 36 below.

In a first series of experiments, expression of CP4 driven by amplicons comprised of the EXP sequences EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) were assayed in transformed wheat leaf protoplasts and compared to CP4 expression levels driven by the constitutive controls, EXP-CaMV.35S-enh+Zm.DnaK:1:1 (SEQ ID NO: 170) and EXP-Os.Act1:1:1 (SEQ ID NO: 164). The average levels of CP4 protein expression expressed as part per million (ppm) is shown in Tables 35 below.

TABLE 35

Average CP4 protein expression in wheat leaf protoplasts.

| Amplicon Template | Amplicon ID | EXP sequence | SEQ ID NO: | CP4 ng/mg total protein Average | CP4 ng/mg total protein STDEV |
|---|---|---|---|---|---|
| | | no DNA | | 0.00 | 0.00 |
| pMON30098 | | GFP (negative control) | | 0.00 | 0.00 |
| pMON19469 | PCR24 | EXP-CaMV.35S-enh + Zm.DnaK:1:1 | 170 | 76.11 | 18.65 |
| pMON30167 | PCR25 | EXP-Os.Act1:1:1 | 164 | 3.83 | 0.73 |
| pMON140896 | PCR41 | EXP-ANDge.Ubq1:1:7 | 5 | 103.46 | 16.31 |
| pMON140917 | PCR42 | EXP-ANDge.Ubq1:1:8 | 8 | 61.48 | 1.99 |
| pMON140897 | PCR43 | EXP-ANDge.Ubq1:1:10 | 10 | 62.65 | 4.58 |
| pMON140898 | PCR44 | EXP-ANDge.Ubq1:1:6 | 12 | 48.74 | 3.09 |
| pMON140899 | PCR45 | EXP-ANDge.Ubq1:1:11 | 14 | 54.91 | 3.50 |
| pMON140900 | PCR46 | EXP-ANDge.Ubq1:1:12 | 16 | 42.81 | 5.97 |
| pMON140904 | PCR50 | EXP-ERIra.Ubq1:1:9 | 22 | 31.26 | 1.69 |
| pMON140905 | PCR51 | EXP-ERIra.Ubq1:1:10 | 25 | 49.82 | 5.96 |
| pMON140906 | PCR52 | EXP-ERIra.Ubq1:1:8 | 27 | 37.43 | 4.52 |
| pMON140907 | PCR53 | EXP-ERIra.Ubq1:1:11 | 29 | 27.17 | 0.96 |
| pMON140908 | PCR54 | EXP-ERIra.Ubq1:1:12 | 31 | 17.41 | 4.13 |
| pMON140913 | PCR19 | EXP-Cl.Ubq1:1:10 | 98 | 66.66 | 13.45 |
| pMON140914 | PCR20 | EXP-Cl.Ubq1:1:13 | 114 | 79.42 | 10.74 |
| pMON140915 | PCR21 | EXP-Cl.Ubq1:1:14 | 115 | 75.53 | 9.32 |
| pMON140916 | PCR22 | EXP-Cl.Ubq1:1:15 | 116 | 0.00 | 0.00 |

As can be seen in Table 31 above, the EXP sequences EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) were able to drive CP4 expression. All of the EXP sequences with the exception of one EXP-Cl.Ubq1:1:15 (SEQ ID NO: 116) drove CP4 expression levels at a much higher level than the constitutive control, EXP-Os.Act1:1:1 (SEQ ID NO: 164). Expression levels were around the same level or lower than that of EXP-CaMV.35S-enh+Zm.DnaK:1:1 (SEQ ID NO: 170) for most of the EXP sequences.

In a second series of experiments, expression of CP4 driven by amplicons comprised of the EXP sequences EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97) were assayed in transformed wheat leaf protoplasts and compared to CP4 expression levels driven by the constitutive control, EXP-Os.Act1:1:1 (SEQ ID NO: 164). The average levels of CP4 protein expression expressed as part per million (ppm) is shown in Tables 32 below.

TABLE 36

Average CP4 protein expression in wheat leaf protoplasts.

| Amplicon Template | Amplicon ID | EXP sequence | SEQ ID NO: | Maize Leaf CP4 mg/total protein Avg | Maize Leaf CP4 mg/total protein StdDev |
|---|---|---|---|---|---|
| pMON30167 | PCR25 | EXP-Os.Act1:1:1 | 164 | 15.84 | 2.12 |
| pMON140913 | PCR19 | EXP-Cl.Ubq1:1:10 | 98 | 736.32 | 79.56 |
| pMON142748 | pMON142748 | EXP-Cl.Ubq1:1:16 | 93 | 593.72 | 80.22 |
| pMON142749 | pMON142749 | EXP-Cl.Ubq1:1:17 | 97 | 763.95 | 86.94 |

As can be seen in Table 36 above, the EXP sequences EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97) were able to drive CP4 expression. Expression levels driven by all three EXP sequences were higher than that of the constitutive control, EXP-Os.Act1:1:1 (SEQ ID NO: 164).

Example 10: Analysis of Regulatory Elements Driving CP4 in Sugarcane Protoplasts This example illustrates the ability of EXP-Sv.Ubq1:1:7 (SEQ ID NO: 128), EXP-Sv.Ubq1:1:8 (SEQ ID NO: 132), EXP-Sv.Ubq1:1:9 (SEQ ID NO: 133), EXP-Zm.UbgM1:1:6 (SEQ ID NO: 137), EXP-Zm.UbgM1:1:8 (SEQ ID NO: 145), EXP-Zm.UbgM1:1:7 (SEQ ID NO: 141), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sb.Ubg4:1:2 (SEQ ID NO: 151), EXP-Sb.Ubg6:1:2 (SEQ ID NO: 153) and EXP-Cl.Ubq1:1:10 (SEQ ID NO: 98) in driving expression of CP4 in sugar cane leaf protoplasts. The EXP sequences were cloned into plant binary transformation plasmid constructs. The resulting vectors contained a right border region from *Agrobacterium tumefaciens*, an ubiquitin EXP sequence operably linked 5' to a plastid targeted glyphosate tolerant EPSPS coding sequence (CP4, U.S. RE39247), operably linked 5' to the T-AGRtu.nos-1:1:13 (SEQ ID NO: 127) or T-CaMV.35S-1:1:1 (SEQ ID NO: 140) 3' UTR and a left border region from *A. tumefaciens* (B-AGRtu.left border). The resulting plasmid constructs were used to transform sugarcane leaf protoplasts cells using PEG transformation method.

Plasmid constructs pMON129203, pMON12904, pMON12905, pMON129210, pMON129211, pMON129212, pMON129200, pMON129201, pMON129202, pMON129219, and pMON129218 are as described in Table 12 above.

Three control plasmids (pMON30167 described above; pMON130803 also comprising EXP-Os.Act1::M (SEQ ID NO: 164); and pMON132804 comprising EXP-P-CaMV.35S-enh-1:1:13/L-CaMV.35S-1:1:2/I-Os.Act1-1:1:19 (SEQ ID NO: 139), with known constitutive regulatory elements driving CP4 were constructed and used to compare the relative CP4 expression levels driven by the ubiquitin EXP sequences listed in Table 37 below.

Sugarcane leaf protoplasts were transformed using a PEG-based transformation method. The mean CP4 expression levels determined by CP4 ELISA are presented in Table 37 below.

TABLE 37

| Mean CP4 Protein Expression in Sugarcane Leaf Protoplast Cells. | | | | | | |
|---|---|---|---|---|---|---|
| | | | Experiment 1 | | Experiment 2 | |
| Plasmid Construct | EXP sequence | SEQ ID NO: | CP4 Average ppm | CP4 STDEV ppm | CP4 Average ppm | CP4 STDEV ppm |
| pMON132804 | EXP-P-CaMV.35S-enh-1:1:13/L-CaMV.35S-1:1:2/I-Os.Act1-1:1:19 | 173 | 557.97 | 194.05 | 283.63 | 95.8 |
| pMON30167 | EXP-Os.Act1:1:1 | 164 | 57.15 | 20.99 | 18.36 | 5.41 |
| pMON130803 | EXP-Os.Act1:1:1 | 164 | 34.26 | 1.61 | 16.57 | 3.71 |
| pMON129203 | EXP-Sv.Ubq1:1:7 | 128 | 89.2 | 32.46 | 56.86 | 9.55 |
| pMON129204 | EXP-Sv.Ubq1:1:8 | 132 | 87.2 | 45.87 | 98.46 | 12.93 |
| pMON129205 | EXP-Sv.Ubq1:1:9 | 133 | 263.57 | 70.14 | 72.53 | 9.25 |
| pMON129210 | EXP-Zm.UbqM1:1:6 | 137 | 353.08 | 29.16 | 199.31 | 41.7 |
| pMON129211 | EXP-Zm.UbqM1:1:8 | 145 | 748.18 | 15.1 | 411.24 | 17.12 |
| pMON129212 | EXP-Zm.UbqM1:1:7 | 141 | 454.88 | 75.77 | 215.06 | 23.22 |
| pMON129200 | EXP-SETit.Ubq1:1:5 | 117 | 150.74 | 63.21 | 91.71 | 41.35 |
| pMON129201 | EXP-SETit.Ubq1:1:7 | 123 | 119.57 | 58.1 | 102.72 | 31.12 |
| pMON129202 | EXP-SETit.Ubq1:1:6 | 124 | 43.79 | 25.77 | 97.63 | 46.07 |
| pMON129219 | EXP-Sb.Ubq4:1:2 | 151 | 95.63 | 38.69 | | |
| pMON129218 | EXP-Sb.Ubq6:1:2 | 153 | 343.34 | 119.2 | 179.75 | 51.16 |
| pMON129221 | EXP-Cl.Ubq1:1:10 | 98 | 374.8 | 205.28 | 258.93 | 38.03 |

As can be seen in Table 37 above, the EXP sequences demonstrated the ability to drive expression CP4 expression in sugarcane protoplasts. The levels of expression were similar to or greater than that of CP4 expression driven by EXP-Os.Act1:1:1 (SEQ ID NO: 164). One EXP sequence, EXP-Zm.UbgM1:1:8 (SEQ ID NO: 145), demonstrated higher levels of expression when compared to EXP-P-CaMV.35S-enh-1:1:13/L-CaMV.35S-1:1:2/I-Os.Act1-1:1:19 (SEQ ID NO: 139) in sugarcane protoplasts.

Example 11: Analysis of Regulatory Elements Driving CP4 in Sugarcane Protoplasts Using CP4 Transgene Cassette Amplicons This example illustrates the ability of EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) in driving expression of the glyphosate tolerance gene CP4 in sugarcane protoplasts. These EXP sequences were cloned into plant binary transformation plasmid constructs. The resulting plant expression vectors were used as amplification templates to produce a transgene cassette amplicon comprised of an ubiquitin EXP sequence operably linked 5' to a plastid targeted glyphosate tolerant EPSPS coding sequence (CP4, U.S. RE39247), operably linked 5' to the T-AGRtu.nos-1:1:13 3' UTR and a left border region from *A. tumefaciens*. The resulting amplicons were used to transform sugarcane leaf protoplasts cells.

Sugarcane leaf protoplasts were transformed using a PEG-based transformation method, as described in Example 2 above. Measurements of both CP4 were conducted using an ELISA-based assay.

Expression of CP4 driven by amplicons comprised of the EXP sequences EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) were assayed in transformed wheat leaf protoplasts and compared to CP4 expression levels driven by the constitutive controls, EXP-CaMV.35S-enh+Zm.DnaK:1:1 (SEQ ID NO: 170) and EXP-Os.Act1:1:1 (SEQ ID NO: 164). The average levels of CP4 protein expression expressed as part per million (ppm) is shown in Table 38 below.

TABLE 38

| Average CP4 protein expression in sugarcane leaf protoplasts. | | | | | |
|---|---|---|---|---|---|
| Amplicon Template | Amplicon ID | EXP sequence | SEQ ID NO: | CP4 ng/mg total protein Average | CP4 ng/mg total protein STDEV |
| pMON19469 | PCR24 | EXP-CaMV.35S-enh + Zm.DnaK:1:1 | 170 | 99.6 | 7.2 |
| pMON30167 | PCR25 | EXP-Os.Act1:1:1 | 164 | 0.0 | 0.0 |
| pMON140896 | PCR41 | EXP-ANDge.Ubq1:1:7 | 5 | 21.9 | 3.3 |
| pMON140917 | PCR42 | EXP-ANDge.Ubq1:1:8 | 8 | 15.4 | 1.9 |
| pMON140897 | PCR43 | EXP-ANDge.Ubq1:1:10 | 10 | 20.7 | 2.2 |

TABLE 38-continued

Average CP4 protein expression in sugarcane leaf protoplasts.

| Amplicon Template | Amplicon ID | EXP sequence | SEQ ID NO: | CP4 ng/mg total protein Average | CP4 ng/mg total protein STDEV |
|---|---|---|---|---|---|
| pMON140898 | PCR44 | EXP-ANDge.Ubq1:1:6 | 12 | 21.8 | 2.8 |
| pMON140899 | PCR45 | EXP-ANDge.Ubq1:1:11 | 14 | 36.9 | 7.2 |
| pMON140900 | PCR46 | EXP-ANDge.Ubq1:1:12 | 16 | 51.7 | 5.6 |
| pMON140904 | PCR50 | EXP-ERIra.Ubq1:1:9 | 22 | 10.3 | 1.1 |
| pMON140905 | PCR51 | EXP-ERIra.Ubq1:1:10 | 25 | 25.3 | 4.7 |
| pMON140906 | PCR52 | EXP-ERIra.Ubq1:1:8 | 27 | 29.9 | 4.6 |
| pMON140907 | PCR53 | EXP-ERIra.Ubq1:1:11 | 29 | 44.0 | 7.1 |
| pMON140908 | PCR54 | EXP-ERIra.Ubq1:1:12 | 31 | 37.0 | 5.4 |
| pMON140913 | PCR19 | EXP-Cl.Ubq1:1:10 | 98 | 19.2 | 1.3 |
| pMON140914 | PCR20 | EXP-Cl.Ubq1:1:13 | 114 | 20.5 | 2.1 |
| pMON140915 | PCR21 | EXP-Cl.Ubq1:1:14 | 115 | 23.2 | 1.6 |
| pMON140916 | PCR22 | EXP-Cl.Ubq1:1:15 | 116 | 0.0 | 0.0 |

As can be seen in Table 38 above, the EXP sequences EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114) and EXP-Cl.Ubq1:1:14 (SEQ ID NO: 115) were able to drive CP4 expression. EXP-Cl.Ubq1:1:15 (SEQ ID NO: 116) did not appear to express CP4 expression in this assay.

Example 12: Analysis of Regulatory Elements Driving GUS in Transgenic Corn

Corn plants were transformed with plant expression vectors containing a EXP sequences driving expression of the β-glucuronidase (GUS) transgene, and the resulting plants were analyzed for GUS protein expression. The ubiquitin EXP sequences were cloned into plant binary transformation plasmid constructs using methods known in the art.

The resulting plant expression vectors contain a right border region from *A. tumefaciens*, a first transgene cassette to assay the EXP sequence operably linked to a coding sequence for β-glucuronidase (GUS) that possesses the processable intron GUS-2, described above, operably linked 5' to the 3' UTR from the rice lipid transfer protein gene (T-Os.LTP-1:1:1, SEQ ID NO: 141); a second transgene selection cassette used for selection of transformed plant cells that confers resistance to the herbicide glyphosate (driven by the rice Actin 1 promoter), and a left border region from *A. tumefaciens*. The resulting plasmids were used to transform corn plants. Table 39 lists the plasmid designations, the EXP sequences and the SEQ ID NOs, which are also described in Table 1.

TABLE 39

Binary plant transformation plasmids and the associated EXP sequences.

| Plasmid Construct | EXP sequence | SEQ ID NO: | Data |
|---|---|---|---|
| pMON142865 | EXP-ANDge.Ubq1:1:8 | 8 | $R_0$ and $R_1$ |
| pMON142864 | EXP-ERIra.Ubq1:1:8 | 27 | $R_0$ and $R_1$ |
| pMON142729 | EXP-Cl.Ubq1:1:12 | 90 | $R_0$ |

TABLE 39-continued

Binary plant transformation plasmids and the associated EXP sequences.

| Plasmid Construct | EXP sequence | SEQ ID NO: | Data |
|---|---|---|---|
| pMON142730 | EXP-Cl.Ubq1:1:11 | 95 | $R_0$ |
| pMON132047 | EXP-Cl.Ubq1:1:23 | 108 | $R_0$ |
| pMON132037 | EXP-SETit.Ubq1:1:10 | 119 | $R_0$ and $F_1$ |
| pMON131957 | EXP-SETit.Ubq1:1:11 | 125 | F1 |
| pMON131958 | EXP-Sv.Ubq1:1:11 | 130 | $R_0$ and $F_1$ |
| pMON131959 | EXP-Sv.Ubq1:1:12 | 136 | $R_0$ |
| pMON131961 | EXP-Zm.UbqM1:1:10 | 139 | $R_0$ |
| pMON131963 | EXP-Zm.UbqM1:1:12 | 143 | $R_0$ |
| pMON131962 | EXP-Zm.UbqM1:1:11 | 149 | $R_0$ |
| pMON132932 | EXP-Sb.Ubq4:1:2 | 151 | $R_0$ |
| pMON132931 | EXP-Sb.Ubq6:1:3 | 155 | $R_0$ |
| pMON132974 | EXP-Sb.Ubq7:1:2 | 157 | $R_0$ and $F_1$ |

Plants were transformed using *Agrobacterium*-mediated transformations, for instance as described in U.S. Patent Application Publication 20090138985.

Histochemical GUS analysis was used for qualitative expression analysis of transformed plants. Whole tissue sections were incubated with GUS staining solution X-Gluc (5-bromo-4-chloro-3-indolyl-b-glucuronide) (1 milligram/milliliter) for an appropriate length of time, rinsed, and visually inspected for blue coloration. GUS activity was qualitatively determined by direct visual inspection or inspection under a microscope using selected plant organs and tissues. The $R_0$ plants are inspected for expression in the roots and leaves as well as the anther, silk and developing seed and embryo 21 days after pollination (21 DAP).

For quantitative analysis, total protein was extracted from selected tissues of transformed corn plants. One microgram of total protein was used with the fluorogenic substrate 4-methyleumbelliferyl-β-D-glucuronide (MUG) in a total reaction volume of 50 microliters. The reaction product, 4-methlyumbelliferone (4-MU), is maximally fluorescent at high pH, where the hydroxyl group is ionized. Addition of a basic solution of sodium carbonate simultaneously stops the assay and adjusts the pH for quantifying the fluorescent product. Fluorescence was measured with excitation at 365 nm, emission at 445 nm using a Fluoromax-3 (Horiba; Kyoto, Japan) with Micromax Reader, with slit width set at excitation 2 nm and emission 3 nm.

The average $R_0$ GUS expression observed for each transformation is presented in Tables 40 and 41 below. The $R_0$ GUS assay performed on transformants transformed with pMON131957 (EXP-SETit.Ubq1:1:11, SEQ ID NO:125) did not pass quality standards. These transformants were assayed at F1 generation and are presented further below in this example.

TABLE 40

Average $R_0$ GUS expression in root and leaf tissue.

| EXP sequence | SEQ ID NO: | V3 Root | V4 Root | V7 Root | VT Root | V3 Leaf | V4 Leaf | V7 Leaf | VT Leaf |
|---|---|---|---|---|---|---|---|---|---|
| EXP-ANDge.Ubq1:1:8 | 8 | nd | 255 | 199 | 70 | nd | 638 | 168 | 130 |
| EXP-ERIra.Ubq1:1:8 | 27 | nd | 477 | 246 | 62 | nd | 888 | 305 | 242 |
| EXP-Cl.Ubq1:1:12 | 90 | nd | 27 | 147 | 52 | nd | 75 | 189 | 199 |
| EXP-Cl.Ubq1:1:11 | 95 | nd | 28 | 77 | 50 | nd | 101 | 177 | 223 |
| EXP-Cl.Ubq1:1:23 | 108 | 0 | nd | 75 | 34 | 201 | nd | 194 | 200 |
| EXP-SETit.Ubq1:1:10 | 119 | 0 | nd | 29 | 57 | 58 | nd | 37 | 46 |
| EXP-Sv.Ubq1:1:11 | 130 | nd | nd | nd | 9 | 20 | nd | 55 | 29 |
| EXP-Sv.Ubq1:1:12 | 136 | 63 | nd | 0 | 28 | 184 | nd | 27 | 16 |
| EXP-Zm.UbqM1:1:10 | 139 | 0 | nd | 237 | 18 | 221 | nd | 272 | 272 |
| EXP-Zm.UbqM1:1:12 | 143 | 0 | nd | 21 | 43 | 234 | nd | 231 | 196 |
| EXP-Zm.UbqM1:1:11 | 149 | 124 | nd | 103 | 112 | 311 | nd | 369 | 297 |
| EXP-Sb.Ubq4:1:2 | 151 | 125 | nd | 0 | 95 | 233 | nd | 150 | 88 |
| EXP-Sb.Ubq6:1:3 | 155 | 154 | nd | 13 | 128 | 53 | nd | 39 | 55 |
| EXP-Sb.Ubq7:1:2 | 157 | 37 | nd | 22 | 18 | 165 | nd | 89 | 177 |

TABLE 41

Average $R_0$ GUS expression in corn reproductive organs (anther, silk) and developing seed (embryo and endosperm).

| EXP sequence | SEQ ID NO: | VT Anther | VT/R1 Silk | 21 DAP Embryo | 21 DAP Endosperm |
|---|---|---|---|---|---|
| EXP-ANDge.Ubq1:1:8 | 8 | 247 | 256 | 24 | 54 |
| EXP-ERIra.Ubq1:1:8 | 27 | 246 | 237 | 36 | 61 |
| EXP-Cl.Ubq1:1:12 | 90 | 420 | 121 | 26 | 220 |
| EXP-Cl.Ubq1:1:11 | 95 | 326 | 227 | 41 | 221 |
| EXP-Cl.Ubq1:1:23 | 108 | 598 | 416 | 212 | 234 |
| EXP-SETit.Ubq1:1:10 | 119 | 132 | 85 | 50 | 63 |
| EXP-Sv.Ubq1:1:11 | 130 | 217 | 3 | 45 | 92 |
| EXP-Sv.Ubq1:1:12 | 136 | 120 | 21 | 49 | 112 |
| EXP-Zm.UbqM1:1:10 | 139 | 261 | 506 | 403 | 376 |
| EXP-Zm.UbqM1:1:12 | 143 | 775 | 362 | 253 | 247 |
| EXP-Zm.UbqM1:1:11 | 149 | 551 | 452 | 234 | 302 |
| EXP-Sb.Ubq4:1:2 | 151 | 213 | 0 | 25 | 79 |
| EXP-Sb.Ubq6:1:3 | 155 | 295 | 87 | 51 | 61 |
| EXP-Sb.Ubq7:1:2 | 157 | 423 | 229 | 274 | 90 |

In $R_0$ corn plants, GUS expression levels in the leaf and root differed amongst the ubiquitin EXP sequences. While all of the EXP sequences demonstrated the ability to drive GUS transgene expression in stably transformed plants, each EXP sequence demonstrated a unique pattern of expression relative to the others. For example, high levels of GUS expression were observed in early stages of root development (V4 and V7) for EXP-ANDge.Ubq1:1:8 (SEQ ID NO: 8) and EXP-ERIra.Ubq1:1:8 (SEQ ID NO: 27) and declined by VT stage. Root expression driven by EXP-Zm.UbgM1:1:10 (SEQ ID NO: 139) demonstrated no expression at V3 but was high at V7 and then dropped by VT stage. Root expression driven by EXP-Zm.UbgM1:1:11 (SEQ ID NO: 149) was maintained to a similar level throughout development from stages V3, V7 through VT. Root expression was observed to increase from early development (V3/V4) to V7 stage and then drop from V7 to V8 stage in plants transformed with EXP-Cl.Ubq1:1:12 (SEQ ID NO: 90), EXP-Cl.Ubq1:1:11 (SEQ ID NO: 95) and EXP-Cl.Ubq1:1:23 (SEQ ID NO: 108). GUS expression levels showed dramatic differences in leaf tissue as well. The highest levels of leaf expression were conferred in early development (V3/V4) with EXP-ANDge.Ubq1:1:8 (SEQ ID NO: 8) and EXP-ERIra.Ubq1:1:8 (SEQ ID NO: 27) which decline at V7 through VT stage. GUS expression is retained from V3 through VT stage using EXP-Zm.UbgM1:1:10 (SEQ ID NO: 139), EXP-Zm.UbgM1:1:11 (SEQ ID NO: 149), EXP-Zm.UbgM1:1:12 (SEQ ID NO: 143) and EXP-Cl.Ubq1:1:23 (SEQ ID NO: 108); and to a lower extent using EXP-SETit.Ubq1:1:10 (SEQ ID NO: 119) and EXP-Sb.Ubg6:1:3 (SEQ ID NO: 155). Expression in the leaf increased from V3 to V7 to VT stage using EXP-Cl.Ubq1:1:12 (SEQ ID NO: 90), EXP-Cl.Ubq1:1:11 (SEQ ID NO: 95) and EXP-Cl.Ubq1:1:23 (SEQ ID NO: 108) while expression declined from V3 to VT stage using EXP-Sv.Ubq1:1:12 (SEQ ID NO: 136) and EXP-Sb.Ubg4:1:2 (SEQ ID NO: 151).

Likewise, with respect to reproductive tissue (anther and silk) and developing seed (21DAP embryo and endosperm) different patterns of expression were observed unique to each EXP sequence. For example, High levels of expression were observed in anther and silk as well as the developing seed using EXP-Zm.UbgM1:1:10 (SEQ ID NO: 139), EXP-Zm.UbgM1:1:11 (SEQ ID NO: 149), EXP-Zm.UbgM1:1:12 (SEQ ID NO: 143) and EXP-Cl.Ubq1:1:23 (SEQ ID NO: 108). Expression was high in the anther and silk but low in the developing seed using EXP-ANDge.Ubq1:1:8 (SEQ ID NO: 8) and EXP-ERIra.Ubq1:1:8 (SEQ ID NO: 27). Expression driven by EXP-Sb.Ubg7:1:2 (SEQ ID NO: 157) was high in reproductive tissue and high in the developing embryo but was lower in the developing endosperm. The EXP sequence, EXP-Sb.Ubg4:1:2 (SEQ ID NO: 151) only demonstrated expression in the anther but not in the silk and expressed much lower in the developing seed. EXP-Sv.Ubq1:1:11 (SEQ ID NO: 130) demonstrated a similar pattern as EXP-Sb.Ubg4:1:2 (SEQ ID NO: 151) with respect to reproductive tissue and developing seed, but whereas EXP-Sb.Ubg4:1:2 (SEQ ID NO: 151) showed expression in root and leaf tissues, EXP-Sv.Ubq1:1:11 (SEQ ID NO: 130) expressed much lower in these same tissues.

$R_0$ generation transformants, selected for single copy insertions were crossed with a non-transgenic LH244 line (resulting in $F_1$) or were self-pollinated (resulting in $R_1$) in order to produce an $F_1$ or $R_1$ population of seeds. In either case, heterozygous $F_1$ or $R_1$ plants were selected for study. GUS expression levels were measured in selected tissues over the course of development as previously described. The $F_1$ or $R_1$ tissues used for this study included: imbibed seed embryo, imbibed seed endosperm, root and coleoptide at 4 days after germination (DAG); leaf and root at V3 stage; root and mature leaf at V8 stage; root, mature leaves, VT stage (at tasseling, prior to reproduction) anther, pollen, leaf and senescing leaf; R1 cob, silk, root and internode; kernel 12 days after pollination (DAP) and; embryo and endosperm 21 and 38 DAP. Selected tissue samples were also analyzed for $F_1$ plants exposed to conditions of drought and cold stress for transformants comprising pMON132037 (EXP-SETit.Ubq1:1:10, SEQ ID NO: 119), pMON131957 (EXP-SETit.Ubq1:1:11, SEQ ID NO: 125), pMON131958 (EXP-Sv.Ubq1:1:11, SEQ ID NO: 130) and pMON132974 (EXP-Sb.Ubg7:1:2, SEQ ID NO: 157). V3 root and leaf tissue was sampled after cold and drought exposure.

Drought stress was induced in $F_1$, V3 plants transformed with pMON132037 (EXP-SETit.Ubq1:1:10, SEQ ID NO: 119), pMON131957 (EXP-SETit.Ubq1:1:11, SEQ ID NO: 125), pMON131958 (EXP-Sv.Ubq1:1:11, SEQ ID NO: 130) and pMON132974 (EXP-Sb.Ubg7:1:2, SEQ ID NO: 157) by withholding watering for 4 days allowing the water content to be reduced by at least 50% of the original water content of the fully watered plant. The drought protocol was comprised essentially of the following steps. V3 stage plants were deprived of water. As a corn plant experiences drought, the shape of the leaf will change from the usual healthy and unfolded appearance to a leaf demonstrating folding at the mid-rib vascular bundle and appearing V-shaped when viewed from the leaf tip to the stem. This change in morphology usually began to occur by about 2 days after the cessation of watering and was shown in earlier experiments to be associated with water loss of around 50% as measured by weight of pots prior to cessation of watering and weight of pots when the leaf curl morphology was observed in un-watered plants. Plants were considered to be under drought conditions, when the leaves showed wilting as evidenced by an inward curling (V-shape) of the leaf. This level of stress is considered to be a form of sub-lethal stress. Once each plant demonstrated drought induction as defined above, the plant was destroyed to acquire both root and leaf samples.

In addition to drought, $F_1$ V3 stage plants transformed with pMON132037 (EXP-SETit.Ubq1:1:10, SEQ ID NO: 119), pMON131957 (EXP-SETit.Ubq1:1:11, SEQ ID NO: 125), pMON131958 (EXP-Sv.Ubq1:1:11, SEQ ID NO: 130) and pMON132974 (EXP-Sb.Ubg7:1:2, SEQ ID NO: 157) were also exposed to conditions of cold to determine if the regulatory elements demonstrated cold-induced expression of GUS. Whole plants were assayed for induction of GUS expression under cold stress at V3 stage. V3 stage corn plants were exposed to a temperature of 12° C. in a growth chamber for 24 hours. Plants in the growth chamber were grown under a white light fluence of 800 micro moles per meter squared per second with a light cycle of ten hours of white light and fourteen hours of darkness. After cold exposure, leaf and root tissues were sampled for quantitative GUS expression.

GUS expression was measured as described above. The average $F_1$ GUS expression determined for each tissue sample is presented in Tables 42 and 43 below.

TABLE 42

Average $F_1$ GUS expression in plants transformed with pMON142864 and pMON142865.

| Organ | pMON142864 | pMON142865 |
|---|---|---|
| V3 Leaf | 86 | 74 |
| V3 Root | 41 | 52 |
| V8 Leaf | 109 | 123 |
| V8 Root | 241 | 252 |
| VT Flower, anthers | 168 | 208 |
| VT Leaf | 158 | 104 |
| R1 Cob | 171 | 224 |
| R1 silk | 314 | 274 |
| R1 Root | 721 | 308 |
| R1 internode | 428 | 364 |
| R2 Seed-12DAP | 109 | 72 |
| R3 Seed-21DAP-Embryo | 45 | 32 |
| R3 Seed-21DAP-Endosperm | 175 | 196 |
| R5 Seed-38DAP-Embryo | 163 | 58 |
| R5 Seed-38DAP-Endosperm | 90 | 69 |

TABLE 43

Average $F_1$ GUS expression in plants transformed with pMON132037, pMON131957, pMON131958 and pMON132974.

| Organ | pMON132037 | pMON131957 | pMON131958 | pMON132974 |
|---|---|---|---|---|
| Imbibed Seed Embryo | 536 | 285 | 288 | 1190 |
| Imbibed Seed Endosperm | 95 | 71 | 73 | 316 |
| Coleoptile-4 DAG | 218 | 60 | 143 | 136 |
| Root-4 DAG | 74 | 33 | 101 | 48 |
| V3 Leaf | 104 | 120 | 66 | 52 |
| V3 Root | 74 | 71 | 81 | 194 |
| V3 Leaf-cold | 73 | 15 | 72 | N/A |
| V3 Root-cold | 113 | 44 | 89 | 49 |
| V3 Leaf-drought | 97 | 344 | 103 | 157 |
| V3 Root-drought | 205 | 153 | 129 | 236 |
| V8 Leaf | 185 | 142 | 77 | 282 |
| V8 Root | 33 | 16 | 61 | 28 |
| VT Flower-anthers | 968 | 625 | 619 | 888 |
| VT Leaf | 138 | 89 | 132 | 268 |
| VT Leaf-senescing | 121 | 100 | 156 | 345 |
| VT Pollen | 610 | 1119 | 332 | 4249 |

TABLE 43-continued

Average $F_1$ GUS expression in plants transformed with pMON132037, pMON131957, pMON131958 and pMON132974.

| Organ | pMON132037 | pMON131957 | pMON131958 | pMON132974 |
|---|---|---|---|---|
| R1 Cob | 291 | 70 | 168 | 127 |
| R1 silk | 164 | 124 | 167 | 101 |
| R1 Root | 36 | 39 | 39 | 21 |
| R1 internode | 255 | 89 | 232 | 141 |
| R2 Seed-12DAP | 138 | 170 | 165 | 169 |
| R3 Seed-21 DAP-Embryo | 94 | 97 | 489 | 389 |
| R3 Seed-21 DAP-Endosperm | 57 | 118 | 52 | 217 |
| R5 Seed-38 DAP-Embryo | 600 | 147 | 377 | 527 |
| R5 Seed-38 DAP-Endosperm | 58 | 36 | 57 | 106 |

In $F_1$ corn plants, GUS expression levels in the various tissues sampled differed amongst the ubiquitin EXP sequences. While all of the EXP sequences demonstrated the ability to drive GUS transgene expression in stably transformed $F_1$ corn plants, each EXP sequence demonstrated a unique pattern of expression relative to the others. For example, R1 root expression is about twice that for EXP-ERIra.Ubq1:1:8 (SEQ ID NO: 27) than EXP-ANDge.Ubq1:1:8 (SEQ ID NO: 8). GUS expression in the developing seed embryo at 38 DAP is almost three fold higher for EXP-ERIra.Ubq1:1:8 (SEQ ID NO: 27) than EXP-ANDge.Ubq1:1:8 (SEQ ID NO: 8). In contrast leaf and root expression at V3 and V8 stage is about the same for EXP-ERIra.Ubq1:1:8 (SEQ ID NO: 27) than EXP-ANDge.Ubq1:1:8 (SEQ ID NO: 8).

The F1 GUS expression in imbided seeds (embryo and endosperm tissues) was much higher in plants transformed with EXP-Sb.Ubg7:1:2 (SEQ ID NO: 157) than in those transformed with EXP-SETit.Ubq1:1:10 (SEQ ID NO: 119), EXP-SETit.Ubq1:1:11 (SEQ ID NO: 125) and EXP-Sv.Ubq1:1:11 (SEQ ID NO: 130). Drought caused an increase in V3 root expression in plants transformed with EXP-SETit.Ubq1:1:10 (SEQ ID NO: 119), EXP-SETit.Ubq1:1:11 (SEQ ID NO: 125), EXP-Sv.Ubq1:1:11 (SEQ ID NO: 130) and EXP-Sb.Ubg7:1:2 (SEQ ID NO: 157), but only increased leaf expression in plants transformed with EXP-SETit.Ubq1:1:11 (SEQ ID NO: 125), EXP-Sv.Ubq1:1:11 (SEQ ID NO: 130) and EXP-Sb.Ubg7:1:2 (SEQ ID NO: 157). The drought enhanced V3 expression was greatest using EXP-SETit.Ubq1:1:11 (SEQ ID NO: 125). Pollen expression was also much higher in plants transformed with EXP-Sb.Ubg7:1:2 (SEQ ID NO: 157) than in those transformed with EXP-SETit.Ubq1:1:10 (SEQ ID NO: 119), EXP-SETit.Ubq1:1:11 (SEQ ID NO: 125) and EXP-Sv.Ubq1:1:11 (SEQ ID NO: 130). Expression in the R1 internode was greatest with EXP-SETit.Ubq1:1:10 (SEQ ID NO: 119) and EXP-Sv.Ubq1:1:11 (SEQ ID NO: 130) and least in plants transformed with EXP-SETit.Ubq1:1:11 (SEQ ID NO: 125).

Each EXP sequence demonstrated the ability to drive transgene expression in stably transformed corn plants. However, each EXP sequence had a pattern of expression for each tissue that was unique and offers an opportunity to select the EXP sequence which will best provide expression of a specific transgene depending upon the tissue expression strategy needed to achieve the desired results. This example demonstrates EXP sequences isolated from homologous genes do not necessarily behave equivalently in the transformed plant and that expression can only be determined through empirical investigation of the properties for each EXP sequence and cannot be predicted based upon the gene homology from which the promoter was derived.

Example 13: Analysis of Regulatory Elements Driving CP4 in Transgenic Corn

Corn plants were transformed with plant expression vectors containing EXP sequences driving expression of the CP4 transgene, and the resulting plants were analyzed for CP4 protein expression.

The EXP sequences EXP-ANDge.Ubq1:1:8 (SEQ ID NO: 8), EXP-ERIra.Ubq1:1:8 (SEQ ID NO: 27), EXP-Cl.Ubq1:1:10 (SEQ ID NO: 98), EXP-Sv.Ubq1:1:9 (SEQ ID NO: 133) and EXP-Zm.UbgM1:1:7 (SEQ ID NO: 141) were cloned into plant binary transformation plasmid constructs. The resulting vectors contained a right border region from *Agrobacterium tumefaciens*, an ubiquitin EXP sequence operably linked 5' to a plastid targeted glyphosate tolerant EPSPS coding sequence (CP4, U.S. RE39247), operably linked 5' to the T-AGRtu.nos-1:1:13 (SEQ ID NO: 127) 3' UTR and a left border region from *A. tumefaciens*. Table 44 below shows the plasmid constructs used to transform corn and the corresponding EXP sequences.

TABLE 44

CP4 plasmid constructs and corresponding EXP sequences used to transform corn.

| Plasmid Construct | EXP sequence | SEQ ID NO: | Data |
|---|---|---|---|
| pMON141619 | EXP-ANDge.Ubq1:1:8 | 8 | $R_0$ and $F_1$ |
| pMON142862 | EXP-ERIra.Ubq1:1:8 | 27 | $R_0$ and $F_1$ |
| pMON129221 | EXP-Cl.Ubq1:1:10 | 98 | $R_0$ and $F_1$ |
| pMON129205 | EXP-Sv.Ubq1:1:9 | 133 | $R_0$ and $F_1$ |
| pMON129212 | EXP-Zm.UbqM1:1:7 | 141 | $R_0$ |

The resulting plasmids were used to transform corn plants. Transformed plants were selected for one or two copies of the inserted T-DNA and grown in the greenhouse. Selected tissues were sampled from the $R_0$ transformed plants at specific stages of development and CP4 protein levels were measured in those tissues using an CP4 ELISA assay. The average CP4 expression observed for each transformation is presented in Tables 45 and 46 below and graphically in FIG. 7.

TABLE 45

Average leaf and root CP4 expression in $R_0$ transformed corn plants.

| EXP sequence | SEQ ID NO: | V4 Leaf | V7 Leaf | VT Leaf | V4 Root | V7 Root | VT Root |
|---|---|---|---|---|---|---|---|
| EXP-ANDge.Ubq1:1:8 | 8 | 20.90 | 18.53 | 25.49 | 11.50 | 26.54 | 17.20 |
| EXP-ERIra.Ubq1:1:8 | 27 | 19.92 | 16.60 | 25.58 | 9.92 | 26.31 | 13.33 |
| EXP-Cl.Ubq1:1:10 | 98 | 10.70 | 12.49 | 17.42 | 7.56 | 13.95 | 6.68 |
| EXP-Sv.Ubq1:1:9 | 133 | 3.72 | 4.34 | 4.48 | 2.90 | 6.99 | 2.78 |
| EXP-Zm.UbqM1:1:7 | 141 | 13.42 | 21.89 | 38.78 | 9.56 | 16.69 | 11.15 |

TABLE 46

Average CP4 expression in reproductive tissue and developing seed in $R_0$ transformed corn plants.

| EXP sequence | SEQ ID NO: | VT Tassel | R1 Silk | R3 Embryo | R3 Endosperm |
|---|---|---|---|---|---|
| EXP-ANDge.Ubq1:1:8 | 8 | 24.14 | 5.55 | 7.29 | 4.91 |
| EXP-ERIra.Ubq1:1:8 | 27 | 19.20 | 10.27 | 12.60 | 4.70 |
| EXP-Cl.Ubq1:1:10 | 98 | 18.70 | 16.21 | 8.26 | 8.82 |
| EXP-Sv.Ubq1:1:9 | 133 | 7.10 | 4.72 | 3.13 | 1.74 |
| EXP-Zm.UbqM1:1:7 | 141 | 67.25 | 11.21 | 7.85 | 10.69 |

As can be seen in Tables 45 and 46, each of the EXP sequences EXP-ANDge.Ubq1:1:8 (SEQ ID NO: 8), EXP-ERIra.Ubq1:1:8 (SEQ ID NO: 27), EXP-Cl.Ubq1:1:10 (SEQ ID NO: 98), EXP-Sv.Ubq1:1:9 (SEQ ID NO: 133) and EXP-Zm.UbqM1:1:7 (SEQ ID NO: 141) was able to drive CP4 expression in all tissues sampled from the $R_0$ transformed plants. Higher expression of CP4 in the root and leaf of transformants comprising EXP-ANDge.Ubq1:1:8 (SEQ ID NO: 8) and EXP-ERIra.Ubq1:1:8 (SEQ ID NO: 27) driving CP4 than EXP-Cl.Ubq1:1:10 (SEQ ID NO: 98) driving CP4 may be related to the level of vegetative tolerance to glyphosate application as observed for these populations of transformants (see Example 14 below).

Each EXP sequence exhibited a unique expression pattern with respect to the level of expression for each tissue sampled. For example, while CP4 expression in leaf, root and tassel were similar for the EXP sequences, EXP-ANDge.Ubq1:1:8 (SEQ ID NO: 8) and EXP-ERIra.Ubq1:1:8 (SEQ ID NO: 27), expression in silk using EXP-ANDge.Ubq1:1:8 (SEQ ID NO: 8) was half that of expression driven by ERIra.Ubq1:1:8 (SEQ ID NO: 21). This might be advantageous for expression of transgenes in which constitutive expression is desired but less expression in silk tissue would be preferred. The EXP sequences demonstrate unique patterns of CP4 constitutive expression in $R_0$ transformed corn plants.

The $R_0$ transformed corn plants were crossed with a non-transgenic LH244 variety to produce F1 seed. The resulting F1 generation seed was analyzed for segregation of the transgene cassette and plants heterozygous for the CP4 cassette were selected for analysis of CP4 expression. Seed was grown in the greenhouse and two groups of plants were produced, one group was sprayed with glyphosate while the other was left unsprayed. Expression of CP4 was analyzed in selected tissues using a standard ELISA based assay. The average CP4 expression is shown in Tables 47 and 48 below.

TABLE 47

Average CP4 expression in $F_1$ transformed corn plants.

| Organ | pMON141619 | pMON142862 | pMON129221 |
|---|---|---|---|
| V4 Leaf | 11.50 | 13.51 | 7.68 |
| V4 Root | 12.48 | 12.60 | 10.29 |
| V7 Leaf | 16.59 | 20.21 | 12.01 |
| V7 Root | 11.00 | 13.62 | 8.15 |
| VT Leaf | 39.88 | 44.85 | 29.42 |
| VT Root | 17.43 | 21.83 | 13.43 |
| VT Flower, anthers | 52.74 | 55.72 | 53.62 |
| R1 Silk | 16.01 | 23.81 | 14.42 |
| R3 Seed-21 DAP-Embryo | 33.29 | 57.96 | 51.64 |
| R3 Seed-21 DAP-Endosperm | 2.99 | 3.20 | 6.44 |

As can be seen in Table 47 above, CP4 expression in leaf and root was higher in $F_1$ transformants transformed with pMON141619 (EXP-ANDge.Ubq1:1:8, SEQ ID NO: 5) and pMON142862 (EXP-ERIra.Ubq1:1:8, SEQ ID NO: 27) than in those transformed with pMON129221 (EXP-Cl.Ubq1:1:10, SEQ ID NO: 98). Expression in the anther tissue was similar for all three EXP sequences while expression in the silk was highest using EXP-ERIra.Ubq1:1:8 (SEQ ID NO: 27). Expression in the developing embryo (21 DAP) was highest in transformants comprising EXP-ERIra.Ubq1:1:8 (SEQ ID NO: 27) and EXP-Cl.Ubq1:1:10 (SEQ ID NO: 98) driving CP4. Expression in the developing endosperm was higher in transformants comprising EXP-Cl.Ubq1:1:10 (SEQ ID NO: 98) driving CP4.

TABLE 48

Average CP4 expression in $F_1$ transformed corn plants.

| Organ | pMON129205 |
|---|---|
| V4 Leaf | 1.73 |
| V4 Root | 2.44 |
| V7 Leaf | 2.84 |
| V7 Root | 1.51 |
| VT Leaf | 3.29 |
| VT Root | 2.63 |
| VT Flower, anthers | 7.52 |
| R1 Silk | 1.99 |
| R3 Seed-21 DAP-Embryo | 3.40 |
| R3 Seed-21 DAP-Endosperm | 1.79 |

As can be seen in Tables 47-48 above, CP4 expression was lower in all tissues of $F_1$ transformants transformed with pMON129205 (EXP-Sv.Ubq1:1:9, SEQ ID NO: 133) than those transformed with pMON141619 (EXP-ANDge.Ubq1:1:8, SEQ ID NO: 8), pMON142862 (EXP-ERIra.Ubq1:1:8, SEQ ID NO: 27) and pMON129221 (EXP-Cl.Ubq1:1:10, SEQ ID NO: 98).

The unique patterns of expression conferred by each of the EXP sequences assayed provide an opportunity to produce a transgenic plant in which expression can be fine-tuned to make small adjustments in transgene expression for optimal performance or effectiveness. In addition, empirical testing of these EXP sequences driving different transgene expression may produce results in which one particular EXP sequence is most suitable for expression of a specific transgene or class of transgenes while another EXP sequence is found to be best for a different transgene or class of transgenes.

Example 14: Analysis of Vegetative Glyphosate Tolerance in $R_0$ Transgenic Corn Plants Corn plants were transformed with plant expression vectors containing EXP sequences driving expression of the CP4 transgene, and the resulting plants were assessed for vegetative and reproductive tolerance to glyphosate application.

$F_1$ transformed corn plants described in Example 13 above transformed with pMON141619, pMON142862, pMON129221, pMON129205 and pMON129212 and comprised of the EXP sequences EXP-ANDge.Ubq1:1:8 (SEQ ID NO: 8), EXP-ERIra.Ubq1:1:8 (SEQ ID NO: 27), EXP-Cl.Ubq1:1:10 (SEQ ID NO: 98), EXP-Sv.Ubq1:1:9 (SEQ ID NO: 133) and EXP-Zm.UbgM1:1:7 (SEQ ID NO: 141), respectively driving CP4 were assessed for both vegetative and reproductive tolerance when sprayed with glyphosate. Ten F1 plants for each event were divided into two groups, the first group consisting of five plants that received glyphosate spray and V4 and V8 stage of development; and a second group of five plants that were left unsprayed (i.e. control). Glyphosate was applied by broadcast foliar spray application using Roundup WeatherMax® at an application rate of 1.5 a.e./acre (a.e. acid equivalent). After seven to ten days, the leaves of each plant were assessed for damage. Vegetative tolerance (Veg Tol in Table 49) was assessed comparing the unsprayed and sprayed plants for each event and a damage rating scale was used to provide a final rating for vegetative tolerance (T=tolerant, NT=not tolerant). In addition seed set was assayed for all of the plants in each event. Seed set measures between control plants and sprayed plants was compared and an assignment of reproductive tolerance (Repro Tol in Table 49) was given for each event based upon the percent seed set of sprayed plants relative to the controls (T=tolerant, NT=not tolerant). Table 49 below shows the vegetative and reproductive tolerance ratings for each event sprayed at V4 and V8 stage. The letter "T" denotes tolerant and "NT" denotes not tolerant.

TABLE 49

Leaf damage ratings of individual transformed corn events at V4 and V8 stage.

| Plasmid Construct | EXP sequence | SEQ ID NO: | Event | Veg Tol V4 | Veg Tol V8 | Repro Tol |
|---|---|---|---|---|---|---|
| pMON141619 | EXP-ANDge.Ubq1:1:8 | 8 | Event 1 | T | T | NT |
| | | | Event 2 | T | T | T |
| | | | Event 3 | T | T | NT |
| | | | Event 4 | T | T | NT |
| | | | Event 5 | T | T | T |
| | | | Event 6 | T | T | NT |
| | | | Event 7 | T | T | T |
| | | | Event 8 | T | T | T |
| | | | Event 9 | T | T | NT |
| pMON142862 | EXP-ERIra.Ubq1:1:8 | 27 | Event 1 | T | T | T |
| | | | Event 2 | T | T | NT |
| | | | Event 3 | T | T | T |
| | | | Event 4 | T | T | T |
| | | | Event 5 | T | T | NT |
| | | | Event 6 | T | T | T |
| | | | Event 7 | T | T | NT |
| | | | Event 8 | T | T | T |
| | | | Event 9 | T | T | T |
| pMON129221 | EXP-Cl.Ubq1:1:10 | 98 | Event 1 | T | T | NT |
| | | | Event 2 | T | T | NT |
| | | | Event 3 | NT | NT | T |
| | | | Event 4 | NT | NT | T |
| | | | Event 5 | T | T | NT |
| | | | Event 6 | NT | NT | T |
| | | | Event 7 | T | T | T |
| pMON129205 | EXP-Sv.Ubq1:1:9 | 133 | Event 1 | NT | NT | |
| | | | Event 2 | NT | NT | NT |
| | | | Event 3 | T | T | NT |
| | | | Event 4 | NT | NT | |
| | | | Event 5 | NT | NT | NT |
| | | | Event 6 | NT | NT | NT |
| | | | Event 7 | NT | NT | NT |
| pMON129212 | EXP-Zm.UbqM1:1:7 | 141 | Event 1 | T | T | |
| | | | Event 2 | T | T | |
| | | | Event 3 | T | T | |
| | | | Event 4 | T | T | |
| | | | Event 5 | T | T | |
| | | | Event 6 | T | T | |
| | | | Event 7 | T | T | |
| | | | Event 8 | T | T | |
| | | | Event 9 | T | T | |
| | | | Event 10 | T | T | |

From Table 49 above, all transformed events assayed comprising CP4 transgene cassettes comprising the EXP sequences EXP-ANDge.Ubq1:1:8 (SEQ ID NO: 8), EXP-ERIra.Ubq1:1:8 (SEQ ID NO: 27) and EXP-Zm.UbgM1:1:7 (SEQ ID NO: 141) demonstrated full vegetative tolerance based upon damage ratings that did not exceed a score of ten. Four events of nine comprising EXP-ANDge.Ubq1:1:8 (SEQ ID NO: 8) and six events of nine comprising EXP-ERIra.Ubq1:1:8 (SEQ ID NO: 27) were both vegetatively and reproductively tolerant to glyphosate application. In contrast, events comprising EXP-Cl.Ubq1:1:10 (SEQ ID NO: 98) were either vegetatively tolerant or reproductively tolerant but not both. Only one event comprising EXP-Sv.Ubq1:1:9 (SEQ ID NO: 133) demonstrated vegetative tolerance and none of the events tested were reproductive tolerant. All events comprising EXP-Zm.UbgM1:1:7 (SEQ ID NO: 141) demonstrated vegetative tolerance but and assessment of reproductive tolerance is still in progress.

Example 15: Analysis of Expression Using Different 3' End Intron/Exon Splice Junction Sequences Corn and Wheat leaf protoplast cells were transformed with plant expression constructs comprising EXP sequences driving GUS expression that comprise the same promoter and leader but have different 3' end nucleotides following the intron/exon splice junction sequence, 5'-AG-3' to see if expression is affected by the slight change in sequence. Expression was also compared to that of two constitutive control plasmids.

Plant expression constructs are built comprising a GUS expression cassette. The resulting vectors are comprised of the *Coix lacryma-jobi* ubiquitin promoter, P-Cl.Ubq1-1:1:1 (SEQ ID NO: 80) operably linked 5' to the leader sequence, L-Cl.Ubq1-1:1:1 (SEQ ID NO: 81), operably linked 5' to an intron element shown in Table 50 below which each comprise different nucleotides at the very 3' end just after the intron/exon splice junction 5'-AG-3' sequence, operably linked 5' to a GUS coding sequence which is operably linked 5' to T-AGRtu.nos-1:1:13 (SEQ ID NO: 127) 3' UTR. Table 50 below shows the plant expression constructs and the corresponding 3' end sequence.

TABLE 50

Plant expression constructs, introns and 3' end sequence following the intron/exon splice junction sequence 5'-AG-3'.

| Plasmid construct | EXP sequence | SEQ ID NO: | Intron Variant | Intron 3' end nucleotides immediately following 3' splice site AG |
|---|---|---|---|---|
| pMON140889 | EXP-Cl.Ubq1:1:10 | 98 | I-Cl.Ubq1-1:1:6 (SEQ ID NO: 94) | GTC |
| pMON146795 | EXP-Cl.Ubq1:1:18 | 99 | I-Cl.Ubq1-1:1:7 (SEQ ID NO: 92) | GTG |
| pMON146796 | EXP-Cl.Ubq1:1:19 | 100 | I-Cl.Ubq1-1:1:8 (SEQ ID NO: 101) | GCG |
| pMON146797 | EXP-Cl.Ubq1:1:20 | 102 | I-Cl.Ubq1-1:1:9 (SEQ ID NO: 103) | GAC |
| pMON146798 | EXP-Cl.Ubq1:1:21 | 104 | I-Cl.Ubq1-1:1:10 (SEQ ID NO: 105) | ACC |
| pMON146799 | EXP-Cl.Ubq1:1:22 | 106 | I-Cl.Ubq1-1:1:11 (SEQ ID NO: 107) | GGG |
| pMON146800 | EXP-Cl.Ubq1:1:23 | 108 | I-Cl.Ubq1-1:1:12 (SEQ ID NO: 109) | GGT |
| pMON146801 | EXP-Cl.Ubq1:1:24 | 110 | I-Cl.Ubq1-1:1:13 (SEQ ID NO: 111) | CGT |
| pMON146802 | EXP-Cl.Ubq1:1:25 | 112 | I-Cl.Ubq1-1:1:14 (SEQ ID NO: 113) | TGT |
| pMON25455 | EXP-Os.Act1:1:9 | 179 | | Constitutive Control |
| pMON65328 | EXP-CaMV.35S-enh + Ta.Lhcb1 + Os.Act1:1:1 | 163 | | Constitutive Control |

Corn and Wheat protoplasts were transformed as previously described and assayed for GUS and luciferase expression. Table 51 below shows the average GUS and RLuc values for both corn and wheat protoplast expression.

TABLE 51

Average GUS and RLuc values for corn and wheat protoplast cells.

| EXP sequence | Intron 3' end nucleotides immed. following 3' splice site AG | Corn Average GUS | Corn Average RLuc | Corn GUS/ RLuc | Wheat Ave. GUS | Wheat Ave. RLuc | Wheat GUS/ RLuc |
|---|---|---|---|---|---|---|---|
| EXP-Cl.Ubq1:1:10 | GTC | 140343.0 | 93870.75 | 1.50 | 40906.25 | 17381.75 | 2.35 |
| EXP-Cl.Ubq1:1:18 | GTG | 143106.25 | 60565.25 | 2.36 | 56709.00 | 17898.75 | 3.17 |
| EXP-Cl.Ubq1:1:19 | GCG | 136326.83 | 88589.75 | 1.54 | 43211.00 | 17352.50 | 2.49 |
| EXP-Cl.Ubq1:1:20 | GAC | 138110.83 | 104751.42 | 1.32 | 31711.50 | 17953.75 | 1.77 |
| EXP-Cl.Ubq1:1:21 | ACC | 137906.75 | 72519.50 | 1.90 | 54164.17 | 17772.83 | 3.05 |
| EXP-Cl.Ubq1:1:22 | GGG | 137306.83 | 92643.42 | 1.48 | 55198.25 | 14476.75 | 3.81 |
| EXP-Cl.Ubq1:1:23 | GGT | 144085.50 | 64351.25 | 2.24 | 43008.83 | 13911.50 | 3.09 |
| EXP-Cl.Ubq1:1:24 | CGT | 142061.50 | 65884.00 | 2.16 | 51210.50 | 15041.00 | 3.40 |
| EXP-Cl.Ubq1:1:25 | TGT | 140353.00 | 61249.50 | 2.29 | 49577.75 | 15348.25 | 3.23 |
| EXP-Os.Act1:1:9 | Constitutive Control | 37665.25 | 65835.50 | 0.57 | 10830.25 | 17716.50 | 0.61 |
| EXP-CaMV.35S-enh+Ta.Lhcb1+Os.Act1:1:1 | Constitutive Control | 49833.75 | 41268.75 | 1.21 | 15598.83 | 14877.50 | 1.05 |

The GUS/RLuc values for each *Coix lacryma-jobi* ubiquitin EXP sequence from PP Table 46 above were used to normalize the expression relative to the two constitutive controls EXP-Os.Act1:1:9 (SEQ ID NO: 179) and EXP-CaMV.35S-enh+Ta.Lhcb1+Os.Act1:1:1 (SEQ ID NO: 163) and are presented in Table 52 below.

TABLE 52

Normalized expression values of the *Coix lacryma-jobi* ubiquitin EXP sequences relative to EXP-Os.Act1:1:9 (SEQ ID NO: 179) and EXP-CaMV.35S-enh + Ta.Lhcb1 + Os.Act1:1:1 (SEQ ID NO: 163).

| EXP sequence | Intron 3' end nucleotides immediately following 3' splice site AG | Corn GUS/RLuc Normalized with respect to EXP-Os.Act1:1:9 | Corn GUS/RLuc Normalized with respect to EXP-CaMV.35S-enh + Ta.Lhcb1 + Os.Act1:1:1 | Wheat GUS/Rluc Normalized with respect to EXP-Os.Act1:1:9 | Wheat GUS/Rluc Normalized with respect to EXP-CaMV.35S-enh + Ta.Lhcb1 + Os.Act1:1:1 |
|---|---|---|---|---|---|
| EXP-Cl.Ubq1:1:10 | GTC | 2.61 | 1.24 | 3.85 | 2.24 |
| EXP-Cl.Ubq1:1:18 | GTG | 4.13 | 1.96 | 5.18 | 3.02 |
| EXP-Cl.Ubq1:1:19 | GCG | 2.69 | 1.27 | 4.07 | 2.38 |
| EXP-Cl.Ubq1:1:20 | GAC | 2.30 | 1.09 | 2.89 | 1.68 |
| EXP-Cl.Ubq1:1:21 | ACC | 3.32 | 1.57 | 4.99 | 2.91 |
| EXP-Cl.Ubq1:1:22 | GGG | 2.59 | 1.23 | 6.24 | 3.64 |
| EXP-Cl.Ubq1:1:23 | GGT | 3.91 | 1.85 | 5.06 | 2.95 |
| EXP-Cl.Ubq1:1:24 | CGT | 3.77 | 1.79 | 5.57 | 3.25 |
| EXP-Cl.Ubq1:1:25 | TGT | 4.01 | 1.90 | 5.28 | 3.08 |
| EXP-Os.Act1:1:9 | Constitutive Control | 1.00 | 0.47 | 1.00 | 0.58 |
| EXP-CaMV.35S-enh + Ta.Lhcb1 + Os.Act1:1:1 | Constitutive Control | 2.11 | 1.00 | 1.72 | 1.00 |

As is shown in Table 52 above, each of the *Coix lacryma-jobi* ubiquitin EXP sequences provided expression that was greater than either constitutive control in both corn and wheat. Expression in corn protoplasts was relatively similar for all of the *Coix* ubiquitin EXP sequences. Expression in wheat was a little more variable. The use of different 3' end nucleotides following the intron/exon splice junction sequence, 5'-AG-3' did not appear to dramatically affect expression of GUS with the exception of GUS driven by EXP-Cl.Ubq1:1:20 (SEQ ID NO: 102). EXP-Cl.Ubq1:1:20 comprises the 3' end nucleotide sequences, 5'-GAC-3' following the intron/exon splice junction 5'-AG-3' sequence and caused expression to drop slightly relative to the other *Coix* ubiquitin EXP sequences. Assessment of the resulting spliced messenger RNA showed that approximately 10% of the mRNA expressed using EXP-Cl.Ubq1:1:20 (SEQ ID NO: 102) to drive GUS expression was improperly spliced. The mRNA resulting from GUS expression using the other *Coix* ubiquitin EXP sequences appeared to process properly. This experiment provides evidence that any of the 3' end nucleotides for any of the intron variants presented in Table 2 of Example 1 with the exception of the 3' end sequence 5'-GAC-3' which is found associated only with the intron element, I-Cl.Ubq1-1:1:9 (SEQ ID NO: 103) should be suitable for use in transgene expression cassettes without significant loss of activity and processing.

Example 16: Enhancers Derived from the Regulatory Elements

Enhancers are derived from the promoter elements provided herein, such as those presented as SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135. The enhancer element may be comprised of one or more cis regulatory elements that, when operably linked 5' or 3' to a promoter element, or operably linked 5' or 3' to additional enhancer elements that are operably linked to a promoter, can enhance or modulate expression of a transgene, or provide expression of a transgene in a specific cell type or plant organ or at a particular time point in development or circadian rhythm. Enhancers are made by removing the TATA box or functionally similar elements and any downstream sequence from the promoters that allow transcription to be initiated from the promoters provided herein as described above, including fragments thereof, in which the TATA box or functionally similar elements and sequence downstream of the TATA box are removed. The enhancer element, E-Cl.Ubq1-1:1:1 (SEQ ID NO: 89) which is derived from the promoter element, P-Cl.Ubq1-1:1:1 is provided herein to demonstrate enhancers derived from a promoter element.

Enhancer elements may be derived from the promoter elements provided herein and cloned using methods known in the art to be operably linked 5' or 3' to a promoter element, or operably linked 5' or 3' to additional enhancer elements that are operably linked to a promoter. Alternatively, enhancer elements are cloned, using methods known in the art, to be operably linked to one or more copies of the enhancer element which are operably linked 5' or 3' to a promoter element, or operably linked 5' or 3' to additional enhancer elements that are operably linked to a promoter. Enhancer elements can also be cloned to be operably linked 5' or 3' to a promoter element derived from a different genus organism, or operably linked 5' or 3' to additional enhancer elements derived from other genus organisms or the same genus organism that are operably linked to a promoter derived from either the same or different genus organism, resulting in a chimeric regulatory element. A GUS expression plant transformation vector is constructed using methods known in the art similar to the constructs described in the previous examples in which the resulting plant expression vectors contain a right border region from *A. tumefaciens*, a first transgene cassette to test the regulatory or a chimeric regulatory element comprised of, a regulatory or chimeric regulatory element, operably linked to an intron derived from the HSP70 heat shock protein of *Z. mays* (I-Zm.DnaK-1:1:1 SEQ ID NO: 144) or any of the introns presented herein or any other intron, operably linked to a coding sequence for β-glucuronidase (GUS) that either possesses a processable intron (GUS-2, SEQ ID NO: 160) or no intron (GUS-1, SEQ ID NO: 159), operably linked to the Nopaline synthase 3' UTR from *A. tumefaciens* (T-AGRtu.nos-1:1:13, SEQ ID NO: 161) or the 3' UTR from the rice lipid transfer protein gene (T-Os.LTP-1:1:1, SEQ ID NO: 175); a second transgene selection cassette used for selection of transformed plant cells that confers resistance to the herbicide glyphosate (driven by the rice Actin 1 promoter), or alternatively, the antibiotic kanamycin (driven by the rice Actin 1 promoter) and a left border region from *A. tumefaciens*. The resulting plasmids are used to transform corn plants or other genus plants by the methods described above or by other *Agrobacterium*-mediated or particle bombardment methods known in the art. Alternatively, protoplast cells derived from corn or other genus plants are transformed using methods known in the art to perform transient assays GUS expression driven by the regulatory element comprising one or more enhancers is evaluated in stable or transient plant assays to determine the effects of the enhancer element on expression of a transgene. Modifications to one or more enhancer elements or duplication of one or more enhancer elements is performed based upon empirical experimentation and the resulting gene expression regulation that is observed using each regulatory element composition. Altering the relative positions of one or more enhancers in the resulting regulatory or chimeric regulatory element may affect the transcriptional activity or specificity of the regulatory or chimeric regulatory element and is determined empirically to identify the best enhancers for the desired transgene expression profile within the corn plant or other genus plant.

Example 17: Analysis of Intron Enhancement of GUS Activity Using Plant Derived Protoplasts An intron is selected based upon experimentation and comparison with an intronless expression vector control to empirically select an intron and configuration within the vector T-DNA element arrangement for optimal expression of a transgene. For example, in the expression of an herbicide resistance gene, such as CP4 which confers tolerance to glyphosate, it is desirable to have transgene expression within the reproductive tissues as well as the vegetative tissues, to prevent the loss of yield when applying the herbicide. An intron in this instance would be selected upon its ability when operably linked to a constitutive promoter, to enhance expression of the herbicide resistance conferring transgene, particularly within the reproductive cells and tissues of the transgenic plant and thus providing both vegetative and reproductive tolerance to the transgenic plant, when sprayed with the herbicide. In most ubiquitin genes, the 5' UTR is comprised of a leader, which has an intron sequence embedded within it. The expression elements derived from such genes are therefore assayed using the entire 5' UTR comprising the promoter, leader, and intron. To achieve different expression profiles or to modulate the level of transgene expression, the intron from such an expression element may be removed or substituted with a heterologous intron.

Introns presented herein as SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182 are identified using genomic DNA contigs in comparison to expressed sequence tag clusters or cDNA contigs to identify exon and intron sequences within the genomic DNA. In addition, 5' UTR or leader sequences are also used to define the intron/exon splice junction of one or more introns under conditions when the gene sequence encodes a leader sequence that is interrupted by one or more introns. Introns are cloned using methods known in the art into a plant transformation vector to be operably linked 3' to a transcriptional regulatory element and leader fragment and operably linked 5' to either a second leader fragment or to coding sequences, for instance as depicted in the two transgene cassettes presented in FIG. 1.

Thus, for instance, a first possible transgene cassette (Transgene Cassette Configuration 1 in FIG. 8) is comprised of a promoter or chimeric promoter element [A], operably linked 5' to a leader element [B], operably linked 5' to a test intron element [C], operably linked to a coding region [D], which is operably linked to a 3' UTR element [E]. Alternatively, a second possible transgene cassette (Transgene Cassette Configuration 2 in FIG. 8) is comprised of a promoter or chimeric promoter element [F], operably linked 5' to a first leader element or first leader element fragment [G], operably linked 5' to a test intron element [H], operably linked 5' to a second leader element or first leader element second fragment [I], operably linked to a coding region [J], which is operably linked to a 3' UTR element [K]. Further, a third possible transgene cassette (Transgene Cassette Configuration 3 in FIG. 8) is comprised of a promoter or chimeric promoter element [L], operably linked 5' to a leader element [M], operably linked 5' to a first fragment of the coding sequence element [N], operably linked 5' to an intron element [O] element, operably linked 5' to a second fragment of the coding sequence element [P], which is operably linked to a 3' UTR element [Q]. Transgene Cassette Configuration 3 is designed to allow splicing of the intron in such a manner as to produce a complete open reading frame without a frame shift between the first and second fragment of the coding sequence.

The first 6 nucleotides on the 5' end and the last 6 nucleotides on the 3' end of the introns presented as SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182 represent nucleotides before and after the intron/exon splice junction, respectively. These short 6 nucleotide sequences, for example, can be modified by having additional sequence appended (i.e. native or artificial) to facilitate cloning of the intron into a plant transformation vector, so long as the first and second nucleotides from the 5' end (GT) and the fourth and fifth nucleotide from the 3' end (AG) of SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182 are preserved, thus preserving the intron/exon splice junction of the intron. As discussed above, it may be preferable to avoid using the nucleotide sequence AT or the nucleotide A just prior to the 5' end of the splice site (GT) and the nucleotide G or the nucleotide sequence TG, respectively just after 3' end of the splice site (AG) to eliminate the potential of unwanted start codons from being formed during processing of the messenger RNA into the final transcript. The sequence around the 5' or 3' end splice junction sites of the intron can thus be modified.

The introns are assayed for an enhancement effect through the ability to enhance expression in transient assay or stable plant assay. For transient assay of intron enhancement, a base plant vector is constructed using methods known in the art. The intron is cloned into a base plant vector which comprises an expression cassette comprised of a constitutive promoter such as the Cauliflower mosaic virus promoter, P-CaMV.35S-enh-1:1:9 (SEQ ID NO: 176), operably linked 5' to a leader element, L-CaMV.35S-1:1:15 (SEQ ID NO: 177 (acacgctg)), operably linked 5' to a test intron element (e.g. one of SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182), operably linked to a coding sequence for β-glucuronidase (GUS) that either possesses a processable intron (GUS-2, SEQ ID NO: 160) or no intron (GUS-1, SEQ ID NO: 159), operably linked to the Nopaline synthase 3' UTR from *A. tumefaciens* (T-AGRtu.nos-1:1:13, SEQ ID NO: 161). Protoplast cells derived from corn or other genus plant tissue are transformed with the base plant vector and luciferase control vectors as described previously in Example 2 above and assayed for activity. To compare the relative ability of the intron to enhance expression, GUS values are expressed as a ratio of GUS to luciferase activity and compared with those levels imparted by a construct comprising the constitutive promoter operably linked to a known intron standard such as that as the intron derived from the HSP70 heat shock protein of *Zea mays*, I-Zm.DnaK-1:1:1 (SEQ ID NO: 178) as well as a construct comprising the constitutive promoter but without an intron operably linked to the promoter.

For stable plant assay of the introns presented as SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182, a GUS expression plant transformation vector is constructed similar to the constructs described in the previous examples in which the resulting plant expression vectors contains a right border region from *A. tumefaciens*, a first transgene cassette to test the intron comprised of a constitutive promoter such as the Cauliflower mosaic virus promoter, P-CaMV.35S-enh-1:1:9 (SEQ ID NO: 176), operably linked 5' to a leader element, L-CaMV.35S-1:1:15 (SEQ ID NO: 177 (acacgctg)), operably linked 5' to a test intron element provided herein, operably linked to a coding sequence for β-glucuronidase (GUS) that either possesses a processable intron (GUS-2, SEQ ID NO: 160) or no intron (GUS-1, SEQ ID NO: 158), operably linked to the Nopaline synthase 3' UTR from *A. tumefaciens* (T-AGRtu.nos-1:1:13, SEQ ID NO: 161); a second transgene selection cassette used for selection of transformed plant cells that confers resistance to glyphosate (driven by the rice Actin 1 promoter), or alternatively, the antibiotic kanamycin (driven by the rice Actin 1 promoter) and a left border region from *A. tumefaciens*. The resulting plasmids are used to transform corn plants or other genus plants by the methods described above or by *Agrobacterium*-mediated methods known in the art. Single-copy or low copy number transformants are selected for comparison to single-copy or low copy number transformed plants, transformed with a plant transformation vector identical to the test vector but without the test intron to determine if the test intron provides an intron mediated enhancement effect.

Any of the introns presented as SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182 can be modified in a number of ways, such as deleting fragments within the intron sequence, which may reduce expression or duplication of fragments with the intron that may enhance expression. In addition, sequences within the intron that may affect the specificity of expression to either particular cells types or tissues and organs can be duplicated or altered or deleted to affect expression and patterns of expression of the transgene. In addition, the introns provided herein can be modified to remove any potential start codons (ATG) that may cause unintentional transcripts from being expressed from improperly spliced introns as different, longer or truncated proteins. Once the intron has been empirically tested, or it has been altered based upon experimentation, the intron is used to enhance expression of a transgene in stably transformed plants that can be of any genus monocot or dicot plant, so long as the intron provides enhancement of the transgene. The intron can also be used to enhance expression in other organisms, such as algae, fungi or animal cells, so long as the intron provides enhancement or attenuation or specificity of expression of the transgene to which it is operably linked.

Having illustrated and described the principles of the present invention, it should be apparent to persons skilled in the art that the invention can be modified in arrangement and detail without departing from such principles. We claim all modifications that are within the spirit and scope of the claims. All publications and published patent documents cited herein are hereby incorporated by reference to the same extent as if each individual publication or patent application is specifically and individually indicated to be incorporated by reference.

What is claimed is:

1. A DNA molecule comprising a DNA sequence selected from the group consisting of:

a) a sequence with at least 95 percent sequence identity to SEQ ID NO: 77 or 78;

b) a sequence comprising SEQ ID NO: 77 or 78; and c) a fragment comprising at least 150 contiguous nucleotides of SEQ ID NO: 77 or 78, wherein the fragment has gene-regulatory activity;

wherein said sequence is operably linked to a heterologous transcribable polynucleotide molecule.

2. The DNA molecule of claim 1, wherein said sequence has at least 97 percent sequence identity to the DNA sequence of SEQ ID NO: 77 or 78.

3. The DNA molecule of claim 1, wherein said sequence has at least 99 percent sequence identity to the DNA sequence of SEQ ID NO: 77 or 78.

4. The DNA molecule of claim 1, wherein the DNA sequence comprises gene regulatory activity.

5. The DNA molecule of claim 1, wherein the heterologous transcribable polynucleotide molecule comprises a gene of agronomic interest.

6. The DNA molecule of claim 5, wherein the gene of agronomic interest confers herbicide tolerance in plants.

7. The DNA molecule of claim 5, wherein the gene of agronomic interest confers pest resistance in plants.

8. A transgenic plant cell comprising the DNA molecule of claim 1.

9. The transgenic plant cell of claim 8, wherein said transgenic plant cell is a monocotyledonous plant cell.

10. The transgenic plant cell of claim 8, wherein said transgenic plant cell is a dicotyledonous plant cell.

11. A transgenic plant, or part thereof, comprising the DNA molecule of claim 1.

12. A progeny plant of the transgenic plant of claim 11, or a part thereof, wherein the progeny plant or part thereof comprises said DNA molecule.

13. A transgenic seed, wherein the seed comprises the DNA molecule of claim 1.

14. A method of producing a commodity product, the method comprising obtaining a transgenic plant or part thereof according to claim 11 and producing the commodity product therefrom.

15. The method of claim 14, wherein the commodity product is selected from the group consisting of protein concentrate, protein isolate, grain, starch, seeds, meal, flour, biomass, and seed oil.

16. A commodity product comprising the DNA molecule of claim 1.

17. The commodity product of claim 16, wherein the commodity product is selected from the group consisting of protein concentrate, protein isolate, grain, starch, seeds, meal, flour, biomass, and seed oil.

18. A method of expressing a transcribable polynucleotide molecule, the method comprising obtaining a transgenic plant according to claim 11 and cultivating the plant, wherein the transcribable polynucleotide is expressed.

19. The DNA molecule of claim 1, wherein said DNA molecule comprises the sequence with at least 95 percent sequence identity to SEQ ID NO: 77 and has promoter activity.

20. The DNA molecule of claim 1, wherein said DNA molecule comprises the sequence with at least 95 percent sequence identity to SEQ ID NO: 78 and has promoter activity.

21. The DNA molecule of claim 1, wherein said DNA molecule comprises the sequence comprising SEQ ID NO: 77.

22. The DNA molecule of claim 1, wherein said DNA molecule comprises the sequence comprising SEQ ID NO: 78.

* * * * *

SEQUENCE LISTING

```
Sequence total quantity: 183
SEQ ID NO: 1           moltype = DNA  length = 3741
FEATURE                Location/Qualifiers
source                 1..3741
                       mol_type = other DNA
                       organism = Andropogon gerardii
SEQUENCE: 1
agcagactcg cattatcgat ggaggggtgg gtttagaacc ctgaaaactg gtactgtttc  60
gaactgaaaa acactgtagc acttttcgtt tgtttgtggt aaatattatc ttactatggt  120
ctaactaggc tcaaaagaat cgtctcgcaa tgtacatcta aattatgcaa ttagttattt  180
tgtttacctg catttcatac tccgagcatg cgtcttttgg tacatttaat gcttcgatgt  240
gatgggaatt ttaaaaattt tggagaaaag ttggtttcta aacacccccg aggacgaaat  300
tggattcggt ctttgacgcg gatgcagcaa ctgcagtgcg caggatacca tcttagccgt  360
tgcgtcgaag ttcgctttgc taacgttttg agaaaattaa accagctttg accaacgtga  420
gacgagcgcc ttacgtggca gtgtaatgga accgggcacg gcaagtttga cgctgtagtg  480
ttagccggtc tcgttacgtt tggcacaact tagttgaatc cggcttccgg caaactatat  540
ggcaagttag acccaagtgt gagccggcca ccgcaagtta ttgggacatt atacgtagga  600
agcaagtgta taataagaat atgagataat gtaagcagct atatgaatca tcacgtcata  660
tttatgttaa gatgaagagg atagaataaa cggtatgtaa atttatagcg agtgatagac  720
gggcacaagg cctcctagct atttccataa atcggatttt gtaagaacaa aaaagaggac  780
ttattataag agaatgtggt aagtaagtat actctctccg tttcaaatta taagttgttt  840
tgattttttt ggtacatcta ttttactatg cattagatat aataatgtgt ctagatacat  900
aacaaaatgg atgaatcaaa aaagtcaaag tgatttacaa tttggaacgg agagagtaag  960
ttcaagccgt caaggcactt ctatgcaacc acagtcaact tgaatgccgc ttgagtgcct  1020
tctcaagttt ttttttcttg caaaaatcat ttcttttttt taaaaaaagt ataatttgga  1080
tcgtgcaaat ttctctctag gtgtgtgtgt gactgtgtga gtaacaattt ctctagttgt  1140
gcgcgactgc tgcttacttt ggagattaca atatctttct aaaatgcttc gattacttat  1200
ttataaaccg tctctaaggc caattgctca agattcattc aacaattgaa acgtctcaca  1260
tgattaaatc atataaagtt tctaagtctt gtttgacaag atttttttag attttcatct  1320
aaattggatg aaactatcaa acactaattt taaaaaatat aagagaagct ccggagataa  1380
aaggtcgtct atgttattat aagagtaaag tcgtctattc tcttcgtccc aacatatata  1440
attctaagca tgaattgctt tctttttgga caaaaggagc atgccacaac acaagaatga  1500
tgtcaccgtc atgcttggat ccttttatgg taaagcttca ccttctataa tctaacaata  1560
gagaaatcag ggaaaaatca tgttttggtt gtttttattt ctaacctcca caataacttt  1620
ggtttaccat tttttgtttg attttagttt tagagaagcg tttataacag gacctaaaat  1680
ctttttttcag tacacagtac aacgcagacg ctcatacacg cacgcacact cacctctatg  1740
aacacacgta agaaaaccct acaccttgag caccttcgaa ggactgagcc ggtaaatata  1800
gagattctcg aagtcactat tagcgcctcg ttgtcaacgg gaatgtcgct taccacttaa  1860
agcataacgc cgagaaatcc cgtaataaat ccagtaaaat acgagcaccc gtgccaagtt  1920
gaatatttga acccgagtgg gtagattcca ccgcaaagga cctaaccaga tcatttcgca  1980
aacaggaact aaaatcggta gagagcccag acaaaagcct ttcctaagag ccactccagt  2040
ggaagcccct actttaggta taaaatgcaa tactagtggg gctcctaaat aaacttctat  2100
ttttcatggc cttctaaaat tcactcccaa accccctagct atagaagtct cttatccatc  2160
ctctaaataa aaatgggagt ctattttatt tcaccagagt tgatcgtaaa tttagtctct  2220
caaattttat aagttgaggg tagaggatga ctggagttgc tctaaacgga cctatcttca  2280
agtgacctca gtgagcccgt ttaacggcgt cgacaagttt aatctaacgg acaccaacca  2340
gagaagagaa ccaccgccag cgccgagcca agcgacgttg acatcttggc gcggcacggc  2400
atctccctgg cgtctggccc cctctcgaga cttccgctcc acctcccacc ggtggcggtt  2460
tccaagtccg ttccgcctcc tctcacacgg cacgaaaccg tgacgggcac cggcagcacg  2520
gggggattcc tttcccaccg ctccttccct ttcccttcct ctcccgccgc tataaatagc  2580
cagccccatc cccagcttct ttccccaacc tcatcttctc tcgtgttgtt cggcacaacc  2640
cgatcgatcc ccaactccct cgtcgtctct cctcgcgagc ctcgtcgatc ccccgcttca  2700
```

```
aggtacggcg atcgattatc ttccctctct ctaccttctc tctcttatag ggcctgctag  2760
ctctgttcct gtttttccat ggctgcgagg tacaatagat cggcgatcca tggttagggc  2820
ctgctagttg tgttcctgtt tttccatggc tgcgaggcac aatagatctg atggcgttat  2880
gatggttaac ttgtcatact cttgcgatct atggtccctt taggagttta ggacatctat  2940
ttaatttcgg atagttcgag atctgtgatc catggttagt accctaggca gtggggttag  3000
atccgtgctg ttatggttcg tagatggatt ctgattgctc agtaactggg aatcctggga  3060
tggttctagc tggttcgcag ataagatcga tttcatgata tgctatatct tgtttggttg  3120
ccgtggttcc gttaaatctg tctgttatga tcttagtctt tgataaggtt cggtcgtgct  3180
agctacgtcc tgtgcagcac ttaattgtca ggtcataatt tttagcatgc ctttttttta  3240
ttggtttggt tttgtctgac tgggctgtag atagtttcaa tctttgtctg actgggctgt  3300
agatagtttc aatctacctg tcggtttatt ttattaaatt tggatctgta tgtgtgtcat  3360
atatcttcat cttttagata tatcgatagg tttatatgtt gctgtcggtt ttttactgtt  3420
cctttatgag atatattcat gcttagatac atgaaacaac gtgctgttac agtttaatag  3480
ttcttgttta tctaataaac aaataaggat aggtatatgc tgcagttagt tttactggta  3540
cttttttga catgaaccta cggcttaata attagtcttc atcaaataaa aagcatattt  3600
tttaattatt tcgatatact tgaatgatgt catatgcagc atctgtgtga atttttggcc  3660
ctgtcttcat atgctgttta tttgtttggg actgtttctt tggttgataa ctcatcctgt  3720
tgtttggtga tccttttgca g                                            3741

SEQ ID NO: 2           moltype = DNA  length = 2603
FEATURE                Location/Qualifiers
source                 1..2603
                       mol_type = other DNA
                       organism = Andropogon gerardii
SEQUENCE: 2
agcagactcg cattatcgat ggaggggtgg gtttagaacc ctgaaaactg gtactgtttc  60
gaactgaaaa acactgtagc acttttcgtt tgtttgtggt aaatattatc ttactatggt  120
ctaactaggc tcaaaagaat cgtctcgcaa tgtacatcta aattatgcaa ttagttattt  180
tgtttacctg catttcatac tccgagcatg cgtcttttgg tacatttaat gcttcgatgt  240
gatgggaatt ttaaaaattt tggagaaaag ttggtttcta aacacccccg aggacgaaat  300
tggattcggt ctttgacgcg gatgcagcaa ctgcagtgcg caggatacca tcttagccgt  360
tgcgtcgaag ttcgctttgc taacgttttg agaaaattaa accagctttg accaacgtga  420
gacgagcgcc ttacgtggca gtgtaatgga accgggcacg gcaagtttga cgctgtagtg  480
ttagccggtc tcgttacgtt tggcacaact tagttgaatc cggcttccgg caaactatat  540
ggcaagttag acccaagtgt gagccggcca ccgcaagtta ttgggacatt atacgtagga  600
agcaagtgta taataagaat atgagataat gtaagcagct atatgaatca tcacgtcata  660
tttatgttaa gatgaagagg atagaataaa cggtatgtaa atttatagcg agtgatagac  720
gggcacaagg cctcctagct atttccataa atcggatttt gtaagaacaa aaaagaggac  780
ttattataag agaatgtggt aagtaagtat actctctccg tttcaaatta taagttgttt  840
tgattttttt ggtacatcta ttttactatg cattagatat aataatgtgt ctagatacat  900
aacaaaatgg atgaatcaaa aaagtcaaag tgatttacaa tttggaacgg agagagtaag  960
ttcaagccgt caaggcactt ctatgcaacc acagtcaact tgaatgccgc ttgagtgcct  1020
tctcaagttt tttttcttg caaaaatcat ttcttttttt taaaaaaagt ataatttgga  1080
tcgtgcaaat ttctctctag gtgtgtgtgt gactgtgtga gtaacaattt ctctagttgt  1140
gcgcgactgc tgcttacttt ggagattaca atatctttct aaaatgcttc gattacttat  1200
ttataaaccg tctctaaggc caattgctca agattcattc aacaattgaa acgtctcaca  1260
tgattaaatc atataaagtt tctaagtctt gtttgacaag attttttag attttcatct  1320
aaattggatg aaactatcaa acactaattt taaaaaatat aagagaagct ccggagataa  1380
aaggtcgtct atgttattat aagagtaaag tcgtctattc tcttcgtccc aacatatata  1440
attctaagca tgaattgctt tctttttgga caaaaggagc atgccacaac acaagaatga  1500
tgtcaccgtc atgcttggat ccttttatgg taaagcttca ccttctataa tctaacaata  1560
gagaaatcag ggaaaaatca tgttttggtt gtttttattt ctaacctcca caataacttt  1620
ggtttaccat tttttgtttg attttagttt tagagaagcg tttataacag gacctaaaat  1680
cttttttcag tacacagtac aacgcagacg ctcatacacg cacgcacact cacctctatg  1740
aacacacgta agaaaaccct acaccttgag caccttcgaa ggactgagcc ggtaaatata  1800
gagattctcg aagtcactat tagcgcctcg ttgtcaacgg gaatgtcgct taccacttaa  1860
agcataacgc cgagaaatcc cgtaataaat ccagtaaaat acgagcaccc gtgccaagtt  1920
gaatatttga acccgagtgg gtagattcca ccgcaaagga cctaaccaga tcatttcgca  1980
aacaggaact aaaatcggta gagagcccag acaaaagcct ttcctaagag ccactccagt  2040
ggaagcccct actttaggta taaaatgcaa tactagtggg gctcctaaat aaacttctat  2100
ttttcatggc cttctaaaat tcactcccaa accccctagct atagaagtct cttatccatc  2160
ctctaaataa aaatgggagt ctattttatt tcaccagagt tgatcgtaaa tttagtctct  2220
caaattttat aagttgaggg tagaggatga ctggagttgc tctaaacgga cctatcttca  2280
agtgacctca gtgagcccgt ttaacggcgt cgacaagttt aatctaacgg acaccaacca  2340
gagaagagaa ccaccgccag cgccgagcca agcgacgttg acatcttggc gcggcacggc  2400
atctccctgg cgtctggccc cctctcgaga cttccgctcc acctcccacc ggtggcggtt  2460
tccaagtccg ttccgcctcc tctcacacgg cacgaaaccg tgacgggcac cggcagcacg  2520
gggggattcc tttcccaccg ctccttccct ttcccttcct ctcccgccgc tataaatagc  2580
cagccccatc cccagcttct ttc                                          2603

SEQ ID NO: 3           moltype = DNA  length = 99
FEATURE                Location/Qualifiers
source                 1..99
                       mol_type = other DNA
                       organism = Andropogon gerardii
SEQUENCE: 3
cccaacctca tcttctctcg tgttgttcgg cacaacccga tcgatcccca actccctcgt  60
cgtctctcct cgcgagcctc gtcgatcccc cgcttcaag                         99
```

```
SEQ ID NO: 4            moltype = DNA  length = 1039
FEATURE                 Location/Qualifiers
source                  1..1039
                        mol_type = other DNA
                        organism = Andropogon gerardii
SEQUENCE: 4
gtacggcgat cgattatctt ccctctctct accttctctc tcttataggg cctgctagct  60
ctgttcctgt ttttccatgg ctgcgaggta caatagatcg gcgatccatg gttagggcct  120
gctagttgtg ttcctgtttt tccatggctg cgaggcacaa tagatctgat ggcgttatga  180
tggttaactt gtcatactct tgcgatctat ggtcccttta ggagtttagg acatctattt  240
aatttcggat agttcgagat ctgtgatcca tggttagtac cctaggcagt ggggttagat  300
ccgtgctgtt atggttcgta gatggattct gattgctcag taactgggaa tcctgggatg  360
gttctagctg gttcgcagat aagatcgatt tcatgatatg ctatatcttg tttggttgcc  420
gtggttccgt taaatctgtc tgttatgatc ttagtctttg ataaggttcg gtcgtgctag  480
ctacgtcctg tgcagcactt aattgtcagg tcataatttt tagcatgcct ttttttattt  540
ggtttggttt tgtctgactg ggctgtagat agtttcaatc tttgtctgac tgggctgtag  600
atagtttcaa tctacctgtc ggtttatttt attaaatttg gatctgtatg tgtgtcatat  660
atcttcatct tttagatata tcgataggtt tatatgttgc tgtcggtttt ttactgttcc  720
tttatgagat atattcatgc ttagatacat gaaacaacgt gctgttacag tttaatagtt  780
cttgtttatc taataaacaa ataaggatag gtatatgctg cagttagttt tactggtact  840
ttttttgaca tgaacctacg gcttaataat tagtcttcat caaataaaaa gcatattttt  900
taattatttc gatatacttg aatgatgtca tatgcagcat ctgtgtgaat ttttggccct  960
gtcttcatat gctgtttatt tgtttgggac tgtttctttg gttgataact catcctgttg  1020
tttggtgatc cttttgcag                                                1039

SEQ ID NO: 5            moltype = DNA  length = 3255
FEATURE                 Location/Qualifiers
source                  1..3255
                        mol_type = other DNA
                        organism = Andropogon gerardii
SEQUENCE: 5
ctcgttacgt ttggcacaac ttagttgaat ccggcttccg gcaaactata tggcaagtta  60
gacccaagtg tgagccggcc accgcaagtt attgggacat tatacgtagg aagcaagtgt  120
ataataagaa tatgagataa tgtaagcagc tatatgaatc atcacgtcat atttatgtta  180
agatgaagag gatagaataa acggtatgta aatttatagc gagtgataga cgggcacaag  240
gcctcctagc tatttccata aatcggattt tgtaagaaca aaaaagagga cttattataa  300
gagaatgtgg taagtaagta tactctctcc gtttcaaatt ataagttgtt ttgatttttt  360
tggtacatct attttactat gcattagata taataatgtg tctagataca taacaaaatg  420
gatgaatcaa aaaagtcaaa gtgatttaca atttggaacg gagagagtaa gttcaagccg  480
tcaaggcact tctatgcaac cacagtcaac ttgaatgccg cttgagtgcc ttctcaagtt  540
tttttttctt gcaaaaatca tttctttttt ttaaaaaaag tataatttgg atcgtgcaaa  600
tttctctcta ggtgtgtgtg tgactgtgtg agtaacaatt tctctagttg tgcgcgactg  660
ctgcttactt tggagattac aatatctttc taaaatgctt cgattactta tttataaacc  720
gtctctaagg ccaattgctc aagattcatt caacaattga aacgtctcac atgattaaat  780
catataaagt ttctaagtct tgtttgacaa gattttttta gattttcatc taaattggat  840
gaaactatca aacactaatt ttaaaaaata taagagaagc tccggagata aaaggtcgtc  900
tatgttatta taagagtaaa gtcgtctatt ctcttcgtcc caacatatat aattctaagc  960
atgaattgct ttctttttgg acaaaaggag catgccacaa cacaagaatg atgtcaccgt  1020
catgcttgga tccttttatg gtaaagcttc accttctata atctaacaat agagaaatca  1080
gggaaaaatc atgttttggt tgtttttatt tctaacctcc acaataactt tggtttacca  1140
tttttgttt gattttagtt ttagagaagc gtttataaca ggacctaaaa tcttttttca  1200
gtacacagta caacgcagac gctcatacac gcacgcacac tcacctctat gaacacacgt  1260
aagaaaaccc tacaccttga gcaccttcga aggactgagc cggtaaatat agagattctc  1320
gaagtcacta ttagcgcctc gttgtcaacg ggaatgtcgc ttaccactta aagcataacg  1380
ccgagaaatc ccgtaataaa tccagtaaaa tacgagcacc cgtgccaagt tgaatatttg  1440
aacccgagtg ggtagattcc accgcaaagg acctaaccag atcatttcgc aaacaggaac  1500
taaaatcggt agagagccca gacaaaagcc tttcctaaga gccactccag tggaagcccc  1560
tactttaggt ataaaatgca atactagtgg ggctcctaaa taaacttcta tttttcatgg  1620
ccttctaaaa ttcactccca aacccctagc tatagaagtc tcttatccat cctctaaata  1680
aaaatgggag tctattttat ttcaccagag ttgatcgtaa atttagtctc tcaaatttta  1740
taagttgagg gtagaggatg actggagttg ctctaaacgg acctatcttc aagtgacctc  1800
agtgagcccg tttaacggcg tcgacaagtt taatctaacg gacaccaacc agagaagaga  1860
accaccgcca gcgccgagcc aagcgacgtt gacatcttgg cgcggcacgg catctccctg  1920
gcgtctggcc ccctctcgag acttccgctc cacctcccac cggtggcggt ttccaagtcc  1980
gttccgcctc ctctcacacg gcacgaaacc gtgacgggca ccggcagcac ggggggattc  2040
ctttcccacc gctccttccc tttcccttcc tctcccgccg ctataaatag ccagccccat  2100
ccccagcttc tttccccaac ctcatcttct ctcgtgttgt tcggcacaac ccgatcgatc  2160
cccaactccc tcgtcgtctc tcctcgcgag cctcgtcgat cccccgcttc aaggtacggc  2220
gatcgattat cttccctctc tctaccttct ctctcttata gggcctgcta gctctgttcc  2280
tgtttttcca tggctgcgag gtacaataga tcggcgatcc atggttaggg cctgctagtt  2340
gtgttcctgt ttttccatgg ctgcgaggca caatagatct gatggcgtta tgatggttaa  2400
cttgtcatac tcttgcgatc tatggtccct ttaggagttt aggacatcta tttaatttcg  2460
gatagttcga gatctgtgat ccatggttag taccctaggc agtggggtta gatccgtgct  2520
gttatggttc gtagatggat tctgattgct cagtaactgg gaatcctggg atggttctag  2580
ctggttcgca gataagatcg atttcatgat atgctatatc ttgtttggtt gccgtggttc  2640
cgttaaatct gtctgttatg atcttagtct ttgataaggt tcggtcgtgc tagctacgtc  2700
ctgtgcagca cttaattgtc aggtcataat ttttagcatg cctttttttt attggtttgg  2760
ttttgtctga ctgggctgta gatagtttca atctttgtct gactgggctg tagatagttt  2820
caatctacct gtcggtttat tttattaaat ttggatctgt atgtgtgtca tatatcttca  2880
```

```
tcttttagat atatcgatag gtttatatgt tgctgtcggt tttttactgt tcctttatga  2940
gatatattca tgcttagata catgaaacaa cgtgctgtta cagtttaata gttcttgttt  3000
atctaataaa caaataagga taggtatatg ctgcagttag ttttactggt actttttttg  3060
acatgaacct acggcttaat aattagtctt catcaaataa aaagcatatt ttttaattat  3120
ttcgatatac ttgaatgatg tcatatgcag catctgtgtg aatttttggc cctgtcttca  3180
tatgctgttt atttgtttgg gactgtttct ttggttgata actcatcctg ttgtttggtg  3240
atccttttgc aggtg                                                   3255

SEQ ID NO: 6           moltype = DNA  length = 2114
FEATURE                Location/Qualifiers
source                 1..2114
                       mol_type = other DNA
                       organism = Andropogon gerardii
SEQUENCE: 6
ctcgttacgt ttggcacaac ttagttgaat ccggcttccg gcaaactata tggcaagtta  60
gacccaagtg tgagccggcc accgcaagtt attgggacat tatacgtagg aagcaagtgt  120
ataataagaa tatgagataa tgtaagcagc tatatgaatc atcacgtcat atttatgtta  180
agatgaagag gatagaataa acggtatgta aatttatagc gagtgataga cgggcacaag  240
gcctcctagc tatttccata aatcggattt tgtaagaaca aaaaagagga cttattataa  300
gagaatgtgg taagtaagta tactctctcc gtttcaaatt ataagttgtt ttgatttttt  360
tggtacatct attttactat gcattagata taataatgtg tctagataca taacaaaatg  420
gatgaatcaa aaaagtcaaa gtgatttaca atttggaacg gagagagtaa gttcaagccg  480
tcaaggcact tctatgcaac cacagtcaac ttgaatgccg cttgagtgcc ttctcaagtt  540
tttttttctt gcaaaaatca tttctttttt ttaaaaaaag tataatttgg atcgtgcaaa  600
tttctctcta ggtgtgtgtg tgactgtgtg agtaacaatt tctctagttg tgcgcgactg  660
ctgcttactt tggagattac aatatctttc taaaatgctt cgattactta tttataaacc  720
gtctctaagg ccaattgctc aagattcatt caacaattga aacgtctcac atgattaaat  780
catataaagt ttctaagtct tgtttgacaa gatttttta gattttcatc taaattggat  840
gaaactatca aacactaatt ttaaaaaata taagagaagc tccggagata aaaggtcgtc  900
tatgttatta taagagtaaa gtcgtctatt ctcttcgtcc caacatatat aattctaagc  960
atgaattgct ttctttttgg acaaaaggag catgccacaa cacaagaatg atgtcaccgt  1020
catgcttgga tccttttatg gtaaagcttc accttctata atctaacaat agagaaatca  1080
gggaaaaatc atgttttggt tgtttttatt tctaacctcc acaataactt tggtttacca  1140
ttttttgttt gattttagtt ttagagaagc gtttataaca ggacctaaaa tcttttttca  1200
gtacacagta caacgcagac gctcatacac gcacgcacac tcacctctat gaacacacgt  1260
aagaaaaccc tacaccttga gcaccttcga aggactgagc cggtaaatat agagattctc  1320
gaagtcacta ttagcgcctc gttgtcaacg ggaatgtcgc ttaccactta aagcataacg  1380
ccgagaaatc ccgtaataaa tccagtaaaa tacgagcacc cgtgccaagt tgaatatttg  1440
aacccgagtg ggtagattcc accgcaaagg acctaaccag atcatttcgc aaacaggaac  1500
taaaatcggt agagagccca gacaaaagcc tttcctaaga gccactccag tggaagcccc  1560
tactttaggt ataaaatgca atactagtgg ggctcctaaa taaacttcta tttttcatgg  1620
ccttctaaaa ttcactccca aacccctagc tatagaagtc tcttatccat cctctaaata  1680
aaaatgggag tctattttat ttcaccagag ttgatcgtaa atttagtctc tcaaatttta  1740
taagttgagg gtagaggatg actggagttg ctctaaacgg acctatcttc aagtgacctc  1800
agtgagcccg tttaacggcg tcgacaagtt taatctaacg gacaccaacc agagaagaga  1860
accaccgcca gcgccgagcc aagcgacgtt gacatcttgg cgcggcacgg catctccctg  1920
gcgtctggcc ccctctcgag acttccgctc cacctcccac cggtggcggt ttccaagtcc  1980
gttccgcctc ctctcacacg gcacgaaacc gtgacgggca ccggcagcac ggggggattc  2040
ctttcccacc gctccttccc tttcccttcc tctcccgccg ctataaatag ccagccccat  2100
ccccagcttc tttc                                                   2114

SEQ ID NO: 7           moltype = DNA  length = 1042
FEATURE                Location/Qualifiers
source                 1..1042
                       mol_type = other DNA
                       organism = Andropogon gerardii
SEQUENCE: 7
gtacggcgat cgattatctt ccctctctct accttctctc tcttataggg cctgctagct  60
ctgttcctgt ttttccatgg ctgcgaggta caatagatcg gcgatccatg gttagggcct  120
gctagttgtg ttcctgtttt tccatggctg cgaggcacaa tagatctgat ggcgttatga  180
tggttaactt gtcatactct tgcgatctat ggtcccttta ggagtttagg acatctattt  240
aatttcggat agttcgagat ctgtgatcca tggttagtac cctaggcagt ggggttagat  300
ccgtgctgtt atggttcgta gatggattct gattgctcag taactgggaa tcctgggatg  360
gttctagctg gttcgcagat aagatcgatt tcatgatatg ctatatcttg tttggttgcc  420
gtggttccgt taaatctgtc tgttatgatc ttagtctttg ataaggttcg gtcgtgctag  480
ctacgtcctg tgcagcactt aattgtcagg tcataatttt tagcatgcct tttttttatt  540
ggtttggttt tgtctgactg ggctgtagat agtttcaatc tttgtctgac tgggctgtag  600
atagtttcaa tctacctgtc ggtttatttt attaaatttg gatctgtatg tgtgtcatat  660
atcttcatct tttagatata tcgataggtt tatatgttgc tgtcggtttt ttactgttcc  720
tttatgagat atattcatgc ttagatacat gaaacaacgt gctgttacag tttaatagtt  780
cttgtttatc taataaacaa ataaggatag gtatatgctg cagttagttt tactggtact  840
ttttttgaca tgaacctacg gcttaataat tagtcttcat caaataaaaa gcatattttt  900
taattatttc gatatacttg aatgatgtca tatgcagcat ctgtgtgaat tttggccct   960
gtcttcatat gctgtttatt tgtttgggac tgtttctttg gttgataact catcctgttg  1020
tttggtgatc cttttgcagg tg                                          1042

SEQ ID NO: 8           moltype = DNA  length = 2785
FEATURE                Location/Qualifiers
source                 1..2785
```

```
                         mol_type = other DNA
                         organism = Andropogon gerardii
SEQUENCE: 8
gttcaagccg tcaaggcact tctatgcaac cacagtcaac ttgaatgccg cttgagtgcc  60
ttctcaagtt tttttttctt gcaaaaatca tttctttttt ttaaaaaaag tataatttgg  120
atcgtgcaaa tttctctcta ggtgtgtgtg tgactgtgtg agtaacaatt tctctagttg  180
tgcgcgactg ctgcttactt tggagattac aatatctttc taaaatgctt cgattactta  240
tttataaacc gtctctaagg ccaattgctc aagattcatt caacaattga aacgtctcac  300
atgattaaat catataaagt ttctaagtct tgtttgacaa gattttttta gattttcatc  360
taaattggat gaaactatca aacactaatt ttaaaaaata taagagaagc tccggagata  420
aaaggtcgtc tatgttatta taagagtaaa gtcgtctatt ctcttcgtcc caacatatat  480
aattctaagc atgaattgct ttctttttgg acaaaaggag catgccacaa cacaagaatg  540
atgtcaccgt catgcttgga tccttttatg gtaaagcttc accttctata atctaacaat  600
agagaaatca gggaaaaatc atgttttggt tgtttttatt tctaacctcc acaataactt  660
tggtttacca tttttttgttt gattttagtt ttagagaagc gtttataaca ggacctaaaa  720
tcttttttca gtacacagta caacgcagac gctcatacac gcacgcacac tcacctctat  780
gaacacacgt aagaaaaccc tacaccttga gcaccttcga aggactgagc cggtaaatat  840
agagattctc gaagtcacta ttagcgcctc gttgtcaacg ggaatgtcgc ttaccactta  900
aagcataacg ccgagaaatc ccgtaataaa tccagtaaaa tacgagcacc cgtgccaagt  960
tgaatatttg aacccgagtg ggtagattcc accgcaaagg acctaaccag atcatttcgc  1020
aaacaggaac taaaatcggt agagagccca gacaaaagcc tttcctaaga gccactccag  1080
tggaagcccc tactttaggt ataaaatgca atactagtgg ggctcctaaa taaacttcta  1140
tttttcatgg ccttctaaaa ttcactccca aacccctagc tatagaagtc tcttatccat  1200
cctctaaata aaaatgggag tctattttat ttcaccagag ttgatcgtaa atttagtctc  1260
tcaaatttta taagttgagg gtagaggatg actggagttg ctctaaacgg acctatcttc  1320
aagtgacctc agtgagcccg tttaacggcg tcgacaagtt taatctaacg gacaccaacc  1380
agagaagaga accaccgcca gcgccgagcc aagcgacgtt gacatcttgg cgcggcacgg  1440
catctccctg gcgtctggcc ccctctcgag acttccgctc cacctcccac cggtggcggt  1500
ttccaagtcc gttccgcctc ctctcacacg gcacgaaacc gtgacgggca ccggcagcac  1560
ggggggattc ctttcccacc gctccttccc tttcccttcc tctcccgccg ctataaatag  1620
ccagccccat ccccagcttc tttccccaac ctcatcttct ctcgtgttgt tcggcacaac  1680
ccgatcgatc cccaactccc tcgtcgtctc tcctcgcgag cctcgtcgat cccccgcttc  1740
aaggtacggc gatcgattat cttccctctc tctaccttct ctctcttata gggcctgcta  1800
gctctgttcc tgtttttcca tggctgcgag gtacaataga tcggcgatcc atggttaggg  1860
cctgctagtt gtgttcctgt ttttccatgg ctgcgaggca caatagatct gatggcgtta  1920
tgatggttaa cttgtcatac tcttgcgatc tatggtccct ttaggagttt aggacatcta  1980
tttaatttcg gatagttcga gatctgtgat ccatggttag taccctaggc agtggggtta  2040
gatccgtgct gttatggttc gtagatggat tctgattgct cagtaactgg gaatcctggg  2100
atggttctag ctggttcgca gataagatcg atttcatgat atgctatatc ttgtttggtt  2160
gccgtggttc cgttaaatct gtctgttatg atcttagtct ttgataaggt tcggtcgtgc  2220
tagctacgtc ctgtgcagca cttaattgtc aggtcataat ttttagcatg ccttttttttt  2280
attggtttgg ttttgtctga ctgggctgta gatagtttca atctttgtct gactgggctg  2340
tagatagttt caatctacct gtcggtttat tttattaaat ttggatctgt atgtgtgtca  2400
tatatcttca tcttttagat atatcgatag gtttatatgt tgctgtcggt tttttactgt  2460
tcctttatga gatatattca tgcttagata catgaaacaa cgtgctgtta cagtttaata  2520
gttcttgttt atctaataaa caaataagga taggtatatg ctgcagttag ttttactggt  2580
acttttttttg acatgaacct acggcttaat aattagtctt catcaaataa aaagcatatt  2640
ttttaattat ttcgatatac ttgaatgatg tcatatgcag catctgtgtg aatttttggc  2700
cctgtcttca tatgctgttt atttgtttgg gactgtttct ttggttgata actcatcctg  2760
ttgtttggtg atccttttgc aggtg                                        2785

SEQ ID NO: 9             moltype = DNA  length = 1644
FEATURE                  Location/Qualifiers
source                   1..1644
                         mol_type = other DNA
                         organism = Andropogon gerardii
SEQUENCE: 9
gttcaagccg tcaaggcact tctatgcaac cacagtcaac ttgaatgccg cttgagtgcc  60
ttctcaagtt tttttttctt gcaaaaatca tttctttttt ttaaaaaaag tataatttgg  120
atcgtgcaaa tttctctcta ggtgtgtgtg tgactgtgtg agtaacaatt tctctagttg  180
tgcgcgactg ctgcttactt tggagattac aatatctttc taaaatgctt cgattactta  240
tttataaacc gtctctaagg ccaattgctc aagattcatt caacaattga aacgtctcac  300
atgattaaat catataaagt ttctaagtct tgtttgacaa gattttttta gattttcatc  360
taaattggat gaaactatca aacactaatt ttaaaaaata taagagaagc tccggagata  420
aaaggtcgtc tatgttatta taagagtaaa gtcgtctatt ctcttcgtcc caacatatat  480
aattctaagc atgaattgct ttctttttgg acaaaaggag catgccacaa cacaagaatg  540
atgtcaccgt catgcttgga tccttttatg gtaaagcttc accttctata atctaacaat  600
agagaaatca gggaaaaatc atgttttggt tgtttttatt tctaacctcc acaataactt  660
tggtttacca tttttttgttt gattttagtt ttagagaagc gtttataaca ggacctaaaa  720
tcttttttca gtacacagta caacgcagac gctcatacac gcacgcacac tcacctctat  780
gaacacacgt aagaaaaccc tacaccttga gcaccttcga aggactgagc cggtaaatat  840
agagattctc gaagtcacta ttagcgcctc gttgtcaacg ggaatgtcgc ttaccactta  900
aagcataacg ccgagaaatc ccgtaataaa tccagtaaaa tacgagcacc cgtgccaagt  960
tgaatatttg aacccgagtg ggtagattcc accgcaaagg acctaaccag atcatttcgc  1020
aaacaggaac taaaatcggt agagagccca gacaaaagcc tttcctaaga gccactccag  1080
tggaagcccc tactttaggt ataaaatgca atactagtgg ggctcctaaa taaacttcta  1140
tttttcatgg ccttctaaaa ttcactccca aacccctagc tatagaagtc tcttatccat  1200
cctctaaata aaaatgggag tctattttat ttcaccagag ttgatcgtaa atttagtctc  1260
tcaaatttta taagttgagg gtagaggatg actggagttg ctctaaacgg acctatcttc  1320
```

```
aagtgacctc agtgagcccg tttaacggcg tcgacaagtt taatctaacg gacaccaacc  1380
agagaagaga accaccgcca gcgccgagcc aagcgacgtt gacatcttgg cgcggcacgg  1440
catctccctg gcgtctggcc ccctctcgag acttccgctc cacctcccac cggtggcggt  1500
ttccaagtcc gttccgcctc ctctcacacg gcacgaaacc gtgacgggca ccggcagcac  1560
ggggggattc ctttcccacc gctccttccc tttcccttcc tctcccgccg ctataaatag  1620
ccagccccat ccccagcttc tttc                                        1644

SEQ ID NO: 10          moltype = DNA  length = 2613
FEATURE                Location/Qualifiers
source                 1..2613
                       mol_type = other DNA
                       organism = Andropogon gerardii
SEQUENCE: 10
tctagttgtg cgcgactgct gcttactttg gagattacaa tatctttcta aaatgcttcg  60
attacttatt tataaaccgt ctctaaggcc aattgctcaa gattcattca acaattgaaa  120
cgtctcacat gattaaatca tataaagttt ctaagtcttg tttgacaaga tttttttaga  180
ttttcatcta aattggatga aactatcaaa cactaatttt aaaaaatata agagaagctc  240
cggagataaa aggtcgtcta tgttattata agagtaaagt cgtctattct cttcgtccca  300
acatatataa ttctaagcat gaattgcttt ctttttggac aaaaggagca tgccacaaca  360
caagaatgat gtcaccgtca tgcttggatc cttttatggt aaagcttcac cttctataat  420
ctaacaatag agaaatcagg gaaaaatcat gttttggttg tttttatttc taacctccac  480
aataactttg gtttaccatt ttttgtttga ttttagtttt agagaagcgt ttataacagg  540
acctaaaatc ttttttcagt acacagtaca acgcagacgc tcatacacgc acgcacactc  600
acctctatga acacacgtaa gaaaacccta caccttgagc accttcgaag gactgagccg  660
gtaaatatag agattctcga agtcactatt agcgcctcgt tgtcaacggg aatgtcgctt  720
accacttaaa gcataacgcc gagaaatccc gtaataaatc cagtaaaata cgagcacccg  780
tgccaagttg aatatttgaa cccgagtggg tagattccac cgcaaaggac ctaaccagat  840
catttcgcaa acaggaacta aaatcggtag agagcccaga caaaagcctt tcctaagagc  900
cactccagtg gaagccccta ctttaggtat aaaatgcaat actagtgggg ctcctaaata  960
aacttctatt tttcatggcc ttctaaaatt cactcccaaa cccctagcta tagaagtctc  1020
ttatccatcc tctaaataaa aatgggagtc tattttattt caccagagtt gatcgtaaat  1080
ttagtctctc aaattttata agttgagggt agaggatgac tggagttgct ctaaacggac  1140
ctatcttcaa gtgacctcag tgagcccgtt taacggcgtc gacaagttta atctaacgga  1200
caccaaccag agaagagaac caccgccagc gccgagccaa gcgacgttga catcttggcg  1260
cggcacggca tctccctggc gtctggcccc ctctcgagac ttccgctcca cctcccaccg  1320
gtggcggttt ccaagtccgt tccgcctcct ctcacacggc acgaaaccgt gacgggcacc  1380
ggcagcacgg ggggattcct ttcccaccgc tccttccctt tcccttcctc tcccgccgct  1440
ataaatagcc agccccatcc ccagcttctt tccccaacct catcttctct cgtgttgttc  1500
ggcacaaccc gatcgatccc caactccctc gtcgtctctc ctcgcgagcc tcgtcgatcc  1560
cccgcttcaa ggtacggcga tcgattatct tccctctctc taccttctct ctcttatagg  1620
gcctgctagc tctgttcctg tttttccatg gctgcgaggt acaatagatc ggcgatccat  1680
ggttagggcc tgctagttgt gttcctgttt ttccatggct gcgaggcaca atagatctga  1740
tggcgttatg atggttaact tgtcatactc ttgcgatcta tggtcccttt aggagtttag  1800
gacatctatt taatttcgga tagttcgaga tctgtgatcc atggttagta ccctaggcag  1860
tggggttaga tccgtgctgt tatggttcgt agatggattc tgattgctca gtaactggga  1920
atcctgggat ggttctagct ggttcgcaga taagatcgat ttcatgatat gctatatctt  1980
gtttggttgc cgtggttccg ttaaatctgt ctgttatgat cttagtcttt gataaggttc  2040
ggtcgtgcta gctacgtcct gtgcagcact taattgtcag gtcataattt ttagcatgcc  2100
tttttttat tggtttggtt ttgtctgact gggctgtaga tagtttcaat ctttgtctga  2160
ctgggctgta gatagtttca atctacctgt cggtttattt tattaaattt ggatctgtat  2220
gtgtgtcata tatcttcatc ttttagatat atcgataggt ttatatgttg ctgtcggttt  2280
tttactgttc ctttatgaga tatattcatg cttagataca tgaaacaacg tgctgttaca  2340
gtttaatagt tcttgtttat ctaataaaca aataaggata ggtatatgct gcagttagtt  2400
ttactggtac ttttttgac atgaacctac ggcttaataa ttagtcttca tcaaataaaa  2460
agcatatttt ttaattattt cgatatactt gaatgatgtc atatgcagca tctgtgtgaa  2520
tttttggccc tgtcttcata tgctgtttat ttgtttggga ctgtttcttt ggttgataac  2580
tcatcctgtt gtttggtgat ccttttgcag gtg                              2613

SEQ ID NO: 11          moltype = DNA  length = 1472
FEATURE                Location/Qualifiers
source                 1..1472
                       mol_type = other DNA
                       organism = Andropogon gerardii
SEQUENCE: 11
tctagttgtg cgcgactgct gcttactttg gagattacaa tatctttcta aaatgcttcg  60
attacttatt tataaaccgt ctctaaggcc aattgctcaa gattcattca acaattgaaa  120
cgtctcacat gattaaatca tataaagttt ctaagtcttg tttgacaaga tttttttaga  180
ttttcatcta aattggatga aactatcaaa cactaatttt aaaaaatata agagaagctc  240
cggagataaa aggtcgtcta tgttattata agagtaaagt cgtctattct cttcgtccca  300
acatatataa ttctaagcat gaattgcttt ctttttggac aaaaggagca tgccacaaca  360
caagaatgat gtcaccgtca tgcttggatc cttttatggt aaagcttcac cttctataat  420
ctaacaatag agaaatcagg gaaaaatcat gttttggttg tttttatttc taacctccac  480
aataactttg gtttaccatt ttttgtttga ttttagtttt agagaagcgt ttataacagg  540
acctaaaatc ttttttcagt acacagtaca acgcagacgc tcatacacgc acgcacactc  600
acctctatga acacacgtaa gaaaacccta caccttgagc accttcgaag gactgagccg  660
gtaaatatag agattctcga agtcactatt agcgcctcgt tgtcaacggg aatgtcgctt  720
accacttaaa gcataacgcc gagaaatccc gtaataaatc cagtaaaata cgagcacccg  780
tgccaagttg aatatttgaa cccgagtggg tagattccac cgcaaaggac ctaaccagat  840
catttcgcaa acaggaacta aaatcggtag agagcccaga caaaagcctt tcctaagagc  900
```

```
cactccagtg gaagccccta ctttaggtat aaaatgcaat actagtgggg ctcctaaata  960
aacttctatt tttcatggcc ttctaaaatt cactcccaaa cccctagcta tagaagtctc  1020
ttatccatcc tctaaataaa aatgggagtc tattttattt caccagagtt gatcgtaaat  1080
ttagtctctc aaattttata agttgagggt agaggatgac tggagttgct ctaaacggac  1140
ctatcttcaa gtgacctcag tgagcccgtt taacggcgtc gacaagttta atctaacgga  1200
caccaaccag agaagagaac caccgccagc gccgagccaa gcgacgttga catcttggcg  1260
cggcacggca tctccctggc gtctggcccc ctctcgagac ttccgctcca cctcccaccg  1320
gtggcggttt ccaagtccgt tccgcctcct ctcacacggc acgaaaccgt gacgggcacc  1380
ggcagcacgg ggggattcct ttcccaccgc tccttccctt tcccttcctc tcccgccgct  1440
ataaatagcc agccccatcc ccagcttctt tc                                1472

SEQ ID NO: 12          moltype = DNA  length = 2255
FEATURE                Location/Qualifiers
source                 1..2255
                       mol_type = other DNA
                       organism = Andropogon gerardii
SEQUENCE: 12
cacaagaatg atgtcaccgt catgcttgga tccttttatg gtaaagcttc accttctata  60
atctaacaat agagaaatca gggaaaaatc atgttttggt tgtttttatt tctaacctcc  120
acaataactt tggtttacca ttttttgttt gattttagtt ttagagaagc gtttataaca  180
ggacctaaaa tctttttttca gtacacagta caacgcagac gctcatacac gcacgcacac  240
tcacctctat gaacacacgt aagaaaaccc tacaccttga gcaccttcga aggactgagc  300
cggtaaatat agagattctc gaagtcacta ttagcgcctc gttgtcaacg ggaatgtcgc  360
ttaccactta aagcataacg ccgagaaatc ccgtaataaa tccagtaaaa tacgagcacc  420
cgtgccaagt tgaatatttg aacccgagtg ggtagattcc accgcaaagg acctaaccag  480
atcatttcgc aaacaggaac taaaatcggt agagagccca gacaaaagcc tttcctaaga  540
gccactccag tggaagcccc tactttaggt ataaaatgca atactagtgg ggctcctaaa  600
taaacttcta tttttcatgg ccttctaaaa ttcactccca aacccctagc tatagaagtc  660
tcttatccat cctctaaata aaaatgggag tctattttat ttcaccagag ttgatcgtaa  720
atttagtctc tcaaatttta taagttgagg gtagaggatg actggagttg ctctaaacgg  780
acctatcttc aagtgacctc agtgagcccg tttaacggcg tcgacaagtt taatctaacg  840
gacaccaacc agagaagaga accaccgcca gcgccgagcc aagcgacgtt gacatcttgg  900
cgcggcacgg catctccctg gcgtctggcc ccctctcgag acttccgctc cacctcccac  960
cggtggcggt ttccaagtcc gttccgcctc ctctcacacg gcacgaaacc gtgacgggca  1020
ccggcagcac ggggggattc ctttcccacc gctccttccc tttcccttcc tctcccgccg  1080
ctataaatag ccagccccat ccccagcttc tttccccaac ctcatcttct ctcgtgttgt  1140
tcggcacaac ccgatcgatc cccaactccc tcgtcgtctc tcctcgcgag cctcgtcgat  1200
cccccgcttc aaggtacggc gatcgattat cttccctctc tctaccttct ctctcttata  1260
gggcctgcta gctctgttcc tgtttttcca tggctgcgag gtacaataga tcggcgatcc  1320
atggttaggg cctgctagtt gtgttcctgt ttttccatgg ctgcgaggca caatagatct  1380
gatggcgtta tgatggttaa cttgtcatac tcttgcgatc tatggtccct ttaggagttt  1440
aggacatcta tttaatttcg gatagttcga gatctgtgat ccatggttag taccctaggc  1500
agtggggtta gatccgtgct gttatggttc gtagatggat tctgattgct cagtaactgg  1560
gaatcctggg atggttctag ctggttcgca gataagatcg atttcatgat atgctatatc  1620
ttgtttggtt gccgtggttc cgttaaatct gtctgttatg atcttagtct ttgataaggt  1680
tcggtcgtgc tagctacgtc ctgtgcagca cttaattgtc aggtcataat ttttagcatg  1740
cctttttttt attggtttgg ttttgtctga ctgggctgta gatagtttca atctttgtct  1800
gactgggctg tagatagttt caatctacct gtcggtttat tttattaaat ttggatctgt  1860
atgtgtgtca tatatcttca tcttttagat atatcgatag gtttatatgt tgctgtcggt  1920
tttttactgt tcctttatga gatatattca tgcttagata catgaaacaa cgtgctgtta  1980
cagtttaata gttcttgttt atctaataaa caaataagga taggtatatg ctgcagttag  2040
ttttactggt actttttttg acatgaacct acggcttaat aattagtctt catcaaataa  2100
aaagcatatt ttttaattat ttcgatatac ttgaatgatg tcatatgcag catctgtgtg  2160
aatttttggc cctgtcttca tatgctgttt atttgtttgg gactgtttct ttggttgata  2220
actcatcctg ttgtttggtg atccttttgc aggtg                             2255

SEQ ID NO: 13          moltype = DNA  length = 1114
FEATURE                Location/Qualifiers
source                 1..1114
                       mol_type = other DNA
                       organism = Andropogon gerardii
SEQUENCE: 13
cacaagaatg atgtcaccgt catgcttgga tccttttatg gtaaagcttc accttctata  60
atctaacaat agagaaatca gggaaaaatc atgttttggt tgtttttatt tctaacctcc  120
acaataactt tggtttacca ttttttgttt gattttagtt ttagagaagc gtttataaca  180
ggacctaaaa tctttttttca gtacacagta caacgcagac gctcatacac gcacgcacac  240
tcacctctat gaacacacgt aagaaaaccc tacaccttga gcaccttcga aggactgagc  300
cggtaaatat agagattctc gaagtcacta ttagcgcctc gttgtcaacg ggaatgtcgc  360
ttaccactta aagcataacg ccgagaaatc ccgtaataaa tccagtaaaa tacgagcacc  420
cgtgccaagt tgaatatttg aacccgagtg ggtagattcc accgcaaagg acctaaccag  480
atcatttcgc aaacaggaac taaaatcggt agagagccca gacaaaagcc tttcctaaga  540
gccactccag tggaagcccc tactttaggt ataaaatgca atactagtgg ggctcctaaa  600
taaacttcta tttttcatgg ccttctaaaa ttcactccca aacccctagc tatagaagtc  660
tcttatccat cctctaaata aaaatgggag tctattttat ttcaccagag ttgatcgtaa  720
atttagtctc tcaaatttta taagttgagg gtagaggatg actggagttg ctctaaacgg  780
acctatcttc aagtgacctc agtgagcccg tttaacggcg tcgacaagtt taatctaacg  840
gacaccaacc agagaagaga accaccgcca gcgccgagcc aagcgacgtt gacatcttgg  900
cgcggcacgg catctccctg gcgtctggcc ccctctcgag acttccgctc cacctcccac  960
cggtggcggt ttccaagtcc gttccgcctc ctctcacacg gcacgaaacc gtgacgggca  1020
```

```
ccggcagcac ggggggattc ctttcccacc gctccttccc tttcccttcc tctcccgccg  1080
ctataaatag ccagccccat ccccagcttc tttc                              1114

SEQ ID NO: 14          moltype = DNA  length = 1912
FEATURE                Location/Qualifiers
source                 1..1912
                       mol_type = other DNA
                       organism = Andropogon gerardii
SEQUENCE: 14
gtcaacggga atgtcgctta ccacttaaag cataacgccg agaaatcccg taataaatcc  60
agtaaaatac gagcacccgt gccaagttga atatttgaac ccgagtgggt agattccacc  120
gcaaaggacc taaccagatc atttcgcaaa caggaactaa aatcggtaga gagcccagac  180
aaaagccttt cctaagagcc actccagtgg aagcccctac tttaggtata aaatgcaata  240
ctagtggggc tcctaaataa acttctattt ttcatggcct tctaaaattc actcccaaac  300
ccctagctat agaagtctct tatccatcct ctaaataaaa atgggagtct attttatttc  360
accagagttg atcgtaaatt tagtctctca aattttataa gttgagggta gaggatgact  420
ggagttgctc taaacggacc tatcttcaag tgacctcagt gagcccgttt aacggcgtcg  480
acaagtttaa tctaacggac accaaccaga gaagagaacc accgccagcg ccgagccaag  540
cgacgttgac atcttggcgc ggcacggcat ctccctggcg tctggccccc tctcgagact  600
tccgctccac ctcccaccgg tggcggtttc caagtccgtt ccgcctcctc tcacacggca  660
cgaaaccgtg acgggcaccg gcagcacggg gggattcctt tcccaccgct ccttcccttt  720
cccttcctct cccgccgcta taaatagcca gccccatccc cagcttcttt ccccaacctc  780
atcttctctc gtgttgttcg gcacaacccg atcgatcccc aactccctcg tcgtctctcc  840
tcgcgagcct cgtcgatccc ccgcttcaag gtacggcgat cgattatctt ccctctctct  900
accttctctc tcttataggg cctgctagct ctgttcctgt ttttccatgg ctgcgaggta  960
caatagatcg gcgatccatg gttagggcct gctagttgtg ttcctgtttt tccatggctg  1020
cgaggcacaa tagatctgat ggcgttatga tggttaactt gtcatactct tgcgatctat  1080
ggtcccttta ggagtttagg acatctattt aatttcggat agttcgagat ctgtgatcca  1140
tggttagtac cctaggcagt ggggttagat ccgtgctgtt atggttcgta gatggattct  1200
gattgctcag taactgggaa tcctgggatg gttctagctg gttcgcagat aagatcgatt  1260
tcatgatatg ctatatcttg tttggttgcc gtggttccgt taaatctgtc tgttatgatc  1320
ttagtctttg ataaggttcg gtcgtgctag ctacgtcctg tgcagcactt aattgtcagg  1380
tcataatttt tagcatgcct ttttttttatt ggtttggttt tgtctgactg ggctgtagat  1440
agtttcaatc tttgtctgac tgggctgtag atagtttcaa tctacctgtc ggtttatttt  1500
attaaatttg gatctgtatg tgtgtcatat atcttcatct tttagatata tcgataggtt  1560
tatatgttgc tgtcggtttt ttactgttcc tttatgagat atattcatgc ttagatacat  1620
gaaacaacgt gctgttacag tttaatagtt cttgtttatc taataaacaa ataaggatag  1680
gtatatgctg cagttagttt tactggtact ttttttgaca tgaacctacg gcttaataat  1740
tagtcttcat caaataaaaa gcatattttt taattatttc gatatacttg aatgatgtca  1800
tatgcagcat ctgtgtgaat ttttggccct gtcttcatat gctgtttatt tgtttgggac  1860
tgtttctttg gttgataact catcctgttg tttggtgatc cttttgcagg tg          1912

SEQ ID NO: 15          moltype = DNA  length = 771
FEATURE                Location/Qualifiers
source                 1..771
                       mol_type = other DNA
                       organism = Andropogon gerardii
SEQUENCE: 15
gtcaacggga atgtcgctta ccacttaaag cataacgccg agaaatcccg taataaatcc  60
agtaaaatac gagcacccgt gccaagttga atatttgaac ccgagtgggt agattccacc  120
gcaaaggacc taaccagatc atttcgcaaa caggaactaa aatcggtaga gagcccagac  180
aaaagccttt cctaagagcc actccagtgg aagcccctac tttaggtata aaatgcaata  240
ctagtggggc tcctaaataa acttctattt ttcatggcct tctaaaattc actcccaaac  300
ccctagctat agaagtctct tatccatcct ctaaataaaa atgggagtct attttatttc  360
accagagttg atcgtaaatt tagtctctca aattttataa gttgagggta gaggatgact  420
ggagttgctc taaacggacc tatcttcaag tgacctcagt gagcccgttt aacggcgtcg  480
acaagtttaa tctaacggac accaaccaga gaagagaacc accgccagcg ccgagccaag  540
cgacgttgac atcttggcgc ggcacggcat ctccctggcg tctggccccc tctcgagact  600
tccgctccac ctcccaccgg tggcggtttc caagtccgtt ccgcctcctc tcacacggca  660
cgaaaccgtg acgggcaccg gcagcacggg gggattcctt tcccaccgct ccttcccttt  720
cccttcctct cccgccgcta taaatagcca gccccatccc cagcttcttt c           771

SEQ ID NO: 16          moltype = DNA  length = 1623
FEATURE                Location/Qualifiers
source                 1..1623
                       mol_type = other DNA
                       organism = Andropogon gerardii
SEQUENCE: 16
cactcccaaa cccctagcta tagaagtctc ttatccatcc tctaaataaa aatgggagtc  60
tattttattt caccagagtt gatcgtaaat ttagtctctc aaattttata agttgagggt  120
agaggatgac tggagttgct ctaaacggac ctatcttcaa gtgacctcag tgagcccgtt  180
taacggcgtc gacaagttta atctaacgga caccaaccag agaagagaac caccgccagc  240
gccgagccaa gcgacgttga catcttggcg cggcacggca tctccctggc gtctggcccc  300
ctctcgagac ttccgctcca cctcccaccg gtggcggttt ccaagtccgt tccgcctcct  360
ctcacacggc acgaaaccgt gacgggcacc ggcagcacgg ggggattcct ttcccaccgc  420
tccttccctt tcccttcctc tcccgccgct ataaatagcc agccccatcc ccagcttctt  480
tccccaacct catcttctct cgtgttgttc ggcacaaccc gatcgatccc caactccctc  540
gtcgtctctc ctcgcgagcc tcgtcgatcc cccgcttcaa ggtacggcga tcgattatct  600
tccctctctc taccttctct ctcttatagg gcctgctagc tctgttcctg tttttccatg  660
```

```
gctgcgaggt acaatagatc ggcgatccat ggttagggcc tgctagttgt gttcctgttt  720
ttccatggct gcgaggcaca atagatctga tggcgttatg atggttaact tgtcatactc  780
ttgcgatcta tggtcccttt aggagtttag gacatctatt taatttcgga tagttcgaga  840
tctgtgatcc atggttagta ccctaggcag tggggttaga tccgtgctgt tatggttcgt  900
agatggattc tgattgctca gtaactggga atcctgggat ggttctagct ggttcgcaga  960
taagatcgat ttcatgatat gctatatctt gtttggttgc cgtggttccg ttaaatctgt  1020
ctgttatgat cttagtcttt gataaggttc ggtcgtgcta gctacgtcct gtgcagcact  1080
taattgtcag gtcataattt ttagcatgcc tttttttat tggtttggtt ttgtctgact  1140
gggctgtaga tagtttcaat ctttgtctga ctgggctgta gatagtttca atctacctgt  1200
cggtttattt tattaaattt ggatctgtat gtgtgtcata tatcttcatc ttttagatat  1260
atcgataggt ttatatgttg ctgtcggttt tttactgttc ctttatgaga tatattcatg  1320
cttagataca tgaaacaacg tgctgttaca gtttaatagt tcttgtttat ctaataaaca  1380
aataaggata ggtatatgct gcagttagtt ttactggtac ttttttgac atgaacctac  1440
ggcttaataa ttagtcttca tcaaataaaa agcatatttt ttaattattt cgatatactt  1500
gaatgatgtc atatgcagca tctgtgtgaa tttttggccc tgtcttcata tgctgtttat  1560
ttgtttggga ctgtttcttt ggttgataac tcatcctgtt gtttggtgat ccttttgcag  1620
gtg                                                                1623

SEQ ID NO: 17          moltype = DNA  length = 482
FEATURE                Location/Qualifiers
source                 1..482
                       mol_type = other DNA
                       organism = Andropogon gerardii
SEQUENCE: 17
cactcccaaa cccctagcta tagaagtctc ttatccatcc tctaaataaa aatgggagtc  60
tattttattt caccagagtt gatcgtaaat ttagtctctc aaattttata agttgagggt  120
agaggatgac tggagttgct ctaaacggac ctatcttcaa gtgacctcag tgagcccgtt  180
taacggcgtc gacaagttta atctaacgga caccaaccag agaagagaac caccgccagc  240
gccgagccaa gcgacgttga catcttggcg cggcacggca tctccctggc gtctggcccc  300
ctctcgagac ttccgctcca cctcccaccg gtggcggttt ccaagtccgt tccgcctcct  360
ctcacacggc acgaaaccgt gacgggcacc ggcagcacgg ggggattcct ttcccaccgc  420
tccttccctt tcccttcctc tcccgccgct ataaatagcc agccccatcc ccagcttctt  480
tc                                                                 482

SEQ ID NO: 18          moltype = DNA  length = 3483
FEATURE                Location/Qualifiers
source                 1..3483
                       mol_type = other DNA
                       organism = Tripidium ravennae
                       sub_species = ravennae
SEQUENCE: 18
gtggccagct tttgttctag ttcaacggcc ccggccttcc gggcacctaa taccctaatt  60
aatctattgc agctaacctc aaaagaaatg catttgcagt tgtctgtccc aatcaatcta  120
ctagcagact tacattatag atggaggaaa ttaaattcag cctttgacgt ggatgcaaca  180
actgcactgc acaggatacc atcttagccg ttgtgtcaaa gtttgctttg ctaaacgttt  240
tgagaaaacc agctttgacc aacgcgagat gagcgcctta cgtttggcac aatgtaatgt  300
aatccggcac ggcaagttag actctgtagt gttagccggc ctctttacgt ttggcatagt  360
ttaattgaat ccggcatggc aagttagacc gtagtgtgag ccggccaacg caagttatta  420
tgacatatgt ataagagcaa gtgtattgtc acgtgatatt tatgttgaga tgaagaagag  480
aaaataaaca gcctgcaaat ttatagcgag tgatagatgg gcacaaggct tcctatttct  540
taaatcagac tttgtaagaa caaaaaaagg acttataaga gaatgggata aaccatatat  600
caatggtgta gtatgttagt atgcattaag atctgactat tatatgagtg agttgttaaa  660
ttcattttag gtgacatggc ccggttaaat tattagccat accctaacag ctctaaaaaa  720
gatatattcg ttgaggcact tttatgcaac cacatagtca acttgaatgc cgcttgagtg  780
cgttctcaag ttttttttct tgcaaattac gctttttttaa gaaagtataa tttggatcgt  840
gcgatttttt ttctctaggt gtgcgtgact gtgtgagtaa caattttgga tctcagaaag  900
gtaataaaag aataatactg ctgcctactt tgaggattac aatatctttc tctaaaatgt  960
tttggtttgt tatttaaacc gtctttaagg ccaattgctc aagattcatt caacaattga  1020
aacgtctcac atgattaaat catataaggt tgctaaggtc ttgtttgaca aggttttttt  1080
tgtggaaatt tcatctaaat ttttgagtga aactatcaaa tactaattta aaaaaggcaa  1140
atttgctgg aggacactgc agaaacgtgt aattggccgg cacaaaccgc caaacggaga  1200
atttgcccag taccattata aattcatgat aaattcatgg ttgtttgcca gtggggctag  1260
ggttcctcgc gtatggtgcg gaatgtggtt tggttcgacc aactcgaact caatccgatc  1320
caaaggggca tcaatagtca ttttagaaag tttctctctc ccgagcagtg gaaatgatta  1380
ttctatttgg cgcgatgtcc accggcaaac aaccacgaat ttgtaatggt actaggcaaa  1440
ttctccgttt ggcggtgtgt gccggccaat tacacgtttt tgcggtgtcc tccgacaaaa  1500
tttgcctttt aaaaacaatt ttataagaga agctccggag ataaaaggcc gtcaatgtta  1560
caagagtgaa gtcgtctact ccctccatcc caaaaaatgt aattctaagt atgagttgta  1620
ttattatttt tggacaaaag gagtatacca caagaatgat atcatcgtca tgcttagatc  1680
ctttttagta aagcttgagc ttctctaaaa gtagagaaat tagaaaaaaa tcacgttttt  1740
gtggtcttga tttctagcct ccacaaaatc tttggtttta cattttttgt ttgattttgg  1800
tttcagaagt ccttatttat atgtgctagt ttggcagcac ttaaaatcgt tagagagagc  1860
ctaaacaaaa gccttttcaa aacgaccttg agccagattg gttgatggcc aaaatttgat  1920
tgtcaaaact taggcaagcc aagattttag cagctatttg gtttggtacc aaaatttgcc  1980
aatgatctgt tcttttgcct tttcaaccgg tttatcagcc gtacttcagc ttattctctc  2040
tcacagaaca ctattgaatc agccgaaaag ccaccgcaga acaggaccag tatctcacaa  2100
atggcatgcc aaatatactc accgtcagtg agcccgttta acggcgtcga caagtctaac  2160
ggccaccaac cagcgaacca ccagcgtcaa gctagccaag cgaagcagac ggccgagacg  2220
ttgacacctt ggcgcgggca tctctctggc cccctctcga gagttccgct ccacctccac  2280
```

```
tggtggcggt ttccaagtcc gttccgcctc ctgctcctcc tcacacggca cgaaaccgtc  2340
acggcaccgg cagcacgggg gattcctttc ccaccgctcc ttccctttcc cttcctcgcc  2400
cgccgtttta aatagccagc cccatcccca gcttctctcc ccgtacggcg atcatcctcc  2460
ctttctctac cttctcttct ctagactagg tcggcgatcc atggttaggg cctgctagtt  2520
ctgttcctgt ttttccgtgg ctgcgaggta caatagatct gatggcgtta tgatggttaa  2580
cttgtcatac tcctgcggtg tgcggtctat agtgctttta ggacatcaat ttgacctggc  2640
tcgttcgaga tcggcgatcc atggttagga ccctaggcgg tggagtcggg ttagatccgc  2700
gctgtttgtg ttagtagatg gatgcgacct ttacttcaga cacgttctga ttgttaactt  2760
gtcagcacct gggagtcctg ggatggttct agctggttcg cagatgagat cgatttcatg  2820
atctgctgta tcttgtttcg ttaggttcct tttaatctat ccgtggtatt atgctaacct  2880
atgatatggt tcgatcgtgc tagctacgtc ctgtgtcata atttttagca tgcccttttt  2940
tgtttggttt tgtctgattg ggctgtagat cagagtatac tgtttcaaac tacctactgg  3000
atatatttat taaatttgaa tctgtatgtg tgtcacatat atcttcataa ttaaaatgga  3060
tggaaagata tatggatagg tacatgtgtt gctgtgggtt ttactggtac tttgttagat  3120
atacatgctt agatacatga agcaacatga tgttacagtt caataattct tgtttaccta  3180
ataaacaaat aaggataggt gtatgttgct gtgggttttg ctggtacttt gttagatata  3240
tatgcttaga tatatgaagc aacatcctgc tacggtttaa taattattgt ttatatctaa  3300
tagacaagcc tgctttttaa ttattttgat atacttggat gatggcatac agcagctatg  3360
tgtggatttt taaataccca gcatcatgag catgcatgac cctgccttag tatgctgttt  3420
atttgcttga gacttctttt tttgttggta ctcacctttt gtagtttggt gactcttctg  3480
cag                                                                3483

SEQ ID NO: 19          moltype = DNA  length = 2536
FEATURE                Location/Qualifiers
source                 1..2536
                       mol_type = other DNA
                       organism = Tripidium ravennae
                       sub_species = ravennae
SEQUENCE: 19
gtggccagct tttgttctag ttcaacggcc ccggccttcc gggcacctaa taccctaatt  60
aatctattgc agctaacctc aaaagaaatg catttgcagt tgtctgtccc aatcaatcta  120
ctagcagact tacattatag atggaggaaa ttaaattcag cctttgacgt ggatgcaaca  180
actgcactgc acaggatacc atcttagccg ttgtgtcaaa gtttgctttg ctaaacgttt  240
tgagaaaacc agctttgacc aacgcgagat gagcgcctta cgtttggcac aatgtaatgt  300
aatccggcac ggcaagttag actctgtagt gttagccggc ctctttacgt ttggcatagt  360
ttaattgaat ccggcatggc aagttagacc gtagtgtgag ccggccaacg caagttatta  420
tgacatatgt ataagagcaa gtgtattgtc acgtgatatt tatgttgaga tgaagaagag  480
aaaataaaca gcctgcaaat ttatagcgag tgatagatgg gcacaaggct tcctatttct  540
taaatcagac tttgtaagaa caaaaaaagg acttataaga gaatgggata aaccatatat  600
caatggtgta gtatgttagt atgcattaag atctgactat tatatgagtg agttgttaaa  660
ttcattttag gtgacatggc ccggttaaat tattagccat accctaacag ctctaaaaaa  720
gatatattcg ttgaggcact tttatgcaac cacatagtca acttgaatgc cgcttgagtg  780
cgttctcaag ttttttttct tgcaaattac gctttttttaa gaaagtataa tttggatcgt  840
gcgatttttt ttctctaggt gtgcgtgact gtgtgagtaa caattttgga tctcagaaag  900
gtaataaaag aataatactg ctgcctactt tgaggattac aatatctttc tctaaaatgt  960
tttggtttgt tatttaaacc gtctttaagg ccaattgctc aagattcatt caacaattga  1020
aacgtctcac atgattaaat catataaggt tgctaaggtc ttgtttgaca aggttttttt  1080
tgtggaaatt tcatctaaat ttttgagtga aactatcaaa tactaattta aaaaaggcaa  1140
attttgctgg aggacactgc agaaacgtgt aattggccgg cacaaaccgc caaacggaga  1200
atttgcccag taccattata aattcatgat aaattcatgg ttgtttgcca gtggggctag  1260
ggttcctcgc gtatggtgcg gaatgtggtt tggttcgacc aactcgaact caatccgatc  1320
caaaggggca tcaatagtca ttttagaaag tttctctctc ccgagcagtg gaaatgatta  1380
ttctatttgg cgcgatgtcc accggcaaac aaccacgaat ttgtaatggt actaggcaaa  1440
ttctccgttt ggcggtgtgt gccggccaat tacacgtttt tgcggtgtcc tccgacaaaa  1500
tttgcctttt aaaaacaatt ttataagaga agctccggag ataaaaggcc gtcaatgtta  1560
caagagtgaa gtcgtctact ccctccatcc caaaaaatgt aattctaagt atgagttgta  1620
ttattatttt tggacaaaag gagtatacca caagaatgat atcatcgtca tgcttagatc  1680
ctttttagta aagcttgagc ttctctaaaa gtagagaaat tagaaaaaaa tcacgttttt  1740
gtggtcttga tttctagcct ccacaaaatc tttggtttta cattttttgt ttgattttgg  1800
tttcagaagt ccttatttat atgtgctagt ttggcagcac ttaaaatcgt tagagagagc  1860
ctaaacaaaa gccttttcaa aacgaccttg agccagattg gttgatggcc aaaatttgat  1920
tgtcaaaact taggcaagcc aagattttag cagctatttg gtttggtacc aaaatttgcc  1980
aatgatctgt tcttttgcct tttcaaccgg tttatcagcc gtacttcagc ttattctctc  2040
tcacagaaca ctattgaatc agccgaaaag ccaccgcaga acaggaccag tatctcacaa  2100
atggcatgcc aaatatactc accgtcagtg agcccgttta acggcgtcga caagtctaac  2160
ggccaccaac cagcgaacca ccagcgtcaa gctagccaag cgaagcagac ggccgagacg  2220
ttgacacctt ggcgcgggca tctctctggc cccctctcga gagttccgct ccacctccac  2280
tggtggcggt ttccaagtcc gttccgcctc ctgctcctcc tcacacggca cgaaaccgtc  2340
acggcaccgg cagcacgggg gattcctttc ccaccgctcc ttccctttcc cttcctcgcc  2400
cgccgtttta aatagccagc cccatcccca gcttctctcc ccaacctcag cttctctcgt  2460
tgttcggagc gcacacacaa cccgatcccc aatcccctcg tctctcctcg cgagcctcgt  2520
cgatccccgc ttcaag                                                  2536

SEQ ID NO: 20          moltype = DNA  length = 94
FEATURE                Location/Qualifiers
source                 1..94
                       mol_type = other DNA
                       organism = Tripidium ravennae
                       sub_species = ravennae
```

```
SEQUENCE: 20
aacctcagct tctctcgttg ttcggagcgc acacacaacc cgatccccaa tcccctcgtc  60
tctcctcgcg agcctcgtcg atccccgctt caag                              94

SEQ ID NO: 21          moltype = DNA  length = 1041
FEATURE                Location/Qualifiers
source                 1..1041
                       mol_type = other DNA
                       organism = Tripidium ravennae
                       sub_species = ravennae
SEQUENCE: 21
gtacggcgat catcctccct ttctctacct tctcttctct agactaggtc ggcgatccat  60
ggttagggcc tgctagttct gttcctgttt ttccgtggct gcgaggtaca atagatctga  120
tggcgttatg atggttaact tgtcatactc ctgcggtgtg cggtctatag tgcttttagg  180
acatcaattt gacctggctc gttcgagatc ggcgatccat ggttaggacc ctaggcggtg  240
gagtcgggtt agatccgcgc tgtttgtgtt agtagatgga tgcgaccttt acttcagaca  300
cgttctgatt gttaacttgt cagcacctgg gagtcctggg atggttctag ctggttcgca  360
gatgagatcg atttcatgat ctgctgtatc ttgtttcgtt aggttccttt taatctatcc  420
gtggtattat gctaacctat gatatggttc gatcgtgcta gctacgtcct gtgtcataat  480
ttttagcatg cccttttttg tttggttttg tctgattggg ctgtagatca gagtatactg  540
tttcaaacta cctactggat atatttatta aatttgaatc tgtatgtgtg tcacatatat  600
cttcataatt aaaatggatg gaaagatata tggataggta catgtgttgc tgtgggtttt  660
actggtactt tgttagatat acatgcttag atacatgaag caacatgatg ttacagttca  720
ataattcttg tttacctaat aaacaaataa ggataggtgt atgttgctgt gggttttgct  780
ggtactttgt tagatatata tgcttagata tatgaagcaa catcctgcta cggtttaata  840
attattgttt atatctaata gacaagcctg ctttttaatt attttgatat acttggatga  900
tggcatacag cagctatgtg tggattttta aatacccagc atcatgagca tgcatgaccc  960
tgccttagta tgctgtttat ttgcttgaga cttctttttt tgttggtact caccttttgt  1020
agtttggtga ctcttctgca g                                           1041

SEQ ID NO: 22          moltype = DNA  length = 3152
FEATURE                Location/Qualifiers
source                 1..3152
                       mol_type = other DNA
                       organism = Tripidium ravennae
                       sub_species = ravennae
SEQUENCE: 22
gtataagagc aagtgtattg tcacgtgata tttatgttga gatgaagaag agaaaataaa  60
cagcctgcaa atttatagcg agtgatagat gggcacaagg cttcctattt cttaaatcag  120
actttgtaag aacaaaaaaa ggacttataa gagaatggga taaaccatat atcaatggtg  180
tagtatgtta gtatgcatta agatctgact attatatgag tgagttgtta aattcatttt  240
aggtgacatg gcccggttaa attattagcc ataccctaac agctctaaaa aagatatatt  300
cgttgaggca cttttatgca accacatagt caacttgaat gccgcttgag tgcgttctca  360
agttttttt cttgcaaatt acgcttttt aagaaagtat aatttggatc gtgcgatttt  420
ttttctctag gtgtgcgtga ctgtgtgagt aacaattttg gatctcagaa aggtaataaa  480
agaataatac tgctgcctac tttgaggatt acaatatctt tctctaaaat gttttggttt  540
gttatttaaa ccgtctttaa ggccaattgc tcaagattca ttcaacaatt gaaacgtctc  600
acatgattaa atcatataag gttgctaagg tcttgtttga caaggttttt tttgtggaaa  660
tttcatctaa atttttgagt gaaactatca aatactaatt taaaaaaggc aaattttgct  720
ggaggacact gcagaaacgt gtaattggcc ggcacaaacc gccaaacgga gaatttgccc  780
agtaccatta taaattcatg ataaattcat ggttgtttgc cagtggggct agggttcctc  840
gcgtatggtg cggaatgtgg tttggttcga ccaactcgaa ctcaatccga tccaaagggg  900
catcaatagt cattttagaa agtttctctc tcccgagcag tggaaatgat tattctattt  960
ggcgcgatgt ccaccggcaa acaaccacga atttgtaatg gtactaggca aattctccgt  1020
ttggcggtgt gtgccggcca attacacgtt tttgcggtgt cctccgacaa aatttgcctt  1080
ttaaaaacaa ttttataaga gaagctccgg agataaaagg ccgtcaatgt tacaagagtg  1140
aagtcgtcta ctccctccat cccaaaaaat gtaattctaa gtatgagttg tattattatt  1200
tttggacaaa aggagtatac cacaagaatg atatcatcgt catgcttaga tcctttttag  1260
taaagcttga gcttctctaa aagtagagaa attagaaaaa aatcacgttt ttgtggtctt  1320
gatttctagc ctccacaaaa tctttggttt tacatttttt gtttgatttt ggtttcagaa  1380
gtccttattt atatgtgcta gtttggcagc acttaaaatc gttagagaga gcctaaacaa  1440
aagccttttc aaaacgacct tgagccagat tggttgatgg ccaaaatttg attgtcaaaa  1500
cttaggcaag ccaagatttt agcagctatt tggtttggta ccaaaatttg ccaatgatct  1560
gttcttttgc cttttcaacc ggtttatcag ccgtacttca gcttattctc tctcacagaa  1620
cactattgaa tcagccgaaa agccaccgca gaacaggacc agtatctcac aaatggcatg  1680
ccaaatatac tcaccgtcag tgagcccgtt taacggcgtc gacaagtcta acggccacca  1740
accagcgaac caccagcgtc aagctagcca agcgaagcag acggccgaga cgttgacacc  1800
ttggcgcggg catctctctg gccccctctc gagagttccg ctccacctcc actggtggcg  1860
gtttccaagt ccgttccgcc tcctgctcct cctcacacgg cacgaaaccg tcacggcacc  1920
ggcagcacgg gggattcctt tcccaccgct ccttcccttt cccttcctcg cccgccgttt  1980
taaatagcca gccccatccc cagcttctct ccccaacctc agcttctctc gttgttcgga  2040
gcgcacacac aacccgatcc ccaatcccct cgtctctcct cgcgagcctc gtcgatcccc  2100
gcttcaaggt acggcgatca tcctcccttt ctctaccttc tcttctctag actaggtcgg  2160
cgatccatgg ttagggcctg ctagttctgt tcctgttttt ccgtggctgc gaggtacaat  2220
agatctgatg gcgttatgat ggttaacttg tcatactcct gcggtgtgcg gtctatagtg  2280
cttttaggac atcaatttga cctggctcgt tcgagatcgg cgatccatgg ttaggaccct  2340
aggcggtgga gtcgggttag atccgcgctg tttgtgttag tagatggatg cgacctttac  2400
ttcagacacg ttctgattgt taacttgtca gcacctggga gtcctgggat ggttctagct  2460
ggttcgcaga tgagatcgat ttcatgatct gctgtatctt gtttcgttag gttcctttta  2520
```

```
atctatccgt ggtattatgc taacctatga tatggttcga tcgtgctagc tacgtcctgt  2580
gtcataattt ttagcatgcc ctttttttgtt tggttttgtc tgattgggct gtagatcaga  2640
gtatactgtt tcaaactacc tactggatat atttattaaa tttgaatctg tatgtgtgtc  2700
acatatatct tcataattaa aatggatgga aagatatatg gataggtaca tgtgttgctg  2760
tgggttttac tggtactttg ttagatatac atgcttagat acatgaagca acatgatgtt  2820
acagttcaat aattcttgtt tacctaataa acaaataagg ataggtgtat gttgctgtgg  2880
gttttgctgg tactttgtta gatatatatg cttagatata tgaagcaaca tcctgctacg  2940
gtttaataat tattgtttat atctaataga caagcctgct ttttaattat tttgatatac  3000
ttggatgatg gcatacagca gctatgtgtg gatttttaaa tacccagcat catgagcatg  3060
catgaccctg ccttagtatg ctgtttattt gcttgagact tcttttttttg ttggtactca  3120
ccttttgtag tttggtgact cttctgcagg tg                                3152
```

```
SEQ ID NO: 23           moltype = DNA  length = 2014
FEATURE                 Location/Qualifiers
source                  1..2014
                        mol_type = other DNA
                        organism = Tripidium ravennae
                        sub_species = ravennae
SEQUENCE: 23
gtataagagc aagtgtattg tcacgtgata tttatgttga gatgaagaag agaaaataaa  60
cagcctgcaa atttatagcg agtgatagat gggcacaagg cttcctattt cttaaatcag  120
actttgtaag aacaaaaaaa ggacttataa gagaatggga taaaccatat atcaatggtg  180
tagtatgtta gtatgcatta agatctgact attatatgag tgagttgtta aattcatttt  240
aggtgacatg gcccggttaa attattagcc ataccctaac agctctaaaa aagatatatt  300
cgttgaggca cttttatgca accacatagt caacttgaat gccgcttgag tgcgttctca  360
agtttttttt cttgcaaatt acgcttttttt aagaaagtat aatttggatc gtgcgatttt  420
ttttctctag gtgtgcgtga ctgtgtgagt aacaattttg gatctcagaa aggtaataaa  480
agaataatac tgctgcctac tttgaggatt acaatatctt tctctaaaat gttttggttt  540
gttatttaaa ccgtctttaa ggccaattgc tcaagattca ttcaacaatt gaaacgtctc  600
acatgattaa atcatataag gttgctaagg tcttgtttga caaggttttt tttgtggaaa  660
tttcatctaa atttttgagt gaaactatca aatactaatt taaaaaaggc aaattttgct  720
ggaggacact gcagaaacgt gtaattggcc ggcacaaacc gccaaacgga gaatttgccc  780
agtaccatta taaattcatg ataaattcat ggttgtttgc cagtggggct agggttcctc  840
gcgtatggtg cggaatgtgg tttggttcga ccaactcgaa ctcaatccga tccaaagggg  900
catcaatagt cattttagaa agtttctctc tcccgagcag tggaaatgat tattctattt  960
ggcgcgatgt ccaccggcaa acaaccacga atttgtaatg gtactaggca aattctccgt  1020
ttggcggtgt gtgccggcca attacacgtt tttgcggtgt cctccgacaa aatttgcctt  1080
ttaaaaacaa ttttataaga gaagctccgg agataaaagg ccgtcaatgt tacaagagtg  1140
aagtcgtcta ctccctccat cccaaaaaat gtaattctaa gtatgagttg tattattatt  1200
tttggacaaa aggagtatac cacaagaatg atatcatcgt catgcttaga tcctttttag  1260
taaagcttga gcttctctaa aagtagagaa attagaaaaa aatcacgttt ttgtggtctt  1320
gatttctagc ctccacaaaa tctttggttt tacatttttt gtttgatttt ggtttcagaa  1380
gtccttattt atatgtgcta gtttggcagc acttaaaatc gttagagaga gcctaaacaa  1440
aagccttttc aaaacgacct tgagccagat tggttgatgg ccaaaatttg attgtcaaaa  1500
cttaggcaag ccaagatttt agcagctatt tggtttggta ccaaaatttg ccaatgatct  1560
gttcttttgc cttttcaacc ggtttatcag ccgtacttca gcttattctc tctcacagaa  1620
cactattgaa tcagccgaaa agccaccgca gaacaggacc agtatctcac aaatggcatg  1680
ccaaatatac tcaccgtcag tgagcccgtt taacggcgtc gacaagtcta acggccacca  1740
accagcgaac caccagcgtc aagctagcca agcgaagcag acggccgaga cgttgacacc  1800
ttggcgcggg catctctctg gccccctctc gagagttccg ctccacctcc actggtggcg  1860
gtttccaagt ccgttccgcc tcctgctcct cctcacacgg cacgaaaccg tcacggcacc  1920
ggcagcacgg gggattcctt tcccaccgct ccttcccttt cccttcctcg cccgccgttt  1980
taaatagcca gccccatccc cagcttctct cccc                            2014
```

```
SEQ ID NO: 24           moltype = DNA  length = 1044
FEATURE                 Location/Qualifiers
source                  1..1044
                        mol_type = other DNA
                        organism = Tripidium ravennae
                        sub_species = ravennae
SEQUENCE: 24
gtacggcgat catcctccct ttctctacct tctcttctct agactaggtc ggcgatccat  60
ggttagggcc tgctagttct gttcctgttt ttccgtggct gcgaggtaca atagatctga  120
tggcgttatg atggttaact tgtcatactc ctgcggtgtg cggtctatag tgcttttagg  180
acatcaattt gacctggctc gttcgagatc ggcgatccat ggttaggacc ctaggcggtg  240
gagtcgggtt agatccgcgc tgtttgtgtt agtagatgga tgcgaccttt acttcagaca  300
cgttctgatt gttaacttgt cagcacctgg gagtcctggg atggttctag ctggttcgca  360
gatgagatcg atttcatgat ctgctgtatc ttgtttcgtt aggttccttt taatctatcc  420
gtggtattat gctaacctat gatatggttc gatcgtgcta gctacgtcct gtgtcataat  480
ttttagcatg cccttttttg tttggttttg tctgattggg ctgtagatca gagtatactg  540
tttcaaacta cctactggat atatttatta aatttgaatc tgtatgtgtg tcacatatat  600
cttcataatt aaaatggatg gaaagatata tggataggta catgtgttgc tgtgggtttt  660
actggtactt tgttagatat acatgcttag atacatgaag caacatgatg ttacagttca  720
ataattcttg tttacctaat aaacaaataa ggataggtgt atgttgctgt gggttttgct  780
ggtactttgt tagatatata tgcttagata tatgaagcaa catcctgcta cggtttaata  840
attattgttt atatctaata gacaagcctg ctttttaatt attttgatat acttggatga  900
tggcatacag cagctatgtg tggattttta aatacccagc atcatgagca tgcatgaccc  960
tgccttagta tgctgtttat ttgcttgaga cttctttttt tgttggtact caccttttgt  1020
agtttggtga ctcttctgca ggtg                                       1044
```

```
SEQ ID NO: 25          moltype = DNA  length = 2663
FEATURE                Location/Qualifiers
source                 1..2663
                       mol_type = other DNA
                       organism = Tripidium ravennae
                       sub_species = ravennae
SEQUENCE: 25
ctgctgccta ctttgaggat tacaatatct ttctctaaaa tgttttggtt tgttatttaa  60
accgtcttta aggccaattg ctcaagattc attcaacaat tgaaacgtct cacatgatta  120
aatcatataa ggttgctaag gtcttgtttg acaaggtttt ttttgtggaa atttcatcta  180
aatttttgag tgaaactatc aaatactaat ttaaaaaagg caaattttgc tggaggacac  240
tgcagaaacg tgtaattggc cggcacaaac cgccaaacgg agaatttgcc cagtaccatt  300
ataaattcat gataaattca tggttgtttg ccagtggggc tagggttcct cgcgtatggt  360
gcggaatgtg gtttggttcg accaactcga actcaatccg atccaaaggg gcatcaatag  420
tcattttaga aagtttctct ctcccgagca gtggaaatga ttattctatt tggcgcgatg  480
tccaccggca aacaaccacg aatttgtaat ggtactaggc aaattctccg tttggcggtg  540
tgtgccggcc aattacacgt ttttgcggtg tcctccgaca aaatttgcct tttaaaaaca  600
attttataag agaagctccg gagataaaag gccgtcaatg ttacaagagt gaagtcgtct  660
actccctcca tcccaaaaaa tgtaattcta agtatgagtt gtattattat ttttggacaa  720
aaggagtata ccacaagaat gatatcatcg tcatgcttag atccttttta gtaaagcttg  780
agcttctcta aaagtagaga aattagaaaa aaatcacgtt tttgtggtct tgatttctag  840
cctccacaaa atctttggtt ttacattttt tgtttgattt tggtttcaga agtccttatt  900
tatatgtgct agtttggcag cacttaaaat cgttagagag agcctaaaca aaagcctttt  960
caaaacgacc ttgagccaga ttggttgatg gccaaaattt gattgtcaaa acttaggcaa  1020
gccaagattt tagcagctat ttggtttggt accaaaattt gccaatgatc tgttcttttg  1080
ccttttcaac cggtttatca gccgtacttc agcttattct ctctcacaga acactattga  1140
atcagccgaa aagccaccgc agaacaggac cagtatctca caaatggcat gccaaatata  1200
ctcaccgtca gtgagcccgt ttaacggcgt cgacaagtct aacggccacc aaccagcgaa  1260
ccaccagcgt caagctagcc aagcgaagca gacggccgag acgttgacac cttggcgcgg  1320
gcatctctct ggccccctct cgagagttcc gctccacctc cactggtggc ggtttccaag  1380
tccgttccgc ctcctgctcc tcctcacacg gcacgaaacc gtcacggcac cggcagcacg  1440
ggggattcct ttcccaccgc tccttccctt tcccttcctc gcccgccgtt ttaaatagcc  1500
agccccatcc ccagcttctc tccccaacct cagcttctct cgttgttcgg agcgcacaca  1560
caacccgatc cccaatcccc tcgtctctcc tcgcgagcct cgtcgatccc cgcttcaagg  1620
tacggcgatc atcctccctt tctctacctt ctcttctcta gactaggtcg gcgatccatg  1680
gttagggcct gctagttctg ttcctgtttt tccgtggctg cgaggtacaa tagatctgat  1740
ggcgttatga tggttaactt gtcatactcc tgcggtgtgc ggtctatagt gcttttagga  1800
catcaatttg acctggctcg ttcgagatcg gcgatccatg gttaggaccc taggcggtgg  1860
agtcgggtta gatccgcgct gtttgtgtta gtagatggat gcgaccttta cttcagacac  1920
gttctgattg ttaacttgtc agcacctggg agtcctggga tggttctagc tggttcgcag  1980
atgagatcga tttcatgatc tgctgtatct tgtttcgtta ggttcctttt aatctatccg  2040
tggtattatg ctaacctatg atatggttcg atcgtgctag ctacgtcctg tgtcataatt  2100
tttagcatgc ccttttttgt ttggttttgt ctgattgggc tgtagatcag agtatactgt  2160
ttcaaactac ctactggata tatttattaa atttgaatct gtatgtgtgt cacatatatc  2220
ttcataatta aaatggatgg aaagatatat ggataggtac atgtgttgct gtgggtttta  2280
ctggtacttt gttagatata catgcttaga tacatgaagc aacatgatgt tacagttcaa  2340
taattcttgt ttacctaata aacaaataag gataggtgta tgttgctgtg ggttttgctg  2400
gtactttgtt agatatatat gcttagatat atgaagcaac atcctgctac ggtttaataa  2460
ttattgttta tatctaatag acaagcctgc tttttaatta ttttgatata cttggatgat  2520
ggcatacagc agctatgtgt ggatttttaa atacccagca tcatgagcat gcatgaccct  2580
gccttagtat gctgtttatt tgcttgagac ttcttttttt gttggtactc accttttgta  2640
gtttggtgac tcttctgcag gtg                                          2663

SEQ ID NO: 26          moltype = DNA  length = 1525
FEATURE                Location/Qualifiers
source                 1..1525
                       mol_type = other DNA
                       organism = Tripidium ravennae
                       sub_species = ravennae
SEQUENCE: 26
ctgctgccta ctttgaggat tacaatatct ttctctaaaa tgttttggtt tgttatttaa  60
accgtcttta aggccaattg ctcaagattc attcaacaat tgaaacgtct cacatgatta  120
aatcatataa ggttgctaag gtcttgtttg acaaggtttt ttttgtggaa atttcatcta  180
aatttttgag tgaaactatc aaatactaat ttaaaaaagg caaattttgc tggaggacac  240
tgcagaaacg tgtaattggc cggcacaaac cgccaaacgg agaatttgcc cagtaccatt  300
ataaattcat gataaattca tggttgtttg ccagtggggc tagggttcct cgcgtatggt  360
gcggaatgtg gtttggttcg accaactcga actcaatccg atccaaaggg gcatcaatag  420
tcattttaga aagtttctct ctcccgagca gtggaaatga ttattctatt tggcgcgatg  480
tccaccggca aacaaccacg aatttgtaat ggtactaggc aaattctccg tttggcggtg  540
tgtgccggcc aattacacgt ttttgcggtg tcctccgaca aaatttgcct tttaaaaaca  600
attttataag agaagctccg gagataaaag gccgtcaatg ttacaagagt gaagtcgtct  660
actccctcca tcccaaaaaa tgtaattcta agtatgagtt gtattattat ttttggacaa  720
aaggagtata ccacaagaat gatatcatcg tcatgcttag atccttttta gtaaagcttg  780
agcttctcta aaagtagaga aattagaaaa aaatcacgtt tttgtggtct tgatttctag  840
cctccacaaa atctttggtt ttacattttt tgtttgattt tggtttcaga agtccttatt  900
tatatgtgct agtttggcag cacttaaaat cgttagagag agcctaaaca aaagcctttt  960
caaaacgacc ttgagccaga ttggttgatg gccaaaattt gattgtcaaa acttaggcaa  1020
gccaagattt tagcagctat ttggtttggt accaaaattt gccaatgatc tgttcttttg  1080
```

-continued

```
ccttttcaac cggtttatca gccgtacttc agcttattct ctctcacaga acactattga  1140
atcagccgaa aagccaccgc agaacaggac cagtatctca caaatggcat gccaaatata  1200
ctcaccgtca gtgagcccgt ttaacggcgt cgacaagtct aacggccacc aaccagcgaa  1260
ccaccagcgt caagctagcc aagcgaagca gacggccgag acgttgacac cttggcgcgg  1320
gcatctctct ggcccctct cgagagttcc gctccacctc cactggtggc ggtttccaag  1380
tccgttccgc ctcctgctcc tcctcacacg gcacgaaacc gtcacggcac cggcagcacg  1440
ggggattcct ttcccaccgc tccttccctt tcccttcctc gcccgccgtt ttaaatagcc  1500
agccccatcc ccagcttctc tcccc                                         1525

SEQ ID NO: 27          moltype = DNA  length = 2182
FEATURE                Location/Qualifiers
source                 1..2182
                       mol_type = other DNA
                       organism = Tripidium ravennae
                       sub_species = ravennae
SEQUENCE: 27
ccaccggcaa acaaccacga atttgtaatg gtactaggca aattctccgt ttggcggtgt  60
gtgccggcca attacacgtt tttgcggtgt cctccgacaa aatttgcctt ttaaaaacaa  120
ttttataaga gaagctccgg agataaaagg ccgtcaatgt tacaagagtg aagtcgtcta  180
ctccctccat cccaaaaaat gtaattctaa gtatgagttg tattattatt tttggacaaa  240
aggagtatac cacaagaatg atatcatcgt catgcttaga tcctttttag taaagcttga  300
gcttctctaa aagtagagaa attagaaaaa aatcacgttt ttgtggtctt gatttctagc  360
ctccacaaaa tctttggttt tacatttttt gtttgatttt ggtttcagaa gtccttattt  420
atatgtgcta gtttggcagc acttaaaatc gttagagaga gcctaaacaa aagccttttc  480
aaaacgacct tgagccagat tggttgatgg ccaaaatttg attgtcaaaa cttaggcaag  540
ccaagatttt agcagctatt tggtttggta ccaaaatttg ccaatgatct gttcttttgc  600
cttttcaacc ggtttatcag ccgtacttca gcttattctc tctcacagaa cactattgaa  660
tcagccgaaa agccaccgca gaacaggacc agtatctcac aaatggcatg ccaaatatac  720
tcaccgtcag tgagcccgtt taacggcgtc gacaagtcta acggccacca accagcgaac  780
caccagcgtc aagctagcca agcgaagcag acggccgaga cgttgacacc ttggcgcggg  840
catctctctg gcccctctc gagagttccg ctccacctcc actggtggcg gtttccaagt  900
ccgttccgcc tcctgctcct cctcacacgg cacgaaaccg tcacggcacc ggcagcacgg  960
gggattcctt tcccaccgct ccttcccttt cccttcctcg cccgccgttt taaatagcca  1020
gccccatccc cagcttctct ccccaacctc agcttctctc gttgttcgga gcgcacacac  1080
aacccgatcc ccaatcccct cgtctctcct cgcgagcctc gtcgatcccc gcttcaaggt  1140
acggcgatca tcctcccttt ctctaccttc tcttctctag actaggtcgg cgatccatgg  1200
ttagggcctg ctagttctgt tcctgttttt ccgtggctgc gaggtacaat agatctgatg  1260
gcgttatgat ggttaacttg tcatactcct gcggtgtgcg gtctatagtg cttttaggac  1320
atcaatttga cctggctcgt tcgagatcgg cgatccatgg ttaggaccct aggcggtgga  1380
gtcgggttag atccgcgctg tttgtgttag tagatggatg cgacctttac ttcagacacg  1440
ttctgattgt taacttgtca gcacctggga gtcctgggat ggttctagct ggttcgcaga  1500
tgagatcgat ttcatgatct gctgtatctt gtttcgttag gttcctttta atctatccgt  1560
ggtattatgc taacctatga tatggttcga tcgtgctagc tacgtcctgt gtcataattt  1620
ttagcatgcc cttttttgtt tggttttgtc tgattgggct gtagatcaga gtatactgtt  1680
tcaaactacc tactggatat atttattaaa tttgaatctg tatgtgtgtc acatatatct  1740
tcataattaa aatggatgga aagatatatg gataggtaca tgtgttgctg tgggttttac  1800
tggtactttg ttagatatac atgcttagat acatgaagca acatgatgtt acagttcaat  1860
aattcttgtt tacctaataa acaaataagg ataggtgtat gttgctgtgg gttttgctgg  1920
tactttgtta gatatatatg cttagatata tgaagcaaca tcctgctacg gtttaataat  1980
tattgtttat atctaataga caagcctgct ttttaattat tttgatatac ttggatgatg  2040
gcatacagca gctatgtgtg gatttttaaa tacccagcat catgagcatg catgaccctg  2100
ccttagtatg ctgtttattt gcttgagact tcttttttttg ttggtactca ccttttgtag  2160
tttggtgact cttctgcagg tg                                            2182

SEQ ID NO: 28          moltype = DNA  length = 1044
FEATURE                Location/Qualifiers
source                 1..1044
                       mol_type = other DNA
                       organism = Tripidium ravennae
                       sub_species = ravennae
SEQUENCE: 28
ccaccggcaa acaaccacga atttgtaatg gtactaggca aattctccgt ttggcggtgt  60
gtgccggcca attacacgtt tttgcggtgt cctccgacaa aatttgcctt ttaaaaacaa  120
ttttataaga gaagctccgg agataaaagg ccgtcaatgt tacaagagtg aagtcgtcta  180
ctccctccat cccaaaaaat gtaattctaa gtatgagttg tattattatt tttggacaaa  240
aggagtatac cacaagaatg atatcatcgt catgcttaga tcctttttag taaagcttga  300
gcttctctaa aagtagagaa attagaaaaa aatcacgttt ttgtggtctt gatttctagc  360
ctccacaaaa tctttggttt tacatttttt gtttgatttt ggtttcagaa gtccttattt  420
atatgtgcta gtttggcagc acttaaaatc gttagagaga gcctaaacaa aagccttttc  480
aaaacgacct tgagccagat tggttgatgg ccaaaatttg attgtcaaaa cttaggcaag  540
ccaagatttt agcagctatt tggtttggta ccaaaatttg ccaatgatct gttcttttgc  600
cttttcaacc ggtttatcag ccgtacttca gcttattctc tctcacagaa cactattgaa  660
tcagccgaaa agccaccgca gaacaggacc agtatctcac aaatggcatg ccaaatatac  720
tcaccgtcag tgagcccgtt taacggcgtc gacaagtcta acggccacca accagcgaac  780
caccagcgtc aagctagcca agcgaagcag acggccgaga cgttgacacc ttggcgcggg  840
catctctctg gcccctctc gagagttccg ctccacctcc actggtggcg gtttccaagt  900
ccgttccgcc tcctgctcct cctcacacgg cacgaaaccg tcacggcacc ggcagcacgg  960
gggattcctt tcccaccgct ccttcccttt cccttcctcg cccgccgttt taaatagcca  1020
gccccatccc cagcttctct cccc                                          1044
```

```
SEQ ID NO: 29          moltype = DNA  length = 1934
FEATURE                Location/Qualifiers
source                 1..1934
                       mol_type = other DNA
                       organism = Tripidium ravennae
                       sub_species = ravennae
SEQUENCE: 29
accacaagaa tgatatcatc gtcatgctta gatccttttt agtaaagctt gagcttctct  60
aaaagtagag aaattagaaa aaaatcacgt ttttgtggtc ttgatttcta gcctccacaa  120
aatctttggt tttacatttt ttgtttgatt ttggtttcag aagtccttat ttatatgtgc  180
tagtttggca gcacttaaaa tcgttagaga gagcctaaac aaaagccttt tcaaaacgac  240
cttgagccag attggttgat ggccaaaatt tgattgtcaa aacttaggca agccaagatt  300
ttagcagcta tttggtttgg taccaaaatt tgccaatgat ctgttctttt gccttttcaa  360
ccggtttatc agccgtactt cagcttattc tctctcacag aacactattg aatcagccga  420
aaagccaccg cagaacagga ccagtatctc acaaatggca tgccaaatat actcaccgtc  480
agtgagcccg tttaacggcg tcgacaagtc taacggccac caaccagcga accaccagcg  540
tcaagctagc caagcgaagc agacggccga gacgttgaca ccttggcgcg ggcatctctc  600
tggccccctc tcgagagttc cgctccacct ccactggtgg cggtttccaa gtccgttccg  660
cctcctgctc ctcctcacac ggcacgaaac cgtcacggca ccggcagcac gggggattcc  720
tttcccaccg ctccttccct ttcccttcct cgcccgccgt tttaaatagc cagccccatc  780
cccagcttct ctccccaacc tcagcttctc tcgttgttcg gagcgcacac acaacccgat  840
ccccaatccc ctcgtctctc ctcgcgagcc tcgtcgatcc ccgcttcaag gtacggcgat  900
catcctccct ttctctacct tctcttctct agactaggtc ggcgatccat ggttagggcc  960
tgctagttct gttcctgttt ttccgtggct gcgaggtaca atagatctga tggcgttatg  1020
atggttaact tgtcatactc ctgcggtgtg cggtctatag tgcttttagg acatcaattt  1080
gacctggctc gttcgagatc ggcgatccat ggttaggacc ctaggcggtg gagtcgggtt  1140
agatccgcgc tgtttgtgtt agtagatgga tgcgaccttt acttcagaca cgttctgatt  1200
gttaacttgt cagcacctgg gagtcctggg atggttctag ctggttcgca gatgagatcg  1260
atttcatgat ctgctgtatc ttgtttcgtt aggttccttt taatctatcc gtggtattat  1320
gctaacctat gatatggttc gatcgtgcta gctacgtcct gtgtcataat ttttagcatg  1380
cccttttttg tttggttttg tctgattggg ctgtagatca gagtatactg tttcaaacta  1440
cctactggat atatttatta aatttgaatc tgtatgtgtg tcacatatat cttcataatt  1500
aaaatggatg gaaagatata tggataggta catgtgttgc tgtgggtttt actggtactt  1560
tgttagatat acatgcttag atacatgaag caacatgatg ttacagttca ataattcttg  1620
tttacctaat aaacaaataa ggataggtgt atgttgctgt gggttttgct ggtactttgt  1680
tagatatata tgcttagata tatgaagcaa catcctgcta cggtttaata attattgttt  1740
atatctaata gacaagcctg ctttttaatt attttgatat acttggatga tggcatacag  1800
cagctatgtg tggattttta aatacccagc atcatgagca tgcatgaccc tgccttagta  1860
tgctgtttat ttgcttgaga cttctttttt tgttggtact caccttttgt agtttggtga  1920
ctcttctgca ggtg                                                     1934

SEQ ID NO: 30          moltype = DNA  length = 796
FEATURE                Location/Qualifiers
source                 1..796
                       mol_type = other DNA
                       organism = Tripidium ravennae
                       sub_species = ravennae
SEQUENCE: 30
accacaagaa tgatatcatc gtcatgctta gatccttttt agtaaagctt gagcttctct  60
aaaagtagag aaattagaaa aaaatcacgt ttttgtggtc ttgatttcta gcctccacaa  120
aatctttggt tttacatttt ttgtttgatt ttggtttcag aagtccttat ttatatgtgc  180
tagtttggca gcacttaaaa tcgttagaga gagcctaaac aaaagccttt tcaaaacgac  240
cttgagccag attggttgat ggccaaaatt tgattgtcaa aacttaggca agccaagatt  300
ttagcagcta tttggtttgg taccaaaatt tgccaatgat ctgttctttt gccttttcaa  360
ccggtttatc agccgtactt cagcttattc tctctcacag aacactattg aatcagccga  420
aaagccaccg cagaacagga ccagtatctc acaaatggca tgccaaatat actcaccgtc  480
agtgagcccg tttaacggcg tcgacaagtc taacggccac caaccagcga accaccagcg  540
tcaagctagc caagcgaagc agacggccga gacgttgaca ccttggcgcg ggcatctctc  600
tggccccctc tcgagagttc cgctccacct ccactggtgg cggtttccaa gtccgttccg  660
cctcctgctc ctcctcacac ggcacgaaac cgtcacggca ccggcagcac gggggattcc  720
tttcccaccg ctccttccct ttcccttcct cgcccgccgt tttaaatagc cagccccatc  780
cccagcttct ctcccc                                                 796

SEQ ID NO: 31          moltype = DNA  length = 1649
FEATURE                Location/Qualifiers
source                 1..1649
                       mol_type = other DNA
                       organism = Tripidium ravennae
                       sub_species = ravennae
SEQUENCE: 31
aggcaagcca agattttagc agctatttgg tttggtacca aaatttgcca atgatctgtt  60
cttttgcctt ttcaaccggt ttatcagccg tacttcagct tattctctct cacagaacac  120
tattgaatca gccgaaaagc caccgcagaa caggaccagt atctcacaaa tggcatgcca  180
aatatactca ccgtcagtga gcccgtttaa cggcgtcgac aagtctaacg gccaccaacc  240
agcgaaccac cagcgtcaag ctagccaagc gaagcagacg gccgagacgt tgacaccttg  300
gcgcgggcat ctctctggcc ccctctcgag agttccgctc cacctccact ggtggcggtt  360
tccaagtccg ttccgcctcc tgctcctcct cacacggcac gaaaccgtca cggcaccggc  420
agcacggggg attcctttcc caccgctcct tccctttccc ttcctcgccc gccgttttaa  480
```

```
atagccagcc ccatccccag cttctctccc caacctcagc ttctctcgtt gttcggagcg  540
cacacacaac ccgatcccca atcccctcgt ctctcctcgc gagcctcgtc gatccccgct  600
tcaaggtacg gcgatcatcc tccctttctc taccttctct tctctagact aggtcggcga  660
tccatggtta gggcctgcta gttctgttcc tgtttttccg tggctgcgag gtacaataga  720
tctgatggcg ttatgatggt taacttgtca tactcctgcg gtgtgcggtc tatagtgctt  780
ttaggacatc aatttgacct ggctcgttcg agatcggcga tccatggtta ggaccctagg  840
cggtggagtc gggttagatc cgcgctgttt gtgttagtag atggatgcga cctttacttc  900
agacacgttc tgattgttaa cttgtcagca cctgggagtc ctgggatggt tctagctggt  960
tcgcagatga gatcgatttc atgatctgct gtatcttgtt tcgttaggtt ccttttaatc  1020
tatccgtggt attatgctaa cctatgatat ggttcgatcg tgctagctac gtcctgtgtc  1080
ataattttta gcatgccctt ttttgtttgg ttttgtctga ttgggctgta gatcagagta  1140
tactgtttca aactacctac tggatatatt tattaaattt gaatctgtat gtgtgtcaca  1200
tatatcttca taattaaaat ggatggaaag atatatggat aggtacatgt gttgctgtgg  1260
gttttactgg tactttgtta gatatacatg cttagataca tgaagcaaca tgatgttaca  1320
gttcaataat tcttgtttac ctaataaaca aataaggata ggtgtatgtt gctgtgggtt  1380
ttgctggtac tttgttagat atatatgctt agatatatga agcaacatcc tgctacggtt  1440
taataattat tgtttatatc taatagacaa gcctgctttt taattatttt gatatacttg  1500
gatgatggca tacagcagct atgtgtggat ttttaaatac ccagcatcat gagcatgcat  1560
gaccctgcct tagtatgctg tttatttgct tgagacttct ttttttgttg gtactcacct  1620
tttgtagttt ggtgactctt ctgcaggtg                                    1649

SEQ ID NO: 32           moltype = DNA  length = 511
FEATURE                 Location/Qualifiers
source                  1..511
                        mol_type = other DNA
                        organism = Tripidium ravennae
                        sub_species = ravennae
SEQUENCE: 32
aggcaagcca agattttagc agctatttgg tttggtacca aaatttgcca atgatctgtt  60
cttttgcctt ttcaaccggt ttatcagccg tacttcagct tattctctct cacagaacac  120
tattgaatca gccgaaaagc caccgcagaa caggaccagt atctcacaaa tggcatgcca  180
aatatactca ccgtcagtga gcccgtttaa cggcgtcgac aagtctaacg gccaccaacc  240
agcgaaccac cagcgtcaag ctagccaagc gaagcagacg gccgagacgt tgacaccttg  300
gcgcgggcat ctctctggcc ccctctcgag agttccgctc cacctccact ggtggcggtt  360
tccaagtccg ttccgcctcc tgctcctcct cacacggcac gaaaccgtca cggcaccggc  420
agcacggggg attcctttcc caccgctcct tccctttccc ttcctcgccc gccgttttaa  480
atagccagcc ccatccccag cttctctccc c                                 511

SEQ ID NO: 33           moltype = DNA  length = 2631
FEATURE                 Location/Qualifiers
source                  1..2631
                        mol_type = other DNA
                        organism = Setaria viridis
SEQUENCE: 33
actgccgcga cacgcctcac tggcgggagg gctccgagcg ctctctcccc ggcggccggc  60
ggagcagcga tctggattgg agagaataga ggaaagagag ggaaaaggag agagatagcg  120
caaagagctg aaaagataag gttgtgcggg ctgtggtgat tagaggacca ctaatccctc  180
catctcctaa tgacgcggtg cccaagacca gtgccgcggc acaccagcgt ctaagtgaac  240
ttccgctaac cttccggtca ttgcgcctga aagatgtcat gtggcgaggc ccccctctca  300
gtagattgcc aactgcctac cgtgccactc ttccatgcat gattgctccc gtctatcccg  360
tttctcacaa cagatagaca acagtaagca tcactaaagc aagcatgtgt agaaccttaa  420
aaaaaggctt atactaccag tatactatca accagcatgc cgtttttgaa gtatccagga  480
ttagaagctt ctactgcgct tttatattat agctgtggac ctgtggtaac ctttctcttt  540
tggcgcttgc ttaatctcgg ccgtgctggt ccatgcttag gcactaggca gagatagagc  600
cgggggtgaa tggggctaaa gctcagctgc tcgaggggcc gtgggctggt ttccactagc  660
ctacagctgt gccacgtgcg gccgcgcaag ccgaagcaag cacgctgagc cgttggacag  720
cttgtcataa tgccattacg tggattacag gtaactggcc ctgtaactac tcgttcggcc  780
atcatcaaac gacgacgtcc gctaggcgac gacacgggta atgcacgcag ccacccaggc  840
gcgcgcgcta gcggagcacg gtcaggtgac acgggcgtcg tgacgcttcc gagttgaagg  900
ggttaacgcc agaaacagtg tttggccagg gtatgaacat aacaaaaaat attcacacga  960
aagaatggaa gtatggagct gctactgtgt aaatgccaag caggaaactc acgcccgcta  1020
acatccaacg gccaacagct cgacgtgccg gtcagcagag acatcggaac actggtgatt  1080
ggtggagccg gcagtatgcg ccccagcacg gccgaggtgg tggtggcccg tggccctgct  1140
gtctgcgcgg ctcgggacaa cttgaaactg ggccaccgcc tcgtcgcaac tcgcaacccg  1200
ttggcggaag aaaggaatgg ctcgtagggg cccgggtaga atccaagaat gttgcgctgg  1260
gcttcgattc acataacatg ggcctgaagc tctaaaacga cggcccggtc accgggcgat  1320
ggaaagagac cggatcctcc tcgtgaattc tggaaggcca cacgagagcg acccaccacc  1380
gacgcggagg agtcgtgcgt ggtccaacac ggccggcggg ctgggctgcg accttaacca  1440
gcaaggcacg ccacgacccg cctcgccctc gaggcataaa taccctccca tcccgttgcc  1500
gcaagactca gatcagattc cgatccccag ttcttcccca atcaccttgt ggtctctcgt  1560
gtcgcggttc ccagggacgc ctccggctcg tcgctcgaca gcgatctccg ccccagcaag  1620
gtatagattc agttccttgc tccgatccca atctggttga gatgttgctc cgatgcgact  1680
tgattatgtc atatatctgc ggtttgcacc gatctgaagc ctagggtttc tcgagcgacc  1740
cagttgtttg caatttgcga tttgctcgtt tgttgcgcat cgtagtttat gtttggagta  1800
atcgaggatt tgtatgcggc gtcggcgcta cctgcttaat cacgccatgt gacgcggtta  1860
cttgcagagg ctgggttagt gggttctgtt atgtcgtgat ctaagaatct agattaggct  1920
cagtcgttct tgctgtcgac tagtttgttt tgatatccat gtagtacaag ttacttaaaa  1980
tttaggtcca atatattttg catgcttttg gcctgttatt cttgccaaca agttgtcctg  2040
gtaaaaagta gatgtgaaag tcacgtattg ggacaaattg atggttaagt gctatagttc  2100
```

```
tatagttctg tgatacatct atctgatttt ttttggtcta ttggtgccta acttatctga  2160
aaatcatgga acatgaggct agtttgatca tggtttagtt cattgtgatt aataatgtat  2220
gatttagtag ctattttggt gatcgtgtca ttttatttgt gaatggaatc attgtatgta  2280
aatgaagcta gttcaggggt tatgatgtag ctggctttgt attctaaagg ctgctattat  2340
tcatccatcg atttcaccta tatgtaatcc agagctttcg atgtgaaatt tgtctgatcc  2400
ttcactagga aggacagaac attgttaata ttttggcaca tctgtcttat tctcatcctt  2460
tgtttgaaca tgttagcctg ttcaaacaga tactgttgta atgtcctagt tatataggta  2520
catatgtgtt ctctattgag tttatggact tttgtgtgtg aagttatatt tcattttgct  2580
caaaactcat gtttgcaagc tttctgacat tattctattg ttctgaaaca g           2631

SEQ ID NO: 34          moltype = DNA  length = 1493
FEATURE                Location/Qualifiers
source                 1..1493
                       mol_type = other DNA
                       organism = Setaria viridis
SEQUENCE: 34
actgccgcga cacgcctcac tggcgggagg gctccgagcg ctctctcccc ggcggccggc  60
ggagcagcga tctggattgg agagaataga ggaaagagag ggaaaaggag agagatagcg  120
caaagagctg aaaagataag gttgtgcggg ctgtggtgat tagaggacca ctaatccctc  180
catctcctaa tgacgcggtg cccaagacca gtgccgcggc acaccagcgt ctaagtgaac  240
ttccgctaac cttccggtca ttgcgcctga aagatgtcat gtggcgaggc ccccctctca  300
gtagattgcc aactgcctac cgtgccactc ttccatgcat gattgctccc gtctatcccg  360
tttctcacaa cagatagaca acagtaagca tcactaaagc aagcatgtgt agaaccttaa  420
aaaaaggctt atactaccag tatactatca accagcatgc cgtttttgaa gtatccagga  480
ttagaagctt ctactgcgct tttatattat agctgtggac ctgtggtaac ctttctcttt  540
tggcgcttgc ttaatctcgg ccgtgctggt ccatgcttag gcactaggca gagatagagc  600
cgggggtgaa tggggctaaa gctcagctgc tcgaggggcc gtgggctggt ttccactagc  660
ctacagctgt gccacgtgcg gccgcgcaag ccgaagcaag cacgctgagc cgttggacag  720
cttgtcataa tgccattacg tggattacag gtaactggcc ctgtaactac tcgttcggcc  780
atcatcaaac gacgacgtcc gctaggcgac gacacgggta atgcacgcag ccacccaggc  840
gcgcgcgcta gcggagcacg gtcaggtgac acgggcgtcg tgacgcttcc gagttgaagg  900
ggttaacgcc agaaacagtg tttggccagg gtatgaacat aacaaaaaat attcacacga  960
aagaatggaa gtatggagct gctactgtgt aaatgccaag caggaaactc acgcccgcta  1020
acatccaacg gccaacagct cgacgtgccg gtcagcagag acatcggaac actggtgatt  1080
ggtggagccg gcagtatgcg ccccagcacg gccgaggtgg tggtggcccg tggccctgct  1140
gtctgcgcgg ctcgggacaa cttgaaactg ggccaccgcc tcgtcgcaac tcgcaacccg  1200
ttggcggaag aaaggaatgg ctcgtagggg cccgggtaga atccaagaat gttgcgctgg  1260
gcttcgattc acataacatg ggcctgaagc tctaaaacga cggcccggtc accgggcgat  1320
ggaaagagac cggatcctcc tcgtgaattc tggaaggcca cacgagagcg acccaccacc  1380
gacgcggagg agtcgtgcgt ggtccaacac ggccggcggg ctgggctgcg accttaacca  1440
gcaaggcacg ccacgacccg cctcgccctc gaggcataaa taccctccca tcc         1493

SEQ ID NO: 35          moltype = DNA  length = 127
FEATURE                Location/Qualifiers
source                 1..127
                       mol_type = other DNA
                       organism = Setaria viridis
SEQUENCE: 35
cgttgccgca agactcagat cagattccga tccccagttc ttccccaatc accttgtggt  60
ctctcgtgtc gcggttccca gggacgcctc cggctcgtcg ctcgacagcg atctccgccc  120
cagcaag                                                            127

SEQ ID NO: 36          moltype = DNA  length = 1011
FEATURE                Location/Qualifiers
source                 1..1011
                       mol_type = other DNA
                       organism = Setaria viridis
SEQUENCE: 36
gtatagattc agttccttgc tccgatccca atctggttga gatgttgctc cgatgcgact  60
tgattatgtc atatatctgc ggtttgcacc gatctgaagc ctagggtttc tcgagcgacc  120
cagttgtttg caatttgcga tttgctcgtt tgttgcgcat cgtagtttat gtttggagta  180
atcgaggatt tgtatgcggc gtcggcgcta cctgcttaat cacgccatgt gacgcggtta  240
cttgcagagg ctgggttagt gggttctgtt atgtcgtgat ctaagaatct agattaggct  300
cagtcgttct tgctgtcgac tagtttgttt tgatatccat gtagtacaag ttacttaaaa  360
tttaggtcca atatattttg catgcttttg gcctgttatt cttgccaaca agttgtcctg  420
gtaaaaagta gatgtgaaag tcacgtattg ggacaaattg atggttaagt gctatagttc  480
tatagttctg tgatacatct atctgatttt ttttggtcta ttggtgccta acttatctga  540
aaatcatgga acatgaggct agtttgatca tggtttagtt cattgtgatt aataatgtat  600
gatttagtag ctattttggt gatcgtgtca ttttatttgt gaatggaatc attgtatgta  660
aatgaagcta gttcaggggt tatgatgtag ctggctttgt attctaaagg ctgctattat  720
tcatccatcg atttcaccta tatgtaatcc agagctttcg atgtgaaatt tgtctgatcc  780
ttcactagga aggacagaac attgttaata ttttggcaca tctgtcttat tctcatcctt  840
tgtttgaaca tgttagcctg ttcaaacaga tactgttgta atgtcctagt tatataggta  900
catatgtgtt ctctattgag tttatggact tttgtgtgtg aagttatatt tcattttgct  960
caaaactcat gtttgcaagc tttctgacat tattctattg ttctgaaaca g           1011

SEQ ID NO: 37          moltype = DNA  length = 2173
FEATURE                Location/Qualifiers
source                 1..2173
```

```
                        mol_type = other DNA
                        organism = Setaria viridis
SEQUENCE: 37
gccgtttttg aagtatccag gattagaagc ttctactgcg cttttatatt atagctgtgg  60
acctgtggta acctttctct tttggcgctt gcttaatctc ggccgtgctg gtccatgctt  120
aggcactagg cagagataga gccgggggtg aatggggcta aagctcagct gctcgagggg  180
ccgtgggctg gtttccacta gcctacagct gtgccacgtg cggccgcgca agccgaagca  240
agcacgctga gccgttggac agcttgtcat aatgccatta cgtggattac aggtaactgg  300
ccctgtaact actcgttcgg ccatcatcaa acgacgacgt ccgctaggcg acgacacggg  360
taatgcacgc agccacccag gcgcgcgcgc tagcggagca cggtcaggtg acacgggcgt  420
cgtgacgctt ccgagttgaa ggggttaacg ccagaaacag tgtttggcca gggtatgaac  480
ataacaaaaa atattcacac gaaagaatgg aagtatggag ctgctactgt gtaaatgcca  540
agcaggaaac tcacgcccgc taacatccaa cggccaacag ctcgacgtgc cggtcagcag  600
agacatcgga acactggtga ttggtggagc cggcagtatg cgccccagca cggccgaggt  660
ggtggtggcc cgtggccctg ctgtctgcgc ggctcgggac aacttgaaac tgggccaccg  720
cctcgtcgca actcgcaacc cgttggcgga agaaaggaat ggctcgtagg ggcccgggta  780
gaatccaaga atgttgcgct gggcttcgat tcacataaca tgggcctgaa gctctaaaac  840
gacggcccgg tcaccgggcg atggaaagag accggatcct cctcgtgaat tctggaaggc  900
cacacgagag cgacccacca ccgacgcgga ggagtcgtgc gtggtccaac acggccggcg  960
ggctgggctg cgaccttaac cagcaaggca cgccacgacc cgcctcgccc tcgaggcata  1020
aataccctcc catcccgttg ccgcaagact cagatcagat tccgatcccc agttcttccc  1080
caatcacctt gtggtctctc gtgtcgcggt tcccagggac gcctccggct cgtcgctcga  1140
cagcgatctc cgccccagca aggtatagat tcagttcctt gctccgatcc caatctggtt  1200
gagatgttgc tccgatgcga cttgattatg tcatatatct gcggtttgca ccgatctgaa  1260
gcctagggtt tctcgagcga cccagttgtt tgcaatttgc gatttgctcg tttgttgcgc  1320
atcgtagttt atgtttggag taatcgagga tttgtatgcg gcgtcggcgc tacctgctta  1380
atcacgccat gtgacgcggt tacttgcaga ggctgggtta gtgggttctg ttatgtcgtg  1440
atctaagaat ctagattagg ctcagtcgtt cttgctgtcg actagtttgt tttgatatcc  1500
atgtagtaca agttacttaa aatttaggtc caatatattt tgcatgcttt tggcctgtta  1560
ttcttgccaa caagttgtcc tggtaaaaag tagatgtgaa agtcacgtat tgggacaaat  1620
tgatggttaa gtgctatagt tctatagttc tgtgatacat ctatctgatt ttttttggtc  1680
tattggtgcc taacttatct gaaaatcatg gaacatgagg ctagtttgat catggtttag  1740
ttcattgtga ttaataatgt atgatttagt agctattttg gtgatcgtgt cattttattt  1800
gtgaatggaa tcattgtatg taaatgaagc tagttcaggg gttatgatgt agctggcttt  1860
gtattctaaa ggctgctatt attcatccat cgatttcacc tatatgtaat ccagagcttt  1920
cgatgtgaaa tttgtctgat ccttcactag gaaggacaga acattgttaa tattttggca  1980
catctgtctt attctcatcc tttgtttgaa catgttagcc tgttcaaaca gatactgttg  2040
taatgtccta gttatatagg tacatatgtg ttctctattg agtttatgga cttttgtgtg  2100
tgaagttata tttcattttg ctcaaaactc atgtttgcaa gctttctgac attattctat  2160
tgttctgaaa cag                                                     2173

SEQ ID NO: 38           moltype = DNA  length = 1035
FEATURE                 Location/Qualifiers
source                  1..1035
                        mol_type = other DNA
                        organism = Setaria viridis
SEQUENCE: 38
gccgtttttg aagtatccag gattagaagc ttctactgcg cttttatatt atagctgtgg  60
acctgtggta acctttctct tttggcgctt gcttaatctc ggccgtgctg gtccatgctt  120
aggcactagg cagagataga gccgggggtg aatggggcta aagctcagct gctcgagggg  180
ccgtgggctg gtttccacta gcctacagct gtgccacgtg cggccgcgca agccgaagca  240
agcacgctga gccgttggac agcttgtcat aatgccatta cgtggattac aggtaactgg  300
ccctgtaact actcgttcgg ccatcatcaa acgacgacgt ccgctaggcg acgacacggg  360
taatgcacgc agccacccag gcgcgcgcgc tagcggagca cggtcaggtg acacgggcgt  420
cgtgacgctt ccgagttgaa ggggttaacg ccagaaacag tgtttggcca gggtatgaac  480
ataacaaaaa atattcacac gaaagaatgg aagtatggag ctgctactgt gtaaatgcca  540
agcaggaaac tcacgcccgc taacatccaa cggccaacag ctcgacgtgc cggtcagcag  600
agacatcgga acactggtga ttggtggagc cggcagtatg cgccccagca cggccgaggt  660
ggtggtggcc cgtggccctg ctgtctgcgc ggctcgggac aacttgaaac tgggccaccg  720
cctcgtcgca actcgcaacc cgttggcgga agaaaggaat ggctcgtagg ggcccgggta  780
gaatccaaga atgttgcgct gggcttcgat tcacataaca tgggcctgaa gctctaaaac  840
gacggcccgg tcaccgggcg atggaaagag accggatcct cctcgtgaat tctggaaggc  900
cacacgagag cgacccacca ccgacgcgga ggagtcgtgc gtggtccaac acggccggcg  960
ggctgggctg cgaccttaac cagcaaggca cgccacgacc cgcctcgccc tcgaggcata  1020
aataccctcc catcc                                                   1035

SEQ ID NO: 39           moltype = DNA  length = 1819
FEATURE                 Location/Qualifiers
source                  1..1819
                        mol_type = other DNA
                        organism = Setaria viridis
SEQUENCE: 39
cacgggtaat gcacgcagcc acccaggcgc gcgcgctagc ggagcacggt caggtgacac  60
gggcgtcgtg acgcttccga gttgaagggg ttaacgccag aaacagtgtt tggccagggt  120
atgaacataa caaaaaatat tcacacgaaa gaatggaagt atggagctgc tactgtgtaa  180
atgccaagca ggaaactcac gcccgctaac atccaacggc caacagctcg acgtgccggt  240
cagcagagac atcggaacac tggtgattgg tggagccggc agtatgcgcc ccagcacggc  300
cgaggtggtg gtggcccgtg gccctgctgt ctgcgcggct cgggacaact tgaaactggg  360
ccaccgcctc gtcgcaactc gcaacccgtt ggcggaagaa aggaatggct cgtaggggcc  420
```

-continued

```
cgggtagaat ccaagaatgt tgcgctgggc ttcgattcac ataacatggg cctgaagctc  480
taaaacgacg gcccggtcac cgggcgatgg aaagagaccg gatcctcctt gtgaattctg  540
gaaggccaca cgagagcgac ccaccaccga cgcggaggag tcgtgcgtgg tccaacacgg  600
ccggcgggct gggctgcgac cttaaccagc aaggcacgcc acgacccgcc tcgccctcga  660
ggcataaata ccctcccatc ccgttgccgc aagactcaga tcagattccg atccccagtt  720
cttccccaat caccttgtgg tctctcgtgt cgcggttccc agggacgcct ccggctcgtc  780
gctcgacagc gatctccgcc ccagcaaggt atagattcag ttccttgctc cgatcccaat  840
ctggttgaga tgttgctccg atgcgacttg attatgtcat atatctgcgg tttgcaccga  900
tctgaagcct agggtttctc gagcgaccca gttgtttgca atttgcgatt tgctcgtttg  960
ttgcgcatcg tagtttatgt ttggagtaat cgaggatttg tatgcggcgt cggcgctacc  1020
tgcttaatca cgccatgtga cgcggttact tgcagaggct gggttagtgg gttctgttat  1080
gtcgtgatct aagaatctag attaggctca gtcgttcttg ctgtcgacta gtttgttttg  1140
atatccatgt agtacaagtt acttaaaatt taggtccaat atattttgca tgcttttggc  1200
ctgttattct tgccaacaag ttgtcctggt aaaaagtaga tgtgaaagtc acgtattggg  1260
acaaattgat ggttaagtgc tatagttcta tagttctgtg atacatctat ctgatttttt  1320
ttggtctatt ggtgcctaac ttatctgaaa atcatggaac atgaggctag tttgatcatg  1380
gtttagttca ttgtgattaa taatgtatga tttagtagct attttggtga tcgtgtcatt  1440
ttatttgtga atggaatcat tgtatgtaaa tgaagctagt tcaggggtta tgatgtagct  1500
ggctttgtat tctaaaggct gctattattc atccatcgat ttcacctata tgtaatccag  1560
agctttcgat gtgaaatttg tctgatcctt cactaggaag gacagaacat tgttaatatt  1620
ttggcacatc tgtcttattc tcatcctttg tttgaacatg ttagcctgtt caaacagata  1680
ctgttgtaat gtcctagtta tataggtaca tatgtgttct ctattgagtt tatggacttt  1740
tgtgtgtgaa gttatatttc attttgctca aaactcatgt ttgcaagctt tctgacatta  1800
ttctattgtt ctgaaacag                                                1819

SEQ ID NO: 40          moltype = DNA  length = 681
FEATURE                Location/Qualifiers
source                 1..681
                       mol_type = other DNA
                       organism = Setaria viridis
SEQUENCE: 40
cacgggtaat gcacgcagcc acccaggcgc gcgcgctagc ggagcacggt caggtgacac  60
gggcgtcgtg acgcttccga gttgaagggg ttaacgccag aaacagtgtt tggccagggt  120
atgaacataa caaaaaatat tcacacgaaa gaatggaagt atggagctgc tactgtgtaa  180
atgccaagca ggaaactcac gcccgctaac atccaacggc caacagctcg acgtgccggt  240
cagcagagac atcggaacac tggtgattgg tggagccggc agtatgcgcc ccagcacggc  300
cgaggtggtg gtggcccgtg gccctgctgt ctgcgcggct cgggacaact tgaaactggg  360
ccaccgcctc gtcgcaactc gcaacccgtt ggcggaagaa aggaatggct cgtaggggcc  420
cgggtagaat ccaagaatgt tgcgctgggc ttcgattcac ataacatggg cctgaagctc  480
taaaacgacg gcccggtcac cgggcgatgg aaagagaccg gatcctcctt gtgaattctg  540
gaaggccaca cgagagcgac ccaccaccga cgcggaggag tcgtgcgtgg tccaacacgg  600
ccggcgggct gggctgcgac cttaaccagc aaggcacgcc acgacccgcc tcgccctcga  660
ggcataaata ccctcccatc c                                            681

SEQ ID NO: 41          moltype = DNA  length = 1922
FEATURE                Location/Qualifiers
source                 1..1922
                       mol_type = other DNA
                       organism = Zea mays
                       sub_species = Mexicana
SEQUENCE: 41
gtcgtgcccc tctctagaga taatgagcat tgcatgtcta agttataaaa aattaccaca  60
tatttttttt tgtcacactt gtgtttgaag tgcagtttat ctatctctat acatatattt  120
aaacttcact atatgaataa tatagtctat agtattaaaa taatatcaat gttttagatg  180
attatataac tgaactgcta gacatggtct aaaggacaac cgagtatttt gacaacatga  240
ctctacagtt ttatcttttt agtgtgcatg tgttcttttt acttttgcaa atagcttcac  300
ctatataata cttcatccat tttattagta catccattta ctaaattttt agtacatcta  360
ttttattcta ttttagcctc taaattaaga aaacttaaac tctattttag tttttttattt  420
aataatttag atataaaata gaataaaata aagtgactaa aaaataacta aataccttttt  480
aagaaataaa aaaactaagg aaccattttt cttgttccga gtagataatg acagcctgtt  540
caacgccgtc gacgagtcta acggacacca accagcgaac cagcagcgtc gcgtcgggcc  600
aagcgaagca gacggcacgg catctctgta gctgcctctg gacccctctc gagagttccg  660
ctccaccgtt ggacttgctc cgctgtcggc atccagaaat tgcgtggcgg agcggcagac  720
gtgagccggc acggcaggcg gcctcctctc acggcaccgg cagctacggg ggattccttt  780
cccaccgctc cttcgctttc ccttcctcgc ccgccgtaat aaatagaccc cctccacacc  840
ctctttcccc aacctcgtgt tcgttcggag cgcgcacaca cacaaccaga tctcccccaa  900
atccacccgt cggcacctcc gcttcaaggt acgccgctca tcctcctccc ccccctctct  960
ctaccttctc tagatcggcg tttcggtcca tggttagggc ccggtagttc tacttctgtt  1020
catgtttgtg ttagatccgt gtttgtgtta gatccgtgct gctagatttc gtacacggat  1080
gcgacctgta catcagacat gttctgattg ctaacttgcc agtgtttctc tttggggaat  1140
cctgggatgg ctctagccgt tccgcagacg ggatcgattt catgaatttt ttttgtttcg  1200
ttgcataggg tttggtttgc ccttttcctt tatttcaata tatgccgtgc acttgtttgt  1260
cgggtcatct tttcatgttt tttttggctt ggttgtgatg atgtggtctg gttgggcggt  1320
cgttctagat cggagtagaa tactgtttca aactacctgg tggatttatt aaaggatctg  1380
tatgtatgtg ccatacatct tcatagttac gagtttaaga tgatggatgg aaatatcgat  1440
ctaggatagg tatacatgtt gatgcgggtt ttactgatgc atatacagag atgctttttt  1500
ttcgcttggt tgtgatgatg tggtctggtc gggcggtcgt tctagatcgg agtagaatac  1560
tgtttcaaac tacctggtgg atttattaat tttggatctg tatgtgtgtc atacatcttc  1620
atagttacga gtttaagatc gatggaaata tcgatctagg ataggtatac atgttgatgt  1680
```

```
gggttttact gatgcatata catggcatat gcagcatcta ttcatatgct ctaaccttga  1740
gtacctatct attataataa acaagtatgt tttataatta ttttgatctt gatatacttg  1800
gatgatggca tatgcagcag ctatatgtgg attttttag  ccctgccttc atacgctatt  1860
tatttgcttg gtactgtttc ttttgtcgat gctcaccctg ttgtttggtg atacttctgc  1920
ag                                                                 1922

SEQ ID NO: 42          moltype = DNA  length = 850
FEATURE                Location/Qualifiers
source                 1..850
                       mol_type = other DNA
                       organism = Zea mays
                       sub_species = Mexicana
SEQUENCE: 42
gtcgtgcccc tctctagaga taatgagcat tgcatgtcta agttataaaa aattaccaca  60
tatttttttt tgtcacactt gtgtttgaag tgcagtttat ctatctctat acatatattt  120
aaacttcact atatgaataa tatagtctat agtattaaaa taatatcaat gttttagatg  180
attatataac tgaactgcta gacatggtct aaaggacaac cgagtatttt gacaacatga  240
ctctacagtt ttatcttttt agtgtgcatg tgttcttttt acttttgcaa atagcttcac  300
ctatataata cttcatccat tttattagta catccattta ctaaattttt agtacatcta  360
ttttattcta ttttagcctc taaattaaga aaacttaaac tctattttag tttttttattt  420
aataatttag atataaaata gaataaaata aagtgactaa aaaataacta aatacctttt  480
aagaaataaa aaaactaagg aaccattttt cttgttccga gtagataatg acagcctgtt  540
caacgccgtc gacgagtcta acggacacca accagcgaac cagcagcgtc gcgtcgggcc  600
aagcgaagca gacggcacgg catctctgta gctgcctctg gacccctctc gagagttccg  660
ctccaccgtt ggacttgctc cgctgtcggc atccagaaat tgcgtggcgg agcggcagac  720
gtgagccggc acggcaggcg gcctcctctc acggcaccgg cagctacggg ggattccttt  780
cccaccgctc cttcgctttc ccttcctcgc ccgccgtaat aaatagaccc cctccacacc  840
ctctttcccc                                                         850

SEQ ID NO: 43          moltype = DNA  length = 78
FEATURE                Location/Qualifiers
source                 1..78
                       mol_type = other DNA
                       organism = Zea mays
                       sub_species = Mexicana
SEQUENCE: 43
aacctcgtgt tcgttcggag cgcgcacaca cacaaccaga tctcccccaa atccacccgt  60
cggcacctcc gcttcaag                                                78

SEQ ID NO: 44          moltype = DNA  length = 994
FEATURE                Location/Qualifiers
source                 1..994
                       mol_type = other DNA
                       organism = Zea mays
                       sub_species = Mexicana
SEQUENCE: 44
gtacgccgct catcctcctc cccccccctct ctctaccttc tctagatcgg cgtttcggtc  60
catggttagg gcccggtagt tctacttctg ttcatgtttg tgttagatcc gtgtttgtgt  120
tagatccgtg ctgctagatt tcgtacacgg atgcgacctg tacatcagac atgttctgat  180
tgctaacttg ccagtgtttc tctttgggga atcctgggat ggctctagcc gttccgcaga  240
cgggatcgat ttcatgaatt ttttttgttt cgttgcatag ggtttggttt gcccttttcc  300
tttatttcaa tatatgccgt gcacttgttt gtcgggtcat cttttcatgt ttttttggc  360
ttggttgtga tgatgtggtc tggttgggcg gtcgttctag atcggagtag aatactgttt  420
caaactacct ggtggattta ttaaaggatc tgtatgtatg tgccatacat cttcatagtt  480
acgagtttaa gatgatggat ggaaatatcg atctaggata ggtatacatg ttgatgcggg  540
ttttactgat gcatatacag agatgctttt ttttcgcttg gttgtgatga tgtggtctgg  600
tcgggcggtc gttctagatc ggagtagaat actgtttcaa actacctggt ggatttatta  660
attttggatc tgtatgtgtg tcatacatct tcatagttac gagtttaaga tcgatggaaa  720
tatcgatcta ggataggtat acatgttgat gtgggtttta ctgatgcata tacatggcat  780
atgcagcatc tattcatatg ctctaacctt gagtacctat ctattataat aaacaagtat  840
gttttataat tattttgatc ttgatatact tggatgatgg catatgcagc agctatatgt  900
ggattttttt agccctgcct tcatacgcta tttatttgct tggtactgtt tcttttgtcg  960
atgctcaccc tgttgtttgg tgatacttct gcag                              994

SEQ ID NO: 45          moltype = DNA  length = 1971
FEATURE                Location/Qualifiers
source                 1..1971
                       mol_type = other DNA
                       organism = Zea mays
                       sub_species = Mexicana
SEQUENCE: 45
gtcgtgcccc tctctagaga taaagagcat tgcatgtcta agttataaaa aattaccaca  60
tatttttttt gtcacacttg tttgaagtgc agtttatcta tctttataca tatatttaaa  120
ctttactcta cgaataatat aatctatagt actacaataa tatcagtgtt ttagagaatc  180
atataaatga acagttagac atggtctaaa ggacaattga gtattttgac aacaggactc  240
tacagtttta tctttttagt gtgcatgtgt tctccttttt tttttgcaaa tagcttcacc  300
tatataatac ttcatccatt ttattagtac atccatttag ggtttagggt taatggtttt  360
tatagactaa ttttttagt acatctattt tattctattt tagcctctaa attaagaaaa  420
ctaaaactct attttagttt ttttatttaa taatttagat ataaaataga ataaaataaa  480
```

-continued

```
gtgactaaaa attaaacaaa taccctttaa gaaattaaaa aaactaagga aacatttttc  540
ttgtttcgag tagataatgc cagcctgtta aacgccgtcg acgagtctaa cggacaccaa  600
ccagcgaacc agcagcgtcg cgtcgggcca agcgaagcag acggcacggc atctctgtcg  660
ctgcctctgg accccctcg agagttccgc tccaccgttg gacttgctcc gctgtcggca  720
tccagaaatt gcgtggcgga gcggcagacg tgagccggca cggcaggcgg cctcctcctc  780
ctctcacggc accggcagct acgggggatt cctttcccac cgctccttcg ctttcccttc  840
ctcgcccgcc gtaataaata gacacccct ccacaccttc tttccccaac ctcgtgttgt  900
tcggagcgca cacacacaca accagatctc ccccaaatcc acccgtcggc acctccgctt  960
caaggtacgc cgctcatcct cccccccccc tctctacctt ctctagatcg gcgttccggt  1020
ccatggttag ggcccggtag ttctacttct gttcatgttt gtgttagatc cgtgtttgtg  1080
ttagatccgt gctgctagcg ttcgtacacg gatgcgacct gtacgtcaga cacgttctga  1140
ttgctaactt gccagtgttt ctctttgggg aatcctggga tggctctagc cgttccgcag  1200
acgggatcga tttcatgatt ttttttgttt cgttgcatag ggtttggttt gccctttcc  1260
tttatttcaa tatatgccgt gcacttgttt gtcgggtcat cttttcatgc ttttttttgt  1320
cttggttgtg atgatgtggt ctggttgggc ggtcgttcta gatcggagaa gaattctgtt  1380
tcaaactacc tggtggattt attaatttg gatctgtatg tgtgtgccat acatattcat  1440
agttacgaat tgaagatgat ggatggaaat atcgatctag gataggtata catgttgatg  1500
cgggttttac tgatgcatat acagagatgc tttttgttcg cttggttgtg atgatgtggt  1560
ctggttgggc ggtcgttcat tcgttctaga tcggagtaga atactgtttc aaactacctg  1620
gtgtatttat taattttgga actgtatgtg tgtgtcatac atcttcatag ttacgagttt  1680
aagatggatg gaaatatcga tctaggatag gtatacatgt tgatgtgggt tttactgatg  1740
catatacatg atggcatatg cagcatctat tcatatgctc taaccttgag tacctatcta  1800
ttataataaa caagtatgtt ttataattat tttgatcttg atatacttgg atgatggcat  1860
atgcagcagc tatatgtgga ttttttagc cctgccttca tacgctattt atttgcttgg  1920
tactgtttct tttgtcgatg ctcaccctgt tgtttggtga tacttctgca g           1971

SEQ ID NO: 46          moltype = DNA  length = 887
FEATURE                Location/Qualifiers
source                 1..887
                       mol_type = other DNA
                       organism = Zea mays
                       sub_species = Mexicana
SEQUENCE: 46
gtcgtgcccc tctctagaga taaagagcat tgcatgtcta agttataaaa aattaccaca  60
tattttttt gtcacacttg tttgaagtgc agtttatcta tctttataca tatatttaaa  120
ctttactcta cgaataatat aatctatagt actacaataa tatcagtgtt ttagagaatc  180
atataaatga acagttagac atggtctaaa ggacaattga gtattttgac aacaggactc  240
tacagtttta tctttttagt gtgcatgtgt tctcctttt tttttgcaaa tagcttcacc  300
tatataatac ttcatccatt ttattagtac atccatttag ggtttagggt taatggtttt  360
tatagactaa tttttttagt acatctattt tattctattt tagcctctaa attaagaaaa  420
ctaaaactct attttagttt ttttatttaa taatttagat ataaaataga ataaaataaa  480
gtgactaaaa attaaacaaa taccctttaa gaaattaaaa aaactaagga aacatttttc  540
ttgtttcgag tagataatgc cagcctgtta aacgccgtcg acgagtctaa cggacaccaa  600
ccagcgaacc agcagcgtcg cgtcgggcca agcgaagcag acggcacggc atctctgtcg  660
ctgcctctgg accccctcg agagttccgc tccaccgttg gacttgctcc gctgtcggca  720
tccagaaatt gcgtggcgga gcggcagacg tgagccggca cggcaggcgg cctcctcctc  780
ctctcacggc accggcagct acgggggatt cctttcccac cgctccttcg ctttcccttc  840
ctcgcccgcc gtaataaata gacacccct ccacaccttc tttcccc                 887

SEQ ID NO: 47          moltype = DNA  length = 77
FEATURE                Location/Qualifiers
source                 1..77
                       mol_type = other DNA
                       organism = Zea mays
                       sub_species = Mexicana
SEQUENCE: 47
aacctcgtgt tgttcggagc gcacacacac acaaccagat ctcccccaaa tccacccgtc  60
ggcacctccg cttcaag                                                 77

SEQ ID NO: 48          moltype = DNA  length = 1007
FEATURE                Location/Qualifiers
source                 1..1007
                       mol_type = other DNA
                       organism = Zea mays
                       sub_species = Mexicana
SEQUENCE: 48
gtacgccgct catcctcccc ccccctctc taccttctct agatcggcgt tccggtccat  60
ggttagggcc cggtagttct acttctgttc atgtttgtgt tagatccgtg tttgtgttag  120
atccgtgctg ctagcgttcg tacacggatg cgacctgtac gtcagacacg ttctgattgc  180
taacttgcca gtgtttctct ttggggaatc ctgggatggc tctagccgtt ccgcagacgg  240
gatcgatttc atgatttttt ttgtttcgtt gcatagggtt tggtttgccc ttttccttta  300
tttcaatata tgccgtgcac ttgtttgtcg ggtcatcttt tcatgctttt ttttgtcttg  360
gttgtgatga tgtggtctgg ttgggcggtc gttctagatc ggagaagaat tctgtttcaa  420
actacctggt ggatttatta attttggatc tgtatgtgtg tgccatacat attcatagtt  480
acgaattgaa gatgatggat ggaaatatcg atctaggata ggtatacatg ttgatgcggg  540
ttttactgat gcatatacag agatgctttt tgttcgcttg gttgtgatga tgtggtctgg  600
ttgggcggtc gttcattcgt tctagatcgg agtagaatac tgtttcaaac tacctggtgt  660
atttattaat tttggaactg tatgtgtgtg tcatacatct tcatagttac gagtttaaga  720
tggatggaaa tatcgatcta ggataggtat acatgttgat gtgggtttta ctgatgcata  780
```

-continued

```
tacatgatgg catatgcagc atctattcat atgctctaac cttgagtacc tatctattat  840
aataaacaag tatgttttat aattattttg atcttgatat acttggatga tggcatatgc  900
agcagctata tgtggatttt tttagccctg ccttcatacg ctatttattt gcttggtact  960
gtttcttttg tcgatgctca ccctgttgtt tggtgatact tctgcag               1007

SEQ ID NO: 49          moltype = DNA  length = 2005
FEATURE                Location/Qualifiers
source                 1..2005
                       mol_type = other DNA
                       organism = Zea mays
                       sub_species = Mexicana
SEQUENCE: 49
gtcgtgcccc tctctagaga taaagagcat tgcatgtcta aagtataaaa aattaccaca  60
tatttttttg tcacacttat ttgaagtgta gtttatctat ctctatacat atatttaaac  120
ttcactctac aaataatata gtctataata ctaaaataat attagtgttt tagaggatca  180
tataaataaa ctgctagaca tggtctaaag gataattgaa tattttgaca atctacagtt  240
ttatcttttt agtgtgcatg tgatctctct gttttttttg caaatagctt gacctatata  300
atacttcatc cattttatta gtacatccat ttaggattta gggttgatgg tttctataga  360
ctaattttta gtacatccat tttattcttt ttagtctcta aatttttttaa aactaaaact  420
ctattttagt tttttattta ataatttaga tataaaatga aataaaataa attgactaca  480
aataaaacaa ataccettta agaaataaaa aaactaagca aacattttte ttgtttcgag  540
tagataatga caggctgttc aacgccgtcg acgagtctaa cggacaccaa ccagcgaacc  600
agcagcgtcg cgtcgggcca agcgaagcag acggcacggc atctctgtag ctgcctctgg  660
acccctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acgggggatt cctttcccac cgctccttcg ctttcccttc ctcgcccgcc  840
gtaataaata gacacccccct ccacaccctc tttccccaac ctcgtgttcg ttcggagcgc  900
acacacacgc aaccagatct cccccaaatc cagccgtcgg cacctccgct tcaaggtacg  960
ccgctcatcc tccccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc ttttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgttgg gtgatacttc tgcag                                        2005

SEQ ID NO: 50          moltype = DNA  length = 877
FEATURE                Location/Qualifiers
source                 1..877
                       mol_type = other DNA
                       organism = Zea mays
                       sub_species = Mexicana
SEQUENCE: 50
gtcgtgcccc tctctagaga taaagagcat tgcatgtcta aagtataaaa aattaccaca  60
tatttttttg tcacacttat ttgaagtgta gtttatctat ctctatacat atatttaaac  120
ttcactctac aaataatata gtctataata ctaaaataat attagtgttt tagaggatca  180
tataaataaa ctgctagaca tggtctaaag gataattgaa tattttgaca atctacagtt  240
ttatcttttt agtgtgcatg tgatctctct gttttttttg caaatagctt gacctatata  300
atacttcatc cattttatta gtacatccat ttaggattta gggttgatgg tttctataga  360
ctaattttta gtacatccat tttattcttt ttagtctcta aatttttttaa aactaaaact  420
ctattttagt tttttattta ataatttaga tataaaatga aataaaataa attgactaca  480
aataaaacaa ataccettta agaaataaaa aaactaagca aacattttte ttgtttcgag  540
tagataatga caggctgttc aacgccgtcg acgagtctaa cggacaccaa ccagcgaacc  600
agcagcgtcg cgtcgggcca agcgaagcag acggcacggc atctctgtag ctgcctctgg  660
acccctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acgggggatt cctttcccac cgctccttcg ctttcccttc ctcgcccgcc  840
gtaataaata gacacccccct ccacaccctc tttcccc                          877

SEQ ID NO: 51          moltype = DNA  length = 78
FEATURE                Location/Qualifiers
source                 1..78
                       mol_type = other DNA
                       organism = Zea mays
                       sub_species = Mexicana
SEQUENCE: 51
aacctcgtgt tcgttcggag cgcacacaca cgcaaccaga tctcccccaa atccagccgt  60
cggcacctcc gcttcaag                                                78
```

```
SEQ ID NO: 52          moltype = DNA  length = 1050
FEATURE                Location/Qualifiers
source                 1..1050
                       mol_type = other DNA
                       organism = Zea mays
                       sub_species = Mexicana
SEQUENCE: 52
gtacgccgct catcctcccc cccccctct ctctaccttc tctagatcgg cgatccggtc  60
catggttagg gcccggtagt tctacttctg ttcatgtttg tgttagagca aacatgttca  120
tgttcatgtt tgtgatgatg tggtctggtt gggcggtcgt tctagatcgg agtaggatac  180
tgtttcaagc tacctggtgg atttattaat tttgtatctg tatgtgtgtg ccatacatct  240
tcatagttac gagtttaaga tgatggatgg aaatatcgat ctaggatagg tatacatgtt  300
gatgcgggtt ttactgatgc atatacagag atgctttttt tctcgcttgg ttgtgatgat  360
atggtctggt tgggcggtcg ttctagatcg gagtagaata ctgtttcaaa ctacctggtg  420
gatttattaa aggataaagg gtcgttctag atcggagtag aatactgttt caaactacct  480
ggtggattta ttaaaggatc tgtatgtatg tgcctacatc ttcatagtta cgagtttaag  540
atgatggatg gaaatatcga tctaggatag gtatacatgt tgatgcgggt tttactgatg  600
catatacaga gatgcttttt ttcgcttggt tgtgatgatg tggtctggtt gggcggtcgt  660
tctagatcgg agtagaatac tgtttcaaac tacctggtgg atttattaat tttgtatctt  720
tatgtgtgtg ccatacatct tcatagttac gagtttaaga tgatggatgg aaatattgat  780
ctaggatagg tatacatgtt gatgtgggtt ttactgatgc atatacatga tggcatatgc  840
ggcatctatt catatgctct aaccttgagt acctatctat tataataaac aagtatgttt  900
tataattatt ttgatcttga tatacttgga tgatggcata tgcagcagct atatgtggat  960
tttttagccc tgccttcata cgctatttat ttgcttggta ctgtttcttt tgtccgatgc  1020
tcaccctgtt gttgggtgat acttctgcag                                  1050

SEQ ID NO: 53          moltype = DNA  length = 2005
FEATURE                Location/Qualifiers
source                 1..2005
                       mol_type = other DNA
                       organism = Zea mays
                       sub_species = Mexicana
SEQUENCE: 53
gtcgtgcccc tctctagaga taaagagcat tgcatgtcta aagtataaaa aattaccaca  60
tatttttttg tcacacttat ttgaagtgta gtttatctat ctctatacat atatttaaac  120
ttcactctac aaataatata gtctataata ctaaaataat attagtgttt tagaggatca  180
tataaataaa ctgctagaca tggtctaaag gataattgaa tattttgaca atctacagtt  240
ttatcttttt agtgtgcatg tgatctctct gtttttttg caaatagctt gacctatata  300
atacttcatc cattttatta gtacatccat ttaggattta gggttgatgg tttctataga  360
ctaattttta gtacatccat tttattcttt ttagtctcta aattttttaa aactaaaact  420
ctattttagt tttttattta ataatttaga tataaaatga aataaaataa attgactaca  480
aataaaacaa ataccottta agaaataaaa aaactaagca aacatttttc ttgtttcgag  540
tagataatga caggctgttc aacgccgtcg acgagtctaa cggacaccaa ccagcgaacc  600
agcagcgtcg cgtcgggcca agcgaagcag acggcacggc atctctgtag ctgcctctgg  660
acccctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acgggggatt cctttcccac cgctccttcg ctttcccttc ctcgcccgcc  840
gtaataaata gacaccccct ccacaccctc tttccccaac ctcgtgttcg ttcggagcgc  900
acacacacgc aaccagatct cccccaaatc cagccgtcgg cacctccgct tcaaggtacg  960
ccgctcatcc tccccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc ttttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgtttg gtgatacttc tgcag                                        2005

SEQ ID NO: 54          moltype = DNA  length = 1050
FEATURE                Location/Qualifiers
source                 1..1050
                       mol_type = other DNA
                       organism = Zea mays
                       sub_species = Mexicana
SEQUENCE: 54
gtacgccgct catcctcccc cccccctct ctctaccttc tctagatcgg cgatccggtc  60
catggttagg gcccggtagt tctacttctg ttcatgtttg tgttagagca aacatgttca  120
tgttcatgtt tgtgatgatg tggtctggtt gggcggtcgt tctagatcgg agtaggatac  180
```

```
tgtttcaagc tacctggtgg atttattaat tttgtatctg tatgtgtgtg ccatacatct  240
tcatagttac gagtttaaga tgatggatgg aaatatcgat ctaggatagg tatacatgtt  300
gatgcgggtt ttactgatgc atatacagag atgctttttt tctcgcttgg ttgtgatgat  360
atggtctggt tgggcggtcg ttctagatcg gagtagaata ctgtttcaaa ctacctggtg  420
gatttattaa aggataaagg gtcgttctag atcggagtag aatactgttt caaactacct  480
ggtggattta ttaaaggatc tgtatgtatg tgcctacatc ttcatagtta cgagtttaag  540
atgatggatg gaaatatcga tctaggatag gtatacatgt tgatgcgggt tttactgatg  600
catatacaga gatgcttttt ttcgcttggt tgtgatgatg tggtctggtt gggcggtcgt  660
tctagatcgg agtagaatac tgtttcaaac tacctggtgg atttattaat tttgtatctt  720
tatgtgtgtg ccatacatct tcatagttac gagtttaaga tgatggatgg aaatattgat  780
ctaggatagg tatacatgtt gatgtgggtt ttactgatgc atatacatga tggcatatgc  840
ggcatctatt catatgctct aaccttgagt acctatctat tataataaac aagtatgttt  900
tataattatt ttgatcttga tatacttgga tgatggcata tgcagcagct atatgtggat  960
tttttagccc tgccttcata cgctatttat ttgcttggta ctgtttcttt tgtccgatgc  1020
tcaccctgtt gtttggtgat acttctgcag                                   1050

SEQ ID NO: 55          moltype = DNA  length = 1632
FEATURE                Location/Qualifiers
source                 1..1632
                       mol_type = other DNA
                       organism = Sorghum bicolor
SEQUENCE: 55
ccaagtccaa atgtcaattc ccttgaagat gatctatttt tatcttttgc attttgttat  60
ggaagtttgc aaatagcaac aaatgctaag tcaatttgcc aaagtctttg gagatgctct  120
tagtctataa ttgaacaata tttgtaaaat acaaaaaaaa atagtactat ttttatttta  180
aaaaattttt ggaagtaaac aaggccgagg atggggaaac ggaagtccaa cacgtcgttt  240
tctaagttgg gctcaaaagc ccatcacgga actgacctgc tatgggtcgg aggagagcgc  300
gtccagatgg ttccagaggc tggtggtggt gggccaaacg cggaactccg ccaccgccac  360
ggcctcgtgc gcaagcgcag cgcgttgccg tgagccgtga cgtaaccctc cgttgcccac  420
gataaaagct ccacccccga ccccggcccc ccgatttccc ctacggacca gtctcccccc  480
gatcgcaatc gcgaattcgt cgcaccatcg gcacgcagac gaacgaagca aggctctccc  540
catcggctcg tcaaggtatg cgttccctag atttgttccc ttcctctctc ggtttgtcta  600
tatatatgca tgtatggtcg attcccgatc tcgtcgattc tcggtttcgc cttccgtacg  660
aagattcgtt tagattgttc atatgttctg ttgtgttacc agattgatcg gatcaacttg  720
atccagttat cttcgctcct ccgattagat ccgtttctat ttcagtatat atatactagt  780
atagtatcta gggttcacac tgttgaccga ctggttactt ggaattgatc cgtgctgagt  840
tcagttgttg ccgtccataa aggcccgtgc tattgtctgt tctgaaacga aatcctgtag  900
atttcttagg gttagtgttc aattcatcaa aaggttgatt agtgaattat caaatttgag  960
agggttaaat cattctcatc atgttgtctc gaatgtaatc ccaaagatat tatagactgt  1020
gtttcgattt gatggattga tttgtgtatc atctaaatca acaaggctaa gtcatcagtt  1080
catagaatca tgtttaggtt tccgttcaat agactagttt tatcaatata taaaattata  1140
agaagggtag ggtaaatcac gttgcctcaa atgccatcct gtatggtttg gtttcaattc  1200
aattagtttg gttgattagg gtatgctctg gattaagatg gttaaatctt ccctagcatc  1260
ttccctgcct atccttactt gatccgtttc ggatatgttg gaagtacagc gagcttattt  1320
catgttgata gtgacccctt tcagattata ctattgaata ttgtatgttt gccacttctg  1380
tatgttgaat tatcctgcta aattagcaat ggaattagca tattggcaat tggtatgcat  1440
ggacctaatc aggacggatg tggttatgtt agtttcaatt cattgtcaat tcattgttca  1500
cctgcgttag atatatatga tgatttttac gtgtagttca tagttcttga gttttggatc  1560
tttcttatct gatatatgct ttcctgtgcc tgtgctttat tgtgtcttac catgcgattt  1620
ttgtctatgc ag                                                      1632

SEQ ID NO: 56          moltype = DNA  length = 401
FEATURE                Location/Qualifiers
source                 1..401
                       mol_type = other DNA
                       organism = Sorghum bicolor
SEQUENCE: 56
ccaagtccaa atgtcaattc ccttgaagat gatctatttt tatcttttgc attttgttat  60
ggaagtttgc aaatagcaac aaatgctaag tcaatttgcc aaagtctttg gagatgctct  120
tagtctataa ttgaacaata tttgtaaaat acaaaaaaaa atagtactat ttttatttta  180
aaaaattttt ggaagtaaac aaggccgagg atggggaaac ggaagtccaa cacgtcgttt  240
tctaagttgg gctcaaaagc ccatcacgga actgacctgc tatgggtcgg aggagagcgc  300
gtccagatgg ttccagaggc tggtggtggt gggccaaacg cggaactccg ccaccgccac  360
ggcctcgtgc gcaagcgcag cgcgttgccg tgagccgtga c                      401

SEQ ID NO: 57          moltype = DNA  length = 154
FEATURE                Location/Qualifiers
source                 1..154
                       mol_type = other DNA
                       organism = Sorghum bicolor
SEQUENCE: 57
gtaaccctcc gttgcccacg ataaaagctc cacccccgac cccggccccc cgatttcccc  60
tacggaccag tctccccccg atcgcaatcg cgaattcgtc gcaccatcgg cacgcagacg  120
aacgaagcaa ggctctcccc atcggctcgt caag                              154

SEQ ID NO: 58          moltype = DNA  length = 1077
FEATURE                Location/Qualifiers
source                 1..1077
                       mol_type = other DNA
```

```
                         organism = Sorghum bicolor
SEQUENCE: 58
gtatgcgttc cctagatttg ttcccttcct ctctcggttt gtctatatat atgcatgtat  60
ggtcgattcc cgatctcgtc gattctcggt ttcgccttcc gtacgaagat tcgtttagat  120
tgttcatatg ttctgttgtg ttaccagatt gatcggatca acttgatcca gttatcttcg  180
ctcctccgat tagatccgtt tctatttcag tatatatata ctagtatagt atctagggtt  240
cacactgttg accgactggt tacttggaat tgatccgtgc tgagttcagt tgttgccgtc  300
cataaaggcc cgtgctattg tctgttctga aacgaaatcc tgtagatttc ttagggttag  360
tgttcaattc atcaaaaggt tgattagtga attatcaaat ttgagagggt taaatcattc  420
tcatcatgtt gtctcgaatg taatcccaaa gatattatag actgtgtttc gatttgatgg  480
attgatttgt gtatcatcta aatcaacaag gctaagtcat cagttcatag aatcatgttt  540
aggtttccgt tcaatagact agttttatca atatataaaa ttataagaag ggtagggtaa  600
atcacgttgc ctcaaatgcc atcctgtatg gtttggtttc aattcaatta gtttggttga  660
ttagggtatg ctctggatta agatggttaa atcttcccta gcatcttccc tgcctatcct  720
tacttgatcc gtttcggata tgttggaagt acagcgagct tatttcatgt tgatagtgac  780
ccctttcaga ttatactatt gaatattgta tgtttgccac ttctgtatgt tgaattatcc  840
tgctaaatta gcaatggaat tagcatattg gcaattggta tgcatggacc taatcaggac  900
ggatgtggtt atgttagttt caattcattg tcaattcatt gttcacctgc gttagatata  960
tatgatgatt tttacgtgta gttcatagtt cttgagtttt ggatctttct tatctgatat  1020
atgctttcct gtgcctgtgc tttattgtgt cttaccatgc gatttttgtc tatgcag     1077

SEQ ID NO: 59            moltype = DNA  length = 2000
FEATURE                  Location/Qualifiers
source                   1..2000
                         mol_type = other DNA
                         organism = Sorghum bicolor
SEQUENCE: 59
cactagctgc gcatgataaa gccacaagcc aaaattaatt attatgggtg agaataaata  60
cgtaccagca ccggccatag aaaaagtaca ttattaaagg tctaatttgg aaacagtctg  120
aaaacgacgt gcgctgcaga ggtaaatgta attttcggca ctaaaaccat tatcaactaa  180
ttcattcaat aacagttatt tagaaaatgt atagctcgct ctaaaaaaac agtttagaaa  240
aacagtcaaa ataattcgac caacaaacag ttaataaggt tcattaaata tataatgcac  300
ggtgctattt gatcttttaa aggaaaaaga ggaatagtcg tgggcgccag gcgggaattg  360
gggcgcggga gtctgccgga cgacgcgttc cgtccgaacg gccggacccg acgaggcccc  420
cccgccgccc cacgtcgcag aaccgtccgt gggtggtaat ctggccgggt acaccagccg  480
tccccttggg cggcctcaca gcactgggct cacacgtgag ttttgttctg ggcttcggat  540
cgcaccatat gggcctcggc atcagaaaga cggggcccgt ctgggataga agagacagga  600
acctcctcgt ggattccaga agccagccac gagcgaccac cgacgcggag gatactcgtc  660
gtccaagtcc aacacggcgg gcgggcgggc ggacgcgtgg gctgggctaa ctgcctaacc  720
ttaacctcca aggcacgcca aggcccgctt ctcccacccg acataaatat ccccccatcc  780
aggcaaggcg cagagcctca gaccagattc cgatcaatca cccataagct ccccccaaat  840
ctgttcctcg tctcccgtct cgcggtttcc tacttccctc ggacgcctcc ggcaagtcgc  900
tcgaccgcgc gattccgccc gctcaaggta tcaactcggt tcaccactcc aatctacgtc  960
tgatttagat gttacttcca tctatgtcta atttagatgt tactccgatg cgattggatt  1020
atgtttatgc ggtttgcact gctctggaaa ctggaatcta gggtttcgag tgatttgatc  1080
gatcgcgatc tgtgatttcg ttgcgccttg tgtatgcttg gagtgatcta ggcttgtata  1140
tgcggcatcg cgatctgacg cggttgcttt gtagaggctg gggtctaggg ctgtgatttt  1200
agaatcaaat aaagctgttc cttaccgtag atgtttccta catgttctgt ccagtactcc  1260
agtgctatat tcacattgtt tgaggcttga gttttgtcga tcagtggtca tgagaaaaat  1320
atatctcatg attttagagg cacctattgg gaaaggtaga tggttccgtt ttacatgttt  1380
tatagacctt gtggcatggc tcctttgttc tatgggtgct ttattttcct gaataacagt  1440
aatgcgagac tggtctatgg gtgctttgac cagtaatgcg agactagtta tttgatcatg  1500
gtgcagttcc tagtgattac gaacaacaat ttggtagctc agttcattca gcattggttt  1560
ctacgatcct tatcatttta cttctgaatg aatttattta tttaagatat tacagtgcaa  1620
taaactgctg tataaatatca gtaacaaact gctattacta gtaaatgcct agattcataa  1680
taattcatta ttctacttga aaatgatctt aggccttttt atgcggtcct acgcatcctt  1740
ccacaggact tgctgtttgt ttgtttttttg taatccctcg ctgggacgca gaatggttca  1800
tctgtgctaa taatttttttt gcatatataa gtttatagtt ctcattattc atgtggctat  1860
ggtagcctgt aaaatctatt gtaataacat attagtcagc catacatctg ttccaacttg  1920
ctcaattgca aatcatatct ccacttaaag cacatgtttg caagctttct gacaagtttc  1980
tttgtgtttg attgaaacag                                               2000

SEQ ID NO: 60            moltype = DNA  length = 791
FEATURE                  Location/Qualifiers
source                   1..791
                         mol_type = other DNA
                         organism = Sorghum bicolor
SEQUENCE: 60
cactagctgc gcatgataaa gccacaagcc aaaattaatt attatgggtg agaataaata  60
cgtaccagca ccggccatag aaaaagtaca ttattaaagg tctaatttgg aaacagtctg  120
aaaacgacgt gcgctgcaga ggtaaatgta attttcggca ctaaaaccat tatcaactaa  180
ttcattcaat aacagttatt tagaaaatgt atagctcgct ctaaaaaaac agtttagaaa  240
aacagtcaaa ataattcgac caacaaacag ttaataaggt tcattaaata tataatgcac  300
ggtgctattt gatcttttaa aggaaaaaga ggaatagtcg tgggcgccag gcgggaattg  360
gggcgcggga gtctgccgga cgacgcgttc cgtccgaacg gccggacccg acgaggcccc  420
cccgccgccc cacgtcgcag aaccgtccgt gggtggtaat ctggccgggt acaccagccg  480
tccccttggg cggcctcaca gcactgggct cacacgtgag ttttgttctg ggcttcggat  540
cgcaccatat gggcctcggc atcagaaaga cggggcccgt ctgggataga agagacagga  600
acctcctcgt ggattccaga agccagccac gagcgaccac cgacgcggag gatactcgtc  660
```

```
gtccaagtcc aacacggcgg gcgggcgggc ggacgcgtgg gctgggctaa ctgcctaacc  720
ttaacctcca aggcacgcca aggcccgctt ctcccacccg acataaatat ccccccatcc  780
aggcaaggcg c                                                       791

SEQ ID NO: 61          moltype = DNA  length = 136
FEATURE                Location/Qualifiers
source                 1..136
                       mol_type = other DNA
                       organism = Sorghum bicolor
SEQUENCE: 61
agagcctcag accagattcc gatcaatcac ccataagctc cccccaaatc tgttcctcgt  60
ctcccgtctc gcggtttcct acttccctcg gacgcctccg gcaagtcgct cgaccgcgcg  120
attccgcccg ctcaag                                                  136

SEQ ID NO: 62          moltype = DNA  length = 1073
FEATURE                Location/Qualifiers
source                 1..1073
                       mol_type = other DNA
                       organism = Sorghum bicolor
SEQUENCE: 62
gtatcaactc ggttcaccac tccaatctac gtctgattta gatgttactt ccatctatgt  60
ctaatttaga tgttactccg atgcgattgg attatgttta tgcggtttgc actgctctgg  120
aaactggaat ctagggtttc gagtgatttg atcgatcgcg atctgtgatt tcgttgcgcc  180
ttgtgtatgc ttggagtgat ctaggcttgt atatgcggca tcgcgatctg acgcggttgc  240
tttgtagagg ctgggggtct aggctgtgat tttagaatca aataaagctg ttccttaccg  300
tagatgtttc ctacatgttc tgtccagtac tccagtgcta tattcacatt gtttgaggct  360
tgagttttgt cgatcagtgg tcatgagaaa aatatatctc atgattttag aggcacctat  420
tgggaaaggt agatggttcc gttttacatg ttttatagac cttgtggcat ggctcctttg  480
ttctatgggt gctttatttt cctgaataac agtaatgcga gactggtcta tgggtgcttt  540
gaccagtaat gcgagactag ttatttgatc atggtgcagt tcctagtgat tacgaacaac  600
aatttggtag ctcagttcat tcagcattgg tttctacgat ccttatcatt ttacttctga  660
atgaatttat ttatttaaga tattacagtg caataaactg ctgtataata tcagtaacaa  720
actgctatta ctagtaaatg cctagattca taataattca ttattctact tgaaaatgat  780
cttaggcctt tttatgcggt cctacgcatc cttccacagg acttgctgtt tgtttgtttt  840
ttgtaatccc tcgctgggac gcagaatggt tcatctgtgc taataatttt tttgcatata  900
taagtttata gttctcatta ttcatgtggc tatggtagcc tgtaaaatct attgtaataa  960
catattagtc agccatacat ctgttccaac ttgctcaatt gcaaatcata tctccactta  1020
aagcacatgt ttgcaagctt tctgacaagt ttctttgtgt ttgattgaaa cag         1073

SEQ ID NO: 63          moltype = DNA  length = 2064
FEATURE                Location/Qualifiers
source                 1..2064
                       mol_type = other DNA
                       organism = Sorghum bicolor
SEQUENCE: 63
cattaaaagt cattatgtgc atgcgtcgta actaacatgg atatgttgct gcactatctc  60
ctcgcactag ctgcgcatga taaagccaca agccaaaatt aattattatg ggtgagaata  120
aatacgtacc agcaccggcc atagaaaaag tacattatta aaggtctaat ttggaaacag  180
tctgaaaacg acgtgcgctg cagaggtaaa tgtaattttc ggcactaaaa ccattatcaa  240
ctaattcatt caataacagt tatttagaaa atgtatagct cgctctaaaa aaacagttta  300
gaaaaacagt caaaataatt cgaccaacaa acagttaata aggttcatta aatatataat  360
gcacggtgct atttgatctt ttaaaggaaa aagaggaata gtcgtgggcg ccaggcggga  420
attggggcgc gggagtctgc cggacgacgc gttccgtccg aacggccgga cccgacgagg  480
cccccccgcc gccccacgtc gcagaaccgt ccgtgggtgg taatctggcc gggtacacca  540
gccgtcccct tgggcggcct cacagcactg ggctcacacg tgagttttgt tctgggcttc  600
ggatcgcacc atatgggcct cggcatcaga aagacggggc ccgtctggga tagaagagac  660
aggaacctcc tcgtggattc cagaagccag ccacgagcga ccaccgacgc ggaggatact  720
cgtcgtccaa gtccaacacg gcgggcgggc gggcggacgc gtgggctggg ctaactgcct  780
aaccttaacc tccaaggcac gccaaggccc gcttctccca cccgacataa atatcccccc  840
atccaggcaa ggcgcagagc ctcagaccag attccgatca atcacccata agctcccccc  900
aaatctgttc ctcgtctccc gtctcgcggt ttcctacttc cctcggacgc ctccggcaag  960
tcgctcgacc gcgcgattcc gcccgctcaa ggtatcaact cggttcacca ctccaatcta  1020
cgtctgattt agatgttact tccatctatg tctaatttag atgttactcc gatgcgattg  1080
gattatgttt atgcggtttg cactgctctg gaaactggaa tctagggttt cgagtgattt  1140
gatcgatcgc gatctgtgat ttcgttgcgc cttgtgtatg cttggagtga tctaggcttg  1200
tatatgcggc atcgcgatct gacgcggttg ctttgtagag gctgggggtc taggctgtga  1260
ttttagaatc aaataaagct gttccttacc gtagatgttt cctacatgtt ctgtccagta  1320
ctccagtgct atattcacat tgtttgaggc ttgagttttg tcgatcagtg gtcatgagaa  1380
aaatatatct catgatttta gaggcaccta ttgggaaagg tagatggttc cgttttacat  1440
gttttataga ccttgtggca tggctccttt gttctatggg tgctttattt tcctgaataa  1500
cagtaatgcg agactggtct atgggtgctt tgaccagtaa tgcgagacta gttatttgat  1560
catggtgcag ttcctagtga ttacgaacaa caatttggta gctcagttca ttcagcattg  1620
gtttctacga tccttatcat tttacttctg aatgaattta tttatttaag atattacagt  1680
gcaataaact gctgtataat atcagtaaca aactgctatt actagtaaat gcctagattc  1740
ataataattc attattctac ttgaaaatga tcttaggcct ttttatgcgg tcctacgcat  1800
ccttccacag gacttgctgt ttgtttgttt tttgtaatcc ctcgctggga cgcagaatgg  1860
ttcatctgtg ctaataattt ttttgcatat ataagtttat agttctcatt attcatgtgg  1920
ctatggtagc ctgtaaaatc tattgtaata acatattagt cagccataca tctgttccaa  1980
cttgctcaat tgcaaatcat atctccactt aaagcacatg tttgcaagct ttctgacaag  2040
```

```
tttctttgtg tttgattgaa acag                                          2064

SEQ ID NO: 64          moltype = DNA  length = 855
FEATURE                Location/Qualifiers
source                 1..855
                       mol_type = other DNA
                       organism = Sorghum bicolor
SEQUENCE: 64
cattaaaagt cattatgtgc atgcgtcgta actaacatgg atatgttgct gcactatctc  60
ctcgcactag ctgcgcatga taaagccaca agccaaaatt aattattatg ggtgagaata  120
aatacgtacc agcaccggcc atagaaaaag tacattatta aaggtctaat ttggaaacag  180
tctgaaaacg acgtgcgctg cagaggtaaa tgtaattttc ggcactaaaa ccattatcaa  240
ctaattcatt caataacagt tatttagaaa atgtatagct cgctctaaaa aaacagttta  300
gaaaaacagt caaaataatt cgaccaacaa acagttaata aggttcatta aatatataat  360
gcacggtgct atttgatctt ttaaaggaaa aagaggaata gtcgtgggcg ccaggcggga  420
attggggcgc gggagtctgc cggacgacgc gttccgtccg aacggccgga cccgacgagg  480
cccccccgcc gccccacgtc gcagaaccgt ccgtgggtgg taatctggcc gggtacacca  540
gccgtcccct tgggcggcct cacagcactg ggctcacacg tgagttttgt tctgggcttc  600
ggatcgcacc atatgggcct cggcatcaga aagacggggc ccgtctggga tagaagagac  660
aggaacctcc tcgtggattc cagaagccag ccacgagcga ccaccgacgc ggaggatact  720
cgtcgtccaa gtccaacacg gcgggcgggc gggcggacgc gtgggctggg ctaactgcct  780
aaccttaacc tccaaggcac gccaaggccc gcttctccca cccgacataa atatcccccc  840
atccaggcaa ggcgc                                                    855

SEQ ID NO: 65          moltype = DNA  length = 2000
FEATURE                Location/Qualifiers
source                 1..2000
                       mol_type = other DNA
                       organism = Sorghum bicolor
SEQUENCE: 65
agaagtaaaa aaaaagttcg tttcagaatc ataaaggtaa gttaaaaaaa gaccatacaa  60
aaaagaggta tttaatgata aactataatc cagaatttgt taggatagta tataagaata  120
agaccttgtt tagtttcaaa aaaatttgca aaattttcca gattcctcgt cacatcaaat  180
ctttagaggt atgcatggag tattaaatat agacaagacc taaataagaa aacatgaaat  240
gttcacgaaa aaaatcaagc caatgcatga tcgaagcaaa cggtatagta acggtgttaa  300
cctgatccat tgatctttgt aatctttaac ggccacctac cgcgggcagc aaacggcgtc  360
cccctcctcg atatctccgc ggcggcctct ggctttttcc gcggaattgc gcggtgggga  420
cggattccac gagaccgcaa cgcaaccgcc tctcgccgct gggccccaca ccgctcggtg  480
ccgtagcccg tagcctcacg ggattctttc tccctcctcc cccgtgtata aattggcttc  540
atcccctccc tgcctcatcc atccaaatcc cactccccaa tcccatcccg tcggagaaat  600
tcatcgaagc gaagcgaagc gaatcctccc gatcctctca aggtacgcga gttttcgaat  660
cccctccaga cccctcgtat gctttccctg ttcgttttcg tcgtagcgtt tgattaggta  720
tgctttccct gttcgtgttc gtcgtagggt tcgattaggt cgtgtgaggc catggcctgc  780
tgtgataaat ttatttgttg ttatatcgga tctgtagtcg atttgggggt cgtggtgtag  840
atccgcgggc tgtgatgaag ttatttggtg tgattgtgct cgcgtgattc tgcgcgttga  900
gctcgagtag atctgatggt tggacgaccg attggttcgt tggctggctg cgctaaggtt  960
gggctgggct catgttgcgt tcgctgttgc gcgtgattcc gcggatggac ttgcgcttga  1020
ttgccgccag atcacgttac gattatgtga tttcgtttgg aactttttag atttgtagct  1080
tctgcttatt atatgacaga tgcgcctact gctcatatgc ctgtggtaaa taatggatgg  1140
ctgtgggtca aactagttga ttgtcgagtc atgtatcata tacaggtgta tagacttgcg  1200
tctaattgtt tgcatgttgc agttatatga tttgttttag attgtttgtt ccactcatct  1260
aggctgtaaa agggacacta cttattagct tgttgtttaa tctttttatt agtagattat  1320
attggtaatg ttttactaat tattattatg ttatatgtga cttctgctca tgcctgatta  1380
taatcataga tcactgtagt tgattgttga atcatgtgtc aaatacccgt atacataaca  1440
ctacacattt gcttagttgt ttccttaact catgcaaatt gaacaccatg tatgatttgc  1500
atggtgctgt aatgttaaat actacagtcc tgttggtact tgtttagtaa gaatctgctt  1560
catacaacta tatgctatgc ctgatgataa tcatatatct ttgtgtaatt aataattagt  1620
tgactgttga ataatgtatc gagtacatac catggcacaa ttgcttagtc acttccttaa  1680
ccatgcatat tgaactgacc ccttcatgtt ctgctgaatt gttctattct gattagacca  1740
tacatcatgt attgcaatct ttatttgcaa ttgtaatgta atggttcggt tctcaaatgt  1800
taaatgctat agttgtgcta ctttctaatg ttaaatgcta tagctgtgct acttgtaaga  1860
tctgcttcat agtttagtta aattaggatg atgagctttg atgctgtaac tttgtttgat  1920
tatgttcata gttgatcagt ttttgttaga ctcacagtaa cttatggtct cactcttctt  1980
ctggtctttg atgtttgcag                                               2000

SEQ ID NO: 66          moltype = DNA  length = 565
FEATURE                Location/Qualifiers
source                 1..565
                       mol_type = other DNA
                       organism = Sorghum bicolor
SEQUENCE: 66
agaagtaaaa aaaaagttcg tttcagaatc ataaaggtaa gttaaaaaaa gaccatacaa  60
aaaagaggta tttaatgata aactataatc cagaatttgt taggatagta tataagaata  120
agaccttgtt tagtttcaaa aaaatttgca aaattttcca gattcctcgt cacatcaaat  180
ctttagaggt atgcatggag tattaaatat agacaagacc taaataagaa aacatgaaat  240
gttcacgaaa aaaatcaagc caatgcatga tcgaagcaaa cggtatagta acggtgttaa  300
cctgatccat tgatctttgt aatctttaac ggccacctac cgcgggcagc aaacggcgtc  360
cccctcctcg atatctccgc ggcggcctct ggctttttcc gcggaattgc gcggtgggga  420
cggattccac gagaccgcaa cgcaaccgcc tctcgccgct gggccccaca ccgctcggtg  480
```

```
ccgtagcccg tagcctcacg ggattctttc tccctcctcc cccgtgtata aattggcttc  540
atcccctccc tgcctcatcc atcca                                        565

SEQ ID NO: 67          moltype = DNA  length = 77
FEATURE                Location/Qualifiers
source                 1..77
                       mol_type = other DNA
                       organism = Sorghum bicolor
SEQUENCE: 67
aatcccactc cccaatccca tcccgtcgga gaaattcatc gaagcgaagc gaagcgaatc  60
ctcccgatcc tctcaag                                                 77

SEQ ID NO: 68          moltype = DNA  length = 1358
FEATURE                Location/Qualifiers
source                 1..1358
                       mol_type = other DNA
                       organism = Sorghum bicolor
SEQUENCE: 68
gtacgcgagt tttcgaatcc cctccagacc cctcgtatgc tttccctgtt cgttttcgtc  60
gtagcgtttg attaggtatg ctttccctgt tcgtgttcgt cgtagggttc gattaggtcg  120
tgtgaggcca tggcctgctg tgataaattt atttgttgtt atatcggatc tgtagtcgat  180
ttgggggtcg tggtgtagat ccgcgggctg tgatgaagtt atttggtgtg attgtgctcg  240
cgtgattctg cgcgttgagc tcgagtagat ctgatggttg gacgaccgat tggttcgttg  300
gctggctgcg ctaaggttgg gctgggctca tgttgcgttc gctgttgcgc gtgattccgc  360
ggatggactt gcgcttgatt gccgccagat cacgttacga ttatgtgatt tcgtttggaa  420
ctttttagat ttgtagcttc tgcttattat atgacagatg cgcctactgc tcatatgcct  480
gtggtaaata atggatggct gtgggtcaaa ctagttgatt gtcgagtcat gtatcatata  540
caggtgtata gacttgcgtc taattgtttg catgttgcag ttatatgatt tgttttagat  600
tgtttgttcc actcatctag gctgtaaaag ggacactact tattagcttg ttgtttaatc  660
tttttattag tagattatat tggtaatgtt ttactaatta ttattatgtt atatgtgact  720
tctgctcatg cctgattata atcatagatc actgtagttg attgttgaat catgtgtcaa  780
atacccgtat acataacact acacatttgc ttagttgttt ccttaactca tgcaaattga  840
acaccatgta tgatttgcat ggtgctgtaa tgttaaatac tacagtcctg ttggtacttg  900
tttagtaaga atctgcttca tacaactata tgctatgcct gatgataatc atatatcttt  960
gtgtaattaa taattagttg actgttgaat aatgtatcga gtacatacca tggcacaatt  1020
gcttagtcac ttccttaacc atgcatattg aactgacccc ttcatgttct gctgaattgt  1080
tctattctga ttagaccata catcatgtat tgcaatcttt atttgcaatt gtaatgtaat  1140
ggttcggttc tcaaatgtta aatgctatag ttgtgctact ttctaatgtt aaatgctata  1200
gctgtgctac ttgtaagatc tgcttcatag tttagttaaa ttaggatgat gagctttgat  1260
gctgtaactt tgtttgatta tgttcatagt tgatcagttt ttgttagact cacagtaact  1320
tatggtctca ctcttcttct ggtctttgat gtttgcag                          1358

SEQ ID NO: 69          moltype = DNA  length = 2622
FEATURE                Location/Qualifiers
source                 1..2622
                       mol_type = other DNA
                       organism = Setaria italica
SEQUENCE: 69
actgccgcga cacgcctcac tggcgggagg gctccgagcg ctctctcccc ggcggccggc  60
ggagcagcga tctggattgg agagaataga ggaaagagag ggaaaaggag agagatagcg  120
caaagagctg aaaagataag gttgtgcggg ctgtggtgat tagaggacca ctaatccctc  180
catctcctaa tgacgcggtg cccaagacca gtgccgcggc acaccagcgt ctaagtgaac  240
ttccgctaac cttccggtca ttgcgcctga aagatgtcat gtggcgaggc ccccctctca  300
gtagattgcc aactgcctac cgtgccactc ttccatgcat gattgctccc gtctatcccg  360
tttctcacaa cagatagaca acagtaagca tcactaaagc aagcatgtgt agaaccttaa  420
aaaaaggctt atactaccag tatactatca accagcatgc cgtttttgaa gtatccagga  480
ttagaagctt ctactgcgct tttatattat agctgtggac ctgtggtaac ctttctcttt  540
tggcgcttgc ttaatctcgg ccgtgctggt ccatgcttag gcactaggca gagatagagc  600
cgggggtgaa tggggctaaa gctcagctgc tcgaggggcc gtgggctggt ttccactagc  660
ctacagctgt gccacgtgcg gccgcgcaag ccgaagcaag cacgctgagc cgttggacag  720
cttgtcataa tgccattacg tggattacac gtaactggcc ctgtaactac tcgttcggcc  780
atcatcaaac gacgacgtcc gctaggcgac gacacgggta atgcacgcag ccacccaggc  840
gcgcgcgcta gcggagcacg gtcaggtgac acgggcgtcg tgacgcttcc gagttgaagg  900
ggttaacgcc agaaacagtg tttggccagg gtatgaacat aacaaaaaat attcacacga  960
aagaatggaa gtatggagct gctactgtgt aaatgccaag caggaaactc acgcccgcta  1020
acatccaacg gccaacagct cgacgtgccg gtcagcagag catcggaaca ctggtgattg  1080
gtggagccgg cagtatgcgc cccagcacgg ccgaggtggt ggtggcccgt ggccctgctg  1140
tctgcgcggc tcgggacaac ttgaaactgg gccaccgcct cgtcgcaact cgcaacccgt  1200
tggcggaaga aaggaatggc tcgtaggggc ccgggtagaa tcgaagaatg ttgcgctggg  1260
cttcgattca cataacatgg gcctgaagct ctaaaacgac ggcccggtcg ccgcgcgatg  1320
gaaagagacc ggatcctcct cgtgaattct ggaaggccac acgagagcga cccaccaccg  1380
acgcggagga gtcgtgcgtg gtccaacacg gccggcgggc tgggctgcga ccttaaccag  1440
caaggcacgc cacgacccgc cccgccctcg aggcataaat accctcccat cccgttgccg  1500
caagactcag atcagattcc gatccccagt tcttccccaa tcaccttgtg gtctctcgtg  1560
tcgcggttcc cagggacgcc tccggctcgt cgctcgacag cgatctccgc cccagcaagg  1620
tatagattca gttccttgct ccgatcccaa tctggttgag atgttgctcc gatgcgactt  1680
gattatgtca tatatctgcg gtttgcaccg atctgaagcc tagggtttct cgagcgaccc  1740
agttatttgc aatttgcgat ttgctcgttt gttgcgcagc gtagtttatg tttggagtaa  1800
tcgaggattt gtatgcggcg tcggcgctac ctgcttaatc acgccatgtg acgcggttac  1860
```

```
ttgcagaggc tgggttctgt tatgtcgtga tctaagaatc tagattaggc tcagtcgttc  1920
ttgctgtcga ctagtttgtt ttgatatcca tgtagtacaa gttacttaaa atttaggtcc  1980
aatatatttt gcatgctttt ggcctgttat tcttgccaac aagttgtcct ggtaaaaagt  2040
agatgtgaaa gtcacgtatt gggacaaatt gatggtttag tgctatagtt ctatagttct  2100
gtgatacatc tatctgattt tttttggtct attggtgcct aacttatctg aaaatcatgg  2160
aacatgaggc tagtttgatc atggtttagt tcattgtgat taataatgta tgatttagta  2220
gctattttgg tgatcgtgtc attttatttg tgaatggaat cattgtatgt aaatgaagct  2280
agttcagggg ttacgatgta gctggctttg tattctaaag gctgctatta ttcatccatc  2340
gatttcacct atatgtaatc cagagctttt gatgtgaaat ttgtctgatc cttcactagg  2400
aaggacagaa cattgttaat attttggcac atctgtctta ttctcatcct ttgtttgaac  2460
atgttagcct gttcaaacag atactgttgt aatgtcctag ttatataggt acatatgtgt  2520
tctctattga gtttatggac ttttgtgtgt gaagttatat ttcattttgc tcaaaactca  2580
tgtttgcaag ctttctgaca ttattctatt gttctgaaac ag                      2622

SEQ ID NO: 70          moltype = DNA  length = 1492
FEATURE                Location/Qualifiers
source                 1..1492
                       mol_type = other DNA
                       organism = Setaria italica
SEQUENCE: 70
actgccgcga cacgcctcac tggcgggagg gctccgagcg ctctctcccc ggcggccggc  60
ggagcagcga tctggattgg agagaataga ggaaagagag ggaaaaggag agagatagcg  120
caaagagctg aaaagataag gttgtgcggg ctgtggtgat tagaggacca ctaatccctc  180
catctcctaa tgacgcggtg cccaagacca gtgccgcggc acaccagcgt ctaagtgaac  240
ttccgctaac cttccggtca ttgcgcctga aagatgtcat gtggcgaggc ccccctctca  300
gtagattgcc aactgcctac cgtgccactc ttccatgcat gattgctccc gtctatcccg  360
tttctcacaa cagatagaca acagtaagca tcactaaagc aagcatgtgt agaaccttaa  420
aaaaaggctt atactaccag tatactatca accagcatgc cgtttttgaa gtatccagga  480
ttagaagctt ctactgcgct tttatattat agctgtggac ctgtggtaac ctttctcttt  540
tggcgcttgc ttaatctcgg ccgtgctggt ccatgcttag gcactaggca gagatagagc  600
cgggggtgaa tggggctaaa gctcagctgc tcgaggggcc gtgggctggt ttccactagc  660
ctacagctgt gccacgtgcg gccgcgcaag ccgaagcaag cacgctgagc cgttggacag  720
cttgtcataa tgccattacg tggattacac gtaactggcc ctgtaactac tcgttcggcc  780
atcatcaaac gacgacgtcc gctaggcgac gacacgggta atgcacgcag ccacccaggc  840
gcgcgcgcta gcggagcacg gtcaggtgac acgggcgtcg tgacgcttcc gagttgaagg  900
ggttaacgcc agaaacagtg tttggccagg gtatgaacat aacaaaaaat attcacacga  960
aagaatggaa gtatggagct gctactgtgt aaatgccaag caggaaactc acgcccgcta  1020
acatccaacg gccaacagct cgacgtgccg gtcagcagag catcggaaca ctggtgattg  1080
gtggagccgg cagtatgcgc cccagcacgg ccgaggtggt ggtggcccgt ggccctgctg  1140
tctgcgcggc tcgggacaac ttgaaactgg gccaccgcct cgtcgcaact cgcaacccgt  1200
tggcggaaga aaggaatggc tcgtaggggc ccgggtagaa tcgaagaatg ttgcgctggg  1260
cttcgattca cataacatgg gcctgaagct ctaaaacgac ggcccggtcg ccgcgcgatg  1320
gaaagagacc ggatcctcct cgtgaattct ggaaggccac acgagagcga cccaccaccg  1380
acgcggagga gtcgtgcgtg gtccaacacg gccggcgggc tgggctgcga ccttaaccag  1440
caaggcacgc cacgacccgc cccgccctcg aggcataaat accctcccat cc          1492

SEQ ID NO: 71          moltype = DNA  length = 127
FEATURE                Location/Qualifiers
source                 1..127
                       mol_type = other DNA
                       organism = Setaria italica
SEQUENCE: 71
cgttgccgca agactcagat cagattccga tccccagttc ttccccaatc accttgtggt  60
ctctcgtgtc gcggttccca gggacgcctc cggctcgtcg ctcgacagcg atctccgccc  120
cagcaag                                                             127

SEQ ID NO: 72          moltype = DNA  length = 1003
FEATURE                Location/Qualifiers
source                 1..1003
                       mol_type = other DNA
                       organism = Setaria italica
SEQUENCE: 72
gtatagattc agttccttgc tccgatccca atctggttga gatgttgctc cgatgcgact  60
tgattatgtc atatatctgc ggtttgcacc gatctgaagc ctagggtttc tcgagcgacc  120
cagttatttg caatttgcga tttgctcgtt tgttgcgcag cgtagtttat gtttggagta  180
atcgaggatt tgtatgcggc gtcggcgcta cctgcttaat cacgccatgt gacgcggtta  240
cttgcagagg ctgggttctg ttatgtcgtg atctaagaat ctagattagg ctcagtcgtt  300
cttgctgtcg actagtttgt tttgatatcc atgtagtaca agttacttaa aatttaggtc  360
caatatattt tgcatgcttt tggcctgtta ttcttgccaa caagttgtcc tggtaaaaag  420
tagatgtgaa agtcacgtat tgggacaaat tgatggttta gtgctatagt tctatagttc  480
tgtgatacat ctatctgatt ttttttggtc tattggtgcc taacttatct gaaaatcatg  540
gaacatgagg ctagtttgat catggtttag ttcattgtga ttaataatgt atgatttagt  600
agctattttg gtgatcgtgt cattttattt gtgaatggaa tcattgtatg taaatgaagc  660
tagttcaggg gttacgatgt agctggcttt gtattctaaa ggctgctatt attcatccat  720
cgatttcacc tatatgtaat ccagagcttt tgatgtgaaa tttgtctgat ccttcactag  780
gaaggacaga acattgttaa tattttggca catctgtctt attctcatcc tttgtttgaa  840
catgttagcc tgttcaaaca gatactgttg taatgtccta gttatatagg tacatatgtg  900
ttctctattg agtttatgga cttttgtgtg tgaagttata tttcattttg ctcaaaactc  960
atgtttgcaa gctttctgac attattctat tgttctgaaa cag                     1003
```

```
SEQ ID NO: 73          moltype = DNA  length = 2622
FEATURE                Location/Qualifiers
source                 1..2622
                       mol_type = other DNA
                       organism = Setaria italica
SEQUENCE: 73
actgccgcga cacgcctcac tggcgggagg gctccgagcg ctctctcccc ggcggccggc  60
ggagcagcga tctggattgg agagaataga ggaaagagag ggaaaaggag agagatagcg  120
caaagagctg aaaagataag gttgtgcggg ctgtggtgat tagaggacca ctaatccctc  180
catctcctaa tgacgcggtg cccaagacca gtgccgcggc acaccagcgt ctaagtgaac  240
ttccgctaac cttccggtca ttgcgcctga aagatgtcat gtggcgaggc ccccctctca  300
gtagattgcc aactgcctac cgtgccactc ttccatgcat gattgctccc gtctatcccg  360
tttctcacaa cagatagaca acagtaagca tcactaaagc aagcatgtgt agaaccttaa  420
aaaaaggctt atactaccag tatactatca accagcatgc cgtttttgaa gtatccagga  480
ttagaagctt ctactgcgct tttatattat agctgtggac ccgtggtaac ctttctcttt  540
tggcgcttgc ttaatctcgg ccgtgctggt ccatgcttag gcactaggca gagatagagc  600
cgggggtgaa tggggctaaa gctcagctgc tcgaggggcc gtgggctggt ttccactagc  660
ctacagctgt gccacgtgcg gccgcgcaag ccgaagcaag cacgctgagc cgttggacag  720
cttgtcataa tgccattacg tggattacac gtaactggcc ctgtaactac tcgttcggcc  780
atcatcaaac gacgacgtcc gctaggcgac gacacgggta atgcacgcag ccacccaggc  840
gcgcgcgcta gcggagcacg gtcaggtgac acgggcgtcg tgacgcttcc gagttgaagg  900
ggttaacgcc agaaacagtg tttggccagg gtatgaacat aacaaaaaat attcacacga  960
aagaatggaa gtatggagct gctactgtgt aaatgccaag caggaaactc acgcccgcta  1020
acatccaacg gccaacagct cgacgtgccg gtcagcagag catcggaaca ctggtgattg  1080
gtggagccgg cagtatgcgc cccagcacgg ccgaggtggt ggtggcccgt ggccctgctg  1140
tctgcgcggc tcgggacaac ttgaaactgg gccaccgcct cgtcgcaact cgcaacccgt  1200
tggcggaaga aaggaatggc tcgtaggggc ccgggtagaa tcgaagaatg ttgcgctggg  1260
cttcgattca cataacatgg gcctgaagct ctaaaacgac ggcccggtcg ccgcgcgatg  1320
gaaagagacc ggatcctcct cgtgaattct ggaaggccac acgagagcga cccaccaccg  1380
acgcggagga gtcgtgcgtg gtccaacacg gccggcgggc tgggctgcga ccttaaccag  1440
caaggcacgc cacgacccgc cccgccctcg aggcataaat accctcccat cccgttgccg  1500
caagactcag atcagattcc gatccccagt tcttccccaa tcaccttgtg gtctctcgtg  1560
tcgcggttcc cagggacgcc tccggctcgt cgctcgacag cgatctccgc cccagcaagg  1620
tatagattca gttccttgct ccgatcccaa tctggttgag atgttgctcc gatgcgactt  1680
gattatgtca tatatctgcg gtttgcaccg atctgaagcc tagggtttct cgagcgaccc  1740
agttatttgc aatttgcgat ttgctcgttt gttgcgcagc gtagtttatg tttggagtaa  1800
tcgaggattt gtatgcggcg tcggcgctac ctgcttaatc acgccatgtg acgcggttac  1860
ttgcagaggc tgggttctgt tatgtcgtga tctaagaatc tagattaggc tcagtcgttc  1920
ttgctgtcga ctagtttgtt ttgatatcca tgtagtacaa gttacttaaa atttaggtcc  1980
aatatatttt gcatgctttt ggcctgttat tcttgccaac aagttgtcct ggtaaaaagt  2040
agatgtgaaa gtcacgtatt gggacaaatt gatggtttag tgctatagtt ctatagttct  2100
gtgatacatc tatctgattt tttttggtct attggtgcct aacttatctg aaaatcatgg  2160
aacatgaggc tagtttgatc atggtttagt tcattgtgat taataatgta tgatttagta  2220
gctattttgg tgatcgtgtc attttatttg tgaatggaat cattgtatgt aaatgaagct  2280
agttcagggg ttacgatgta gctggctttg tattctaaag gctgctatta ttcatccatc  2340
gatttcacct atatgtaatc cagagctttt gatgtgaaat ttgtctgatc cttcactagg  2400
aaggacagaa cattgttaat attttggcac atctgtctta ttctcatcct ttgtttgaac  2460
atgttagcct gttcaaacag atactgttgt aatgtcctag ttatataggt acatatgtgt  2520
tctctattga gtttatggac ttttgtgtgt gaagttatat ttcattttgc tcaaaactca  2580
tgtttgcaag ctttctgaca ttattctatt gttctgaaac ag                     2622

SEQ ID NO: 74          moltype = DNA  length = 1492
FEATURE                Location/Qualifiers
source                 1..1492
                       mol_type = other DNA
                       organism = Setaria italica
SEQUENCE: 74
actgccgcga cacgcctcac tggcgggagg gctccgagcg ctctctcccc ggcggccggc  60
ggagcagcga tctggattgg agagaataga ggaaagagag ggaaaaggag agagatagcg  120
caaagagctg aaaagataag gttgtgcggg ctgtggtgat tagaggacca ctaatccctc  180
catctcctaa tgacgcggtg cccaagacca gtgccgcggc acaccagcgt ctaagtgaac  240
ttccgctaac cttccggtca ttgcgcctga aagatgtcat gtggcgaggc ccccctctca  300
gtagattgcc aactgcctac cgtgccactc ttccatgcat gattgctccc gtctatcccg  360
tttctcacaa cagatagaca acagtaagca tcactaaagc aagcatgtgt agaaccttaa  420
aaaaaggctt atactaccag tatactatca accagcatgc cgtttttgaa gtatccagga  480
ttagaagctt ctactgcgct tttatattat agctgtggac ccgtggtaac ctttctcttt  540
tggcgcttgc ttaatctcgg ccgtgctggt ccatgcttag gcactaggca gagatagagc  600
cgggggtgaa tggggctaaa gctcagctgc tcgaggggcc gtgggctggt ttccactagc  660
ctacagctgt gccacgtgcg gccgcgcaag ccgaagcaag cacgctgagc cgttggacag  720
cttgtcataa tgccattacg tggattacac gtaactggcc ctgtaactac tcgttcggcc  780
atcatcaaac gacgacgtcc gctaggcgac gacacgggta atgcacgcag ccacccaggc  840
gcgcgcgcta gcggagcacg gtcaggtgac acgggcgtcg tgacgcttcc gagttgaagg  900
ggttaacgcc agaaacagtg tttggccagg gtatgaacat aacaaaaaat attcacacga  960
aagaatggaa gtatggagct gctactgtgt aaatgccaag caggaaactc acgcccgcta  1020
acatccaacg gccaacagct cgacgtgccg gtcagcagag catcggaaca ctggtgattg  1080
gtggagccgg cagtatgcgc cccagcacgg ccgaggtggt ggtggcccgt ggccctgctg  1140
tctgcgcggc tcgggacaac ttgaaactgg gccaccgcct cgtcgcaact cgcaacccgt  1200
tggcggaaga aaggaatggc tcgtaggggc ccgggtagaa tcgaagaatg ttgcgctggg  1260
```

```
cttcgattca cataacatgg gcctgaagct ctaaaacgac ggcccggtcg ccgcgcgatg  1320
gaaagagacc ggatcctcct cgtgaattct ggaaggccac acgagagcga cccaccaccg  1380
acgcggagga gtcgtgcgtg gtccaacacg gccggcgggc tgggctgcga ccttaaccag  1440
caaggcacgc cacgacccgc cccgccctcg aggcataaat accctcccat cc          1492

SEQ ID NO: 75          moltype = DNA  length = 2164
FEATURE                Location/Qualifiers
source                 1..2164
                       mol_type = other DNA
                       organism = Setaria italica
SEQUENCE: 75
gccgtttttg aagtatccag gattagaagc ttctactgcg cttttatatt atagctgtgg  60
acctgtggta acctttctct tttggcgctt gcttaatctc ggccgtgctg gtccatgctt  120
aggcactagg cagagataga gccgggggtg aatggggcta aagctcagct gctcgagggg  180
ccgtgggctg gtttccacta gcctacagct gtgccacgtg cggccgcgca agccgaagca  240
agcacgctga gccgttggac agcttgtcat aatgccatta cgtggattac acgtaactgg  300
ccctgtaact actcgttcgg ccatcatcaa acgacgacgt ccgctaggcg acgacacggg  360
taatgcacgc agccacccag gcgcgcgcgc tagcggagca cggtcaggtg acacgggcgt  420
cgtgacgctt ccgagttgaa ggggttaacg ccagaaacag tgtttggcca gggtatgaac  480
ataacaaaaa atattcacac gaaagaatgg aagtatggag ctgctactgt gtaaatgcca  540
agcaggaaac tcacgcccgc taacatccaa cggccaacag ctcgacgtgc cggtcagcag  600
agcatcggaa cactggtgat tggtggagcc ggcagtatgc gccccagcac ggccgaggtg  660
gtggtggccc gtggccctgc tgtctgcgcg gctcgggaca acttgaaact gggccaccgc  720
ctcgtcgcaa ctcgcaaccc gttggcggaa gaaaggaatg gctcgtaggg gcccgggtag  780
aatcgaagaa tgttgcgctg ggcttcgatt cacataacat gggcctgaag ctctaaaacg  840
acggcccggt cgccgcgcga tggaaagaga ccggatcctc ctcgtgaatt ctggaaggcc  900
acacgagagc gacccaccac cgacgcggag gagtcgtgcg tggtccaaca cggccggcgg  960
gctgggctgc gaccttaacc agcaaggcac gccacgaccc gccccgccct cgaggcataa  1020
ataccctccc atcccgttgc cgcaagactc agatcagatt ccgatcccca gttcttcccc  1080
aatcaccttg tggtctctcg tgtcgcggtt cccagggacg cctccggctc gtcgctcgac  1140
agcgatctcc gccccagcaa ggtatagatt cagttccttg ctccgatccc aatctggttg  1200
agatgttgct ccgatgcgac ttgattatgt catatatctg cggtttgcac cgatctgaag  1260
cctagggttt ctcgagcgac ccagttattt gcaatttgcg atttgctcgt ttgttgcgca  1320
gcgtagttta tgtttggagt aatcgaggat ttgtatgcgg cgtcggcgct acctgcttaa  1380
tcacgccatg tgacgcggtt acttgcagag gctgggttct gttatgtcgt gatctaagaa  1440
tctagattag gctcagtcgt tcttgctgtc gactagtttg ttttgatatc catgtagtac  1500
aagttactta aaatttaggt ccaatatatt ttgcatgctt ttggcctgtt attcttgcca  1560
acaagttgtc ctggtaaaaa gtagatgtga aagtcacgta ttgggacaaa ttgatggttt  1620
agtgctatag ttctatagtt ctgtgataca tctatctgat ttttttggt ctattggtgc  1680
ctaacttatc tgaaaatcat ggaacatgag gctagtttga tcatggttta gttcattgtg  1740
attaataatg tatgatttag tagctatttt ggtgatcgtg tcattttatt tgtgaatgga  1800
atcattgtat gtaaatgaag ctagttcagg ggttacgatg tagctggctt tgtattctaa  1860
aggctgctat tattcatcca tcgatttcac ctatatgtaa tccagagctt ttgatgtgaa  1920
atttgtctga tccttcacta ggaaggacag aacattgtta atattttggc acatctgtct  1980
tattctcatc ctttgtttga acatgttagc ctgttcaaac agatactgtt gtaatgtcct  2040
agttatatag gtacatatgt gttctctatt gagtttatgg acttttgtgt gtgaagttat  2100
atttcatttt gctcaaaact catgtttgca agctttctga cattattcta ttgttctgaa  2160
acag                                                               2164

SEQ ID NO: 76          moltype = DNA  length = 1034
FEATURE                Location/Qualifiers
source                 1..1034
                       mol_type = other DNA
                       organism = Setaria italica
SEQUENCE: 76
gccgtttttg aagtatccag gattagaagc ttctactgcg cttttatatt atagctgtgg  60
acctgtggta acctttctct tttggcgctt gcttaatctc ggccgtgctg gtccatgctt  120
aggcactagg cagagataga gccgggggtg aatggggcta aagctcagct gctcgagggg  180
ccgtgggctg gtttccacta gcctacagct gtgccacgtg cggccgcgca agccgaagca  240
agcacgctga gccgttggac agcttgtcat aatgccatta cgtggattac acgtaactgg  300
ccctgtaact actcgttcgg ccatcatcaa acgacgacgt ccgctaggcg acgacacggg  360
taatgcacgc agccacccag gcgcgcgcgc tagcggagca cggtcaggtg acacgggcgt  420
cgtgacgctt ccgagttgaa ggggttaacg ccagaaacag tgtttggcca gggtatgaac  480
ataacaaaaa atattcacac gaaagaatgg aagtatggag ctgctactgt gtaaatgcca  540
agcaggaaac tcacgcccgc taacatccaa cggccaacag ctcgacgtgc cggtcagcag  600
agcatcggaa cactggtgat tggtggagcc ggcagtatgc gccccagcac ggccgaggtg  660
gtggtggccc gtggccctgc tgtctgcgcg gctcgggaca acttgaaact gggccaccgc  720
ctcgtcgcaa ctcgcaaccc gttggcggaa gaaaggaatg gctcgtaggg gcccgggtag  780
aatcgaagaa tgttgcgctg ggcttcgatt cacataacat gggcctgaag ctctaaaacg  840
acggcccggt cgccgcgcga tggaaagaga ccggatcctc ctcgtgaatt ctggaaggcc  900
acacgagagc gacccaccac cgacgcggag gagtcgtgcg tggtccaaca cggccggcgg  960
gctgggctgc gaccttaacc agcaaggcac gccacgaccc gccccgccct cgaggcataa  1020
ataccctccc atcc                                                     1034

SEQ ID NO: 77          moltype = DNA  length = 1810
FEATURE                Location/Qualifiers
source                 1..1810
                       mol_type = other DNA
                       organism = Setaria italica
```

```
SEQUENCE: 77
cacgggtaat gcacgcagcc acccaggcgc gcgcgctagc ggagcacggt caggtgacac  60
gggcgtcgtg acgcttccga gttgaagggg ttaacgccag aaacagtgtt tggccagggt  120
atgaacataa caaaaaatat tcacacgaaa gaatggaagt atggagctgc tactgtgtaa  180
atgccaagca ggaaactcac gcccgctaac atccaacggc caacagctcg acgtgccggt  240
cagcagagca tcggaacact ggtgattggt ggagccggca gtatgcgccc cagcacggcc  300
gaggtggtgg tggcccgtgg ccctgctgtc tgcgcggctc gggacaactt gaaactgggc  360
caccgcctcg tcgcaactcg caacccgttg gcggaagaaa ggaatggctc gtaggggccc  420
gggtagaatc gaagaatgtt gcgctgggct tcgattcaca taacatgggc ctgaagctct  480
aaaacgacgg cccggtcgcc gcgcgatgga aagagaccgg atcctcctcg tgaattctgg  540
aaggccacac gagagcgacc caccaccgac gcggaggagt cgtgcgtggt ccaacacggc  600
cggcgggctg ggctgcgacc ttaaccagca aggcacgcca cgacccgccc cgccctcgag  660
gcataaatac cctcccatcc cgttgccgca agactcagat cagattccga tccccagttc  720
ttccccaatc accttgtggt ctctcgtgtc gcggttccca gggacgcctc cggctcgtcg  780
ctcgacagcg atctccgccc cagcaaggta tagattcagt tccttgctcc gatcccaatc  840
tggttgagat gttgctccga tgcgacttga ttatgtcata tatctgcggt ttgcaccgat  900
ctgaagccta gggtttctcg agcgacccag ttatttgcaa tttgcgattt gctcgtttgt  960
tgcgcagcgt agtttatgtt tggagtaatc gaggatttgt atgcggcgtc ggcgctacct  1020
gcttaatcac gccatgtgac gcggttactt gcagaggctg ggttctgtta tgtcgtgatc  1080
taagaatcta gattaggctc agtcgttctt gctgtcgact agtttgtttt gatatccatg  1140
tagtacaagt tacttaaaat ttaggtccaa tatattttgc atgcttttgg cctgttattc  1200
ttgccaacaa gttgtcctgg taaaaagtag atgtgaaagt cacgtattgg gacaaattga  1260
tggtttagtg ctatagttct atagttctgt gatacatcta tctgattttt tttggtctat  1320
tggtgcctaa cttatctgaa aatcatggaa catgaggcta gtttgatcat ggtttagttc  1380
attgtgatta ataatgtatg atttagtagc tattttggtg atcgtgtcat tttatttgtg  1440
aatggaatca ttgtatgtaa atgaagctag ttcaggggtt acgatgtagc tggctttgta  1500
ttctaaaggc tgctattatt catccatcga tttcacctat atgtaatcca gagcttttga  1560
tgtgaaattt gtctgatcct tcactaggaa ggacagaaca ttgttaatat tttggcacat  1620
ctgtcttatt ctcatccttt gtttgaacat gttagcctgt tcaaacagat actgttgtaa  1680
tgtcctagtt atataggtac atatgtgttc tctattgagt ttatggactt ttgtgtgtga  1740
agttatattt cattttgctc aaaactcatg tttgcaagct ttctgacatt attctattgt  1800
tctgaaacag                                                          1810

SEQ ID NO: 78          moltype = DNA  length = 680
FEATURE                Location/Qualifiers
source                 1..680
                       mol_type = other DNA
                       organism = Setaria italica
SEQUENCE: 78
cacgggtaat gcacgcagcc acccaggcgc gcgcgctagc ggagcacggt caggtgacac  60
gggcgtcgtg acgcttccga gttgaagggg ttaacgccag aaacagtgtt tggccagggt  120
atgaacataa caaaaaatat tcacacgaaa gaatggaagt atggagctgc tactgtgtaa  180
atgccaagca ggaaactcac gcccgctaac atccaacggc caacagctcg acgtgccggt  240
cagcagagca tcggaacact ggtgattggt ggagccggca gtatgcgccc cagcacggcc  300
gaggtggtgg tggcccgtgg ccctgctgtc tgcgcggctc gggacaactt gaaactgggc  360
caccgcctcg tcgcaactcg caacccgttg gcggaagaaa ggaatggctc gtaggggccc  420
gggtagaatc gaagaatgtt gcgctgggct tcgattcaca taacatgggc ctgaagctct  480
aaaacgacgg cccggtcgcc gcgcgatgga aagagaccgg atcctcctcg tgaattctgg  540
aaggccacac gagagcgacc caccaccgac gcggaggagt cgtgcgtggt ccaacacggc  600
cggcgggctg ggctgcgacc ttaaccagca aggcacgcca cgacccgccc cgccctcgag  660
gcataaatac cctcccatcc                                               680

SEQ ID NO: 79          moltype = DNA  length = 1940
FEATURE                Location/Qualifiers
source                 1..1940
                       mol_type = other DNA
                       organism = Coix lacryma-jobi
SEQUENCE: 79
agcagactcg cattatcgat ggagctctac caaactggcc ctaggcatta acctaccatg  60
gatcacatcg taaaaaaaaa accctaccat ggatcctatc tgttttcttt ttgccctgaa  120
agagtgaagt catcatcata tttaccatgg cgcgcgtagg agcgcttcgt cgaagaccca  180
taggggggcg gtactcgcac cgtggttgtt tcctgttatg taatatcgga tgggggagca  240
gtcggctagg ttggtcccat cggtactggt cgtcccctag tgcgctagat gcgcgatgtt  300
tgtcctcaaa aactcttttc ttcttaataa caatcatacg caaatttttt gcgtattcga  360
gaaaaaaaga agattctatc tgtttttttt ttgaaatggc tccaatttat aggaggagcc  420
cgtttaacgg cgtcgacaaa tctaacggac accaaccagc gaatgagcga acccaccagc  480
gccaagctag ccaagcgaag cagacggccg agacgctgac acccttgcct tggcgcggca  540
tctccgtcgc tggctcgctg gctctggccc cttcgcgaga gttccggtcc acctccacct  600
gtgtcggttt ccaactccgt tccgccttcg cgtgggactt gttccgttca tccgttggcg  660
gcatccggaa attgcgtggc gtagagcacg gggccctcct ctcacacggc acggaaccgt  720
cacgagctca cggcaccggc agcacggcgg ggattccttc cccaccaccg ctccttccct  780
ttcccttcct cgcccgccat cataaatagc caccctccc agcttccttc gccacatcct  840
ctcatcatct tctctcgtgt agcacgcgca gcccgatccc caatcccctc tcctcgcgag  900
cctcgtcgat ccctcgcttc aaggtatggc tatcgtcctt cctctctctc tctttacctt  960
atctagatcg gcgatccatg gttagggcct gctagttctc cgttcgtgtt tgtcgatggc  1020
tgtgaggcac aatagatccg tcggcgttat gatggttagc ctgtcatgct cttgcgatct  1080
gtggttcctt taggaaaggc attaatttaa tccctgatgg ttcgagatcg gtgatccatg  1140
gttagtaccc taagctgtgg agtcgggttt agatccgcgc tgttcgtagg cgatctgttc  1200
tgattgttaa cttgtcagta cctgcgaatc ctcggtggtt ctagctggtt cggagatcag  1260
```

```
atcgattcca ttatctgcta tacatcttgt ttcgttgcct aggctccgtt taatctatcc  1320
atcgtatgat gttagccttt gatatgattc gatcgtgcta gctatgtcct gtggacttaa  1380
ttgtcaggtc ctaattttta ggaagactgt tccaaaccat ctgctggatt tattaaattt  1440
ggatctggat gtgtcacata caccttcata attaaaatgg atggaaatat ctcttatctt  1500
ttagatatgg ataggcattt atatgatgct gtgagtttta ctagtacttt cttagaatat  1560
atgtactttt ttagacggaa tattgatatg tatacatgtg tagatacatg aagcaacatg  1620
ctgctgtagt ctaataattc ctgttcatct aataatcaag tatgtatatg ttctgtgtgt  1680
tttattggta tttgattaga tatatacatg cttagataca tacatgaagc agcatgctgc  1740
tacagtttaa tcattattgt ttatccaata aacaaacatg ctttttaatt tatcttgata  1800
tgcttggatg acggaatatg cagagatttt aagtacccag catcatgagc atgcatgacc  1860
ctgcgttagt atgctgttta tttgcttgag actctttctt ttgtagatac tcaccctgtt  1920
ttctggtgat cctactgcag                                              1940

SEQ ID NO: 80          moltype = DNA  length = 837
FEATURE                Location/Qualifiers
source                 1..837
                       mol_type = other DNA
                       organism = Coix lacryma-jobi
SEQUENCE: 80
agcagactcg cattatcgat ggagctctac caaactggcc ctaggcatta acctaccatg  60
gatcacatcg taaaaaaaaa accctaccat ggatcctatc tgttttcttt ttgccctgaa  120
agagtgaagt catcatcata tttaccatgg cgcgcgtagg agcgcttcgt cgaagaccca  180
taggggggcg gtactcgcac cgtggttgtt tcctgttatg taatatcgga tgggggagca  240
gtcggctagg ttggtcccat cggtactggt cgtcccctag tgcgctagat gcgcgatgtt  300
tgtcctcaaa aactcttttc ttcttaataa caatcatacg caaatttttt gcgtattcga  360
gaaaaaaaga agattctatc tgtttttttt ttgaaatggc tccaatttat aggaggagcc  420
cgtttaacgg cgtcgacaaa tctaacggac accaaccagc gaatgagcga acccaccagc  480
gccaagctag ccaagcgaag cagacggccg agacgctgac acccttgcct tggcgcggca  540
tctccgtcgc tggctcgctg gctctggccc cttcgcgaga gttccggtcc acctccacct  600
gtgtcggttt ccaactccgt tccgccttcg cgtgggactt gttccgttca tccgttggcg  660
gcatccggaa attgcgtggc gtagagcacg gggccctcct ctcacacggc acggaaccgt  720
cacgagctca cggcaccggc agcacggcgg ggattccttc cccaccaccg ctccttccct  780
ttcccttcct cgcccgccat cataaatagc cacccctccc agcttccttc gccacat     837

SEQ ID NO: 81          moltype = DNA  length = 86
FEATURE                Location/Qualifiers
source                 1..86
                       mol_type = other DNA
                       organism = Coix lacryma-jobi
SEQUENCE: 81
cctctcatca tcttctctcg tgtagcacgc gcagcccgat ccccaatccc ctctcctcgc  60
gagcctcgtc gatccctcgc ttcaag                                       86

SEQ ID NO: 82          moltype = DNA  length = 1017
FEATURE                Location/Qualifiers
source                 1..1017
                       mol_type = other DNA
                       organism = Coix lacryma-jobi
SEQUENCE: 82
gtatggctat cgtccttcct ctctctctct ttaccttatc tagatcggcg atccatggtt  60
agggcctgct agttctccgt tcgtgtttgt cgatggctgt gaggcacaat agatccgtcg  120
gcgttatgat ggttagcctg tcatgctctt gcgatctgtg gttcctttag gaaaggcatt  180
aatttaatcc ctgatggttc gagatcggtg atccatggtt agtaccctaa gctgtggagt  240
cgggtttaga tccgcgctgt tcgtaggcga tctgttctga ttgttaactt gtcagtacct  300
gcgaatcctc ggtggttcta gctggttcgg agatcagatc gattccatta tctgctatac  360
atcttgtttc gttgcctagg ctccgtttaa tctatccatc gtatgatgtt agcctttgat  420
atgattcgat cgtgctagct atgtcctgtg gacttaattg tcaggtccta atttttagga  480
agactgttcc aaaccatctg ctggatttat taaatttgga tctggatgtg tcacatacac  540
cttcataatt aaaatggatg gaaatatctc ttatctttta gatatggata ggcatttata  600
tgatgctgtg agttttacta gtactttctt agaatatatg tacttttttta gacggaatat  660
tgatatgtat acatgtgtag atacatgaag caacatgctg ctgtagtcta ataattcctg  720
ttcatctaat aatcaagtat gtatatgttc tgtgtgtttt attggtattt gattagatat  780
atacatgctt agatacatac atgaagcagc atgctgctac agtttaatca ttattgttta  840
tccaataaac aaacatgctt tttaatttat cttgatatgc ttggatgacg gaatatgcag  900
agattttaag tacccagcat catgagcatg catgaccctg cgttagtatg ctgtttattt  960
gcttgagact ctttcttttg tagatactca ccctgtttc tggtgatcct actgcag     1017

SEQ ID NO: 83          moltype = DNA  length = 1845
FEATURE                Location/Qualifiers
source                 1..1845
                       mol_type = other DNA
                       organism = Coix lacryma-jobi
SEQUENCE: 83
ctatctgttt tctttttgcc ctgaaagagt gaagtcatca tcatatttac catggcgcgc  60
gtaggagcgc ttcgtcgaag acccataggg gggcggtact cgcaccgtgg ttgtttcctg  120
ttatgtaata tcggatgggg gagcagtcgg ctaggttggt cccatcggta ctggtcgtcc  180
cctagtgcgc tagatgcgcg atgtttgtcc tcaaaaactc ttttcttctt aataacaatc  240
atacgcaaat tttttgcgta ttcgagaaaa aaagaagatt ctatctgttt ttttttgaa   300
atggctccaa tttataggag gagcccgttt aacggcgtcg acaaatctaa cggacaccaa  360
```

```
ccagcgaatg agcgaaccca ccagcgccaa gctagccaag cgaagcagac ggccgagacg  420
ctgacaccct tgccttggcg cggcatctcc gtcgctggct cgctggctct ggccccttcg  480
cgagagttcc ggtccacctc cacctgtgtc ggtttccaac tccgttccgc cttcgcgtgg  540
gacttgttcc gttcatccgt tggcggcatc cggaaattgc gtggcgtaga gcacggggcc  600
ctcctctcac acggcacgga accgtcacga gctcacggca ccggcagcac ggcggggatt  660
ccttccccac caccgctcct tccctttccc ttcctcgccc gccatcataa atagccaccc  720
ctcccagctt ccttcgccac atcctctcat catcttctct cgtgtagcac gcgcagcccg  780
atccccaatc ccctctcctc gcgagcctcg tcgatccctc gcttcaaggt atggctatcg  840
tccttcctct ctctctcttt accttatcta gatcggcgat ccatggttag ggcctgctag  900
ttctccgttc gtgtttgtcg atggctgtga ggcacaatag atccgtcggc gttatgatgg  960
ttagcctgtc atgctcttgc gatctgtggt tcctttagga aaggcattaa tttaatccct  1020
gatggttcga gatcggtgat ccatggttag taccctaagc tgtggagtcg ggtttagatc  1080
cgcgctgttc gtaggcgatc tgttctgatt gttaacttgt cagtacctgc gaatcctcgg  1140
tggttctagc tggttcggag atcagatcga ttccattatc tgctatacat cttgtttcgt  1200
tgcctaggct ccgtttaatc tatccatcgt atgatgttag cctttgatat gattcgatcg  1260
tgctagctat gtcctgtgga cttaattgtc aggtcctaat tttaggaag actgttccaa  1320
accatctgct ggatttatta aatttggatc tggatgtgtc acatacacct tcataattaa  1380
aatggatgga aatatctctt atcttttaga tatggatagg catttatatg atgctgtgag  1440
ttttactagt actttcttag aatatatgta ctttttttaga cggaatattg atatgtatac  1500
atgtgtagat acatgaagca acatgctgct gtagtctaat aattcctgtt catctaataa  1560
tcaagtatgt atatgttctg tgtgttttat tggtatttga ttagatatat acatgcttag  1620
atacatacat gaagcagcat gctgctacag tttaatcatt attgtttatc caataaacaa  1680
acatgctttt taatttatct tgatatgctt ggatgacgga atatgcagag attttaagta  1740
cccagcatca tgagcatgca tgaccctgcg ttagtatgct gtttatttgc ttgagactct  1800
ttcttttgta gatactcacc ctgttttctg gtgatcctac tgcag                  1845
```

```
SEQ ID NO: 84          moltype = DNA  length = 742
FEATURE                Location/Qualifiers
source                 1..742
                       mol_type = other DNA
                       organism = Coix lacryma-jobi
SEQUENCE: 84
ctatctgttt tctttttgcc ctgaaagagt gaagtcatca tcatatttac catggcgcgc  60
gtaggagcgc ttcgtcgaag acccataggg gggcggtact cgcaccgtgg ttgtttcctg  120
ttatgtaata tcggatgggg gagcagtcgg ctaggttggt cccatcggta ctggtcgtcc  180
cctagtgcgc tagatgcgcg atgtttgtcc tcaaaaactc ttttcttctt aataacaatc  240
atacgcaaat tttttgcgta ttcgagaaaa aaagaagatt ctatctgttt ttttttgaa  300
atggctccaa tttataggag gagcccgttt aacggcgtcg acaaatctaa cggacaccaa  360
ccagcgaatg agcgaaccca ccagcgccaa gctagccaag cgaagcagac ggccgagacg  420
ctgacaccct tgccttggcg cggcatctcc gtcgctggct cgctggctct ggccccttcg  480
cgagagttcc ggtccacctc cacctgtgtc ggtttccaac tccgttccgc cttcgcgtgg  540
gacttgttcc gttcatccgt tggcggcatc cggaaattgc gtggcgtaga gcacggggcc  600
ctcctctcac acggcacgga accgtcacga gctcacggca ccggcagcac ggcggggatt  660
ccttccccac caccgctcct tccctttccc ttcctcgccc gccatcataa atagccaccc  720
ctcccagctt ccttcgccac at                                           742
```

```
SEQ ID NO: 85          moltype = DNA  length = 1504
FEATURE                Location/Qualifiers
source                 1..1504
                       mol_type = other DNA
                       organism = Coix lacryma-jobi
SEQUENCE: 85
caaatctaac ggacaccaac cagcgaatga gcgaacccac cagcgccaag ctagccaagc  60
gaagcagacg gccgagacgc tgacaccctt gccttggcgc ggcatctccg tcgctggctc  120
gctggctctg gccccttcgc gagagttccg gtccacctcc acctgtgtcg gtttccaact  180
ccgttccgcc ttcgcgtggg acttgttccg ttcatccgtt ggcggcatcc ggaaattgcg  240
tggcgtagag cacggggccc tcctctcaca cggcacggaa ccgtcacgag ctcacggcac  300
cggcagcacg gcggggattc cttccccacc accgctcctt ccctttccct tcctcgcccg  360
ccatcataaa tagccacccc tcccagcttc cttcgccaca tcctctcatc atcttctctc  420
gtgtagcacg cgcagcccga tccccaatcc cctctcctcg cgagcctcgt cgatccctcg  480
cttcaaggta tggctatcgt ccttcctctc tctctcttta ccttatctag atcggcgatc  540
catggttagg gcctgctagt tctccgttcg tgtttgtcga tggctgtgag gcacaataga  600
tccgtcggcg ttatgatggt tagcctgtca tgctcttgcg atctgtggtt cctttaggaa  660
aggcattaat ttaatccctg atggttcgag atcggtgatc catggttagt accctaagct  720
gtggagtcgg gtttagatcc gcgctgttcg taggcgatct gttctgattg ttaacttgtc  780
agtacctgcg aatcctcggt ggttctagct ggttcggaga tcagatcgat tccattatct  840
gctatacatc ttgtttcgtt gcctaggctc cgtttaatct atccatcgta tgatgttagc  900
ctttgatatg attcgatcgt gctagctatg tcctgtggac ttaattgtca ggtcctaatt  960
tttaggaaga ctgttccaaa ccatctgctg gatttattaa atttggatct ggatgtgtca  1020
catacacctt cataattaaa atggatggaa atatctctta tcttttagat atggataggc  1080
atttatatga tgctgtgagt tttactagta ctttcttaga atatatgtac ttttttagac  1140
ggaatattga tatgtataca tgtgtagata catgaagcaa catgctgctg tagtctaata  1200
attcctgttc atctaataat caagtatgta tatgttctgt gtgttttatt ggtatttgat  1260
tagatatata catgcttaga tacatacatg aagcagcatg ctgctacagt ttaatcatta  1320
ttgtttatcc aataaacaaa catgcttttt aatttatctt gatatgcttg gatgacggaa  1380
tatgcagaga ttttaagtac ccagcatcat gagcatgcat gaccctgcgt tagtatgctg  1440
tttatttgct tgagactctt tcttttgtag atactcaccc tgttttctgg tgatcctact  1500
gcag                                                               1504
```

```
SEQ ID NO: 86          moltype = DNA  length = 401
FEATURE                Location/Qualifiers
source                 1..401
                       mol_type = other DNA
                       organism = Coix lacryma-jobi
SEQUENCE: 86
caaatctaac ggacaccaac cagcgaatga gcgaacccac cagcgccaag ctagccaagc  60
gaagcagacg gccgagacgc tgacaccctt gccttggcgc ggcatctccg tcgctggctc  120
gctggctctg gccccttcgc gagagttccg gtccacctcc acctgtgtcg gtttccaact  180
ccgttccgcc ttcgcgtggg acttgttccg ttcatccgtt ggcggcatcc ggaaattgcg  240
tggcgtagag cacggggccc tcctctcaca cggcacggaa ccgtcacgag ctcacggcac  300
cggcagcacg gcggggattc cttccccacc accgctcctt ccctttccct tcctcgcccg  360
ccatcataaa tagccacccc tcccagcttc cttcgccaca t                      401

SEQ ID NO: 87          moltype = DNA  length = 1157
FEATURE                Location/Qualifiers
source                 1..1157
                       mol_type = other DNA
                       organism = Coix lacryma-jobi
SEQUENCE: 87
ccttcctcgc ccgccatcat aaatagccac ccctcccagc ttccttcgcc acatcctctc  60
atcatcttct ctcgtgtagc acgcgcagcc cgatccccaa tcccctctcc tcgcgagcct  120
cgtcgatccc tcgcttcaag gtatggctat cgtccttcct ctctctctct ttaccttatc  180
tagatcggcg atccatggtt agggcctgct agttctccgt tcgtgtttgt cgatggctgt  240
gaggcacaat agatccgtcg gcgttatgat ggttagcctg tcatgctctt gcgatctgtg  300
gttcctttag gaaaggcatt aatttaatcc ctgatggttc gagatcggtg atccatggtt  360
agtaccctaa gctgtggagt cgggtttaga tccgcgctgt tcgtaggcga tctgttctga  420
ttgttaactt gtcagtacct gcgaatcctc ggtggttcta gctggttcgg agatcagatc  480
gattccatta tctgctatac atcttgtttc gttgcctagg ctccgtttaa tctatccatc  540
gtatgatgtt agcctttgat atgattcgat cgtgctagct atgtcctgtg gacttaattg  600
tcaggtccta atttttagga agactgttcc aaaccatctg ctggatttat taaatttgga  660
tctggatgtg tcacatacac cttcataatt aaaatggatg gaaatatctc ttatctttta  720
gatatggata ggcatttata tgatgctgtg agttttacta gtactttctt agaatatatg  780
tacttttttta gacggaatat tgatatgtat acatgtgtag atacatgaag caacatgctg  840
ctgtagtcta ataattcctg ttcatctaat aatcaagtat gtatatgttc tgtgtgtttt  900
attggtattt gattagatat atacatgctt agatacatac atgaagcagc atgctgctac  960
agtttaatca ttattgttta tccaataaac aaacatgctt tttaatttat cttgatatgc  1020
ttggatgacg gaatatgcag agattttaag tacccagcat catgagcatg catgaccctg  1080
cgttagtatg ctgtttattt gcttgagact ctttcttttg tagatactca ccctgttttc  1140
tggtgatcct actgcag                                                 1157

SEQ ID NO: 88          moltype = DNA  length = 54
FEATURE                Location/Qualifiers
source                 1..54
                       mol_type = other DNA
                       organism = Coix lacryma-jobi
SEQUENCE: 88
ccttcctcgc ccgccatcat aaatagccac ccctcccagc ttccttcgcc acat        54

SEQ ID NO: 89          moltype = DNA  length = 798
FEATURE                Location/Qualifiers
source                 1..798
                       mol_type = other DNA
                       organism = Coix lacryma-jobi
SEQUENCE: 89
agcagactcg cattatcgat ggagctctac caaactggcc ctaggcatta acctaccatg  60
gatcacatcg taaaaaaaaa accctaccat ggatcctatc tgttttcttt ttgccctgaa  120
agagtgaagt catcatcata tttaccatgg cgcgcgtagg agcgcttcgt cgaagaccca  180
taggggggcg gtactcgcac cgtggttgtt tcctgttatg taatatcgga tgggggagca  240
gtcggctagg ttggtcccat cggtactggt cgtcccctag tgcgctagat gcgcgatgtt  300
tgtcctcaaa aactcttttc ttcttaataa caatcatacg caaatttttt gcgtattcga  360
gaaaaaaaga agattctatc tgtttttttt ttgaaatggc tccaatttat aggaggagcc  420
cgtttaacgg cgtcgacaaa tctaacggac accaaccagc gaatgagcga acccaccagc  480
gccaagctag ccaagcgaag cagacggccg agacgctgac acccttgcct tggcgcggca  540
tctccgtcgc tggctcgctg gctctggccc cttcgcgaga gttccggtcc acctccacct  600
gtgtcggttt ccaactccgt tccgccttcg cgtgggactt gttccgttca tccgttggcg  660
gcatccggaa attgcgtggc gtagagcacg gggccctcct ctcacacggc acggaaccgt  720
cacgagctca cggcaccggc agcacggcgg ggattccttc cccaccaccg ctccttccct  780
ttcccttcct cgcccgcc                                                798

SEQ ID NO: 90          moltype = DNA  length = 3393
FEATURE                Location/Qualifiers
source                 1..3393
                       mol_type = other DNA
                       organism = Coix lacryma-jobi
SEQUENCE: 90
ggttctatac aacaccacac actgtgtgag tgtgtgacca gtggccaact tttgttcagt  60
tcaacgatcc tggcctttcc gggcacccaa tacactaatt aatctattgc agctaacctc  120
aaaagaaatg catttgcagt tgtctgtcct aatcaatcta ctagcagact cacattattg  180
```

```
atgtaggaaa taaaattcag cctgtgacgt ggatgcaaca actgcactgc acaggatacc  240
atcttagccg ttgtgtcaca atttgctttg ctaatgtttt gagaaaccca gctttgacaa  300
acgtaagatc gatgagggcc ttacgtttgg cacaatatgt attgtaatcc ggcacggcaa  360
gttagactcg gtagtgttta gccggcatct ttatgtttgg cacaatttaa tttaattcgg  420
catggtaggt tagactgcag cgtgagccgg tcattgcaag ttattatgac atgttagagc  480
atctccaaca agttggaaaa aatgacttgg tatatcatgg tatatcatga gttttagcaa  540
cttattaatt catttgacaa gtaaaaaaaa gatccctctt caacaatttg ctattccaac  600
tcgctaaaat aaaaaaaaat taggctcacc taggccgatc tgcgttgccg cgggagagga  660
gggtaaaaga ttttgcgcta ggagaggtgg aggaacaggg cgcgggagcc ggccacggtg  720
aaatcacggg atagcaacct cacccgcgcg cgcaaattta cgcgtgtggc atggaggaat  780
agaaagttgg aaaagatagc aagttcattt agggagttgt tggagaagaa tatttgtgct  840
tttaccaaat ttataagaat agcaagtgag aatagagagt tgttggagat gctcaacaaa  900
tatacacaat aaagtggtat aataagcggc aagttattat gacatatata agagcaagta  960
tacaataagg tgaactgtta tatcgatcga tttttttttg agcacatatc gatcgaattt  1020
attgtaagat agaaaagaga agatataaaa acttatagtg atgaacaata ataatataaa  1080
gattattttt aaactatgaa aacaataacc gaactactcg ctctcttcta attagtaaag  1140
taaaggcttc tcattgtata tatataaaaa aattcgttct gatttcttat attcaagacg  1200
gggagagtgc tgagtgctaa cttactagtc tacgagagaa gcttcaaatc aaacagtgta  1260
ctatagggct tacacaattt ttctgaggga agcgattgtc tgaaatgaac taaaaggctg  1320
agagctggaa aaagtagctt attctgattc tgtgaagtga ttctccatgc tgattttaaa  1380
agtttatgat aaaaaatcaa agagaataac tttcagccac agaatcactt ctctcagaga  1440
atcaacttat atggagaatc agaatcagat ggagctctac caaactggcc ctaggcatta  1500
acctaccatg gatcacatcg taaaaaaaaa accctaccat ggatcctatc tgttttcttt  1560
ttgccctgaa agagtgaagt catcatcata tttaccatgg cgcgcgtagg agcgcttcgt  1620
cgaagaccca tagggggggcg gtactcgcac cgtggttgtt tcctgttatg taatatcgga  1680
tgggggagca gtcggctagg ttggtcccat cggtactggt cgtcccctag tgcgctagat  1740
gcgcgatgtt tgtcctcaaa aactcttttc ttcttaataa caatcatacg caaatttttt  1800
gcgtattcga gaaaaaaaga agattctatc tgtttttttt ttgaaatggc tccaatttat  1860
aggaggagcc cgtttaacgg cgtcgacaaa tctaacggac accaaccagc gaatgagcga  1920
acccaccagc gccaagctag ccaagcgaag cagacggccg agacgctgac acccttgcct  1980
tggcgcggca tctccgtcgc tggctcgctg gctctggccc cttcgcgaga gttccggtcc  2040
acctccacct gtgtcggttt ccaactccgt tccgccttcg cgtgggactt gttccgttca  2100
tccgttggcg gcatccggaa attgcgtggc gtagagcacg gggccctcct ctcacacggc  2160
acggaaccgt cacgagctca cggcaccggc agcacggcgg ggattccttc cccaccaccg  2220
ctccttccct ttcccttcct cgcccgccat cataaatagc cacccctccc agcttccttc  2280
gccacatcct ctcatcatct tctctcgtgt agcacgcgca gcccgatccc caatcccctc  2340
tcctcgcgag cctcgtcgat ccctcgcttc aaggtatggc tatcgtcctt cctctctctc  2400
tctttacctt atctagatcg gcgatccatg gttagggcct gctagttctc cgttcgtgtt  2460
tgtcgatggc tgtgaggcac aatagatccg tcggcgttat gatggttagc ctgtcatgct  2520
cttgcgatct gtggttcctt taggaaaggc attaatttaa tccctgatgg ttcgagatcg  2580
gtgatccatg gttagtaccc taagctgtgg agtcgggttt agatccgcgc tgttcgtagg  2640
cgatctgttc tgattgttaa cttgtcagta cctgcgaatc ctcggtggtt ctagctggtt  2700
cggagatcag atcgattcca ttatctgcta tacatcttgt ttcgttgcct aggctccgtt  2760
taatctatcc atcgtatgat gttagccttt gatatgattc gatcgtgcta gctatgtcct  2820
gtggacttaa ttgtcaggtc ctaattttta ggaagactgt tccaaaccat ctgctggatt  2880
tattaaattt ggatctggat gtgtcacata caccttcata attaaaatgg atggaaatat  2940
ctcttatctt ttagatatgg ataggcattt atatgatgct gtgagtttta ctagtacttt  3000
cttagaatat atgtactttt ttagacggaa tattgatatg tatacatgtg tagatacatg  3060
aagcaacatg ctgctgtagt ctaataattc ctgttcatct aataatcaag tatgtatatg  3120
ttctgtgtgt tttattggta tttgattaga tatatacatg cttagataca tacatgaagc  3180
agcatgctgc tacagtttaa tcattattgt ttatccaata aacaaacatg ctttttaatt  3240
tatcttgata tgcttggatg acggaatatg cagagatttt aagtacccag catcatgagc  3300
atgcatgacc ctgcgttagt atgctgttta tttgcttgag actctttctt ttgtagatac  3360
tcaccctgtt ttctggtgat cctactgcag gtg                                3393

SEQ ID NO: 91          moltype = DNA  length = 2287
FEATURE                Location/Qualifiers
source                 1..2287
                       mol_type = other DNA
                       organism = Coix lacryma-jobi
SEQUENCE: 91
ggttctatac aacaccacac actgtgtgag tgtgtgacca gtggccaact tttgttcagt  60
tcaacgatcc tggcctttcc gggcacccaa tacactaatt aatctattgc agctaacctc  120
aaaagaaatg catttgcagt tgtctgtcct aatcaatcta ctagcagact cacattattg  180
atgtaggaaa taaaattcag cctgtgacgt ggatgcaaca actgcactgc acaggatacc  240
atcttagccg ttgtgtcaca atttgctttg ctaatgtttt gagaaaccca gctttgacaa  300
acgtaagatc gatgagggcc ttacgtttgg cacaatatgt attgtaatcc ggcacggcaa  360
gttagactcg gtagtgttta gccggcatct ttatgtttgg cacaatttaa tttaattcgg  420
catggtaggt tagactgcag cgtgagccgg tcattgcaag ttattatgac atgttagagc  480
atctccaaca agttggaaaa aatgacttgg tatatcatgg tatatcatga gttttagcaa  540
cttattaatt catttgacaa gtaaaaaaaa gatccctctt caacaatttg ctattccaac  600
tcgctaaaat aaaaaaaaat taggctcacc taggccgatc tgcgttgccg cgggagagga  660
gggtaaaaga ttttgcgcta ggagaggtgg aggaacaggg cgcgggagcc ggccacggtg  720
aaatcacggg atagcaacct cacccgcgcg cgcaaattta cgcgtgtggc atggaggaat  780
agaaagttgg aaaagatagc aagttcattt agggagttgt tggagaagaa tatttgtgct  840
tttaccaaat ttataagaat agcaagtgag aatagagagt tgttggagat gctcaacaaa  900
tatacacaat aaagtggtat aataagcggc aagttattat gacatatata agagcaagta  960
tacaataagg tgaactgtta tatcgatcga tttttttttg agcacatatc gatcgaattt  1020
attgtaagat agaaaagaga agatataaaa acttatagtg atgaacaata ataatataaa  1080
```

```
gattatttttt aaactatgaa aacaataacc gaactactcg ctctcttcta attagtaaag  1140
taaaggcttc tcattgtata tatataaaaa aattcgttct gatttcttat attcaagacg  1200
gggagagtgc tgagtgctaa cttactagtc tacgagagaa gcttcaaatc aaacagtgta  1260
ctatagggct tacacaattt ttctgaggga agcgattgtc tgaaatgaac taaaaggctg  1320
agagctggaa aaagtagctt attctgattc tgtgaagtga ttctccatgc tgattttaaa  1380
agtttatgat aaaaaatcaa agagaataac tttcagccac agaatcactt ctctcagaga  1440
atcaacttat atggagaatc agaatcagat ggagctctac caaactggcc ctaggcatta  1500
acctaccatg gatcacatcg taaaaaaaaa accctaccat ggatcctatc tgttttcttt  1560
ttgccctgaa agagtgaagt catcatcata tttaccatgg cgcgcgtagg agcgcttcgt  1620
cgaagaccca tagggggcg gtactcgcac cgtggttgtt tcctgttatg taatatcgga  1680
tgggggagca gtcggctagg ttggtcccat cggtactggt cgtcccctag tgcgctagat  1740
gcgcgatgtt tgtcctcaaa aactcttttc ttcttaataa caatcatacg caaatttttt  1800
gcgtattcga gaaaaaaaga agattctatc tgtttttttt ttgaaatggc tccaatttat  1860
aggaggagcc cgtttaacgg cgtcgacaaa tctaacggac accaaccagc gaatgagcga  1920
acccaccagc gccaagctag ccaagcgaag cagacggccg agacgctgac acccttgcct  1980
tggcgcggca tctccgtcgc tggctcgctg gctctggccc cttcgcgaga gttccggtcc  2040
acctccacct gtgtcggttt ccaactccgt tccgccttcg cgtgggactt gttccgttca  2100
tccgttggcg gcatccggaa attgcgtggc gtagagcacg gggccctcct ctcacacggc  2160
acggaaccgt cacgagctca cggcaccggc agcacggcgg ggattccttc cccaccaccg  2220
ctccttccct ttcccttcct cgcccgccat cataaatagc caccccctccc agcttccttc  2280
gccacat                                                             2287
```

```
SEQ ID NO: 92          moltype = DNA  length = 1020
FEATURE                Location/Qualifiers
source                 1..1020
                       mol_type = other DNA
                       organism = Coix lacryma-jobi
SEQUENCE: 92
gtatggctat cgtccttcct ctctctctct ttaccttatc tagatcggcg atccatggtt  60
agggcctgct agttctccgt tcgtgtttgt cgatggctgt gaggcacaat agatccgtcg  120
gcgttatgat ggttagcctg tcatgctctt gcgatctgtg gttcctttag gaaaggcatt  180
aatttaatcc ctgatggttc gagatcggtg atccatggtt agtaccctaa gctgtggagt  240
cgggtttaga tccgcgctgt tcgtaggcga tctgttctga ttgttaactt gtcagtacct  300
gcgaatcctc ggtggttcta gctggttcgg agatcagatc gattccatta tctgctatac  360
atcttgtttc gttgcctagg ctccgtttaa tctatccatc gtatgatgtt agcctttgat  420
atgattcgat cgtgctagct atgtcctgtg gacttaattg tcaggtccta atttttagga  480
agactgttcc aaaccatctg ctggatttat taaatttgga tctggatgtg tcacatacac  540
cttcataatt aaaatggatg gaaatatctc ttatctttta gatatggata ggcatttata  600
tgatgctgtg agttttacta gtactttctt agaatatatg tacttttttta gacggaatat  660
tgatatgtat acatgtgtag atacatgaag caacatgctg ctgtagtcta ataattcctg  720
ttcatctaat aatcaagtat gtatatgttc tgtgtgtttt attggtattt gattagatat  780
atacatgctt agatacatac atgaagcagc atgctgctac agtttaatca ttattgttta  840
tccaataaac aaacatgctt tttaatttat cttgatatgc ttggatgacg gaatatgcag  900
agattttaag tacccagcat catgagcatg catgaccctg cgttagtatg ctgtttattt  960
gcttgagact ctttcttttg tagatactca ccctgttttc tggtgatcct actgcaggtg  1020
```

```
SEQ ID NO: 93          moltype = DNA  length = 3393
FEATURE                Location/Qualifiers
source                 1..3393
                       mol_type = other DNA
                       organism = Coix lacryma-jobi
SEQUENCE: 93
ggttctatac aacaccacac actgtgtgag tgtgtgacca gtggccaact tttgttcagt  60
tcaacgatcc tggcctttcc gggcacccaa tacactaatt aatctattgc agctaacctc  120
aaaagaaatg catttgcagt tgtctgtcct aatcaatcta ctagcagact cacattattg  180
atgtaggaaa taaaattcag cctgtgacgt ggatgcaaca actgcactgc acaggatacc  240
atcttagccg ttgtgtcaca atttgctttg ctaatgtttt gagaaaccca gctttgacaa  300
acgtaagatc gatgagggcc ttacgtttgg cacaatatgt attgtaatcc ggcacggcaa  360
gttagactcg gtagtgttta gccggcatct ttatgtttgg cacaatttaa tttaattcgg  420
catggtaggt tagactgcag cgtgagccgg tcattgcaag ttattatgac atgttagagc  480
atctccaaca agttggaaaa aatgacttgg tatatcatgg tatatcatga gttttagcaa  540
cttattaatt catttgacaa gtaaaaaaaa gatccctctt caacaatttg ctattccaac  600
tcgctaaaat aaaaaaaaat taggctcacc taggccgatc tgcgttgccg cgggagagga  660
gggtaaaaga ttttgcgcta ggagaggtgg aggaacaggg cgcgggagcc ggccacggtg  720
aaatcacggg atagcaacct cacccgcgcg cgcaaattta cgcgtgtggc atggaggaat  780
agaaagttgg aaaagatagc aagttcattt agggagttgt tggagaagaa tatttgtgct  840
tttaccaaat ttataagaat agcaagtgag aatagagagt tgttggagat gctcaacaaa  900
tatacacaat aaagtggtat aataagcggc aagttattat gacatatata agagcaagta  960
tacaataagg tgaactgtta tatcgatcga tttttttttg agcacatatc gatcgaattt  1020
attgtaagat agaaaagaga agatataaaa acttatagtg atgaacaata ataatataaa  1080
gattatttttt aaactatgaa aacaataacc gaactactcg ctctcttcta attagtaaag  1140
taaaggcttc tcattgtata tatataaaaa aattcgttct gatttcttat attcaagacg  1200
gggagagtgc tgagtgctaa cttactagtc tacgagagaa gcttcaaatc aaacagtgta  1260
ctatagggct tacacaattt ttctgaggga agcgattgtc tgaaatgaac taaaaggctg  1320
agagctggaa aaagtagctt attctgattc tgtgaagtga ttctccatgc tgattttaaa  1380
agtttatgat aaaaaatcaa agagaataac tttcagccac agaatcactt ctctcagaga  1440
atcaacttat atggagaatc agaatcagat ggagctctac caaactggcc ctaggcatta  1500
acctaccatg gatcacatcg taaaaaaaaa accctaccat ggatcctatc tgttttcttt  1560
ttgccctgaa agagtgaagt catcatcata tttaccatgg cgcgcgtagg agcgcttcgt  1620
```

```
cgaagaccca taggggggcg gtactcgcac cgtggttgtt tcctgttatg taatatcgga  1680
tgggggagca gtcggctagg ttggtcccat cggtactggt cgtcccctag tgcgctagat  1740
gcgcgatgtt tgtcctcaaa aactcttttc ttcttaataa caatcatacg caaatttttt  1800
gcgtattcga gaaaaaaaga agattctatc tgtttttttt ttgaaatggc tccaatttat  1860
aggaggagcc cgtttaacgg cgtcgacaaa tctaacggac accaaccagc gaatgagcga  1920
acccaccagc gccaagctag ccaagcgaag cagacggccg agacgctgac acccttgcct  1980
tggcgcggca tctccgtcgc tggctcgctg gctctggccc cttcgcgaga gttccggtcc  2040
acctccacct gtgtcggttt ccaactccgt tccgccttcg cgtgggactt gttccgttca  2100
tccgttggcg gcatccggaa attgcgtggc gtagagcacg gggccctcct ctcacacggc  2160
acggaaccgt cacgagctca cggcaccggc agcacggcgg ggattccttc cccaccaccg  2220
ctccttccct ttcccttcct cgcccgccat cataaatagc caccccctccc agcttccttc  2280
gccacatcct ctcatcatct tctctcgtgt agcacgcgca gcccgatccc caatcccctc  2340
tcctcgcgag cctcgtcgat ccctcgcttc aaggtatggc tatcgtcctt cctctctctc  2400
tctttacctt atctagatcg gcgatccatg gttagggcct gctagttctc cgttcgtgtt  2460
tgtcgatggc tgtgaggcac aatagatccg tcggcgttat gatggttagc ctgtcatgct  2520
cttgcgatct gtggttcctt taggaaaggc attaatttaa tccctgatgg ttcgagatcg  2580
gtgatccatg gttagtaccc taagctgtgg agtcgggttt agatccgcgc tgttcgtagg  2640
cgatctgttc tgattgttaa cttgtcagta cctgcgaatc ctcggtggtt ctagctggtt  2700
cggagatcag atcgattcca ttatctgcta tacatcttgt ttcgttgcct aggctccgtt  2760
taatctatcc atcgtatgat gttagccttt gatatgattc gatcgtgcta gctatgtcct  2820
gtggacttaa ttgtcaggtc ctaattttta ggaagactgt tccaaaccat ctgctggatt  2880
tattaaattt ggatctggat gtgtcacata caccttcata attaaaatgg atggaaatat  2940
ctcttatctt ttagatatgg ataggcattt atatgatgct gtgagtttta ctagtacttt  3000
cttagaatat atgtactttt ttagacggaa tattgatatg tatacatgtg tagatacatg  3060
aagcaacatg ctgctgtagt ctaataattc ctgttcatct aataatcaag tatgtatatg  3120
ttctgtgtgt tttattggta tttgattaga tatatacatg cttagataca tacatgaagc  3180
agcatgctgc tacagtttaa tcattattgt ttatccaata aacaaacatg ctttttaatt  3240
tatcttgata tgcttggatg acggaatatg cagagatttt aagtacccag catcatgagc  3300
atgcatgacc ctgcgttagt atgctgttta tttgcttgag actctttctt ttgtagatac  3360
tcaccctgtt ttctggtgat cctactgcag gtc                               3393
```

```
SEQ ID NO: 94           moltype = DNA  length = 1020
FEATURE                 Location/Qualifiers
source                  1..1020
                        mol_type = other DNA
                        organism = Coix lacryma-jobi
SEQUENCE: 94
gtatggctat cgtccttcct ctctctctct ttaccttatc tagatcggcg atccatggtt  60
agggcctgct agttctccgt tcgtgtttgt cgatggctgt gaggcacaat agatccgtcg  120
gcgttatgat ggttagcctg tcatgctctt gcgatctgtg gttcctttag gaaaggcatt  180
aatttaatcc ctgatggttc gagatcggtg atccatggtt agtaccctaa gctgtggagt  240
cgggtttaga tccgcgctgt tcgtaggcga tctgttctga ttgttaactt gtcagtacct  300
gcgaatcctc ggtggttcta gctggttcgg agatcagatc gattccatta tctgctatac  360
atcttgtttc gttgcctagg ctccgtttaa tctatccatc gtatgatgtt agcctttgat  420
atgattcgat cgtgctagct atgtcctgtg gacttaattg tcaggtccta atttttagga  480
agactgttcc aaaccatctg ctggatttat taaatttgga tctggatgtg tcacatacac  540
cttcataatt aaaatggatg gaaatatctc ttatctttta gatatggata ggcatttata  600
tgatgctgtg agttttacta gtactttctt agaatatatg tacttttttta gacggaatat  660
tgatatgtat acatgtgtag atacatgaag caacatgctg ctgtagtcta ataattcctg  720
ttcatctaat aatcaagtat gtatatgttc tgtgtgtttt attggtattt gattagatat  780
atacatgctt agatacatac atgaagcagc atgctgctac agtttaatca ttattgttta  840
tccaataaac aaacatgctt tttaatttat cttgatatgc ttggatgacg gaatatgcag  900
agattttaag tacccagcat catgagcatg catgaccctg cgttagtatg ctgtttattt  960
gcttgagact ctttcttttg tagatactca ccctgttttc tggtgatcct actgcaggtc  1020
```

```
SEQ ID NO: 95           moltype = DNA  length = 2166
FEATURE                 Location/Qualifiers
source                  1..2166
                        mol_type = other DNA
                        organism = Coix lacryma-jobi
SEQUENCE: 95
gtctacgaga gaagcttcaa atcaaacagt gtactatagg gcttacacaa tttttctgag  60
ggaagcgatt gtctgaaatg aactaaaagg ctgagagctg gaaaaagtag cttattctga  120
ttctgtgaag tgattctcca tgctgatttt aaaagtttat gataaaaaat caaagagaat  180
aactttcagc cacagaatca cttctctcag agaatcaact tatatggaga atcagaatca  240
gatggagctc taccaaactg gccctaggca ttaacctacc atggatcaca tcgtaaaaaa  300
aaaaccctac catggatcct atctgttttc tttttgccct gaaagagtga agtcatcatc  360
atatttacca tggcgcgcgt aggagcgctt cgtcgaagac ccatagggggg gcggtactcg  420
caccgtggtt gtttcctgtt atgtaatatc ggatggggga gcagtcggct aggttggtcc  480
catcggtact ggtcgtcccc tagtgcgcta gatgcgcgat gtttgtcctc aaaaactctt  540
ttcttcttaa taacaatcat acgcaaattt tttgcgtatt cgagaaaaaa agaagattct  600
atctgttttt tttttgaaat ggctccaatt tataggagga gcccgtttaa cggcgtcgac  660
aaatctaacg gacaccaacc agcgaatgag cgaacccacc agcgccaagc tagccaagcg  720
aagcagacgg ccgagacgct gacacccttg ccttggcgcg gcatctccgt cgctggctcg  780
ctggctctgg ccccttcgcg agagttccgg tccacctcca cctgtgtcgg tttccaactc  840
cgttccgcct tcgcgtggga cttgttccgt tcatccgttg gcggcatccg gaaattgcgt  900
ggcgtagagc acggggccct cctctcacac ggcacggaac cgtcacgagc tcacggcacc  960
ggcagcacgg cggggattcc ttccccacca ccgctccttc cctttccctt cctcgcccgc  1020
catcataaat agccacccct cccagcttcc ttcgccacat cctctcatca tcttctctcg  1080
```

```
tgtagcacgc gcagcccgat ccccaatccc ctctcctcgc gagcctcgtc gatccctcgc  1140
ttcaaggtat ggctatcgtc cttcctctct ctctctttac cttatctaga tcggcgatcc  1200
atggttaggg cctgctagtt ctccgttcgt gtttgtcgat ggctgtgagg cacaatagat  1260
ccgtcggcgt tatgatggtt agcctgtcat gctcttgcga tctgtggttc ctttaggaaa  1320
ggcattaatt taatccctga tggttcgaga tcggtgatcc atggttagta ccctaagctg  1380
tggagtcggg tttagatccg cgctgttcgt aggcgatctg ttctgattgt taacttgtca  1440
gtacctgcga atcctcggtg gttctagctg gttcggagat cagatcgatt ccattatctg  1500
ctatacatct tgtttcgttg cctaggctcc gtttaatcta tccatcgtat gatgttagcc  1560
tttgatatga ttcgatcgtg ctagctatgt cctgtggact taattgtcag gtcctaattt  1620
ttaggaagac tgttccaaac catctgctgg atttattaaa tttggatctg gatgtgtcac  1680
atacaccttc ataattaaaa tggatggaaa tatctcttat cttttagata tggataggca  1740
tttatatgat gctgtgagtt ttactagtac tttcttagaa tatatgtact tttttagacg  1800
gaatattgat atgtatacat gtgtagatac atgaagcaac atgctgctgt agtctaataa  1860
ttcctgttca tctaataatc aagtatgtat atgttctgtg tgttttattg gtatttgatt  1920
agatatatac atgcttagat acatacatga agcagcatgc tgctacagtt taatcattat  1980
tgtttatcca ataaacaaac atgcttttta atttatcttg atatgcttgg atgacggaat  2040
atgcagagat tttaagtacc cagcatcatg agcatgcatg accctgcgtt agtatgctgt  2100
ttatttgctt gagactcttt cttttgtaga tactcaccct gttttctggt gatcctactg  2160
caggtg                                                             2166

SEQ ID NO: 96          moltype = DNA  length = 1060
FEATURE                Location/Qualifiers
source                 1..1060
                       mol_type = other DNA
                       organism = Coix lacryma-jobi
SEQUENCE: 96
gtctacgaga gaagcttcaa atcaaacagt gtactatagg gcttacacaa tttttctgag  60
ggaagcgatt gtctgaaatg aactaaaagg ctgagagctg gaaaaagtag cttattctga  120
ttctgtgaag tgattctcca tgctgatttt aaaagtttat gataaaaaat caaagagaat  180
aactttcagc cacagaatca cttctctcag agaatcaact tatatggaga atcagaatca  240
gatggagctc taccaaactg gccctaggca ttaacctacc atggatcaca tcgtaaaaaa  300
aaaaccctac catggatcct atctgttttc tttttgccct gaaagagtga agtcatcatc  360
atatttacca tggcgcgcgt aggagcgctt cgtcgaagac ccataggggg gcggtactcg  420
caccgtggtt gtttcctgtt atgtaatatc ggatggggga gcagtcggct aggttggtcc  480
catcggtact ggtcgtcccc tagtgcgcta gatgcgcgat gtttgtcctc aaaaactctt  540
ttcttcttaa taacaatcat acgcaaattt tttgcgtatt cgagaaaaaa agaagattct  600
atctgttttt tttttgaaat ggctccaatt tataggagga gcccgtttaa cggcgtcgac  660
aaatctaacg gacaccaacc agcgaatgag cgaacccacc agcgccaagc tagccaagcg  720
aagcagacgg ccgagacgct gacacccttg ccttggcgcg gcatctccgt cgctggctcg  780
ctggctctgg ccccttcgcg agagttccgg tccacctcca cctgtgtcgg tttccaactc  840
cgttccgcct tcgcgtggga cttgttccgt tcatccgttg gcggcatccg gaaattgcgt  900
ggcgtagagc acggggccct cctctcacac ggcacggaac cgtcacgagc tcacggcacc  960
ggcagcacgg cggggattcc ttccccacca ccgctccttc cctttccctt cctcgcccgc  1020
catcataaat agccacccct cccagcttcc ttcgccacat                        1060

SEQ ID NO: 97          moltype = DNA  length = 2166
FEATURE                Location/Qualifiers
source                 1..2166
                       mol_type = other DNA
                       organism = Coix lacryma-jobi
SEQUENCE: 97
gtctacgaga gaagcttcaa atcaaacagt gtactatagg gcttacacaa tttttctgag  60
ggaagcgatt gtctgaaatg aactaaaagg ctgagagctg gaaaaagtag cttattctga  120
ttctgtgaag tgattctcca tgctgatttt aaaagtttat gataaaaaat caaagagaat  180
aactttcagc cacagaatca cttctctcag agaatcaact tatatggaga atcagaatca  240
gatggagctc taccaaactg gccctaggca ttaacctacc atggatcaca tcgtaaaaaa  300
aaaaccctac catggatcct atctgttttc tttttgccct gaaagagtga agtcatcatc  360
atatttacca tggcgcgcgt aggagcgctt cgtcgaagac ccataggggg gcggtactcg  420
caccgtggtt gtttcctgtt atgtaatatc ggatggggga gcagtcggct aggttggtcc  480
catcggtact ggtcgtcccc tagtgcgcta gatgcgcgat gtttgtcctc aaaaactctt  540
ttcttcttaa taacaatcat acgcaaattt tttgcgtatt cgagaaaaaa agaagattct  600
atctgttttt tttttgaaat ggctccaatt tataggagga gcccgtttaa cggcgtcgac  660
aaatctaacg gacaccaacc agcgaatgag cgaacccacc agcgccaagc tagccaagcg  720
aagcagacgg ccgagacgct gacacccttg ccttggcgcg gcatctccgt cgctggctcg  780
ctggctctgg ccccttcgcg agagttccgg tccacctcca cctgtgtcgg tttccaactc  840
cgttccgcct tcgcgtggga cttgttccgt tcatccgttg gcggcatccg gaaattgcgt  900
ggcgtagagc acggggccct cctctcacac ggcacggaac cgtcacgagc tcacggcacc  960
ggcagcacgg cggggattcc ttccccacca ccgctccttc cctttccctt cctcgcccgc  1020
catcataaat agccacccct cccagcttcc ttcgccacat cctctcatca tcttctctcg  1080
tgtagcacgc gcagcccgat ccccaatccc ctctcctcgc gagcctcgtc gatccctcgc  1140
ttcaaggtat ggctatcgtc cttcctctct ctctctttac cttatctaga tcggcgatcc  1200
atggttaggg cctgctagtt ctccgttcgt gtttgtcgat ggctgtgagg cacaatagat  1260
ccgtcggcgt tatgatggtt agcctgtcat gctcttgcga tctgtggttc ctttaggaaa  1320
ggcattaatt taatccctga tggttcgaga tcggtgatcc atggttagta ccctaagctg  1380
tggagtcggg tttagatccg cgctgttcgt aggcgatctg ttctgattgt taacttgtca  1440
gtacctgcga atcctcggtg gttctagctg gttcggagat cagatcgatt ccattatctg  1500
ctatacatct tgtttcgttg cctaggctcc gtttaatcta tccatcgtat gatgttagcc  1560
tttgatatga ttcgatcgtg ctagctatgt cctgtggact taattgtcag gtcctaattt  1620
ttaggaagac tgttccaaac catctgctgg atttattaaa tttggatctg gatgtgtcac  1680
```

```
atacaccttc ataattaaaa tggatggaaa tatctcttat cttttagata tggataggca  1740
tttatatgat gctgtgagtt ttactagtac tttcttagaa tatatgtact tttttagacg  1800
gaatattgat atgtatacat gtgtagatac atgaagcaac atgctgctgt agtctaataa  1860
ttcctgttca tctaataatc aagtatgtat atgttctgtg tgttttattg gtatttgatt  1920
agatatatac atgcttagat acatacatga agcagcatgc tgctacagtt taatcattat  1980
tgtttatcca ataaacaaac atgcttttta atttatcttg atatgcttgg atgacggaat  2040
atgcagagat tttaagtacc cagcatcatg agcatgcatg accctgcgtt agtatgctgt  2100
ttatttgctt gagactcttt cttttgtaga tactcaccct gttttctggt gatcctactg  2160
caggtc                                                             2166

SEQ ID NO: 98          moltype = DNA  length = 1943
FEATURE                Location/Qualifiers
source                 1..1943
                       mol_type = other DNA
                       organism = Coix lacryma-jobi
SEQUENCE: 98
agcagactcg cattatcgat ggagctctac caaactggcc ctaggcatta acctaccatg  60
gatcacatcg taaaaaaaaa accctaccat ggatcctatc tgttttcttt ttgccctgaa  120
agagtgaagt catcatcata tttaccatgg cgcgcgtagg agcgcttcgt cgaagaccca  180
tagggggcg gtactcgcac cgtggttgtt tcctgttatg taatatcgga tgggggagca  240
gtcggctagg ttggtcccat cggtactggt cgtcccctag tgcgctagat gcgcgatgtt  300
tgtcctcaaa aactcttttc ttcttaataa caatcatacg caaatttttt gcgtattcga  360
gaaaaaaaga agattctatc tgtttttttt ttgaaatggc tccaatttat aggaggagcc  420
cgtttaacgg cgtcgacaaa tctaacggac accaaccagc gaatgagcga acccaccagc  480
gccaagctag ccaagcgaag cagacggccg agacgctgac acccttgcct tggcgcggca  540
tctccgtcgc tggctcgctg gctctggccc cttcgcgaga gttccggtcc acctccacct  600
gtgtcggttt ccaactccgt tccgccttcg cgtgggactt gttccgttca tccgttggcg  660
gcatccggaa attgcgtggc gtagagcacg gggccctcct ctcacacggc acggaaccgt  720
cacgagctca cggcaccggc agcacggcgg ggattccttc cccaccaccg ctccttccct  780
ttcccttcct cgcccgccat cataaatagc cacccctccc agcttccttc gccacatcct  840
ctcatcatct tctctcgtgt agcacgcgca gcccgatccc caatcccctc tcctcgcgag  900
cctcgtcgat ccctcgcttc aaggtatggc tatcgtcctt cctctctctc tctttacctt  960
atctagatcg gcgatccatg gttagggcct gctagttctc cgttcgtgtt tgtcgatggc  1020
tgtgaggcac aatagatccg tcggcgttat gatggttagc ctgtcatgct cttgcgatct  1080
gtggttcctt taggaaaggc attaatttaa tccctgatgg ttcgagatcg gtgatccatg  1140
gttagtaccc taagctgtgg agtcgggttt agatccgcgc tgttcgtagg cgatctgttc  1200
tgattgttaa cttgtcagta cctgcgaatc ctcggtggtt ctagctggtt cggagatcag  1260
atcgattcca ttatctgcta tacatcttgt ttcgttgcct aggctccgtt taatctatcc  1320
atcgtatgat gttagccttt gatatgattc gatcgtgcta gctatgtcct gtggacttaa  1380
ttgtcaggtc ctaattttta ggaagactgt tccaaaccat ctgctggatt tattaaattt  1440
ggatctggat gtgtcacata caccttcata attaaaatgg atggaaatat ctcttatctt  1500
ttagatatgg ataggcattt atatgatgct gtgagtttta ctagtacttt cttagaatat  1560
atgtactttt ttagacggaa tattgatatg tatacatgtg tagatacatg aagcaacatg  1620
ctgctgtagt ctaataattc ctgttcatct aataatcaag tatgtatatg ttctgtgtgt  1680
tttattggta tttgattaga tatatacatg cttagataca tacatgaagc agcatgctgc  1740
tacagtttaa tcattattgt ttatccaata aacaaacatg ctttttaatt tatcttgata  1800
tgcttggatg acggaatatg cagagatttt aagtacccag catcatgagc atgcatgacc  1860
ctgcgttagt atgctgttta tttgcttgag actctttctt ttgtagatac tcaccctgtt  1920
ttctggtgat cctactgcag gtc                                          1943

SEQ ID NO: 99          moltype = DNA  length = 1943
FEATURE                Location/Qualifiers
source                 1..1943
                       mol_type = other DNA
                       organism = Coix lacryma-jobi
SEQUENCE: 99
agcagactcg cattatcgat ggagctctac caaactggcc ctaggcatta acctaccatg  60
gatcacatcg taaaaaaaaa accctaccat ggatcctatc tgttttcttt ttgccctgaa  120
agagtgaagt catcatcata tttaccatgg cgcgcgtagg agcgcttcgt cgaagaccca  180
tagggggcg gtactcgcac cgtggttgtt tcctgttatg taatatcgga tgggggagca  240
gtcggctagg ttggtcccat cggtactggt cgtcccctag tgcgctagat gcgcgatgtt  300
tgtcctcaaa aactcttttc ttcttaataa caatcatacg caaatttttt gcgtattcga  360
gaaaaaaaga agattctatc tgtttttttt ttgaaatggc tccaatttat aggaggagcc  420
cgtttaacgg cgtcgacaaa tctaacggac accaaccagc gaatgagcga acccaccagc  480
gccaagctag ccaagcgaag cagacggccg agacgctgac acccttgcct tggcgcggca  540
tctccgtcgc tggctcgctg gctctggccc cttcgcgaga gttccggtcc acctccacct  600
gtgtcggttt ccaactccgt tccgccttcg cgtgggactt gttccgttca tccgttggcg  660
gcatccggaa attgcgtggc gtagagcacg gggccctcct ctcacacggc acggaaccgt  720
cacgagctca cggcaccggc agcacggcgg ggattccttc cccaccaccg ctccttccct  780
ttcccttcct cgcccgccat cataaatagc cacccctccc agcttccttc gccacatcct  840
ctcatcatct tctctcgtgt agcacgcgca gcccgatccc caatcccctc tcctcgcgag  900
cctcgtcgat ccctcgcttc aaggtatggc tatcgtcctt cctctctctc tctttacctt  960
atctagatcg gcgatccatg gttagggcct gctagttctc cgttcgtgtt tgtcgatggc  1020
tgtgaggcac aatagatccg tcggcgttat gatggttagc ctgtcatgct cttgcgatct  1080
gtggttcctt taggaaaggc attaatttaa tccctgatgg ttcgagatcg gtgatccatg  1140
gttagtaccc taagctgtgg agtcgggttt agatccgcgc tgttcgtagg cgatctgttc  1200
tgattgttaa cttgtcagta cctgcgaatc ctcggtggtt ctagctggtt cggagatcag  1260
atcgattcca ttatctgcta tacatcttgt ttcgttgcct aggctccgtt taatctatcc  1320
atcgtatgat gttagccttt gatatgattc gatcgtgcta gctatgtcct gtggacttaa  1380
```

```
ttgtcaggtc ctaattttta ggaagactgt tccaaaccat ctgctggatt tattaaattt  1440
ggatctggat gtgtcacata caccttcata attaaaatgg atggaaatat ctcttatctt  1500
ttagatatgg ataggcattt atatgatgct gtgagtttta ctagtacttt cttagaatat  1560
atgtactttt ttagacggaa tattgatatg tatacatgtg tagatacatg aagcaacatg  1620
ctgctgtagt ctaataattc ctgttcatct aataatcaag tatgtatatg ttctgtgtgt  1680
tttattggta tttgattaga tatatacatg cttagataca tacatgaagc agcatgctgc  1740
tacagtttaa tcattattgt ttatccaata aacaaacatg ctttttaatt tatcttgata  1800
tgcttggatg acggaatatg cagagatttt aagtacccag catcatgagc atgcatgacc  1860
ctgcgttagt atgctgttta tttgcttgag actctttctt ttgtagatac tcaccctgtt  1920
ttctggtgat cctactgcag gtg                                          1943

SEQ ID NO: 100          moltype = DNA  length = 1943
FEATURE                 Location/Qualifiers
source                  1..1943
                        mol_type = other DNA
                        organism = Coix lacryma-jobi
SEQUENCE: 100
agcagactcg cattatcgat ggagctctac caaactggcc ctaggcatta acctaccatg  60
gatcacatcg taaaaaaaaa accctaccat ggatcctatc tgttttcttt ttgccctgaa  120
agagtgaagt catcatcata tttaccatgg cgcgcgtagg agcgcttcgt cgaagaccca  180
taggggggcg gtactcgcac cgtggttgtt tcctgttatg taatatcgga tgggggagca  240
gtcggctagg ttggtcccat cggtactggt cgtcccctag tgcgctagat gcgcgatgtt  300
tgtcctcaaa aactcttttc ttcttaataa caatcatacg caaatttttt gcgtattcga  360
gaaaaaaaga agattctatc tgtttttttt ttgaaatggc tccaatttat aggaggagcc  420
cgtttaacgg cgtcgacaaa tctaacggac accaaccagc gaatgagcga acccaccagc  480
gccaagctag ccaagcgaag cagacggccg agacgctgac acccttgcct tggcgcggca  540
tctccgtcgc tggctcgctg gctctggccc cttcgcgaga gttccggtcc acctccacct  600
gtgtcggttt ccaactccgt tccgccttcg cgtgggactt gttccgttca tccgttggcg  660
gcatccggaa attgcgtggc gtagagcacg gggccctcct ctcacacggc acggaaccgt  720
cacgagctca cggcaccggc agcacggcgg ggattccttc cccaccaccg ctccttccct  780
ttcccttcct cgcccgccat cataaatagc cacccctccc agcttccttc gccacatcct  840
ctcatcatct tctctcgtgt agcacgcgca gcccgatccc caatcccctc tcctcgcgag  900
cctcgtcgat ccctcgcttc aaggtatggc tatcgtcctt cctctctctc tctttacctt  960
atctagatcg gcgatccatg gttagggcct gctagttctc cgttcgtgtt tgtcgatggc  1020
tgtgaggcac aatagatccg tcggcgttat gatggttagc ctgtcatgct cttgcgatct  1080
gtggttcctt taggaaaggc attaatttaa tccctgatgg ttcgagatcg gtgatccatg  1140
gttagtaccc taagctgtgg agtcgggttt agatccgcgc tgttcgtagg cgatctgttc  1200
tgattgttaa cttgtcagta cctgcgaatc ctcggtggtt ctagctggtt cggagatcag  1260
atcgattcca ttatctgcta tacatcttgt ttcgttgcct aggctccgtt taatctatcc  1320
atcgtatgat gttagccttt gatatgattc gatcgtgcta gctatgtcct gtggacttaa  1380
ttgtcaggtc ctaattttta ggaagactgt tccaaaccat ctgctggatt tattaaattt  1440
ggatctggat gtgtcacata caccttcata attaaaatgg atggaaatat ctcttatctt  1500
ttagatatgg ataggcattt atatgatgct gtgagtttta ctagtacttt cttagaatat  1560
atgtactttt ttagacggaa tattgatatg tatacatgtg tagatacatg aagcaacatg  1620
ctgctgtagt ctaataattc ctgttcatct aataatcaag tatgtatatg ttctgtgtgt  1680
tttattggta tttgattaga tatatacatg cttagataca tacatgaagc agcatgctgc  1740
tacagtttaa tcattattgt ttatccaata aacaaacatg ctttttaatt tatcttgata  1800
tgcttggatg acggaatatg cagagatttt aagtacccag catcatgagc atgcatgacc  1860
ctgcgttagt atgctgttta tttgcttgag actctttctt ttgtagatac tcaccctgtt  1920
ttctggtgat cctactgcag gcg                                          1943

SEQ ID NO: 101          moltype = DNA  length = 1020
FEATURE                 Location/Qualifiers
source                  1..1020
                        mol_type = other DNA
                        organism = Coix lacryma-jobi
SEQUENCE: 101
gtatggctat cgtccttcct ctctctctct ttaccttatc tagatcggcg atccatggtt  60
agggcctgct agttctccgt tcgtgtttgt cgatggctgt gaggcacaat agatccgtcg  120
gcgttatgat ggttagcctg tcatgctctt gcgatctgtg gttcctttag gaaaggcatt  180
aatttaatcc ctgatggttc gagatcggtg atccatggtt agtaccctaa gctgtggagt  240
cgggtttaga tccgcgctgt tcgtaggcga tctgttctga ttgttaactt gtcagtacct  300
gcgaatcctc ggtggttcta gctggttcgg agatcagatc gattccatta tctgctatac  360
atcttgtttc gttgcctagg ctccgtttaa tctatccatc gtatgatgtt agcctttgat  420
atgattcgat cgtgctagct atgtcctgtg gacttaattg tcaggtccta atttttagga  480
agactgttcc aaaccatctg ctggatttat taaatttgga tctggatgtg tcacatacac  540
cttcataatt aaaatggatg gaaatatctc ttatctttta gatatggata ggcatttata  600
tgatgctgtg agttttacta gtactttctt agaatatatg tacttttttta gacggaatat  660
tgatatgtat acatgtgtag atacatgaag caacatgctg ctgtagtcta ataattcctg  720
ttcatctaat aatcaagtat gtatatgttc tgtgtgtttt attggtattt gattagatat  780
atacatgctt agatacatac atgaagcagc atgctgctac agtttaatca ttattgttta  840
tccaataaac aaacatgctt tttaatttat cttgatatgc ttggatgacg gaatatgcag  900
agattttaag tacccagcat catgagcatg catgaccctg cgttagtatg ctgtttattt  960
gcttgagact ctttcttttg tagatactca ccctgttttc tggtgatcct actgcaggcg  1020

SEQ ID NO: 102          moltype = DNA  length = 1943
FEATURE                 Location/Qualifiers
source                  1..1943
                        mol_type = other DNA
```

```
                         organism = Coix lacryma-jobi
SEQUENCE: 102
agcagactcg cattatcgat ggagctctac caaactggcc ctaggcatta acctaccatg  60
gatcacatcg taaaaaaaaa accctaccat ggatcctatc tgttttcttt ttgccctgaa  120
agagtgaagt catcatcata tttaccatgg cgcgcgtagg agcgcttcgt cgaagaccca  180
taggggggcg gtactcgcac cgtggttgtt tcctgttatg taatatcgga tgggggagca  240
gtcggctagg ttggtcccat cggtactggt cgtcccctag tgcgctagat gcgcgatgtt  300
tgtcctcaaa aactcttttc ttcttaataa caatcatacg caaatttttt gcgtattcga  360
gaaaaaaaga agattctatc tgtttttttt ttgaaatggc tccaatttat aggaggagcc  420
cgtttaacgg cgtcgacaaa tctaacggac accaaccagc gaatgagcga acccaccagc  480
gccaagctag ccaagcgaag cagacggccg agacgctgac acccttgcct tggcgcggca  540
tctccgtcgc tggctcgctg gctctggccc cttcgcgaga gttccggtcc acctccacct  600
gtgtcggttt ccaactccgt tccgccttcg cgtgggactt gttccgttca tccgttggcg  660
gcatccggaa attgcgtggc gtagagcacg gggccctcct ctcacacggc acggaaccgt  720
cacgagctca cggcaccggc agcacggcgg ggattccttc cccaccaccg ctccttccct  780
ttcccttcct cgcccgccat cataaatagc cacccctccc agcttccttc gccacatcct  840
ctcatcatct tctctcgtgt agcacgcgca gcccgatccc caatcccctc tcctcgcgag  900
cctcgtcgat ccctcgcttc aaggtatggc tatcgtcctt cctctctctc tctttacctt  960
atctagatcg gcgatccatg gttagggcct gctagttctc cgttcgtgtt tgtcgatggc  1020
tgtgaggcac aatagatccg tcggcgttat gatggttagc ctgtcatgct cttgcgatct  1080
gtggttcctt taggaaaggc attaatttaa tccctgatgg ttcgagatcg gtgatccatg  1140
gttagtaccc taagctgtgg agtcgggttt agatccgcgc tgttcgtagg cgatctgttc  1200
tgattgttaa cttgtcagta cctgcgaatc ctcggtggtt ctagctggtt cggagatcag  1260
atcgattcca ttatctgcta tacatcttgt ttcgttgcct aggctccgtt taatctatcc  1320
atcgtatgat gttagccttt gatatgattc gatcgtgcta gctatgtcct gtggacttaa  1380
ttgtcaggtc ctaattttta ggaagactgt tccaaaccat ctgctggatt tattaaattt  1440
ggatctggat gtgtcacata caccttcata attaaaatgg atggaaatat ctcttatctt  1500
ttagatatgg ataggcattt atatgatgct gtgagtttta ctagtacttt cttagaatat  1560
atgtactttt ttagacggaa tattgatatg tatacatgtg tagatacatg aagcaacatg  1620
ctgctgtagt ctaataattc ctgttcatct aataatcaag tatgtatatg ttctgtgtgt  1680
tttattggta tttgattaga tatatacatg cttagataca tacatgaagc agcatgctgc  1740
tacagtttaa tcattattgt ttatccaata aacaaacatg ctttttaatt tatcttgata  1800
tgcttggatg acggaatatg cagagatttt aagtacccag catcatgagc atgcatgacc  1860
ctgcgttagt atgctgttta tttgcttgag actctttctt ttgtagatac tcaccctgtt  1920
ttctggtgat cctactgcag gac                                          1943

SEQ ID NO: 103           moltype = DNA  length = 1020
FEATURE                  Location/Qualifiers
source                   1..1020
                         mol_type = other DNA
                         organism = Coix lacryma-jobi
SEQUENCE: 103
gtatggctat cgtccttcct ctctctctct ttaccttatc tagatcggcg atccatggtt  60
agggcctgct agttctccgt tcgtgtttgt cgatggctgt gaggcacaat agatccgtcg  120
gcgttatgat ggttagcctg tcatgctctt gcgatctgtg gttcctttag gaaaggcatt  180
aatttaatcc ctgatggttc gagatcggtg atccatggtt agtaccctaa gctgtggagt  240
cgggtttaga tccgcgctgt tcgtaggcga tctgttctga ttgttaactt gtcagtacct  300
gcgaatcctc ggtggttcta gctggttcgg agatcagatc gattccatta tctgctatac  360
atcttgtttc gttgcctagg ctccgtttaa tctatccatc gtatgatgtt agcctttgat  420
atgattcgat cgtgctagct atgtcctgtg gacttaattg tcaggtccta atttttagga  480
agactgttcc aaaccatctg ctggatttat taaatttgga tctggatgtg tcacatacac  540
cttcataatt aaaatggatg gaaatatctc ttatctttta gatatggata ggcatttata  600
tgatgctgtg agttttacta gtactttctt agaatatatg tacttttttta gacggaatat  660
tgatatgtat acatgtgtag atacatgaag caacatgctg ctgtagtcta ataattcctg  720
ttcatctaat aatcaagtat gtatatgttc tgtgtgtttt attggtattt gattagatat  780
atacatgctt agatacatac atgaagcagc atgctgctac agtttaatca ttattgttta  840
tccaataaac aaacatgctt tttaatttat cttgatatgc ttggatgacg gaatatgcag  900
agattttaag tacccagcat catgagcatg catgaccctg cgttagtatg ctgtttattt  960
gcttgagact ctttcttttg tagatactca ccctgttttc tggtgatcct actgcaggac  1020

SEQ ID NO: 104           moltype = DNA  length = 1943
FEATURE                  Location/Qualifiers
source                   1..1943
                         mol_type = other DNA
                         organism = Coix lacryma-jobi
SEQUENCE: 104
agcagactcg cattatcgat ggagctctac caaactggcc ctaggcatta acctaccatg  60
gatcacatcg taaaaaaaaa accctaccat ggatcctatc tgttttcttt ttgccctgaa  120
agagtgaagt catcatcata tttaccatgg cgcgcgtagg agcgcttcgt cgaagaccca  180
taggggggcg gtactcgcac cgtggttgtt tcctgttatg taatatcgga tgggggagca  240
gtcggctagg ttggtcccat cggtactggt cgtcccctag tgcgctagat gcgcgatgtt  300
tgtcctcaaa aactcttttc ttcttaataa caatcatacg caaatttttt gcgtattcga  360
gaaaaaaaga agattctatc tgtttttttt ttgaaatggc tccaatttat aggaggagcc  420
cgtttaacgg cgtcgacaaa tctaacggac accaaccagc gaatgagcga acccaccagc  480
gccaagctag ccaagcgaag cagacggccg agacgctgac acccttgcct tggcgcggca  540
tctccgtcgc tggctcgctg gctctggccc cttcgcgaga gttccggtcc acctccacct  600
gtgtcggttt ccaactccgt tccgccttcg cgtgggactt gttccgttca tccgttggcg  660
gcatccggaa attgcgtggc gtagagcacg gggccctcct ctcacacggc acggaaccgt  720
cacgagctca cggcaccggc agcacggcgg ggattccttc cccaccaccg ctccttccct  780
```

```
ttcccttcct cgcccgccat cataaatagc cacccctccc agcttccttc gccacatcct  840
ctcatcatct tctctcgtgt agcacgcgca gcccgatccc caatcccctc tcctcgcgag  900
cctcgtcgat ccctcgcttc aaggtatggc tatcgtcctt cctctctctc tctttacctt  960
atctagatcg gcgatccatg gttagggcct gctagttctc cgttcgtgtt tgtcgatggc  1020
tgtgaggcac aatagatccg tcggcgttat gatggttagc ctgtcatgct cttgcgatct  1080
gtggttcctt taggaaaggc attaatttaa tccctgatgg ttcgagatcg gtgatccatg  1140
gttagtaccc taagctgtgg agtcgggttt agatccgcgc tgttcgtagg cgatctgttc  1200
tgattgttaa cttgtcagta cctgcgaatc ctcggtggtt ctagctggtt cggagatcag  1260
atcgattcca ttatctgcta tacatcttgt ttcgttgcct aggctccgtt taatctatcc  1320
atcgtatgat gttagccttt gatatgattc gatcgtgcta gctatgtcct gtggacttaa  1380
ttgtcaggtc ctaattttta ggaagactgt tccaaaccat ctgctggatt tattaaattt  1440
ggatctggat gtgtcacata caccttcata attaaaatgg atggaaatat ctcttatctt  1500
ttagatatgg ataggcattt atatgatgct gtgagtttta ctagtacttt cttagaatat  1560
atgtactttt ttagacggaa tattgatatg tatacatgtg tagatacatg aagcaacatg  1620
ctgctgtagt ctaataattc ctgttcatct aataatcaag tatgtatatg ttctgtgtgt  1680
tttattggta tttgattaga tatatacatg cttagataca tacatgaagc agcatgctgc  1740
tacagtttaa tcattattgt ttatccaata aacaaacatg ctttttaatt tatcttgata  1800
tgcttggatg acggaatatg cagagatttt aagtacccag catcatgagc atgcatgacc  1860
ctgcgttagt atgctgttta tttgcttgag actctttctt ttgtagatac tcaccctgtt  1920
ttctggtgat cctactgcag acc                                          1943
```

```
SEQ ID NO: 105          moltype = DNA  length = 1020
FEATURE                 Location/Qualifiers
source                  1..1020
                        mol_type = other DNA
                        organism = Coix lacryma-jobi
SEQUENCE: 105
gtatggctat cgtccttcct ctctctctct ttaccttatc tagatcggcg atccatggtt  60
agggcctgct agttctccgt tcgtgtttgt cgatggctgt gaggcacaat agatccgtcg  120
gcgttatgat ggttagcctg tcatgctctt gcgatctgtg gttcctttag gaaaggcatt  180
aatttaatcc ctgatggttc gagatcggtg atccatggtt agtaccctaa gctgtggagt  240
cgggtttaga tccgcgctgt tcgtaggcga tctgttctga ttgttaactt gtcagtacct  300
gcgaatcctc ggtggttcta gctggttcgg agatcagatc gattccatta tctgctatac  360
atcttgtttc gttgcctagg ctccgtttaa tctatccatc gtatgatgtt agcctttgat  420
atgattcgat cgtgctagct atgtcctgtg gacttaattg tcaggtccta atttttagga  480
agactgttcc aaaccatctg ctggatttat taaatttgga tctggatgtg tcacatacac  540
cttcataatt aaaatggatg gaaatatctc ttatctttta gatatggata ggcatttata  600
tgatgctgtg agttttacta gtactttctt agaatatatg tacttttta gacggaatat  660
tgatatgtat acatgtgtag atacatgaag caacatgctg ctgtagtcta ataattcctg  720
ttcatctaat aatcaagtat gtatatgttc tgtgtgtttt attggtattt gattagatat  780
atacatgctt agatacatac atgaagcagc atgctgctac agtttaatca ttattgttta  840
tccaataaac aaacatgctt tttaatttat cttgatatgc ttggatgacg gaatatgcag  900
agattttaag tacccagcat catgagcatg catgaccctg cgttagtatg ctgtttattt  960
gcttgagact ctttcttttg tagatactca ccctgttttc tggtgatcct actgcagacc  1020
```

```
SEQ ID NO: 106          moltype = DNA  length = 1943
FEATURE                 Location/Qualifiers
source                  1..1943
                        mol_type = other DNA
                        organism = Coix lacryma-jobi
SEQUENCE: 106
agcagactcg cattatcgat ggagctctac caaactggcc ctaggcatta acctaccatg  60
gatcacatcg taaaaaaaaa accctaccat ggatcctatc tgttttcttt ttgccctgaa  120
agagtgaagt catcatcata tttaccatgg cgcgcgtagg agcgcttcgt cgaagaccca  180
taggggggcg gtactcgcac cgtggttgtt tcctgttatg taatatcgga tgggggagca  240
gtcggctagg ttggtcccat cggtactggt cgtcccctag tgcgctagat gcgcgatgtt  300
tgtcctcaaa aactcttttc ttcttaataa caatcatacg caaatttttt gcgtattcga  360
gaaaaaaaga agattctatc tgtttttttt ttgaaatggc tccaatttat aggaggagcc  420
cgtttaacgg cgtcgacaaa tctaacggac accaaccagc gaatgagcga acccaccagc  480
gccaagctag ccaagcgaag cagacggccg agacgctgac acccttgcct tggcgcggca  540
tctccgtcgc tggctcgctg gctctggccc cttcgcgaga gttccggtcc acctccacct  600
gtgtcggttt ccaactccgt tccgccttcg cgtgggactt gttccgttca tccgttggcg  660
gcatccggaa attgcgtggc gtagagcacg gggccctcct ctcacacggc acggaaccgt  720
cacgagctca cggcaccggc agcacggcgg ggattccttc cccaccaccg ctccttccct  780
ttcccttcct cgcccgccat cataaatagc cacccctccc agcttccttc gccacatcct  840
ctcatcatct tctctcgtgt agcacgcgca gcccgatccc caatcccctc tcctcgcgag  900
cctcgtcgat ccctcgcttc aaggtatggc tatcgtcctt cctctctctc tctttacctt  960
atctagatcg gcgatccatg gttagggcct gctagttctc cgttcgtgtt tgtcgatggc  1020
tgtgaggcac aatagatccg tcggcgttat gatggttagc ctgtcatgct cttgcgatct  1080
gtggttcctt taggaaaggc attaatttaa tccctgatgg ttcgagatcg gtgatccatg  1140
gttagtaccc taagctgtgg agtcgggttt agatccgcgc tgttcgtagg cgatctgttc  1200
tgattgttaa cttgtcagta cctgcgaatc ctcggtggtt ctagctggtt cggagatcag  1260
atcgattcca ttatctgcta tacatcttgt ttcgttgcct aggctccgtt taatctatcc  1320
atcgtatgat gttagccttt gatatgattc gatcgtgcta gctatgtcct gtggacttaa  1380
ttgtcaggtc ctaattttta ggaagactgt tccaaaccat ctgctggatt tattaaattt  1440
ggatctggat gtgtcacata caccttcata attaaaatgg atggaaatat ctcttatctt  1500
ttagatatgg ataggcattt atatgatgct gtgagtttta ctagtacttt cttagaatat  1560
atgtactttt ttagacggaa tattgatatg tatacatgtg tagatacatg aagcaacatg  1620
ctgctgtagt ctaataattc ctgttcatct aataatcaag tatgtatatg ttctgtgtgt  1680
```

```
tttattggta tttgattaga tatatacatg cttagataca tacatgaagc agcatgctgc  1740
tacagtttaa tcattattgt ttatccaata aacaaacatg ctttttaatt tatcttgata  1800
tgcttggatg acggaatatg cagagatttt aagtacccag catcatgagc atgcatgacc  1860
ctgcgttagt atgctgttta tttgcttgag actctttctt ttgtagatac tcaccctgtt  1920
ttctggtgat cctactgcag ggg                                          1943

SEQ ID NO: 107         moltype = DNA  length = 1020
FEATURE                Location/Qualifiers
source                 1..1020
                       mol_type = other DNA
                       organism = Coix lacryma-jobi
SEQUENCE: 107
gtatggctat cgtccttcct ctctctctct ttaccttatc tagatcggcg atccatggtt  60
agggcctgct agttctccgt tcgtgtttgt cgatggctgt gaggcacaat agatccgtcg  120
gcgttatgat ggttagcctg tcatgctctt gcgatctgtg gttcctttag gaaaggcatt  180
aatttaatcc ctgatggttc gagatcggtg atccatggtt agtaccctaa gctgtggagt  240
cgggtttaga tccgcgctgt tcgtaggcga tctgttctga ttgttaactt gtcagtacct  300
gcgaatcctc ggtggttcta gctggttcgg agatcagatc gattccatta tctgctatac  360
atcttgtttc gttgcctagg ctccgtttaa tctatccatc gtatgatgtt agcctttgat  420
atgattcgat cgtgctagct atgtcctgtg gacttaattg tcaggtccta atttttagga  480
agactgttcc aaaccatctg ctggatttat taaatttgga tctggatgtg tcacatacac  540
cttcataatt aaaatggatg gaaatatctc ttatctttta gatatggata ggcatttata  600
tgatgctgtg agttttacta gtactttctt agaatatatg tacttttttta gacggaatat  660
tgatatgtat acatgtgtag atacatgaag caacatgctg ctgtagtcta ataattcctg  720
ttcatctaat aatcaagtat gtatatgttc tgtgtgtttt attggtattt gattagatat  780
atacatgctt agatacatac atgaagcagc atgctgctac agtttaatca ttattgttta  840
tccaataaac aaacatgctt tttaatttat cttgatatgc ttggatgacg gaatatgcag  900
agattttaag tacccagcat catgagcatg catgaccctg cgttagtatg ctgtttattt  960
gcttgagact ctttcttttg tagatactca ccctgttttc tggtgatcct actgcagggg  1020

SEQ ID NO: 108         moltype = DNA  length = 1943
FEATURE                Location/Qualifiers
source                 1..1943
                       mol_type = other DNA
                       organism = Coix lacryma-jobi
SEQUENCE: 108
agcagactcg cattatcgat ggagctctac caaactggcc ctaggcatta acctaccatg  60
gatcacatcg taaaaaaaaa accctaccat ggatcctatc tgttttcttt ttgccctgaa  120
agagtgaagt catcatcata tttaccatgg cgcgcgtagg agcgcttcgt cgaagaccca  180
taggggggcg gtactcgcac cgtggttgtt tcctgttatg taatatcgga tgggggagca  240
gtcggctagg ttggtcccat cggtactggt cgtcccctag tgcgctagat gcgcgatgtt  300
tgtcctcaaa aactcttttc ttcttaataa caatcatacg caaatttttt gcgtattcga  360
gaaaaaaaga agattctatc tgtttttttt ttgaaatggc tccaatttat aggaggagcc  420
cgtttaacgg cgtcgacaaa tctaacggac accaaccagc gaatgagcga acccaccagc  480
gccaagctag ccaagcgaag cagacggccg agacgctgac acccttgcct tggcgcggca  540
tctccgtcgc tggctcgctg gctctggccc cttcgcgaga gttccggtcc acctccacct  600
gtgtcggttt ccaactccgt tccgccttcg cgtgggactt gttccgttca tccgttggcg  660
gcatccggaa attgcgtggc gtagagcacg gggccctcct ctcacacggc acggaaccgt  720
cacgagctca cggcaccggc agcacggcgg ggattccttc cccaccaccg ctccttccct  780
ttcccttcct cgcccgccat cataaatagc cacccctccc agcttccttc gccacatcct  840
ctcatcatct tctctcgtgt agcacgcgca gcccgatccc caatcccctc tcctcgcgag  900
cctcgtcgat ccctcgcttc aaggtatggc tatcgtcctt cctctctctc tctttacctt  960
atctagatcg gcgatccatg gttagggcct gctagttctc cgttcgtgtt tgtcgatggc  1020
tgtgaggcac aatagatccg tcggcgttat gatggttagc ctgtcatgct cttgcgatct  1080
gtggttcctt taggaaaggc attaatttaa tccctgatgg ttcgagatcg gtgatccatg  1140
gttagtaccc taagctgtgg agtcgggttt agatccgcgc tgttcgtagg cgatctgttc  1200
tgattgttaa cttgtcagta cctgcgaatc ctcggtggtt ctagctggtt cggagatcag  1260
atcgattcca ttatctgcta tacatcttgt ttcgttgcct aggctccgtt taatctatcc  1320
atcgtatgat gttagccttt gatatgattc gatcgtgcta gctatgtcct gtggacttaa  1380
ttgtcaggtc ctaattttta ggaagactgt tccaaaccat ctgctggatt tattaaattt  1440
ggatctggat gtgtcacata caccttcata attaaaatgg atggaaatat ctcttatctt  1500
ttagatatgg ataggcattt atatgatgct gtgagtttta ctagtacttt cttagaatat  1560
atgtactttt ttagacggaa tattgatatg tatacatgtg tagatacatg aagcaacatg  1620
ctgctgtagt ctaataattc ctgttcatct aataatcaag tatgtatatg ttctgtgtgt  1680
tttattggta tttgattaga tatatacatg cttagataca tacatgaagc agcatgctgc  1740
tacagtttaa tcattattgt ttatccaata aacaaacatg ctttttaatt tatcttgata  1800
tgcttggatg acggaatatg cagagatttt aagtacccag catcatgagc atgcatgacc  1860
ctgcgttagt atgctgttta tttgcttgag actctttctt ttgtagatac tcaccctgtt  1920
ttctggtgat cctactgcag ggt                                          1943

SEQ ID NO: 109         moltype = DNA  length = 1020
FEATURE                Location/Qualifiers
source                 1..1020
                       mol_type = other DNA
                       organism = Coix lacryma-jobi
SEQUENCE: 109
gtatggctat cgtccttcct ctctctctct ttaccttatc tagatcggcg atccatggtt  60
agggcctgct agttctccgt tcgtgtttgt cgatggctgt gaggcacaat agatccgtcg  120
gcgttatgat ggttagcctg tcatgctctt gcgatctgtg gttcctttag gaaaggcatt  180
```

```
aatttaatcc ctgatggttc gagatcggtg atccatggtt agtaccctaa gctgtggagt  240
cgggtttaga tccgcgctgt tcgtaggcga tctgttctga ttgttaactt gtcagtacct  300
gcgaatcctc ggtggttcta gctggttcgg agatcagatc gattccatta tctgctatac  360
atcttgtttc gttgcctagg ctccgtttaa tctatccatc gtatgatgtt agcctttgat  420
atgattcgat cgtgctagct atgtcctgtg gacttaattg tcaggtccta atttttagga  480
agactgttcc aaaccatctg ctggatttat taaatttgga tctggatgtg tcacatacac  540
cttcataatt aaaatggatg gaaatatctc ttatctttta gatatggata ggcatttata  600
tgatgctgtg agttttacta gtactttctt agaatatatg tacttttttta gacggaatat  660
tgatatgtat acatgtgtag atacatgaag caacatgctg ctgtagtcta ataattcctg  720
ttcatctaat aatcaagtat gtatatgttc tgtgtgtttt attggtattt gattagatat  780
atacatgctt agatacatac atgaagcagc atgctgctac agtttaatca ttattgttta  840
tccaataaac aaacatgctt tttaatttat cttgatatgc ttggatgacg gaatatgcag  900
agattttaag tacccagcat catgagcatg catgaccctg cgttagtatg ctgtttattt  960
gcttgagact ctttcttttg tagatactca ccctgttttc tggtgatcct actgcagggt  1020

SEQ ID NO: 110         moltype = DNA  length = 1943
FEATURE                Location/Qualifiers
source                 1..1943
                       mol_type = other DNA
                       organism = Coix lacryma-jobi
SEQUENCE: 110
agcagactcg cattatcgat ggagctctac caaactggcc ctaggcatta acctaccatg  60
gatcacatcg taaaaaaaaa accctaccat ggatcctatc tgttttcttt ttgccctgaa  120
agagtgaagt catcatcata tttaccatgg cgcgcgtagg agcgcttcgt cgaagaccca  180
taggggggcg gtactcgcac cgtggttgtt tcctgttatg taatatcgga tgggggagca  240
gtcggctagg ttggtcccat cggtactggt cgtcccctag tgcgctagat gcgcgatgtt  300
tgtcctcaaa aactcttttc ttcttaataa caatcatacg caaatttttt gcgtattcga  360
gaaaaaaaga agattctatc tgtttttttt ttgaaatggc tccaatttat aggaggagcc  420
cgtttaacgg cgtcgacaaa tctaacggac accaaccagc gaatgagcga acccaccagc  480
gccaagctag ccaagcgaag cagacggccg agacgctgac acccttgcct tggcgcggca  540
tctccgtcgc tggctcgctg gctctggccc cttcgcgaga gttccggtcc acctccacct  600
gtgtcggttt ccaactccgt tccgccttcg cgtgggactt gttccgttca tccgttggcg  660
gcatccggaa attgcgtggc gtagagcacg gggccctcct ctcacacggc acggaaccgt  720
cacgagctca cggcaccggc agcacggcgg ggattccttc cccaccaccg ctccttccct  780
ttcccttcct cgcccgccat cataaatagc caccccctccc agcttccttc gccacatcct  840
ctcatcatct tctctcgtgt agcacgcgca gcccgatccc caatcccctc tcctcgcgag  900
cctcgtcgat ccctcgcttc aaggtatggc tatcgtcctt cctctctctc tctttacctt  960
atctagatcg gcgatccatg gttagggcct gctagttctc cgttcgtgtt tgtcgatggc  1020
tgtgaggcac aatagatccg tcggcgttat gatggttagc ctgtcatgct cttgcgatct  1080
gtggttcctt taggaaaggc attaatttaa tccctgatgg ttcgagatcg gtgatccatg  1140
gttagtaccc taagctgtgg agtcgggttt agatccgcgc tgttcgtagg cgatctgttc  1200
tgattgttaa cttgtcagta cctgcgaatc ctcggtggtt ctagctggtt cggagatcag  1260
atcgattcca ttatctgcta tacatcttgt ttcgttgcct aggctccgtt taatctatcc  1320
atcgtatgat gttagccttt gatatgattc gatcgtgcta gctatgtcct gtggacttaa  1380
ttgtcaggtc ctaattttta ggaagactgt tccaaaccat ctgctggatt tattaaattt  1440
ggatctggat gtgtcacata caccttcata attaaaatgg atggaaatat ctcttatctt  1500
ttagatatgg ataggcattt atatgatgct gtgagtttta ctagtacttt cttagaatat  1560
atgtactttt ttagacggaa tattgatatg tatacatgtg tagatacatg aagcaacatg  1620
ctgctgtagt ctaataattc ctgttcatct aataatcaag tatgtatatg ttctgtgtgt  1680
tttattggta tttgattaga tatatacatg cttagataca tacatgaagc agcatgctgc  1740
tacagtttaa tcattattgt ttatccaata aacaaacatg ctttttaatt tatcttgata  1800
tgcttggatg acggaatatg cagagatttt aagtacccag catcatgagc atgcatgacc  1860
ctgcgttagt atgctgttta tttgcttgag actctttctt ttgtagatac tcaccctgtt  1920
ttctggtgat cctactgcag cgt                                         1943

SEQ ID NO: 111         moltype = DNA  length = 1020
FEATURE                Location/Qualifiers
source                 1..1020
                       mol_type = other DNA
                       organism = Coix lacryma-jobi
SEQUENCE: 111
gtatggctat cgtccttcct ctctctctct ttaccttatc tagatcggcg atccatggtt  60
agggcctgct agttctccgt tcgtgtttgt cgatggctgt gaggcacaat agatccgtcg  120
gcgttatgat ggttagcctg tcatgctctt gcgatctgtg gttcctttag gaaaggcatt  180
aatttaatcc ctgatggttc gagatcggtg atccatggtt agtaccctaa gctgtggagt  240
cgggtttaga tccgcgctgt tcgtaggcga tctgttctga ttgttaactt gtcagtacct  300
gcgaatcctc ggtggttcta gctggttcgg agatcagatc gattccatta tctgctatac  360
atcttgtttc gttgcctagg ctccgtttaa tctatccatc gtatgatgtt agcctttgat  420
atgattcgat cgtgctagct atgtcctgtg gacttaattg tcaggtccta atttttagga  480
agactgttcc aaaccatctg ctggatttat taaatttgga tctggatgtg tcacatacac  540
cttcataatt aaaatggatg gaaatatctc ttatctttta gatatggata ggcatttata  600
tgatgctgtg agttttacta gtactttctt agaatatatg tacttttttta gacggaatat  660
tgatatgtat acatgtgtag atacatgaag caacatgctg ctgtagtcta ataattcctg  720
ttcatctaat aatcaagtat gtatatgttc tgtgtgtttt attggtattt gattagatat  780
atacatgctt agatacatac atgaagcagc atgctgctac agtttaatca ttattgttta  840
tccaataaac aaacatgctt tttaatttat cttgatatgc ttggatgacg gaatatgcag  900
agattttaag tacccagcat catgagcatg catgaccctg cgttagtatg ctgtttattt  960
gcttgagact ctttcttttg tagatactca ccctgttttc tggtgatcct actgcagcgt  1020
```

```
SEQ ID NO: 112          moltype = DNA  length = 1943
FEATURE                 Location/Qualifiers
source                  1..1943
                        mol_type = other DNA
                        organism = Coix lacryma-jobi
SEQUENCE: 112
agcagactcg cattatcgat ggagctctac caaactggcc ctaggcatta acctaccatg  60
gatcacatcg taaaaaaaaa accctaccat ggatcctatc tgttttcttt ttgccctgaa  120
agagtgaagt catcatcata tttaccatgg cgcgcgtagg agcgcttcgt cgaagaccca  180
taggggggcg gtactcgcac cgtggttgtt tcctgttatg taatatcgga tgggggagca  240
gtcggctagg ttggtcccat cggtactggt cgtcccctag tgcgctagat gcgcgatgtt  300
tgtcctcaaa aactcttttc ttcttaataa caatcatacg caaatttttt gcgtattcga  360
gaaaaaaaga agattctatc tgtttttttt ttgaaatggc tccaatttat aggaggagcc  420
cgtttaacgg cgtcgacaaa tctaacggac accaaccagc gaatgagcga acccaccagc  480
gccaagctag ccaagcgaag cagacggccg agacgctgac acccttgcct tggcgcggca  540
tctccgtcgc tggctcgctg gctctggccc cttcgcgaga gttccggtcc acctccacct  600
gtgtcggttt ccaactccgt tccgccttcg cgtgggactt gttccgttca tccgttggcg  660
gcatccggaa attgcgtggc gtagagcacg gggccctcct ctcacacggc acggaaccgt  720
cacgagctca cggcaccggc agcacggcgg ggattccttc cccaccaccg ctccttccct  780
ttcccttcct cgcccgccat cataaatagc cacccctccc agcttccttc gccacatcct  840
ctcatcatct tctctcgtgt agcacgcgca gcccgatccc caatcccctc tcctcgcgag  900
cctcgtcgat ccctcgcttc aaggtatggc tatcgtcctt cctctctctc tctttacctt  960
atctagatcg gcgatccatg gttagggcct gctagttctc cgttcgtgtt tgtcgatggc  1020
tgtgaggcac aatagatccg tcggcgttat gatggttagc ctgtcatgct cttgcgatct  1080
gtggttcctt taggaaaggc attaatttaa tccctgatgg ttcgagatcg gtgatccatg  1140
gttagtaccc taagctgtgg agtcgggttt agatccgcgc tgttcgtagg cgatctgttc  1200
tgattgttaa cttgtcagta cctgcgaatc ctcggtggtt ctagctggtt cggagatcag  1260
atcgattcca ttatctgcta tacatcttgt ttcgttgcct aggctccgtt taatctatcc  1320
atcgtatgat gttagccttt gatatgattc gatcgtgcta gctatgtcct gtggacttaa  1380
ttgtcaggtc ctaattttta ggaagactgt tccaaaccat ctgctggatt tattaaattt  1440
ggatctggat gtgtcacata caccttcata attaaaatgg atggaaatat ctcttatctt  1500
ttagatatgg ataggcattt atatgatgct gtgagtttta ctagtacttt cttagaatat  1560
atgtactttt ttagacggaa tattgatatg tatacatgtg tagatacatg aagcaacatg  1620
ctgctgtagt ctaataattc ctgttcatct aataatcaag tatgtatatg ttctgtgtgt  1680
tttattggta tttgattaga tatatacatg cttagataca tacatgaagc agcatgctgc  1740
tacagtttaa tcattattgt ttatccaata aacaaacatg ctttttaatt tatcttgata  1800
tgcttggatg acggaatatg cagagatttt aagtacccag catcatgagc atgcatgacc  1860
ctgcgttagt atgctgttta tttgcttgag actctttctt ttgtagatac tcaccctgtt  1920
ttctggtgat cctactgcag tgt                                          1943

SEQ ID NO: 113          moltype = DNA  length = 1020
FEATURE                 Location/Qualifiers
source                  1..1020
                        mol_type = other DNA
                        organism = Coix lacryma-jobi
SEQUENCE: 113
gtatggctat cgtccttcct ctctctctct ttaccttatc tagatcggcg atccatggtt  60
agggcctgct agttctccgt tcgtgtttgt cgatggctgt gaggcacaat agatccgtcg  120
gcgttatgat ggttagcctg tcatgctctt gcgatctgtg gttcctttag gaaaggcatt  180
aatttaatcc ctgatggttc gagatcggtg atccatggtt agtaccctaa gctgtggagt  240
cgggtttaga tccgcgctgt tcgtaggcga tctgttctga ttgttaactt gtcagtacct  300
gcgaatcctc ggtggttcta gctggttcgg agatcagatc gattccatta tctgctatac  360
atcttgtttc gttgcctagg ctccgtttaa tctatccatc gtatgatgtt agcctttgat  420
atgattcgat cgtgctagct atgtcctgtg gacttaattg tcaggtccta atttttagga  480
agactgttcc aaaccatctg ctggatttat taaatttgga tctggatgtg tcacatacac  540
cttcataatt aaaatggatg gaaatatctc ttatctttta gatatggata ggcatttata  600
tgatgctgtg agttttacta gtactttctt agaatatatg tacttttttta gacggaatat  660
tgatatgtat acatgtgtag atacatgaag caacatgctg ctgtagtcta ataattcctg  720
ttcatctaat aatcaagtat gtatatgttc tgtgtgtttt attggtattt gattagatat  780
atacatgctt agatacatac atgaagcagc atgctgctac agtttaatca ttattgttta  840
tccaataaac aaacatgctt tttaatttat cttgatatgc ttggatgacg gaatatgcag  900
agattttaag tacccagcat catgagcatg catgaccctg cgttagtatg ctgtttattt  960
gcttgagact ctttcttttg tagatactca ccctgttttc tggtgatcct actgcagtgt  1020

SEQ ID NO: 114          moltype = DNA  length = 1848
FEATURE                 Location/Qualifiers
source                  1..1848
                        mol_type = other DNA
                        organism = Coix lacryma-jobi
SEQUENCE: 114
ctatctgttt tctttttgcc ctgaaagagt gaagtcatca tcatatttac catggcgcgc  60
gtaggagcgc ttcgtcgaag acccataggg gggcggtact cgcaccgtgg ttgtttcctg  120
ttatgtaata tcggatgggg gagcagtcgg ctaggttggt cccatcggta ctggtcgtcc  180
cctagtgcgc tagatgcgcg atgtttgtcc tcaaaaactc ttttcttctt aataacaatc  240
atacgcaaat tttttgcgta ttcgagaaaa aaagaagatt ctatctgttt ttttttgaa  300
atggctccaa tttataggag gagcccgttt aacggcgtcg acaaatctaa cggacaccaa  360
ccagcgaatg agcgaaccca ccagcgccaa gctagccaag cgaagcagac ggccgagacg  420
ctgacaccct tgccttggcg cggcatctcc gtcgctggct cgctggctct ggccccttcg  480
cgagagttcc ggtccacctc cacctgtgtc ggtttccaac tccgttccgc cttcgcgtgg  540
```

```
gacttgttcc gttcatccgt tggcggcatc cggaaattgc gtggcgtaga gcacggggcc  600
ctcctctcac acggcacgga accgtcacga gctcacggca ccggcagcac ggcggggatt  660
ccttccccac caccgctcct tccctttccc ttcctcgccc gccatcataa atagccaccc  720
ctcccagctt ccttcgccac atcctctcat catcttctct cgtgtagcac gcgcagcccg  780
atccccaatc ccctctcctc gcgagcctcg tcgatccctc gcttcaaggt atggctatcg  840
tccttcctct ctctctcttt accttatcta gatcggcgat ccatggttag ggcctgctag  900
ttctccgttc gtgtttgtcg atggctgtga ggcacaatag atccgtcggc gttatgatgg  960
ttagcctgtc atgctcttgc gatctgtggt tcctttagga aaggcattaa tttaatccct  1020
gatggttcga gatcggtgat ccatggttag taccctaagc tgtggagtcg ggtttagatc  1080
cgcgctgttc gtaggcgatc tgttctgatt gttaacttgt cagtacctgc gaatcctcgg  1140
tggttctagc tggttcggag atcagatcga ttccattatc tgctatacat cttgtttcgt  1200
tgcctaggct ccgtttaatc tatccatcgt atgatgttag cctttgatat gattcgatcg  1260
tgctagctat gtcctgtgga cttaattgtc aggtcctaat ttttaggaag actgttccaa  1320
accatctgct ggatttatta aatttggatc tggatgtgtc acatacacct tcataattaa  1380
aatggatgga aatatctctt atcttttaga tatggatagg catttatatg atgctgtgag  1440
ttttactagt actttcttag aatatatgta ctttttttaga cggaatattg atatgtatac  1500
atgtgtagat acatgaagca acatgctgct gtagtctaat aattcctgtt catctaataa  1560
tcaagtatgt atatgttctg tgtgttttat tggtatttga ttagatatat acatgcttag  1620
atacatacat gaagcagcat gctgctacag tttaatcatt attgtttatc caataaacaa  1680
acatgctttt taatttatct tgatatgctt ggatgacgga atatgcagag attttaagta  1740
cccagcatca tgagcatgca tgaccctgcg ttagtatgct gtttatttgc ttgagactct  1800
ttcttttgta gatactcacc ctgttttctg gtgatcctac tgcaggtc              1848
```

```
SEQ ID NO: 115         moltype = DNA  length = 1507
FEATURE                Location/Qualifiers
source                 1..1507
                       mol_type = other DNA
                       organism = Coix lacryma-jobi
SEQUENCE: 115
caaatctaac ggacaccaac cagcgaatga gcgaacccac cagcgccaag ctagccaagc  60
gaagcagacg gccgagacgc tgacaccctt gccttggcgc ggcatctccg tcgctggctc  120
gctggctctg gccccttcgc gagagttccg gtccacctcc acctgtgtcg gtttccaact  180
ccgttccgcc ttcgcgtggg acttgttccg ttcatccgtt ggcggcatcc ggaaattgcg  240
tggcgtagag cacggggccc tcctctcaca cggcacggaa ccgtcacgag ctcacggcac  300
cggcagcacg gcggggattc cttccccacc accgctcctt ccctttccct tcctcgcccg  360
ccatcataaa tagccacccc tcccagcttc cttcgccaca tcctctcatc atcttctctc  420
gtgtagcacg cgcagcccga tccccaatcc cctctcctcg cgagcctcgt cgatccctcg  480
cttcaaggta tggctatcgt ccttcctctc tctctcttta ccttatctag atcggcgatc  540
catggttagg gcctgctagt tctccgttcg tgtttgtcga tggctgtgag gcacaataga  600
tccgtcggcg ttatgatggt tagcctgtca tgctcttgcg atctgtggtt cctttaggaa  660
aggcattaat ttaatccctg atggttcgag atcggtgatc catggttagt accctaagct  720
gtggagtcgg gtttagatcc gcgctgttcg taggcgatct gttctgattg ttaacttgtc  780
agtacctgcg aatcctcggt ggttctagct ggttcggaga tcagatcgat tccattatct  840
gctatacatc ttgtttcgtt gcctaggctc cgtttaatct atccatcgta tgatgttagc  900
ctttgatatg attcgatcgt gctagctatg tcctgtggac ttaattgtca ggtcctaatt  960
tttaggaaga ctgttccaaa ccatctgctg gatttattaa atttggatct ggatgtgtca  1020
catacacctt cataattaaa atggatggaa atatctctta tcttttagat atggataggc  1080
atttatatga tgctgtgagt tttactagta ctttcttaga atatatgtac ttttttagac  1140
ggaatattga tatgtataca tgtgtagata catgaagcaa catgctgctg tagtctaata  1200
attcctgttc atctaataat caagtatgta tatgttctgt gtgttttatt ggtatttgat  1260
tagatatata catgcttaga tacatacatg aagcagcatg ctgctacagt ttaatcatta  1320
ttgtttatcc aataaacaaa catgcttttt aatttatctt gatatgcttg gatgacggaa  1380
tatgcagaga ttttaagtac ccagcatcat gagcatgcat gaccctgcgt tagtatgctg  1440
tttatttgct tgagactctt tcttttgtag atactcaccc tgttttctgg tgatcctact  1500
gcaggtc                                                            1507
```

```
SEQ ID NO: 116         moltype = DNA  length = 1160
FEATURE                Location/Qualifiers
source                 1..1160
                       mol_type = other DNA
                       organism = Coix lacryma-jobi
SEQUENCE: 116
ccttcctcgc ccgccatcat aaatagccac ccctcccagc ttccttcgcc acatcctctc  60
atcatcttct ctcgtgtagc acgcgcagcc cgatccccaa tcccctctcc tcgcgagcct  120
cgtcgatccc tcgcttcaag gtatggctat cgtccttcct ctctctctct ttaccttatc  180
tagatcggcg atccatggtt agggcctgct agttctccgt tcgtgtttgt cgatggctgt  240
gaggcacaat agatccgtcg gcgttatgat ggttagcctg tcatgctctt gcgatctgtg  300
gttcctttag gaaaggcatt aatttaatcc ctgatggttc gagatcggtg atccatggtt  360
agtaccctaa gctgtggagt cgggtttaga tccgcgctgt tcgtaggcga tctgttctga  420
ttgttaactt gtcagtacct gcgaatcctc ggtggttcta gctggttcgg agatcagatc  480
gattccatta tctgctatac atcttgtttc gttgcctagg ctccgtttaa tctatccatc  540
gtatgatgtt agcctttgat atgattcgat cgtgctagct atgtcctgtg gacttaattg  600
tcaggtccta atttttagga agactgttcc aaaccatctg ctggatttat taaatttgga  660
tctggatgtg tcacatacac cttcataatt aaaatggatg gaaatatctc ttatctttta  720
gatatggata ggcatttata tgatgctgtg agttttacta gtactttctt agaatatatg  780
tactttttta gacggaatat tgatatgtat acatgtgtag atacatgaag caacatgctg  840
ctgtagtcta ataattcctg ttcatctaat aatcaagtat gtatatgttc tgtgtgtttt  900
attggtattt gattagatat atacatgctt agatacatac atgaagcagc atgctgctac  960
agtttaatca ttattgttta tccaataaac aaacatgctt tttaatttat cttgatatgc  1020
```

```
ttggatgacg gaatatgcag agattttaag tacccagcat catgagcatg catgaccctg  1080
cgttagtatg ctgtttattt gcttgagact ctttcttttg tagatactca ccctgttttc  1140
tggtgatcct actgcaggtc                                              1160

SEQ ID NO: 117         moltype = DNA  length = 2625
FEATURE                Location/Qualifiers
source                 1..2625
                       mol_type = other DNA
                       organism = Setaria italica
SEQUENCE: 117
actgccgcga cacgcctcac tggcgggagg gctccgagcg ctctctcccc ggcggccggc  60
ggagcagcga tctggattgg agagaataga ggaaagagag ggaaaaggag agagatagcg  120
caaagagctg aaaagataag gttgtgcggg ctgtggtgat tagaggacca ctaatccctc  180
catctcctaa tgacgcggtg cccaagacca gtgccgcggc acaccagcgt ctaagtgaac  240
ttccgctaac cttccggtca ttgcgcctga aagatgtcat gtggcgaggc ccccctctca  300
gtagattgcc aactgcctac cgtgccactc ttccatgcat gattgctccc gtctatcccg  360
tttctcacaa cagatagaca acagtaagca tcactaaagc aagcatgtgt agaaccttaa  420
aaaaaggctt atactaccag tatactatca accagcatgc cgtttttgaa gtatccagga  480
ttagaagctt ctactgcgct tttatattat agctgtggac ctgtggtaac ctttctcttt  540
tggcgcttgc ttaatctcgg ccgtgctggt ccatgcttag gcactaggca gagatagagc  600
cgggggtgaa tggggctaaa gctcagctgc tcgaggggcc gtgggctggt ttccactagc  660
ctacagctgt gccacgtgcg gccgcgcaag ccgaagcaag cacgctgagc cgttggacag  720
cttgtcataa tgccattacg tggattacac gtaactggcc ctgtaactac tcgttcggcc  780
atcatcaaac gacgacgtcc gctaggcgac gacacgggta atgcacgcag ccacccaggc  840
gcgcgcgcta gcggagcacg gtcaggtgac acgggcgtcg tgacgcttcc gagttgaagg  900
ggttaacgcc agaaacagtg tttggccagg gtatgaacat aacaaaaaat attcacacga  960
aagaatggaa gtatggagct gctactgtgt aaatgccaag caggaaactc acgcccgcta  1020
acatccaacg gccaacagct cgacgtgccg gtcagcagag catcggaaca ctggtgattg  1080
gtggagccgg cagtatgcgc cccagcacgg ccgaggtggt ggtggcccgt ggccctgctg  1140
tctgcgcggc tcgggacaac ttgaaactgg gccaccgcct cgtcgcaact cgcaacccgt  1200
tggcggaaga aaggaatggc tcgtaggggc ccgggtagaa tcgaagaatg ttgcgctggg  1260
cttcgattca cataacatgg gcctgaagct ctaaaacgac ggcccggtcg ccgcgcgatg  1320
gaaagagacc ggatcctcct cgtgaattct ggaaggccac acgagagcga cccaccaccg  1380
acgcggagga gtcgtgcgtg gtccaacacg gccggcgggc tgggctgcga ccttaaccag  1440
caaggcacgc cacgacccgc cccgccctcg aggcataaat accctcccat cccgttgccg  1500
caagactcag atcagattcc gatccccagt tcttccccaa tcaccttgtg gtctctcgtg  1560
tcgcggttcc cagggacgcc tccggctcgt cgctcgacag cgatctccgc cccagcaagg  1620
tatagattca gttccttgct ccgatcccaa tctggttgag atgttgctcc gatgcgactt  1680
gattatgtca tatatctgcg gtttgcaccg atctgaagcc tagggtttct cgagcgaccc  1740
agttatttgc aatttgcgat ttgctcgttt gttgcgcagc gtagtttatg tttggagtaa  1800
tcgaggattt gtatgcggcg tcggcgctac ctgcttaatc acgccatgtg acgcggttac  1860
ttgcagaggc tgggttctgt tatgtcgtga tctaagaatc tagattaggc tcagtcgttc  1920
ttgctgtcga ctagtttgtt ttgatatcca tgtagtacaa gttacttaaa atttaggtcc  1980
aatatatttt gcatgctttt ggcctgttat tcttgccaac aagttgtcct ggtaaaaagt  2040
agatgtgaaa gtcacgtatt gggacaaatt gatggtttag tgctatagtt ctatagttct  2100
gtgatacatc tatctgattt tttttggtct attggtgcct aacttatctg aaaatcatgg  2160
aacatgaggc tagtttgatc atggtttagt tcattgtgat taataatgta tgatttagta  2220
gctattttgg tgatcgtgtc attttatttg tgaatggaat cattgtatgt aaatgaagct  2280
agttcagggg ttacgatgta gctggctttg tattctaaag gctgctatta ttcatccatc  2340
gatttcacct atatgtaatc cagagctttt gatgtgaaat ttgtctgatc cttcactagg  2400
aaggacagaa cattgttaat attttggcac atctgtctta ttctcatcct ttgtttgaac  2460
atgttagcct gttcaaacag atactgttgt aatgtcctag ttatataggt acatatgtgt  2520
tctctattga gtttatggac ttttgtgtgt gaagttatat ttcattttgc tcaaaactca  2580
tgtttgcaag ctttctgaca ttattctatt gttctgaaac aggtg                  2625

SEQ ID NO: 118         moltype = DNA  length = 1006
FEATURE                Location/Qualifiers
source                 1..1006
                       mol_type = other DNA
                       organism = Setaria italica
SEQUENCE: 118
gtatagattc agttccttgc tccgatccca atctggttga gatgttgctc cgatgcgact  60
tgattatgtc atatatctgc ggtttgcacc gatctgaagc ctagggtttc tcgagcgacc  120
cagttatttg caatttgcga tttgctcgtt tgttgcgcag cgtagtttat gtttggagta  180
atcgaggatt tgtatgcggc gtcggcgcta cctgcttaat cacgccatgt gacgcggtta  240
cttgcagagg ctgggttctg ttatgtcgtg atctaagaat ctagattagg ctcagtcgtt  300
cttgctgtcg actagtttgt tttgatatcc atgtagtaca agttacttaa aatttaggtc  360
caatatattt tgcatgcttt tggcctgtta ttcttgccaa caagttgtcc tggtaaaaag  420
tagatgtgaa agtcacgtat tgggacaaat tgatggttta gtgctatagt tctatagttc  480
tgtgatacat ctatctgatt ttttttggtc tattggtgcc taacttatct gaaaatcatg  540
gaacatgagg ctagtttgat catggtttag ttcattgtga ttaataatgt atgatttagt  600
agctattttg gtgatcgtgt cattttattt gtgaatggaa tcattgtatg taaatgaagc  660
tagttcaggg gttacgatgt agctggcttt gtattctaaa ggctgctatt attcatccat  720
cgatttcacc tatatgtaat ccagagcttt tgatgtgaaa tttgtctgat ccttcactag  780
gaaggacaga acattgttaa tattttggca catctgtctt attctcatcc tttgtttgaa  840
catgttagcc tgttcaaaca gatactgttg taatgtccta gttatatagg tacatatgtg  900
ttctctattg agtttatgga cttttgtgtg tgaagttata tttcattttg ctcaaaactc  960
atgtttgcaa gctttctgac attattctat tgttctgaaa caggtg                 1006
```

```
SEQ ID NO: 119          moltype = DNA  length = 2625
FEATURE                 Location/Qualifiers
source                  1..2625
                        mol_type = other DNA
                        organism = Setaria italica
SEQUENCE: 119
actgccgcga cacgcctcac tggcgggagg gctccgagcg ctctctcccc ggcggccggc  60
ggagcagcga tctggattgg agagaataga ggaaagagag ggaaaaggag agagatagcg  120
caaagagctg aaaagataag gttgtgcggg ctgtggtgat tagaggacca ctaatccctc  180
catctcctaa tgacgcggtg cccaagacca gtgccgcggc acaccagcgt ctaagtgaac  240
ttccgctaac cttccggtca ttgcgcctga aagatgtcat gtggcgaggc ccccctctca  300
gtagattgcc aactgcctac cgtgccactc ttccatgcat gattgctccc gtctatcccg  360
tttctcacaa cagatagaca acagtaagca tcactaaagc aagcatgtgt agaaccttaa  420
aaaaaggctt atactaccag tatactatca accagcatgc cgtttttgaa gtatccagga  480
ttagaagctt ctactgcgct tttatattat agctgtggac ccgtggtaac ctttctcttt  540
tggcgcttgc ttaatctcgg ccgtgctggt ccatgcttag gcactaggca gagatagagc  600
cgggggtgaa tggggctaaa gctcagctgc tcgaggggcc gtgggctggt ttccactagc  660
ctacagctgt gccacgtgcg gccgcgcaag ccgaagcaag cacgctgagc cgttggacag  720
cttgtcataa tgccattacg tggattacac gtaactggcc ctgtaactac tcgttcggcc  780
atcatcaaac gacgacgtcc gctaggcgac gacacgggta atgcacgcag ccacccaggc  840
gcgcgcgcta gcggagcacg gtcaggtgac acgggcgtcg tgacgcttcc gagttgaagg  900
ggttaacgcc agaaacagtg tttggccagg gtatgaacat aacaaaaaat attcacacga  960
aagaatggaa gtatggagct gctactgtgt aaatgccaag caggaaactc acgcccgcta  1020
acatccaacg gccaacagct cgacgtgccg gtcagcagag catcggaaca ctggtgattg  1080
gtggagccgg cagtatgcgc cccagcacgg ccgaggtggt ggtggcccgt ggccctgctg  1140
tctgcgcggc tcgggacaac ttgaaactgg gccaccgcct cgtcgcaact cgcaacccgt  1200
tggcggaaga aaggaatggc tcgtaggggc ccgggtagaa tcgaagaatg ttgcgctggg  1260
cttcgattca cataacatgg gcctgaagct ctaaaacgac ggcccggtcg ccgcgcgatg  1320
gaaagagacc ggatcctcct cgtgaattct ggaaggccac acgagagcga cccaccaccg  1380
acgcggagga gtcgtgcgtg gtccaacacg gccggcgggc tgggctgcga ccttaaccag  1440
caaggcacgc cacgacccgc cccgccctcg aggcataaat accctcccat cccgttgccg  1500
caagactcag atcagattcc gatccccagt tcttccccaa tcaccttgtg gtctctcgtg  1560
tcgcggttcc cagggacgcc tccggctcgt cgctcgacag cgatctccgc cccagcaagg  1620
tatagattca gttccttgct ccgatcccaa tctggttgag atgttgctcc gatgcgactt  1680
gattatgtca tatatctgcg gtttgcaccg atctgaagcc tagggtttct cgagcgaccc  1740
agttatttgc aatttgcgat ttgctcgttt gttgcgcagc gtagtttatg tttggagtaa  1800
tcgaggattt gtatgcggcg tcggcgctac ctgcttaatc acgccatgtg acgcggttac  1860
ttgcagaggc tgggttctgt tatgtcgtga tctaagaatc tagattaggc tcagtcgttc  1920
ttgctgtcga ctagtttgtt ttgatatcca tgtagtacaa gttacttaaa atttaggtcc  1980
aatatatttt gcatgctttt ggcctgttat tcttgccaac aagttgtcct ggtaaaaagt  2040
agatgtgaaa gtcacgtatt gggacaaatt gatggtttag tgctatagtt ctatagttct  2100
gtgatacatc tatctgattt tttttggtct attggtgcct aacttatctg aaaatcatgg  2160
aacatgaggc tagtttgatc atggtttagt tcattgtgat taataatgta tgatttagta  2220
gctattttgg tgatcgtgtc attttatttg tgaatggaat cattgtatgt aaatgaagct  2280
agttcagggg ttacgatgta gctggctttg tattctaaag gctgctatta ttcatccatc  2340
gatttcacct atatgtaatc cagagctttt gatgtgaaat ttgtctgatc cttcactagg  2400
aaggacagaa cattgttaat attttggcac atctgtctta ttctcatcct ttgtttgaac  2460
atgttagcct gttcaaacag atactgttgt aatgtcctag ttatataggt acatatgtgt  2520
tctctattga gtttatggac ttttgtgtgt gaagttatat ttcattttgc tcaaaactca  2580
tgtttgcaag ctttctgaca ttattctatt gttctgaaac agggt                  2625

SEQ ID NO: 120          moltype = DNA  length = 1006
FEATURE                 Location/Qualifiers
source                  1..1006
                        mol_type = other DNA
                        organism = Setaria italica
SEQUENCE: 120
gtatagattc agttccttgc tccgatccca atctggttga gatgttgctc cgatgcgact  60
tgattatgtc atatatctgc ggtttgcacc gatctgaagc ctagggtttc tcgagcgacc  120
cagttatttg caatttgcga tttgctcgtt tgttgcgcag cgtagtttat gtttggagta  180
atcgaggatt tgtatgcggc gtcggcgcta cctgcttaat cacgccatgt gacgcggtta  240
cttgcagagg ctgggttctg ttatgtcgtg atctaagaat ctagattagg ctcagtcgtt  300
cttgctgtcg actagtttgt tttgatatcc atgtagtaca agttacttaa aatttaggtc  360
caatatattt tgcatgcttt tggcctgtta ttcttgccaa caagttgtcc tggtaaaaag  420
tagatgtgaa agtcacgtat tgggacaaat tgatggttta gtgctatagt tctatagttc  480
tgtgatacat ctatctgatt ttttttggtc tattggtgcc taacttatct gaaaatcatg  540
gaacatgagg ctagtttgat catggtttag ttcattgtga ttaataatgt atgatttagt  600
agctattttg gtgatcgtgt cattttattt gtgaatggaa tcattgtatg taaatgaagc  660
tagttcaggg gttacgatgt agctggcttt gtattctaaa ggctgctatt attcatccat  720
cgatttcacc tatatgtaat ccagagcttt tgatgtgaaa tttgtctgat ccttcactag  780
gaaggacaga acattgttaa tattttggca catctgtctt attctcatcc tttgtttgaa  840
catgttagcc tgttcaaaca gatactgttg taatgtccta gttatatagg tacatatgtg  900
ttctctattg agtttatgga cttttgtgtg tgaagttata tttcattttg ctcaaaactc  960
atgtttgcaa gctttctgac attattctat tgttctgaaa cagggt                 1006

SEQ ID NO: 121          moltype = DNA  length = 2625
FEATURE                 Location/Qualifiers
source                  1..2625
                        mol_type = other DNA
```

organism = Setaria italica

SEQUENCE: 121

```
actgccgcga cacgcctcac tggcgggagg gctccgagcg ctctctcccc ggcggccggc  60
ggagcagcga tctggattgg agagaataga ggaaagagag ggaaaaggag agagatagcg  120
caaagagctg aaaagataag gttgtgcggg ctgtggtgat tagaggacca ctaatccctc  180
catctcctaa tgacgcggtg cccaagacca gtgccgcggc acaccagcgt ctaagtgaac  240
ttccgctaac cttccggtca ttgcgcctga aagatgtcat gtggcgaggc ccccctctca  300
gtagattgcc aactgcctac cgtgccactc ttccatgcat gattgctccc gtctatcccg  360
tttctcacaa cagatagaca acagtaagca tcactaaagc aagcatgtgt agaaccttaa  420
aaaaaggctt atactaccag tatactatca accagcatgc cgtttttgaa gtatccagga  480
ttagaagctt ctactgcgct tttatattat agctgtggac ccgtggtaac ctttctcttt  540
tggcgcttgc ttaatctcgg ccgtgctggt ccatgcttag gcactaggca gagatagagc  600
cgggggtgaa tggggctaaa gctcagctgc tcgaggggcc gtgggctggt ttccactagc  660
ctacagctgt gccacgtgcg gccgcgcaag ccgaagcaag cacgctgagc cgttggacag  720
cttgtcataa tgccattacg tggattacac gtaactggcc ctgtaactac tcgttcggcc  780
atcatcaaac gacgacgtcc gctaggcgac gacacgggta atgcacgcag ccacccaggc  840
gcgcgcgcta gcggagcacg gtcaggtgac acgggcgtcg tgacgcttcc gagttgaagg  900
ggttaacgcc agaaacagtg tttggccagg gtatgaacat aacaaaaaat attcacacga  960
aagaatggaa gtatggagct gctactgtgt aaatgccaag caggaaactc acgcccgcta  1020
acatccaacg gccaacagct cgacgtgccg gtcagcagag catcggaaca ctggtgattg  1080
gtggagccgg cagtatgcgc cccagcacgg ccgaggtggt ggtggcccgt ggccctgctg  1140
tctgcgcggc tcgggacaac ttgaaactgg gccaccgcct cgtcgcaact cgcaacccgt  1200
tggcggaaga aaggaatggc tcgtaggggc ccgggtagaa tcgaagaatg ttgcgctggg  1260
cttcgattca cataacatgg gcctgaagct ctaaaacgac ggcccggtcg ccgcgcgatg  1320
gaaagagacc ggatcctcct cgtgaattct ggaaggccac acgagagcga cccaccaccg  1380
acgcggagga gtcgtgcgtg gtccaacacg gccggcgggc tgggctgcga ccttaaccag  1440
caaggcacgc cacgacccgc cccgccctcg aggcataaat accctcccat cccgttgccg  1500
caagactcag atcagattcc gatccccagt tcttccccaa tcaccttgtg gtctctcgtg  1560
tcgcggttcc cagggacgcc tccggctcgt cgctcgacag cgatctccgc cccagcaagg  1620
tatagattca gttccttgct ccgatcccaa tctggttgag atgttgctcc gatgcgactt  1680
gattatgtca tatatctgcg gtttgcaccg atctgaagcc tagggtttct cgagcgaccc  1740
agttatttgc aatttgcgat ttgctcgttt gttgcgcagc gtagtttatg tttggagtaa  1800
tcgaggattt gtatgcggcg tcggcgctac ctgcttaatc acgccatgtg acgcggttac  1860
ttgcagaggc tgggttctgt tatgtcgtga tctaagaatc tagattaggc tcagtcgttc  1920
ttgctgtcga ctagtttgtt ttgatatcca tgtagtacaa gttacttaaa atttaggtcc  1980
aatatatttt gcatgctttt ggcctgttat tcttgccaac aagttgtcct ggtaaaaagt  2040
agatgtgaaa gtcacgtatt gggacaaatt gatggtttag tgctatagtt ctatagttct  2100
gtgatacatc tatctgattt tttttggtct attggtgcct aacttatctg aaaatcatgg  2160
aacatgaggc tagtttgatc atggtttagt tcattgtgat taataatgta tgatttagta  2220
gctattttgg tgatcgtgtc attttatttg tgaatggaat cattgtatgt aaatgaagct  2280
agttcagggg ttacgatgta gctggctttg tattctaaag gctgctatta ttcatccatc  2340
gatttcacct atatgtaatc cagagctttt gatgtgaaat ttgtctgatc cttcactagg  2400
aaggacagaa cattgttaat attttggcac atctgtctta ttctcatcct ttgtttgaac  2460
atgttagcct gttcaaacag atactgttgt aatgtcctag ttatataggt acatatgtgt  2520
tctctattga gtttatggac ttttgtgtgt gaagttatat ttcattttgc tcaaaactca  2580
tgtttgcaag ctttctgaca ttattctatt gttctgaaac agacc                 2625
```

SEQ ID NO: 122 moltype = DNA length = 1006
FEATURE Location/Qualifiers
source 1..1006
mol_type = other DNA
organism = Setaria italica

SEQUENCE: 122

```
gtatagattc agttccttgc tccgatccca atctggttga gatgttgctc cgatgcgact  60
tgattatgtc atatatctgc ggtttgcacc gatctgaagc ctagggtttc tcgagcgacc  120
cagttatttg caatttgcga tttgctcgtt tgttgcgcag cgtagtttat gtttggagta  180
atcgaggatt tgtatgcggc gtcggcgcta cctgcttaat cacgccatgt gacgcggtta  240
cttgcagagg ctgggttctg ttatgtcgtg atctaagaat ctagattagg ctcagtcgtt  300
cttgctgtcg actagtttgt tttgatatcc atgtagtaca agttacttaa aatttaggtc  360
caatatattt tgcatgcttt tggcctgtta ttcttgccaa caagttgtcc tggtaaaaag  420
tagatgtgaa agtcacgtat tgggacaaat tgatggttta gtgctatagt tctatagttc  480
tgtgatacat ctatctgatt ttttttggtc tattggtgcc taacttatct gaaaatcatg  540
gaacatgagg ctagtttgat catggtttag ttcattgtga ttaataatgt atgatttagt  600
agctattttg gtgatcgtgt cattttattt gtgaatggaa tcattgtatg taaatgaagc  660
tagttcaggg gttacgatgt agctggcttt gtattctaaa ggctgctatt attcatccat  720
cgatttcacc tatatgtaat ccagagcttt tgatgtgaaa tttgtctgat ccttcactag  780
gaaggacaga acattgttaa tattttggca catctgtctt attctcatcc tttgtttgaa  840
catgttagcc tgttcaaaca gatactgttg taatgtccta gttatatagg tacatatgtg  900
ttctctattg agtttatgga cttttgtgtg tgaagttata tttcattttg ctcaaaactc  960
atgtttgcaa gctttctgac attattctat tgttctgaaa cagacc                1006
```

SEQ ID NO: 123 moltype = DNA length = 2167
FEATURE Location/Qualifiers
source 1..2167
mol_type = other DNA
organism = Setaria italica

SEQUENCE: 123

```
gccgtttttg aagtatccag gattagaagc ttctactgcg cttttatatt atagctgtgg  60
acctgtggta acctttctct tttggcgctt gcttaatctc ggccgtgctg gtccatgctt  120
```

```
aggcactagg cagagataga gccgggggtg aatggggcta aagctcagct gctcgagggg  180
ccgtgggctg gtttccacta gcctacagct gtgccacgtg cggccgcgca agccgaagca  240
agcacgctga gccgttggac agcttgtcat aatgccatta cgtggattac acgtaactgg  300
ccctgtaact actcgttcgg ccatcatcaa acgacgacgt ccgctaggcg acgacacggg  360
taatgcacgc agccacccag gcgcgcgcgc tagcggagca cggtcaggtg acacgggcgt  420
cgtgacgctt ccgagttgaa ggggttaacg ccagaaacag tgtttggcca gggtatgaac  480
ataacaaaaa atattcacac gaaagaatgg aagtatggag ctgctactgt gtaaatgcca  540
agcaggaaac tcacgcccgc taacatccaa cggccaacag ctcgacgtgc cggtcagcag  600
agcatcggaa cactggtgat tggtggagcc ggcagtatgc gccccagcac ggccgaggtg  660
gtggtggccc gtggccctgc tgtctgcgcg gctcgggaca acttgaaact gggccaccgc  720
ctcgtcgcaa ctcgcaaccc gttggcggaa gaaaggaatg gctcgtaggg gcccgggtag  780
aatcgaagaa tgttgcgctg ggcttcgatt cacataacat gggcctgaag ctctaaaacg  840
acggcccggt cgccgcgcga tggaaagaga ccggatcctc ctcgtgaatt ctggaaggcc  900
acacgagagc gacccaccac cgacgcggag gagtcgtgcg tggtccaaca cggccggcgg  960
gctgggctgc gaccttaacc agcaaggcac gccacgaccc gccccgccct cgaggcataa  1020
ataccctccc atcccgttgc cgcaagactc agatcagatt ccgatcccca gttcttcccc  1080
aatcaccttg tggtctctcg tgtcgcggtt cccagggacg cctccggctc gtcgctcgac  1140
agcgatctcc gccccagcaa ggtatagatt cagttccttg ctccgatccc aatctggttg  1200
agatgttgct ccgatgcgac ttgattatgt catatatctg cggtttgcac cgatctgaag  1260
cctagggttt ctcgagcgac ccagttattt gcaatttgcg atttgctcgt ttgttgcgca  1320
gcgtagttta tgtttggagt aatcgaggat ttgtatgcgg cgtcggcgct acctgcttaa  1380
tcacgccatg tgacgcggtt acttgcagag gctgggttct gttatgtcgt gatctaagaa  1440
tctagattag gctcagtcgt tcttgctgtc gactagtttg ttttgatatc catgtagtac  1500
aagttactta aaatttaggt ccaatatatt ttgcatgctt ttggcctgtt attcttgcca  1560
acaagttgtc ctggtaaaaa gtagatgtga aagtcacgta ttgggacaaa ttgatggttt  1620
agtgctatag ttctatagtt ctgtgataca tctatctgat ttttttggt ctattggtgc  1680
ctaacttatc tgaaaatcat ggaacatgag gctagtttga tcatggttta gttcattgtg  1740
attaataatg tatgatttag tagctatttt ggtgatcgtg tcatttttatt tgtgaatgga  1800
atcattgtat gtaaatgaag ctagttcagg ggttacgatg tagctggctt tgtattctaa  1860
aggctgctat tattcatcca tcgatttcac ctatatgtaa tccagagctt ttgatgtgaa  1920
atttgtctga tccttcacta ggaaggacag aacattgtta atattttggc acatctgtct  1980
tattctcatc ctttgtttga acatgttagc ctgttcaaac agatactgtt gtaatgtcct  2040
agttatatag gtacatatgt gttctctatt gagtttatgg acttttgtgt gtgaagttat  2100
atttcatttt gctcaaaact catgtttgca agctttctga cattattcta ttgttctgaa  2160
acaggtg                                                            2167
```

```
SEQ ID NO: 124          moltype = DNA  length = 1813
FEATURE                 Location/Qualifiers
source                  1..1813
                        mol_type = other DNA
                        organism = Setaria italica
SEQUENCE: 124
cacgggtaat gcacgcagcc acccaggcgc gcgcgctagc ggagcacggt caggtgacac  60
gggcgtcgtg acgcttccga gttgaagggg ttaacgccag aaacagtgtt tggccagggt  120
atgaacataa caaaaaatat tcacacgaaa gaatggaagt atggagctgc tactgtgtaa  180
atgccaagca ggaaactcac gcccgctaac atccaacggc caacagctcg acgtgccggt  240
cagcagagca tcggaacact ggtgattggt ggagccggca gtatgcgccc cagcacggcc  300
gaggtggtgg tggcccgtgg ccctgctgtc tgcgcggctc gggacaactt gaaactgggc  360
caccgcctcg tcgcaactcg caacccgttg gcggaagaaa ggaatggctc gtaggggccc  420
gggtagaatc gaagaatgtt gcgctgggct tcgattcaca taacatgggc ctgaagctct  480
aaaacgacgg cccggtcgcc gcgcgatgga aagagaccgg atcctcctcg tgaattctgg  540
aaggccacac gagagcgacc caccaccgac gcggaggagt cgtgcgtggt ccaacacggc  600
cggcgggctg ggctgcgacc ttaaccagca aggcacgcca cgacccgccc cgccctcgag  660
gcataaatac cctcccatcc cgttgccgca agactcagat cagattccga tccccagttc  720
ttccccaatc accttgtggt ctctcgtgtc gcggttccca gggacgcctc cggctcgtcg  780
ctcgacagcg atctccgccc cagcaaggta tagattcagt tccttgctcc gatcccaatc  840
tggttgagat gttgctccga tgcgacttga ttatgtcata tatctgcggt ttgcaccgat  900
ctgaagccta gggtttctcg agcgacccag ttatttgcaa tttgcgattt gctcgtttgt  960
tgcgcagcgt agtttatgtt tggagtaatc gaggatttgt atgcggcgtc ggcgctacct  1020
gcttaatcac gccatgtgac gcggttactt gcagaggctg ggttctgtta tgtcgtgatc  1080
taagaatcta gattaggctc agtcgttctt gctgtcgact agtttgtttt gatatccatg  1140
tagtacaagt tacttaaaat ttaggtccaa tatattttgc atgcttttgg cctgttattc  1200
ttgccaacaa gttgtcctgg taaaaagtag atgtgaaagt cacgtattgg gacaaattga  1260
tggtttagtg ctatagttct atagttctgt gatacatcta tctgattttt tttggtctat  1320
tggtgcctaa cttatctgaa aatcatggaa catgaggcta gtttgatcat ggtttagttc  1380
attgtgatta ataatgtatg atttagtagc tattttggtg atcgtgtcat tttatttgtg  1440
aatggaatca ttgtatgtaa atgaagctag ttcaggggtt acgatgtagc tggctttgta  1500
ttctaaaggc tgctattatt catccatcga tttcacctat atgtaatcca gagcttttga  1560
tgtgaaattt gtctgatcct tcactaggaa ggacagaaca ttgttaatat tttggcacat  1620
ctgtcttatt ctcatccttt gtttgaacat gttagcctgt tcaaacagat actgttgtaa  1680
tgtcctagtt atataggtac atatgtgttc tctattgagt ttatggactt ttgtgtgtga  1740
agttatattt cattttgctc aaaactcatg tttgcaagct ttctgacatt attctattgt  1800
tctgaaacag gtg                                                     1813
```

```
SEQ ID NO: 125          moltype = DNA  length = 1813
FEATURE                 Location/Qualifiers
source                  1..1813
                        mol_type = other DNA
                        organism = Setaria italica
```

SEQUENCE: 125
cacgggtaat gcacgcagcc acccaggcgc gcgcgctagc ggagcacggt caggtgacac 60
gggcgtcgtg acgcttccga gttgaagggg ttaacgccag aaacagtgtt tggccagggt 120
atgaacataa caaaaaatat tcacacgaaa gaatggaagt atggagctgc tactgtgtaa 180
atgccaagca ggaaactcac gcccgctaac atccaacggc caacagctcg acgtgccggt 240
cagcagagca tcggaacact ggtgattggt ggagccggca gtatgcgccc cagcacggcc 300
gaggtggtgg tggcccgtgg ccctgctgtc tgcgcggctc gggacaactt gaaactgggc 360
caccgcctcg tcgcaactcg caacccgttg gcggaagaaa ggaatggctc gtaggggccc 420
gggtagaatc gaagaatgtt gcgctgggct tcgattcaca taacatgggc ctgaagctct 480
aaaacgacgg cccggtcgcc gcgcgatgga aagagaccgg atcctcctcg tgaattctgg 540
aaggccacac gagagcgacc caccaccgac gcggaggagt cgtgcgtggt ccaacacggc 600
cggcgggctg ggctgcgacc ttaaccagca aggcacgcca cgacccgccc cgccctcgag 660
gcataaatac cctcccatcc cgttgccgca agactcagat cagattccga tccccagttc 720
ttccccaatc accttgtggt ctctcgtgtc gcggttccca gggacgcctc cggctcgtcg 780
ctcgacagcg atctccgccc cagcaaggta tagattcagt tccttgctcc gatcccaatc 840
tggttgagat gttgctccga tgcgacttga ttatgtcata tatctgcggt ttgcaccgat 900
ctgaagccta gggtttctcg agcgacccag ttatttgcaa tttgcgattt gctcgtttgt 960
tgcgcagcgt agtttatgtt tggagtaatc gaggatttgt atgcggcgtc ggcgctacct 1020
gcttaatcac gccatgtgac gcggttactt gcagaggctg ggttctgtta tgtcgtgatc 1080
taagaatcta gattaggctc agtcgttctt gctgtcgact agtttgtttt gatatccatg 1140
tagtacaagt tacttaaaat ttaggtccaa tatattttgc atgcttttgg cctgttattc 1200
ttgccaacaa gttgtcctgg taaaaagtag atgtgaaagt cacgtattgg gacaaattga 1260
tggtttagtg ctatagttct atagttctgt gatacatcta tctgattttt tttggtctat 1320
tggtgcctaa cttatctgaa aatcatggaa catgaggcta gtttgatcat ggtttagttc 1380
attgtgatta ataatgtatg atttagtagc tattttggtg atcgtgtcat tttatttgtg 1440
aatggaatca ttgtatgtaa atgaagctag ttcaggggtt acgatgtagc tggctttgta 1500
ttctaaaggc tgctattatt catccatcga tttcacctat atgtaatcca gagcttttga 1560
tgtgaaattt gtctgatcct tcactaggaa ggacagaaca ttgttaatat tttggcacat 1620
ctgtcttatt ctcatccttt gtttgaacat gttagcctgt tcaaacagat actgttgtaa 1680
tgtcctagtt atataggtac atatgtgttc tctattgagt ttatggactt ttgtgtgtga 1740
agttatattt cattttgctc aaaactcatg tttgcaagct ttctgacatt attctattgt 1800
tctgaaacag ggt 1813

SEQ ID NO: 126 moltype = DNA length = 1813
FEATURE Location/Qualifiers
source 1..1813
mol_type = other DNA
organism = Setaria italica
SEQUENCE: 126
cacgggtaat gcacgcagcc acccaggcgc gcgcgctagc ggagcacggt caggtgacac 60
gggcgtcgtg acgcttccga gttgaagggg ttaacgccag aaacagtgtt tggccagggt 120
atgaacataa caaaaaatat tcacacgaaa gaatggaagt atggagctgc tactgtgtaa 180
atgccaagca ggaaactcac gcccgctaac atccaacggc caacagctcg acgtgccggt 240
cagcagagca tcggaacact ggtgattggt ggagccggca gtatgcgccc cagcacggcc 300
gaggtggtgg tggcccgtgg ccctgctgtc tgcgcggctc gggacaactt gaaactgggc 360
caccgcctcg tcgcaactcg caacccgttg gcggaagaaa ggaatggctc gtaggggccc 420
gggtagaatc gaagaatgtt gcgctgggct tcgattcaca taacatgggc ctgaagctct 480
aaaacgacgg cccggtcgcc gcgcgatgga aagagaccgg atcctcctcg tgaattctgg 540
aaggccacac gagagcgacc caccaccgac gcggaggagt cgtgcgtggt ccaacacggc 600
cggcgggctg ggctgcgacc ttaaccagca aggcacgcca cgacccgccc cgccctcgag 660
gcataaatac cctcccatcc cgttgccgca agactcagat cagattccga tccccagttc 720
ttccccaatc accttgtggt ctctcgtgtc gcggttccca gggacgcctc cggctcgtcg 780
ctcgacagcg atctccgccc cagcaaggta tagattcagt tccttgctcc gatcccaatc 840
tggttgagat gttgctccga tgcgacttga ttatgtcata tatctgcggt ttgcaccgat 900
ctgaagccta gggtttctcg agcgacccag ttatttgcaa tttgcgattt gctcgtttgt 960
tgcgcagcgt agtttatgtt tggagtaatc gaggatttgt atgcggcgtc ggcgctacct 1020
gcttaatcac gccatgtgac gcggttactt gcagaggctg ggttctgtta tgtcgtgatc 1080
taagaatcta gattaggctc agtcgttctt gctgtcgact agtttgtttt gatatccatg 1140
tagtacaagt tacttaaaat ttaggtccaa tatattttgc atgcttttgg cctgttattc 1200
ttgccaacaa gttgtcctgg taaaaagtag atgtgaaagt cacgtattgg gacaaattga 1260
tggtttagtg ctatagttct atagttctgt gatacatcta tctgattttt tttggtctat 1320
tggtgcctaa cttatctgaa aatcatggaa catgaggcta gtttgatcat ggtttagttc 1380
attgtgatta ataatgtatg atttagtagc tattttggtg atcgtgtcat tttatttgtg 1440
aatggaatca ttgtatgtaa atgaagctag ttcaggggtt acgatgtagc tggctttgta 1500
ttctaaaggc tgctattatt catccatcga tttcacctat atgtaatcca gagcttttga 1560
tgtgaaattt gtctgatcct tcactaggaa ggacagaaca ttgttaatat tttggcacat 1620
ctgtcttatt ctcatccttt gtttgaacat gttagcctgt tcaaacagat actgttgtaa 1680
tgtcctagtt atataggtac atatgtgttc tctattgagt ttatggactt ttgtgtgtga 1740
agttatattt cattttgctc aaaactcatg tttgcaagct ttctgacatt attctattgt 1800
tctgaaacag ggc 1813

SEQ ID NO: 127 moltype = DNA length = 1006
FEATURE Location/Qualifiers
source 1..1006
mol_type = other DNA
organism = Setaria italica
SEQUENCE: 127
gtatagattc agttccttgc tccgatccca atctggttga gatgttgctc cgatgcgact 60
tgattatgtc atatatctgc ggtttgcacc gatctgaagc ctagggtttc tcgagcgacc 120

```
cagttatttg caatttgcga tttgctcgtt tgttgcgcag cgtagtttat gtttggagta  180
atcgaggatt tgtatgcggc gtcggcgcta cctgcttaat cacgccatgt gacgcggtta  240
cttgcagagg ctgggttctg ttatgtcgtg atctaagaat ctagattagg ctcagtcgtt  300
cttgctgtcg actagtttgt tttgatatcc atgtagtaca agttacttaa aatttaggtc  360
caatatattt tgcatgcttt tggcctgtta ttcttgccaa caagttgtcc tggtaaaaag  420
tagatgtgaa agtcacgtat tgggacaaat tgatggttta gtgctatagt tctatagttc  480
tgtgatacat ctatctgatt ttttttggtc tattggtgcc taacttatct gaaaatcatg  540
gaacatgagg ctagtttgat catggtttag ttcattgtga ttaataatgt atgatttagt  600
agctattttg gtgatcgtgt cattttattt gtgaatggaa tcattgtatg taaatgaagc  660
tagttcaggg gttacgatgt agctggcttt gtattctaaa ggctgctatt attcatccat  720
cgatttcacc tatatgtaat ccagagcttt tgatgtgaaa tttgtctgat ccttcactag  780
gaaggacaga acattgttaa tattttggca catctgtctt attctcatcc tttgtttgaa  840
catgttagcc tgttcaaaca gatactgttg taatgtccta gttatatagg tacatatgtg  900
ttctctattg agtttatgga cttttgtgtg tgaagttata tttcattttg ctcaaaactc  960
atgtttgcaa gctttctgac attattctat tgttctgaaa cagggc                 1006
```

```
SEQ ID NO: 128          moltype = DNA  length = 2634
FEATURE                 Location/Qualifiers
source                  1..2634
                        mol_type = other DNA
                        organism = Setaria viridis
SEQUENCE: 128
actgccgcga cacgcctcac tggcgggagg gctccgagcg ctctctcccc ggcggccggc  60
ggagcagcga tctggattgg agagaataga ggaaagagag ggaaaaggag agagatagcg  120
caaagagctg aaaagataag gttgtgcggg ctgtggtgat tagaggacca ctaatccctc  180
catctcctaa tgacgcggtg cccaagacca gtgccgcggc acaccagcgt ctaagtgaac  240
ttccgctaac cttccggtca ttgcgcctga aagatgtcat gtggcgaggc ccccctctca  300
gtagattgcc aactgcctac cgtgccactc ttccatgcat gattgctccc gtctatcccg  360
tttctcacaa cagatagaca acagtaagca tcactaaagc aagcatgtgt agaaccttaa  420
aaaaaggctt atactaccag tatactatca accagcatgc cgtttttgaa gtatccagga  480
ttagaagctt ctactgcgct tttatattat agctgtggac ctgtggtaac ctttctcttt  540
tggcgcttgc ttaatctcgg ccgtgctggt ccatgcttag gcactaggca gagatagagc  600
cgggggtgaa tggggctaaa gctcagctgc tcgaggggcc gtgggctggt ttccactagc  660
ctacagctgt gccacgtgcg gccgcgcaag ccgaagcaag cacgctgagc cgttggacag  720
cttgtcataa tgccattacg tggattacag gtaactggcc ctgtaactac tcgttcggcc  780
atcatcaaac gacgacgtcc gctaggcgac gacacgggta atgcacgcag ccacccaggc  840
gcgcgcgcta gcggagcacg gtcaggtgac acgggcgtcg tgacgcttcc gagttgaagg  900
ggttaacgcc agaaacagtg tttggccagg gtatgaacat aacaaaaaat attcacacga  960
aagaatggaa gtatggagct gctactgtgt aaatgccaag caggaaactc acgcccgcta  1020
acatccaacg gccaacagct cgacgtgccg gtcagcagag acatcggaac actggtgatt  1080
ggtggagccg gcagtatgcg ccccagcacg gccgaggtgg tggtggcccg tggccctgct  1140
gtctgcgcgg ctcgggacaa cttgaaactg ggccaccgcc tcgtcgcaac tcgcaacccg  1200
ttggcggaag aaaggaatgg ctcgtagggg cccgggtaga atccaagaat gttgcgctgg  1260
gcttcgattc acataacatg ggcctgaagc tctaaaacga cggcccggtc accgggcgat  1320
ggaaagagac cggatcctcc tcgtgaattc tggaaggcca cacgagagcg acccaccacc  1380
gacgcggagg agtcgtgcgt ggtccaacac ggccggcggg ctgggctgcg accttaacca  1440
gcaaggcacg ccacgacccg cctcgccctc gaggcataaa taccctccca tcccgttgcc  1500
gcaagactca gatcagattc cgatccccag ttcttcccca atcaccttgt ggtctctcgt  1560
gtcgcggttc ccagggacgc ctccggctcg tcgctcgaca gcgatctccg ccccagcaag  1620
gtatagattc agttccttgc tccgatccca atctggttga gatgttgctc cgatgcgact  1680
tgattatgtc atatatctgc ggtttgcacc gatctgaagc ctagggtttc tcgagcgacc  1740
cagttgtttg caatttgcga tttgctcgtt tgttgcgcat cgtagtttat gtttggagta  1800
atcgaggatt tgtatgcggc gtcggcgcta cctgcttaat cacgccatgt gacgcggtta  1860
cttgcagagg ctgggttagt gggttctgtt atgtcgtgat ctaagaatct agattaggct  1920
cagtcgttct tgctgtcgac tagtttgttt tgatatccat gtagtacaag ttacttaaaa  1980
tttaggtcca atatattttg catgcttttg gcctgttatt cttgccaaca agttgtcctg  2040
gtaaaaagta gatgtgaaag tcacgtattg ggacaaattg atggttaagt gctatagttc  2100
tatagttctg tgatacatct atctgatttt ttttggtcta ttggtgccta acttatctga  2160
aaatcatgga acatgaggct agtttgatca tggtttagtt cattgtgatt aataatgtat  2220
gatttagtag ctattttggt gatcgtgtca ttttatttgt gaatggaatc attgtatgta  2280
aatgaagcta gttcaggggt tatgatgtag ctggctttgt attctaaagg ctgctattat  2340
tcatccatcg atttcaccta tatgtaatcc agagctttcg atgtgaaatt tgtctgatcc  2400
ttcactagga aggacagaac attgttaata ttttggcaca tctgtcttat tctcatcctt  2460
tgtttgaaca tgttagcctg ttcaaacaga tactgttgta atgtcctagt tatataggta  2520
catatgtgtt ctctattgag tttatggact tttgtgtgtg aagttatatt tcattttgct  2580
caaaactcat gtttgcaagc tttctgacat tattctattg ttctgaaaca ggtg         2634
```

```
SEQ ID NO: 129          moltype = DNA  length = 1014
FEATURE                 Location/Qualifiers
source                  1..1014
                        mol_type = other DNA
                        organism = Setaria viridis
SEQUENCE: 129
gtatagattc agttccttgc tccgatccca atctggttga gatgttgctc cgatgcgact  60
tgattatgtc atatatctgc ggtttgcacc gatctgaagc ctagggtttc tcgagcgacc  120
cagttgtttg caatttgcga tttgctcgtt tgttgcgcat cgtagtttat gtttggagta  180
atcgaggatt tgtatgcggc gtcggcgcta cctgcttaat cacgccatgt gacgcggtta  240
cttgcagagg ctgggttagt gggttctgtt atgtcgtgat ctaagaatct agattaggct  300
cagtcgttct tgctgtcgac tagtttgttt tgatatccat gtagtacaag ttacttaaaa  360
```

```
tttaggtcca atatatttg catgcttttg gcctgttatt cttgccaaca agttgtcctg  420
gtaaaaagta gatgtgaaag tcacgtattg ggacaaattg atggttaagt gctatagttc  480
tatagttctg tgatacatct atctgatttt ttttggtcta ttggtgccta acttatctga  540
aaatcatgga acatgaggct agtttgatca tggtttagtt cattgtgatt aataatgtat  600
gatttagtag ctattttggt gatcgtgtca ttttatttgt gaatggaatc attgtatgta  660
aatgaagcta gttcaggggt tatgatgtag ctggctttgt attctaaagg ctgctattat  720
tcatccatcg atttcaccta tatgtaatcc agagctttcg atgtgaaatt tgtctgatcc  780
ttcactagga aggacagaac attgttaata ttttggcaca tctgtcttat tctcatcctt  840
tgtttgaaca tgttagcctg ttcaaacaga tactgttgta atgtcctagt tatataggta  900
catatgtgtt ctctattgag tttatggact tttgtgtgtg aagttatatt tcattttgct  960
caaaactcat gtttgcaagc tttctgacat tattctattg ttctgaaaca ggtg        1014

SEQ ID NO: 130         moltype = DNA  length = 2634
FEATURE                Location/Qualifiers
source                 1..2634
                       mol_type = other DNA
                       organism = Setaria viridis
SEQUENCE: 130
actgccgcga cacgcctcac tggcgggagg gctccgagcg ctctctcccc ggcggccggc  60
ggagcagcga tctggattgg agagaataga ggaaagagag ggaaaaggag agagatagcg  120
caaagagctg aaaagataag gttgtgcggg ctgtggtgat tagaggacca ctaatccctc  180
catctcctaa tgacgcggtg cccaagacca gtgccgcggc acaccagcgt ctaagtgaac  240
ttccgctaac cttccggtca ttgcgcctga aagatgtcat gtggcgaggc ccccctctca  300
gtagattgcc aactgcctac cgtgccactc ttccatgcat gattgctccc gtctatcccg  360
tttctcacaa cagatagaca acagtaagca tcactaaagc aagcatgtgt agaaccttaa  420
aaaaaggctt atactaccag tatactatca accagcatgc cgtttttgaa gtatccagga  480
ttagaagctt ctactgcgct tttatattat agctgtggac ctgtggtaac ctttctcttt  540
tggcgcttgc ttaatctcgg ccgtgctggt ccatgcttag gcactaggca gagatagagc  600
cgggggtgaa tggggctaaa gctcagctgc tcgaggggcc gtgggctggt ttccactagc  660
ctacagctgt gccacgtgcg gccgcgcaag ccgaagcaag cacgctgagc cgttggacag  720
cttgtcataa tgccattacg tggattacag gtaactggcc ctgtaactac tcgttcggcc  780
atcatcaaac gacgacgtcc gctaggcgac gacacgggta atgcacgcag ccacccaggc  840
gcgcgcgcta gcggagcacg gtcaggtgac acgggcgtcg tgacgcttcc gagttgaagg  900
ggttaacgcc agaaacagtg tttggccagg gtatgaacat aacaaaaaat attcacacga  960
aagaatggaa gtatggagct gctactgtgt aaatgccaag caggaaactc acgcccgcta  1020
acatccaacg gccaacagct cgacgtgccg gtcagcagag acatcggaac actggtgatt  1080
ggtggagccg gcagtatgcg ccccagcacg gccgaggtgg tggtggcccg tggccctgct  1140
gtctgcgcgg ctcgggacaa cttgaaactg ggccaccgcc tcgtcgcaac tcgcaacccg  1200
ttggcggaag aaaggaatgg ctcgtagggg cccgggtaga atccaagaat gttgcgctgg  1260
gcttcgattc acataacatg ggcctgaagc tctaaaacga cggcccggtc accgggcgat  1320
ggaaagagac cggatcctcc tcgtgaattc tggaaggcca cacgagagcg acccaccacc  1380
gacgcggagg agtcgtgcgt ggtccaacac ggccggcggg ctgggctgcg accttaacca  1440
gcaaggcacg ccacgacccg cctcgccctc gaggcataaa taccctccca tcccgttgcc  1500
gcaagactca gatcagattc cgatccccag ttcttcccca atcaccttgt ggtctctcgt  1560
gtcgcggttc ccagggacgc ctccggctcg tcgctcgaca gcgatctccg ccccagcaag  1620
gtatagattc agttccttgc tccgatccca atctggttga gatgttgctc cgatgcgact  1680
tgattatgtc atatatctgc ggtttgcacc gatctgaagc ctagggtttc tcgagcgacc  1740
cagttgtttg caatttgcga tttgctcgtt tgttgcgcat cgtagtttat gtttggagta  1800
atcgaggatt tgtatgcggc gtcggcgcta cctgcttaat cacgccatgt gacgcggtta  1860
cttgcagagg ctgggttagt gggttctgtt atgtcgtgat ctaagaatct agattaggct  1920
cagtcgttct tgctgtcgac tagtttgttt tgatatccat gtagtacaag ttacttaaaa  1980
tttaggtcca atatatttg catgcttttg gcctgttatt cttgccaaca agttgtcctg  2040
gtaaaaagta gatgtgaaag tcacgtattg ggacaaattg atggttaagt gctatagttc  2100
tatagttctg tgatacatct atctgatttt ttttggtcta ttggtgccta acttatctga  2160
aaatcatgga acatgaggct agtttgatca tggtttagtt cattgtgatt aataatgtat  2220
gatttagtag ctattttggt gatcgtgtca ttttatttgt gaatggaatc attgtatgta  2280
aatgaagcta gttcaggggt tatgatgtag ctggctttgt attctaaagg ctgctattat  2340
tcatccatcg atttcaccta tatgtaatcc agagctttcg atgtgaaatt tgtctgatcc  2400
ttcactagga aggacagaac attgttaata ttttggcaca tctgtcttat tctcatcctt  2460
tgtttgaaca tgttagcctg ttcaaacaga tactgttgta atgtcctagt tatataggta  2520
catatgtgtt ctctattgag tttatggact tttgtgtgtg aagttatatt tcattttgct  2580
caaaactcat gtttgcaagc tttctgacat tattctattg ttctgaaaca gggt        2634

SEQ ID NO: 131         moltype = DNA  length = 1014
FEATURE                Location/Qualifiers
source                 1..1014
                       mol_type = other DNA
                       organism = Setaria viridis
SEQUENCE: 131
gtatagattc agttccttgc tccgatccca atctggttga gatgttgctc cgatgcgact  60
tgattatgtc atatatctgc ggtttgcacc gatctgaagc ctagggtttc tcgagcgacc  120
cagttgtttg caatttgcga tttgctcgtt tgttgcgcat cgtagtttat gtttggagta  180
atcgaggatt tgtatgcggc gtcggcgcta cctgcttaat cacgccatgt gacgcggtta  240
cttgcagagg ctgggttagt gggttctgtt atgtcgtgat ctaagaatct agattaggct  300
cagtcgttct tgctgtcgac tagtttgttt tgatatccat gtagtacaag ttacttaaaa  360
tttaggtcca atatatttg catgcttttg gcctgttatt cttgccaaca agttgtcctg  420
gtaaaaagta gatgtgaaag tcacgtattg ggacaaattg atggttaagt gctatagttc  480
tatagttctg tgatacatct atctgatttt ttttggtcta ttggtgccta acttatctga  540
aaatcatgga acatgaggct agtttgatca tggtttagtt cattgtgatt aataatgtat  600
```

```
gatttagtag ctattttggt gatcgtgtca ttttatttgt gaatggaatc attgtatgta  660
aatgaagcta gttcaggggt tatgatgtag ctggctttgt attctaaagg ctgctattat  720
tcatccatcg atttcaccta tatgtaatcc agagctttcg atgtgaaatt tgtctgatcc  780
ttcactagga aggacagaac attgttaata ttttggcaca tctgtcttat tctcatcctt  840
tgtttgaaca tgttagcctg ttcaaacaga tactgttgta atgtcctagt tatataggta  900
catatgtgtt ctctattgag tttatggact tttgtgtgtg aagttatatt tcattttgct  960
caaaactcat gtttgcaagc tttctgacat tattctattg ttctgaaaca gggt        1014

SEQ ID NO: 132          moltype = DNA  length = 2176
FEATURE                 Location/Qualifiers
source                  1..2176
                        mol_type = other DNA
                        organism = Setaria viridis
SEQUENCE: 132
gccgtttttg aagtatccag gattagaagc ttctactgcg cttttatatt atagctgtgg  60
acctgtggta acctttctct tttggcgctt gcttaatctc ggccgtgctg gtccatgctt  120
aggcactagg cagagataga gccgggggtg aatggggcta aagctcagct gctcgagggg  180
ccgtgggctg gtttccacta gcctacagct gtgccacgtg cggccgcgca agccgaagca  240
agcacgctga gccgttggac agcttgtcat aatgccatta cgtggattac aggtaactgg  300
ccctgtaact actcgttcgg ccatcatcaa acgacgacgt ccgctaggcg acgacacggg  360
taatgcacgc agccacccag gcgcgcgcgc tagcggagca cggtcaggtg acacgggcgt  420
cgtgacgctt ccgagttgaa ggggttaacg ccagaaacag tgtttggcca gggtatgaac  480
ataacaaaaa atattcacac gaaagaatgg aagtatggag ctgctactgt gtaaatgcca  540
agcaggaaac tcacgcccgc taacatccaa cggccaacag ctcgacgtgc cggtcagcag  600
agacatcgga acactggtga ttggtggagc cggcagtatg cgccccagca cggccgaggt  660
ggtggtggcc cgtggccctg ctgtctgcgc ggctcgggac aacttgaaac tgggccaccg  720
cctcgtcgca actcgcaacc cgttggcgga agaaaggaat ggctcgtagg ggcccgggta  780
gaatccaaga atgttgcgct gggcttcgat tcacataaca tgggcctgaa gctctaaaac  840
gacggcccgg tcaccgggcg atggaaagag accggatcct cctcgtgaat tctggaaggc  900
cacacgagag cgacccacca ccgacgcgga ggagtcgtgc gtggtccaac acggccggcg  960
ggctgggctg cgaccttaac cagcaaggca cgccacgacc cgcctcgccc tcgaggcata  1020
aataccctcc catcccgttg ccgcaagact cagatcagat tccgatcccc agttcttccc  1080
caatcacctt gtggtctctc gtgtcgcggt tcccagggac gcctccggct cgtcgctcga  1140
cagcgatctc cgccccagca aggtatagat tcagttcctt gctccgatcc caatctggtt  1200
gagatgttgc tccgatgcga cttgattatg tcatatatct gcggtttgca ccgatctgaa  1260
gcctagggtt tctcgagcga cccagttgtt tgcaatttgc gatttgctcg tttgttgcgc  1320
atcgtagttt atgtttggag taatcgagga tttgtatgcg gcgtcggcgc tacctgctta  1380
atcacgccat gtgacgcggt tacttgcaga ggctgggtta gtgggttctg ttatgtcgtg  1440
atctaagaat ctagattagg ctcagtcgtt cttgctgtcg actagtttgt tttgatatcc  1500
atgtagtaca agttacttaa aatttaggtc caatatattt tgcatgcttt tggcctgtta  1560
ttcttgccaa caagttgtcc tggtaaaaag tagatgtgaa agtcacgtat tgggacaaat  1620
tgatggttaa gtgctatagt tctatagttc tgtgatacat ctatctgatt ttttttggtc  1680
tattggtgcc taacttatct gaaaatcatg gaacatgagg ctagtttgat catggtttag  1740
ttcattgtga ttaataatgt atgatttagt agctattttg gtgatcgtgt cattttattt  1800
gtgaatggaa tcattgtatg taaatgaagc tagttcaggg gttatgatgt agctggcttt  1860
gtattctaaa ggctgctatt attcatccat cgatttcacc tatatgtaat ccagagcttt  1920
cgatgtgaaa tttgtctgat ccttcactag gaaggacaga acattgttaa tattttggca  1980
catctgtctt attctcatcc tttgtttgaa catgttagcc tgttcaaaca gatactgttg  2040
taatgtccta gttatatagg tacatatgtg ttctctattg agtttatgga cttttgtgtg  2100
tgaagttata tttcattttg ctcaaaactc atgtttgcaa gctttctgac attattctat  2160
tgttctgaaa caggtg                                                  2176

SEQ ID NO: 133          moltype = DNA  length = 1822
FEATURE                 Location/Qualifiers
source                  1..1822
                        mol_type = other DNA
                        organism = Setaria viridis
SEQUENCE: 133
cacgggtaat gcacgcagcc acccaggcgc gcgcgctagc ggagcacggt caggtgacac  60
gggcgtcgtg acgcttccga gttgaagggg ttaacgccag aaacagtgtt tggccagggt  120
atgaacataa caaaaaatat tcacacgaaa gaatggaagt atggagctgc tactgtgtaa  180
atgccaagca ggaaactcac gcccgctaac atccaacggc caacagctcg acgtgccggt  240
cagcagagac atcggaacac tggtgattgg tggagccggc agtatgcgcc ccagcacggc  300
cgaggtggtg gtggcccgtg gccctgctgt ctgcgcggct cgggacaact tgaaactggg  360
ccaccgcctc gtcgcaactc gcaacccgtt ggcggaagaa aggaatggct cgtaggggcc  420
cgggtagaat ccaagaatgt tgcgctgggc ttcgattcac ataacatggg cctgaagctc  480
taaaacgacg gcccggtcac cgggcgatgg aaagagaccg gatcctcctt gtgaattctg  540
gaaggccaca cgagagcgac ccaccaccga cgcggaggag tcgtgcgtgg tccaacacgg  600
ccggcgggct gggctgcgac cttaaccagc aaggcacgcc acgacccgcc tcgccctcga  660
ggcataaata ccctcccatc ccgttgccgc aagactcaga tcagattccg atccccagtt  720
cttccccaat caccttgtgg tctctcgtgt cgcggttccc agggacgcct ccggctcgtc  780
gctcgacagc gatctccgcc ccagcaaggt atagattcag ttccttgctc cgatcccaat  840
ctggttgaga tgttgctccg atgcgacttg attatgtcat atatctgcgg tttgcaccga  900
tctgaagcct agggtttctc gagcgaccca gttgtttgca atttgcgatt tgctcgtttg  960
ttgcgcatcg tagtttatgt ttggagtaat cgaggatttg tatgcggcgt cggcgctacc  1020
tgcttaatca cgccatgtga cgcggttact tgcagaggct gggttagtgg gttctgttat  1080
gtcgtgatct aagaatctag attaggctca gtcgttcttg ctgtcgacta gtttgttttg  1140
atatccatgt agtacaagtt acttaaaatt taggtccaat atattttgca tgcttttggc  1200
ctgttattct tgccaacaag ttgtcctggt aaaaagtaga tgtgaaagtc acgtattggg  1260
```

```
acaaattgat ggttaagtgc tatagttcta tagttctgtg atacatctat ctgatttttt  1320
ttggtctatt ggtgcctaac ttatctgaaa atcatggaac atgaggctag tttgatcatg  1380
gtttagttca ttgtgattaa taatgtatga tttagtagct attttggtga tcgtgtcatt  1440
ttatttgtga atggaatcat tgtatgtaaa tgaagctagt tcaggggtta tgatgtagct  1500
ggctttgtat tctaaaggct gctattattc atccatcgat ttcacctata tgtaatccag  1560
agctttcgat gtgaaatttg tctgatcctt cactaggaag gacagaacat tgttaatatt  1620
ttggcacatc tgtcttattc tcatcctttg tttgaacatg ttagcctgtt caaacagata  1680
ctgttgtaat gtcctagtta tataggtaca tatgtgttct ctattgagtt tatggacttt  1740
tgtgtgtgaa gttatatttc attttgctca aaactcatgt ttgcaagctt tctgacatta  1800
ttctattgtt ctgaaacagg tg                                            1822
```

```
SEQ ID NO: 134          moltype = DNA  length = 1822
FEATURE                 Location/Qualifiers
source                  1..1822
                        mol_type = other DNA
                        organism = Setaria viridis
SEQUENCE: 134
cacgggtaat gcacgcagcc acccaggcgc gcgcgctagc ggagcacggt caggtgacac  60
gggcgtcgtg acgcttccga gttgaagggg ttaacgccag aaacagtgtt tggccagggt  120
atgaacataa caaaaaatat tcacacgaaa gaatggaagt atggagctgc tactgtgtaa  180
atgccaagca ggaaactcac gcccgctaac atccaacggc caacagctcg acgtgccggt  240
cagcagagac atcggaacac tggtgattgg tggagccggc agtatgcgcc ccagcacggc  300
cgaggtggtg gtggcccgtg gccctgctgt ctgcgcggct cgggacaact tgaaactggg  360
ccaccgcctc gtcgcaactc gcaacccgtt ggcggaagaa aggaatggct cgtaggggcc  420
cgggtagaat ccaagaatgt tgcgctgggc ttcgattcac ataacatggg cctgaagctc  480
taaaacgacg gcccggtcac cgggcgatgg aaagagaccg gatcctcctc gtgaattctg  540
gaaggccaca cgagagcgac ccaccaccga cgcggaggag tcgtgcgtgg tccaacacgg  600
ccggcgggct gggctgcgac cttaaccagc aaggcacgcc acgacccgcc tcgccctcga  660
ggcataaata ccctcccatc ccgttgccgc aagactcaga tcagattccg atccccagtt  720
cttccccaat caccttgtgg tctctcgtgt cgcggttccc agggacgcct ccggctcgtc  780
gctcgacagc gatctccgcc ccagcaaggt atagattcag ttccttgctc cgatcccaat  840
ctggttgaga tgttgctccg atgcgacttg attatgtcat atatctgcgg tttgcaccga  900
tctgaagcct agggtttctc gagcgaccca gttgtttgca atttgcgatt tgctcgtttg  960
ttgcgcatcg tagtttatgt ttggagtaat cgaggatttg tatgcggcgt cggcgctacc  1020
tgcttaatca cgccatgtga cgcggttact tgcagaggct gggttagtgg gttctgttat  1080
gtcgtgatct aagaatctag attaggctca gtcgttcttg ctgtcgacta gtttgttttg  1140
atatccatgt agtacaagtt acttaaaatt taggtccaat atattttgca tgcttttggc  1200
ctgttattct tgccaacaag ttgtcctggt aaaaagtaga tgtgaaagtc acgtattggg  1260
acaaattgat ggttaagtgc tatagttcta tagttctgtg atacatctat ctgatttttt  1320
ttggtctatt ggtgcctaac ttatctgaaa atcatggaac atgaggctag tttgatcatg  1380
gtttagttca ttgtgattaa taatgtatga tttagtagct attttggtga tcgtgtcatt  1440
ttatttgtga atggaatcat tgtatgtaaa tgaagctagt tcaggggtta tgatgtagct  1500
ggctttgtat tctaaaggct gctattattc atccatcgat ttcacctata tgtaatccag  1560
agctttcgat gtgaaatttg tctgatcctt cactaggaag gacagaacat tgttaatatt  1620
ttggcacatc tgtcttattc tcatcctttg tttgaacatg ttagcctgtt caaacagata  1680
ctgttgtaat gtcctagtta tataggtaca tatgtgttct ctattgagtt tatggacttt  1740
tgtgtgtgaa gttatatttc attttgctca aaactcatgt ttgcaagctt tctgacatta  1800
ttctattgtt ctgaaacagg tg                                            1822
```

```
SEQ ID NO: 135          moltype = DNA  length = 681
FEATURE                 Location/Qualifiers
source                  1..681
                        mol_type = other DNA
                        organism = Setaria viridis
SEQUENCE: 135
cacgggtaat gcacgcagcc acccaggcgc gcgcgctagc ggagcacggt caggtgacac  60
gggcgtcgtg acgcttccga gttgaagggg ttaacgccag aaacagtgtt tggccagggt  120
atgaacataa caaaaaatat tcacacgaaa gaatggaagt atggagctgc tactgtgtaa  180
atgccaagca ggaaactcac gcccgctaac atccaacggc caacagctcg acgtgccggt  240
cagcagagac atcggaacac tggtgattgg tggagccggc agtatgcgcc ccagcacggc  300
cgaggtggtg gtggcccgtg gccctgctgt ctgcgcggct cgggacaact tgaaactggg  360
ccaccgcctc gtcgcaactc gcaacccgtt ggcggaagaa aggaatggct cgtaggggcc  420
cgggtagaat ccaagaatgt tgcgctgggc ttcgattcac ataacatggg cctgaagctc  480
taaaacgacg gcccggtcac cgggcgatgg aaagagaccg gatcctcctc gtgaattctg  540
gaaggccaca cgagagcgac ccaccaccga cgcggaggag tcgtgcgtgg tccaacacgg  600
ccggcgggct gggctgcgac cttaaccagc aaggcacgcc acgacccgcc tcgccctcga  660
ggcataaata ccctcccatc c                                             681
```

```
SEQ ID NO: 136          moltype = DNA  length = 1822
FEATURE                 Location/Qualifiers
source                  1..1822
                        mol_type = other DNA
                        organism = Setaria viridis
SEQUENCE: 136
cacgggtaat gcacgcagcc acccaggcgc gcgcgctagc ggagcacggt caggtgacac  60
gggcgtcgtg acgcttccga gttgaagggg ttaacgccag aaacagtgtt tggccagggt  120
atgaacataa caaaaaatat tcacacgaaa gaatggaagt atggagctgc tactgtgtaa  180
atgccaagca ggaaactcac gcccgctaac atccaacggc caacagctcg acgtgccggt  240
cagcagagac atcggaacac tggtgattgg tggagccggc agtatgcgcc ccagcacggc  300
```

```
cgaggtggtg gtggcccgtg gccctgctgt ctgcgcggct cgggacaact tgaaactggg  360
ccaccgcctc gtcgcaactc gcaacccgtt ggcggaagaa aggaatggct cgtaggggcc  420
cgggtagaat ccaagaatgt tgcgctgggc ttcgattcac ataacatggg cctgaagctc  480
taaaacgacg gcccggtcac cgggcgatgg aaagagaccg gatcctcctt gtgaattctg  540
gaaggccaca cgagagcgac ccaccaccga cgcggaggag tcgtgcgtgg tccaacacgg  600
ccggcgggct gggctgcgac cttaaccagc aaggcacgcc acgacccgcc tcgccctcga  660
ggcataaata ccctcccatc ccgttgccgc aagactcaga tcagattccg atccccagtt  720
cttccccaat caccttgtgg tctctcgtgt cgcggttccc agggacgcct ccggctcgtc  780
gctcgacagc gatctccgcc ccagcaaggt atagattcag ttccttgctc cgatcccaat  840
ctggttgaga tgttgctccg atgcgacttg attatgtcat atatctgcgg tttgcaccga  900
tctgaagcct agggtttctc gagcgaccca gttgtttgca atttgcgatt tgctcgtttg  960
ttgcgcatcg tagtttatgt ttggagtaat cgaggatttg tatgcggcgt cggcgctacc  1020
tgcttaatca cgccatgtga cgcggttact tgcagaggct gggttagtgg gttctgttat  1080
gtcgtgatct aagaatctag attaggctca gtcgttcttg ctgtcgacta gtttgttttg  1140
atatccatgt agtacaagtt acttaaaatt taggtccaat atattttgca tgcttttggc  1200
ctgttattct tgccaacaag ttgtcctggt aaaaagtaga tgtgaaagtc acgtattggg  1260
acaaattgat ggttaagtgc tatagttcta tagttctgtg atacatctat ctgatttttt  1320
ttggtctatt ggtgcctaac ttatctgaaa atcatggaac atgaggctag tttgatcatg  1380
gtttagttca ttgtgattaa taatgtatga tttagtagct attttggtga tcgtgtcatt  1440
ttatttgtga atggaatcat tgtatgtaaa tgaagctagt tcaggggtta tgatgtagct  1500
ggctttgtat tctaaaggct gctattattc atccatcgat ttcacctata tgtaatccag  1560
agctttcgat gtgaaatttg tctgatcctt cactaggaag gacagaacat tgttaatatt  1620
ttggcacatc tgtcttattc tcatcctttg tttgaacatg ttagcctgtt caaacagata  1680
ctgttgtaat gtcctagtta tataggtaca tatgtgttct ctattgagtt tatggacttt  1740
tgtgtgtgaa gttatatttc attttgctca aaactcatgt ttgcaagctt tctgacatta  1800
ttctattgtt ctgaaacagg gt                                          1822

SEQ ID NO: 137         moltype = DNA  length = 1925
FEATURE                Location/Qualifiers
source                 1..1925
                       mol_type = other DNA
                       organism = Zea mays
                       sub_species = Mexicana
SEQUENCE: 137
gtcgtgcccc tctctagaga taatgagcat tgcatgtcta agttataaaa aattaccaca  60
tatttttttt tgtcacactt gtgtttgaag tgcagtttat ctatctctat acatatattt  120
aaacttcact atatgaataa tatagtctat agtattaaaa taatatcaat gttttagatg  180
attatataac tgaactgcta gacatggtct aaaggacaac cgagtatttt gacaacatga  240
ctctacagtt ttatcttttt agtgtgcatg tgttcttttt acttttgcaa atagcttcac  300
ctatataata cttcatccat tttattagta catccattta ctaaattttt agtacatcta  360
ttttattcta ttttagcctc taaattaaga aaacttaaac tctattttag ttttttattt  420
aataatttag atataaaata gaataaaata aagtgactaa aaaataacta aatacctttt  480
aagaaataaa aaaactaagg aaccattttt cttgttccga gtagataatg acagcctgtt  540
caacgccgtc gacgagtcta acggacacca accagcgaac cagcagcgtc gcgtcgggcc  600
aagcgaagca gacggcacgg catctctgta gctgcctctg gacccctctc gagagttccg  660
ctccaccgtt ggacttgctc cgctgtcggc atccagaaat tgcgtggcgg agcggcagac  720
gtgagccggc acggcaggcg gcctcctctc acggcaccgg cagctacggg ggattccttt  780
cccaccgctc cttcgctttc ccttcctcgc ccgccgtaat aaatagaccc cctccacacc  840
ctctttcccc aacctcgtgt tcgttcggag cgcgcacaca cacaaccaga tctcccccaa  900
atccacccgt cggcacctcc gcttcaaggt acgccgctca tcctcctccc ccccctctct  960
ctaccttctc tagatcggcg tttcggtcca tggttagggc ccggtagttc tacttctgtt  1020
catgtttgtg ttagatccgt gtttgtgtta gatccgtgct gctagatttc gtacacggat  1080
gcgacctgta catcagacat gttctgattg ctaacttgcc agtgtttctc tttggggaat  1140
cctgggatgg ctctagccgt tccgcagacg ggatcgattt catgaatttt ttttgtttcg  1200
ttgcataggg tttggtttgc ccttttcctt tatttcaata tatgccgtgc acttgtttgt  1260
cgggtcatct tttcatgttt tttttggctt ggttgtgatg atgtggtctg gttgggcggt  1320
cgttctagat cggagtagaa tactgtttca aactacctgg tggatttatt aaaggatctg  1380
tatgtatgtg ccatacatct tcatagttac gagtttaaga tgatggatgg aaatatcgat  1440
ctaggatagg tatacatgtt gatgcgggtt ttactgatgc atatacagag atgctttttt  1500
ttcgcttggt tgtgatgatg tggtctggtc gggcggtcgt tctagatcgg agtagaatac  1560
tgtttcaaac tacctggtgg atttattaat tttggatctg tatgtgtgtc atacatcttc  1620
atagttacga gtttaagatc gatggaaata tcgatctagg ataggtatac atgttgatgt  1680
gggttttact gatgcatata catggcatat gcagcatcta ttcatatgct ctaaccttga  1740
gtacctatct attataataa acaagtatgt tttataatta ttttgatctt gatatacttg  1800
gatgatggca tatgcagcag ctatatgtgg atttttttag ccctgccttc atacgctatt  1860
tatttgcttg gtactgtttc ttttgtcgat gctcaccctg ttgtttggtg atacttctgc  1920
aggtc                                                             1925

SEQ ID NO: 138         moltype = DNA  length = 997
FEATURE                Location/Qualifiers
source                 1..997
                       mol_type = other DNA
                       organism = Zea mays
                       sub_species = Mexicana
SEQUENCE: 138
gtacgccgct catcctcctc cccccccctct ctctaccttc tctagatcgg cgtttcggtc  60
catggttagg gcccggtagt tctacttctg ttcatgtttg tgttagatcc gtgtttgtgt  120
tagatccgtg ctgctagatt tcgtacacgg atgcgacctg tacatcagac atgttctgat  180
tgctaacttg ccagtgtttc tctttgggga atcctgggat ggctctagcc gttccgcaga  240
```

```
cgggatcgat ttcatgaatt ttttttgttt cgttgcatag ggtttggttt gccctttcc  300
tttatttcaa tatatgccgt gcacttgttt gtcgggtcat cttttcatgt tttttttggc  360
ttggttgtga tgatgtggtc tggttgggcg gtcgttctag atcggagtag aatactgttt  420
caaactacct ggtggattta ttaaaggatc tgtatgtatg tgccatacat cttcatagtt  480
acgagtttaa gatgatggat ggaaatatcg atctaggata ggtatacatg ttgatgcggg  540
ttttactgat gcatatacag agatgctttt ttttcgcttg gttgtgatga tgtggtctgg  600
tcgggcggtc gttctagatc ggagtagaat actgtttcaa actacctggt ggatttatta  660
attttggatc tgtatgtgtg tcatacatct tcatagttac gagtttaaga tcgatggaaa  720
tatcgatcta ggataggtat acatgttgat gtgggtttta ctgatgcata tacatggcat  780
atgcagcatc tattcatatg ctctaacctt gagtacctat ctattataat aaacaagtat  840
gttttataat tattttgatc ttgatatact tggatgatgg catatgcagc agctatatgt  900
ggattttttt agccctgcct tcatacgcta tttatttgct tggtactgtt tcttttgtcg  960
atgctcaccc tgttgtttgg tgatacttct gcaggtc                          997

SEQ ID NO: 139         moltype = DNA  length = 1925
FEATURE                Location/Qualifiers
source                 1..1925
                       mol_type = other DNA
                       organism = Zea mays
                       sub_species = Mexicana
SEQUENCE: 139
gtcgtgcccc tctctagaga taatgagcat tgcatgtcta agttataaaa aattaccaca  60
tatttttttt tgtcacactt gtgtttgaag tgcagtttat ctatctctat acatatattt  120
aaacttcact atatgaataa tatagtctat agtattaaaa taatatcaat gttttagatg  180
attatataac tgaactgcta gacatggtct aaaggacaac cgagtatttt gacaacatga  240
ctctacagtt ttatcttttt agtgtgcatg tgttcttttt acttttgcaa atagcttcac  300
ctatataata cttcatccat tttattagta catccattta ctaaattttt agtacatcta  360
ttttattcta ttttagcctc taaattaaga aaacttaaac tctattttag tttttttattt  420
aataatttag atataaaata gaataaaata aagtgactaa aaaataacta aataccttttt  480
aagaaataaa aaaactaagg aaccattttt cttgttccga gtagataatg acagcctgtt  540
caacgccgtc gacgagtcta acggacacca accagcgaac cagcagcgtc gcgtcgggcc  600
aagcgaagca gacggcacgg catctctgta gctgcctctg gacccctctc gagagttccg  660
ctccaccgtt ggacttgctc cgctgtcggc atccagaaat tgcgtggcgg agcggcagac  720
gtgagccggc acggcaggcg gcctcctctc acggcaccgg cagctacggg ggattccttt  780
cccaccgctc cttcgctttc ccttcctcgc ccgccgtaat aaatagaccc cctccacacc  840
ctctttcccc aacctcgtgt tcgttcggag cgcgcacaca cacaaccaga tctcccccaa  900
atccacccgt cggcacctcc gcttcaaggt acgccgctca tcctcctccc cccctctct  960
ctaccttctc tagatcggcg tttcggtcca tggttagggc ccggtagttc tacttctgtt  1020
catgtttgtg ttagatccgt gtttgtgtta gatccgtgct gctagatttc gtacacggat  1080
gcgacctgta catcagacat gttctgattg ctaacttgcc agtgtttctc tttggggaat  1140
cctgggatgg ctctagccgt tccgcagacg ggatcgattt catgaatttt ttttgtttcg  1200
ttgcataggg tttggtttgc ccttttcctt tatttcaata tatgccgtgc acttgtttgt  1260
cgggtcatct tttcatgttt tttttggctt ggttgtgatg atgtggtctg gttgggcggt  1320
cgttctagat cggagtagaa tactgtttca aactacctgg tggatttatt aaaggatctg  1380
tatgtatgtg ccatacatct tcatagttac gagtttaaga tgatggatgg aaatatcgat  1440
ctaggatagg tatacatgtt gatgcgggtt ttactgatgc atatacagag atgctttttt  1500
ttcgcttggt tgtgatgatg tggtctggtc gggcggtcgt tctagatcgg agtagaatac  1560
tgtttcaaac tacctggtgg atttattaat tttggatctg tatgtgtgtc atacatcttc  1620
atagttacga gtttaagatc gatggaaata tcgatctagg ataggtatac atgttgatgt  1680
gggttttact gatgcatata catggcatat gcagcatcta ttcatatgct ctaaccttga  1740
gtacctatct attataataa acaagtatgt tttataatta ttttgatctt gatatacttg  1800
gatgatggca tatgcagcag ctatatgtgg attttttttag ccctgccttc atacgctatt  1860
tatttgcttg gtactgtttc ttttgtcgat gctcaccctg ttgtttggtg atacttctgc  1920
agggt                                                             1925

SEQ ID NO: 140         moltype = DNA  length = 997
FEATURE                Location/Qualifiers
source                 1..997
                       mol_type = other DNA
                       organism = Zea mays
                       sub_species = Mexicana
SEQUENCE: 140
gtacgccgct catcctcctc cccccccctct ctctaccttc tctagatcgg cgtttcggtc  60
catggttagg gcccggtagt tctacttctg ttcatgtttg tgttagatcc gtgtttgtgt  120
tagatccgtg ctgctagatt tcgtacacgg atgcgacctg tacatcagac atgttctgat  180
tgctaacttg ccagtgtttc tctttgggga atcctgggat ggctctagcc gttccgcaga  240
cgggatcgat ttcatgaatt ttttttgttt cgttgcatag ggtttggttt gccctttcc  300
tttatttcaa tatatgccgt gcacttgttt gtcgggtcat cttttcatgt tttttttggc  360
ttggttgtga tgatgtggtc tggttgggcg gtcgttctag atcggagtag aatactgttt  420
caaactacct ggtggattta ttaaaggatc tgtatgtatg tgccatacat cttcatagtt  480
acgagtttaa gatgatggat ggaaatatcg atctaggata ggtatacatg ttgatgcggg  540
ttttactgat gcatatacag agatgctttt ttttcgcttg gttgtgatga tgtggtctgg  600
tcgggcggtc gttctagatc ggagtagaat actgtttcaa actacctggt ggatttatta  660
attttggatc tgtatgtgtg tcatacatct tcatagttac gagtttaaga tcgatggaaa  720
tatcgatcta ggataggtat acatgttgat gtgggtttta ctgatgcata tacatggcat  780
atgcagcatc tattcatatg ctctaacctt gagtacctat ctattataat aaacaagtat  840
gttttataat tattttgatc ttgatatact tggatgatgg catatgcagc agctatatgt  900
ggattttttt agccctgcct tcatacgcta tttatttgct tggtactgtt tcttttgtcg  960
atgctcaccc tgttgtttgg tgatacttct gcagggt                          997
```

```
SEQ ID NO: 141          moltype = DNA  length = 1974
FEATURE                 Location/Qualifiers
source                  1..1974
                        mol_type = other DNA
                        organism = Zea mays
                        sub_species = Mexicana
SEQUENCE: 141
gtcgtgcccc tctctagaga taaagagcat tgcatgtcta agttataaaa aattaccaca  60
tatttttttt gtcacacttg tttgaagtgc agtttatcta tctttataca tatatttaaa  120
ctttactcta cgaataatat aatctatagt actacaataa tatcagtgtt ttagagaatc  180
atataaatga acagttagac atggtctaaa ggacaattga gtattttgac aacaggactc  240
tacagtttta tctttttagt gtgcatgtgt tctccttttt tttttgcaaa tagcttcacc  300
tatataatac ttcatccatt ttattagtac atccatttag ggtttagggt taatggtttt  360
tatagactaa ttttttttagt acatctattt tattctattt tagcctctaa attaagaaaa  420
ctaaaactct attttagttt ttttatttaa taatttagat ataaaataga ataaaataaa  480
gtgactaaaa attaaacaaa taccctttaa gaaattaaaa aaactaagga aacatttttc  540
ttgtttcgag tagataatgc cagcctgtta aacgccgtcg acgagtctaa cggacaccaa  600
ccagcgaacc agcagcgtcg cgtcgggcca agcgaagcag acggcacggc atctctgtcg  660
ctgcctctgg acccctctcg agagttccgc tccaccgttg gacttgctcc gctgtcggca  720
tccagaaatt gcgtggcgga gcggcagacg tgagccggca cggcaggcgg cctcctcctc  780
ctctcacggc accggcagct acgggggatt cctttcccac cgctccttcg ctttcccttc  840
ctcgcccgcc gtaataaata gacaccccct ccacaccttc tttccccaac ctcgtgttgt  900
tcggagcgca cacacacaca accagatctc ccccaaatcc acccgtcggc acctccgctt  960
caaggtacgc cgctcatcct cccccccccc tctctacctt ctctagatcg gcgttccggt  1020
ccatggttag ggcccggtag ttctacttct gttcatgttt gtgttagatc cgtgtttgtg  1080
ttagatccgt gctgctagcg ttcgtacacg gatgcgacct gtacgtcaga cacgttctga  1140
ttgctaactt gccagtgttt ctctttgggg aatcctggga tggctctagc cgttccgcag  1200
acgggatcga tttcatgatt ttttttgttt cgttgcatag ggtttggttt gccctttttcc  1260
tttatttcaa tatatgccgt gcacttgttt gtcgggtcat cttttcatgc ttttttttgt  1320
cttggttgtg atgatgtggt ctggttgggc ggtcgttcta gatcggagaa gaattctgtt  1380
tcaaactacc tggtggattt attaattttg gatctgtatg tgtgtgccat acatattcat  1440
agttacgaat tgaagatgat ggatggaaat atcgatctag gataggtata catgttgatg  1500
cgggttttac tgatgcatat acagagatgc tttttgttcg cttggttgtg atgatgtggt  1560
ctggttgggc ggtcgttcat tcgttctaga tcggagtaga atactgtttc aaactacctg  1620
gtgtatttat taattttgga actgtatgtg tgtgtcatac atcttcatag ttacgagttt  1680
aagatggatg gaaatatcga tctaggatag gtatacatgt tgatgtgggt tttactgatg  1740
catatacatg atggcatatg cagcatctat tcatatgctc taaccttgag tacctatcta  1800
ttataataaa caagtatgtt ttataattat tttgatcttg atatacttgg atgatggcat  1860
atgcagcagc tatatgtgga tttttttagc cctgccttca tacgctattt atttgcttgg  1920
tactgtttct tttgtcgatg ctcaccctgt tgtttggtga tacttctgca ggtc        1974

SEQ ID NO: 142          moltype = DNA  length = 1010
FEATURE                 Location/Qualifiers
source                  1..1010
                        mol_type = other DNA
                        organism = Zea mays
                        sub_species = Mexicana
SEQUENCE: 142
gtacgccgct catcctcccc cccccctctc taccttctct agatcggcgt tccggtccat  60
ggttagggcc cggtagttct acttctgttc atgtttgtgt tagatccgtg tttgtgttag  120
atccgtgctg ctagcgttcg tacacggatg cgacctgtac gtcagacacg ttctgattgc  180
taacttgcca gtgtttctct ttggggaatc ctgggatggc tctagccgtt ccgcagacgg  240
gatcgatttc atgatttttt ttgtttcgtt gcatagggtt tggtttgccc ttttccttta  300
tttcaatata tgccgtgcac ttgtttgtcg ggtcatcttt tcatgctttt ttttgtcttg  360
gttgtgatga tgtggtctgg ttgggcggtc gttctagatc ggagaagaat tctgtttcaa  420
actacctggt ggatttatta attttggatc tgtatgtgtg tgccatacat attcatagtt  480
acgaattgaa gatgatggat ggaaatatcg atctaggata ggtatacatg ttgatgcggg  540
ttttactgat gcatatacag agatgctttt tgttcgcttg gttgtgatga tgtggtctgg  600
ttgggcggtc gttcattcgt tctagatcgg agtagaatac tgtttcaaac tacctggtgt  660
atttattaat tttggaactg tatgtgtgtg tcatacatct tcatagttac gagtttaaga  720
tggatggaaa tatcgatcta ggataggtat acatgttgat gtgggtttta ctgatgcata  780
tacatgatgg catatgcagc atctattcat atgctctaac cttgagtacc tatctattat  840
aataaacaag tatgttttat aattattttg atcttgatat acttggatga tggcatatgc  900
agcagctata tgtggatttt tttagccctg ccttcatacg ctatttattt gcttggtact  960
gtttcttttg tcgatgctca ccctgttgtt tggtgatact tctgcaggtc            1010

SEQ ID NO: 143          moltype = DNA  length = 1974
FEATURE                 Location/Qualifiers
source                  1..1974
                        mol_type = other DNA
                        organism = Zea mays
                        sub_species = Mexicana
SEQUENCE: 143
gtcgtgcccc tctctagaga taaagagcat tgcatgtcta agttataaaa aattaccaca  60
tatttttttt gtcacacttg tttgaagtgc agtttatcta tctttataca tatatttaaa  120
ctttactcta cgaataatat aatctatagt actacaataa tatcagtgtt ttagagaatc  180
atataaatga acagttagac atggtctaaa ggacaattga gtattttgac aacaggactc  240
tacagtttta tctttttagt gtgcatgtgt tctccttttt tttttgcaaa tagcttcacc  300
```

```
tatataatac ttcatccatt ttattagtac atccatttag ggtttagggt taatggtttt  360
tatagactaa tttttttagt acatctattt tattctattt tagcctctaa attaagaaaa  420
ctaaaactct attttagttt ttttatttaa taatttagat ataaaataga ataaaataaa  480
gtgactaaaa attaaacaaa taccctttaa gaaattaaaa aaactaagga aacatttttc  540
ttgtttcgag tagataatgc cagcctgtta aacgccgtcg acgagtctaa cggacaccaa  600
ccagcgaacc agcagcgtcg cgtcgggcca agcgaagcag acggcacggc atctctgtcg  660
ctgcctctgg acccctctcg agagttccgc tccaccgttg gacttgctcc gctgtcggca  720
tccagaaatt gcgtggcgga gcggcagacg tgagccggca cggcaggcgg cctcctcctc  780
ctctcacggc accggcagct acgggggatt cctttcccac cgctccttcg ctttcccttc  840
ctcgcccgcc gtaataaata gacaccccct ccacaccttc tttccccaac ctcgtgttgt  900
tcggagcgca cacacacaca accagatctc ccccaaatcc acccgtcggc acctccgctt  960
caaggtacgc cgctcatcct ccccccccc tctctacctt ctctagatcg gcgttccggt  1020
ccatggttag ggcccggtag ttctacttct gttcatgttt gtgttagatc cgtgtttgtg  1080
ttagatccgt gctgctagcg ttcgtacacg gatgcgacct gtacgtcaga cacgttctga  1140
ttgctaactt gccagtgttt ctctttgggg aatcctggga tggctctagc cgttccgcag  1200
acgggatcga tttcatgatt ttttttgttt cgttgcatag ggtttggttt gcccttttcc  1260
tttatttcaa tatatgccgt gcacttgttt gtcgggtcat cttttcatgc ttttttttgt  1320
cttggttgtg atgatgtggt ctggttgggc ggtcgttcta gatcggagaa gaattctgtt  1380
tcaaactacc tggtggattt attaatttttg gatctgtatg tgtgtgccat acatattcat  1440
agttacgaat tgaagatgat ggatggaaat atcgatctag gataggtata catgttgatg  1500
cgggttttac tgatgcatat acagagatgc tttttgttcg cttggttgtg atgatgtggt  1560
ctggttgggc ggtcgttcat tcgttctaga tcggagtaga atactgtttc aaactacctg  1620
gtgtatttat taattttgga actgtatgtg tgtgtcatac atcttcatag ttacgagttt  1680
aagatggatg gaaatatcga tctaggatag gtatacatgt tgatgtgggt tttactgatg  1740
catatacatg atggcatatg cagcatctat tcatatgctc taaccttgag tacctatcta  1800
ttataataaa caagtatgtt ttataattat tttgatcttg atatacttgg atgatggcat  1860
atgcagcagc tatatgtgga tttttttagc cctgccttca tacgctattt atttgcttgg  1920
tactgtttct tttgtcgatg ctcaccctgt tgtttggtga tacttctgca gggt        1974
```

```
SEQ ID NO: 144          moltype = DNA  length = 1010
FEATURE                 Location/Qualifiers
source                  1..1010
                        mol_type = other DNA
                        organism = Zea mays
                        sub_species = Mexicana
SEQUENCE: 144
gtacgccgct catcctcccc cccccctctc taccttctct agatcggcgt tccggtccat  60
ggttagggcc cggtagttct acttctgttc atgtttgtgt tagatccgtg tttgtgttag  120
atccgtgctg ctagcgttcg tacacggatg cgacctgtac gtcagacacg ttctgattgc  180
taacttgcca gtgtttctct ttggggaatc ctgggatggc tctagccgtt ccgcagacgg  240
gatcgatttc atgatttttt ttgtttcgtt gcatagggtt tggtttgccc ttttccttta  300
tttcaatata tgccgtgcac ttgtttgtcg ggtcatcttt tcatgctttt ttttgtcttg  360
gttgtgatga tgtggtctgg ttgggcggtc gttctagatc ggagaagaat tctgtttcaa  420
actacctggt ggatttatta attttggatc tgtatgtgtg tgccatacat attcatagtt  480
acgaattgaa gatgatggat ggaaatatcg atctaggata ggtatacatg ttgatgcggg  540
ttttactgat gcatatacag agatgctttt tgttcgcttg gttgtgatga tgtggtctgg  600
ttgggcggtc gttcattcgt tctagatcgg agtagaatac tgtttcaaac tacctggtgt  660
atttattaat tttggaactg tatgtgtgtg tcatacatct tcatagttac gagtttaaga  720
tggatggaaa tatcgatcta ggataggtat acatgttgat gtgggtttta ctgatgcata  780
tacatgatgg catatgcagc atctattcat atgctctaac cttgagtacc tatctattat  840
aataaacaag tatgttttat aattattttg atcttgatat acttggatga tggcatatgc  900
agcagctata tgtggatttt tttagccctg ccttcatacg ctatttattt gcttggtact  960
gtttcttttg tcgatgctca ccctgttgtt tggtgatact tctgcagggt            1010
```

```
SEQ ID NO: 145          moltype = DNA  length = 2008
FEATURE                 Location/Qualifiers
source                  1..2008
                        mol_type = other DNA
                        organism = Zea mays
                        sub_species = Mexicana
SEQUENCE: 145
gtcgtgcccc tctctagaga taaagagcat tgcatgtcta aagtataaaa aattaccaca  60
tattttttg tcacacttat ttgaagtgta gtttatctat ctctatacat atatttaaac  120
ttcactctac aaataatata gtctataata ctaaaataat attagtgttt tagaggatca  180
tataaataaa ctgctagaca tggtctaaag gataattgaa tattttgaca atctacagtt  240
ttatcttttt agtgtgcatg tgatctctct gttttttttg caaatagctt gacctatata  300
atacttcatc cattttatta gtacatccat ttaggattta gggttgatgg tttctataga  360
ctaattttta gtacatccat tttattcttt ttagtctcta aattttttaa aactaaaact  420
ctatttagt ttttattta ataatttaga tataaaatga aataaaataa attgactaca  480
aataaaacaa atacccttta agaaataaaa aaactaagca aacatttttc ttgtttcgag  540
tagataatga caggctgttc aacgccgtcg acgagtctaa cggacaccaa ccagcgaacc  600
agcagcgtcg cgtcgggcca agcgaagcag acggcacggc atctctgtag ctgcctctgg  660
acccctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acgggggatt cctttcccac cgctccttcg ctttcccttc ctcgcccgcc  840
gtaataaata gacaccccct ccacaccctc tttccccaac ctcgtgttcg ttcggagcgc  900
acacacacgc aaccagatct cccccaaatc cagccgtcgg cacctccgct tcaaggtacg  960
ccgctcatcc tccccccccc cctctctcta ccttctctag atcggcgatc cggtccatgg  1020
ttagggcccg gtagttctac ttctgttcat gtttgtgtta gagcaaacat gttcatgttc  1080
```

```
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc tttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgttgg gtgatacttc tgcaggtc                                     2008
```

```
SEQ ID NO: 146          moltype = DNA  length = 1053
FEATURE                 Location/Qualifiers
source                  1..1053
                        mol_type = other DNA
                        organism = Zea mays
                        sub_species = Mexicana
SEQUENCE: 146
gtacgccgct catcctcccc cccccctct ctctaccttc tctagatcgg cgatccggtc  60
catggttagg gcccggtagt tctacttctg ttcatgtttg tgttagagca aacatgttca  120
tgttcatgtt tgtgatgatg tggtctggtt gggcggtcgt tctagatcgg agtaggatac  180
tgtttcaagc tacctggtgg atttattaat tttgtatctg tatgtgtgtg ccatacatct  240
tcatagttac gagtttaaga tgatggatgg aaatatcgat ctaggatagg tatacatgtt  300
gatgcgggtt ttactgatgc atatacagag atgctttttt tctcgcttgg ttgtgatgat  360
atggtctggt tgggcggtcg ttctagatcg gagtagaata ctgtttcaaa ctacctggtg  420
gatttattaa aggataaagg gtcgttctag atcggagtag aatactgttt caaactacct  480
ggtggattta ttaaaggatc tgtatgtatg tgcctacatc ttcatagtta cgagtttaag  540
atgatggatg gaaatatcga tctaggatag gtatacatgt tgatgcgggt tttactgatg  600
catatacaga gatgcttttt ttcgcttggt tgtgatgatg tggtctggtt gggcggtcgt  660
tctagatcgg agtagaatac tgtttcaaac tacctggtgg atttattaat tttgtatctt  720
tatgtgtgtg ccatacatct tcatagttac gagtttaaga tgatggatgg aaatattgat  780
ctaggatagg tatacatgtt gatgtgggtt ttactgatgc atatacatga tggcatatgc  840
ggcatctatt catatgctct aaccttgagt acctatctat tataataaac aagtatgttt  900
tataattatt ttgatcttga tatacttgga tgatggcata tgcagcagct atatgtggat  960
tttttagccc tgccttcata cgctatttat ttgcttggta ctgtttcttt tgtccgatgc  1020
tcaccctgtt gttgggtgat acttctgcag gtc                               1053
```

```
SEQ ID NO: 147          moltype = DNA  length = 2008
FEATURE                 Location/Qualifiers
source                  1..2008
                        mol_type = other DNA
                        organism = Zea mays
                        sub_species = Mexicana
SEQUENCE: 147
gtcgtgcccc tctctagaga taaagagcat tgcatgtcta aagtataaaa aattaccaca  60
tattttttg tcacacttat ttgaagtgta gtttatctat ctctatacat atatttaaac  120
ttcactctac aaataatata gtctataata ctaaaataat attagtgttt tagaggatca  180
tataaataaa ctgctagaca tggtctaaag gataattgaa tattttgaca atctacagtt  240
ttatcttttt agtgtgcatg tgatctctct gttttttttg caaatagctt gacctatata  300
atacttcatc cattttatta gtacatccat ttaggattta gggttgatgg tttctataga  360
ctaattttta gtacatccat tttattcttt ttagtctcta aatttttaa aactaaaact  420
ctattttagt tttttattta ataatttaga tataaaatga aataaaataa attgactaca  480
aataaaacaa ataccctta agaaataaaa aaactaagca aacattttc ttgtttcgag  540
tagataatga caggctgttc aacgccgtcg acgagtctaa cggacaccaa ccagcgaacc  600
agcagcgtcg cgtcgggcca agcgaagcag acggcacggc atctctgtag ctgcctctgg  660
acccctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acgggggatt cctttcccac cgctccttcg ctttcccttc ctcgcccgcc  840
gtaataaata gacaccccct ccacaccctc tttccccaac ctcgtgttcg ttcggagcgc  900
acacacacgc aaccagatct cccccaaatc cagccgtcgg cacctccgct tcaaggtacg  960
ccgctcatcc tcccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc tttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
```

```
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgtttg gtgatacttc tgcaggtc                                     2008

SEQ ID NO: 148          moltype = DNA  length = 1053
FEATURE                 Location/Qualifiers
source                  1..1053
                        mol_type = other DNA
                        organism = Zea mays
                        sub_species = Mexicana
SEQUENCE: 148
gtacgccgct catcctcccc cccccctct ctctaccttc tctagatcgg cgatccggtc  60
catggttagg gcccggtagt tctacttctg ttcatgtttg tgttagagca aacatgttca  120
tgttcatgtt tgtgatgatg tggtctggtt gggcggtcgt tctagatcgg agtaggatac  180
tgtttcaagc tacctggtgg atttattaat tttgtatctg tatgtgtgtg ccatacatct  240
tcatagttac gagtttaaga tgatggatgg aaatatcgat ctaggatagg tatacatgtt  300
gatgcgggtt ttactgatgc atatacagag atgctttttt tctcgcttgg ttgtgatgat  360
atggtctggt tgggcggtcg ttctagatcg gagtagaata ctgtttcaaa ctacctggtg  420
gatttattaa aggataaagg gtcgttctag atcggagtag aatactgttt caaactacct  480
ggtggattta ttaaaggatc tgtatgtatg tgcctacatc ttcatagtta cgagtttaag  540
atgatggatg gaaatatcga tctaggatag gtatacatgt tgatgcgggt tttactgatg  600
catatacaga gatgcttttt ttcgcttggt tgtgatgatg tggtctggtt gggcggtcgt  660
tctagatcgg agtagaatac tgtttcaaac tacctggtgg atttattaat tttgtatctt  720
tatgtgtgtg ccatacatct tcatagttac gagtttaaga tgatggatgg aaatattgat  780
ctaggatagg tatacatgtt gatgtgggtt ttactgatgc atatacatga tggcatatgc  840
ggcatctatt catatgctct aaccttgagt acctatctat tataataaac aagtatgttt  900
tataattatt ttgatcttga tatacttgga tgatggcata tgcagcagct atatgtggat  960
tttttagccc tgccttcata cgctatttat ttgcttggta ctgtttcttt tgtccgatgc  1020
tcaccctgtt gtttggtgat acttctgcag gtc                               1053

SEQ ID NO: 149          moltype = DNA  length = 2008
FEATURE                 Location/Qualifiers
source                  1..2008
                        mol_type = other DNA
                        organism = Zea mays
                        sub_species = Mexicana
SEQUENCE: 149
gtcgtgcccc tctctagaga taaagagcat tgcatgtcta aagtataaaa aattaccaca  60
tattttttg tcacacttat ttgaagtgta gtttatctat ctctatacat atatttaaac  120
ttcactctac aaataatata gtctataata ctaaaataat attagtgttt tagaggatca  180
tataaataaa ctgctagaca tggtctaaag gataattgaa tattttgaca atctacagtt  240
ttatcttttt agtgtgcatg tgatctctct gtttttttg caaatagctt gacctatata  300
atacttcatc cattttatta gtacatccat ttaggattta gggttgatgg tttctataga  360
ctaattttta gtacatccat tttattcttt ttagtctcta aatttttaa aactaaaact  420
ctattttagt tttttattta ataatttaga tataaaatga aataaaataa attgactaca  480
aataaaacaa ataccccttta agaaataaaa aaactaagca aacatttttc ttgtttcgag  540
tagataatga caggctgttc aacgccgtcg acgagtctaa cggacaccaa ccagcgaacc  600
agcagcgtcg cgtcgggcca agcgaagcag acggcacggc atctctgtag ctgcctctgg  660
acccctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acgggggatt cctttcccac cgctccttcg ctttcccttc ctcgcccgcc  840
gtaataaata gacaccccct ccacaccctc tttccccaac ctcgtgttcg ttcggagcgc  900
acacacacgc aaccagatct cccccaaatc cagccgtcgg cacctccgct tcaaggtacg  960
ccgctcatcc tcccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc tttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgttgg gtgatacttc tgcagggt                                     2008

SEQ ID NO: 150          moltype = DNA  length = 1053
FEATURE                 Location/Qualifiers
source                  1..1053
                        mol_type = other DNA
                        organism = Zea mays
```

```
                         sub_species = Mexicana
SEQUENCE: 150
gtacgccgct catcctcccc cccccccctct ctctaccttc tctagatcgg cgatccggtc  60
catggttagg gcccggtagt tctacttctg ttcatgtttg tgttagagca aacatgttca  120
tgttcatgtt tgtgatgatg tggtctggtt gggcggtcgt tctagatcgg agtaggatac  180
tgtttcaagc tacctggtgg atttattaat tttgtatctg tatgtgtgtg ccatacatct  240
tcatagttac gagtttaaga tgatggatgg aaatatcgat ctaggatagg tatacatgtt  300
gatgcgggtt ttactgatgc atatacagag atgctttttt tctcgcttgg ttgtgatgat  360
atggtctggt tgggcggtcg ttctagatcg gagtagaata ctgtttcaaa ctacctggtg  420
gatttattaa aggataaagg gtcgttctag atcggagtag aatactgttt caaactacct  480
ggtggattta ttaaaggatc tgtatgtatg tgcctacatc ttcatagtta cgagtttaag  540
atgatggatg gaaatatcga tctaggatag gtatacatgt tgatgcgggt tttactgatg  600
catatacaga gatgcttttt ttcgcttggt tgtgatgatg tggtctggtt gggcggtcgt  660
tctagatcgg agtagaatac tgtttcaaac tacctggtgg atttattaat tttgtatctt  720
tatgtgtgtg ccatacatct tcatagttac gagtttaaga tgatggatgg aaatattgat  780
ctaggatagg tatacatgtt gatgtgggtt ttactgatgc atatacatga tggcatatgc  840
ggcatctatt catatgctct aaccttgagt acctatctat tataataaac aagtatgttt  900
tataattatt ttgatcttga tatacttgga tgatggcata tgcagcagct atatgtggat  960
tttttagccc tgccttcata cgctatttat ttgcttggta ctgtttcttt tgtccgatgc  1020
tcaccctgtt gttgggtgat acttctgcag ggt                               1053

SEQ ID NO: 151          moltype = DNA  length = 1635
FEATURE                 Location/Qualifiers
source                  1..1635
                        mol_type = other DNA
                        organism = Sorghum bicolor
SEQUENCE: 151
ccaagtccaa atgtcaattc ccttgaagat gatctatttt tatcttttgc attttgttat  60
ggaagtttgc aaatagcaac aaatgctaag tcaatttgcc aaagtctttg gagatgctct  120
tagtctataa ttgaacaata tttgtaaaat acaaaaaaaa atagtactat ttttatttta  180
aaaaattttt ggaagtaaac aaggccgagg atggggaaac ggaagtccaa cacgtcgttt  240
tctaagttgg gctcaaaagc ccatcacgga actgacctgc tatgggtcgg aggagagcgc  300
gtccagatgg ttccagaggc tggtggtggt gggccaaacg cggaactccg ccaccgccac  360
ggcctcgtgc gcaagcgcag cgcgttgccg tgagccgtga cgtaaccctc cgttgcccac  420
gataaaagct ccacccccga ccccggcccc ccgatttccc ctacggacca gtctccccccc  480
gatcgcaatc gcgaattcgt cgcaccatcg gcacgcagac gaacgaagca aggctctccc  540
catcggctcg tcaaggtatg cgttccctag atttgttccc ttcctctctc ggtttgtcta  600
tatatatgca tgtatggtcg attcccgatc tcgtcgattc tcggtttcgc cttccgtacg  660
aagattcgtt tagattgttc atatgttctg ttgtgttacc agattgatcg gatcaacttg  720
atccagttat cttcgctcct ccgattagat ccgtttctat ttcagtatat atatactagt  780
atagtatcta gggttcacac tgttgaccga ctggttactt ggaattgatc cgtgctgagt  840
tcagttgttg ccgtccataa aggcccgtgc tattgtctgt tctgaaacga aatcctgtag  900
atttcttagg gttagtgttc aattcatcaa aaggttgatt agtgaattat caaatttgag  960
agggttaaat cattctcatc atgttgtctc gaatgtaatc ccaaagatat tatagactgt  1020
gtttcgattt gatggattga tttgtgtatc atctaaatca acaaggctaa gtcatcagtt  1080
catagaatca tgtttaggtt tccgttcaat agactagttt tatcaatata taaaattata  1140
agaagggtag ggtaaatcac gttgcctcaa atgccatcct gtatggtttg gtttcaattc  1200
aattagtttg gttgattagg gtatgctctg gattaagatg gttaaatctt ccctagcatc  1260
ttccctgcct atccttactt gatccgtttc ggatatgttg gaagtacagc gagcttattt  1320
catgttgata gtgacccctt tcagattata ctattgaata ttgtatgttt gccacttctg  1380
tatgttgaat tatcctgcta aattagcaat ggaattagca tattggcaat tggtatgcat  1440
ggacctaatc aggacggatg tggttatgtt agtttcaatt cattgtcaat tcattgttca  1500
cctgcgttag atatatatga tgatttttac gtgtagttca tagttcttga gttttggatc  1560
tttcttatct gatatatgct ttcctgtgcc tgtgctttat tgtgtcttac catgcgattt  1620
ttgtctatgc aggtc                                                   1635

SEQ ID NO: 152          moltype = DNA  length = 1080
FEATURE                 Location/Qualifiers
source                  1..1080
                        mol_type = other DNA
                        organism = Sorghum bicolor
SEQUENCE: 152
gtatgcgttc cctagatttg ttcccttcct ctctcggttt gtctatatat atgcatgtat  60
ggtcgattcc cgatctcgtc gattctcggt ttcgccttcc gtacgaagat tcgtttagat  120
tgttcatatg ttctgttgtg ttaccagatt gatcggatca acttgatcca gttatcttcg  180
ctcctccgat tagatccgtt tctatttcag tatatatata ctagtatagt atctagggtt  240
cacactgttg accgactggt tacttggaat tgatccgtgc tgagttcagt tgttgccgtc  300
cataaaggcc cgtgctattg tctgttctga aacgaaatcc tgtagatttc ttagggttag  360
tgttcaattc atcaaaaggt tgattagtga attatcaaat ttgagagggt taaatcattc  420
tcatcatgtt gtctcgaatg taatcccaaa gatattatag actgtgtttc gatttgatgg  480
attgatttgt gtatcatcta aatcaacaag gctaagtcat cagttcatag aatcatgttt  540
aggtttccgt tcaatagact agttttatca atatataaaa ttataagaag ggtagggtaa  600
atcacgttgc ctcaaatgcc atcctgtatg gtttggtttc aattcaatta gtttggttga  660
ttagggtatg ctctggatta agatggttaa atcttcccta gcatcttccc tgcctatcct  720
tacttgatcc gtttcggata tgttggaagt acagcgagct tatttcatgt tgatagtgac  780
ccctttcaga ttatactatt gaatattgta tgtttgccac ttctgtatgt tgaattatcc  840
tgctaaatta gcaatggaat tagcatattg gcaattggta tgcatggacc taatcaggac  900
ggatgtggtt atgttagttt caattcattg tcaattcatt gttcacctgc gttagatata  960
tatgatgatt tttacgtgta gttcatagtt cttgagtttt ggatctttct tatctgatat  1020
```

```
atgctttcct gtgcctgtgc tttattgtgt cttaccatgc gatttttgtc tatgcaggtc  1080

SEQ ID NO: 153         moltype = DNA  length = 2067
FEATURE                Location/Qualifiers
source                 1..2067
                       mol_type = other DNA
                       organism = Sorghum bicolor
SEQUENCE: 153
cattaaaagt cattatgtgc atgcgtcgta actaacatgg atatgttgct gcactatctc  60
ctcgcactag ctgcgcatga taaagccaca agccaaaatt aattattatg ggtgagaata  120
aatacgtacc agcaccggcc atagaaaaag tacattatta aaggtctaat ttggaaacag  180
tctgaaaacg acgtgcgctg cagaggtaaa tgtaattttc ggcactaaaa ccattatcaa  240
ctaattcatt caataacagt tatttagaaa atgtatagct cgctctaaaa aaacagttta  300
gaaaaacagt caaaataatt cgaccaacaa acagttaata aggttcatta aatatataat  360
gcacggtgct atttgatctt ttaaaggaaa aagaggaata gtcgtgggcg ccaggcggga  420
attggggcgc gggagtctgc cggacgacgc gttccgtccg aacggccgga cccgacgagg  480
ccccccgcc gccccacgtc gcagaaccgt ccgtgggtgg taatctggcc gggtacacca  540
gccgtcccct tgggcggcct cacagcactg ggctcacacg tgagttttgt tctgggcttc  600
ggatcgcacc atatgggcct cggcatcaga aagacggggc ccgtctggga tagaagagac  660
aggaacctcc tcgtggattc cagaagccag ccacgagcga ccaccgacgc ggaggatact  720
cgtcgtccaa gtccaacacg gcgggcgggc gggcggacgc gtgggctggg ctaactgcct  780
aaccttaacc tccaaggcac gccaaggccc gcttctccca cccgacataa atatcccccc  840
atccaggcaa ggcgcagagc ctcagaccag attccgatca atcacccata agctcccccc  900
aaatctgttc ctcgtctccc gtctcgcggt ttcctacttc cctcggacgc ctccggcaag  960
tcgctcgacc gcgcgattcc gcccgctcaa ggtatcaact cggttcacca ctccaatcta  1020
cgtctgattt agatgttact tccatctatg tctaatttag atgttactcc gatgcgattg  1080
gattatgttt atgcggtttg cactgctctg gaaactggaa tctagggttt cgagtgattt  1140
gatcgatcgc gatctgtgat ttcgttgcgc cttgtgtatg cttggagtga tctaggcttg  1200
tatatgcggc atcgcgatct gacgcggttg ctttgtagag gctgggggtc taggctgtga  1260
ttttagaatc aaataaagct gttccttacc gtagatgttt cctacatgtt ctgtccagta  1320
ctccagtgct atattcacat tgtttgaggc ttgagttttg tcgatcagtg gtcatgagaa  1380
aaatatatct catgatttta gaggcaccta ttgggaaagg tagatggttc cgttttacat  1440
gttttataga ccttgtggca tggctccttt gttctatggg tgctttattt tcctgaataa  1500
cagtaatgcg agactggtct atgggtgctt tgaccagtaa tgcgagacta gttatttgat  1560
catggtgcag ttcctagtga ttacgaacaa caatttggta gctcagttca ttcagcattg  1620
gtttctacga tccttatcat tttacttctg aatgaattta tttatttaag atattacagt  1680
gcaataaact gctgtataat atcagtaaca aactgctatt actagtaaat gcctagattc  1740
ataataattc attattctac ttgaaaatga tcttaggcct tttatgcgg tcctacgcat  1800
ccttccacag gacttgctgt ttgtttgttt tttgtaatcc ctcgctggga cgcagaatgg  1860
ttcatctgtg ctaataattt ttttgcatat ataagtttat agttctcatt attcatgtgg  1920
ctatggtagc ctgtaaaatc tattgtaata acatattagt cagccataca tctgttccaa  1980
cttgctcaat tgcaaatcat atctccactt aaagcacatg tttgcaagct ttctgacaag  2040
tttctttgtg tttgattgaa acaggtg                                     2067

SEQ ID NO: 154         moltype = DNA  length = 1076
FEATURE                Location/Qualifiers
source                 1..1076
                       mol_type = other DNA
                       organism = Sorghum bicolor
SEQUENCE: 154
gtatcaactc ggttcaccac tccaatctac gtctgattta gatgttactt ccatctatgt  60
ctaatttaga tgttactccg atgcgattgg attatgttta tgcggtttgc actgctctgg  120
aaactggaat ctagggtttc gagtgatttg atcgatcgcg atctgtgatt tcgttgcgcc  180
ttgtgtatgc ttggagtgat ctaggcttgt atatgcggca tcgcgatctg acgcggttgc  240
tttgtagagg ctgggggtct aggctgtgat tttagaatca aataaagctg ttccttaccg  300
tagatgtttc ctacatgttc tgtccagtac tccagtgcta tattcacatt gtttgaggct  360
tgagttttgt cgatcagtgg tcatgagaaa aatatatctc atgattttag aggcacctat  420
tgggaaaggt agatggttcc gttttacatg ttttatagac cttgtggcat ggctcctttg  480
ttctatgggt gctttatttt cctgaataac agtaatgcga gactggtcta tgggtgcttt  540
gaccagtaat gcgagactag ttatttgatc atggtgcagt tcctagtgat tacgaacaac  600
aatttggtag ctcagttcat tcagcattgg tttctacgat ccttatcatt ttacttctga  660
atgaatttat ttatttaaga tattacagtg caataaactg ctgtataata tcagtaacaa  720
actgctatta ctagtaaatg cctagattca taataattca ttattctact tgaaaatgat  780
cttaggcctt ttatgcggt cctacgcatc cttccacagg acttgctgtt tgtttgtttt  840
ttgtaatccc tcgctgggac gcagaatggt tcatctgtgc taataatttt tttgcatata  900
taagtttata gttctcatta ttcatgtggc tatggtagcc tgtaaaatct attgtaataa  960
catattagtc agccatacat ctgttccaac ttgctcaatt gcaaatcata tctccactta  1020
aagcacatgt ttgcaagctt tctgacaagt ttctttgtgt ttgattgaaa caggtg      1076

SEQ ID NO: 155         moltype = DNA  length = 2067
FEATURE                Location/Qualifiers
source                 1..2067
                       mol_type = other DNA
                       organism = Sorghum bicolor
SEQUENCE: 155
cattaaaagt cattatgtgc atgcgtcgta actaacatgg atatgttgct gcactatctc  60
ctcgcactag ctgcgcatga taaagccaca agccaaaatt aattattatg ggtgagaata  120
aatacgtacc agcaccggcc atagaaaaag tacattatta aaggtctaat ttggaaacag  180
tctgaaaacg acgtgcgctg cagaggtaaa tgtaattttc ggcactaaaa ccattatcaa  240
```

```
ctaattcatt caataacagt tatttagaaa atgtatagct cgctctaaaa aaacagttta  300
gaaaaacagt caaaataatt cgaccaacaa acagttaata aggttcatta aatatataat  360
gcacggtgct atttgatctt ttaaaggaaa aagaggaata gtcgtgggcg ccaggcggga  420
attggggcgc gggagtctgc cggacgacgc gttccgtccg aacggccgga cccgacgagg  480
cccccccgcc gccccacgtc gcagaaccgt ccgtgggtgg taatctggcc gggtacacca  540
gccgtcccct tgggcggcct cacagcactg ggctcacacg tgagttttgt tctgggcttc  600
ggatcgcacc atatgggcct cggcatcaga aagacggggc ccgtctggga tagaagagac  660
aggaacctcc tcgtggattc cagaagccag ccacgagcga ccaccgacgc ggaggatact  720
cgtcgtccaa gtccaacacg gcgggcgggc gggcggacgc gtgggctggg ctaactgcct  780
aaccttaacc tccaaggcac gccaaggccc gcttctccca cccgacataa atatcccccc  840
atccaggcaa ggcgcagagc ctcagaccag attccgatca atcacccata agctcccccc  900
aaatctgttc ctcgtctccc gtctcgcggt ttcctacttc cctcggacgc ctccggcaag  960
tcgctcgacc gcgcgattcc gcccgctcaa ggtatcaact cggttcacca ctccaatcta  1020
cgtctgattt agatgttact tccatctatg tctaatttag atgttactcc gatgcgattg  1080
gattatgttt atgcggtttg cactgctctg gaaactggaa tctagggttt cgagtgattt  1140
gatcgatcgc gatctgtgat ttcgttgcgc cttgtgtatg cttggagtga tctaggcttg  1200
tatatgcggc atcgcgatct gacgcggttg ctttgtagag gctgggggtc taggctgtga  1260
ttttagaatc aaataaagct gttccttacc gtagatgttt cctacatgtt ctgtccagta  1320
ctccagtgct atattcacat tgtttgaggc ttgagttttg tcgatcagtg gtcatgagaa  1380
aaatatatct catgatttta gaggcaccta ttgggaaagg tagatggttc cgttttacat  1440
gttttataga ccttgtggca tggctccttt gttctatggg tgctttattt tcctgaataa  1500
cagtaatgcg agactggtct atgggtgctt tgaccagtaa tgcgagacta gttatttgat  1560
catggtgcag ttcctagtga ttacgaacaa caatttggta gctcagttca ttcagcattg  1620
gtttctacga tccttatcat tttacttctg aatgaattta tttatttaag atattacagt  1680
gcaataaact gctgtataat atcagtaaca aactgctatt actagtaaat gcctagattc  1740
ataataattc attattctac ttgaaaatga tcttaggcct ttttatgcgg tcctacgcat  1800
ccttccacag gacttgctgt ttgtttgttt tttgtaatcc ctcgctggga cgcagaatgg  1860
ttcatctgtg ctaataattt ttttgcatat ataagtttat agttctcatt attcatgtgg  1920
ctatggtagc ctgtaaaatc tattgtaata acatattagt cagccataca tctgttccaa  1980
cttgctcaat tgcaaatcat atctccactt aaagcacatg tttgcaagct ttctgacaag  2040
tttctttgtg tttgattgaa acagggt                                      2067
```

```
SEQ ID NO: 156          moltype = DNA  length = 1076
FEATURE                 Location/Qualifiers
source                  1..1076
                        mol_type = other DNA
                        organism = Sorghum bicolor
SEQUENCE: 156
gtatcaactc ggttcaccac tccaatctac gtctgattta gatgttactt ccatctatgt  60
ctaatttaga tgttactccg atgcgattgg attatgttta tgcggtttgc actgctctgg  120
aaactggaat ctagggtttc gagtgatttg atcgatcgcg atctgtgatt tcgttgcgcc  180
ttgtgtatgc ttggagtgat ctaggcttgt atatgcggca tcgcgatctg acgcggttgc  240
tttgtagagg ctgggggtct aggctgtgat tttagaatca aataaagctg ttccttaccg  300
tagatgtttc ctacatgttc tgtccagtac tccagtgcta tattcacatt gtttgaggct  360
tgagttttgt cgatcagtgg tcatgagaaa aatatatctc atgattttag aggcacctat  420
tgggaaaggt agatggttcc gttttacatg ttttatagac cttgtggcat ggctcctttg  480
ttctatgggt gctttatttt cctgaataac agtaatgcga gactggtcta tgggtgcttt  540
gaccagtaat gcgagactag ttatttgatc atggtgcagt tcctagtgat tacgaacaac  600
aatttggtag ctcagttcat tcagcattgg tttctacgat ccttatcatt ttacttctga  660
atgaatttat ttatttaaga tattacagtg caataaactg ctgtataata tcagtaacaa  720
actgctatta ctagtaaatg cctagattca taataattca ttattctact tgaaaatgat  780
cttaggcctt tttatgcggt cctacgcatc cttccacagg acttgctgtt tgtttgtttt  840
ttgtaatccc tcgctgggac gcagaatggt tcatctgtgc taataatttt tttgcatata  900
taagtttata gttctcatta ttcatgtggc tatggtagcc tgtaaaatct attgtaataa  960
catattagtc agccatacat ctgttccaac ttgctcaatt gcaaatcata tctccactta  1020
aagcacatgt ttgcaagctt tctgacaagt ttctttgtgt ttgattgaaa cagggt      1076
```

```
SEQ ID NO: 157          moltype = DNA  length = 2003
FEATURE                 Location/Qualifiers
source                  1..2003
                        mol_type = other DNA
                        organism = Sorghum bicolor
SEQUENCE: 157
agaagtaaaa aaaaagttcg tttcagaatc ataaaggtaa gttaaaaaaa gaccatacaa  60
aaaagaggta tttaatgata aactataatc cagaatttgt taggatagta tataagaata  120
agaccttgtt tagtttcaaa aaaatttgca aaattttcca gattcctcgt cacatcaaat  180
ctttagaggt atgcatggag tattaaatat agacaagacc taaataagaa aacatgaaat  240
gttcacgaaa aaaatcaagc caatgcatga tcgaagcaaa cggtatagta acggtgttaa  300
cctgatccat tgatctttgt aatctttaac ggccacctac cgcgggcagc aaacggcgtc  360
cccctcctcg atatctccgc ggcggcctct ggctttttcc gcggaattgc gcggtgggga  420
cggattccac gagaccgcaa cgcaaccgcc tctcgccgct gggcccccaca ccgctcggtg  480
ccgtagcccg tagcctcacg ggattctttc tccctcctcc cccgtgtata aattggcttc  540
atcccctccc tgcctcatcc atccaaatcc cactccccaa tcccatcccg tcggagaaat  600
tcatcgaagc gaagcgaagc gaatcctccc gatcctctca aggtacgcga gttttcgaat  660
cccctccaga cccctcgtat gctttccctg ttcgttttcg tcgtagcgtt tgattaggta  720
tgctttccct gttcgtgttc gtcgtagggt tcgattaggt cgtgtgaggc catggcctgc  780
tgtgataaat ttatttgttg ttatatcgga tctgtagtcg atttgggggt cgtggtgtag  840
atccgcgggc tgtgatgaag ttatttggtg tgattgtgct cgcgtgattc tgcgcgttga  900
gctcgagtag atctgatggt tggacgaccg attggttcgt tggctggctg cgctaaggtt  960
```

```
gggctgggct catgttgcgt tcgctgttgc gcgtgattcc gcggatggac ttgcgcttga  1020
ttgccgccag atcacgttac gattatgtga tttcgtttgg aactttttag atttgtagct  1080
tctgcttatt atatgacaga tgcgcctact gctcatatgc ctgtggtaaa taatggatgg  1140
ctgtgggtca aactagttga ttgtcgagtc atgtatcata tacaggtgta tagacttgcg  1200
tctaattgtt tgcatgttgc agttatatga tttgttttag attgtttgtt ccactcatct  1260
aggctgtaaa agggacacta cttattagct tgttgtttaa tctttttatt agtagattat  1320
attggtaatg ttttactaat tattattatg ttatatgtga cttctgctca tgcctgatta  1380
taatcataga tcactgtagt tgattgttga atcatgtgtc aaatacccgt atacataaca  1440
ctacacattt gcttagttgt ttccttaact catgcaaatt gaacaccatg tatgatttgc  1500
atggtgctgt aatgttaaat actacagtcc tgttggtact tgtttagtaa gaatctgctt  1560
catacaacta tatgctatgc ctgatgataa tcatatatct ttgtgtaatt aataattagt  1620
tgactgttga ataatgtatc gagtacatac catggcacaa ttgcttagtc acttccttaa  1680
ccatgcatat tgaactgacc ccttcatgtt ctgctgaatt gttctattct gattagacca  1740
tacatcatgt attgcaatct ttatttgcaa ttgtaatgta atggttcggt tctcaaatgt  1800
taaatgctat agttgtgcta ctttctaatg ttaaatgcta tagctgtgct acttgtaaga  1860
tctgcttcat agtttagtta aattaggatg atgagctttg atgctgtaac tttgtttgat  1920
tatgttcata gttgatcagt ttttgttaga ctcacagtaa cttatggtct cactcttctt  1980
ctggtctttg atgtttgcag cgg                                          2003

SEQ ID NO: 158          moltype = DNA  length = 1361
FEATURE                 Location/Qualifiers
source                  1..1361
                        mol_type = other DNA
                        organism = Sorghum bicolor
SEQUENCE: 158
gtacgcgagt tttcgaatcc cctccagacc cctcgtatgc tttccctgtt cgttttcgtc  60
gtagcgtttg attaggtatg ctttccctgt tcgtgttcgt cgtagggttc gattaggtcg  120
tgtgaggcca tggcctgctg tgataaattt atttgttgtt atatcggatc tgtagtcgat  180
ttgggggtcg tggtgtagat ccgcgggctg tgatgaagtt atttggtgtg attgtgctcg  240
cgtgattctg cgcgttgagc tcgagtagat ctgatggttg gacgaccgat tggttcgttg  300
gctggctgcg ctaaggttgg gctgggctca tgttgcgttc gctgttgcgc gtgattccgc  360
ggatggactt gcgcttgatt gccgccagat cacgttacga ttatgtgatt tcgtttggaa  420
ctttttagat ttgtagcttc tgcttattat atgacagatg cgcctactgc tcatatgcct  480
gtggtaaata atggatggct gtgggtcaaa ctagttgatt gtcgagtcat gtatcatata  540
caggtgtata gacttgcgtc taattgtttg catgttgcag ttatatgatt tgttttagat  600
tgtttgttcc actcatctag gctgtaaaag ggacactact tattagcttg ttgtttaatc  660
tttttattag tagattatat tggtaatgtt ttactaatta ttattatgtt atatgtgact  720
tctgctcatg cctgattata atcatagatc actgtagttg attgttgaat catgtgtcaa  780
atacccgtat acataacact acacatttgc ttagttgttt ccttaactca tgcaaattga  840
acaccatgta tgatttgcat ggtgctgtaa tgttaaatac tacagtcctg ttggtacttg  900
tttagtaaga atctgcttca tacaactata tgctatgcct gatgataatc atatatcttt  960
gtgtaattaa taattagttg actgttgaat aatgtatcga gtacatacca tggcacaatt  1020
gcttagtcac ttccttaacc atgcatattg aactgacccc ttcatgttct gctgaattgt  1080
tctattctga ttagaccata catcatgtat tgcaatcttt atttgcaatt gtaatgtaat  1140
ggttcggttc tcaaatgtta aatgctatag ttgtgctact ttctaatgtt aaatgctata  1200
gctgtgctac ttgtaagatc tgcttcatag tttagttaaa ttaggatgat gagctttgat  1260
gctgtaactt tgtttgatta tgttcatagt tgatcagttt ttgttagact cacagtaact  1320
tatggtctca ctcttcttct ggtctttgat gtttgcagcg g                      1361

SEQ ID NO: 159          moltype = DNA  length = 1812
FEATURE                 Location/Qualifiers
source                  1..1812
                        mol_type = other DNA
                        organism = synthetic construct
SEQUENCE: 159
atggtccgtc ctgtagaaac cccaacccgt gaaatcaaaa aactcgacgg cctgtgggca  60
ttcagtctgg atcgcgaaaa ctgtggaatt gatcagcgtt ggtgggaaag cgcgttacaa  120
gaaagccggg caattgctgt gccaggcagt tttaacgatc agttcgccga tgcagatatt  180
cgtaattatg cgggcaacgt ctggtatcag cgcgaagtct ttataccgaa aggttgggca  240
ggccagcgta tcgtgctgcg tttcgatgcg gtcactcatt acggcaaagt gtgggtcaat  300
aatcaggaag tgatggagca tcagggcggc tatacgccat ttgaagccga tgtcacgccg  360
tatgttattg ccgggaaaag tgtacgtatc accgtttgtg tgaacaacga actgaactgg  420
cagactatcc cgccgggaat ggtgattacc gacgaaaacg gcaagaaaaa gcagtcttac  480
ttccatgatt tctttaacta tgccggaatc catcgcagcg taatgctcta caccacgccg  540
aacacctggg tggacgatat caccgtggtg acgcatgtcg cgcaagactg taaccacgcg  600
tctgttgact ggcaggtggt ggccaatggt gatgtcagcg ttgaactgcg tgatgcggat  660
caacaggtgg ttgcaactgg acaaggcact agcgggactt tgcaagtggt gaatccgcac  720
ctctggcaac cgggtgaagg ttatctctat gaactgtgcg tcacagccaa aagccagaca  780
gagtgtgata tctacccgct tcgcgtcggc atccggtcag tggcagtgaa gggcgaacag  840
ttcctgatta accacaaacc gttctacttt actggctttg gtcgtcatga agatgcggac  900
ttgcgtggca aaggattcga taacgtgctg atggtgcacg accacgcatt aatggactgg  960
attggggcca actcctaccg tacctcgcat tacccttacg ctgaagagat gctcgactgg  1020
gcagatgaac atggcatcgt ggtgattgat gaaactgctg ctgtcggctt taacctctct  1080
ttaggcattg gtttcgaagc gggcaacaag ccgaaagaac tgtacagcga agaggcagtc  1140
aacggggaaa ctcagcaagc gcacttacag gcgattaaag agctgatagc gcgtgacaaa  1200
aaccacccaa gcgtggtgat gtggagtatt gccaacgaac cggatacccg tccgcaaggt  1260
gcacgggaat atttcgcgcc actggcggaa gcaacgcgta aactcgaccc gacgcgtccg  1320
atcacctgcg tcaatgtaat gttctgcgac gctcacaccg ataccatcag cgatctcttt  1380
gatgtgctgt gcctgaaccg ttattacgga tggtatgtcc aaagcggcga tttggaaacg  1440
```

```
gcagagaagg tactggaaaa agaacttctg gcctggcagg agaaactgca tcagccgatt  1500
atcatcaccg aatacggcgt ggatacgtta gccgggctgc actcaatgta caccgacatg  1560
tggagtgaag agtatcagtg tgcatggctg gatatgtatc accgcgtctt tgatcgcgtc  1620
agcgccgtcg tcggtgaaca ggtatggaat ttcgccgatt ttgcgacctc gcaaggcata  1680
ttgcgcgttg gcggtaacaa gaaagggatc ttcactcgcg accgcaaacc gaagtcggcg  1740
gcttttctgc tgcaaaaacg ctggactggc atgaacttcg gtgaaaaacc gcagcaggga  1800
ggcaaacaat ga                                                       1812

SEQ ID NO: 160         moltype = DNA  length = 2001
FEATURE                Location/Qualifiers
source                 1..2001
                       mol_type = other DNA
                       organism = synthetic construct
SEQUENCE: 160
atggtccgtc ctgtagaaac cccaacccgt gaaatcaaaa aactcgacgg cctgtgggca  60
ttcagtctgg atcgcgaaaa ctgtggaatt gatcagcgtt ggtgggaaag cgcgttacaa  120
gaaagccggg caattgctgt gccaggcagt tttaacgatc agttcgccga tgcagatatt  180
cgtaattatg cgggcaacgt ctggtatcag cgcgaagtct ttataccgaa aggttgggca  240
ggccagcgta tcgtgctgcg tttcgatgcg gtcactcatt acggcaaagt gtgggtcaat  300
aatcaggaag tgatggagca tcagggcggc tatacgccat ttgaagccga tgtcacgccg  360
tatgttattg ccgggaaaag tgtacgtaag tttctgcttc tacctttgat atatatataa  420
taattatcat taattagtag taatataata tttcaaatat ttttttcaaa ataaaagaat  480
gtagtatata gcaattgctt ttctgtagtt tataagtgtg tatattttaa tttataactt  540
ttctaatata tgaccaaaat ttgttgatgt gcaggtatca ccgtttgtgt gaacaacgaa  600
ctgaactggc agactatccc gccgggaatg gtgattaccg acgaaaacgg caagaaaaag  660
cagtcttact tccatgattt ctttaactat gccggaatcc atcgcagcgt aatgctctac  720
accacgccga acacctgggt ggacgatatc accgtggtga cgcatgtcgc gcaagactgt  780
aaccacgcgt ctgttgactg gcaggtggtg gccaatggtg atgtcagcgt tgaactgcgt  840
gatgcggatc aacaggtggt tgcaactgga caaggcacta gcgggacttt gcaagtggtg  900
aatccgcacc tctggcaacc gggtgaaggt tatctctatg aactgtgcgt cacagccaaa  960
agccagacag agtgtgatat ctacccgctt cgcgtcggca tccggtcagt ggcagtgaag  1020
ggcgaacagt tcctgattaa ccacaaaccg ttctacttta ctggctttgg tcgtcatgaa  1080
gatgcggact tgcgtggcaa aggattcgat aacgtgctga tggtgcacga ccacgcatta  1140
atggactgga ttggggccaa ctcctaccgt acctcgcatt acccttacgc tgaagagatg  1200
ctcgactggg cagatgaaca tggcatcgtg gtgattgatg aaactgctgc tgtcggcttt  1260
aacctctctt taggcattgg tttcgaagcg ggcaacaagc cgaaagaact gtacagcgaa  1320
gaggcagtca acggggaaac tcagcaagcg cacttacagg cgattaaaga gctgatagcg  1380
cgtgacaaaa accacccaag cgtggtgatg tggagtattg ccaacgaacc ggatacccgt  1440
ccgcaaggtg cacgggaata tttcgcgcca ctggcggaag caacgcgtaa actcgacccg  1500
acgcgtccga tcacctgcgt caatgtaatg ttctgcgacg ctcacaccga taccatcagc  1560
gatctctttg atgtgctgtg cctgaaccgt tattacggat ggtatgtcca aagcggcgat  1620
ttggaaacgg cagagaaggt actggaaaaa gaacttctgg cctggcagga gaaactgcat  1680
cagccgatta tcatcaccga atacggcgtg gatacgttag ccgggctgca ctcaatgtac  1740
accgacatgt ggagtgaaga gtatcagtgt gcatggctgg atatgtatca ccgcgtcttt  1800
gatcgcgtca gcgccgtcgt cggtgaacag gtatggaatt tcgccgattt tgcgacctcg  1860
caaggcatat tgcgcgttgg cggtaacaag aaagggatct tcactcgcga ccgcaaaccg  1920
aagtcggcgg cttttctgct gcaaaaacgc tggactggca tgaacttcgg tgaaaaaccg  1980
cagcagggag gcaaacaatg a                                             2001

SEQ ID NO: 161         moltype = DNA  length = 253
FEATURE                Location/Qualifiers
source                 1..253
                       mol_type = other DNA
                       organism = Agrobacterium tumefaciens
SEQUENCE: 161
gatcgttcaa acatttggca ataaagtttc ttaagattga atcctgttgc cggtcttgcg  60
atgattatca tataatttct gttgaattac gttaagcatg taataattaa catgtaatgc  120
atgacgttat ttatgagatg ggtttttatg attagagtcc cgcaattata catttaatac  180
gcgatagaaa acaaaatata gcgcgcaaac taggataaat tatcgcgcgc ggtgtcatct  240
atgttactag atc                                                     253

SEQ ID NO: 162         moltype = DNA  length = 210
FEATURE                Location/Qualifiers
source                 1..210
                       mol_type = other DNA
                       organism = Triticum aestivum
SEQUENCE: 162
ctgcatgcgt ttggacgtat gctcattcag gttggagcca atttggttga tgtgtgtgcg  60
agttcttgcg agtctgatga gacatctctg tattgtgttt ctttccccag tgttttctgt  120
acttgtgtaa tcggctaatc gccaacagat tcggcgatga ataaatgaga aataaattgt  180
tctgattttg agtgcaaaaa aaaaggaatt                                    210

SEQ ID NO: 163         moltype = DNA  length = 1204
FEATURE                Location/Qualifiers
source                 1..1204
                       mol_type = other DNA
                       organism = synthetic construct
SEQUENCE: 163
ggtccgattg agacttttca acaaagggta atatccggaa acctcctcgg attccattgc  60
```

```
ccagctatct gtcactttat tgtgaagata gtggaaaagg aaggtggctc ctacaaatgc  120
catcattgcg ataaaggaaa ggccatcgtt gaagatgcct ctgccgacag tggtcccaaa  180
gatggacccc cacccacgag gagcatcgtg gaaaaagaag acgttccaac cacgtcttca  240
aagcaagtgg attgatgtga tggtccgatt gagacttttc aacaaagggt aatatccgga  300
aacctcctcg gattccattg cccagctatc tgtcacttta ttgtgaagat agtggaaaag  360
gaaggtggct cctacaaatg ccatcattgc gataaaggaa aggccatcgt tgaagatgcc  420
tctgccgaca gtggtcccaa agatggaccc ccacccacga ggagcatcgt ggaaaaagaa  480
gacgttccaa ccacgtcttc aaagcaagtg gattgatgtg atatctccac tgacgtaagg  540
gatgacgcac aatcccacta tccttcgcaa gacccttcct ctatataagg aagttcattt  600
catttggaga ggacacgctg acaagctgac tctagcagat cctctagaac catcttccac  660
acactcaagc cacactattg gagaacacac agggacaaca caccataaga tccaagggag  720
gcctccgccg ccgccggtaa ccaccccgcc cctctcctct ttctttctcc gtttttttt   780
ccgtctcggt ctcgatcttt ggccttggta gtttgggtgg gcgagaggcg gcttcgtgcg  840
cgcccagatc ggtgcgcggg aggggcggga tctcgcggct ggggctctcg ccggcgtgga  900
tccggcccgg atctcgcggg gaatggggct ctcggatgta gatctgcgat ccgccgttgt  960
tgggggagat gatgggggt ttaaaatttc cgccgtgcta aacaagatca ggaagagggg  1020
aaaagggcac tatggtttat atttttatat atttctgctg cttcgtcagg cttagatgtg  1080
ctagatcttt ctttcttctt tttgtgggta gaatttgaat ccctcagcat tgttcatcgg  1140
tagtttttct tttcatgatt tgtgacaaat gcagcctcgt gcggagcttt tttgtaggta  1200
gaag                                                               1204
```

```
SEQ ID NO: 164         moltype = DNA  length = 1399
FEATURE                Location/Qualifiers
source                 1..1399
                       mol_type = other DNA
                       organism = Oryza sativa
SEQUENCE: 164
tcgaggtcat tcatatgctt gagaagagag tcgggatagt ccaaaataaa acaaaggtaa  60
gattacctgg tcaaaagtga aaacatcagt taaaaggtgg tataaagtaa aatatcggta  120
ataaaaggtg gcccaaagtg aaatttactc ttttctacta ttataaaaat tgaggatgtt  180
tttgtcggta ctttgatacg tcatttttgt atgaattggt ttttaagttt attcgctttt  240
ggaaatgcat atctgtattt gagtcgggtt ttaagttcgt ttgcttttgt aaatacagag  300
ggatttgtat aagaaatatc tttagaaaaa cccatatgct aatttgacat aatttttgag  360
aaaaatatat attcaggcga attctcacaa tgaacaataa taagattaaa atagctttcc  420
cccgttgcag cgcatgggta ttttttctag taaaaataaa agataaactt agactcaaaa  480
catttacaaa aacaacccct aaagttccta aagcccaaag tgctatccac gatccatagc  540
aagcccagcc caacccaacc caacccaacc caccccagtc cagccaactg gacaatagtc  600
tccacacccc cccactatca ccgtgagttg tccgcacgca ccgcacgtct cgcagccaaa  660
aaaaaaaaga aagaaaaaaa agaaaaagaa aaaacagcag gtgggtccgg gtcgtggggg  720
ccggaaacgc gaggaggatc gcgagccagc gacgaggccg gccctccctc cgcttccaaa  780
gaaacgcccc ccatcgccac tatatacata ccccccccctc tcctcccatc cccccaaccc  840
taccaccacc accaccacca cctccacctc ctcccccctc gctgccggac gacgagctcc  900
tccccccctcc ccctccgccg ccgccgcgcc ggtaaccacc ccgcccctct cctctttctt  960
tctccgtttt tttttccgtc tcggtctcga tctttggcct tggtagtttg ggtgggcgag  1020
aggcggcttc gtgcgcgccc agatcggtgc gcgggagggg cgggatctcg cggctggggc  1080
tctcgccggc gtggatccgg cccggatctc gcggggaatg gggctctcgg atgtagatct  1140
gcgatccgcc gttgttgggg gagatgatgg ggggtttaaa atttccgccg tgctaaacaa  1200
gatcaggaag aggggaaaag ggcactatgg tttatatttt tatatatttc tgctgcttcg  1260
tcaggcttag atgtgctaga tctttctttc ttctttttgt gggtagaatt tgaatccctc  1320
agcattgttc atcggtagtt tttcttttca tgatttgtga caaatgcagc ctcgtgcgga  1380
gctttttttgt aggtagaag                                              1399
```

```
SEQ ID NO: 165         moltype = DNA  length = 2181
FEATURE                Location/Qualifiers
source                 1..2181
                       mol_type = other DNA
                       organism = Oryza sativa
SEQUENCE: 165
gacaacaaca tgcttctcat caacatggag ggaagaggga gggagaaagt gtcgcctggt  60
cacctccatt gtcacactag ccactggcca gctctcccac accaccaatg ccaggggcga  120
gctttagcac agccaccgct tcacctccac caccgcacta ccctagcttc gcccaacagc  180
caccgtcaac gcctcctctc cgtcaacata agagagagag agaagaggag agtagccatg  240
tggggaggag gaatagtaca tggggcctac cgtttggcaa gttattttgg gttgccaagt  300
taggccaata aggggaggga tttggccatc cggttggaaa ggttattggg gtagtatctt  360
tttactagaa ttgtcaaaaa aaaatagttt gagagccatt tggagaggat gttgcctgtt  420
agaggtgctc ttaggacatc aaattccata aaaacatcag aaaaattctc tcgatgaaga  480
tttataacca ctaaaactgc cctcaattcg aagggagttc aaaacaatta aaatcatgtt  540
cgaattgagt ttcaatttca ctttaacccc tttgaaatct caatggtaaa acatcaaccc  600
gtcaggtagc atggttcttt ttattccttt caaaaagagt taattacaaa cagaatcaaa  660
actaacagtt aggcccaagg cccatccgag caaacaatag atcatgggcc aggcctgcca  720
ccaccctccc cctcctggct cccgctcttg aatttcaaaa tccaaaaata tcggcacgac  780
tggccgccga cggagcgggc ggaaaatgac ggaacaaccc ctcgaattct accccaacta  840
cgcccaccaa cccacacgcc actgacaatc cggtcccacc cttgtgggcc cacctacaag  900
cgagacgtca gtcgctcgca gcaaccagtg ggcccacctc ccagtgagcg gcgggtagat  960
ctggactctt acccacccac actaaacaaa acggcatgaa tattttgcac taaaaccctc  1020
agaaaaattc cgatattcca aaccagtaca gttcctgacc gttggaggag ccaaagtgga  1080
gcggagtgta aaattgggaa acttaatcga gggggttaaa cgcaaaaacg ccgaggcgcc  1140
tcccgctcta tagaaagggg aggagtggga ggtggaaacc ctaccacacc gcagagaaag  1200
gcgtcttcgt actcgcctct ctccgcgccc tcctccgccg ccgctcgccg ccgttcgtct  1260
```

```
ccgccgccac cggctagcca tccaggtaaa acaaacaaaa acggatctga tgcttccatt  1320
cctccgtttc tcgtagtagc gcgcttcgat ctgtgggtgg atctgggtga tcctggggtg  1380
tggttcgttc tgtttgatag atctgtcggt ggatctggcc ttctgtggtt gtcgatgtcc  1440
ggatctgcgt tttgatcagt ggtagttcgt ggatctggcg aaatgttttg gatctggcag  1500
tgagacgcta agaatcggga aatgatgcaa tattaggggg gtttcggatg gggatccact  1560
gaattagtct gtctccctgc tgataatctg ttcctttttg gtagatctgg ttagtgtatg  1620
tttgtttcgg atagatctga tcaatgcttg tttgtttttt caaattttct acctaggttg  1680
tataggaatg gcatgcggat ctggttggat tgccatgatc cgtgctgaaa tgcccctttg  1740
gttgatggat cttgatattt tactgctgtt cacctagatt tgtactcccg tttatactta  1800
atttgttgct tattatgaat agatctgtaa cttaggcaca tgtatggacg gagtatgtgg  1860
atctgtagta tgtacattgc tgcgagctaa gaactatttc agagcaagca cagaaaaaaa  1920
tatttagaca gattgggcaa ctatttgatg gtctttggta tcatgctttg tagtgctcgt  1980
ttctgcgtag taatcttttg atctgatctg aagataggtg ctattatatt cttaaaggtc  2040
attagaacgc tatctgaaag gctgtattat gtggattggt tcacctgtga ctccctgttc  2100
gtcttgtctt gataaatcct gtgataaaaa aaattcttaa ggcgtaattt gttgaaatct  2160
tgttttgtcc tatgcagcct g                                           2181
```

```
SEQ ID NO: 166         moltype = DNA  length = 1653
FEATURE                Location/Qualifiers
source                 1..1653
                       mol_type = other DNA
                       organism = synthetic construct
SEQUENCE: 166
atggaagacg ccaaaaacat aaagaaaggc ccggcgccat tctatcctct agaggatgga  60
accgctggag agcaactgca taaggctatg aagagatacg ccctggttcc tggaacaatt  120
gcttttacag atgcacatat cgaggtgaac atcacgtacg cggaatactt cgaaatgtcc  180
gttcggttgg cagaagctat gaaacgatat gggctgaata caaatcacag aatcgtcgta  240
tgcagtgaaa actctcttca attctttatg ccggtgttgg gcgcgttatt tatcggagtt  300
gcagttgcgc ccgcgaacga catttataat gaacgtgaat tgctcaacag tatgaacatt  360
tcgcagccta ccgtagtgtt tgtttccaaa aaggggttgc aaaaaatttt gaacgtgcaa  420
aaaaaattac caataatcca gaaaattatt atcatggatt ctaaaacgga ttaccaggga  480
tttcagtcga tgtacacgtt cgtcacatct catctacctc ccggttttaa tgaatacgat  540
tttgtaccag agtcctttga tcgtgacaaa acaattgcac tgataatgaa ttcctctgga  600
tctactgggt tacctaaggg tgtggccctt ccgcatagaa ctgcctgcgt cagattctcg  660
catgccagag atcctatttt tggcaatcaa atcattccgg atactgcgat tttaagtgtt  720
gttccattcc atcacggttt tggaatgttt actacactcg gatatttgat atgtggattt  780
cgagtcgtct taatgtatag atttgaagaa gagctgtttt tacgatccct tcaggattac  840
aaaattcaaa gtgcgttgct agtaccaacc ctattttcat tcttcgccaa aagcactctg  900
attgacaaat acgatttatc taatttacac gaaattgctt ctgggggcgc acctctttcg  960
aaagaagtcg gggaagcggt tgcaaaacgc ttccatcttc cagggatacg acaaggatat  1020
gggctcactg agactacatc agctattctg attacacccg agggggatga taaaccgggc  1080
gcggtcggta aagttgttcc atttttttgaa gcgaaggttg tggatctgga taccgggaaa  1140
acgctgggcg ttaatcagag aggcgaatta tgtgtcagag gacctatgat tatgtccggt  1200
tatgtaaaca atccggaagc gaccaacgcc ttgattgaca aggatggatg gctacattct  1260
ggagacatag cttactggga cgaagacgaa cacttcttca tagttgaccg cttgaagtct  1320
ttaattaaat acaaaggata tcaggtggcc cccgctgaat tggaatcgat attgttacaa  1380
caccccaaca tcttcgacgc gggcgtggca ggtcttcccg acgatgacgc cggtgaactt  1440
cccgccgccg ttgttgtttt ggagcacgga aagacgatga cggaaaaaga gatcgtggat  1500
tacgtcgcca gtcaagtaac aaccgcgaaa aagttgcgcg gaggagttgt gtttgtggac  1560
gaagtaccga aaggtcttac cggaaaactc gacgcaagaa aaatcagaga gatcctcata  1620
aaggccaaga agggcggaaa gtccaaattg taa                              1653
```

```
SEQ ID NO: 167         moltype = DNA  length = 936
FEATURE                Location/Qualifiers
source                 1..936
                       mol_type = other DNA
                       organism = synthetic construct
SEQUENCE: 167
atggcttcca aggtgtacga ccccgagcaa cgcaaacgca tgatcactgg gcctcagtgg  60
tgggctcgct gcaagcaaat gaacgtgctg gactccttca tcaactacta tgattccgag  120
aagcacgccg agaacgccgt gatttttctg catggtaacg ctgcctccag ctacctgtgg  180
aggcacgtcg tgcctcacat cgagcccgtg gctagatgca tcatccctga tctgatcgga  240
atgggtaagt ccggcaagag cgggaatggc tcatatcgcc tcctggatca ctacaagtac  300
ctcaccgctt ggttcgagct gctgaacctt ccaaagaaaa tcatctttgt gggccacgac  360
tggggggctt gtctggcctt tcactactcc tacgagcacc aagacaagat caaggccatc  420
gtccatgctg agagtgtcgt ggacgtgatc gagtcctggg acgagtggcc tgacatcgag  480
gaggatatcg ccctgatcaa gagcgaagag ggcgagaaaa tggtgcttga gaataacttc  540
ttcgtcgaga ccatgctccc aagcaagatc atgcggaaac tggagcctga ggagttcgct  600
gcctacctgg agccattcaa ggagaagggc gaggttagac ggcctaccct ctcctggcct  660
cgcgagatcc ctctcgttaa gggaggcaag cccgacgtcg tccagattgt ccgcaactac  720
aacgcctacc ttcgggccag cgacgatctg cctaagatgt tcatcgagtc cgaccctggg  780
ttcttttcca acgctattgt cgagggagct aagaagttcc ctaacaccga gttcgtgaag  840
gtgaagggcc tccacttcag ccaggaggac gctccagatg aaatgggtaa gtacatcaag  900
agcttcgtgg agcgcgtgct gaagaacgag cagtaa                           936
```

```
SEQ ID NO: 168         moltype = DNA  length = 675
FEATURE                Location/Qualifiers
source                 1..675
                       mol_type = other DNA
```

```
                         organism = synthetic construct
SEQUENCE: 168
ggtccgatgt gagacttttc aacaaagggt aatatccgga aacctcctcg gattccattg  60
cccagctatc tgtcacttta ttgtgaagat agtggaaaag gaaggtggct cctacaaatg  120
ccatcattgc gataaaggaa aggccatcgt tgaagatgcc tctgccgaca gtggtcccaa  180
agatggaccc ccacccacga ggagcatcgt ggaaaaagaa gacgttccaa ccacgtcttc  240
aaagcaagtg gattgatgtg atggtccgat gtgagacttt tcaacaaagg gtaatatccg  300
gaaacctcct cggattccat tgcccagcta tctgtcactt tattgtgaag atagtggaaa  360
aggaaggtgg ctcctacaaa tgccatcatt gcgataaagg aaaggccatc gttgaagatg  420
cctctgccga cagtggtccc aaagatggac ccccacccac gaggagcatc gtggaaaaag  480
aagacgttcc aaccacgtct tcaaagcaag tggattgatg tgatatctcc actgacgtaa  540
gggatgacgc acaatcccac tatccttcgc aagacccttc ctctatataa ggaagttcat  600
ttcatttgga gaggaaccat cttccacaca ctcaagccac actattggag aacacacagg  660
gacaacacac cataa                                                   675

SEQ ID NO: 169           moltype = DNA  length = 622
FEATURE                  Location/Qualifiers
source                   1..622
                         mol_type = other DNA
                         organism = Cauliflower mosaic virus
SEQUENCE: 169
ggtccgattg agacttttca acaaagggta atatccggaa acctcctcgg attccattgc  60
ccagctatct gtcactttat tgtgaagata gtggaaaagg aaggtggctc ctacaaatgc  120
catcattgcg ataaaggaaa ggccatcgtt gaagatgcct ctgccgacag tggtcccaaa  180
gatggacccc cacccacgag gagcatcgtg gaaaaagaag acgttccaac cacgtcttca  240
aagcaagtgg attgatgtga tggtccgatt gagacttttc aacaaagggt aatatccgga  300
aacctcctcg gattccattg cccagctatc tgtcacttta ttgtgaagat agtggaaaag  360
gaaggtggct cctacaaatg ccatcattgc gataaaggaa aggccatcgt tgaagatgcc  420
tctgccgaca gtggtcccaa agatggaccc ccacccacga ggagcatcgt ggaaaaagaa  480
gacgttccaa ccacgtcttc aaagcaagtg gattgatgtg atatctccac tgacgtaagg  540
gatgacgcac aatcccacta tctagacgca agacccttcc tctatataag gaagttcatt  600
tcatttggag aggacacgct ga                                           622

SEQ ID NO: 170           moltype = DNA  length = 1446
FEATURE                  Location/Qualifiers
source                   1..1446
                         mol_type = other DNA
                         organism = synthetic construct
SEQUENCE: 170
ggtccgattg agacttttca acaaagggta atatccggaa acctcctcgg attccattgc  60
ccagctatct gtcactttat tgtgaagata gtggaaaagg aaggtggctc ctacaaatgc  120
catcattgcg ataaaggaaa ggccatcgtt gaagatgcct ctgccgacag tggtcccaaa  180
gatggacccc cacccacgag gagcatcgtg gaaaaagaag acgttccaac cacgtcttca  240
aagcaagtgg attgatgtga tggtccgatt gagacttttc aacaaagggt aatatccgga  300
aacctcctcg gattccattg cccagctatc tgtcacttta ttgtgaagat agtggaaaag  360
gaaggtggct cctacaaatg ccatcattgc gataaaggaa aggccatcgt tgaagatgcc  420
tctgccgaca gtggtcccaa agatggaccc ccacccacga ggagcatcgt ggaaaaagaa  480
gacgttccaa ccacgtcttc aaagcaagtg gattgatgtg atatctccac tgacgtaagg  540
gatgacgcac aatcccacta tccttcgcaa gacccttcct ctatataagg aagttcattt  600
catttggaga ggacacgctg acaagctgac tctagcagat ctaccgtctt cggtacgcgc  660
tcactccgcc ctctgccttt gttactgcca cgtttctctg aatgctctct tgtgtggtga  720
ttgctgagag tggtttagct ggatctagaa ttacactctg aaatcgtgtt ctgcctgtgc  780
tgattacttg ccgtcctttg tagcagcaaa atatagggac atggtagtac gaaacgaaga  840
tagaacctac acagcaatac gagaaatgtg taatttggtg cttagcggta tttatttaag  900
cacatgttgg tgttataggg cacttggatt cagaagtttg ctgttaattt aggcacaggc  960
ttcatactac atgggtcaat agtataggga ttcatattat aggcgatact ataataattt  1020
gttcgtctgc agagcttatt atttgccaaa attagatatt cctattctgt ttttgtttgt  1080
gtgctgttaa attgttaacg cctgaaggaa taaatataaa tgacgaaatt ttgatgttta  1140
tctctgctcc tttattgtga ccataagtca agatcagatg cacttgtttt aaatattgtt  1200
gtctgaagaa ataagtactg acagtatttt gatgcattga tctgcttgtt tgttgtaaca  1260
aaatttaaaa ataaagagtt tcctttttgt tgctctcctt acctcctgat ggtatctagt  1320
atctaccaac tgacactata ttgcttctct ttacatacgt atcttgctcg atgccttctc  1380
cctagtgttg accagtgtta ctcacatagt ctttgctcat ttcattgtaa tgcagatacc  1440
aagcgg                                                             1446

SEQ ID NO: 171           moltype = DNA  length = 1165
FEATURE                  Location/Qualifiers
source                   1..1165
                         mol_type = other DNA
                         organism = synthetic construct
SEQUENCE: 171
ggtccgatgt gagacttttc aacaaagggt aatatccgga aacctcctcg gattccattg  60
cccagctatc tgtcacttta ttgtgaagat agtggaaaag gaaggtggct cctacaaatg  120
ccatcattgc gataaaggaa aggccatcgt tgaagatgcc tctgccgaca gtggtcccaa  180
agatggaccc ccacccacga ggagcatcgt ggaaaaagaa gacgttccaa ccacgtcttc  240
aaagcaagtg gattgatgtg atggtccgat gtgagacttt tcaacaaagg gtaatatccg  300
gaaacctcct cggattccat tgcccagcta tctgtcactt tattgtgaag atagtggaaa  360
aggaaggtgg ctcctacaaa tgccatcatt gcgataaagg aaaggccatc gttgaagatg  420
cctctgccga cagtggtccc aaagatggac ccccacccac gaggagcatc gtggaaaaag  480
```

```
aagacgttcc aaccacgtct tcaaagcaag tggattgatg tgatatctcc actgacgtaa  540
gggatgacgc acaatcccac tatccttcgc aagacccttc ctctatataa ggaagttcat  600
ttcatttgga gaggacacgc tgacaagctg actctagcag atcctctaga accatcttcc  660
acacactcaa gccacactat tggagaacac acagggacaa cacaccataa gatccaaggg  720
aggcctccgc cgccgccggt aaccaccccg cccctctcct ctttctttct ccgttttttt  780
ttccgtctcg gtctcgatct ttggccttgg tagtttgggt gggcgagagg cggcttcgtg  840
cgcgcccaga tcggtgcgcg ggaggggcgg gatctcgcgg ggaatggggc tctcggatgt  900
agatctgcga tccgccgttg ttgggggaga tgatgggggg tttaaaattt gcgccgtgct  960
aaacaagatc aggaagaggg gaaaagggca ctatggttta tatttttata tatttctgct  1020
gcttcgtcag gcttagatgt gctagatctt tctttcttct ttttgtgggt agaatttgaa  1080
tccctcagca ttgttcatcg gtagtttttc ttttcatgat ttgtgacaaa tgcagcctcg  1140
tgcggagctt ttttgtaggt agaag                                        1165

SEQ ID NO: 172         moltype = DNA  length = 1751
FEATURE                Location/Qualifiers
source                 1..1751
                       mol_type = other DNA
                       organism = synthetic construct
SEQUENCE: 172
tcgaggtcat tcatatgctt gagaagagag tcgggatagt ccaaaataaa acaaaggtaa  60
gattacctgg tcaaaagtga aaacatcagt taaaaggtgg tataaagtaa aatatcggta  120
ataaaaggtg gcccaaagtg aaatttactc ttttctacta ttataaaaat tgaggatgtt  180
tttgtcggta ctttgatacg tcatttttgt atgaattggt ttttaagttt attcgctttt  240
ggaaatgcat atctgtattt gagtcgggtt ttaagttcgt ttgcttttgt aaatacagag  300
ggatttgtat aagaaatatc tttagaaaaa cccatatgct aatttgacat aatttttgag  360
aaaaatatat attcaggcga attagcttag gcctcatcgt tgaagatgcc tctgccgaca  420
gtggtcccaa agatggaccc ccacccacga ggagcatcgt ggaaaaagaa gacgttccaa  480
ccacgtcttc aaagcaagtg gattgatgtg atatctccac tgacgtaagg gatgacgcac  540
aatcccacta tccttcgagg cctcatcgtt gaagatgcct ctgccgacag tggtcccaaa  600
gatggacccc cacccacgag gagcatcgtg gaaaaagaag acgttccaac cacgtcttca  660
aagcaagtgg attgatgtga tatctccact gacgtaaggg atgacgcaca atcccactat  720
ccttcgaagc taattctcac aatgaacaat aataagatta aaatagcttt cccccgttgc  780
agcgcatggg tattttttct agtaaaaata aaagataaac ttagactcaa aacatttaca  840
aaaacaaccc ctaaagttcc taaagcccaa agtgctatcc acgatccata gcaagcccag  900
cccaacccaa cccaacccaa cccaccccag tccagccaac tggacaatag tctccacacc  960
cccccactat caccgtgagt tgtccgcacg caccgcacgt ctcgcagcca aaaaaaaaaa  1020
gaaagaaaaa aaagaaaaag aaaaaacagc aggtgggtcc gggtcgtggg ggccggaaac  1080
gcgaggagga tcgcgagcca gcgacgaggc cggccctccc tccgcttcca aagaaacgcc  1140
ccccatcgcc actatataca tacccccccc tctcctccca tccccccaac cctaccacca  1200
ccaccaccac cacctccacc tcctccccc tcgctgccgg acgacgagct cctccccccct  1260
ccccctccgc cgccgccgcg ccggtaacca ccccgcccct ctcctctttc tttctccgtt  1320
tttttttccg tctcggtctc gatctttggc cttggtagtt tgggtgggcg agaggcggct  1380
tcgtgcgcgc ccagatcggt gcgcgggagg ggcgggatct cgcggctggg gctctcgccg  1440
gcgtggatcc ggcccggatc tcgcggggaa tggggctctc ggatgtagat ctgcgatccg  1500
ccgttgttgg gggagatgat ggggggttta aaatttccgc cgtgctaaac aagatcagga  1560
agaggggaaa agggcactat ggtttatatt tttatatatt tctgctgctt cgtcaggctt  1620
agatgtgcta gatctttctt tcttcttttt gtgggtagaa tttgaatccc tcagcattgt  1680
tcatcggtag tttttctttt catgatttgt gacaaatgca gcctcgtgcg gagctttttt  1740
gtaggtagaa g                                                       1751

SEQ ID NO: 173         moltype = DNA  length = 1101
FEATURE                Location/Qualifiers
source                 1..1101
                       mol_type = other DNA
                       organism = synthetic construct
SEQUENCE: 173
ggtccgattg agacttttca acaaagggta atatccggaa acctcctcgg attccattgc  60
ccagctatct gtcactttat tgtgaagata gtggaaaagg aaggtggctc ctacaaatgc  120
catcattgcg ataaaggaaa ggccatcgtt gaagatgcct ctgccgacag tggtcccaaa  180
gatggacccc cacccacgag gagcatcgtg gaaaaagaag acgttccaac cacgtcttca  240
aagcaagtgg attgatgtga tggtccgatt gagacttttc aacaaagggt aatatccgga  300
aacctcctcg gattccattg cccagctatc tgtcacttta ttgtgaagat agtggaaaag  360
gaaggtggct cctacaaatg ccatcattgc gataaaggaa aggccatcgt tgaagatgcc  420
tctgccgaca gtggtcccaa agatggaccc ccacccacga ggagcatcgt ggaaaaagaa  480
gacgttccaa ccacgtcttc aaagcaagtg gattgatgtg atatctccac tgacgtaagg  540
gatgacgcac aatcccacta tccttcgcaa gacccttcct ctatataagg aagttcattt  600
catttggaga ggacacgctg accgccgccg ccggtaacca ccccgcccct ctcctctttc  660
tttctccgtt tttttttccg tctcggtctc gatctttggc cttggtagtt tgggtgggcg  720
agaggcggct tcgtgcgcgc ccagatcggt gcgcgggagg ggcgggatct cgcggctggg  780
gctctcgccg gcgtggatcc ggcccggatc tcgcggggaa tggggctctc ggatgtagat  840
ctgcgatccg ccgttgttgg gggagatgat ggggggttta aaatttccgc cgtgctaaac  900
aagatcagga agaggggaaa agggcactat ggtttatatt tttatatatt tctgctgctt  960
cgtcaggctt agatgtgcta gatctttctt tcttcttttt gtgggtagaa tttgaatccc  1020
tcagcattgt tcatcggtag tttttctttt catgatttgt gacaaatgca gcctcgtgcg  1080
gagctttttt gtaggtagaa g                                            1101

SEQ ID NO: 174         moltype = DNA  length = 200
FEATURE                Location/Qualifiers
source                 1..200
```

```
                         mol_type = other DNA
                         organism = Cauliflower mosaic virus
SEQUENCE: 174
aaatcaccag tctctctcta caaatctatc tctctctatt tttctccaga ataatgtgtg  60
agtagttccc agataaggga attagggttc ttatagggtt tcgctcatgt gttgagcata  120
taagaaaccc ttagtatgta tttgtatttg taaaatactt ctatcaataa aatttctaat  180
tcctaaaacc aaaatccagt                                              200

SEQ ID NO: 175           moltype = DNA  length = 300
FEATURE                  Location/Qualifiers
source                   1..300
                         mol_type = other DNA
                         organism = Oryza sativa
SEQUENCE: 175
attaatcgat cctccgatcc cttaattacc ataccattac accatgcatc aatatccata  60
tatatataaa ccctttcgca cgtacttata ctatgttttg tcatacatat atatgtgtcg  120
aacgatcgat ctatcactga tatgatatga ttgatccatc agcctgatct ctgtatcttg  180
ttatttgtat accgtcaaat aaaagtttct tccacttgtg ttaataatta gctactctca  240
tctcatgaac cctatatata actagtttaa tttgctgtca attgaacatg atgatcgatg  300

SEQ ID NO: 176           moltype = DNA  length = 623
FEATURE                  Location/Qualifiers
source                   1..623
                         mol_type = other DNA
                         organism = Cauliflower mosaic virus
SEQUENCE: 176
ggtccgatgt gagacttttc aacaaagggt aatatccgga aacctcctcg gattccattg  60
cccagctatc tgtcacttta ttgtgaagat agtggaaaag gaaggtggct cctacaaatg  120
ccatcattgc gataaaggaa aggccatcgt tgaagatgcc tctgccgaca gtggtcccaa  180
agatggaccc ccacccacga ggagcatcgt ggaaaaagaa gacgttccaa ccacgtcttc  240
aaagcaagtg gattgatgtg atggtccgat gtgagacttt tcaacaaagg gtaatatccg  300
gaaacctcct cggattccat tgcccagcta tctgtcactt tattgtgaag atagtggaaa  360
aggaaggtgg ctcctacaaa tgccatcatt gcgataaagg aaaggccatc gttgaagatg  420
cctctgccga cagtggtccc aaagatggac ccccacccac gaggagcatc gtggaaaaag  480
aagacgttcc aaccacgtct tcaaagcaag tggattgatg tgatatctcc actgacgtaa  540
gggatgacgc acaatcccac tatccttcgc aagacccttc ctctatataa ggaagttcat  600
ttcatttgga gaggacacgc tga                                          623

SEQ ID NO: 177           moltype =   length =
SEQUENCE: 177
000

SEQ ID NO: 178           moltype = DNA  length = 804
FEATURE                  Location/Qualifiers
source                   1..804
                         mol_type = other DNA
                         organism = Zea mays
SEQUENCE: 178
accgtcttcg gtacgcgctc actccgccct ctgcctttgt tactgccacg tttctctgaa  60
tgctctcttg tgtggtgatt gctgagagtg gtttagctgg atctagaatt acactctgaa  120
atcgtgttct gcctgtgctg attacttgcc gtcctttgta gcagcaaaat atagggacat  180
ggtagtacga aacgaagata gaacctacac agcaatacga gaaatgtgta atttggtgct  240
tagcggtatt tatttaagca catgttggtg ttatagggca cttggattca gaagtttgct  300
gttaatttag gcacaggctt catactacat gggtcaatag tatagggatt catattatag  360
gcgatactat aataatttgt tcgtctgcag agcttattat ttgccaaaat tagatattcc  420
tattctgttt ttgtttgtgt gctgttaaat tgttaacgcc tgaaggaata aatataaatg  480
acgaaatttt gatgtttatc tctgctcctt tattgtgacc ataagtcaag atcagatgca  540
cttgttttaa atattgttgt ctgaagaaat aagtactgac agtattttga tgcattgatc  600
tgcttgtttg ttgtaacaaa atttaaaaat aaagagtttc ctttttgttg ctctccttac  660
ctcctgatgg tatctagtat ctaccaactg acactatatt gcttctcttt acatacgtat  720
cttgctcgat gccttctccc tagtgttgac cagtgttact cacatagtct ttgctcattt  780
cattgtaatg cagataccaa gcgg                                         804

SEQ ID NO: 179           moltype = DNA  length = 1396
FEATURE                  Location/Qualifiers
source                   1..1396
                         mol_type = other DNA
                         organism = Oryza sativa
SEQUENCE: 179
tcgaggtcat tcatatgctt gagaagagag tcgggatagt ccaaaataaa acaaaggtaa  60
gattacctgg tcaaaagtga aaacatcagt taaaaggtgg tataaagtaa aatatcggta  120
ataaaaggtg gcccaaagtg aaatttactc ttttctacta ttataaaaat tgaggatgtt  180
tttgtcggta ctttgatacg tcatttttgt atgaattggt ttttaagttt attcgctttt  240
ggaaatgcat atctgtattt gagtcgggtt ttaagttcgt ttgcttttgt aaatacagag  300
ggatttgtat aagaaatatc tttagaaaaa cccatatgct aatttgacat aatttttgag  360
aaaaatatat attcaggcga attctcacaa tgaacaataa taagattaaa atagctttcc  420
cccgttgcag cgcatgggta ttttttctag taaaaataaa agataaactt agactcaaaa  480
catttacaaa aacaacccct aaagttccta aagcccaaag tgctatccac gatccatagc  540
aagcccagcc caacccaacc caacccagcc caccccagtc cagccaactg gacaatagtc  600
```

```
tccacacccc cccactatca ccgtgagttg tccgcacgca ccgcacgtct cgcagccaaa  660
aaaaaaaaga aagaaaaaaa agaaaaagaa aaaacagcag gtgggtccgg gtcgtggggg  720
ccggaaacgc gaggaggatc gcgagccagc gacgaggccg gccctccctc cgcttccaaa  780
gaaacgcccc ccatcgccac tatatacata cccccccctc tcctcccatc cccccaaccc  840
taccaccacc accaccacca cctccacctc ctcccccctc gctgccggac gacgagctcc  900
tccccccctcc ccctccgccg ccgccgcgcc ggtaaccacc ccgcccctct cctctttctt  960
tctccgtttt tttttccgtc tcggtctcga tctttggcct tggtagtttg ggtgggcgag  1020
aggcggcttc gtgccgccca gatcggtgcg cgggaggggc gggatctcgc ggctggctct  1080
cgcccccgtg gatccggccc ggatctcgcg gggaatgggg ctctcggatg tagatctgcg  1140
atccgccgtt gttggggccg atgatggggc ccttaaaatt tccgccgtgc taaacaagat  1200
caggaagagg ggaaaagggc actatggttt atatttttat atatttctgc tgcttcgtca  1260
ggcttagatg tgctagatct ttctttcttc tttttgtggg tagaatttaa tccctcagca  1320
ttgttcatcg gtagtttttc ttttcatgat tcgtgacaaa tgcagcctcg tgcggacgtt  1380
tttttgtagg tagaag                                                 1396
```

```
SEQ ID NO: 180          moltype = DNA  length = 2625
FEATURE                 Location/Qualifiers
source                  1..2625
                        mol_type = other DNA
                        organism = Setaria italica
SEQUENCE: 180
actgccgcga cacgcctcac tggcgggagg gctccgagcg ctctctcccc ggcggccggc  60
ggagcagcga tctggattgg agagaataga ggaaagagag ggaaaaggag agagatagcg  120
caaagagctg aaaagataag gttgtgcggg ctgtggtgat tagaggacca ctaatccctc  180
catctcctaa tgacgcggtg cccaagacca gtgccgcggc acaccagcgt ctaagtgaac  240
ttccgctaac cttccggtca ttgcgcctga aagatgtcat gtggcgaggc ccccctctca  300
gtagattgcc aactgcctac cgtgccactc ttccatgcat gattgctccc gtctatcccg  360
tttctcacaa cagatagaca acagtaagca tcactaaagc aagcatgtgt agaaccttaa  420
aaaaaggctt atactaccag tatactatca accagcatgc cgtttttgaa gtatccagga  480
ttagaagctt ctactgcgct tttatattat agctgtggac ccgtggtaac ctttctcttt  540
tggcgcttgc ttaatctcgg ccgtgctggt ccatgcttag gcactaggca gagatagagc  600
cgggggtgaa tggggctaaa gctcagctgc tcgaggggcc gtgggctggt ttccactagc  660
ctacagctgt gccacgtgcg gccgcgcaag ccgaagcaag cacgctgagc cgttggacag  720
cttgtcataa tgccattacg tggattacac gtaactggcc ctgtaactac tcgttcggcc  780
atcatcaaac gacgacgtcc gctaggcgac gacacgggta atgcacgcag ccacccaggc  840
gcgcgcgcta gcggagcacg gtcaggtgac acgggcgtcg tgacgcttcc gagttgaagg  900
ggttaacgcc agaaacagtg tttggccagg gtatgaacat aacaaaaaat attcacacga  960
aagaatggaa gtatggagct gctactgtgt aaatgccaag caggaaactc acgcccgcta  1020
acatccaacg gccaacagct cgacgtgccg gtcagcagag catcggaaca ctggtgattg  1080
gtggagccgg cagtatgcgc cccagcacgg ccgaggtggt ggtggcccgt ggccctgctg  1140
tctgcgcggc tcgggacaac ttgaaactgg gccaccgcct cgtcgcaact cgcaacccgt  1200
tggcggaaga aaggaatggc tcgtaggggc ccgggtagaa tcgaagaatg ttgcgctggg  1260
cttcgattca cataacatgg gcctgaagct ctaaaacgac ggcccggtcg ccgcgcgatg  1320
gaaagagacc ggatcctcct cgtgaattct ggaaggccac acgagagcga cccaccaccg  1380
acgcggagga gtcgtgcgtg gtccaacacg gccggcgggc tgggctgcga ccttaaccag  1440
caaggcacgc cacgacccgc cccgccctcg aggcataaat accctcccat cccgttgccg  1500
caagactcag atcagattcc gatccccagt tcttccccaa tcaccttgtg gtctctcgtg  1560
tcgcggttcc cagggacgcc tccggctcgt cgctcgacag cgatctccgc cccagcaagg  1620
tatagattca gttccttgct ccgatcccaa tctggttgag atgttgctcc gatgcgactt  1680
gattatgtca tatatctgcg gtttgcaccg atctgaagcc tagggtttct cgagcgaccc  1740
agttatttgc aatttgcgat ttgctcgttt gttgcgcagc gtagtttatg tttggagtaa  1800
tcgaggattt gtatgcggcg tcggcgctac ctgcttaatc acgccatgtg acgcggttac  1860
ttgcagaggc tgggttctgt tatgtcgtga tctaagaatc tagattaggc tcagtcgttc  1920
ttgctgtcga ctagtttgtt ttgatatcca tgtagtacaa gttacttaaa atttaggtcc  1980
aatatatttt gcatgctttt ggcctgttat tcttgccaac aagttgtcct ggtaaaaagt  2040
agatgtgaaa gtcacgtatt gggacaaatt gatggtttag tgctatagtt ctatagttct  2100
gtgatacatc tatctgattt tttttggtct attggtgcct aacttatctg aaaatcatgg  2160
aacatgaggc tagtttgatc atggtttagt tcattgtgat taataatgta tgatttagta  2220
gctattttgg tgatcgtgtc attttatttg tgaatggaat cattgtatgt aaatgaagct  2280
agttcagggg ttacgatgta gctggctttg tattctaaag gctgctatta ttcatccatc  2340
gatttcacct atatgtaatc cagagctttt gatgtgaaat ttgtctgatc cttcactagg  2400
aaggacagaa cattgttaat attttggcac atctgtctta ttctcatcct ttgtttgaac  2460
atgttagcct gttcaaacag atactgttgt aatgtcctag ttatataggt acatatgtgt  2520
tctctattga gtttatggac ttttgtgtgt gaagttatat ttcattttgc tcaaaactca  2580
tgtttgcaag ctttctgaca ttattctatt gttctgaaac aggtg                 2625
```

```
SEQ ID NO: 181          moltype = DNA  length = 2008
FEATURE                 Location/Qualifiers
source                  1..2008
                        mol_type = other DNA
                        organism = Zea mays
                        sub_species = Mexicana
SEQUENCE: 181
gtcgtgcccc tctctagaga taaagagcat tgcatgtcta aagtataaaa aattaccaca  60
tattttttttg tcacacttat ttgaagtgta gtttatctat ctctatacat atatttaaac  120
ttcactctac aaataatata gtctataata ctaaaataat attagtgttt tagaggatca  180
tataaataaa ctgctagaca tggtctaaag gataattgaa tattttgaca atctacagtt  240
ttatcttttt agtgtgcatg tgatctctct gttttttttg caaatagctt gacctatata  300
atacttcatc cattttatta gtacatccat ttaggattta gggttgatgg tttctataga  360
```

```
ctaattttta gtacatccat tttattcttt ttagtctcta aatttttaa aactaaaact  420
ctattttagt tttttattta ataatttaga tataaaatga aataaaataa attgactaca  480
aataaaacaa atacccttta agaaataaaa aaactaagca aacattttc ttgtttcgag  540
tagataatga caggctgttc aacgccgtcg acgagtctaa cggacaccaa ccagcgaacc  600
agcagcgtcg cgtcgggcca agcgaagcag acggcacggc atctctgtag ctgcctctgg  660
acccctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acgggggatt cctttcccac cgctccttcg ctttcccttc ctcgcccgcc  840
gtaataaata gacacccccct ccacaccctc tttccccaac ctcgtgttcg ttcggagcgc  900
acacacacgc aaccagatct cccccaaatc cagccgtcgg cacctccgct tcaaggtacg  960
ccgctcatcc tcccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc ttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgttgg gtgatacttc tgcagcgg                                     2008

SEQ ID NO: 182          moltype = DNA  length = 1053
FEATURE                 Location/Qualifiers
source                  1..1053
                        mol_type = other DNA
                        organism = Zea mays
                        sub_species = Mexicana
SEQUENCE: 182
gtacgccgct catcctcccc cccccctct ctctaccttc tctagatcgg cgatccggtc  60
catggttagg gcccggtagt tctacttctg ttcatgtttg tgttagagca aacatgttca  120
tgttcatgtt tgtgatgatg tggtctggtt gggcggtcgt tctagatcgg agtaggatac  180
tgtttcaagc tacctggtgg atttattaat tttgtatctg tatgtgtgtg ccatacatct  240
tcatagttac gagtttaaga tgatggatgg aaatatcgat ctaggatagg tatacatgtt  300
gatgcgggtt ttactgatgc atatacagag atgctttttt tctcgcttgg ttgtgatgat  360
atggtctggt tgggcggtcg ttctagatcg gagtagaata ctgtttcaaa ctacctggtg  420
gatttattaa aggataaagg gtcgttctag atcggagtag aatactgttt caaactacct  480
ggtggattta ttaaaggatc tgtatgtatg tgcctacatc ttcatagtta cgagtttaag  540
atgatggatg gaaatatcga tctaggatag gtatacatgt tgatgcgggt tttactgatg  600
catatacaga gatgcttttt ttcgcttggt tgtgatgatg tggtctggtt gggcggtcgt  660
tctagatcgg agtagaatac tgtttcaaac tacctggtgg atttattaat tttgtatctt  720
tatgtgtgtg ccatacatct tcatagttac gagtttaaga tgatggatgg aaatattgat  780
ctaggatagg tatacatgtt gatgtgggtt ttactgatgc atatacatga tggcatatgc  840
ggcatctatt catatgctct aaccttgagt acctatctat tataataaac aagtatgttt  900
tataattatt ttgatcttga tatacttgga tgatggcata tgcagcagct atatgtggat  960
tttttagccc tgccttcata cgctatttat ttgcttggta ctgtttcttt tgtccgatgc  1020
tcaccctgtt gttgggtgat acttctgcag cgg                              1053

SEQ ID NO: 183          moltype = DNA  length = 2625
FEATURE                 Location/Qualifiers
source                  1..2625
                        mol_type = other DNA
                        organism = Setaria italica
SEQUENCE: 183
actgccgcga cacgcctcac tggcgggagg gctccgagcg ctctctcccc ggcggccggc  60
ggagcagcga tctggattgg agagaataga ggaaagagag ggaaaaggag agagatagcg  120
caaagagctg aaaagataag gttgtgcggg ctgtggtgat tagaggacca ctaatccctc  180
catctcctaa tgacgcggtg cccaagacca gtgccgcggc acaccagcgt ctaagtgaac  240
ttccgctaac cttccggtca ttgcgcctga aagatgtcat gtggcgaggc ccccctctca  300
gtagattgcc aactgcctac cgtgccactc ttccatgcat gattgctccc gtctatcccg  360
tttctcacaa cagatagaca acagtaagca tcactaaagc aagcatgtgt agaaccttaa  420
aaaaaggctt atactaccag tatactatca accagcatgc cgtttttgaa gtatccagga  480
ttagaagctt ctactgcgct tttatattat agctgtggac ccgtggtaac ctttctcttt  540
tggcgcttgc ttaatctcgg ccgtgctggt ccatgcttag gcactaggca gagatagagc  600
cgggggtgaa tggggctaaa gctcagctgc tcgaggggcc gtgggctggt ttccactagc  660
ctacagctgt gccacgtgcg gccgcgcaag ccgaagcaag cacgctgagc cgttggacag  720
cttgtcataa tgccattacg tggattacac gtaactggcc ctgtaactac tcgttcggcc  780
atcatcaaac gacgacgtcc gctaggcgac gacacgggta atgcacgcag ccacccaggc  840
gcgcgcgcta gcggagcacg gtcaggtgac acgggcgtcg tgacgcttcc gagttgaagg  900
ggttaacgcc agaaacagtg tttggccagg gtatgaacat aacaaaaaat attcacacga  960
aagaatggaa gtatggagct gctactgtgt aaatgccaag caggaaactc acgcccgcta  1020
acatccaacg gccaacagct cgacgtgccg gtcagcagag catcggaaca ctggtgattg  1080
```

-continued

```
gtggagccgg cagtatgcgc cccagcacgg ccgaggtggt ggtggcccgt ggccctgctg  1140
tctgcgcggc tcgggacaac ttgaaactgg gccaccgcct cgtcgcaact cgcaacccgt  1200
tggcggaaga aaggaatggc tcgtaggggc ccgggtagaa tcgaagaatg ttgcgctggg  1260
cttcgattca cataacatgg gcctgaagct ctaaaacgac ggcccggtcg ccgcgcgatg  1320
gaaagagacc ggatcctcct cgtgaattct ggaaggccac acgagagcga cccaccaccg  1380
acgcggagga gtcgtgcgtg gtccaacacg gccggcgggc tgggctgcga ccttaaccag  1440
caaggcacgc cacgacccgc cccgccctcg aggcataaat accctcccat cccgttgccg  1500
caagactcag atcagattcc gatccccagt tcttccccaa tcaccttgtg gtctctcgtg  1560
tcgcggttcc cagggacgcc tccggctcgt cgctcgacag cgatctccgc cccagcaagg  1620
tatagattca gttccttgct ccgatcccaa tctggttgag atgttgctcc gatgcgactt  1680
gattatgtca tatatctgcg gtttgcaccg atctgaagcc tagggtttct cgagcgaccc  1740
agttatttgc aatttgcgat ttgctcgttt gttgcgcagc gtagtttatg tttggagtaa  1800
tcgaggattt gtatgcggcg tcggcgctac ctgcttaatc acgccatgtg acgcggttac  1860
ttgcagaggc tgggttctgt tatgtcgtga tctaagaatc tagattaggc tcagtcgttc  1920
ttgctgtcga ctagtttgtt ttgatatcca tgtagtacaa gttacttaaa atttaggtcc  1980
aatatatttt gcatgctttt ggcctgttat tcttgccaac aagttgtcct ggtaaaaagt  2040
agatgtgaaa gtcacgtatt gggacaaatt gatggtttag tgctatagtt ctatagttct  2100
gtgatacatc tatctgattt tttttggtct attggtgcct aacttatctg aaaatcatgg  2160
aacatgaggc tagtttgatc atggtttagt tcattgtgat taataatgta tgatttagta  2220
gctattttgg tgatcgtgtc attttatttg tgaatggaat cattgtatgt aaatgaagct  2280
agttcagggg ttacgatgta gctggctttg tattctaaag gctgctatta ttcatccatc  2340
gatttcacct atatgtaatc cagagctttt gatgtgaaat ttgtctgatc cttcactagg  2400
aaggacagaa cattgttaat attttggcac atctgtctta ttctcatcct ttgtttgaac  2460
atgttagcct gttcaaacag atactgttgt aatgtcctag ttatataggt acatatgtgt  2520
tctctattga gtttatggac ttttgtgtgt gaagttatat ttcattttgc tcaaaactca  2580
tgtttgcaag ctttctgaca ttattctatt gttctgaaac aggtg                  2625
```